(12) United States Patent
Jackson et al.

(10) Patent No.: US 11,819,249 B2
(45) Date of Patent: Nov. 21, 2023

(54) PIVOTAL BONE ANCHOR ASSEMBLY HAVING TWIST-IN-PLACE INSERT WITH FORCED INTERFERENCE DOWNWARD DISPLACEMENT

(71) Applicant: Roger P. Jackson, Prairie Village, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 0 days.

(21) Appl. No.: 18/045,113

(22) Filed: Oct. 7, 2022

(65) Prior Publication Data

US 2023/0113760 A1 Apr. 13, 2023

Related U.S. Application Data

(63) Continuation of application No. 17/536,942, filed on Nov. 29, 2021, now Pat. No. 11,464,549, which is a continuation of application No. 17/228,345, filed on Apr. 12, 2021, now Pat. No. 11,185,352, which is a continuation of application No. 16/942,273, filed on Jul. 29, 2020, now Pat. No. 10,973,555, which is a continuation of application No. 16/538,443, filed on Aug. 12, 2019, now Pat. No. 10,765,456, which is a
(Continued)

(51) Int. Cl.
*A61B 17/70* (2006.01)
*A61B 17/86* (2006.01)
*A61B 90/00* (2016.01)

(52) U.S. Cl.
CPC ........ *A61B 17/7037* (2013.01); *A61B 17/702* (2013.01); *A61B 17/7008* (2013.01); *A61B 17/864* (2013.01); *A61B 17/8605* (2013.01); *A61B 17/8615* (2013.01); *A61B 17/8685* (2013.01); *A61B 17/705* (2013.01); *A61B 17/7031* (2013.01); *A61B 17/7091* (2013.01); *A61B 2090/037* (2016.02)

(58) Field of Classification Search
CPC ............................................... A61B 2017/564
See application file for complete search history.

(56) References Cited

U.S. PATENT DOCUMENTS 5,501,684 A 3/1996 Schlapfer
5,584,834 A 12/1996 Errico et al.
(Continued)

*Primary Examiner* — Sameh R Boles
(74) *Attorney, Agent, or Firm* — Polsinelli PC

(57) ABSTRACT

A receiver assembly includes a receiver having a first channel, a through-space with internal recesses beneath a guide and advancement structure, and internal ridges projecting inwardly below the internal recesses. The assembly also includes an insert having a second channel, side structures protruding laterally outward below top surfaces, and opposed lower extensions extending downwardly below the second channel, with the insert being loadable into the through-space with the second channel in non-alignment with the first channel. The insert is the non-threadably rotatable within the through-space to align the second channel with the first channel and to move the side structures into the internal recesses above the internal ridges, with a subsequent forced downward displacement of the insert within the through-space causing the side structures to frictionally engage the internal ridges to inhibit the insert from moving upward within the through-space.

18 Claims, 122 Drawing Sheets

Related U.S. Application Data continuation of application No. 16/516,576, filed on Jul. 19, 2019, now Pat. No. 10,765,455, which is a continuation of application No. 15/663,316, filed on Jul. 28, 2017, now Pat. No. 10,441,319, which is a continuation of application No. 15/239,515, filed on Aug. 17, 2016, now Pat. No. 9,956,006, which is a continuation of application No. 14/052,265, filed on Oct. 11, 2013, now abandoned, which is a continuation of application No. 12/924,802, filed on Oct. 5, 2010, now Pat. No. 8,556,938, and a continuation-in-part of application No. 12/802,849, filed on Jun. 15, 2010, now abandoned.

(60) Provisional application No. 61/403,915, filed on Sep. 23, 2010, provisional application No. 61/403,696, filed on Sep. 20, 2010, provisional application No. 61/402,959, filed on Sep. 8, 2010, provisional application No. 61/400,504, filed on Jul. 29, 2010, provisional application No. 61/398,807, filed on Jul. 1, 2010, provisional application No. 61/396,390, filed on May 26, 2010, provisional application No. 61/395,752, filed on May 17, 2010, provisional application No. 61/395,564, filed on May 14, 2010, provisional application No. 61/343,737, filed on May 3, 2010, provisional application No. 61/336,911, filed on Jan. 28, 2010, provisional application No. 61/278,240, filed on Oct. 5, 2009, provisional application No. 61/270,754, filed on Jul. 13, 2009, provisional application No. 61/268,708, filed on Jun. 15, 2009.

(56) References Cited

U.S. PATENT DOCUMENTS

| | | |
|---|---|---|
| 5,672,176 A | 9/1997 | Biedermann et al. |
| 5,735,853 A | 4/1998 | Olerud |
| 5,891,145 A | 4/1999 | Morrison et al. |
| 6,063,090 A | 5/2000 | Schlapfer |
| 6,146,383 A | 11/2000 | Studer et al. |
| 6,241,731 B1 | 6/2001 | Fiz |
| 6,280,442 B1 | 8/2001 | Barker et al. |
| 6,626,908 B2 | 9/2003 | Cooper et al. |
| 6,648,888 B1 | 11/2003 | Shluzas |
| 6,660,004 B2 | 12/2003 | Barker et al. |
| 6,716,214 B1 | 4/2004 | Jackson |
| 6,740,086 B2 | 5/2004 | Richelsoph |
| 6,837,889 B2 | 1/2005 | Shluzas |
| 6,945,975 B2 | 9/2005 | Dalton |
| 7,001,389 B1 | 2/2006 | Navarro et al. |
| 7,066,937 B2 | 6/2006 | Shluzas |
| 7,160,300 B2 | 1/2007 | Jackson |
| 7,179,261 B2 | 2/2007 | Sicvol et al. |
| 7,186,255 B2 | 3/2007 | Baynham |
| 7,306,606 B2 | 12/2007 | Sasing |
| 7,322,981 B2 | 1/2008 | Jackson |
| 7,491,218 B2 | 2/2009 | Landry et al. |
| 7,530,992 B2 | 5/2009 | Biedermann et al. |
| 7,604,655 B2 | 10/2009 | Warnick |
| 7,618,444 B2 | 11/2009 | Shluzas |
| 7,625,396 B2 | 12/2009 | Jackson |
| 7,766,945 B2 | 8/2010 | Nilsson et al. |
| 7,776,067 B2 | 8/2010 | Jackson |
| 7,811,310 B2 | 10/2010 | Baker et al. |
| 7,833,251 B1 | 11/2010 | Ahlgren et al. |
| 7,857,834 B2 | 12/2010 | Boschert |
| 7,875,065 B2 | 1/2011 | Jackson |
| 7,901,436 B2 | 3/2011 | Baccelli |
| 7,922,748 B2 | 4/2011 | Hoffman |
| 7,947,065 B2 | 5/2011 | Hammill et al. |
| 8,021,397 B2 | 9/2011 | Farris et al. |
| 8,034,089 B2 | 10/2011 | Matthis et al. |
| 8,048,112 B2 | 11/2011 | Suziki et al. |
| 8,048,126 B2 | 11/2011 | Altarac et al. |
| 8,066,744 B2 | 11/2011 | Justis et al. |
| 8,133,262 B2 | 3/2012 | Whipple |
| 8,137,386 B2 | 3/2012 | Jackson |
| 8,206,422 B2 | 6/2012 | Hestad et al. |
| 8,277,485 B2 | 10/2012 | Krishna et al. |
| 8,353,932 B2 | 1/2013 | Jackson |
| 8,361,129 B2 | 1/2013 | Chao |
| 8,377,102 B2 | 2/2013 | Jackson |
| 8,382,805 B2 | 2/2013 | Wang et al. |
| 8,430,914 B2 | 4/2013 | Spratt et al. |
| 8,444,681 B2 | 5/2013 | Jackson et al. |
| 8,506,609 B2 | 8/2013 | Biedermann et al. |
| 8,591,558 B2 | 11/2013 | Matthis et al. |
| 8,814,913 B2 | 8/2014 | Jackson |
| 8,876,869 B1 | 11/2014 | Schafer et al. |
| 8,986,349 B1 | 3/2015 | German |
| 9,168,069 B2 | 10/2015 | Jackson |
| 9,393,047 B2 | 7/2016 | Jackson et al. |
| 9,439,681 B2 | 9/2016 | Keyer et al. |
| 9,456,853 B2 | 10/2016 | Jackson |
| 9,480,517 B2 | 11/2016 | Jackson et al. |
| 9,504,496 B2 | 11/2016 | Jackson et al. |
| 9,572,599 B1 | 2/2017 | Casey et al. |
| 9,717,534 B2 | 8/2017 | Jackson et al. |
| 9,883,892 B2 | 2/2018 | Jackson et al. |
| 9,895,172 B2 | 2/2018 | Biedermann et al. |
| 9,907,574 B2 | 3/2018 | Jackson et al. |
| 9,918,745 B2 | 3/2018 | Jackson |
| 9,956,006 B2 | 5/2018 | Jackson |
| 9,980,743 B2 | 5/2018 | Jackson et al. |
| 9,980,753 B2 | 5/2018 | Jackson |
| 10,172,649 B2 | 1/2019 | Jackson et al. |
| 10,179,010 B2 | 1/2019 | Jackson et al. |
| 10,363,070 B2 | 7/2019 | Jackson et al. |
| 10,456,173 B1 | 10/2019 | Casey et al. |
| 2002/0022842 A1 | 2/2002 | Horvath et al. |
| 2002/0026193 A1* | 2/2002 | Barker ............ A61B 17/7037 606/328 |
| 2002/0133159 A1 | 9/2002 | Jackson |
| 2002/0143341 A1 | 10/2002 | Biedermann et al. |
| 2002/0193794 A1 | 12/2002 | Taylor |
| 2004/0039383 A1 | 2/2004 | Jackson |
| 2004/0049196 A1 | 3/2004 | Jackson |
| 2004/0167526 A1 | 8/2004 | Jackson |
| 2004/0267264 A1 | 12/2004 | Konieczynski et al. |
| 2005/0080415 A1 | 4/2005 | Keyer et al. |
| 2005/0228379 A1 | 10/2005 | Jackson |
| 2005/0240180 A1 | 10/2005 | Vienney |
| 2005/0261687 A1 | 11/2005 | Garamszegi |
| 2006/0025771 A1 | 2/2006 | Jackson |
| 2006/0058788 A1 | 3/2006 | Hammer |
| 2006/0155277 A1 | 7/2006 | Metz-Stavenhagen |
| 2006/0173454 A1 | 8/2006 | Spitler et al. |
| 2006/0200131 A1 | 9/2006 | Chao et al. |
| 2006/0217716 A1 | 9/2006 | Baker |
| 2006/0293664 A1 | 12/2006 | Schumacher |
| 2007/0088357 A1 | 4/2007 | Johnson et al. |
| 2007/0090238 A1 | 4/2007 | Justis |
| 2007/0093826 A1 | 4/2007 | Hawkes et al. |
| 2007/0093827 A1 | 4/2007 | Warnick |
| 2007/0118117 A1 | 5/2007 | Altarac et al. |
| 2007/0118123 A1 | 5/2007 | Strausbaugh et al. |
| 2007/0123862 A1 | 5/2007 | Warnick |
| 2007/0161999 A1 | 7/2007 | Biedermann et al. |
| 2007/0233087 A1 | 10/2007 | Schlapfer |
| 2007/0270813 A1 | 11/2007 | Garamszegi |
| 2007/0270831 A1 | 11/2007 | Dewey et al. |
| 2008/0045953 A1 | 2/2008 | Garamszegi |
| 2008/0086132 A1 | 4/2008 | Biedermann et al. |
| 2008/0132957 A1 | 6/2008 | Matthis et al. |
| 2008/0140135 A1 | 6/2008 | Konieczynski et al. |
| 2008/0140136 A1 | 6/2008 | Jackson |
| 2008/0147129 A1 | 6/2008 | Biedermann et al. |
| 2008/0154315 A1 | 6/2008 | Jackson |
| 2008/0161863 A1 | 7/2008 | Arnold et al. |
| 2008/0215100 A1 | 9/2008 | Matthis et al. |

(56) References Cited

U.S. PATENT DOCUMENTS

| | | |
|---|---|---|
| 2008/0221681 A1 | 9/2008 | Trieu et al. |
| 2008/0234761 A1 | 9/2008 | Jackson |
| 2008/0269809 A1 | 10/2008 | Garamszegi |
| 2008/0294202 A1 | 11/2008 | Peterson et al. |
| 2008/0319490 A1 | 12/2008 | Jackson |
| 2009/0012567 A1 | 1/2009 | Biedermann et al. |
| 2009/0062865 A1 | 3/2009 | Schumacher |
| 2009/0062866 A1 | 3/2009 | Jackson |
| 2009/0062867 A1 | 3/2009 | Schumacher |
| 2009/0069852 A1 | 3/2009 | Farris et al. |
| 2009/0069853 A1 | 3/2009 | Schumacher |
| 2009/0105769 A1 | 4/2009 | Rock et al. |
| 2009/0204155 A1 | 8/2009 | Aschmann |
| 2010/0004692 A1 | 1/2010 | Biedermann |
| 2010/0023061 A1 | 1/2010 | Randol et al. |
| 2010/0087865 A1 | 4/2010 | Biedermann et al. |
| 2010/0094343 A1 | 4/2010 | Pham et al. |
| 2010/0094349 A1 | 4/2010 | Hammer et al. |
| 2010/0100137 A1 | 4/2010 | Justis et al. |
| 2010/0152787 A1 | 6/2010 | Walsh et al. |
| 2010/0234902 A1 | 9/2010 | Biedermann et al. |
| 2010/0256686 A1 | 10/2010 | Fisher |
| 2010/0262195 A1 | 10/2010 | Jackson |
| 2010/0274288 A1 | 10/2010 | Prevost et al. |
| 2010/0298891 A1 | 11/2010 | Jackson |
| 2010/0305621 A1 | 12/2010 | Wang et al. |
| 2011/0040338 A1 | 2/2011 | Jackson |
| 2011/0077694 A1 | 3/2011 | Biedermann et al. |
| 2011/0213424 A1 | 9/2011 | Biedermann et al. |
| 2011/0282399 A1 | 11/2011 | Jackson |
| 2012/0010661 A1 | 1/2012 | Farris et al. |
| 2012/0046699 A1 | 2/2012 | Jones et al. |
| 2012/0165881 A1 | 6/2012 | Biedermann et al. |
| 2012/0179210 A1 | 7/2012 | Garamszegi |
| 2012/0179212 A1 | 7/2012 | Jackson et al. |
| 2012/0265257 A1 | 10/2012 | Jackson |
| 2012/0303070 A1 | 11/2012 | Jackson |
| 2012/0310290 A1 | 12/2012 | Jackson |
| 2013/0060292 A1 | 3/2013 | Jackson |
| 2013/0072981 A1 | 3/2013 | Jackson |
| 2013/0079830 A1 | 3/2013 | Garamszegi et al. |
| 2013/0131730 A1 | 5/2013 | Jackson et al. |
| 2013/0144346 A1 | 6/2013 | Jackson et al. |
| 2013/0268006 A1 | 10/2013 | Garamszegi |
| 2013/0345756 A1 | 12/2013 | Berrevoets et al. |
| 2014/0058454 A1 | 2/2014 | Hammer |
| 2014/0081334 A1 | 3/2014 | Jackson |
| 2014/0128927 A1 | 5/2014 | Jackson |
| 2014/0135854 A1 | 5/2014 | Dec et al. |
| 2014/0163619 A1 | 6/2014 | Harvey |
| 2014/0172018 A1 | 6/2014 | Gephart et al. |
| 2014/0172023 A1 | 6/2014 | Garamszegi |
| 2014/0379031 A1 | 12/2014 | Biedermann et al. |
| 2015/0182260 A1 | 7/2015 | Jackson et al. |
| 2016/0045228 A1 | 2/2016 | Biedermann et al. |
| 2016/0220280 A1 | 8/2016 | Jackson |
| 2016/0367293 A1 | 12/2016 | Keyer et al. |
| 2017/0189074 A1 | 7/2017 | Biedermann et al. |
| 2017/0265902 A1 | 9/2017 | Jackson |
| 2017/0333086 A1 | 11/2017 | Jackson |
| 2017/0354443 A1 | 12/2017 | Jackson |
| 2018/0000523 A1 | 1/2018 | Jackson |
| 2018/0098795 A1 | 4/2018 | Jackson |
| 2018/0250036 A1 | 9/2018 | Jackson et al. |
| 2018/0325560 A1 | 11/2018 | Jackson et al. |
| 2018/0360499 A9 | 12/2018 | Jackson |
| 2019/0059953 A1 | 2/2019 | Keyer |
| 2019/0117271 A1 | 4/2019 | Jackson et al. |
| 2019/0142468 A1 | 5/2019 | Jackson et al. |
| 2019/0216511 A1 | 7/2019 | Jackson et al. |
| 2019/0247093 A1 | 8/2019 | Jackson et al. |
| 2019/0282278 A1 | 9/2019 | Schlapfer et al. |
| 2019/0307489 A1 | 10/2019 | Jackson et al. |
| 2019/0336174 A1 | 11/2019 | Jackson et al. |
| 2019/0357945 A1 | 11/2019 | Jackson et al. |
| 2019/0365425 A1 | 12/2019 | Casey et al. |
| 2019/0365430 A1 | 12/2019 | Jackson et al. |
| 2020/0030004 A1 | 1/2020 | Jackson et al. |
| 2020/0030005 A1 | 1/2020 | Jackson et al. |
| 2020/0069337 A1 | 3/2020 | Jackson et al. |

\* cited by examiner

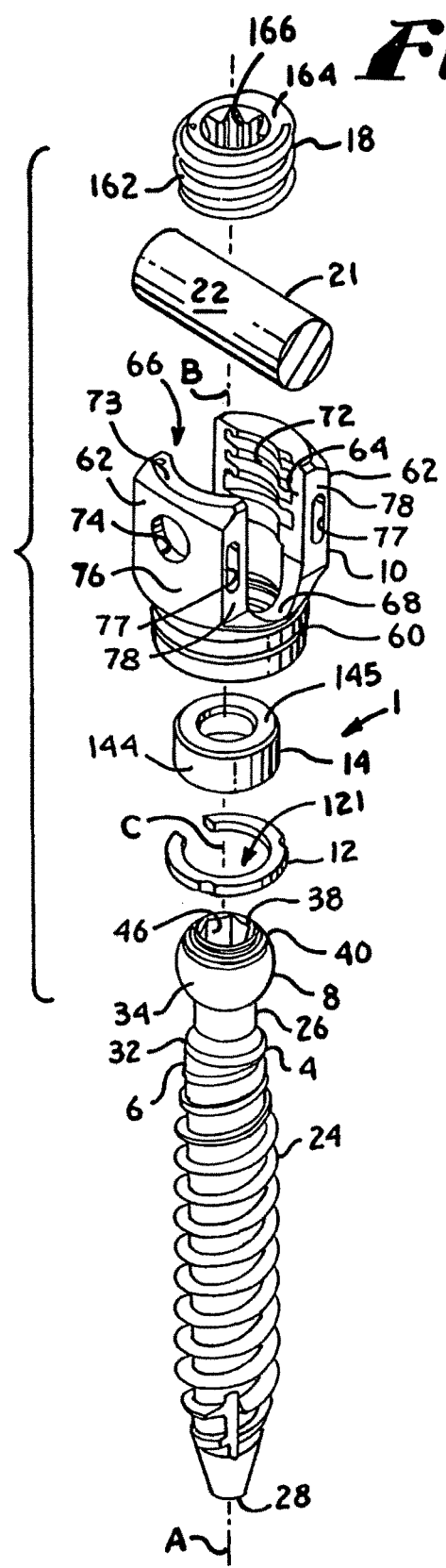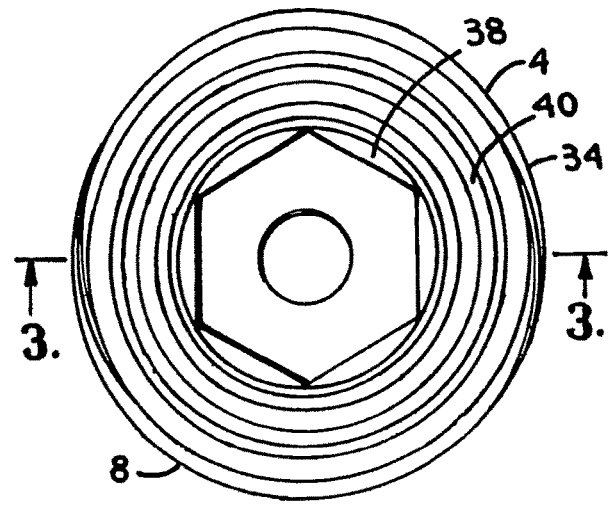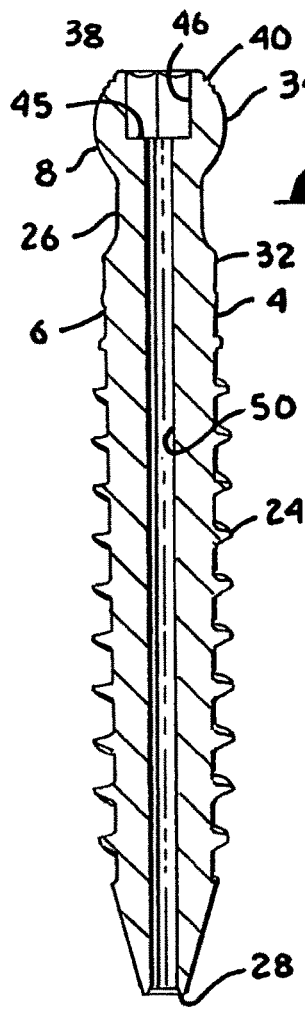

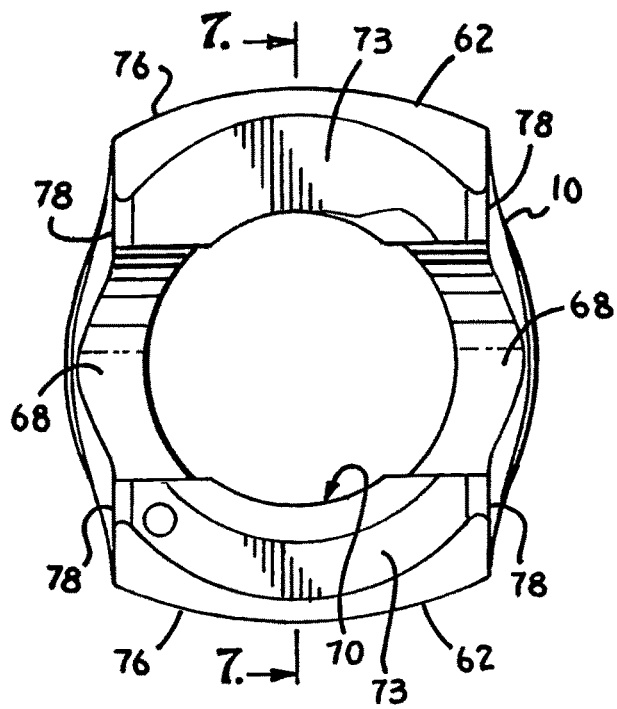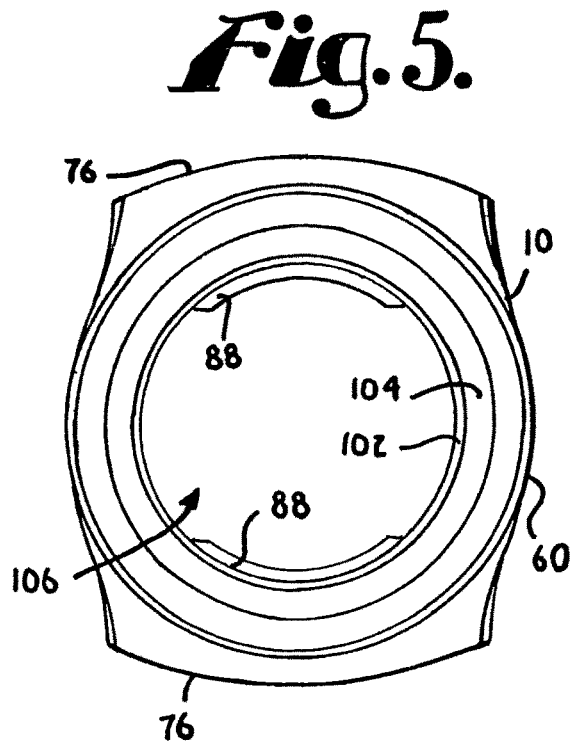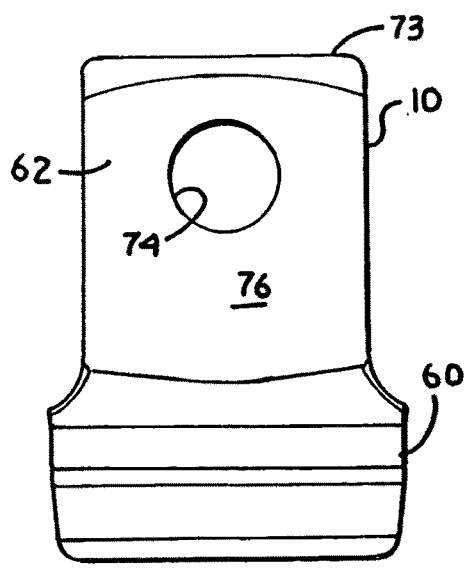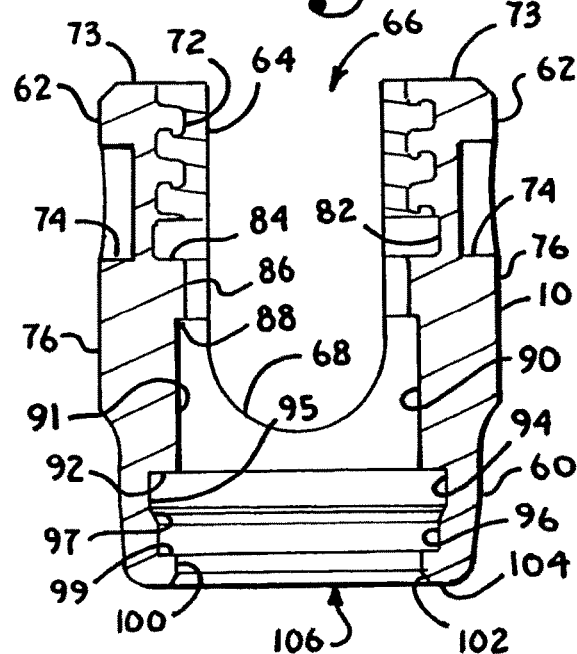

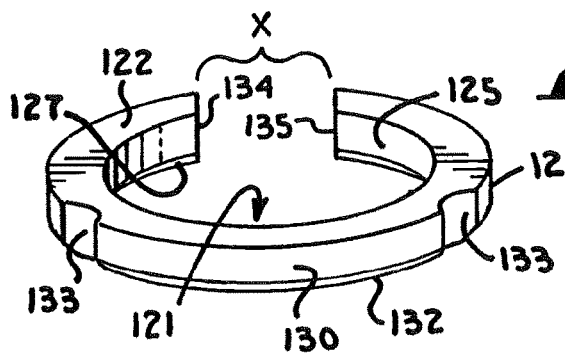
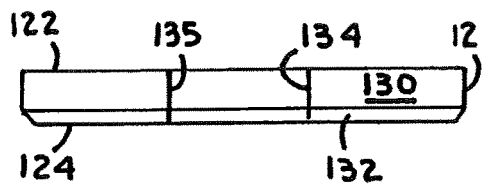
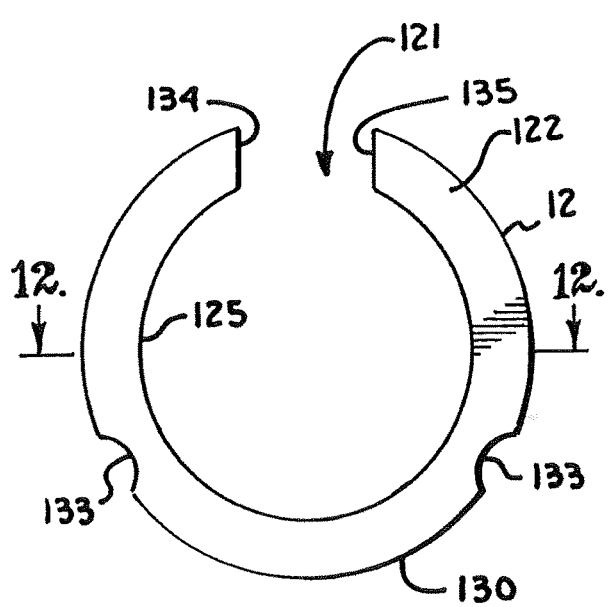
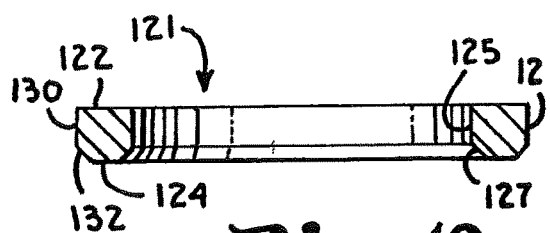
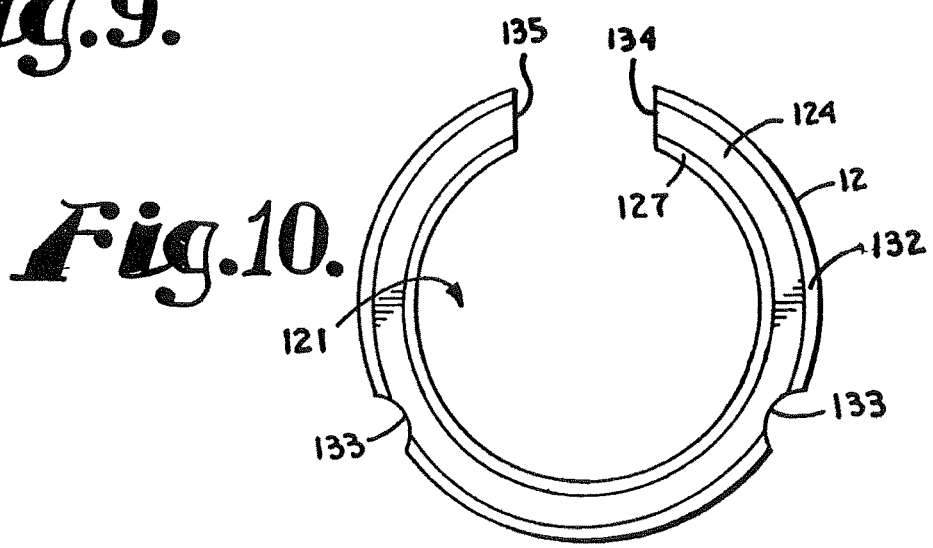

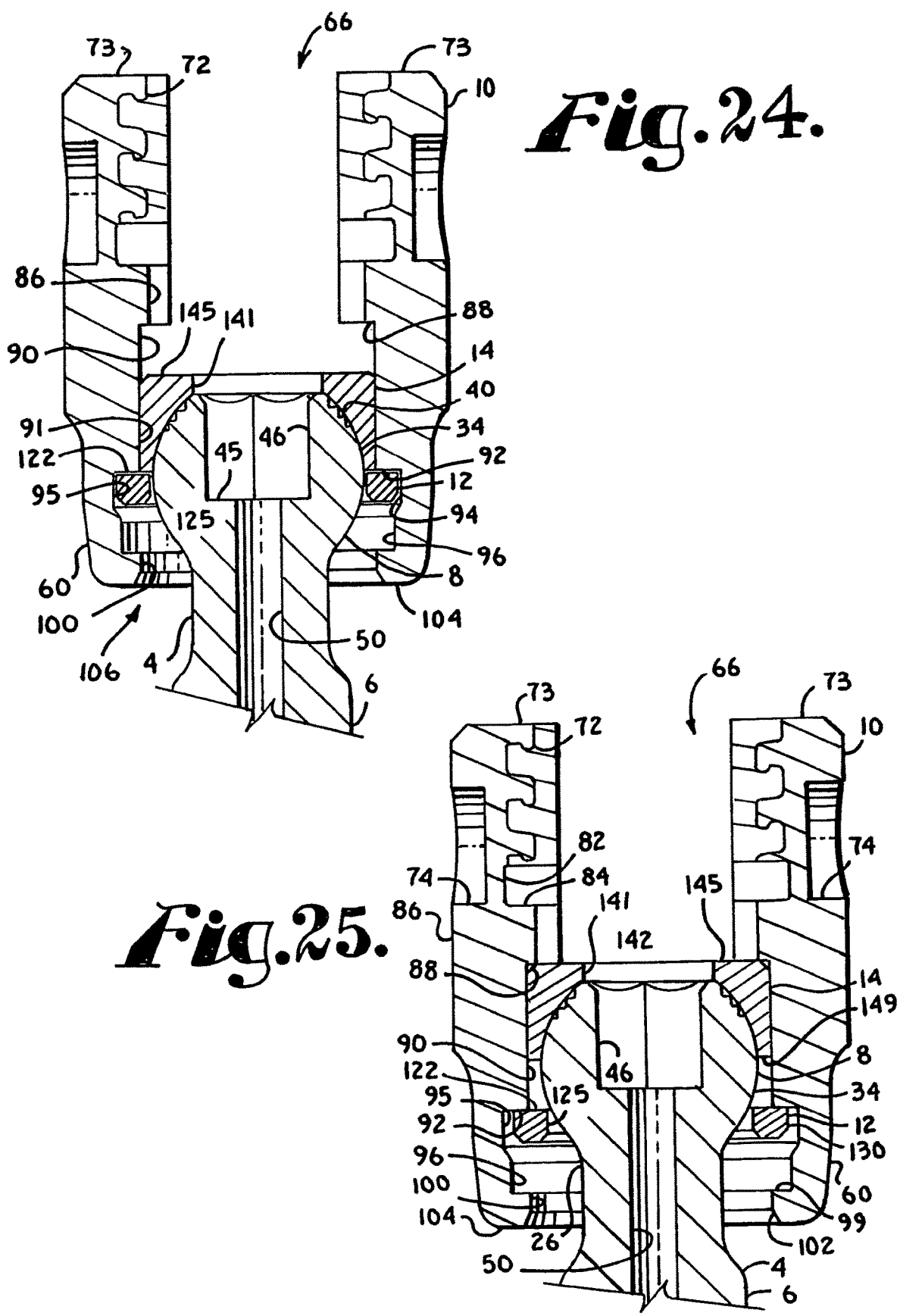

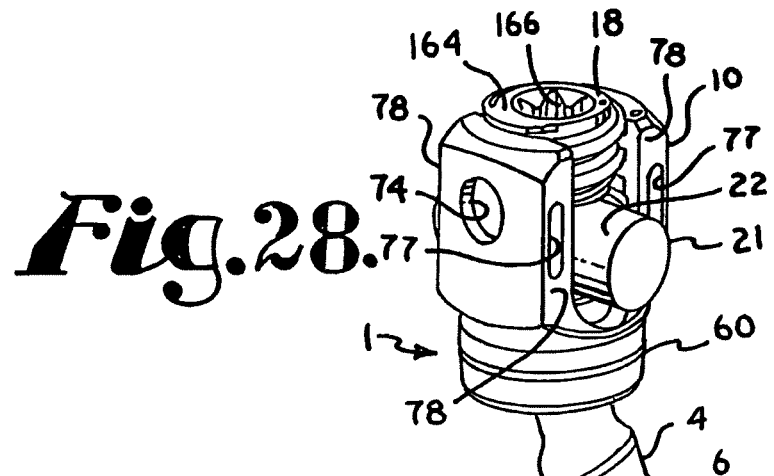
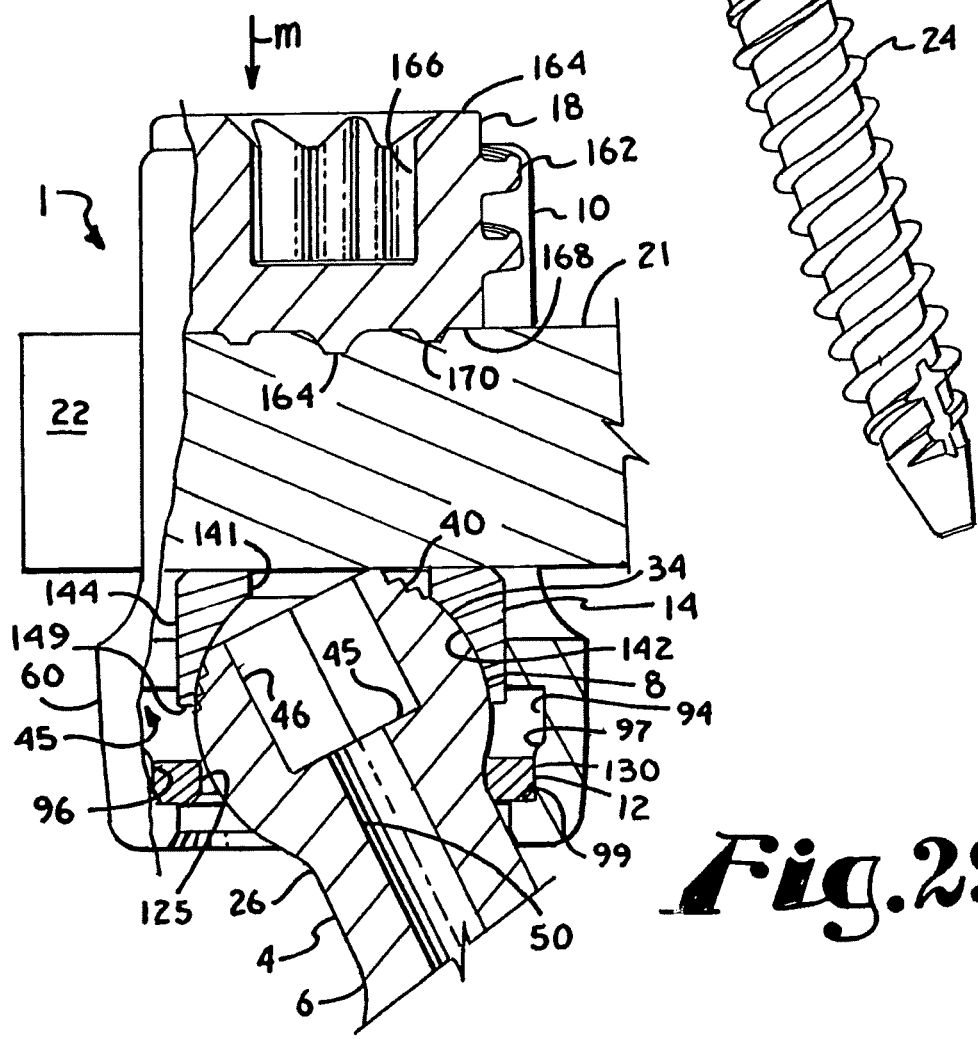

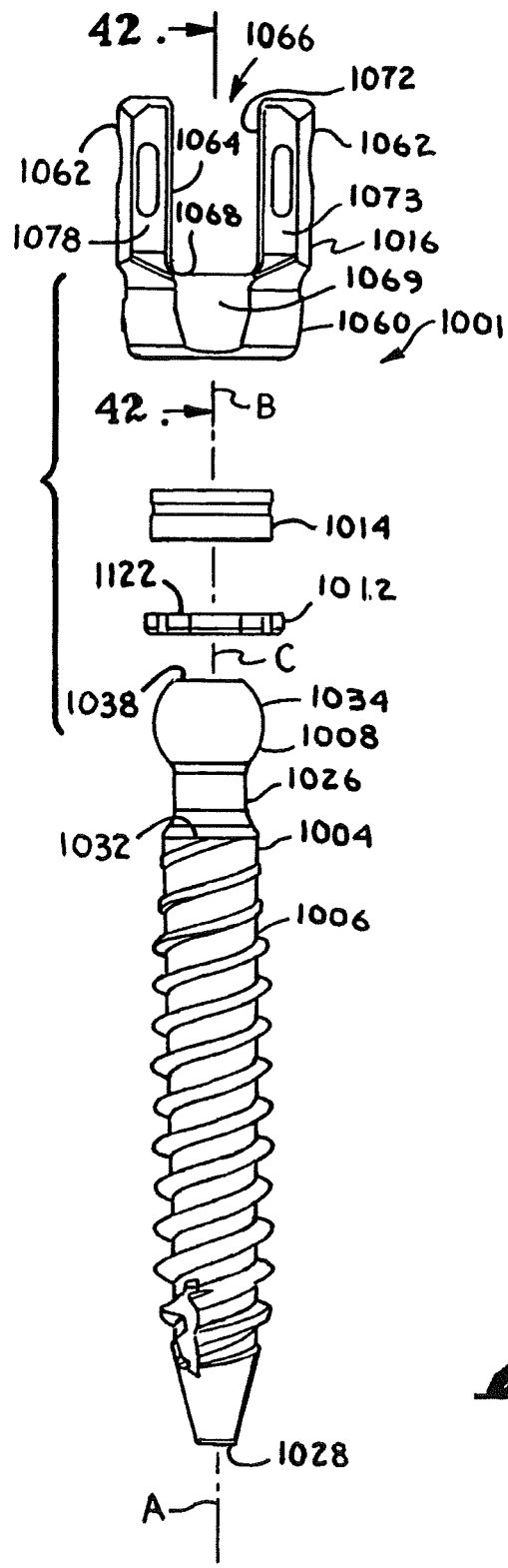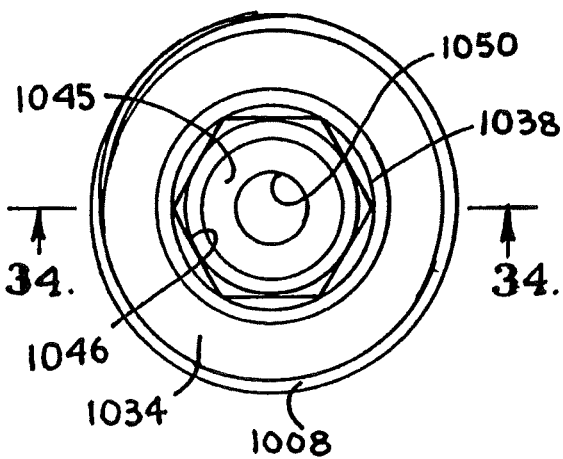

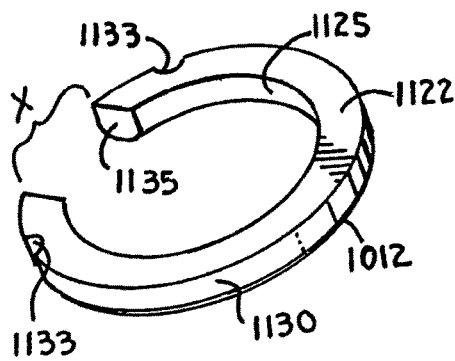
Fig.35.
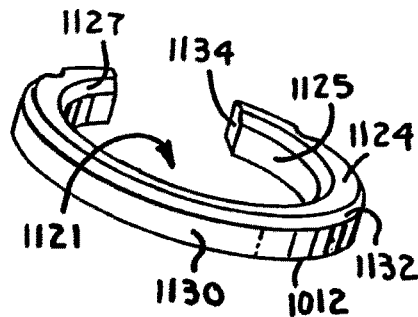
Fig.36.
Fig.38.
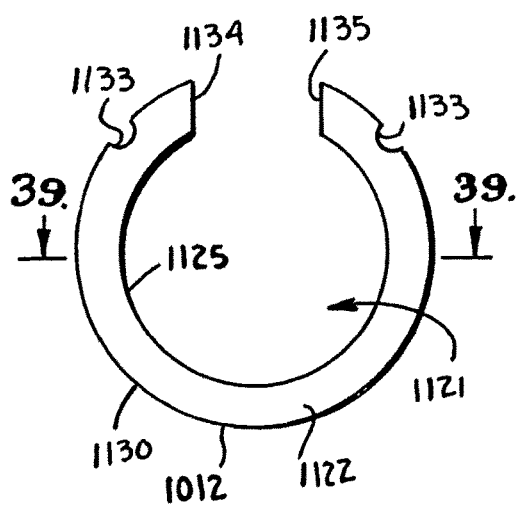
Fig.37.
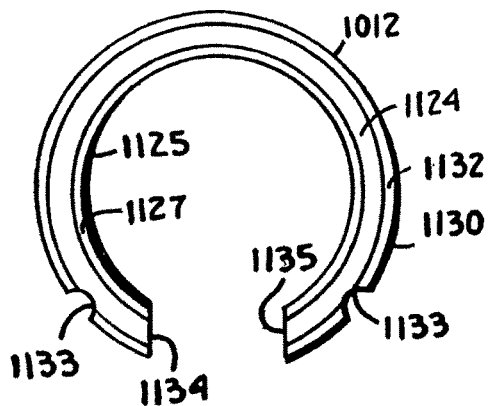
Fig.39.
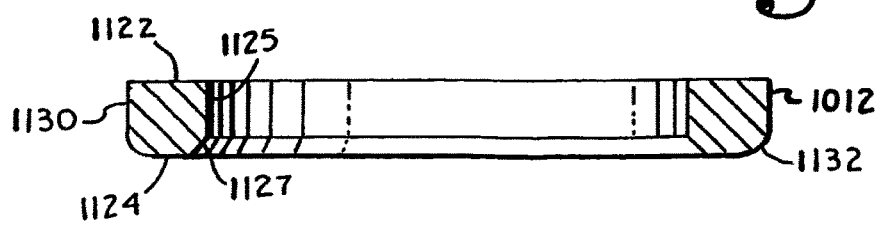

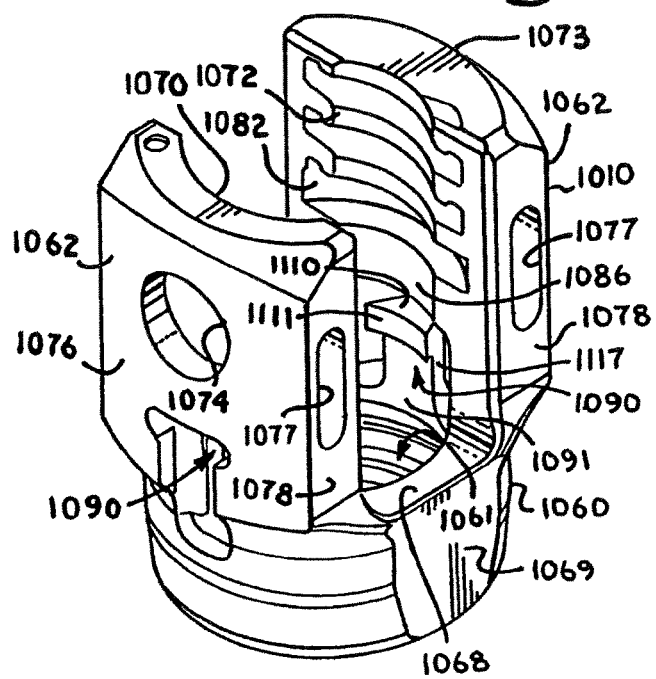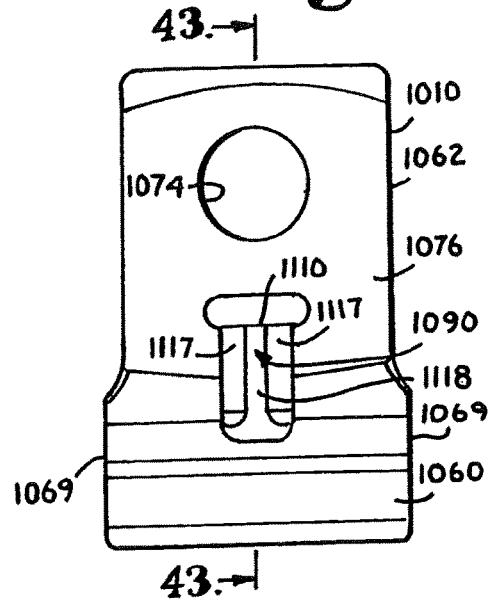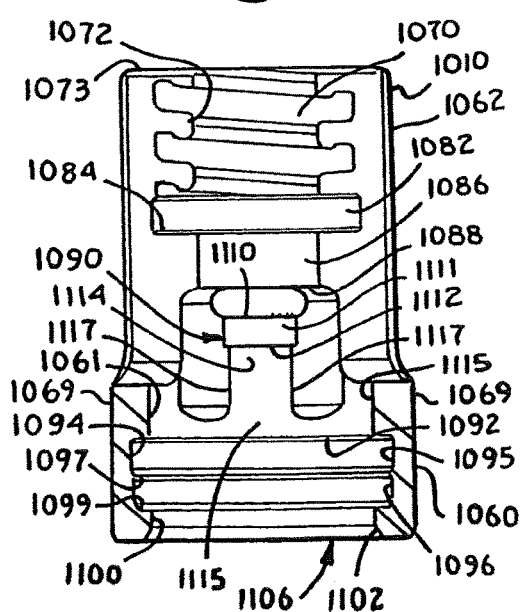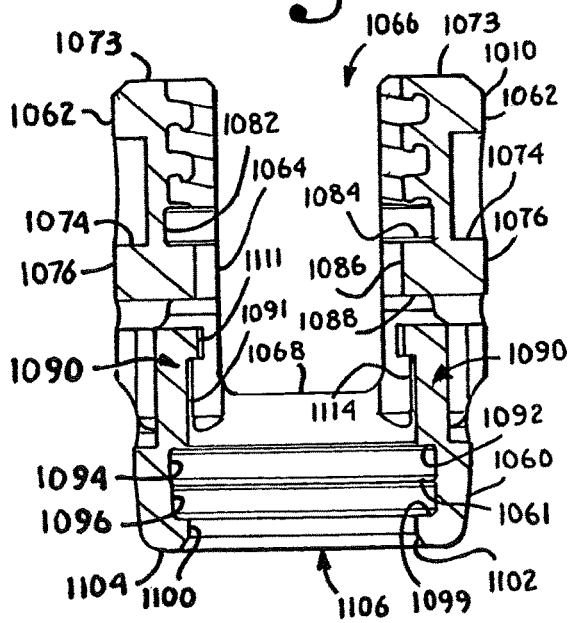

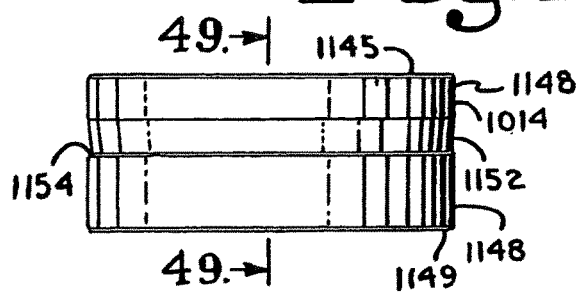
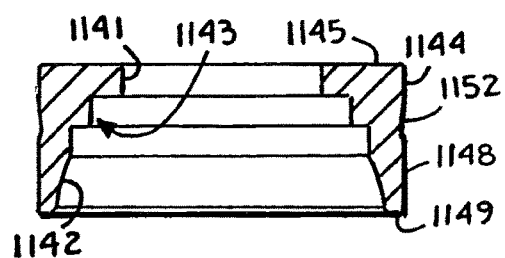
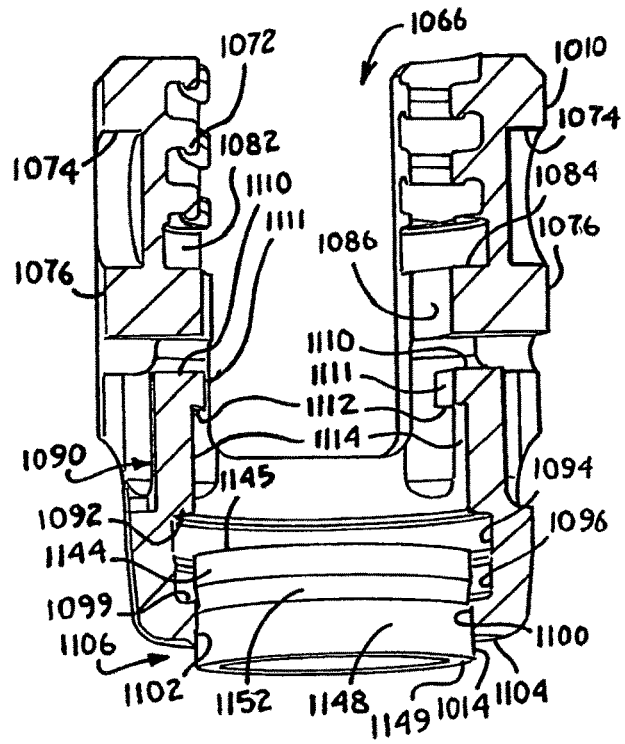
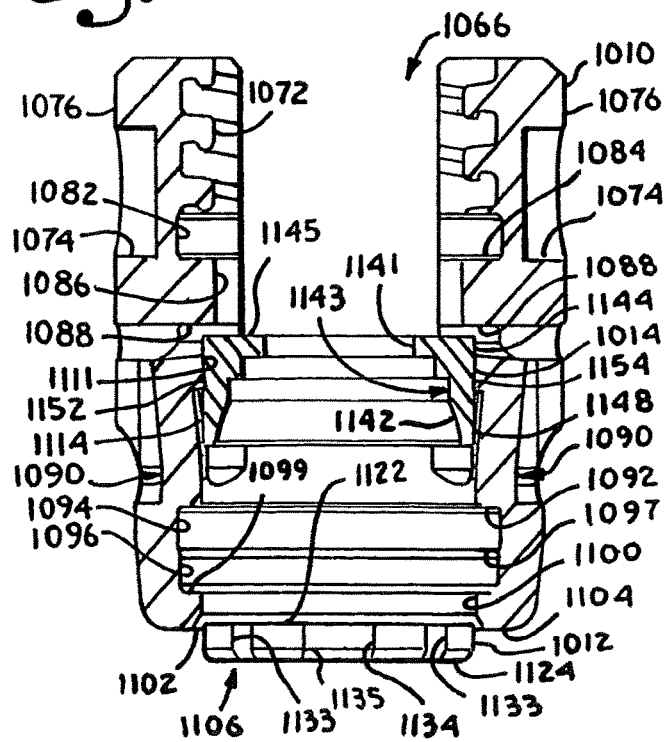

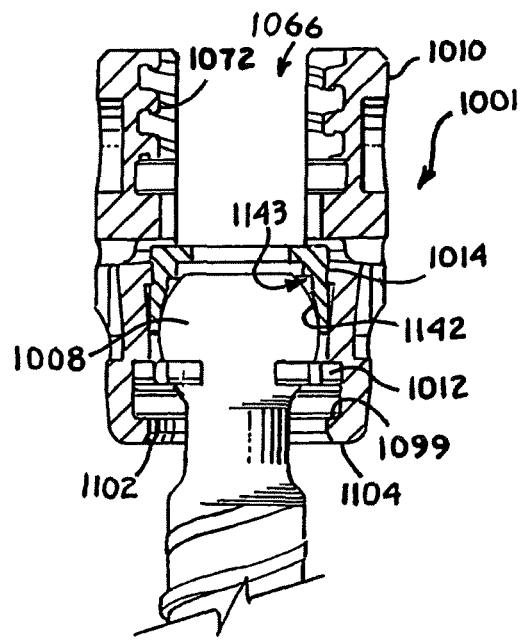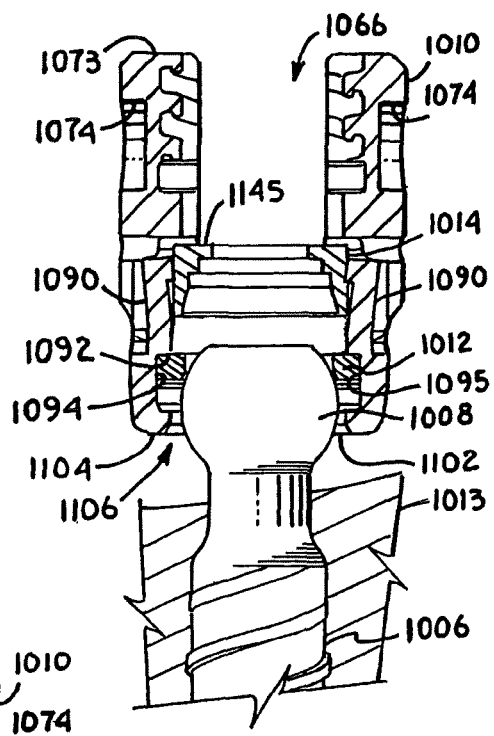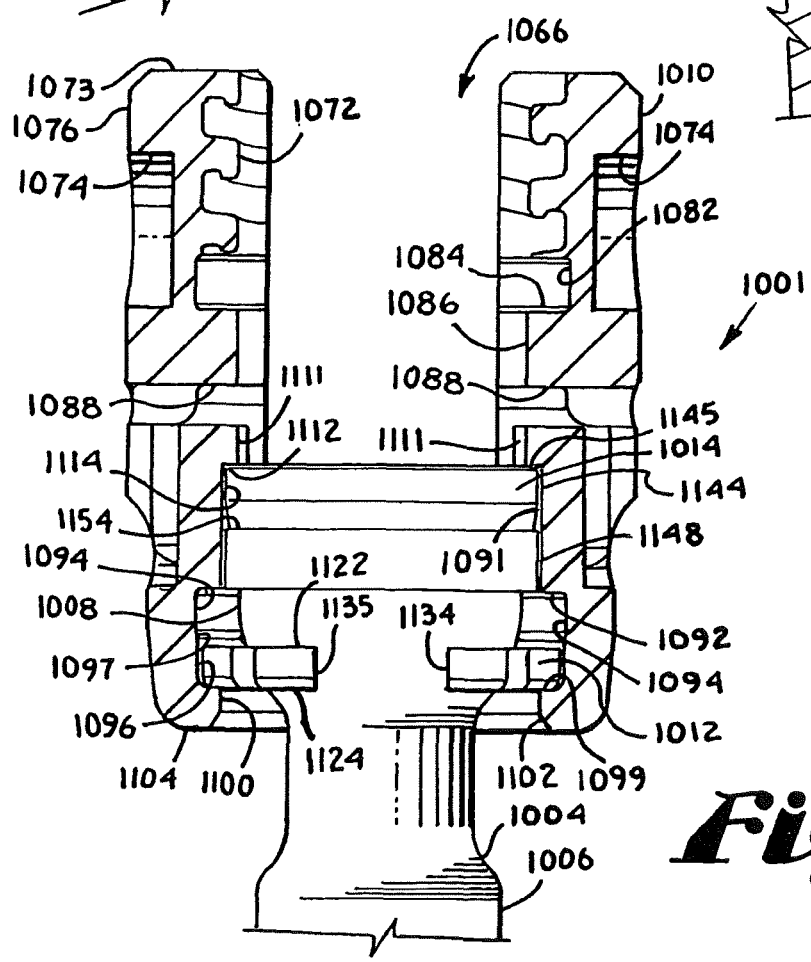

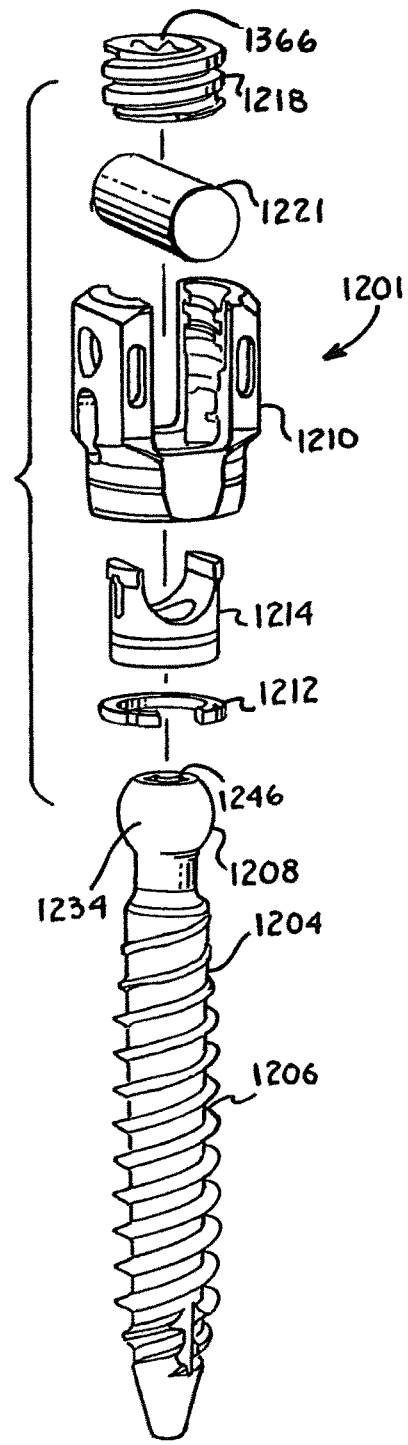
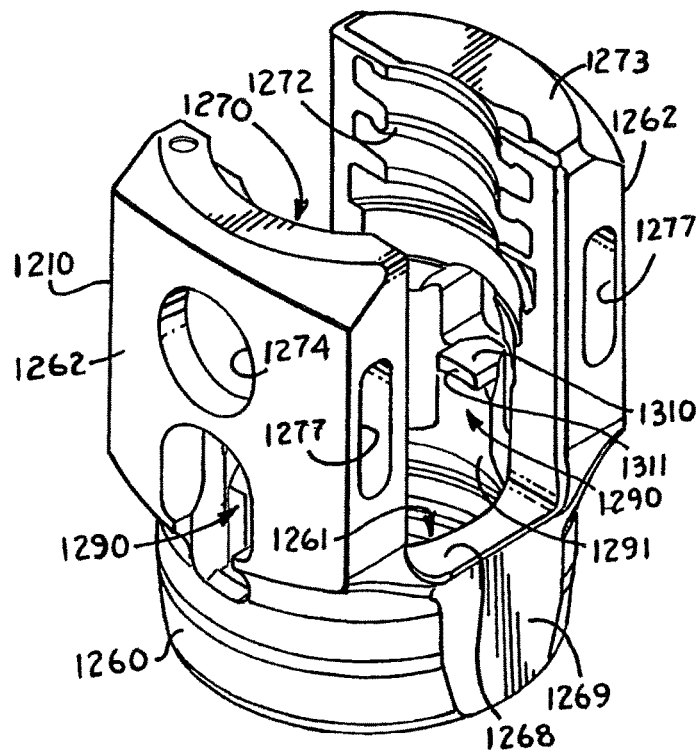
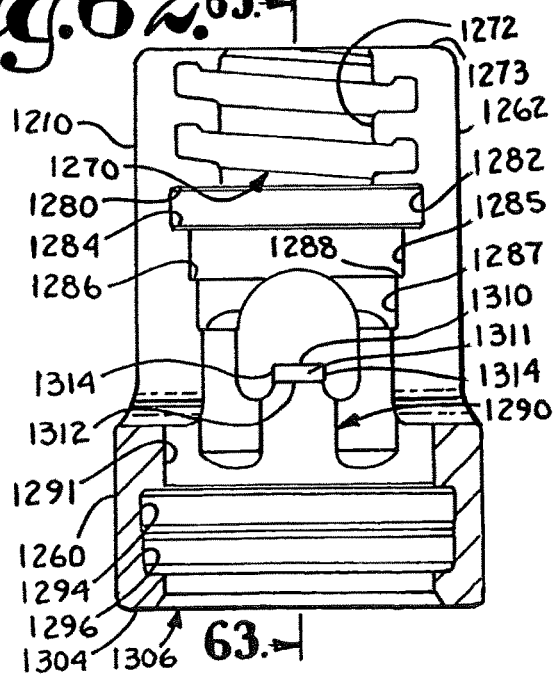

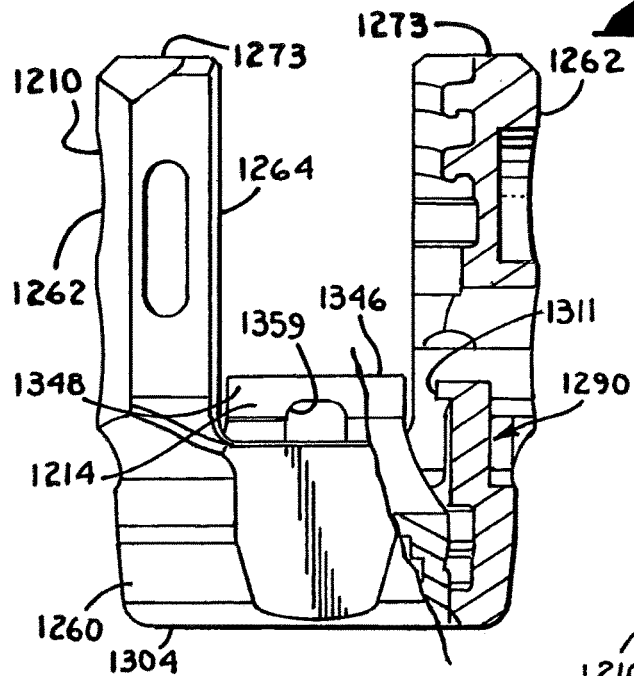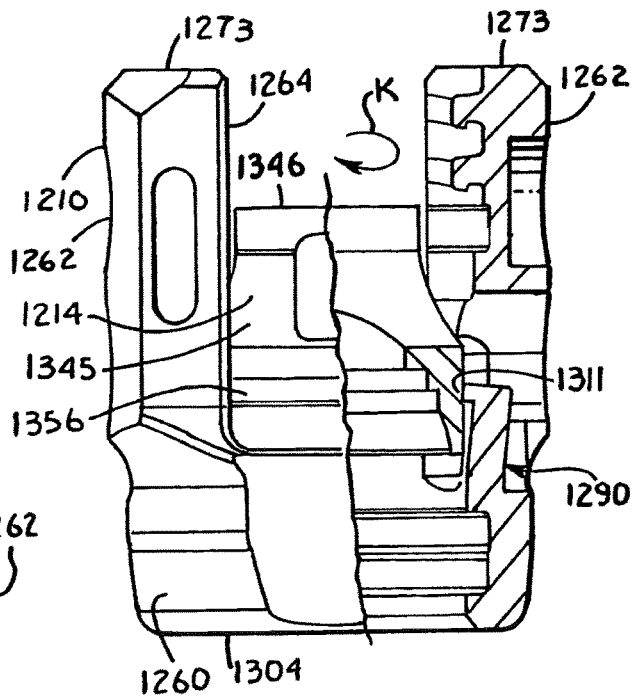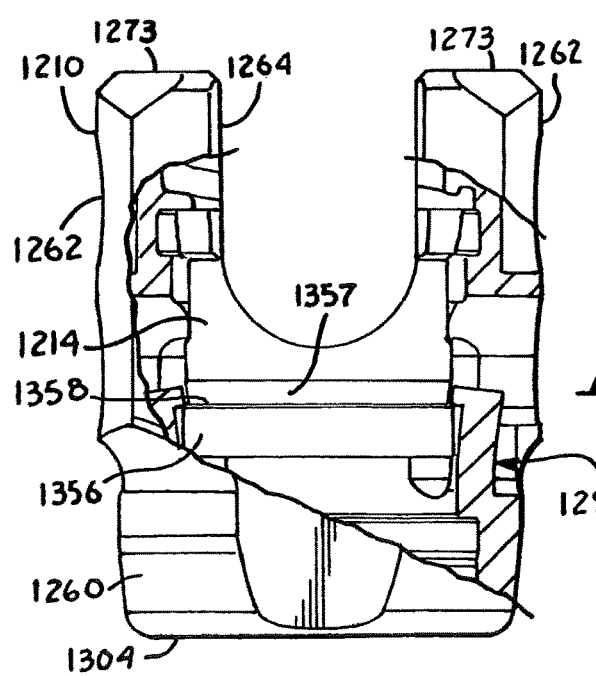

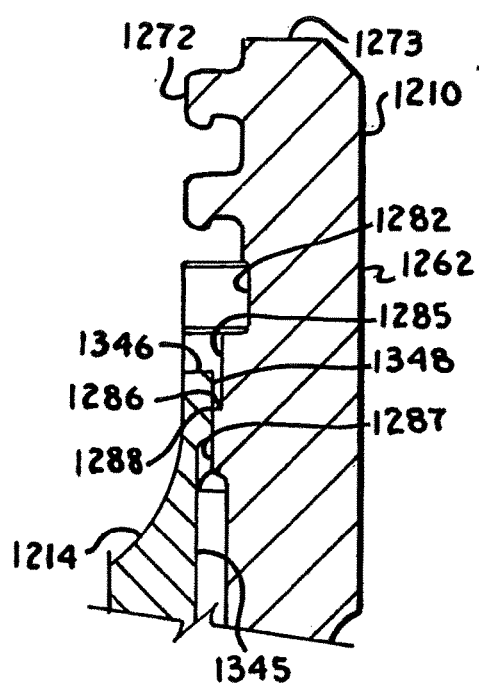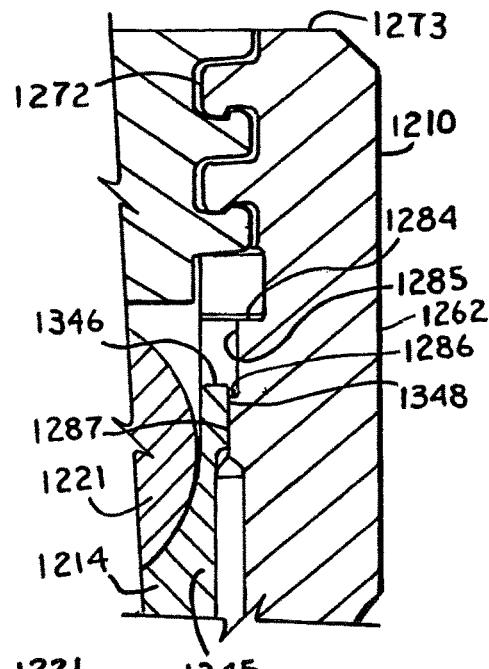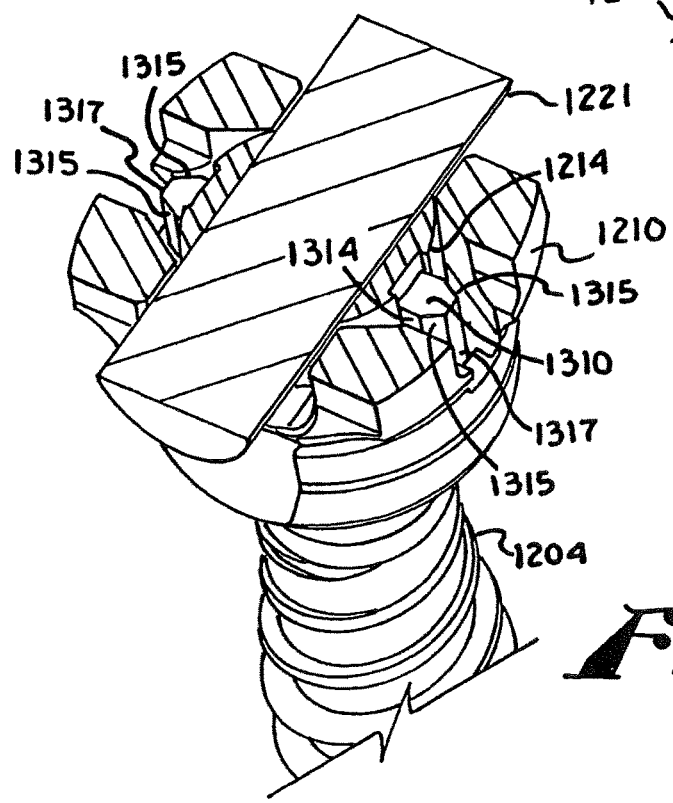

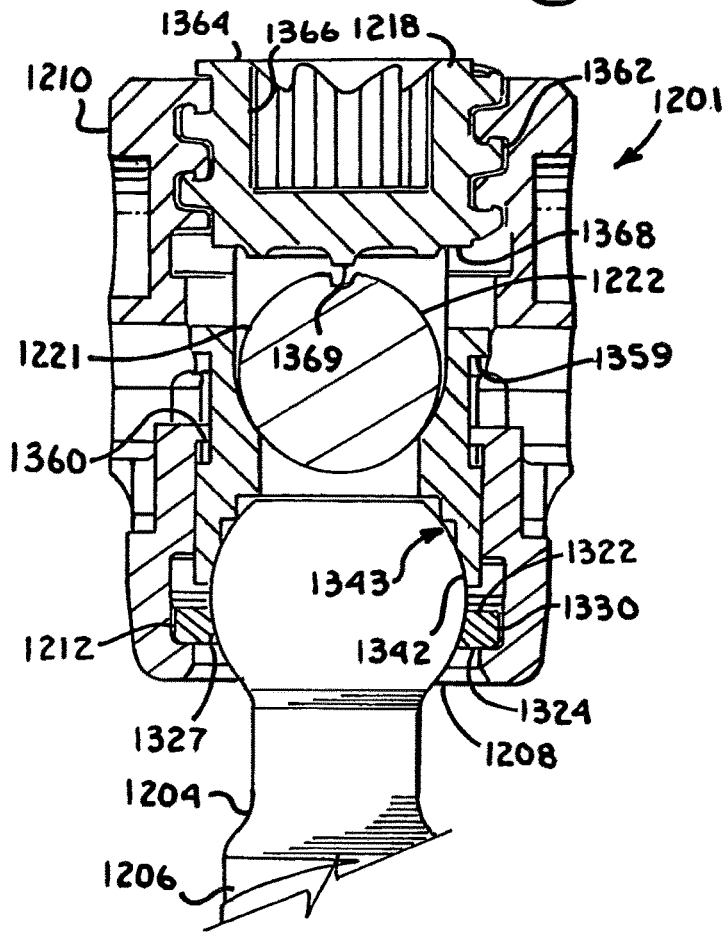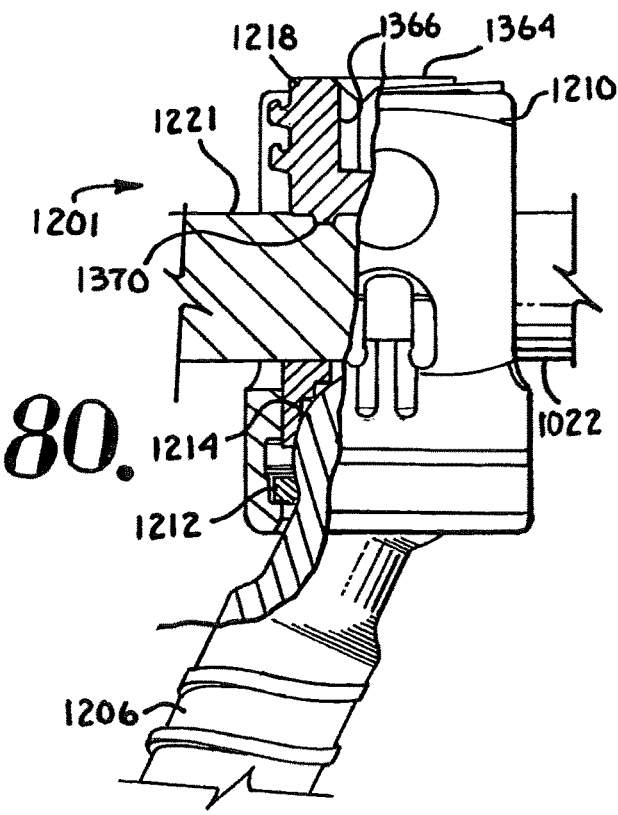

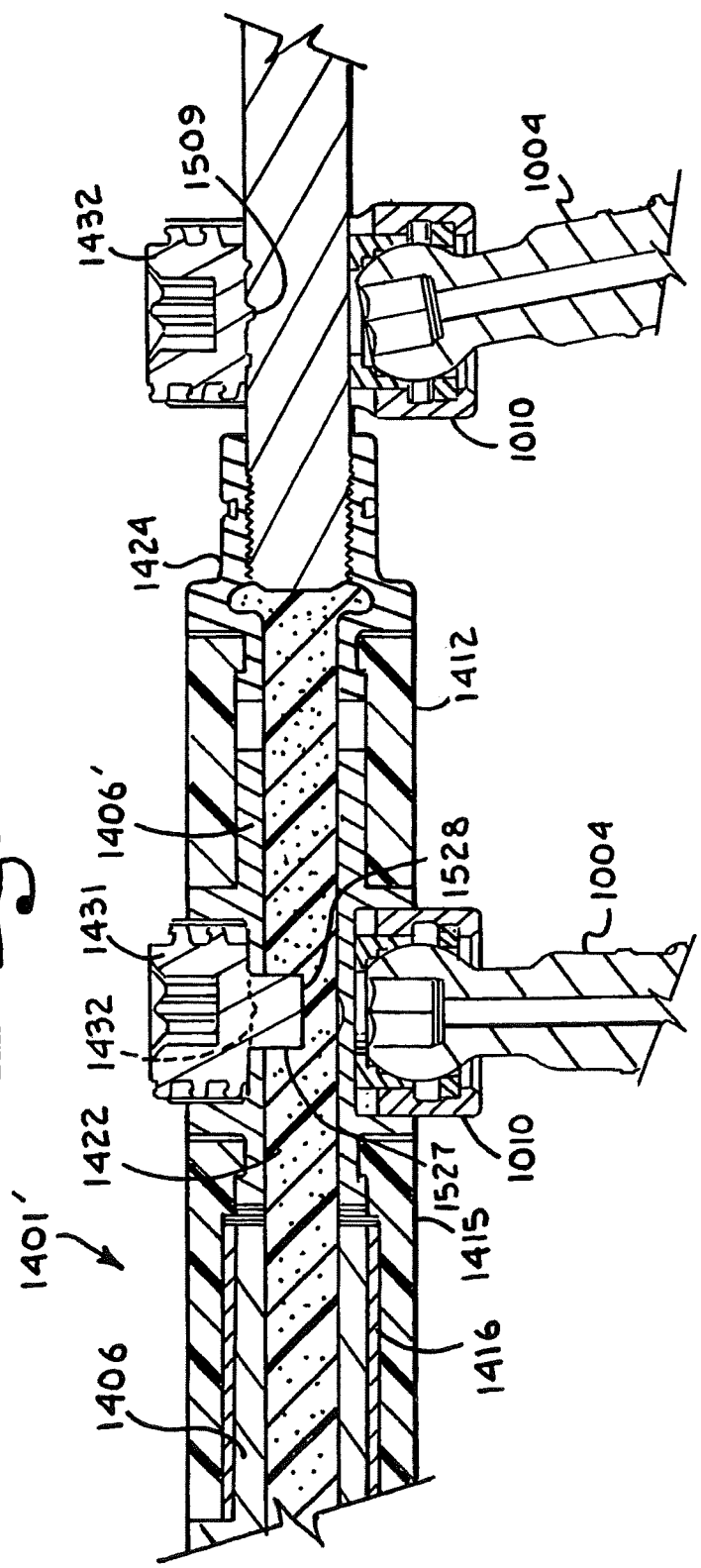

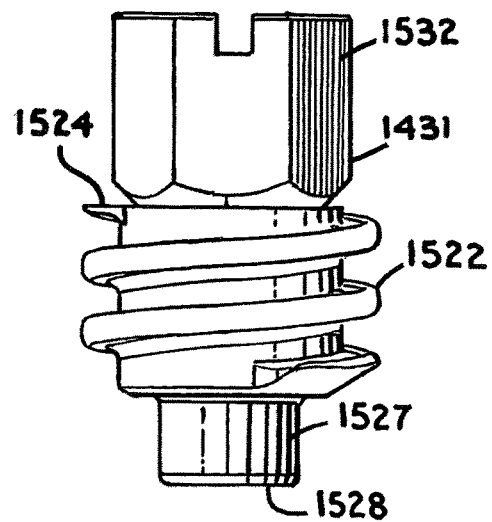
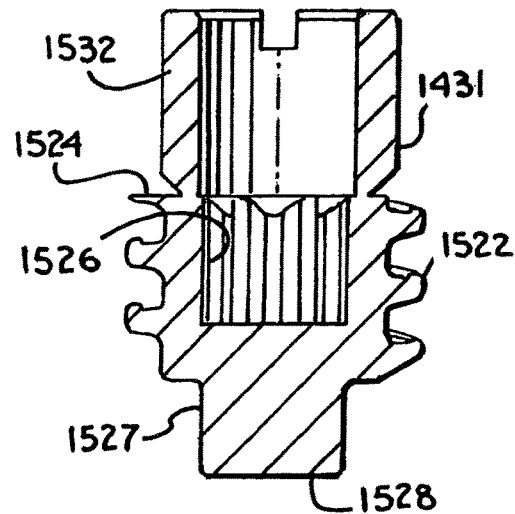
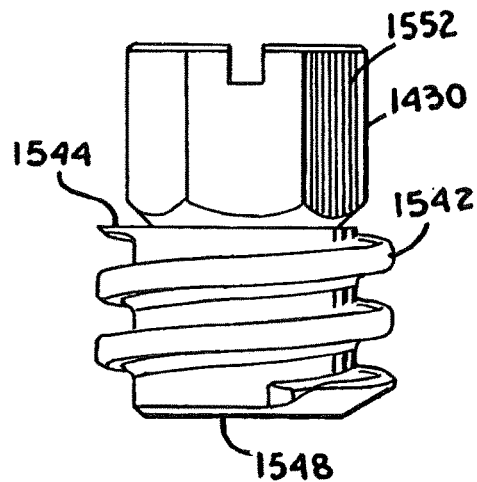
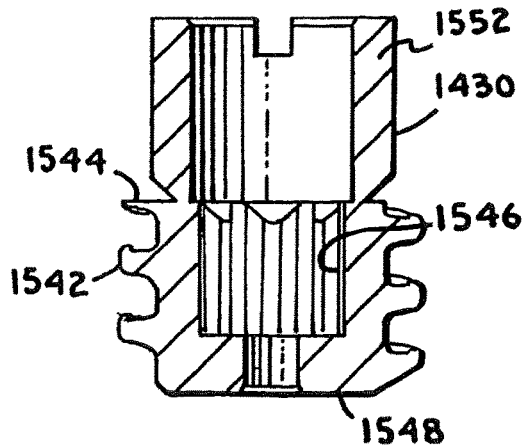

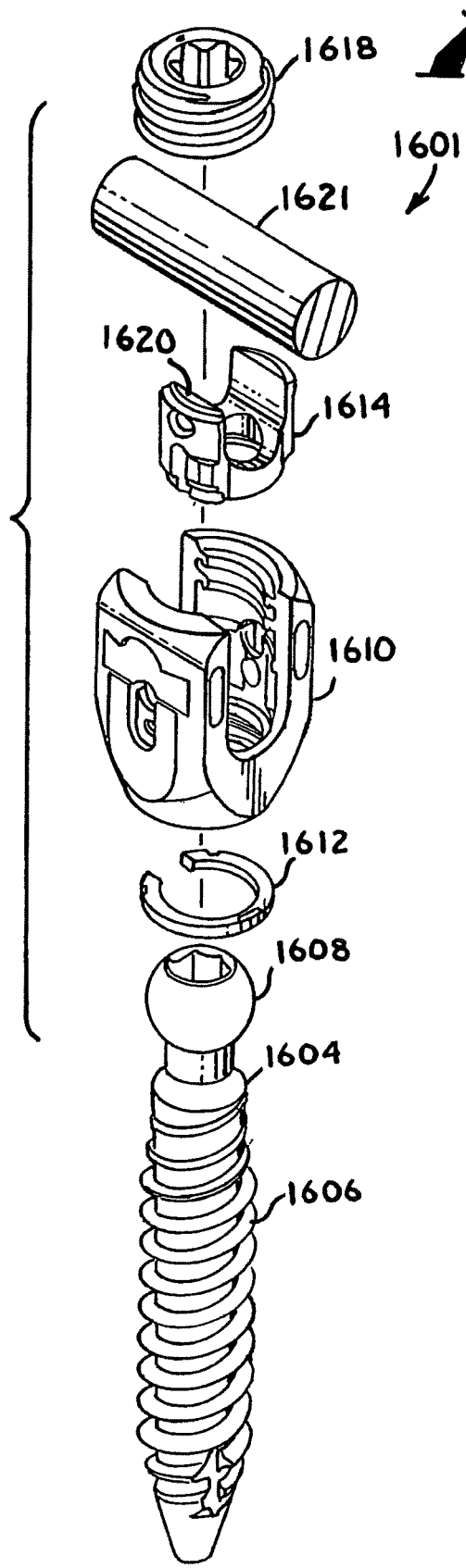
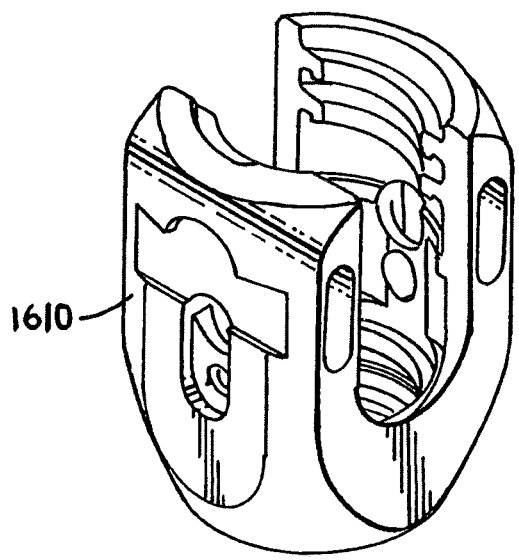
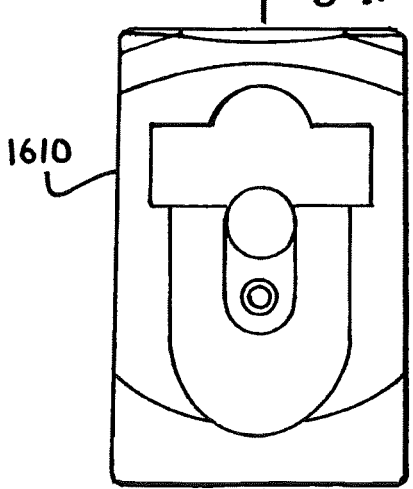

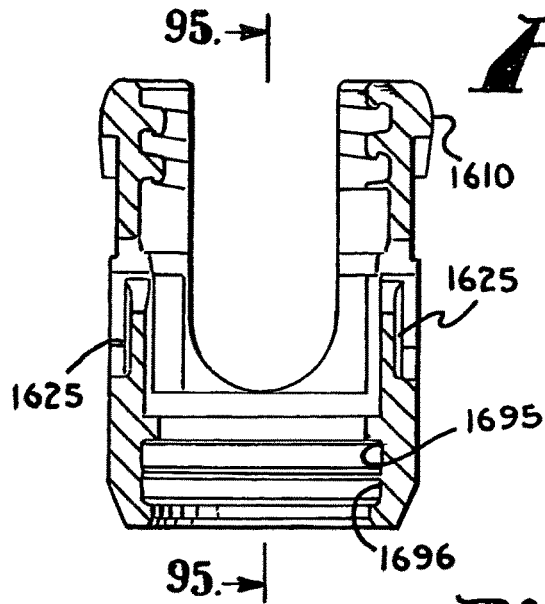
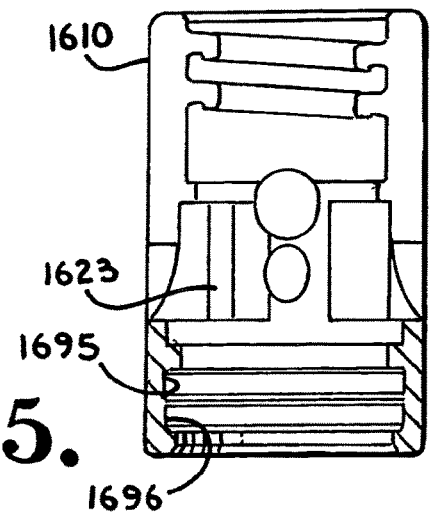
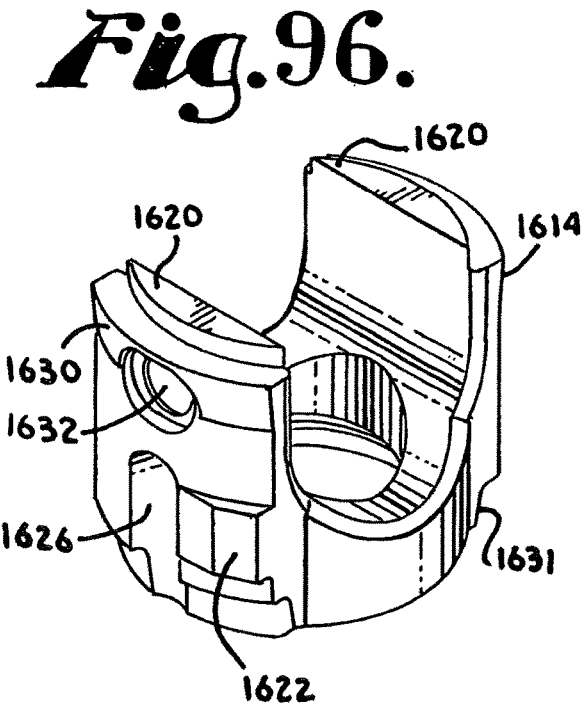
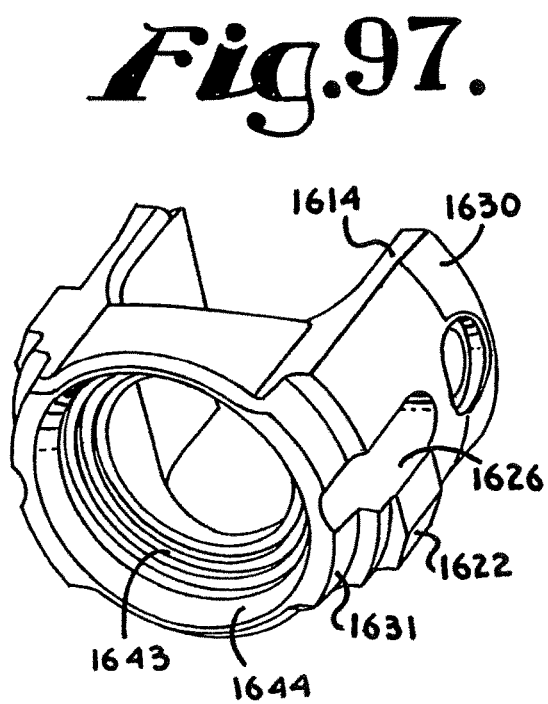

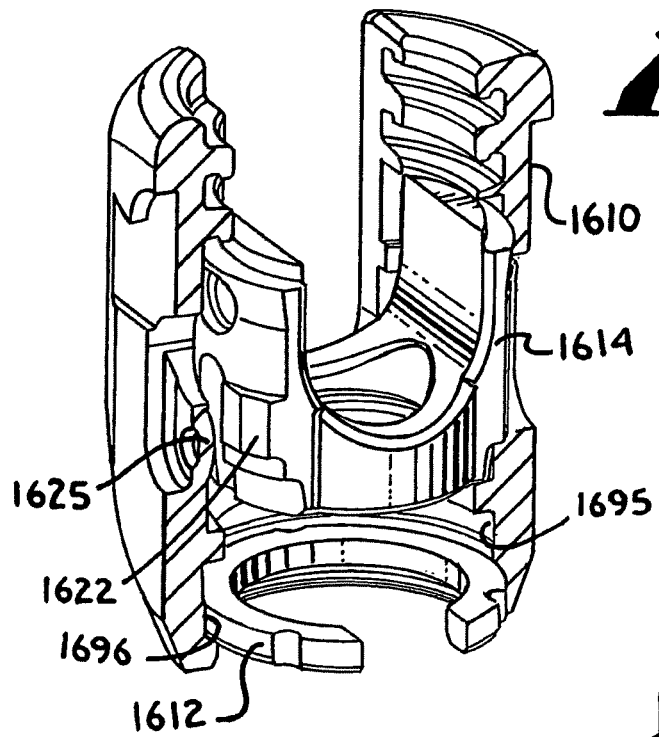
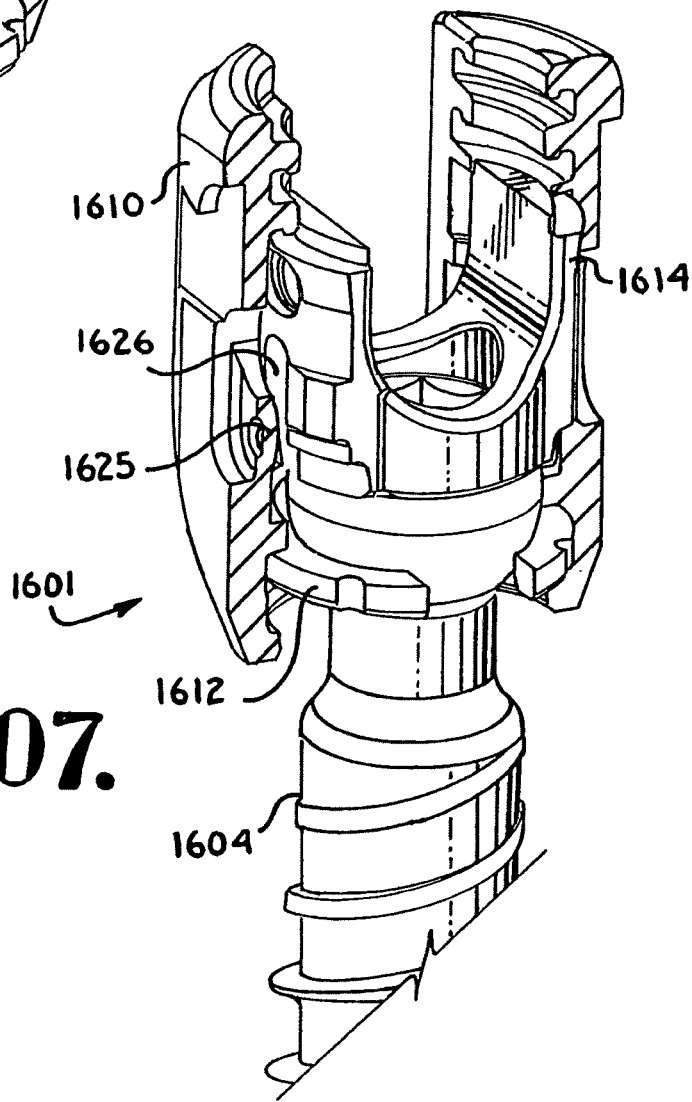

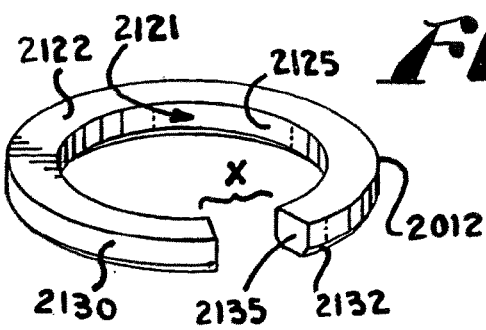
Fig.118.
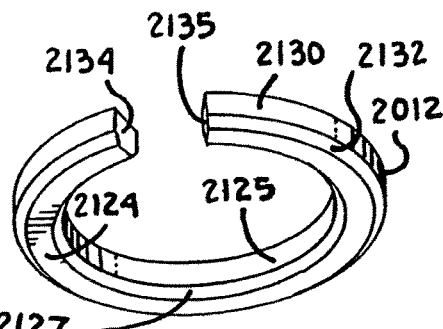
Fig.119.
Fig.120.
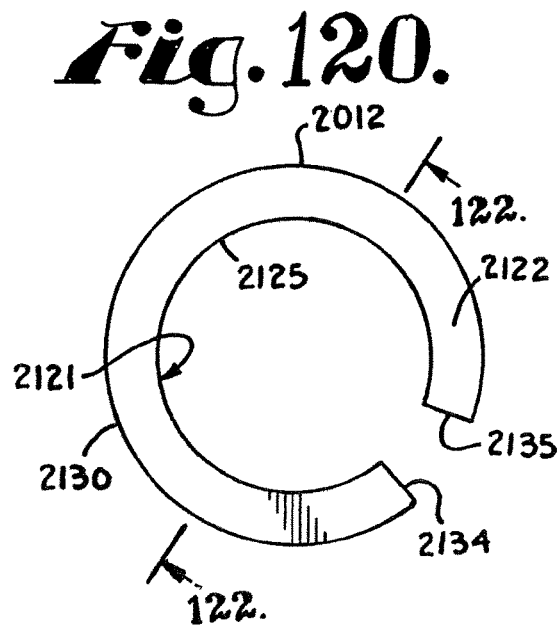
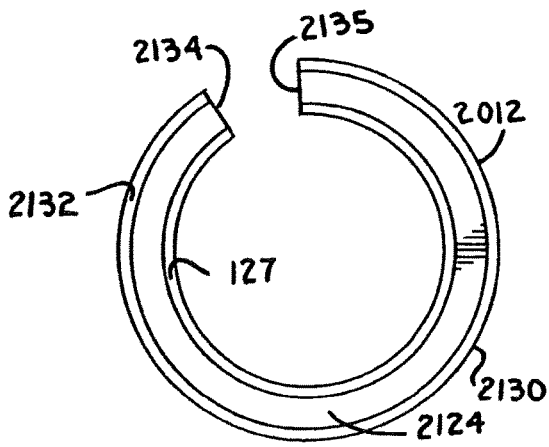
Fig.121.
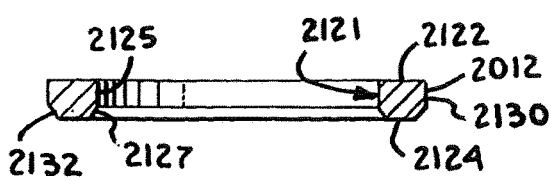
Fig.122.

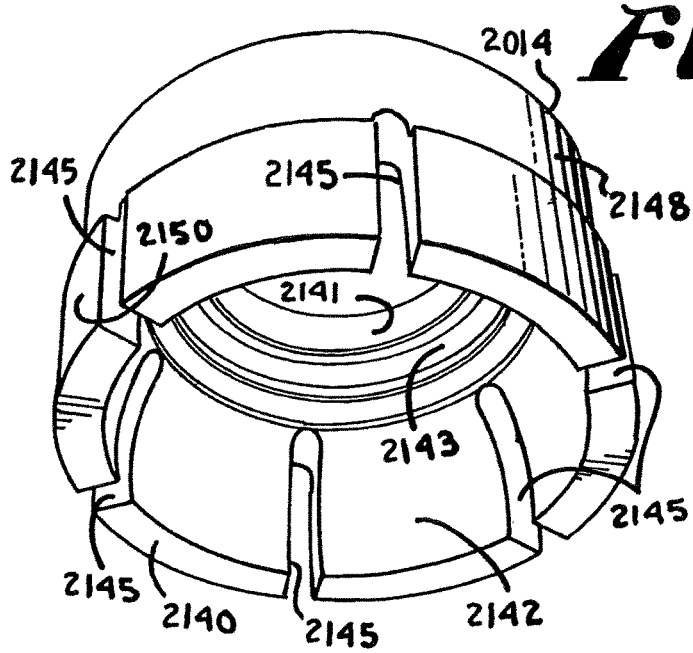
*Fig.*123.
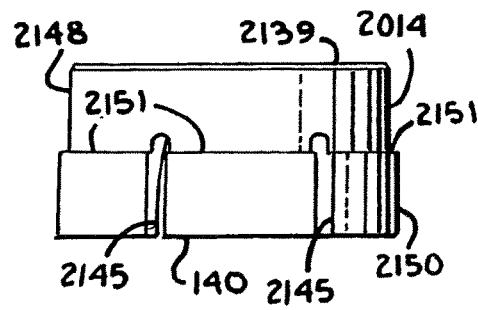
*Fig.*124.
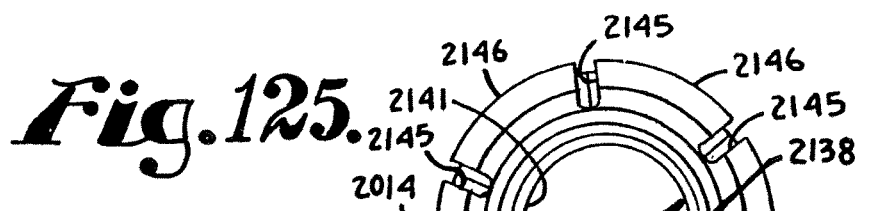
*Fig.*125.
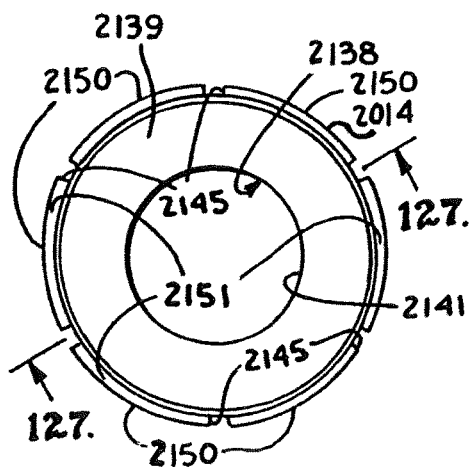
*Fig.*126.
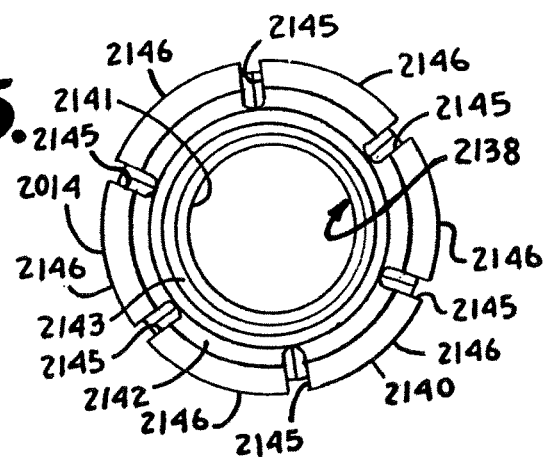
*Fig.*127.

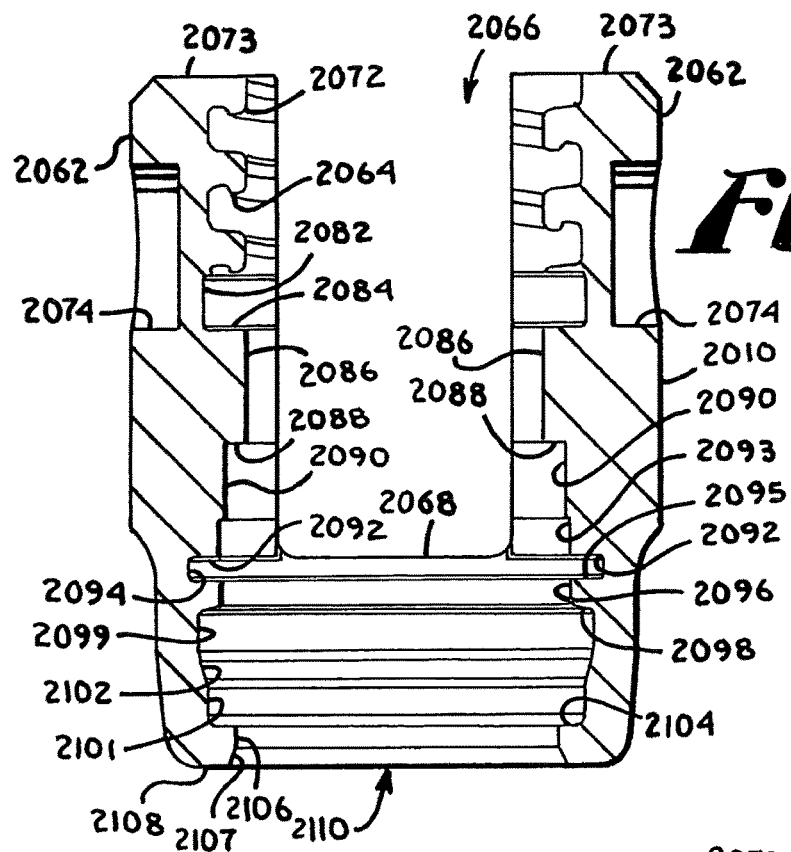
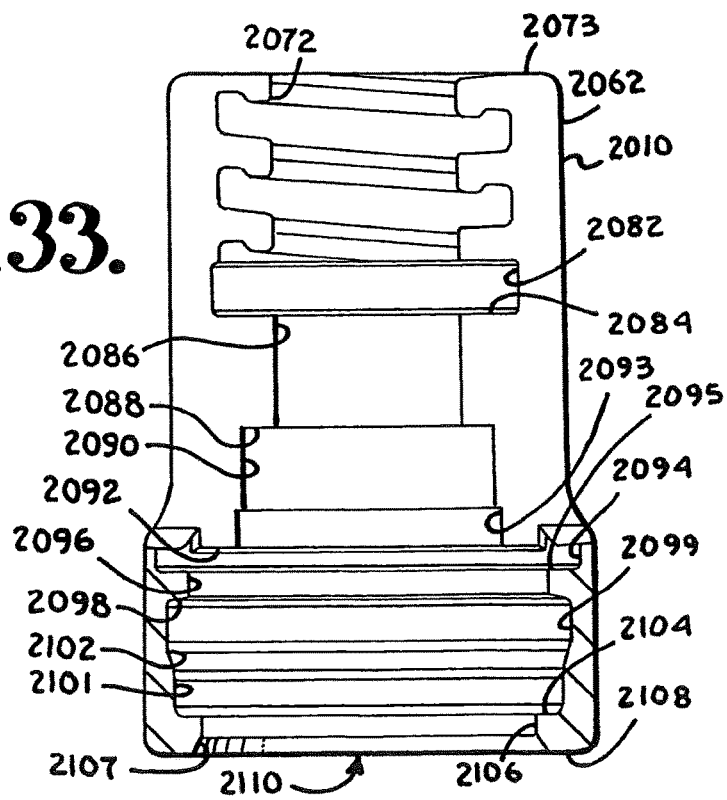

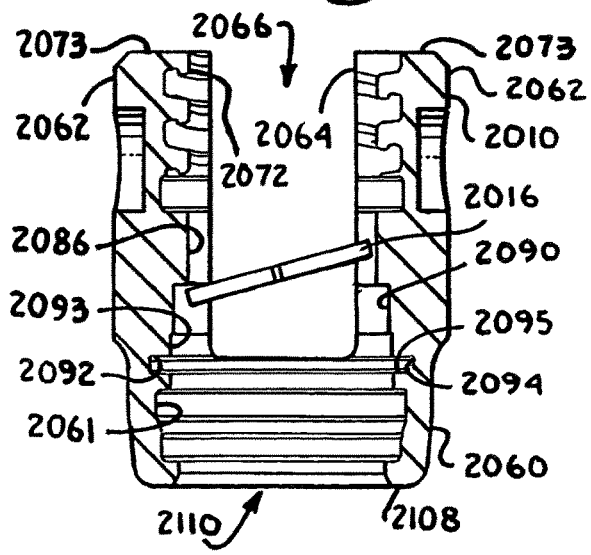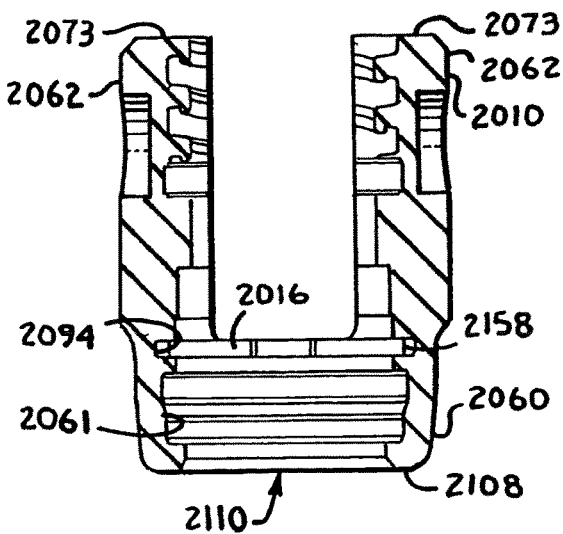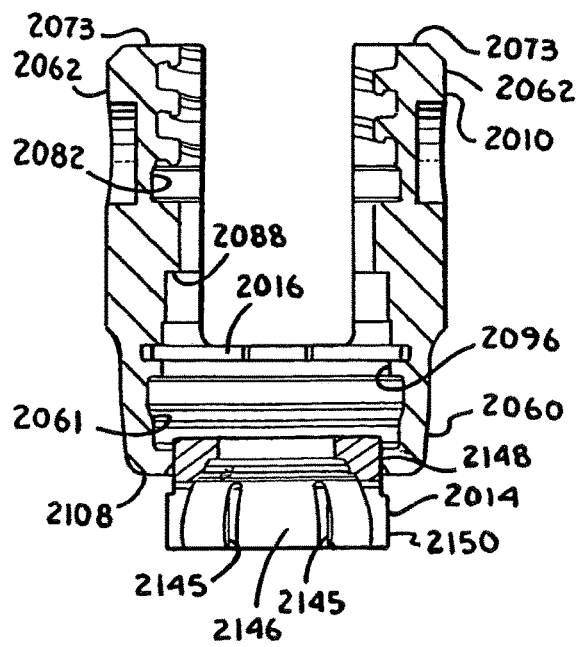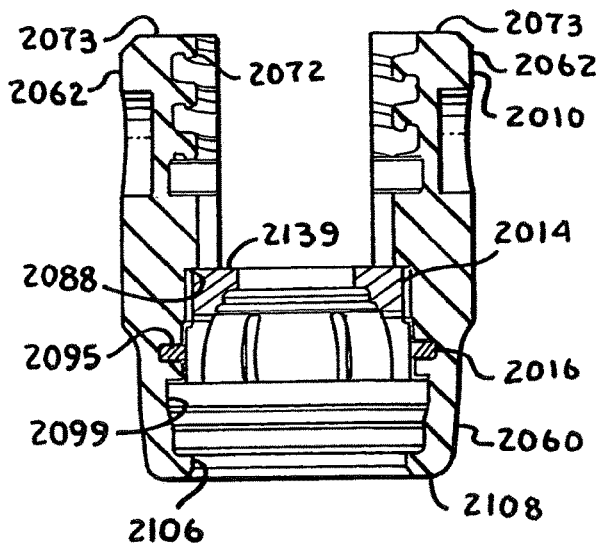

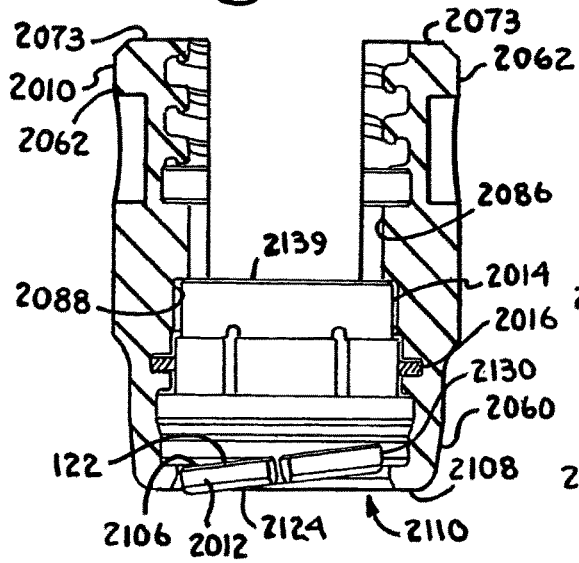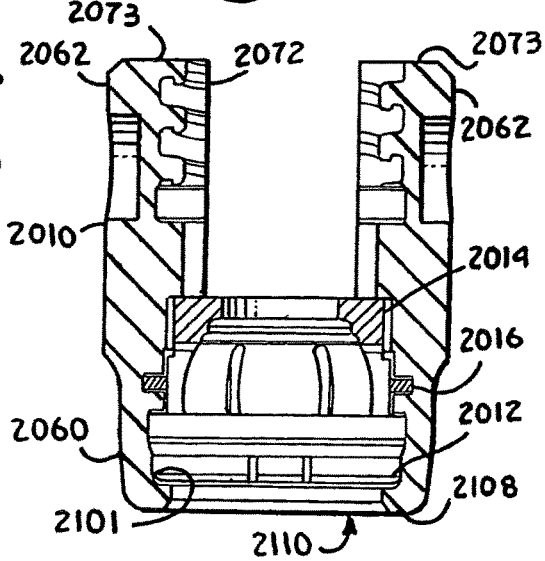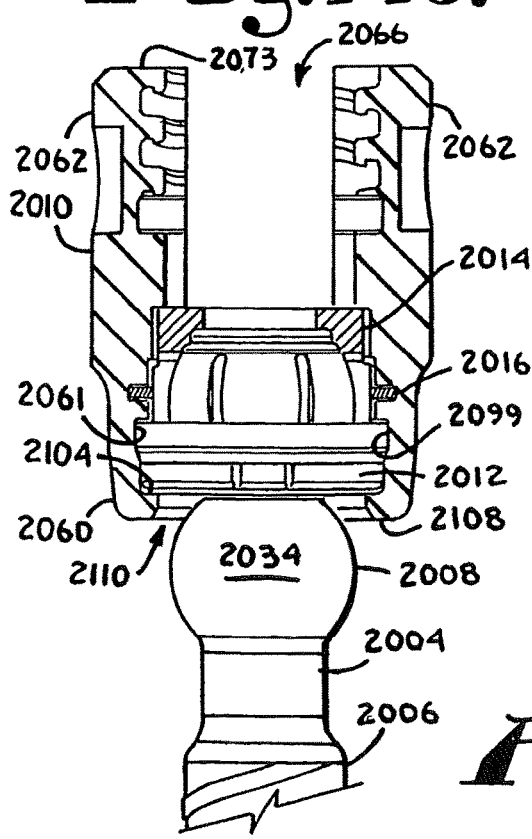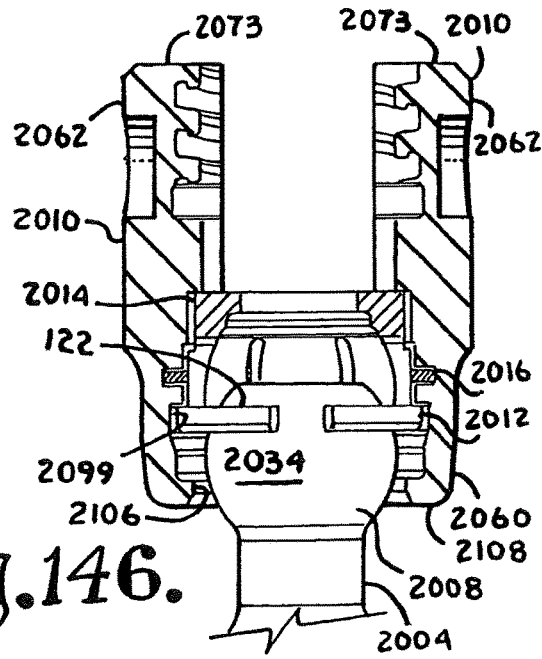

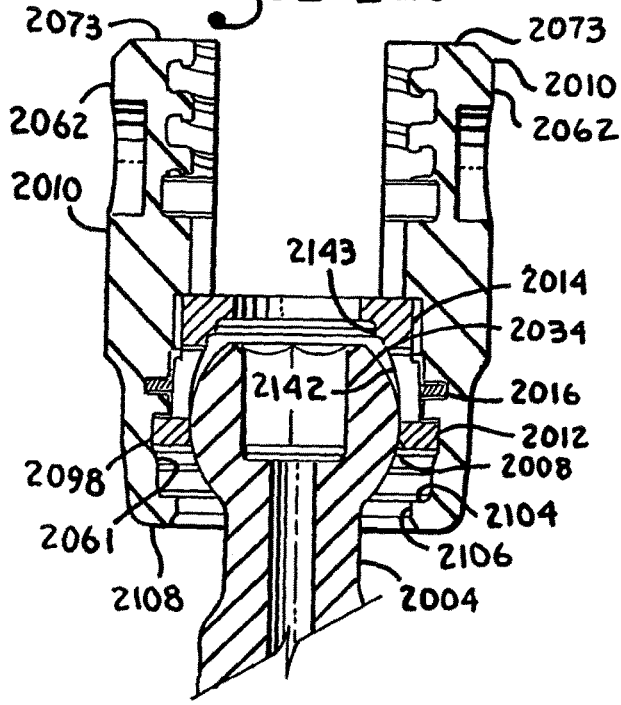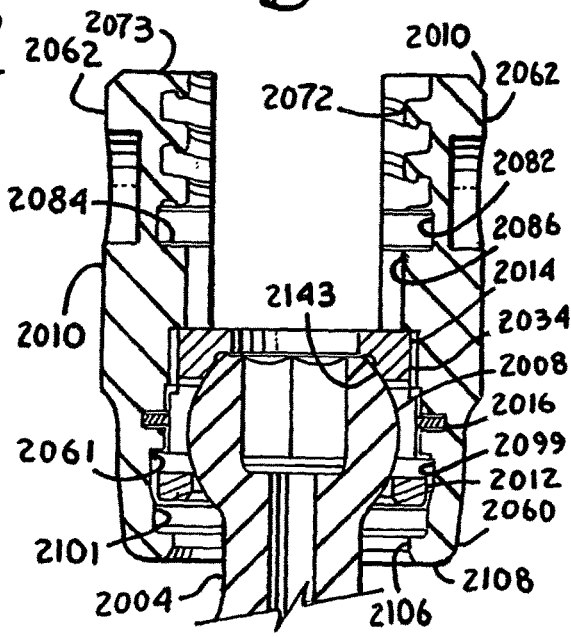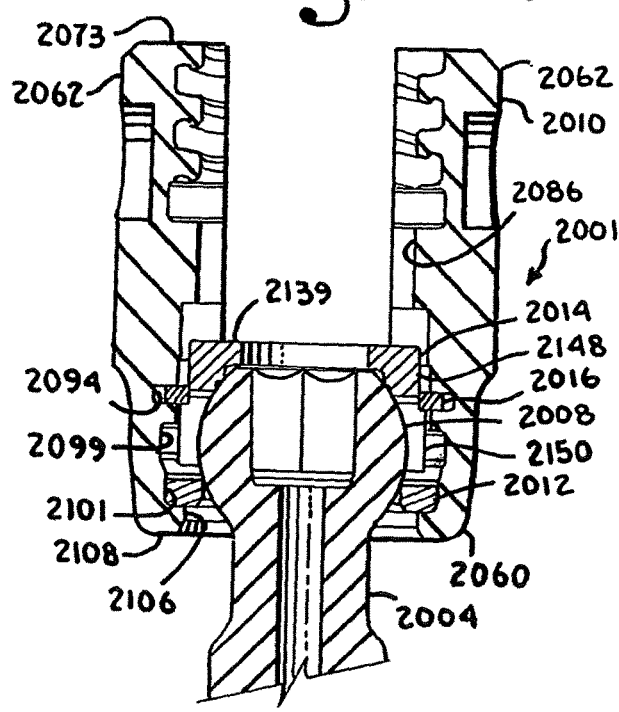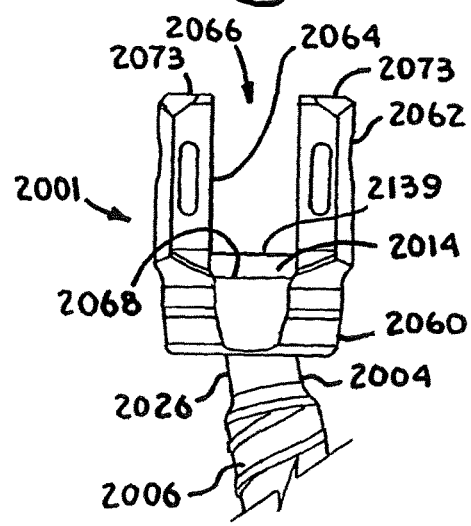

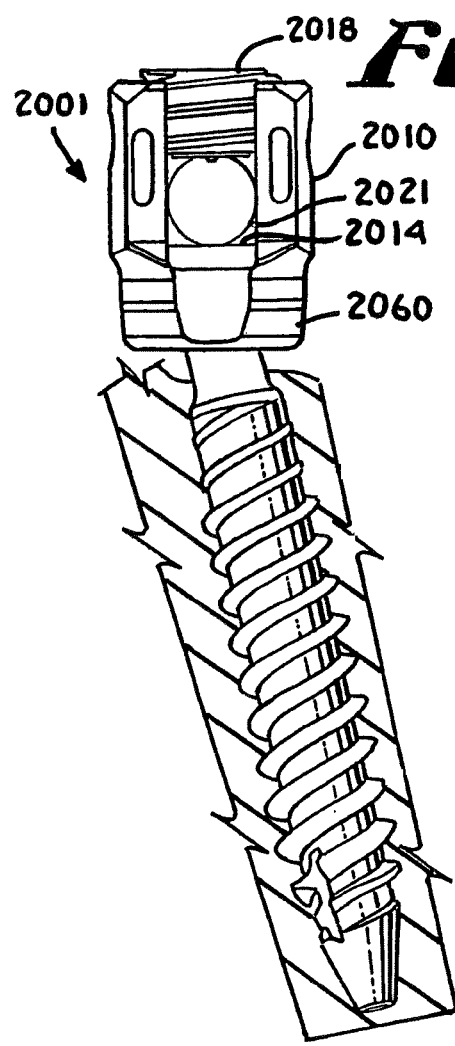
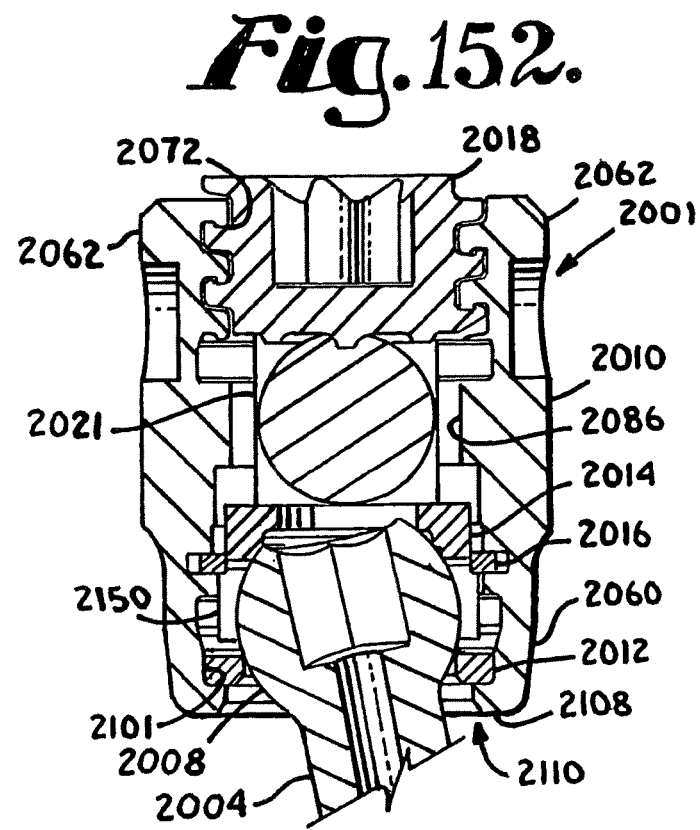

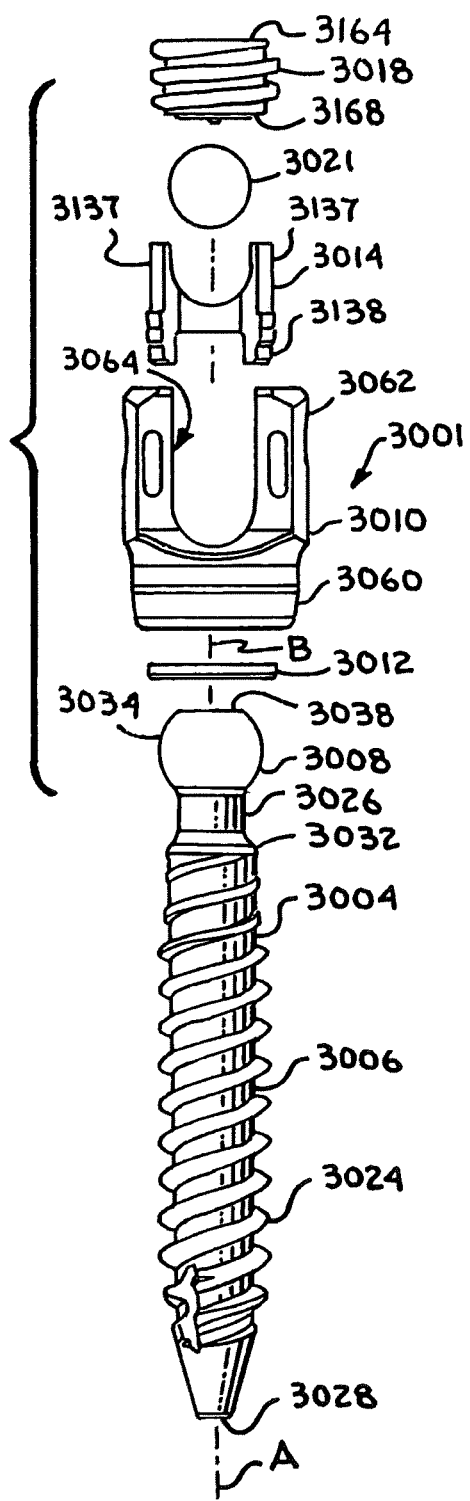
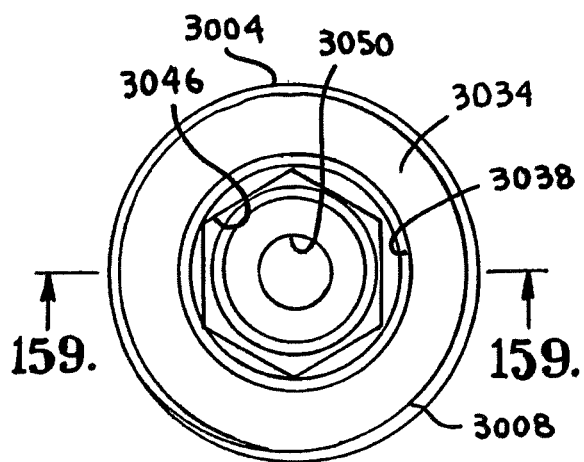
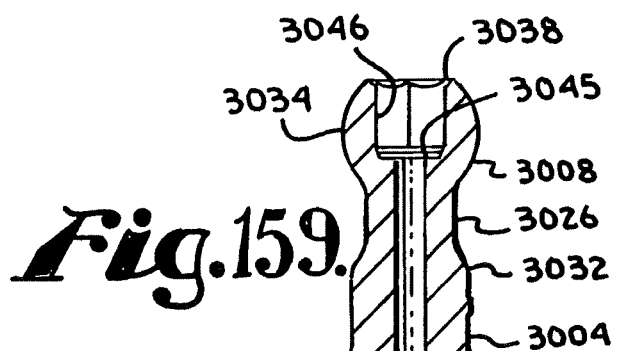
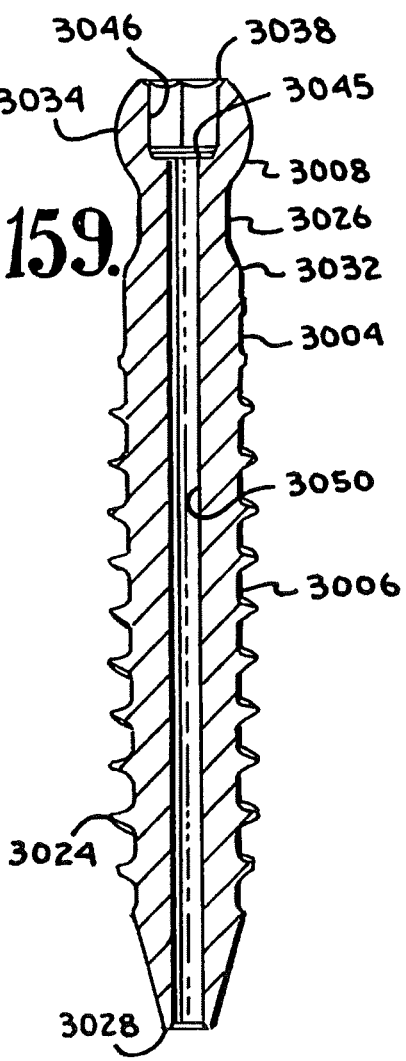

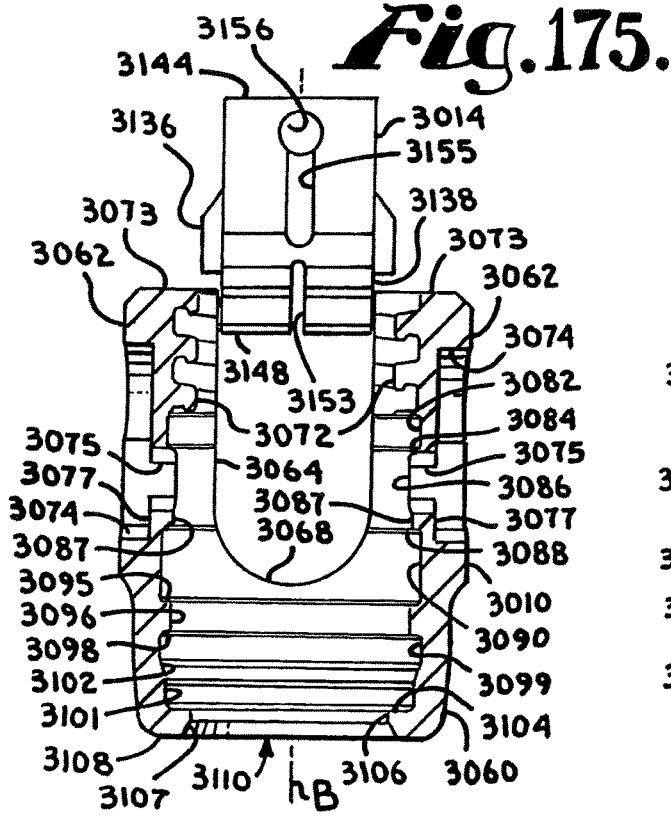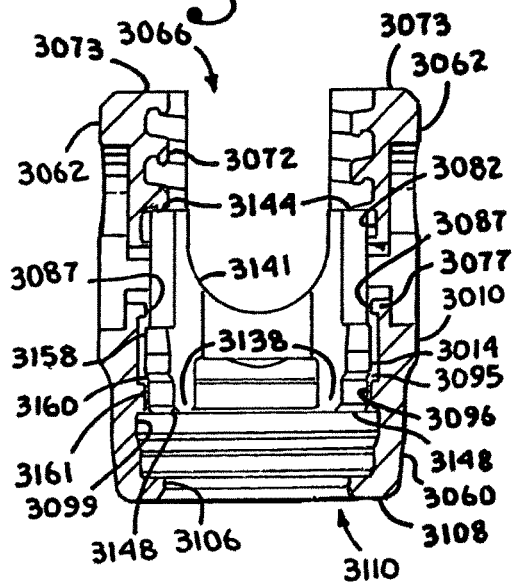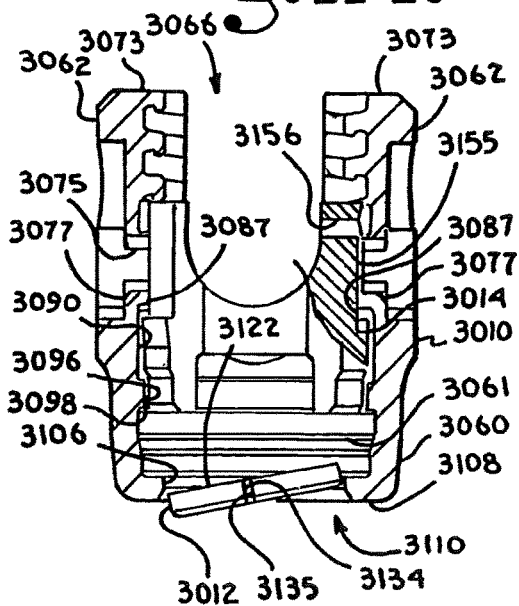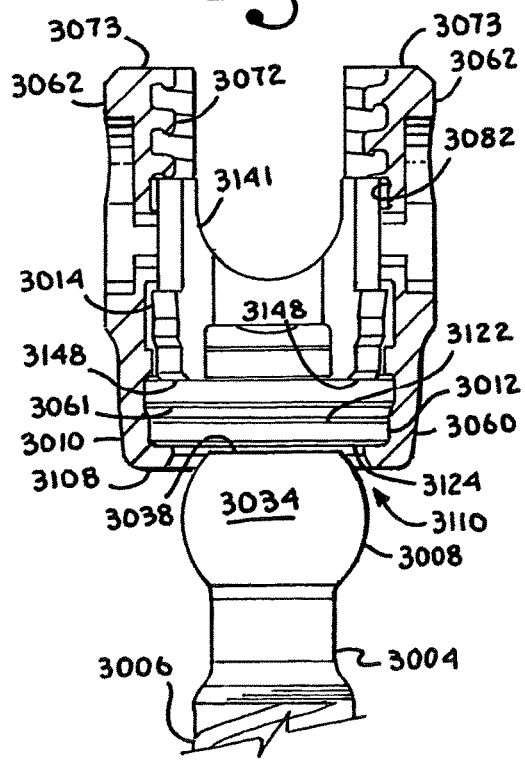

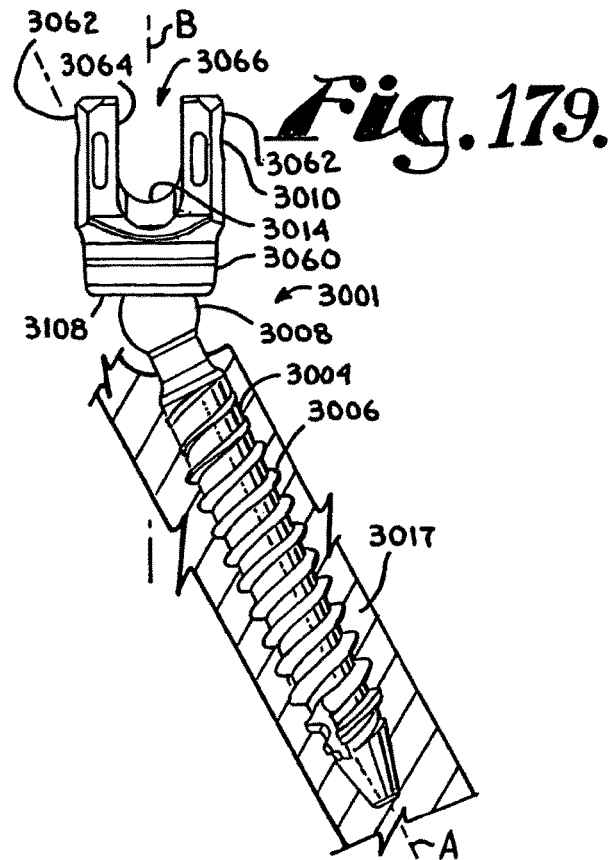
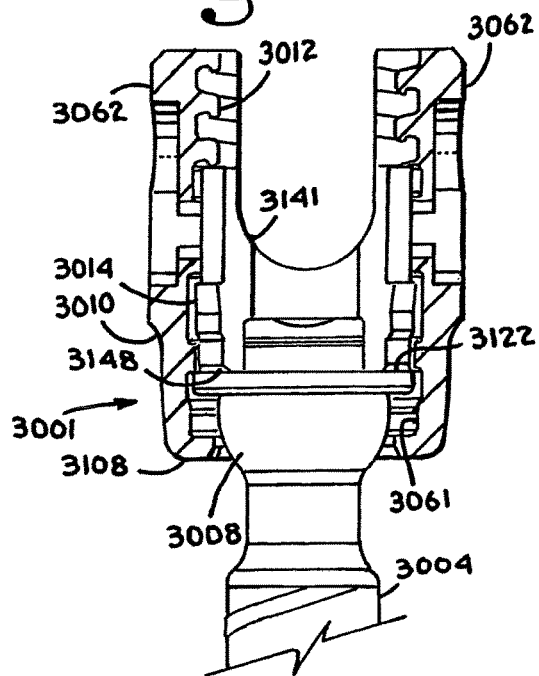
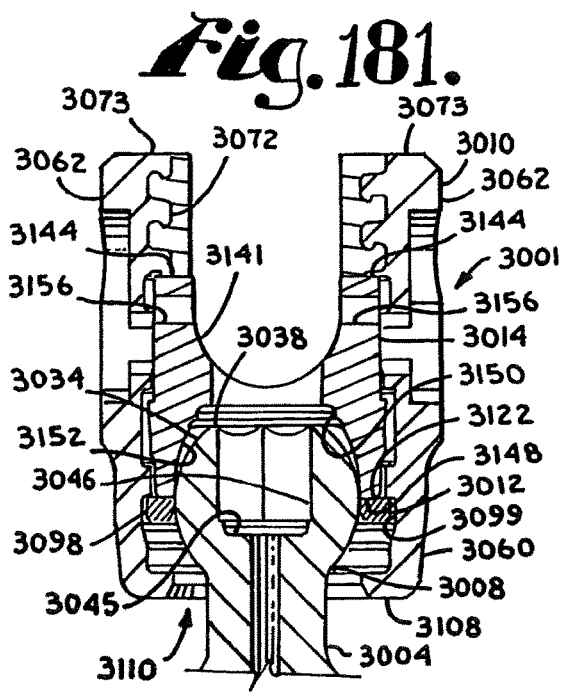
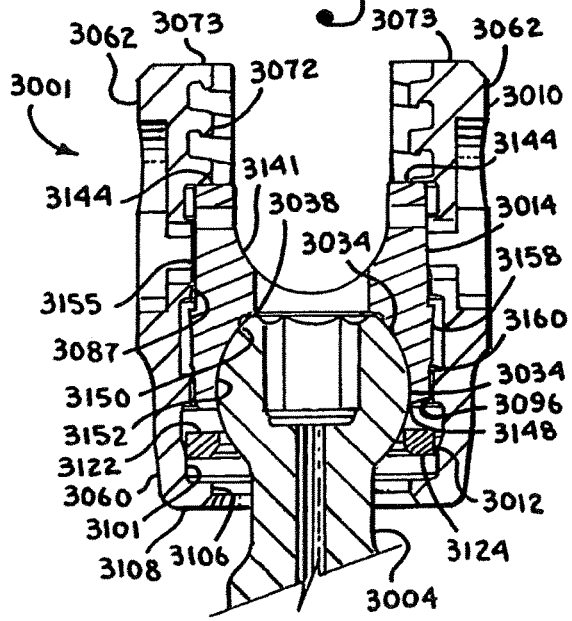

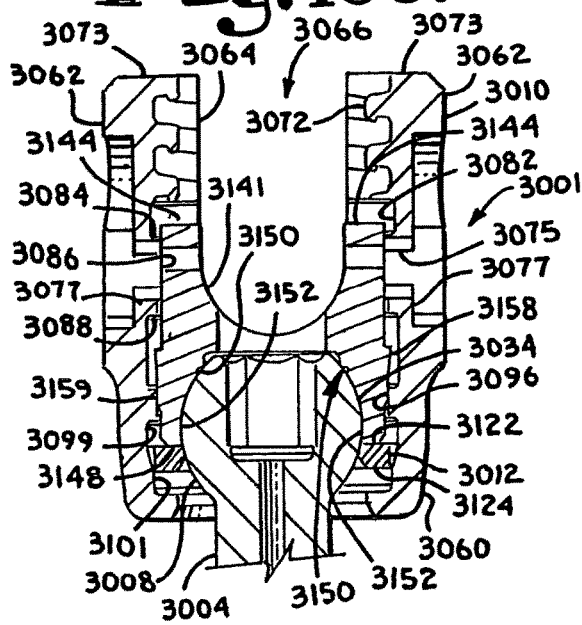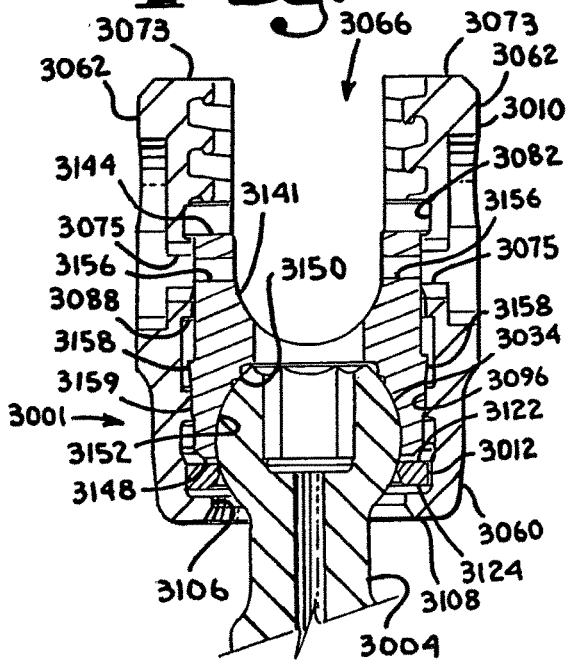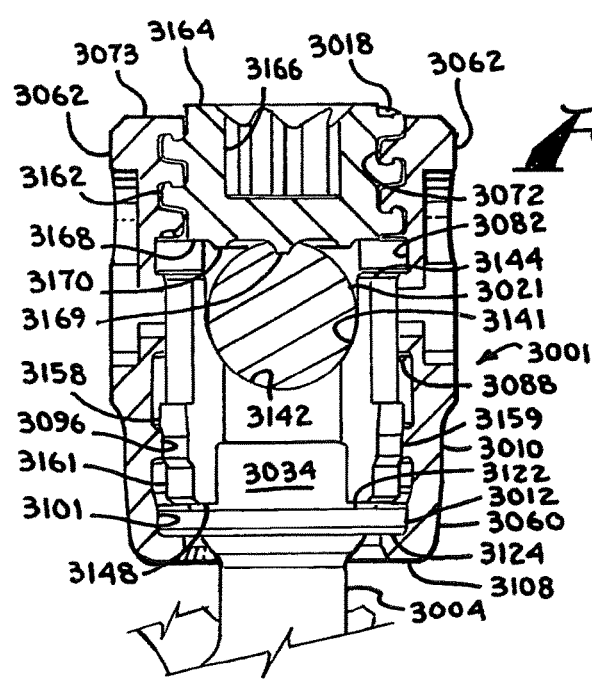

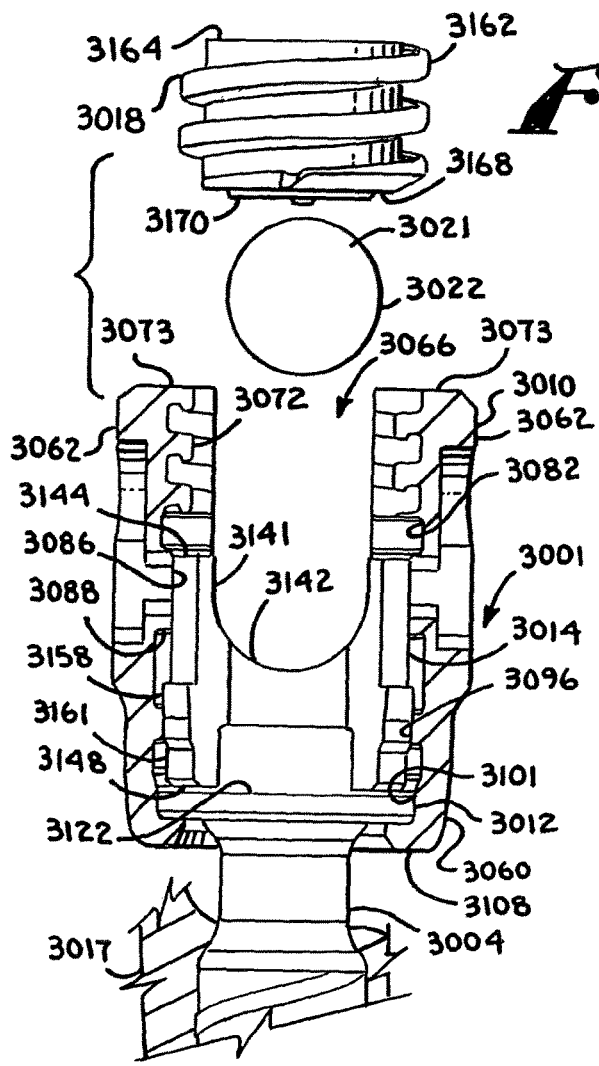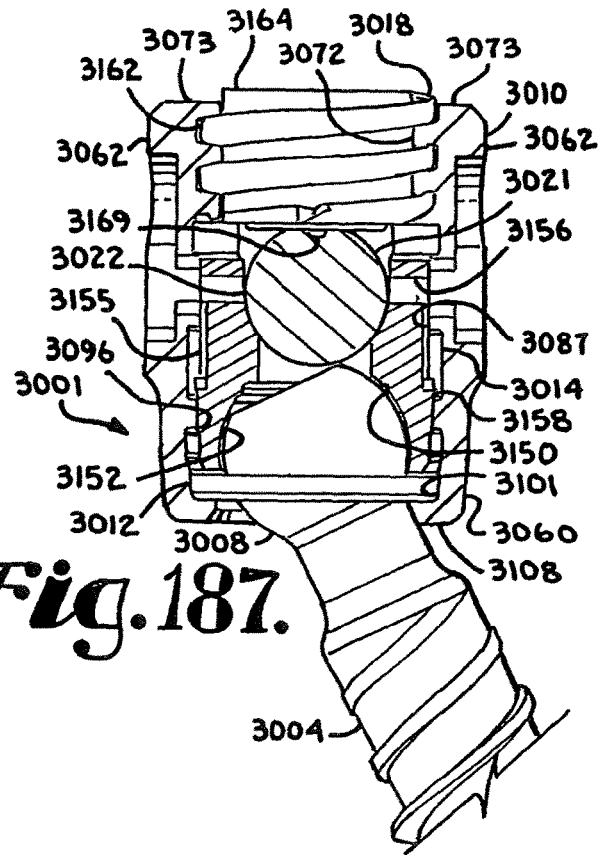

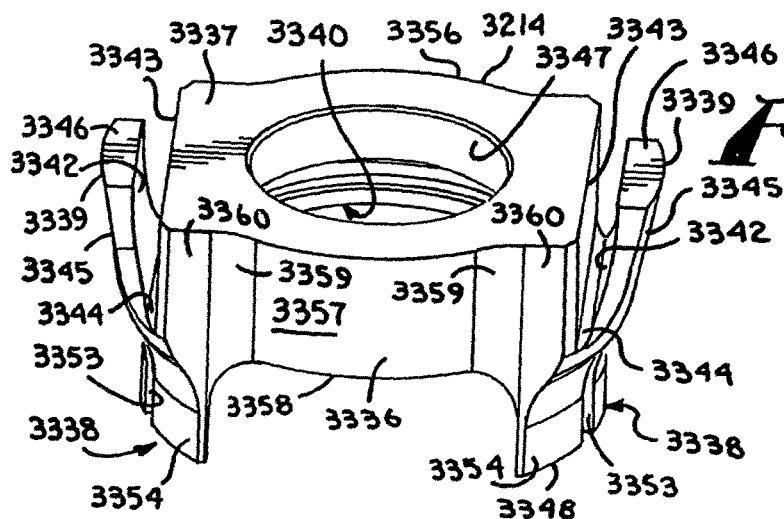
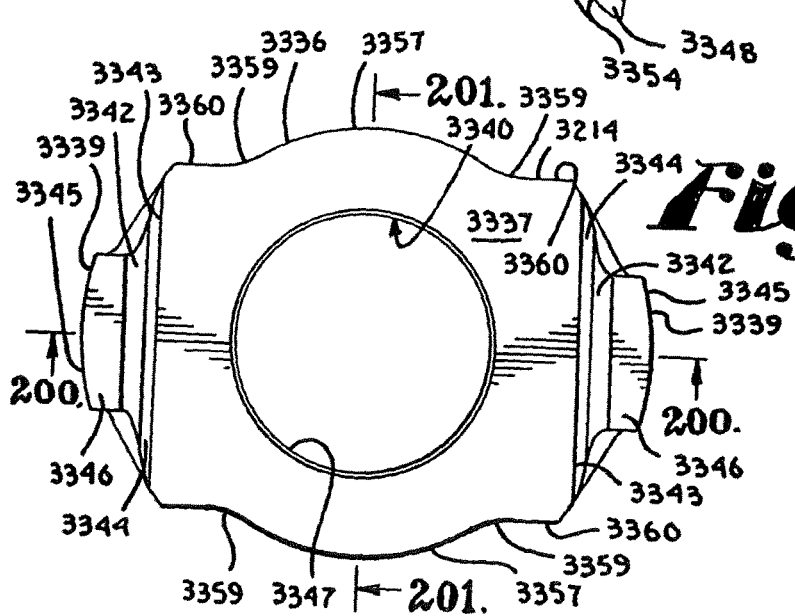

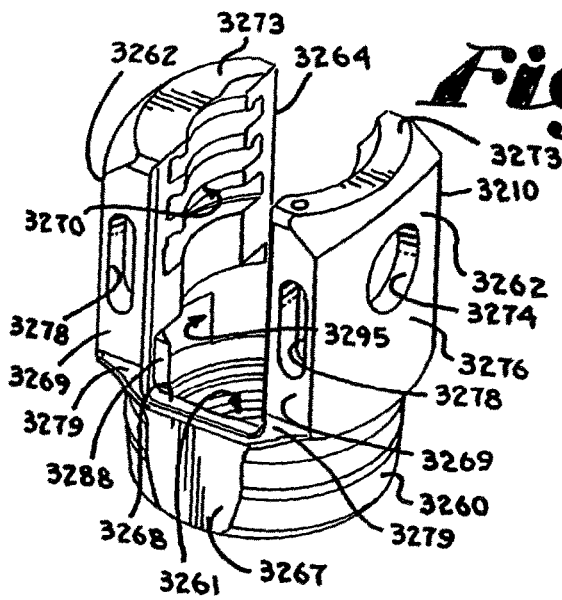
Fig.202.
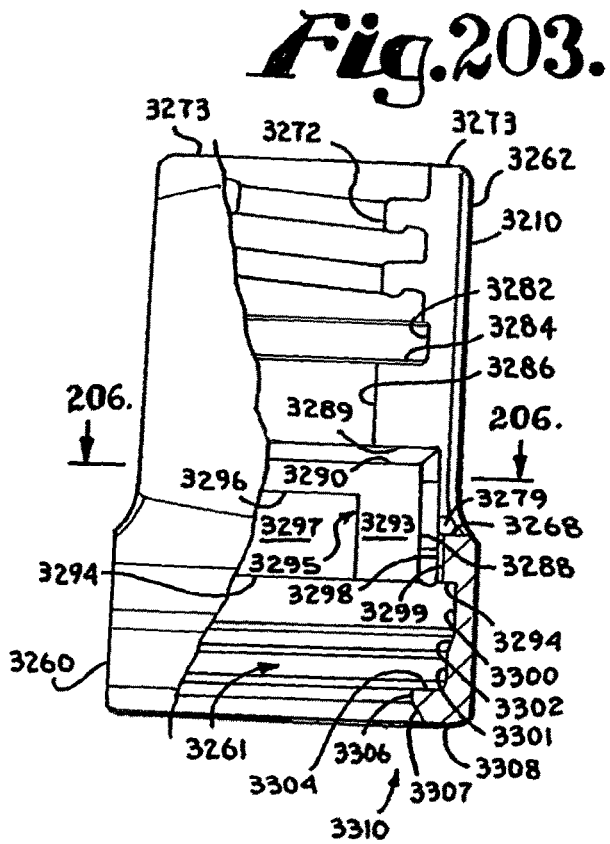
Fig.203.
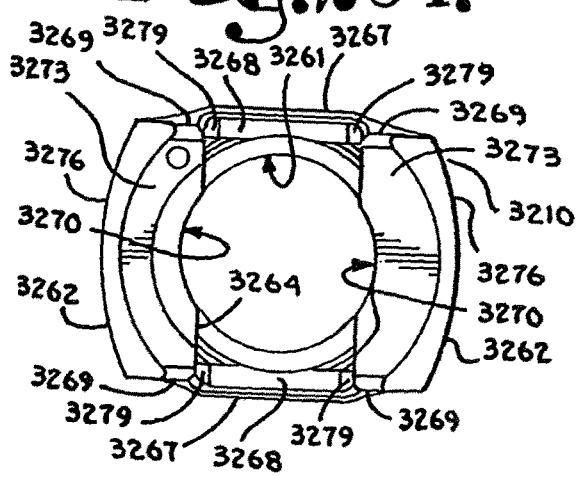
Fig.204.
Fig.205.

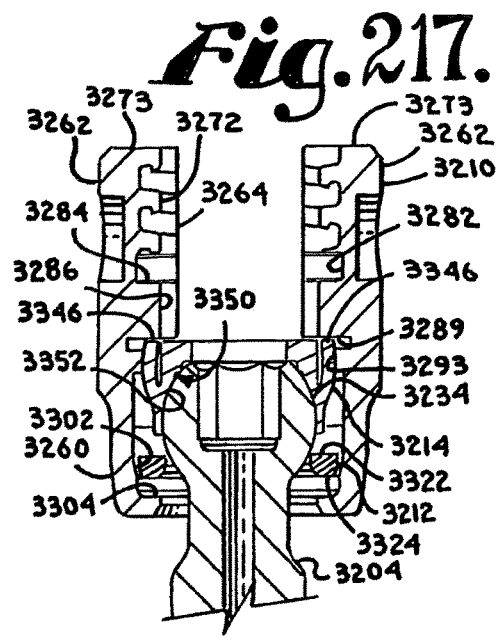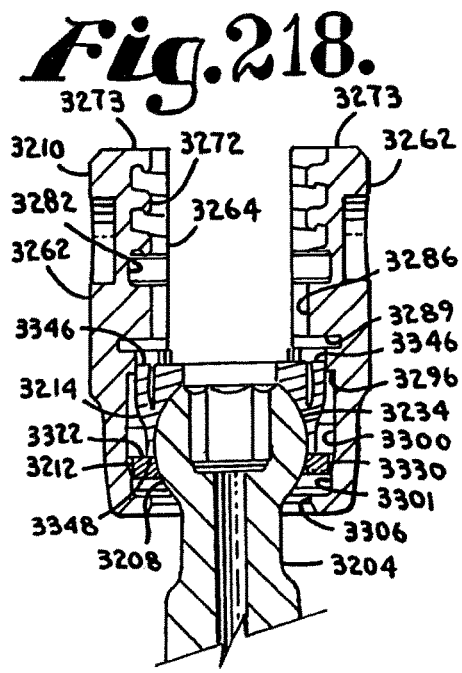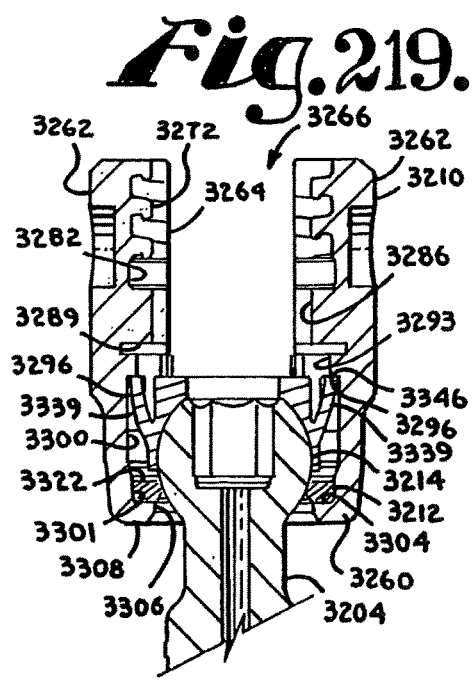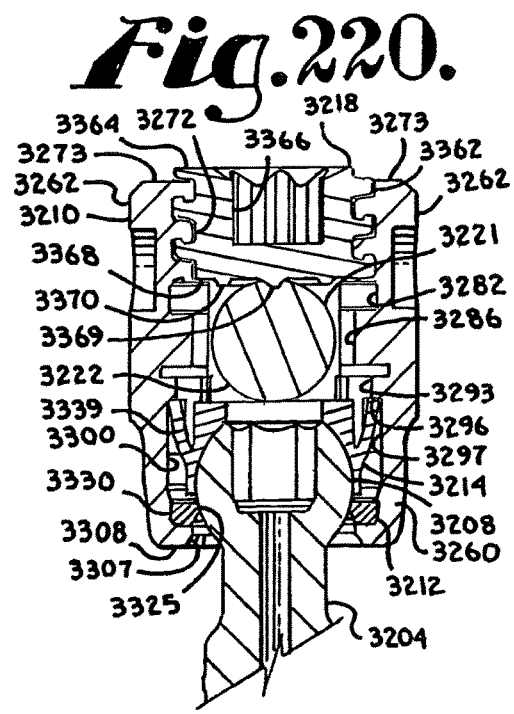

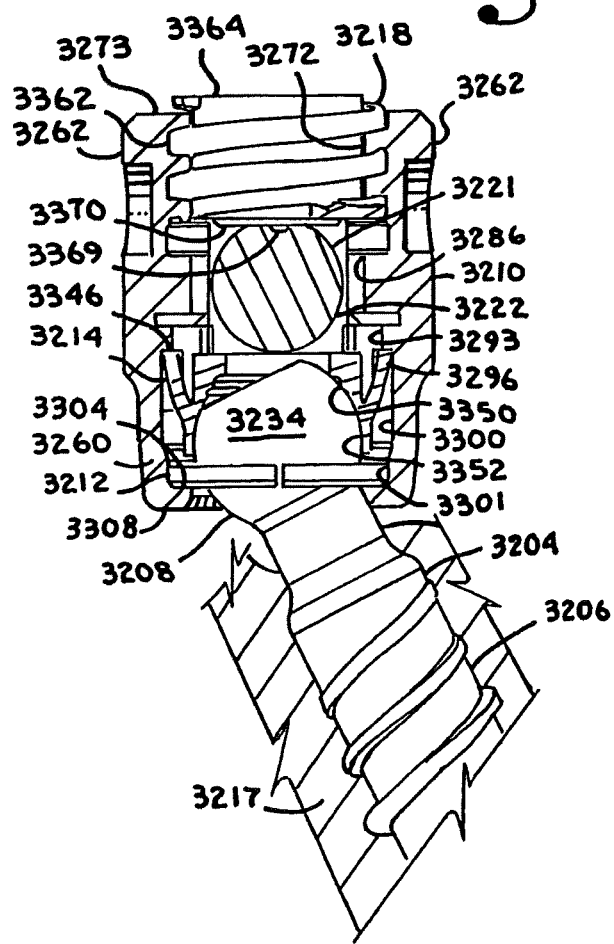

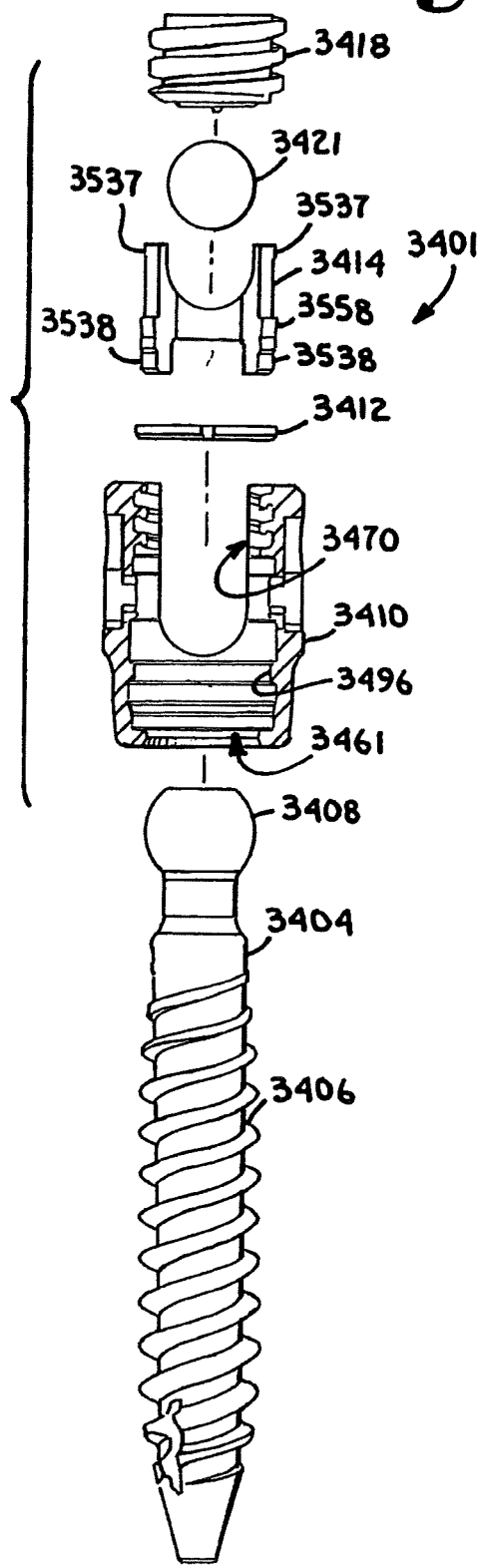
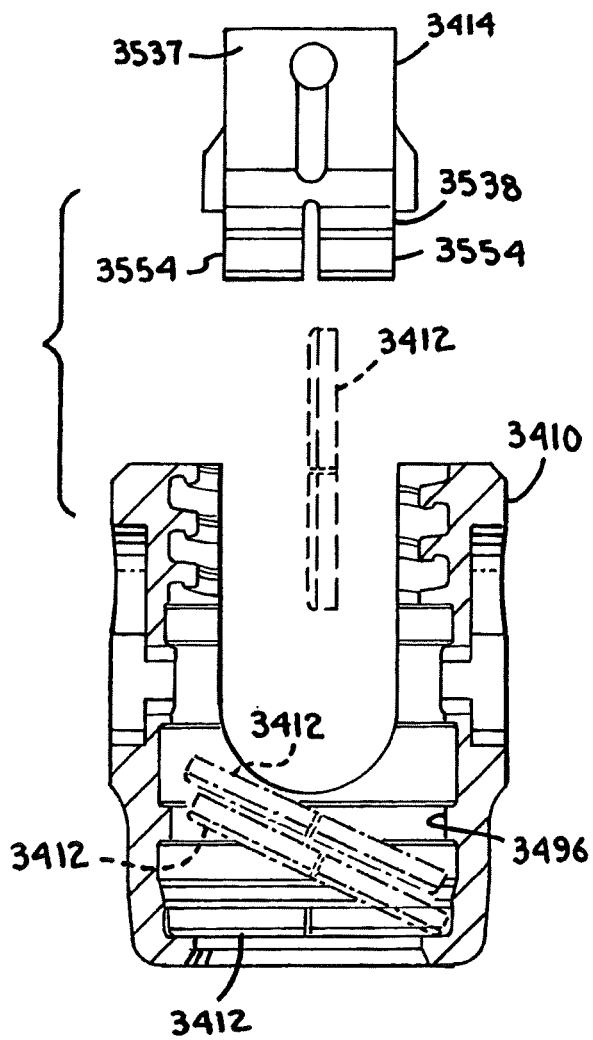

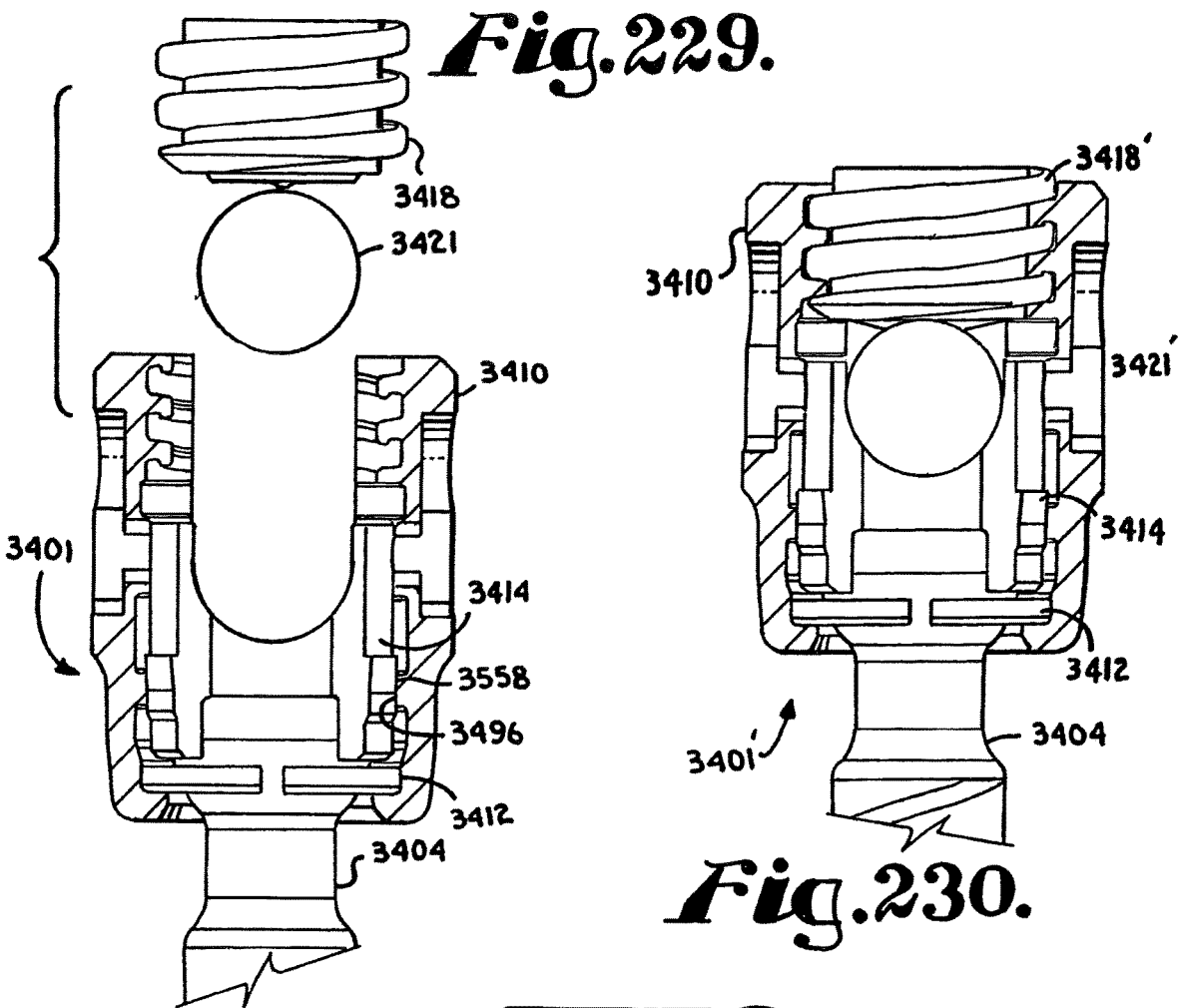
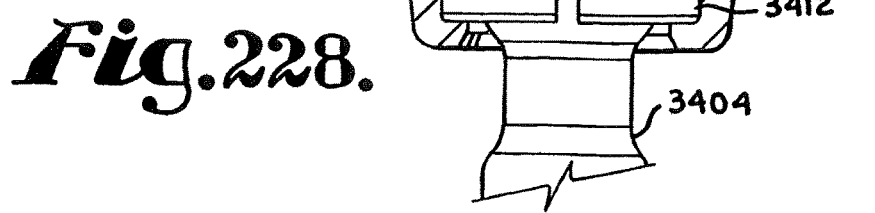

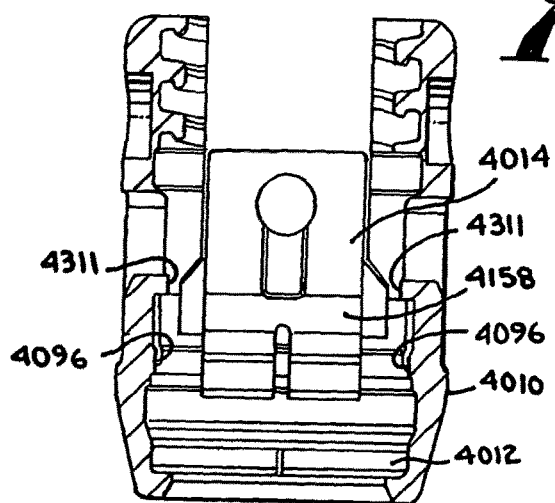
Fig.238.
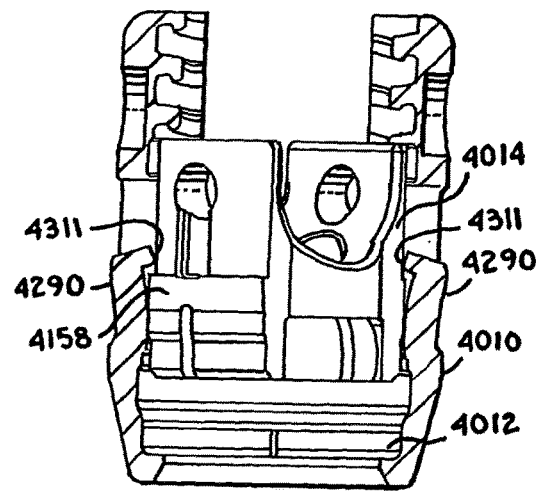
Fig.239.
Fig.240.
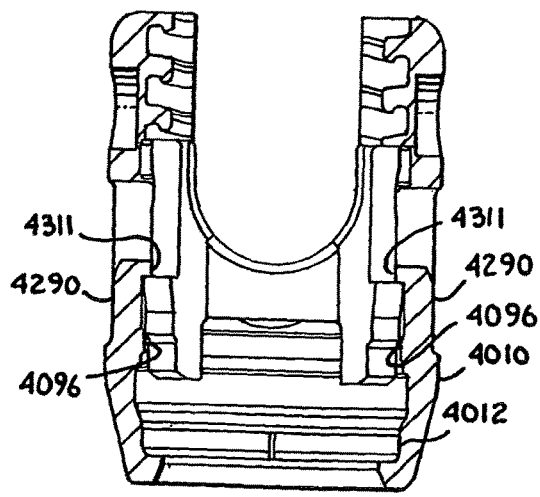
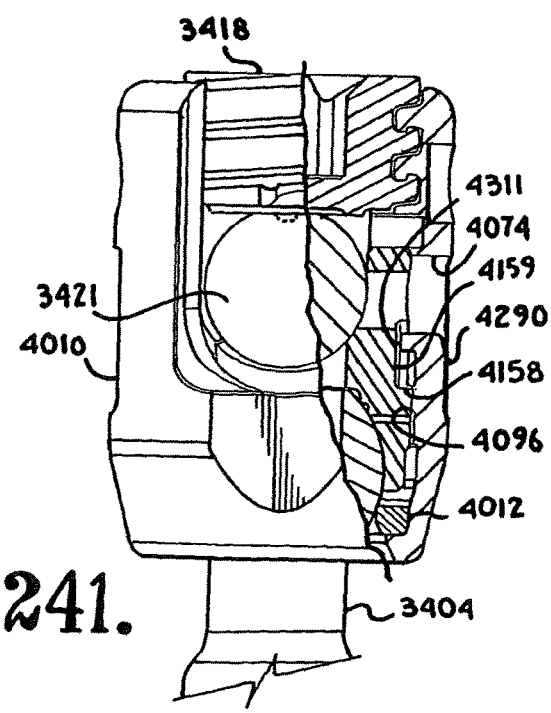
Fig.241.

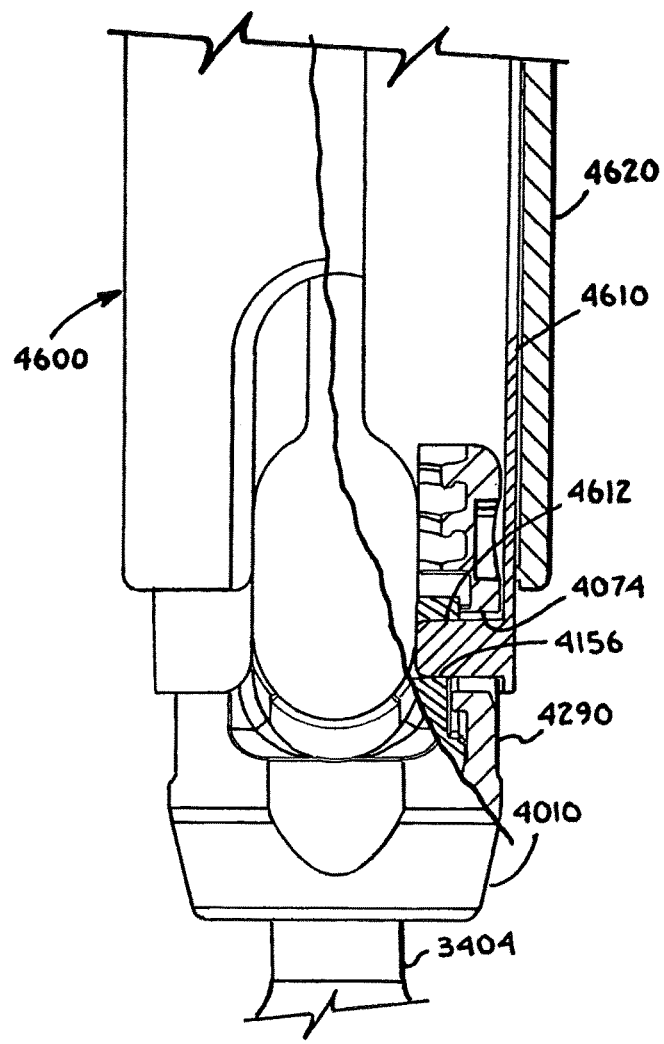
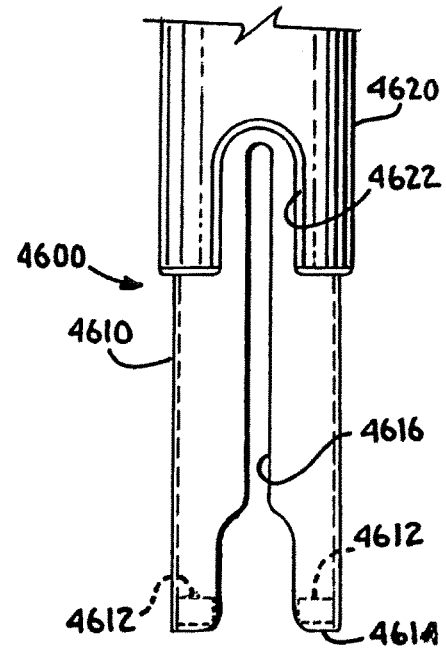
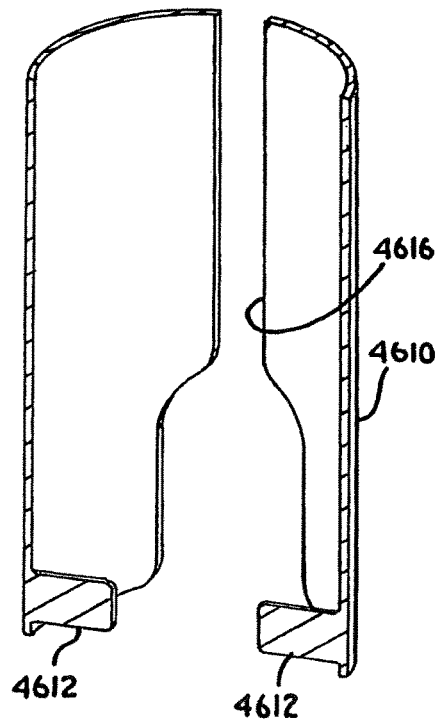
Fig.242.
Fig.243.
Fig.244.

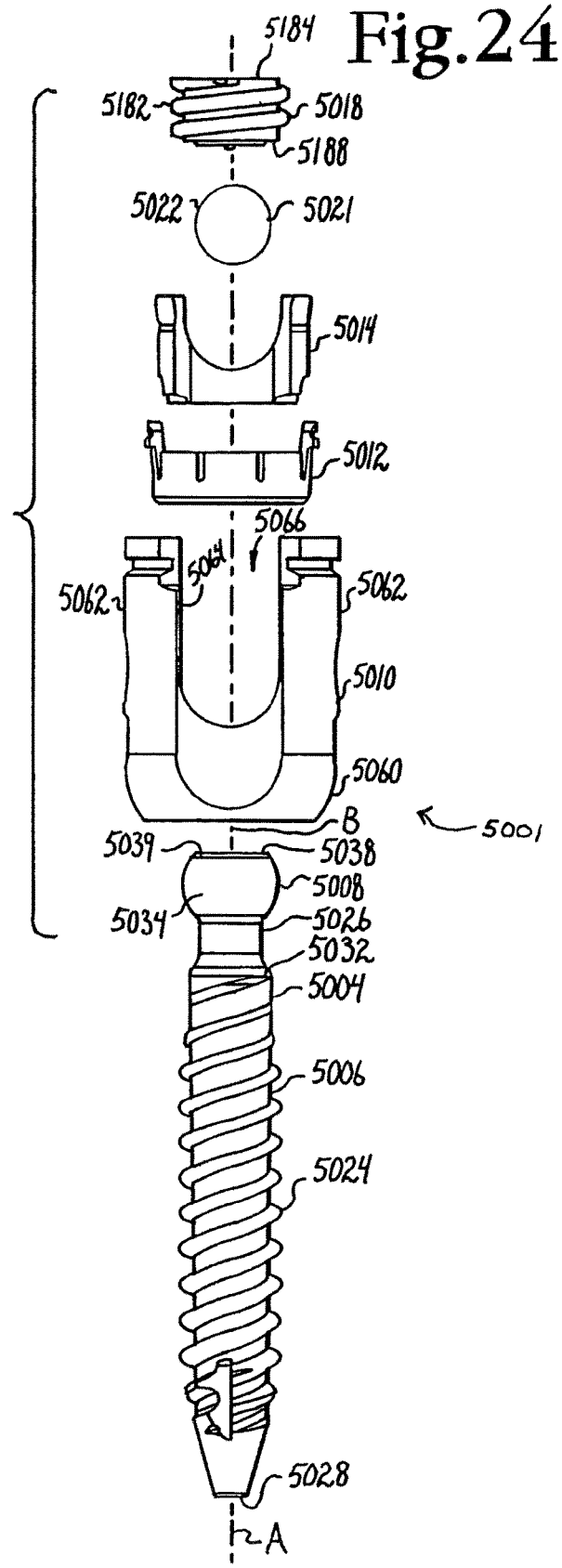
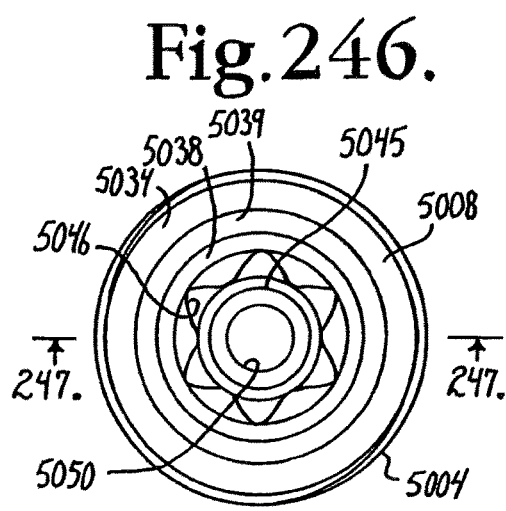
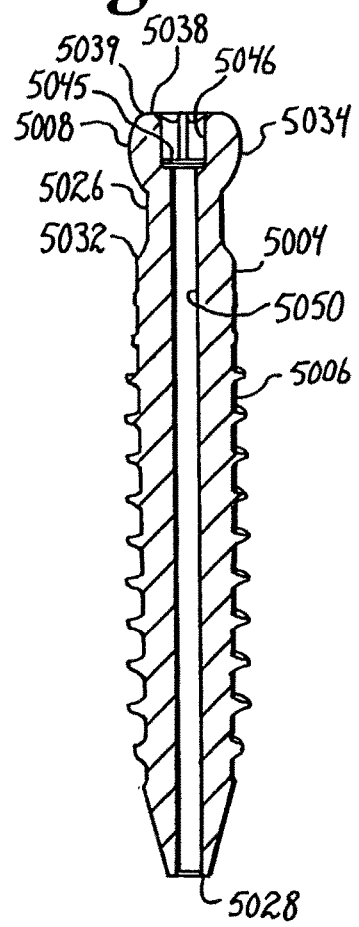
Fig. 245.
Fig. 246.
Fig. 247.

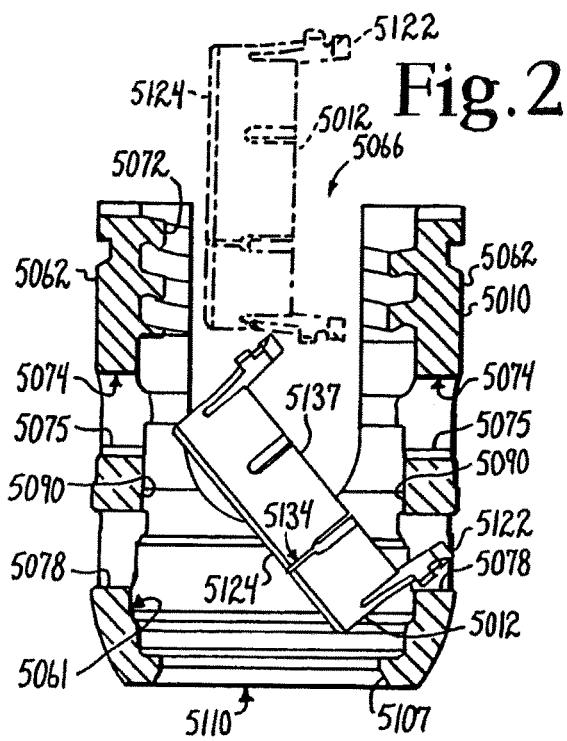
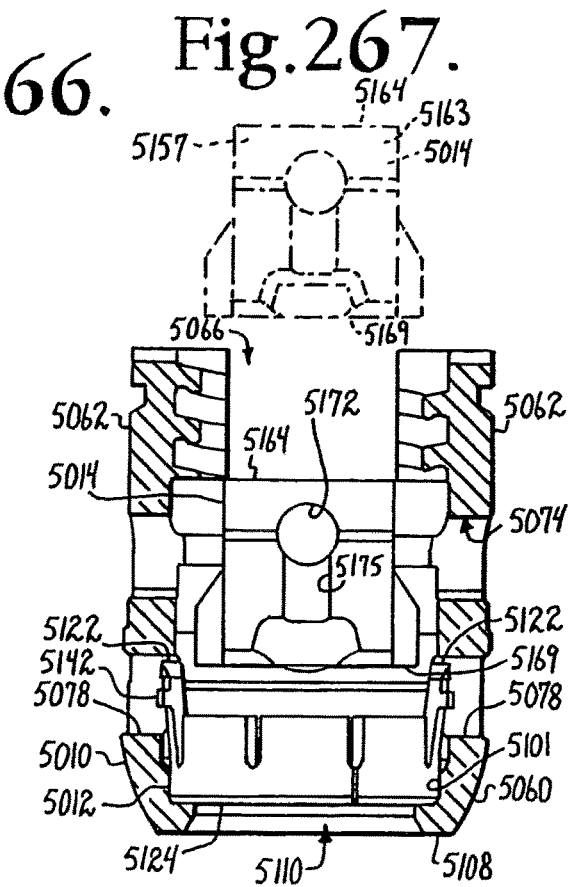
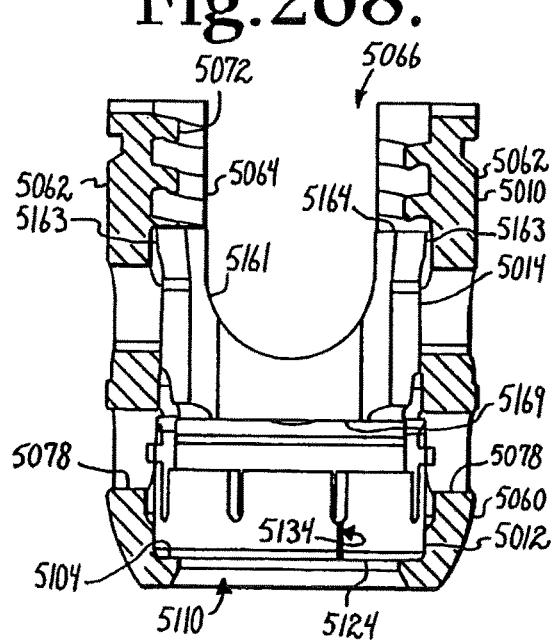
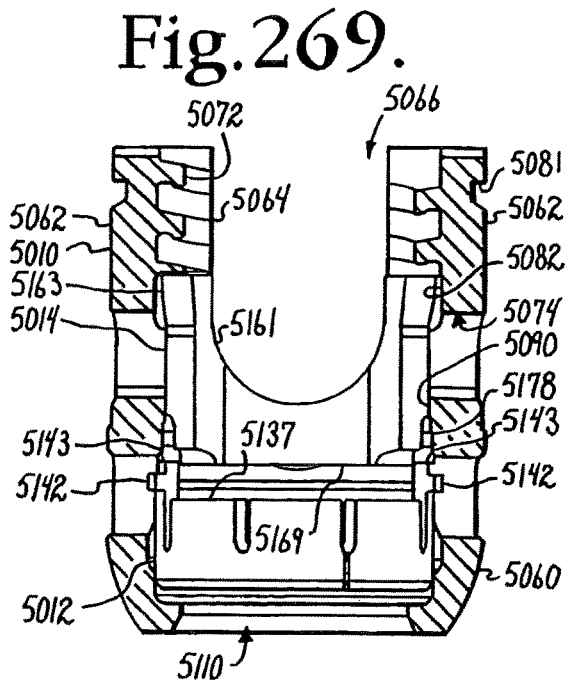

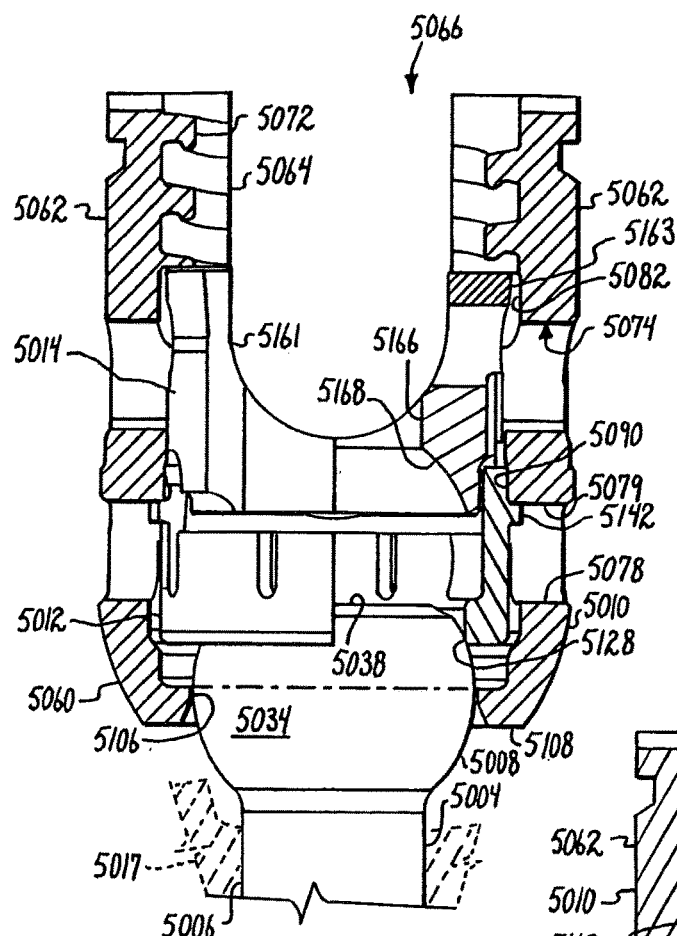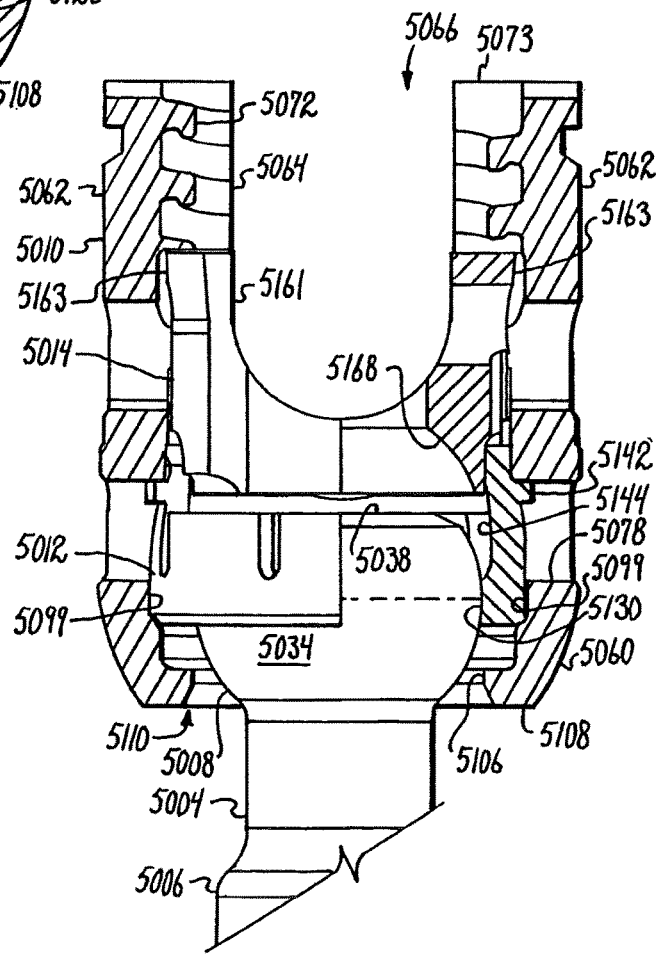

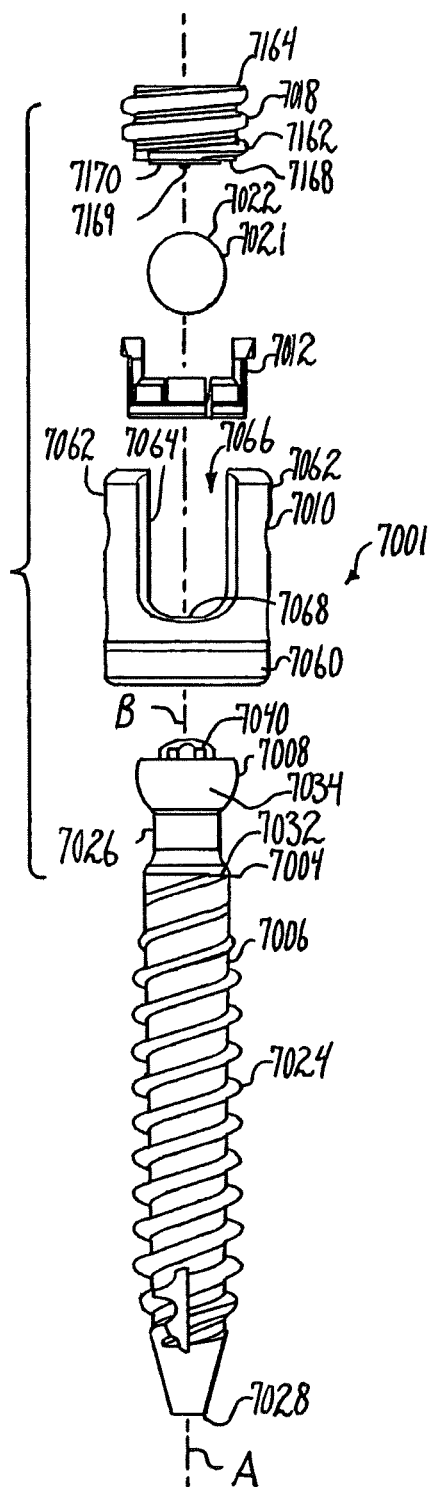
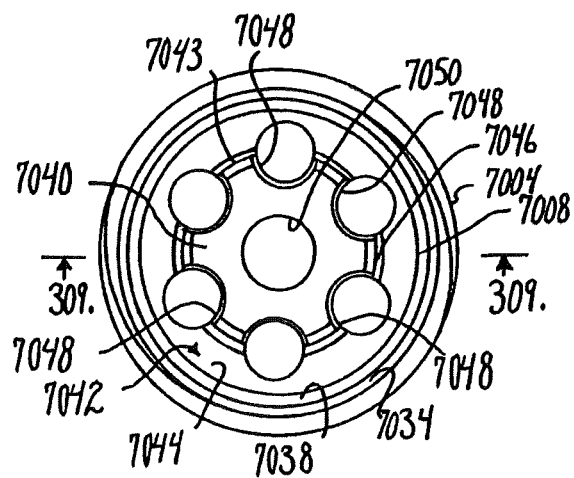
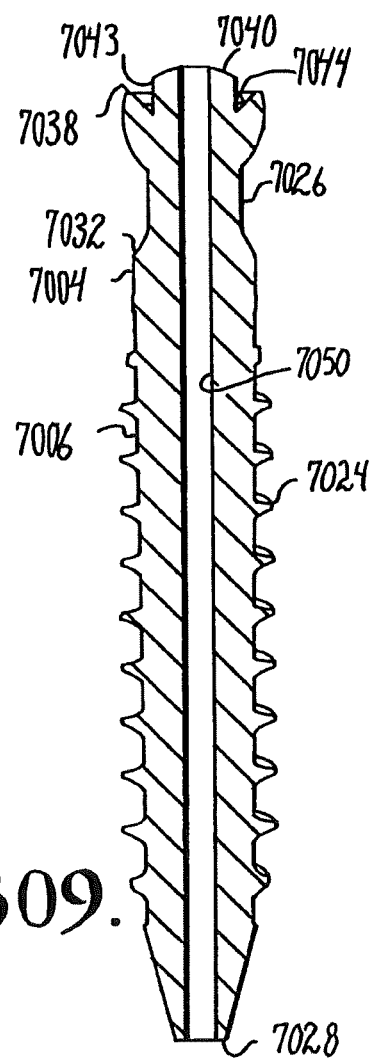
Fig. 307.
Fig. 308.
Fig. 309.

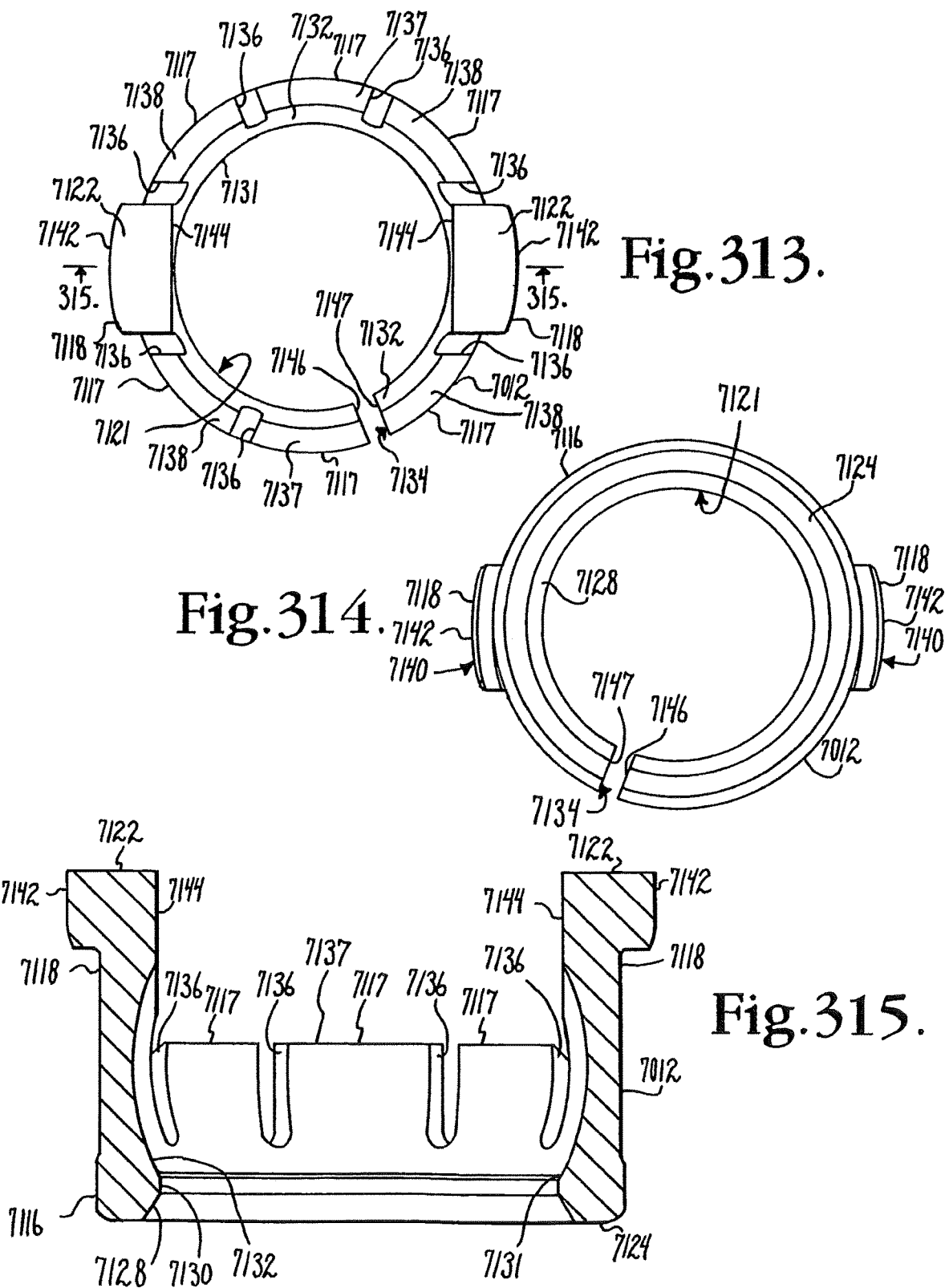

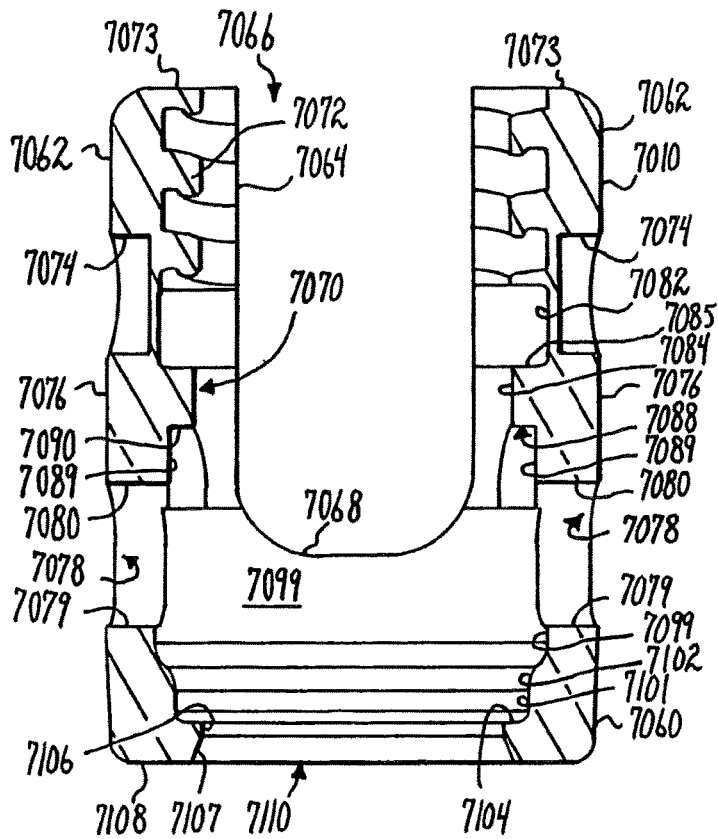
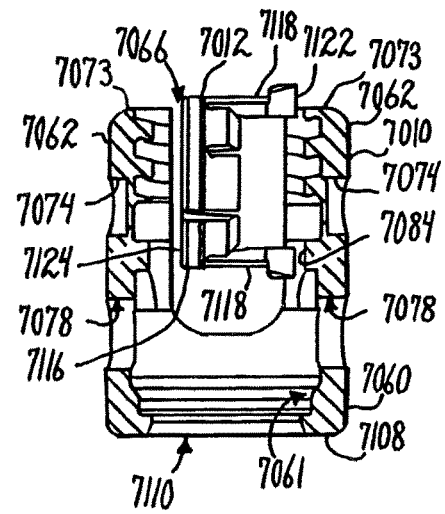
Fig.320.
Fig.321.
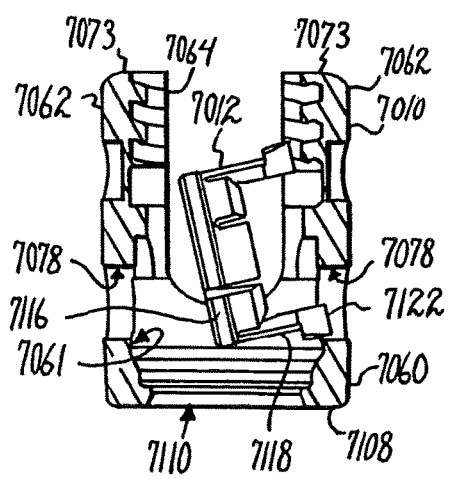
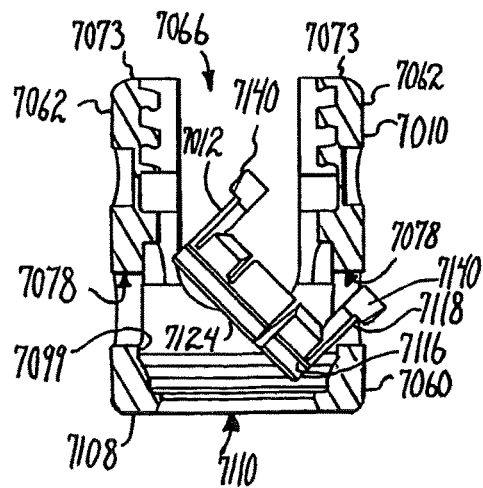
Fig.322.
Fig.323.

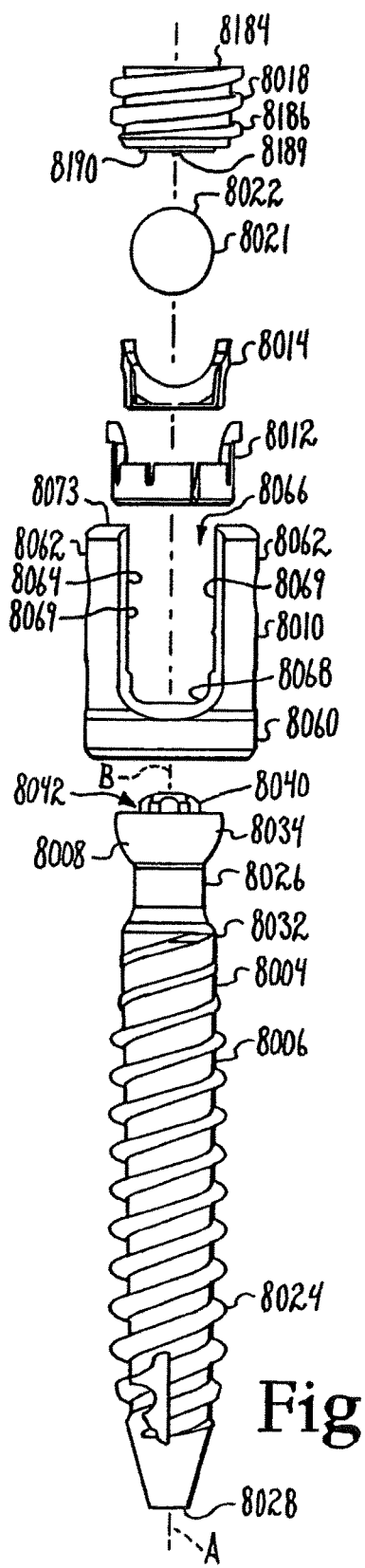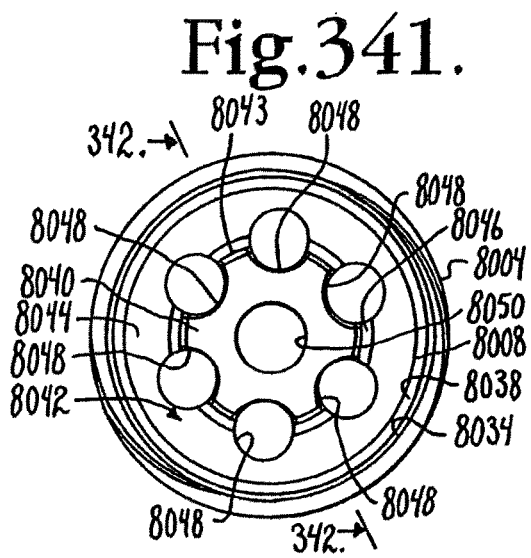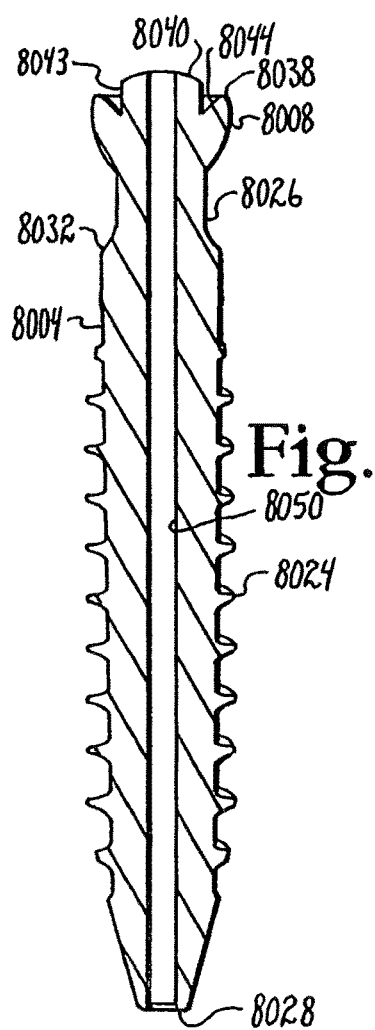

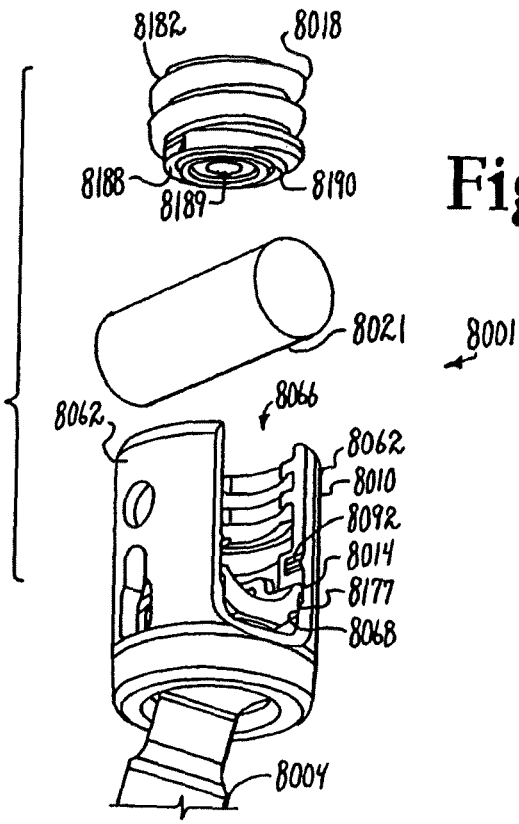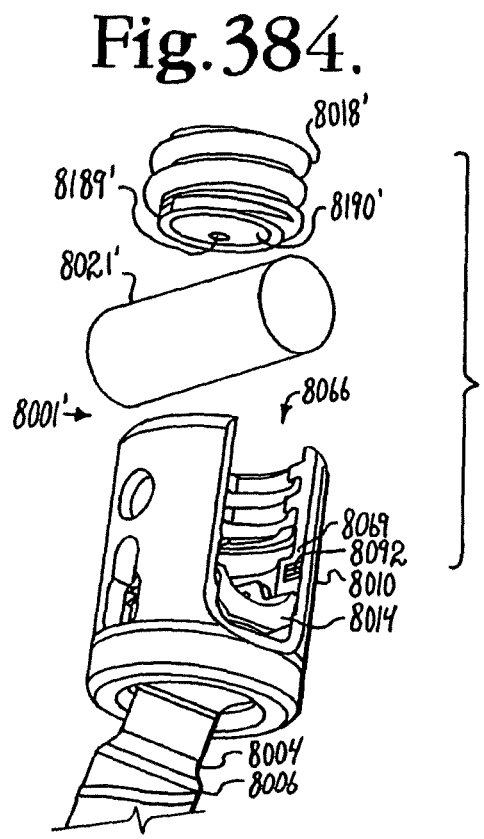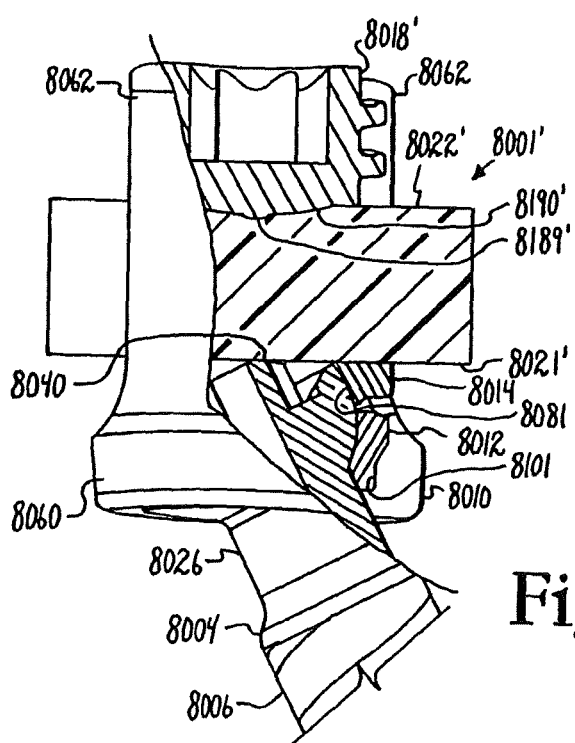
Fig.383.
Fig.384.
Fig.385.

PIVOTAL BONE ANCHOR ASSEMBLY HAVING TWIST-IN-PLACE INSERT WITH FORCED INTERFERENCE DOWNWARD DISPLACEMENT

CROSS-REFERENCE TO RELATED APPLICATIONS

This application is a continuation of U.S. application Ser. No. 17/536,942, filed Nov. 29, 2021, now U.S. Pat. No. 11,464,549, which is a continuation of U.S. application Ser. No. 17/228,345, filed Apr. 12, 2021, now U.S. Pat. No. 11,185,352, which is a continuation of U.S. application Ser. No. 16/942,273, filed Jul. 29, 2020, now U.S. Pat. No. 10,973,555, which is a continuation of U.S. application Ser. No. 16/538,443, filed Aug. 12, 2019, now U.S. Pat. No. 10,765,456, which is a continuation of U.S. application Ser. No. 16/516,576, filed Jul. 19, 2019, now U.S. Pat. No. 10,765,455, which is continuation of U.S. application Ser. No. 15/663,316, filed Jul. 28, 2017, now U.S. Pat. No. 10,441,319, which is a continuation of U.S. application Ser. No. 15/239,515, filed Aug. 17, 2016, now U.S. Pat. No. 9,956,006, which is a continuation of U.S. application Ser. No. 14/052,265, filed Oct. 11, 2013, now abandoned, which is a continuation of U.S. application Ser. No. 12/924,802, filed Oct. 5, 2010, now U.S. Pat. No. 8,556,938, each of which is incorporated by reference in its entirety herein and for all purposes.

U.S. application Ser. No. 12/924,802 claims the benefit of priority from the following: U.S. Provisional Application No. 61/403,915, filed Sep. 23, 2010, U.S. Provisional Application No. 61/403,696, filed Sep. 20, 2010; U.S. Provisional Application No. 61/402,959, filed Sep. 8, 2010; U.S. Provisional Application No. 61/400,504, filed Jul. 29, 2010; U.S. Provisional Application No. 61/398,807, filed Jul. 1, 2010; U.S. Provisional Application No. 61/396,390, filed May 26, 2010; U.S. Provisional Application No. 61/395,752, filed May 17, 2010; U.S. Provisional Application No. 61/395,564, filed May 14, 2010, U.S. Provisional Application No. 61/343,737, filed May 3, 2010; U.S. Provisional Application No. 61/336,911, filed Jan. 28, 2010; and U.S. Provisional Application No. 61/278,240, filed Oct. 5, 2009; each of which is incorporated by reference in its entirety herein and for all purposes.

U.S. application Ser. No. 14/052,265 is also a continuation-in-part of U.S. patent application Ser. No. 12/802,849, filed Jun. 15, 2010, now abandoned, which claims the benefit of priority from the following: U.S. Provisional Application No. 61/396,390, filed May 26, 2010; U.S. Provisional Application No. 61/395,752, filed May 17, 2010; U.S. Provisional Application No. 61/395,564, filed May 14, 2010; U.S. Provisional Application No. 61/336,911, filed Jan. 28, 2010; U.S. Provisional Application No. 61/270,754, filed Jul. 13, 2009; and U.S. Provisional Application No. 61/268,708, filed Jun. 15, 2009, each of which is incorporated by reference in its entirety herein and for all purposes.

BACKGROUND OF THE INVENTION

The present invention is directed to polyaxial bone screws for use in bone surgery, particularly spinal surgery.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the head is achieved by fixing such position relative to the shank during a final stage of a medical procedure when a rod or other longitudinal connecting member is inserted into the head or receiver, followed by a locking screw or other closure.

SUMMARY OF THE INVENTION

A polyaxial bone anchor assembly according to the invention includes a receiver defining a chamber communicating with a channel, the channel sized and shaped for receiving a portion of a longitudinal connecting member. The bone anchor further includes a shank having an upper portion and a retainer located in the chamber, the retainer being expandable in the chamber about the shank upper portion and receiving the upper portion therethrough to capture the upper portion in the chamber. The retainer is in a non-tapered locking engagement with the shank upper portion when the shank is in a locked orientation with respect to the receiver. The bone anchor assembly may include a variety of inserts, including compression inserts that may or may not have a lock and release feature as well as inserts having a super structure to provide a non-floppy friction fit between the insert and the shank upper portion when the shank is not otherwise locked in place with respect to the receiver. Furthermore, in some embodiments, the retainer may have super structure to provide a friction-fit insert.

A pre-assembled receiver, retainer and alternative insert may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the retainer and expanding the resilient retainer portion out into an expansion portion of the receiver cavity followed by return of the retainer back to an original neutral shape thereof after the hemisphere of the shank head or upper portion passes through an open body portion of the retainer. The shank head may also enter into a friction fit super structure of either the retainer or an insert, panels or surfaces of the friction fit portion of the retainer or insert snapping or gripping onto the shank head as or after the retainer returns to a neutral or close to neutral orientation, providing a non-floppy connection between the retainer or insert and the shank head. The friction fit between the shank head and the retainer or insert is temporary. In several of illustrated embodiments, when the shank is ultimately locked between the compression insert and the retainer non-tapered body, the friction fit portions of the retainer or insert typically are no longer in a friction fit engagement with the shank head. The final fixation typically occurs as a result of locking expansion type of contact between the shank head and the expandable retainer and expansion type of engagement between the retainer and the receiver cavity. In some embodiments, when the polyaxial mechanism is locked, an insert or a retainer portion is wedged against a surface of the receiver, allowing for adjustment or removal of the rod or other connecting member without loss of a desired angular relationship between the shank and the receiver.

Objects of the invention include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged and partial exploded perspective view of a polyaxial bone screw assembly according to the present invention including a shank, a receiver, a retainer in the form of a spring ring and a compression insert and also shown with a closure top and a longitudinal connecting member in the form of a rod.

FIG. 2 is an enlarged top plan view of the shank of FIG. 1.

FIG. 3 is reduced cross-sectional view taken along the line 3-3 of FIG. 2.

FIG. 4 is an enlarged top plan view of the receiver of FIG. 1.

FIG. 5 is a bottom plan view of the receiver of FIG. 4.

FIG. 6 is a side elevational view of the receiver of FIG. 4.

FIG. 7 is a cross-sectional view taken along the line 7-7 of FIG. 4.

FIG. 8 is an enlarged perspective view of the retainer of FIG. 1.

FIG. 9 is a top plan view of the retainer of FIG. 8.

FIG. 10 is a bottom plan view of the retainer of FIG. 8.

FIG. 11 is a front elevational view of the retainer of FIG. 8.

FIG. 12 is a cross-sectional view taken along the line 12-12 of FIG. 9.

FIG. 24 is an enlarged and partial front elevational view of the shank, receiver, compression insert and retainer of FIG. 1, with portions broken away to show the detail thereof and shown in a stage of assembly subsequent to that shown in FIG. 23.

FIG. 25 is a partial front elevational view with portions broken away, similar to FIG. 24, showing a subsequent stage of assembly.

FIG. 28 is an enlarged perspective view of the entire assembly of FIG. 1 shown with the shank at an angle with respect to the receiver as shown in FIG. 27.

FIG. 29 is an enlarged and partial side elevational view of the assembly of FIG. 28 with portions broken away to show the detail thereof.

FIG. 32 is an enlarged and partial exploded front elevational view of another polyaxial bone screw assembly according to the present invention including a shank, a receiver, a retainer in the form of a spring ring and a compression insert.

FIG. 33 is an enlarged top plan view of the shank of FIG. 32.

FIG. 34 is reduced cross-sectional view taken along the line 34-34 of FIG. 33.

FIG. 35 is an enlarged perspective view of the retainer of FIG. 32.

FIG. 36 is another perspective view of the retainer of FIG. 32.

FIG. 37 is a top plan view of the retainer of FIG. 35.

FIG. 38 is a bottom plan view of the retainer of FIG. 35.

FIG. 39 is a cross-sectional view taken along the line 39-39 of FIG. 37.

FIG. 40 is an enlarged perspective view of the receiver of FIG. 32.

FIG. 41 is a side elevational view of the receiver of FIG. 40.

FIG. 42 is an enlarged cross-sectional view taken along the line 42-42 of FIG. 32.

FIG. 43 is a cross-sectional view taken along the line 43-43 of FIG. 41.

FIG. 48 is a front elevational view of the compression insert of FIG. 45.

FIG. 49 is a cross-sectional view taken along the line 49-49 of FIG. 48.

FIG. 50 is an enlarged and partial perspective view of the receiver and compression insert of FIG. 32 with portions of the receiver broken away to show the detail thereof and shown in an early stage of assembly.

FIG. 51 is an enlarged and partial front elevational view of the receiver, compression insert and retainer (shown in a compressed position) of FIG. 32 with portions of the receiver and compression insert broken away to show the detail thereof and shown in a stage of assembly subsequent to that shown in FIG. 50.

FIG. 54 is a reduced and partial front elevational view of the implanted shank of FIG. 53 and further showing an early stage of assembly of the shank with the pre-assembled receiver, compression insert and retainer of FIG. 52, also with portions broken away to show the detail thereof.

FIG. 55 is a partial front elevational view of the shank, receiver, compression insert and retainer of FIG. 54, with portions broken away to show the detail thereof and shown in a stage of assembly subsequent to that shown in FIG. 54.

FIG. 56 is an enlarged and partial front elevational view with portions broken away, similar to FIG. 55, showing a subsequent stage of assembly.

FIG. 60 is an exploded perspective view of a another embodiment of a polyaxial bone screw assembly according to the present invention including a shank, a receiver, a retainer in the form of a spring ring and a compression insert.

FIG. 61 is an enlarged perspective view of the receiver of FIG. 60.

FIG. 62 is a reduced side elevational view of the receiver of FIG. 61 with portions broken away to show the detail thereof.

FIG. 69 is an enlarged front elevational view of the receiver of FIG. 60 with portions broken away to show the detail thereof shown in a stage of assembly with the insert subsequent to that shown in FIG. 68, the insert in enlarged side elevational view with portions broken away to show the detail thereof.

FIG. 70 is an enlarged front elevational view of the receiver of FIG. 60 with portions broken away to show the detail thereof shown in a stage of assembly with the insert subsequent to that shown in FIG. 69, the insert in enlarged side elevational view with portions broken away to show the detail thereof.

FIG. 71 is an enlarged front elevational view of the receiver of FIG. 60 with portions broken away to show the detail thereof shown in a stage of assembly with the insert subsequent to that shown in FIG. 70, the insert in enlarged front elevational view.

FIG. 76 is an enlarged and partial front elevational view of the assembly shown in FIG. 74 with different portions broken away to show the detail thereof.

FIG. 77 is an enlarged and partial front elevational view of the assembly shown in FIG. 75 with different portions broken away to show the detail thereof.

FIG. 78 is a partial perspective view of the assembly of FIG. 75 with portions broken away to show the detail thereof.

FIG. 79 is a partial front elevational view with portions broken away, similar to FIG. 75 but showing the closure top and rod in a loosened position while the insert, shank, retainer and receiver remain in the locked position shown in FIG. 75.

FIG. 80 is an enlarged and partial side elevational view of the assembly of FIG. 60 with portions broken away to show the detail thereof and the shank shown at an angle with respect to the receiver.

FIG. 84 is a reduced and partial side elevational view of two bone screw assemblies according to FIG. 60, with portions broken away to show the detail thereof and shown with a multi-piece longitudinal connecting member, also shown with portions broken away, the connecting member having an inner cord and outer sleeves and spacers, also shown attached to a solid rod.

FIG. 85 is an enlarged front elevational view of an alternative closure top also shown in FIG. 84.

FIG. 86 is a front elevational view of the closure top of FIG. 85 with portions broken away to show the detail thereof.

FIG. 87 is an enlarged front elevational view of another alternative closure top (not shown in FIG. 84).

FIG. 88 is a front elevational view of the closure top of FIG. 87 with portions broken away to show the detail thereof.

FIG. 91 is an exploded perspective view of another embodiment of a polyaxial bone screw assembly according to the present invention including a shank, a receiver, a retainer in the form of a spring ring and a compression insert and shown with a closure top and a deformable rod.

FIG. 92 is an enlarged perspective view of the receiver of FIG. 91.

FIG. 93 is a side elevational view of the receiver of FIG. 92.

FIG. 94 is a cross-sectional view taken along the line 94-94 of FIG. 93.

FIG. 95 is a cross-sectional view taken along the line 95-95 of FIG. 94.

FIG. 96 is an enlarged perspective view of the insert of FIG. 91.

FIG. 97 is a second perspective view of the insert of FIG. 96.

FIG. 106 is an enlarged and partial perspective view of the receiver, insert and retainer of FIG. 91 with portions broken away to show the detail thereof.

FIG. 107 is an enlarged and partial perspective view of the receiver, insert and retainer and shown assembled with the shank of FIG. 91 and with portions broken away to show the detail thereof.

FIG. 118 is an enlarged perspective view of the lower retainer of FIG. 115.

FIG. 119 is another perspective view of the retainer of FIG. 118.

FIG. 120 is a top plan view of the retainer of FIG. 118

FIG. 121 is a bottom plan view of the retainer of FIG. 118.

FIG. 122 is a cross-sectional view taken along the line 122-122 of FIG. 120.

FIG. 123 is an enlarged perspective view of the friction fit crown insert of FIG. 115.

FIG. 124 is a reduced front elevational view of the insert of FIG. 123.

FIG. 125 is a reduced bottom plan view of the insert of FIG. 123.

FIG. 126 is a reduced top plan view of the insert of FIG. 123.

FIG. 127 is a cross-sectional view taken along the line 127-127 of FIG. 126.

FIG. 128 is an enlarged perspective view of the receiver of FIG. 115.

FIG. 129 is a second perspective view of the receiver of FIG. 128.

FIG. 130 is a top plan view of the receiver of FIG. 128.

FIG. 131 is a bottom plan view of the receiver of FIG. 128.

Figure 130:
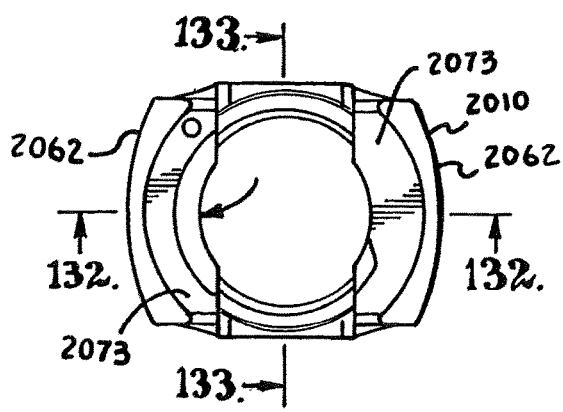
Figure 131:
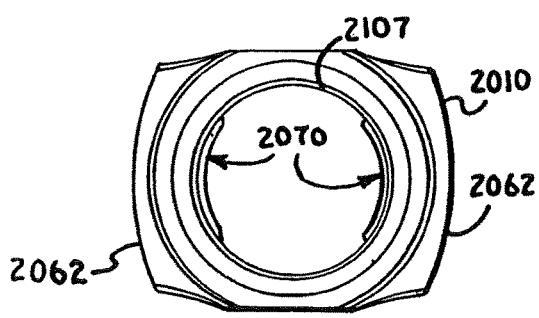

FIG. 132 is an enlarged cross-sectional view taken along the line 132-132 of FIG. 130.

FIG. 133 is an enlarged cross-sectional view taken along the line 133-133 of FIG. 130.

Figure 115:
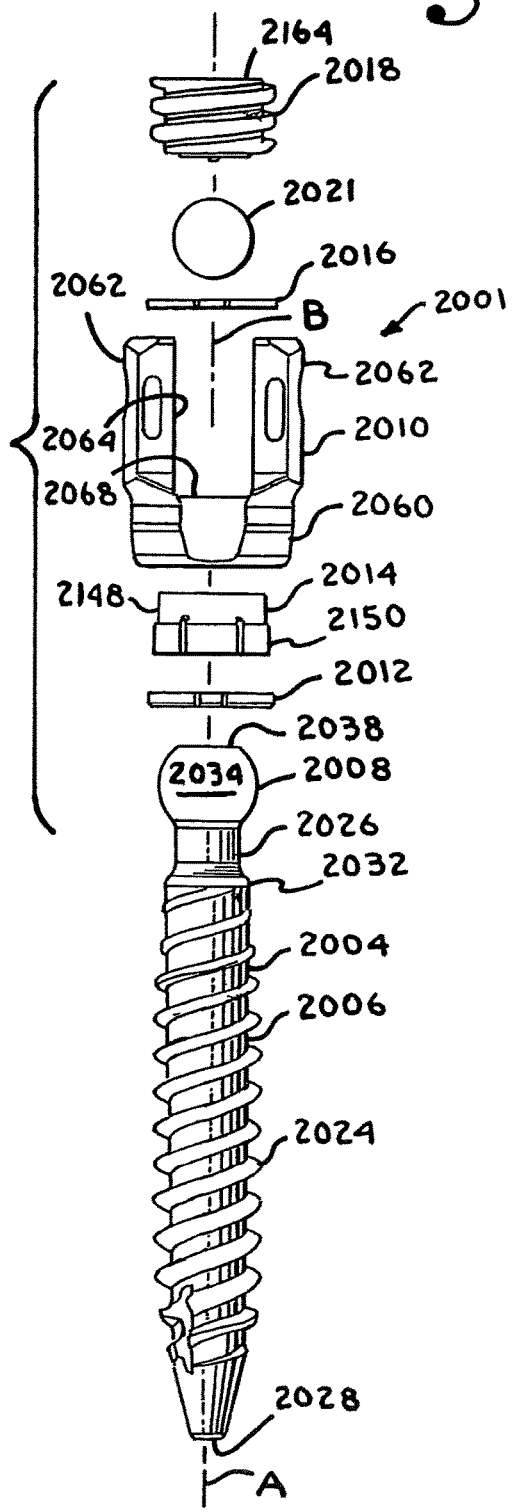
FIG. 115 is an exploded perspective view of another embodiment of a polyaxial bone screw assembly according to the present invention including a shank, a receiver, upper and lower open retainer rings and a friction fit crown compression insert, further shown with a portion of a longitudinal connecting member in the form of a rod and a closure top.
Figure 134:
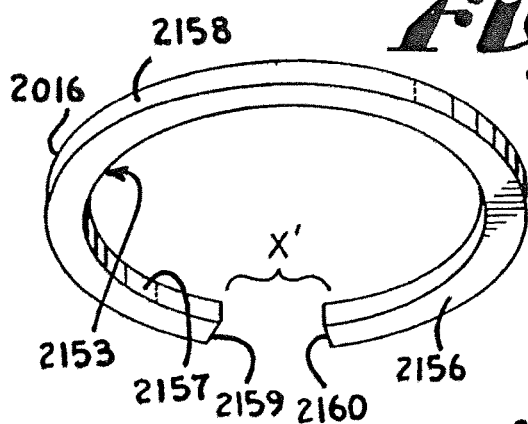

FIG. 134 is an enlarged perspective view of the upper retainer of FIG. 115.

Figure 135:
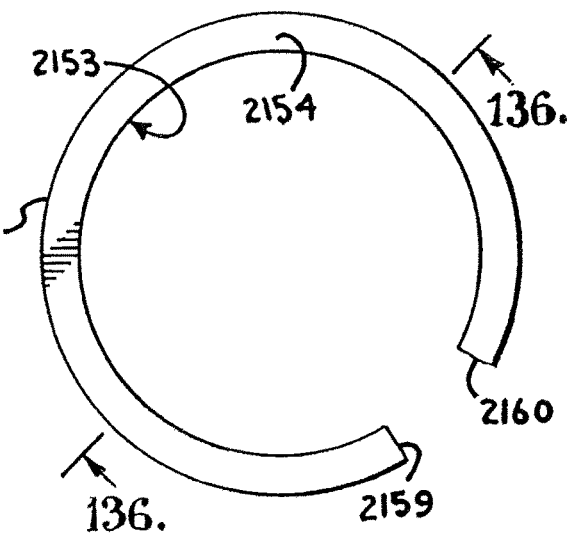

FIG. 135 is an enlarged top plan view of the retainer of FIG. 134.

Figure 136:
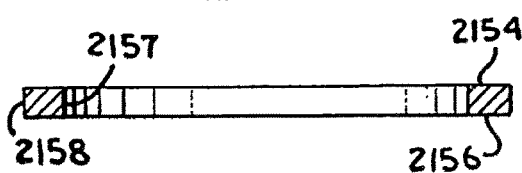

FIG. 136 is a cross-sectional view taken along the line 136-136 of FIG. 135.

Figure 137:
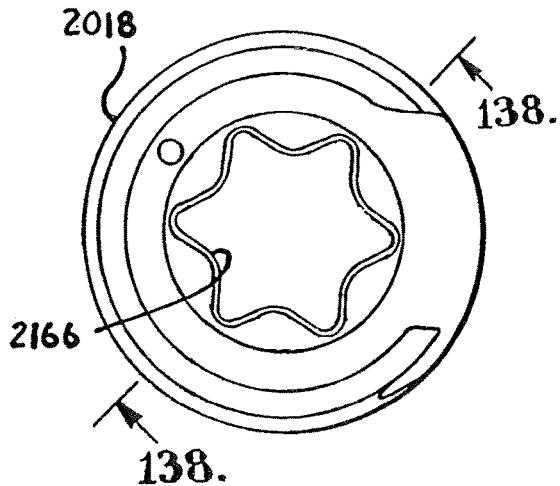

FIG. 137 is an enlarged top plan view of the closure top of FIG. 115.

Figure 138:
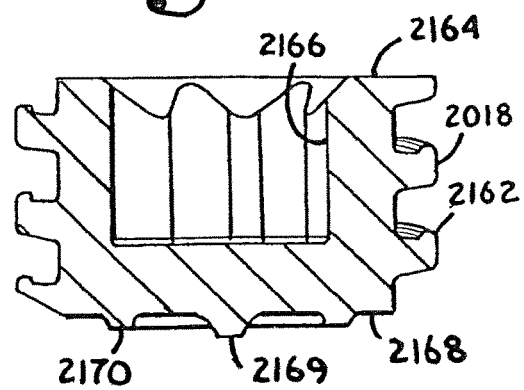

FIG. 138 is a cross-sectional view taken along the line 138-138 of FIG. 137.

FIG. 139 is an enlarged front elevational view of the receiver and upper retainer of FIG. 115 with portions of the receiver broken away to show the detail thereof, the upper retainer being shown in a compressed insertion stage of assembly.

FIG. 140 is a front elevational view with portions broken away, similar to FIG. 139, showing the upper retainer in a neutral position, assembled within the receiver.

FIG. 141 is a front elevational view with portions broken away, similar to FIG. 140 and further showing the friction fit compression insert of FIG. 115 in an initial stage of assembly with the receiver.

FIG. 142 is a front elevational view with portions broken away, similar to FIG. 141, showing the compression insert uploaded into the receiver and in engagement with the upper retainer, the upper retainer in an expanded position.

FIG. 143 is a front elevational view with portions broken away, similar to FIG. 142 and further showing the lower retainer of FIG. 115 in front elevation and in a compressed state, the lower retainer being shown in a stage of uploading into the receiver.

FIG. 144 is a front elevational view with portions broken away, similar to FIG. 143 showing the lower retainer within the receiver and in a neutral non-compressed state.

FIG. 145 is a front elevational view with portions broken away, similar to FIG. 144 and further showing a shank of FIG. 115 in partial front elevation.

FIG. 146 is a partial front elevational view with portions broken away, similar to FIG. 145 showing the shank in a stage of assembly with the lower retainer ring, the lower retainer ring being pushed up into engagement with the compression insert.

FIG. 147 is a partial front elevational view with portions broken away, similar to FIG. 146, showing the lower retainer in an expanded state about an upper portion of the shank, the shank upper portion in a stage of assembly with the compression insert.

FIG. 148 is a partial front elevational view with portions broken away, similar to FIG. 147, the shank upper portion in frictional engagement with the compression insert and the lower retainer in a substantially neutral state.

FIG. 149 is a partial front elevational view with portions broken away, similar to FIG. 148, the shank upper portion and attached compression insert being in a downward, fully assembled position, the upper retainer being in a substantially neutral state.

FIG. 150 is a reduced partial front elevational view of the assembly of FIG. 149, shown with the shank pivoted at an angle with respect to the receiver.

FIG. 151 is a front elevational view of the assembly of FIG. 150, shown in a vertebra and in a locked position with the rod portion and closure top of FIG. 115.

FIG. 152 is an enlarged and partial front elevational view of the assembly of FIG. 151 with portions broken away to show the detail thereof.

Figure 153:
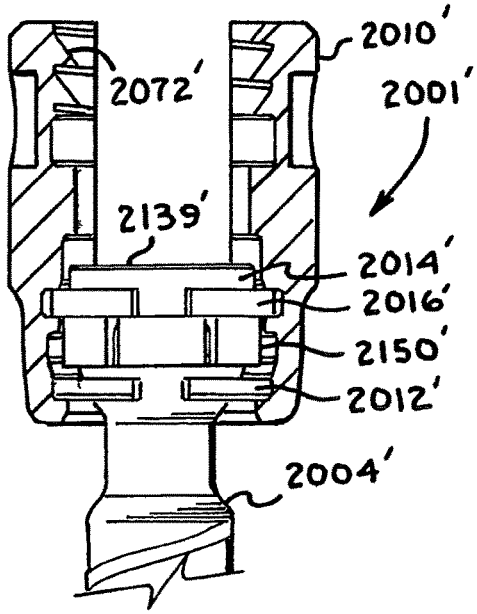

FIG. 153 is a partial front elevational view of an alternative embodiment of a bone screw assembly, substantially similar to the bone screw assembly shown in FIG. 115, shown with portions broken away to show the detail thereof.

Figure 154:
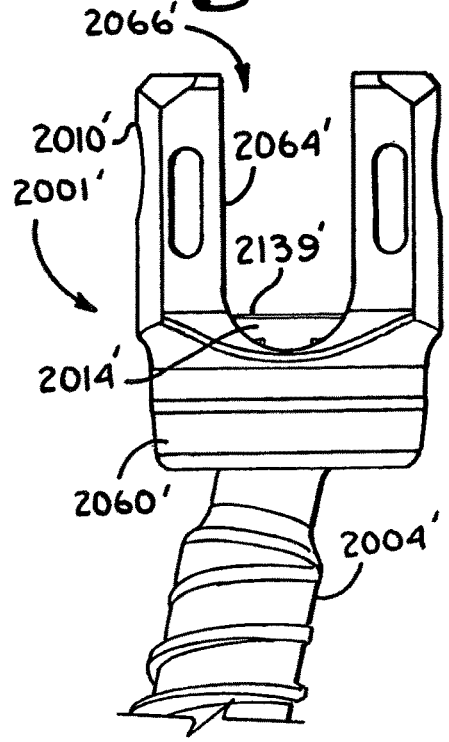

FIG. 154 is another partial front elevational view of the bone screw assembly of FIG. 153, shown with the shank disposed at an angle with respect to the receiver.

Figure 155:
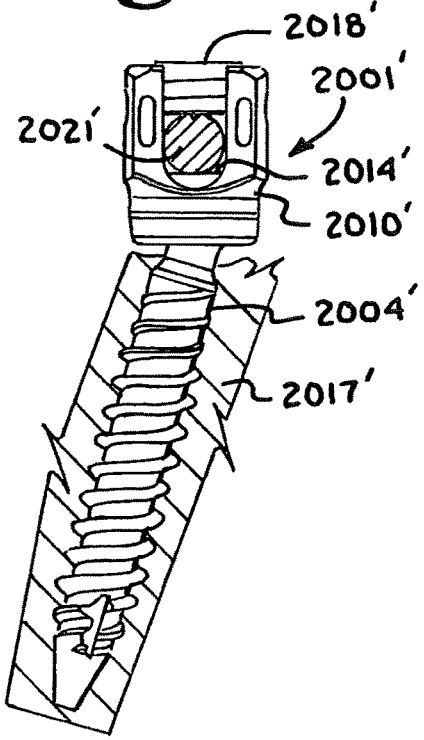

FIG. 155 is a reduced front elevational view, similar to FIG. 154, showing the bone screw assembly with a rod and closure top.

Figure 156:
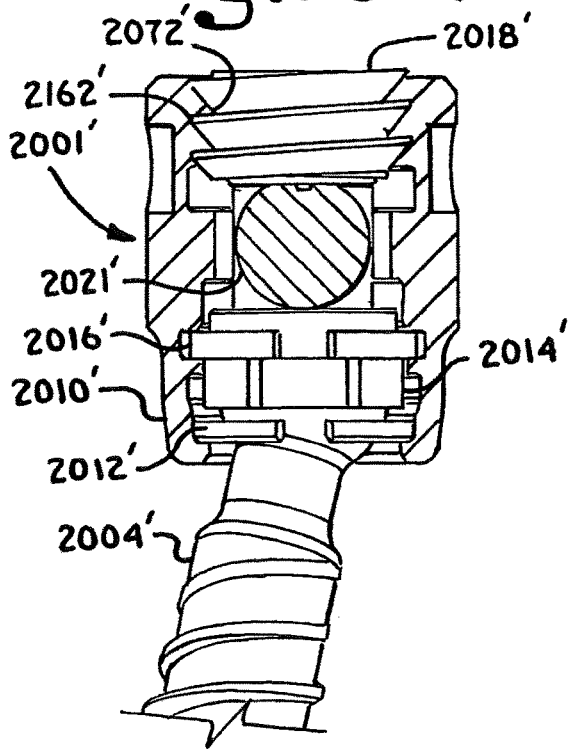

FIG. 156 is an enlarged front elevational view of the assembly of FIG. 155 with portions broken away to show the detail thereof.

FIG. 157 is an exploded perspective view of another polyaxial bone screw assembly according to the present invention including a shank, a receiver, a retainer in the form of an open ring and a friction fit crown compression insert, further shown with a portion of a longitudinal connecting member in the form of a rod and a closure top.

FIG. 158 is an enlarged top plan view of the shank of FIG. 157.

FIG. 159 is reduced cross-sectional view taken along the line 159-159 of FIG. 158.

Figure 160:
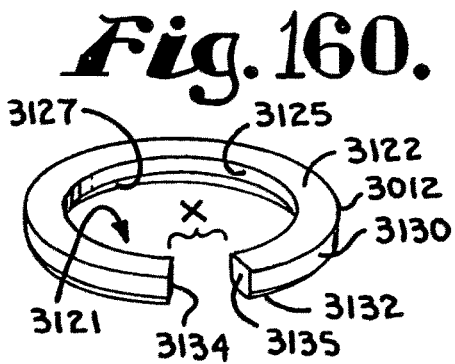

FIG. 160 is an enlarged perspective view of the retainer of FIG. 157.

Figure 161:
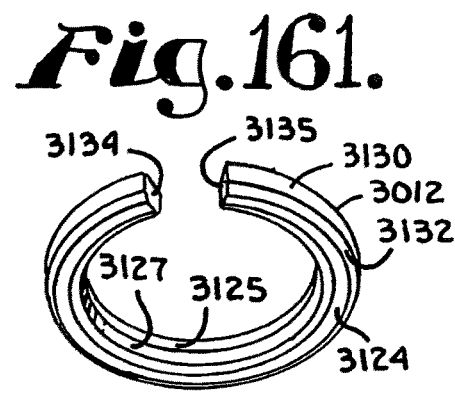

FIG. 161 is another perspective view of the retainer of FIG. 160.

Figure 162:
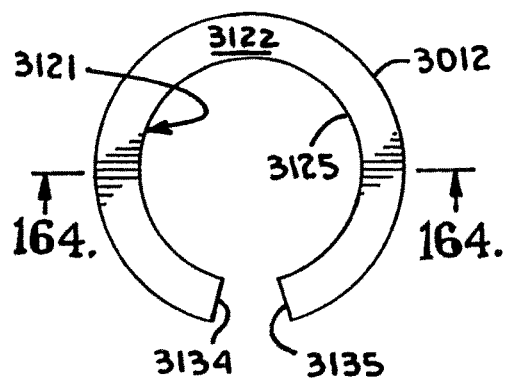

FIG. 162 is a top plan view of the retainer of FIG. 160.

Figure 163:
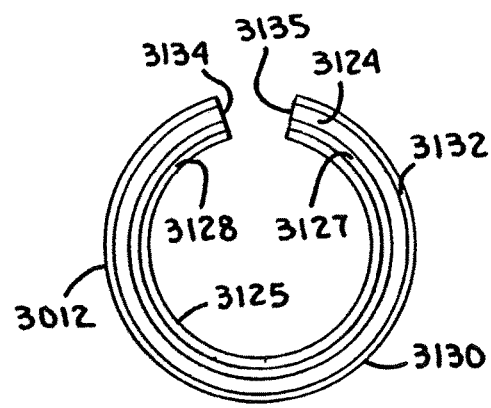

FIG. 163 is a bottom plan view of the retainer of FIG. 160.

Figure 164:
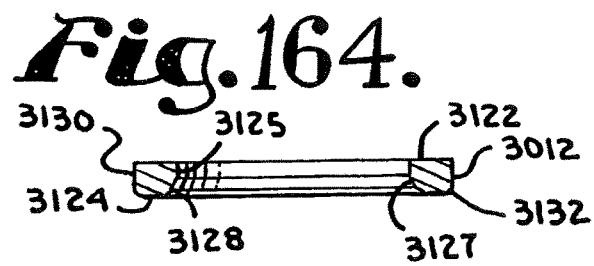

FIG. 164 is a cross-sectional view taken along the line 164-164 of FIG. 162.

Figure 165:
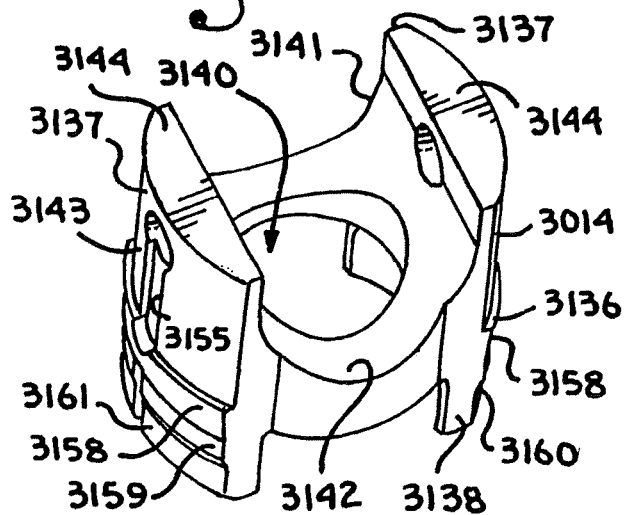

FIG. 165 is an enlarged perspective view of the friction fit crown insert of FIG. 157.

Figure 166:
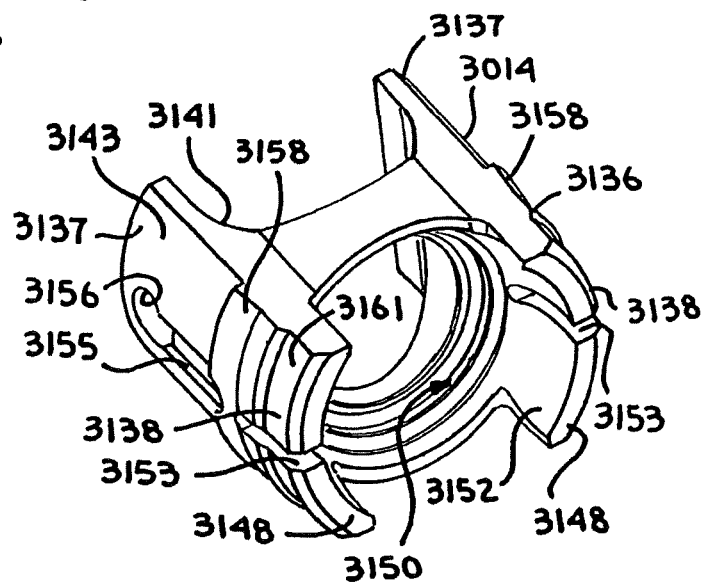

FIG. 166 is another perspective view of the insert of FIG. 165.

Figure 167:
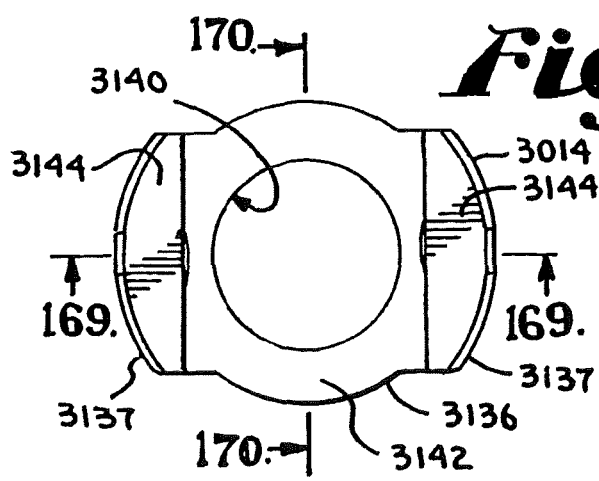

FIG. 167 is a top plan view of the insert of FIG. 165.

Figure 168:
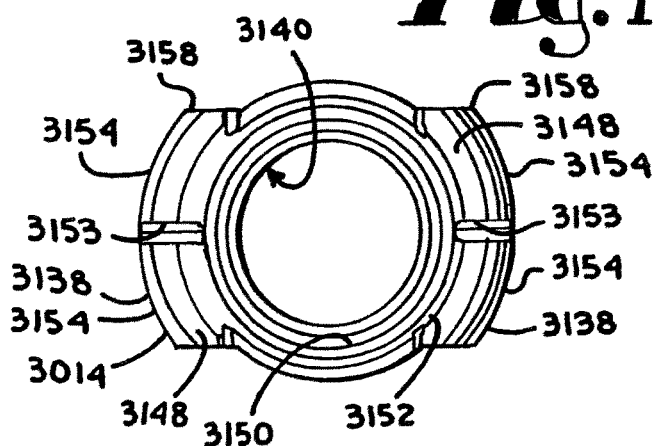

FIG. 168 is a bottom plan view of the insert of FIG. 165.

Figure 169:
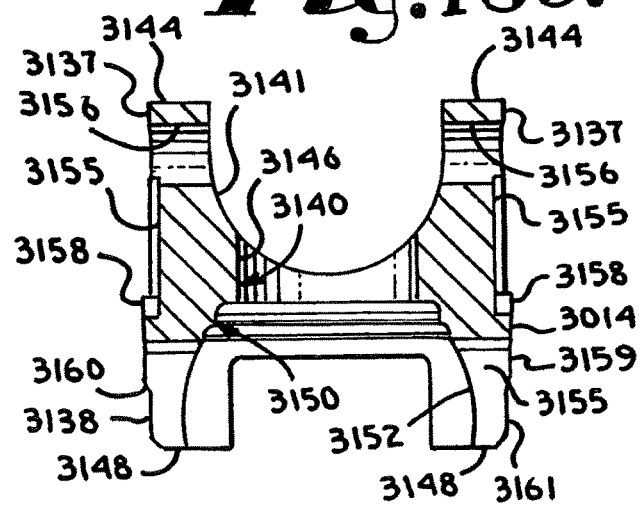

FIG. 169 is a cross-sectional view taken along the line 169-169 of FIG. 167.

Figure 170:
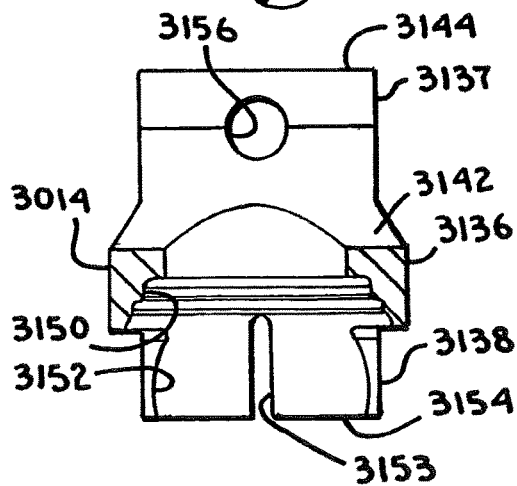

FIG. 170 is a cross-sectional view taken along the line 170-170 of FIG. 167.

Figure 171:
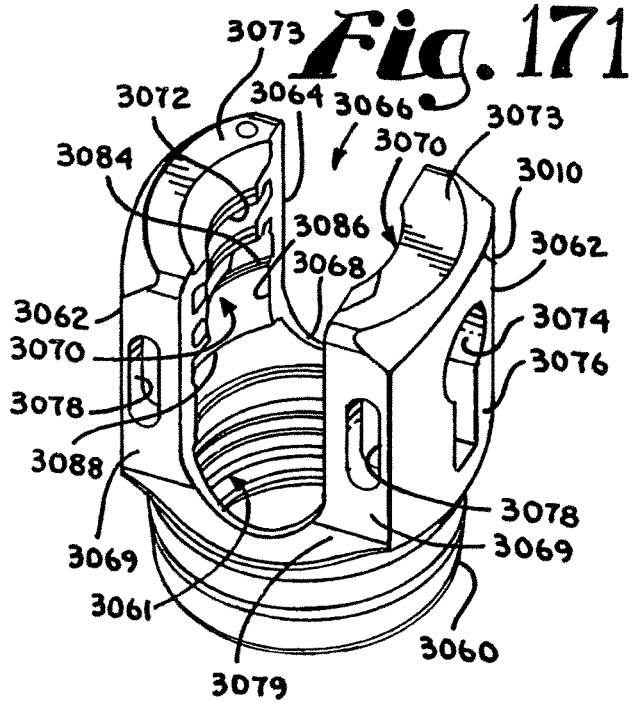

FIG. 171 is an enlarged perspective view of the receiver of FIG. 157.

Figure 172:
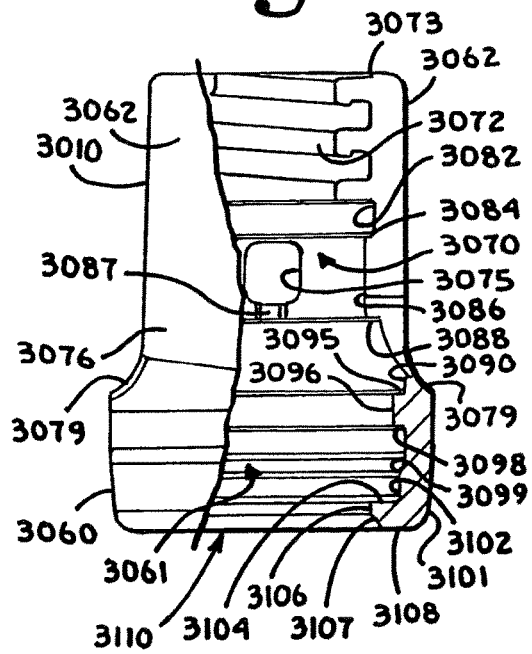

FIG. 172 is a side elevational view of the receiver of FIG. 171 with portions broken away to show the detail thereof.

Figure 173:
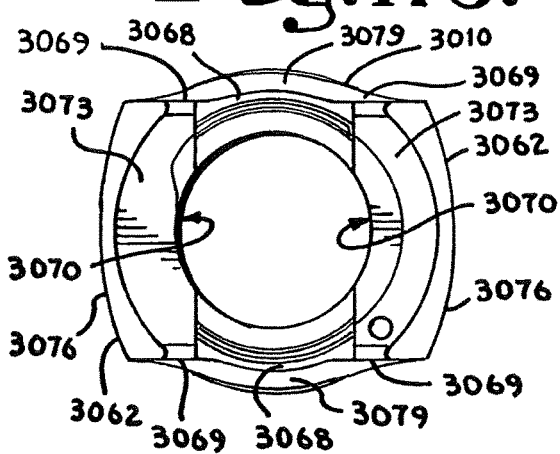

FIG. 173 is a top plan view of the receiver of FIG. 171.

Figure 174:
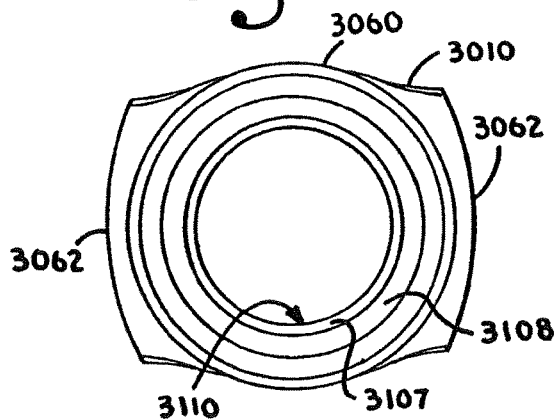

FIG. 174 is a bottom plan view of the receiver of FIG. 171.

FIG. 175 is an enlarged side elevational view of the insert of FIG. 157 and a front elevational view of the receiver of FIG. 157 with portions of the receiver broken away to show the detail thereof, the insert being shown downloaded into the receiver in an insertion stage of assembly.

FIG. 176 is a reduced front elevational view of the receiver, with portions broken away, similar to FIG. 175, showing the insert of FIG. 175 also in reduced front elevational view, the insert having been lowered into the receiver and rotated there-within during an assembly stage subsequent to that shown in FIG. 175.

FIG. 177 is a front elevational view with portions broken away, similar to FIG. 176 and further showing the retainer of FIG. 157 in front elevation and in a compressed state, the retainer being shown in a stage of uploading into the receiver.

FIG. 178 is a front elevational view with portions broken away, similar to FIG. 177 showing the retainer within the receiver and in a neutral non-compressed state and further showing a shank of FIG. 157 in partial front elevation being uploaded into the receiver.

FIG. 179 is a reduced front elevational view similar to FIG. 178 showing an alternative assembly stage in which the shank of FIG. 157 is first implanted in a vertebra, followed by assembly with the receiver, retainer and insert.

FIG. 180 is a partial front elevational view with portions broken away, similar to FIG. 178 showing the shank in a stage of assembly with the retainer, the retainer being pushed up into engagement with the crown insert.

FIG. 181 is a partial front elevational view with portions broken away, similar to FIG. 180, showing the retainer in an expanded state about an upper portion of the shank, the shank upper portion in a stage of assembly with the insert.

FIG. 182 is a partial front elevational view with portions broken away, similar to FIG. 181, the shank upper portion in frictional engagement with the insert and the retainer in a substantially neutral state.

FIG. 183 is a partial front elevational view with portions broken away, similar to FIG. 182, the shank upper portion with attached insert being shown pulled down slightly from the position shown in FIG. 182, the insert being placed into frictional engagement with the receiver.

FIG. 184 is a partial front elevational view with portions broken away, similar to FIG. 183, the shank upper portion and attached insert being in a downward, fully assembled position, the insert being further wedged against inner surfaces of the receiver.

FIG. 185 is a partial front elevational view of the assembly of FIG. 184 with portions broken away to show the detail thereof and further shown in a locked position with a rod and closure top of FIG. 157.

FIG. 186 is a partial front elevational view with portions broken away, similar to FIG. 185 showing the assembly remaining in the locked position of FIG. 185 when the rod and closure top are removed.

FIG. 187 is a reduced and partial front elevational view with portions broken away, similar to FIG. 185, showing a locked assembly wherein the shank is disposed at an angle with respect to the receiver.

Figure 188:
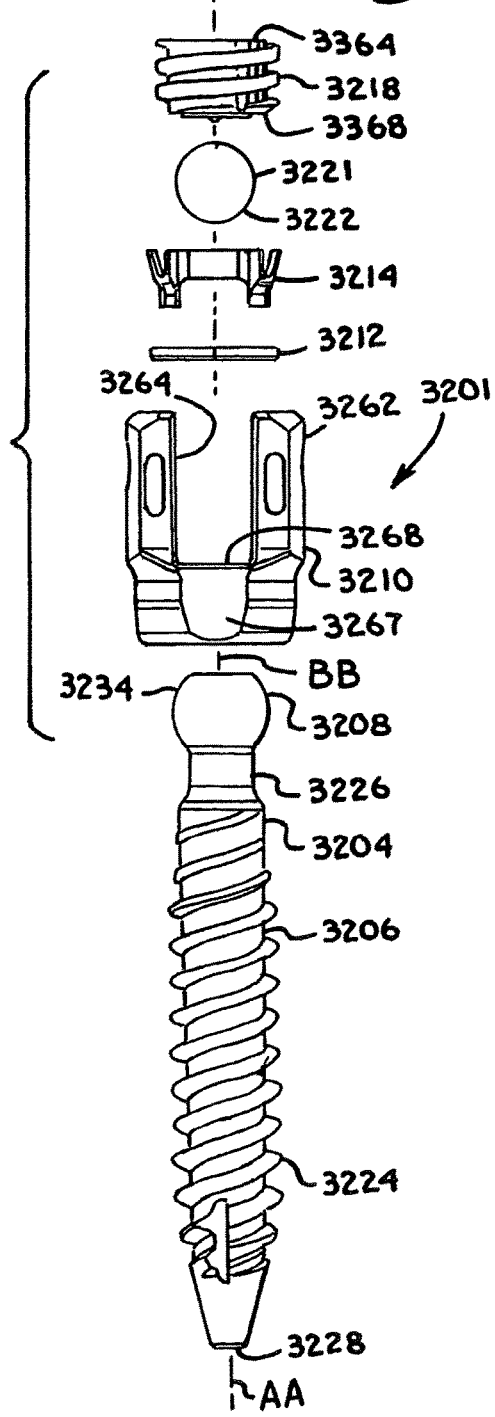

FIG. 188 is an exploded perspective view of another embodiment of a polyaxial bone screw assembly according to the present invention including a shank, a receiver, a retainer in the form of a top-loadable open ring and a friction fit crown compression insert, the assembly further shown with a portion of a longitudinal connecting member in the form of a rod and a closure top.

Figure 189:
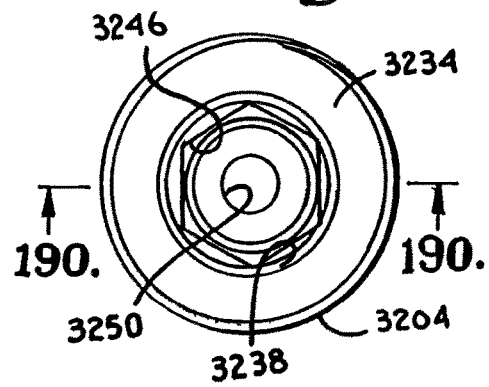

FIG. 189 is an enlarged top plan view of the shank of FIG. 188.

Figure 190:
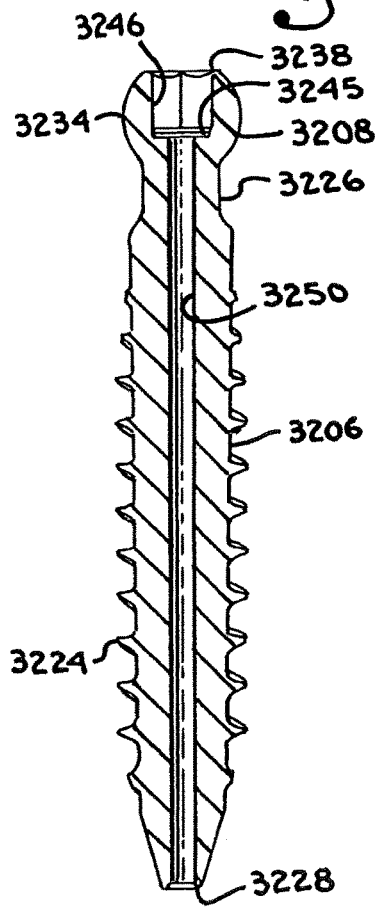

FIG. 190 is reduced cross-sectional view taken along the line 190-190 of FIG. 189.

Figure 191:
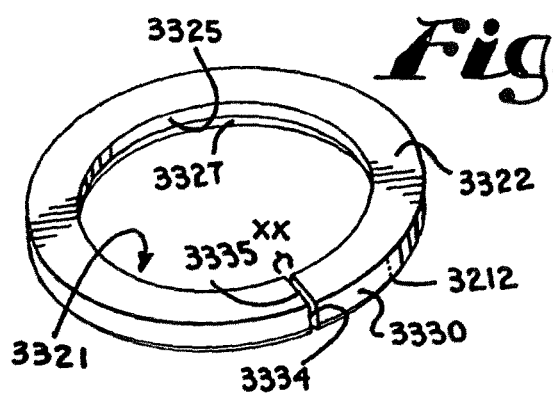

FIG. 191 is an enlarged perspective view of the retainer of FIG. 188.

Figure 192:
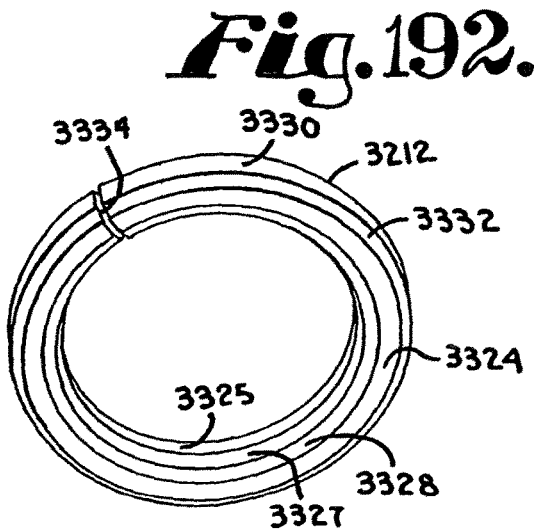

FIG. 192 is another perspective view of the retainer of FIG. 191.

Figure 193:
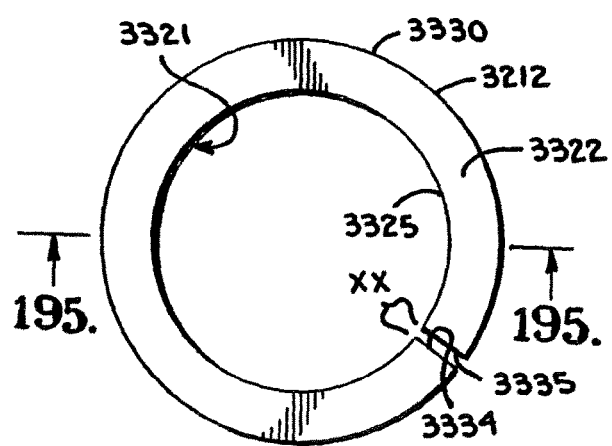

FIG. 193 is a top plan view of the retainer of FIG. 191.

Figure 194:
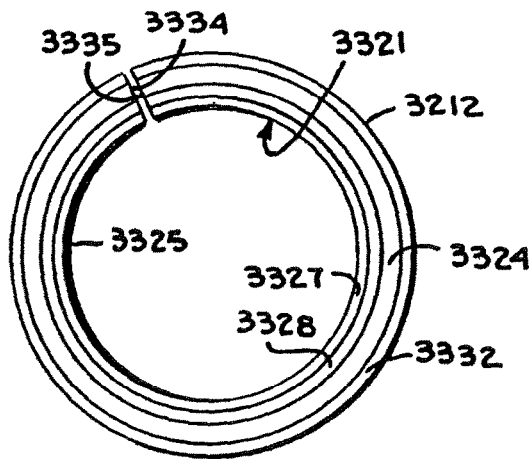

FIG. 194 is a bottom plan view of the retainer of FIG. 191.

Figure 195:
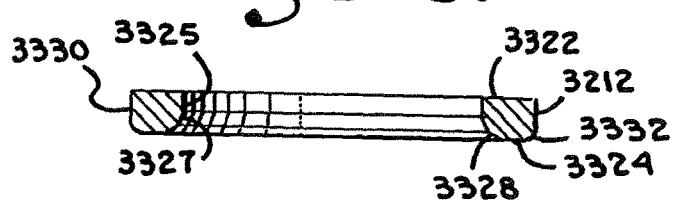

FIG. 195 is a cross-sectional view taken along the line 195-195 of FIG. 193.

FIG. 196 is an enlarged perspective view of the friction fit crown insert of FIG. 188.

FIG. 197 is another perspective view of the insert of FIG. 196.

FIG. 198 is a top plan view of the insert of FIG. 196.

Figure 199:
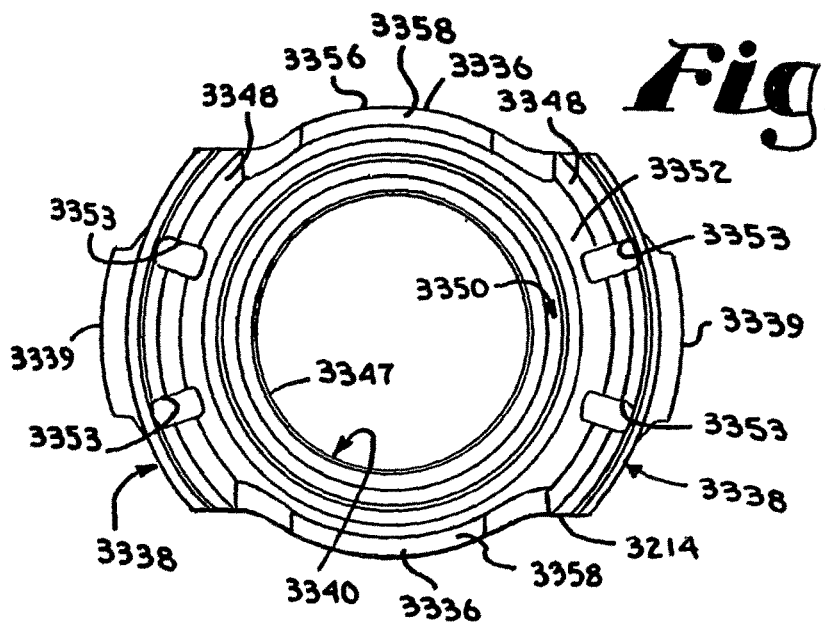

FIG. 199 is a bottom plan view of the insert of FIG. 196.

Figure 200:
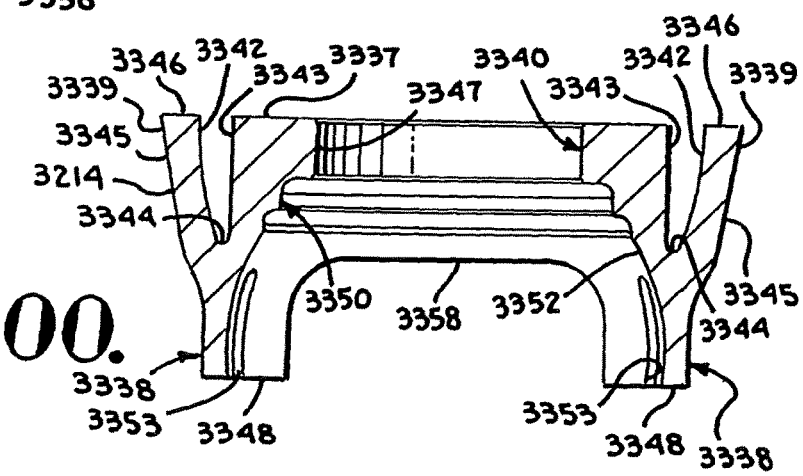

FIG. 200 is a cross-sectional view taken along the line 200-200 of FIG. 198.

Figure 201:
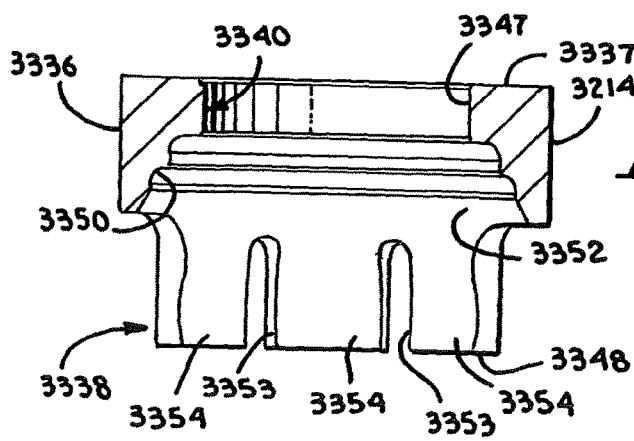

FIG. 201 is a cross-sectional view taken along the line 201-201 of FIG. 198.

FIG. 202 is an enlarged perspective view of the receiver of FIG. 188.

FIG. 203 is an enlarged side elevational view of the receiver of FIG. 202 with portions broken away to show the detail thereof.

FIG. 204 is a top plan view of the receiver of FIG. 202.

FIG. 205 is a bottom plan view of the receiver of FIG. 202.

Figure 206:
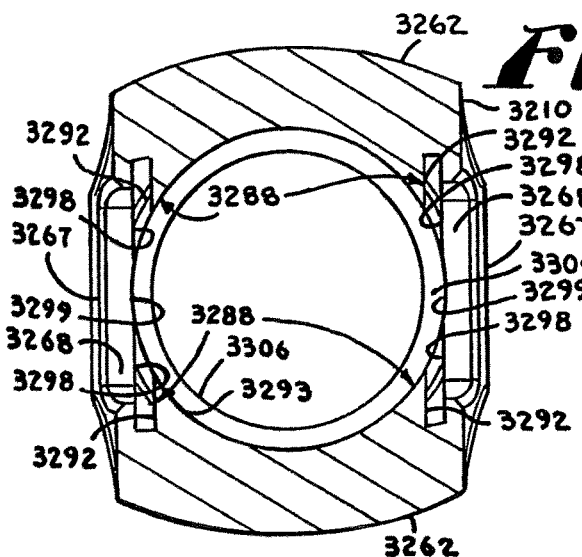

FIG. 206 is an enlarged cross-sectional view taken along the line 206-206 of FIG. 203.

Figure 207:
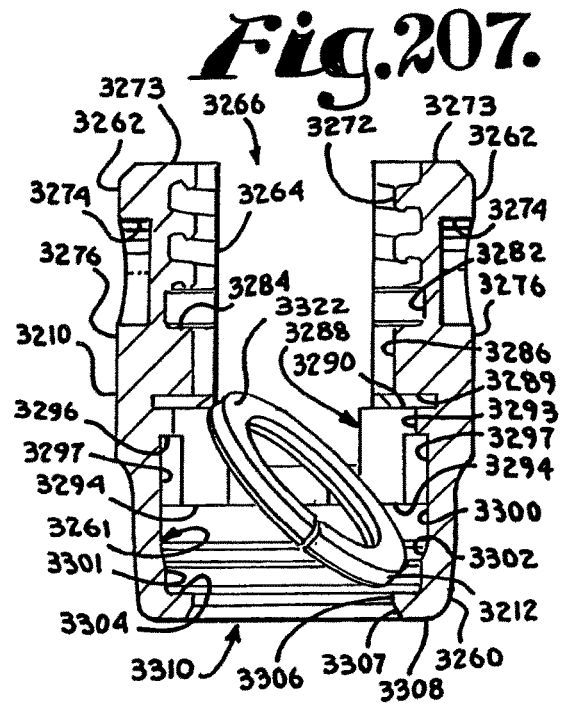

FIG. 207 is an enlarged front elevational view of the receiver of FIG. 188 with portions broken away to show the detail thereof, shown with the retainer of FIG. 188 in perspective view being top loaded into the receiver during an early stage of assembly.

Figure 208:
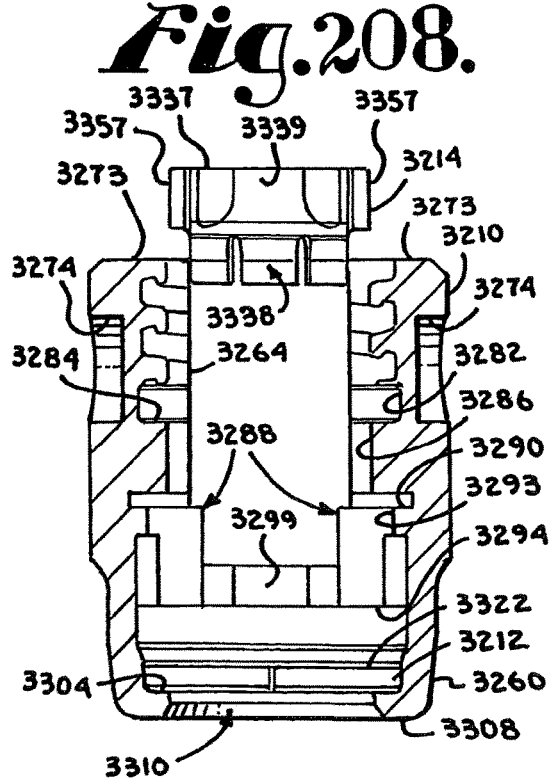

FIG. 208 is an enlarged side elevational view of the insert of FIG. 188 and a front elevational view of the receiver and retainer of FIG. 207 with portions broken away to show the detail thereof, the insert being shown top loaded into the receiver.

Figure 209:
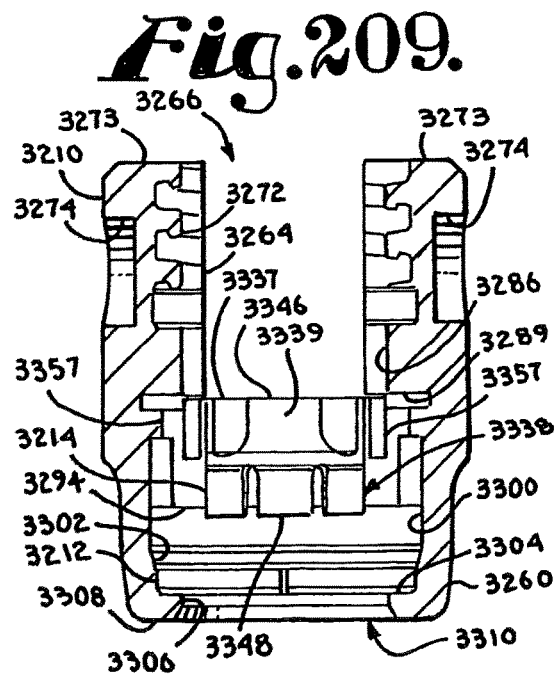

FIG. 209 is a front elevational view of the receiver and retainer, with portions broken away, similar to FIG. 208, showing the insert of FIG. 208 in side elevation lowered into the receiver.

Figure 210:
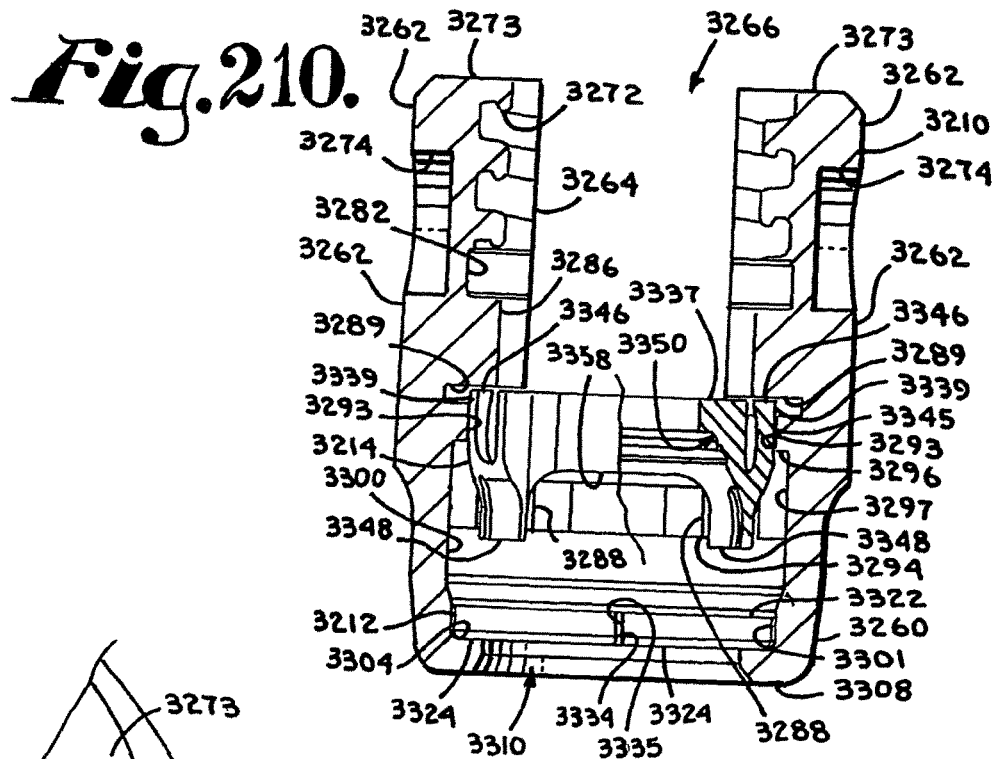

FIG. 210 is an enlarged front elevational view of the receiver, retainer and insert, with portions broken away, similar to FIG. 209, the insert having been rotated into an assembled position within the receiver.

Figure 211:
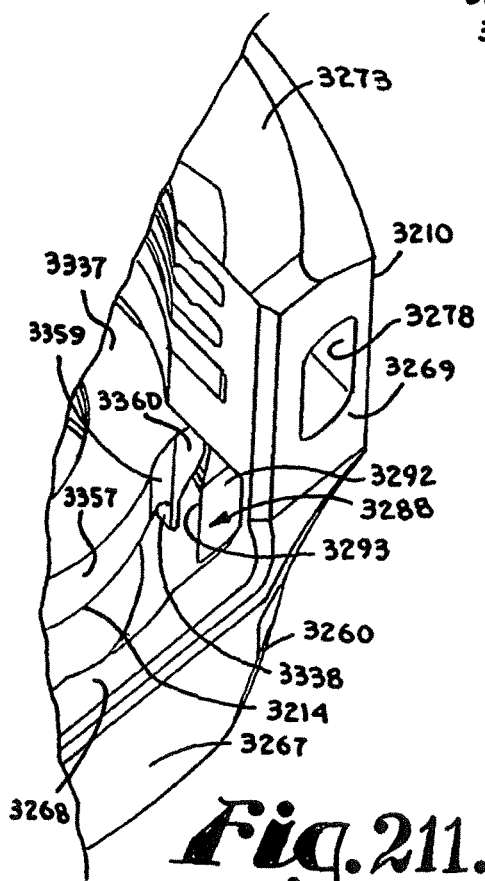

FIG. 211 is an enlarged and partial perspective view of the receiver, retainer and insert of FIG. 210.

Figure 212:
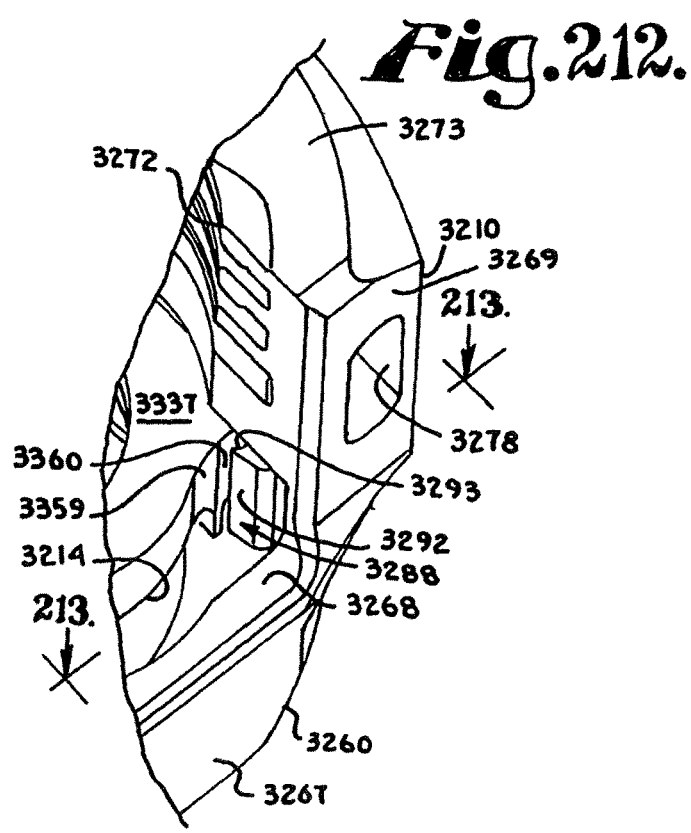

FIG. 212 is a partial perspective view, similar to FIG. 211 showing holding tabs of the receiver bent against the insert to prohibit further rotation thereof.

Figure 213:
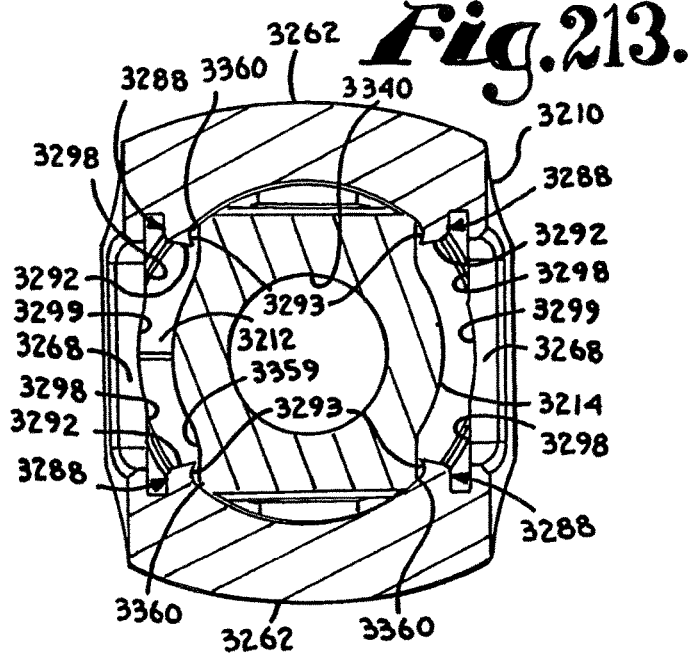

FIG. 213 is a cross-sectional view taken along the line 213-213 of FIG. 212.

Figure 214:
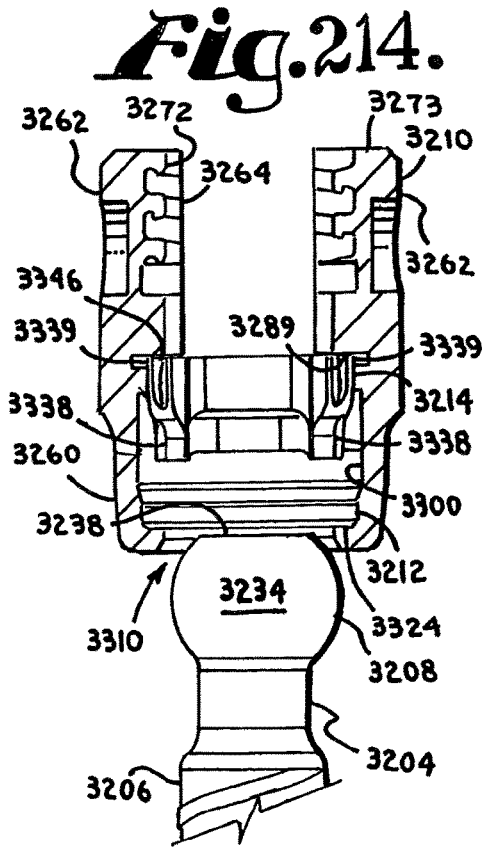

FIG. 214 is a reduced front elevational view with portions broken away, similar to FIG. 210 shown subsequent to the assembly step shown in FIGS. 212 and 213 and further showing the shank of FIG. 188 in partial front elevation being uploaded into the receiver.

Figure 215:
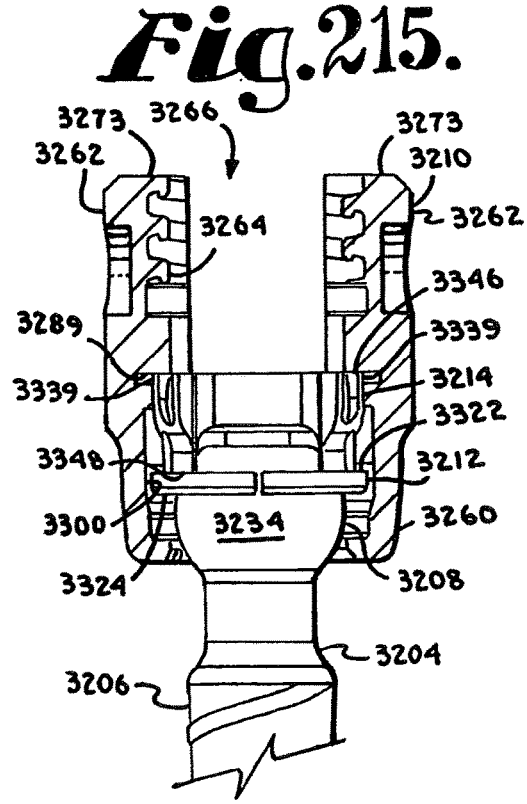

FIG. 215 is a front elevational view with portions broken away, similar to FIG. 214 showing the shank in a stage of assembly with the retainer, the retainer being pushed up into engagement with the crown insert.

Figure 216:
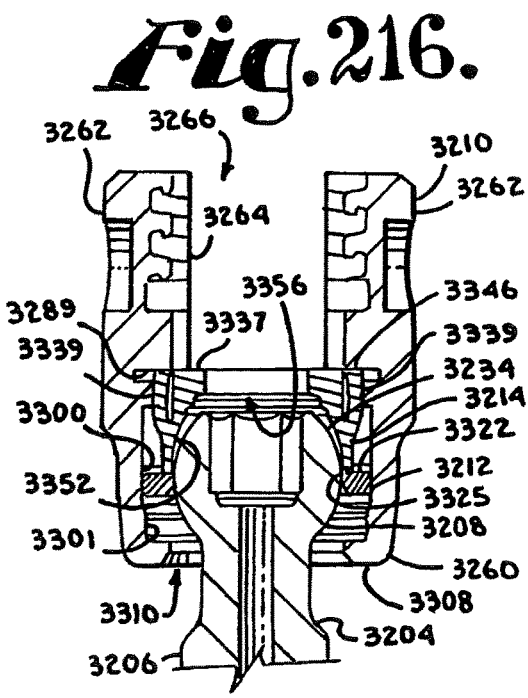

FIG. 216 is a partial front elevational view with portions broken away, similar to FIG. 215, showing the retainer in an expanded state about an upper portion of the shank, the shank upper portion in a stage of assembly with the insert.

FIG. 217 is a partial front elevational view with portions broken away, similar to FIG. 216, the shank upper portion in frictional engagement with the insert and the retainer in a substantially neutral state.

FIG. 218 is a partial front elevational view with portions broken away, similar to FIG. 217, the shank upper portion with attached insert being shown pulled down slightly from the position shown in FIG. 217.

FIG. 219 is a partial front elevational view with portions broken away, similar to FIG. 218, the shank upper portion and attached insert being in a downward, fully assembled position, the insert being allowed to expand under a ledge surface of the receiver.

FIG. 220 is a partial front elevational view of the assembly of FIG. 219 with portions broken away to show the detail thereof and further shown in a locked position with a rod and closure top of FIG. 188.

FIG. 221 is a partial front elevational view with portions broken away, similar to FIG. 220, showing a locked assembly wherein the shank is disposed at an angle with respect to the receiver.

FIG. 222 is an exploded front elevational view with portions broken away of another embodiment of a polyaxial bone screw assembly according to the present invention including a shank, a receiver, a retainer in the form of a top-loadable open ring and a lock and release friction fit crown compression insert, the assembly further shown with a portion of a longitudinal connecting member in the form of a rod and a closure top.

FIG. 223 is an enlarged front elevational view, with portions broken away of the receiver and retainer of FIG. 222 showing stages of assembly of the retainer in phantom and with the insert of FIG. 222 shown in side elevational view prior to insertion and rotation into place within the receiver.

Figure 224:
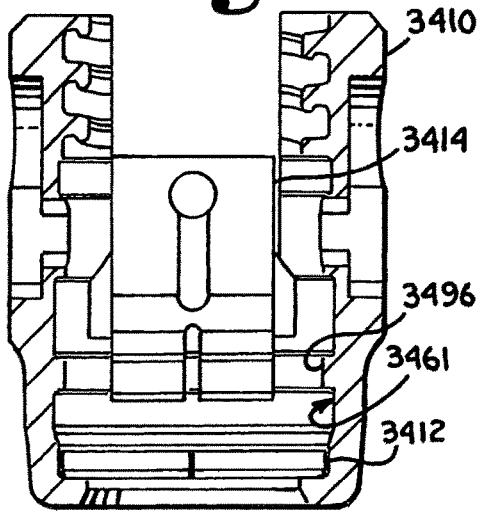

FIG. 224 is a front elevational view of the retainer and receiver of FIG. 223 with portions broken away and a side elevational view of the insert of FIG. 223 in a stage of assembly just prior to rotation within the receiver.

Figure 225:
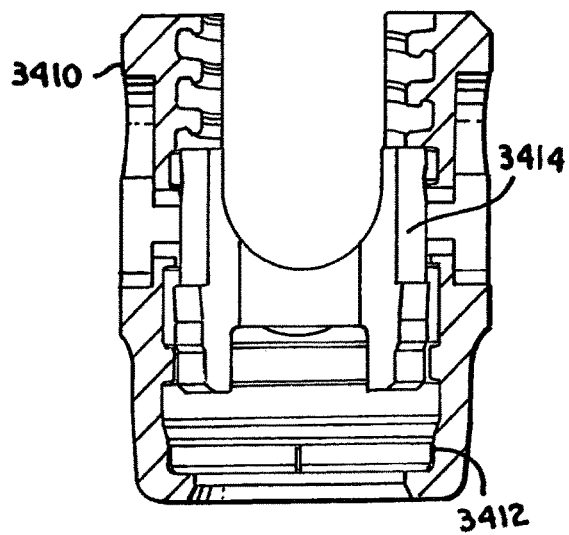

FIG. 225 is a front elevational view with portions broken away, similar to FIG. 224, showing the insert after rotation thereof within the receiver.

Figure 226:
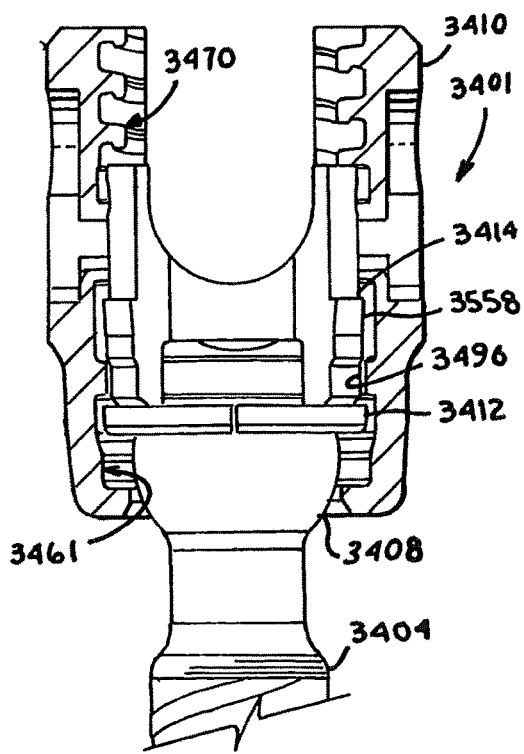

FIG. 226 is a front elevational view with portions broken away, similar to FIG. 225 further showing the shank of FIG. 222 in partial front elevation and in an assembly step with the receiver and retainer.

Figure 227:
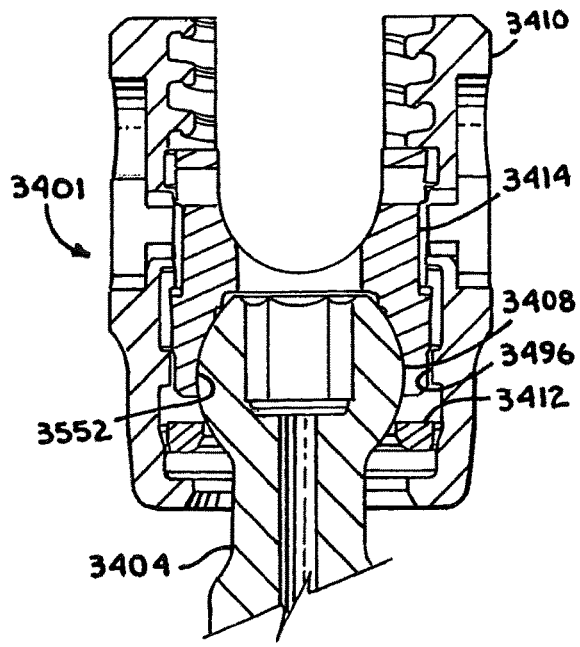

FIG. 227 is a partial front elevational view with portions broken away showing an assembly step subsequent to that shown in FIG. 226.

FIG. 228 is a partial front elevational view with portions broken away showing an assembly step subsequent to that shown in FIG. 227 with the rod and closure of FIG. 222, also in front elevation.

FIG. 229 is a partial front elevational view with portions broken away, similar to FIG. 228, showing the shank being retained and locked in place by the insert when the rod and closure top are removed.

FIG. 230 is a partial front elevational view with portions broken away, similar to FIG. 228, showing the rod and closure top being replaced by an alternative deformable rod and cooperating alternative closure top.

Figure 231:
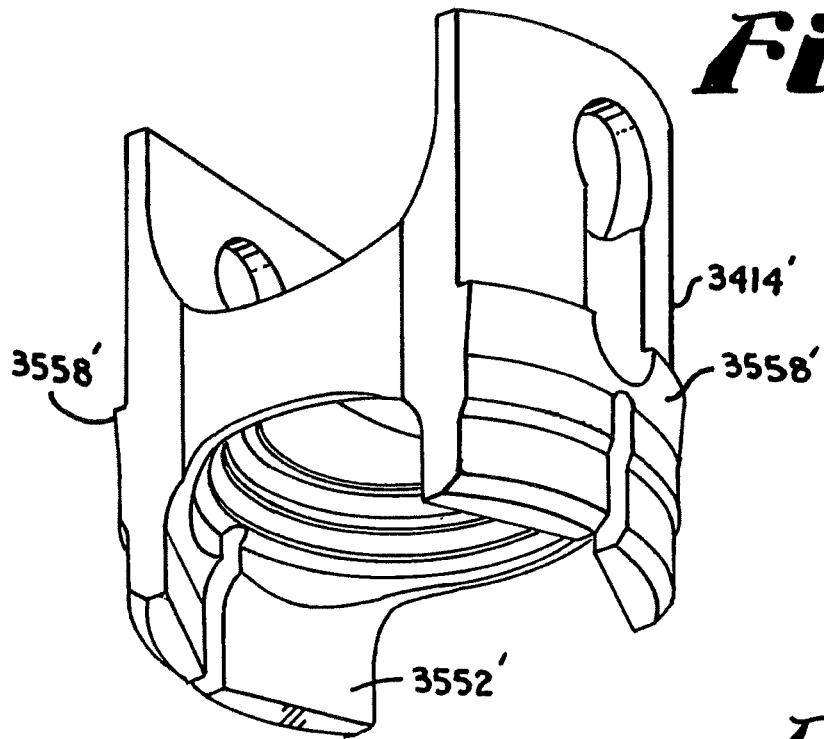

FIG. 231 is an enlarged perspective view of an alternative locking insert for use with the assembly of FIG. 222 in lieu of the insert that is shown in FIG. 222.

Figure 232:
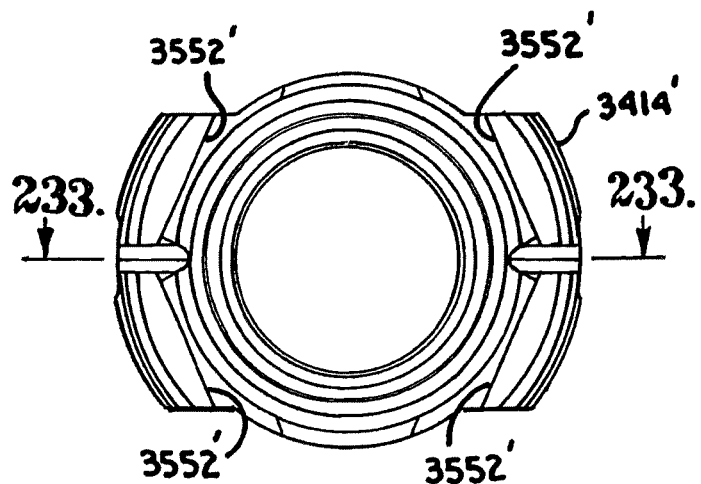

FIG. 232 is a reduced bottom plan view of the insert shown in FIG. 231.

Figure 233:
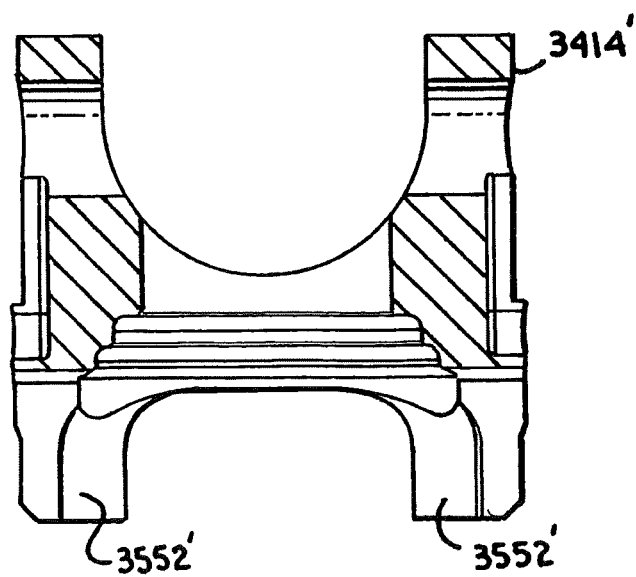

FIG. 233 is an enlarged cross-sectional view taken along the line 233-233 of FIG. 232.

Figure 234:
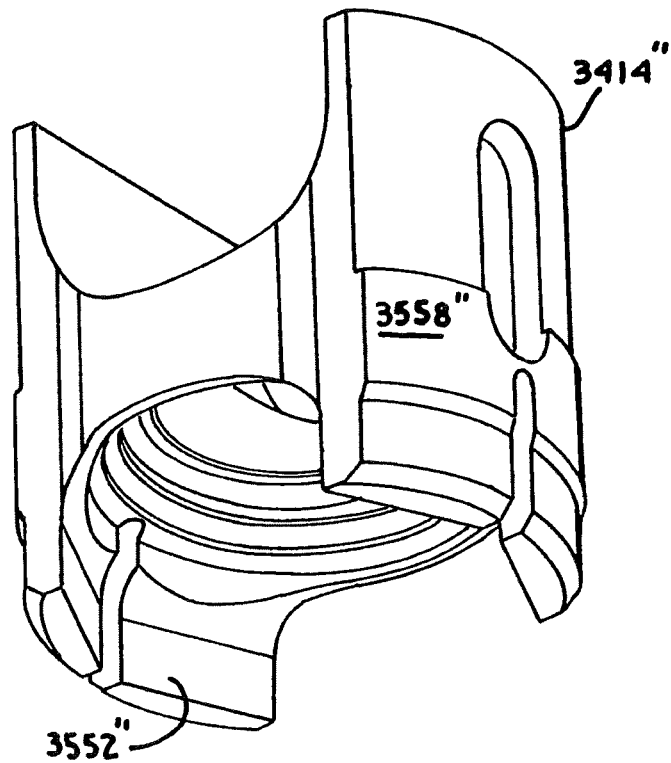

FIG. 234 is an enlarged perspective view of another alternative non-locking insert for use with the assembly of FIG. 222 in lieu of the insert shown in FIG. 222.

Figure 235:
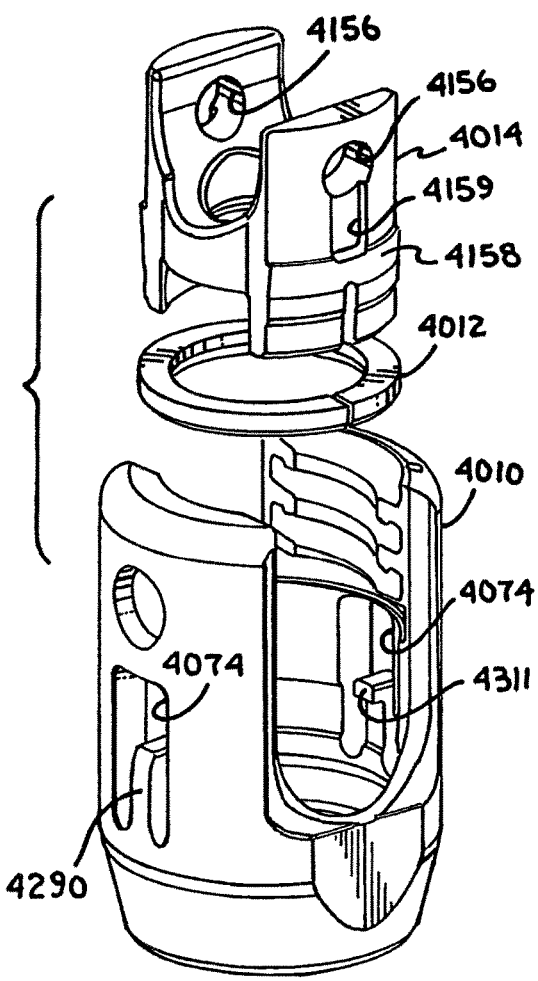

FIG. 235 is an exploded perspective view of a receiver, retainer ring and insert of another embodiment of a polyaxial bone screw assembly according to the invention that is substantially similar to the assembly shown in FIG. 222.

Figure 236:
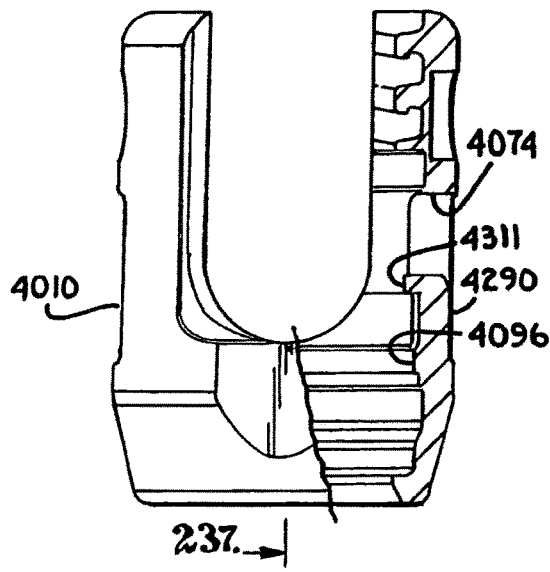

FIG. 236 is a front elevational view of the receiver of FIG. 235 shown with portions broken away to show the detail thereof.

Figure 237:
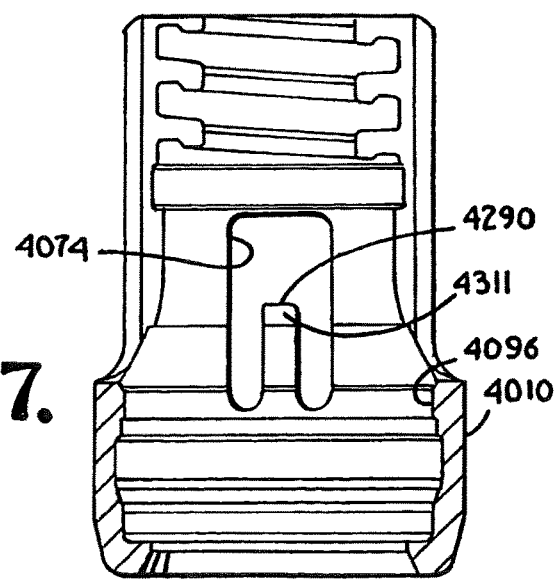

FIG. 237 is a cross-sectional view taken along the line 237-237 of FIG. 236.

FIG. 238 is a front elevational view of the retainer and receiver of FIG. 235 with portions broken away and a side elevational view of the insert of FIG. 235 in a stage of assembly just prior to rotation within the receiver.

FIG. 239 is a front elevational view with portions broken away, similar to FIG. 238, showing the insert being rotated within the receiver.

FIG. 240 is a front elevational view with portions broken away, similar to FIG. 239, shown subsequent to rotation of the insert within the receiver.

FIG. 241 is a partial front elevational view with portions broken away, similar to FIG. 240 and further showing assembly with a shank, a rod and a closure top of FIG. 222.

FIG. 242 is a partial front elevational view with portions broken away, similar to FIG. 241, showing the rod and closure top removed and further showing unlocking of the insert from the receiver with a two-piece tool having an inner insert engaging portion and an outer tubular holding portion.

FIG. 243 is a reduced and partial front elevational view of the two-piece tool of FIG. 242, holding prongs of the inner insert engaging portion being shown in phantom.

FIG. 244 is a partial front elevational view of the inner insert engaging portion of the tool shown in FIG. 242 with portions broken away to show the detail thereof.

FIG. 245 is an exploded front elevational view of another polyaxial bone screw assembly according to the present invention including a shank, a receiver, an open friction fit retainer and a compression insert, further shown with a portion of a longitudinal connecting member in the form of a rod and a closure top.

FIG. 246 is an enlarged top plan view of the shank of FIG. 245.

FIG. 247 is reduced cross-sectional view taken along the line 247-247 of FIG. 246.

Figure 248:
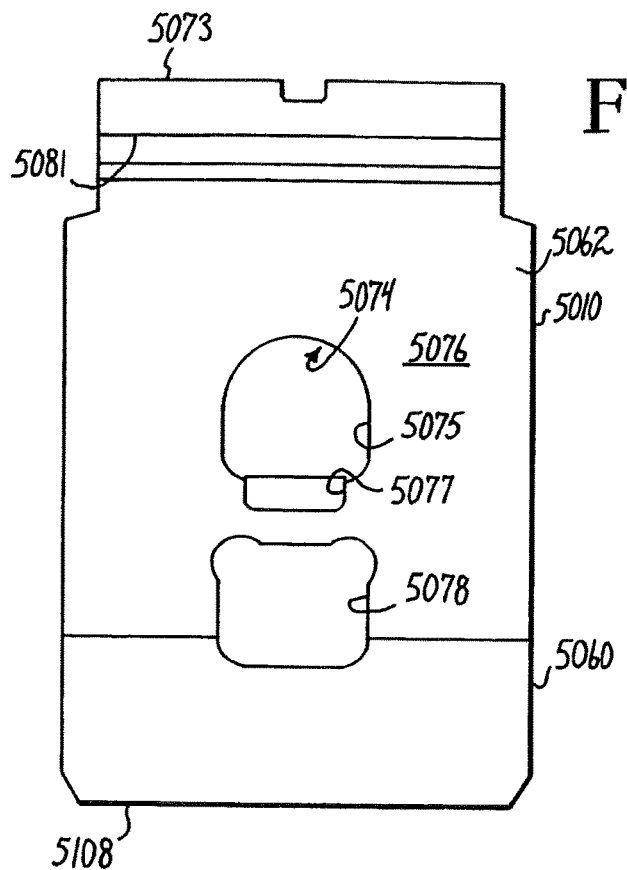

FIG. 248 is an enlarged side elevational view of the receiver of FIG. 245.

Figure 249:
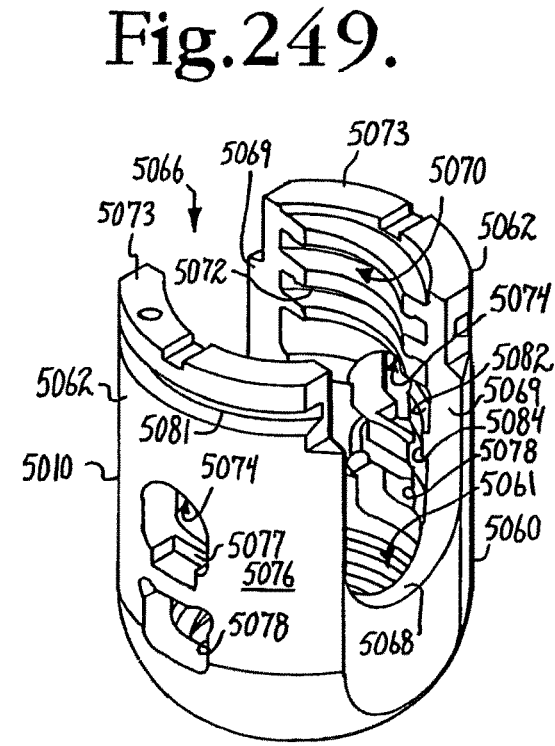

FIG. 249 is a reduced perspective view of the receiver of FIG. 248.

Figure 250:
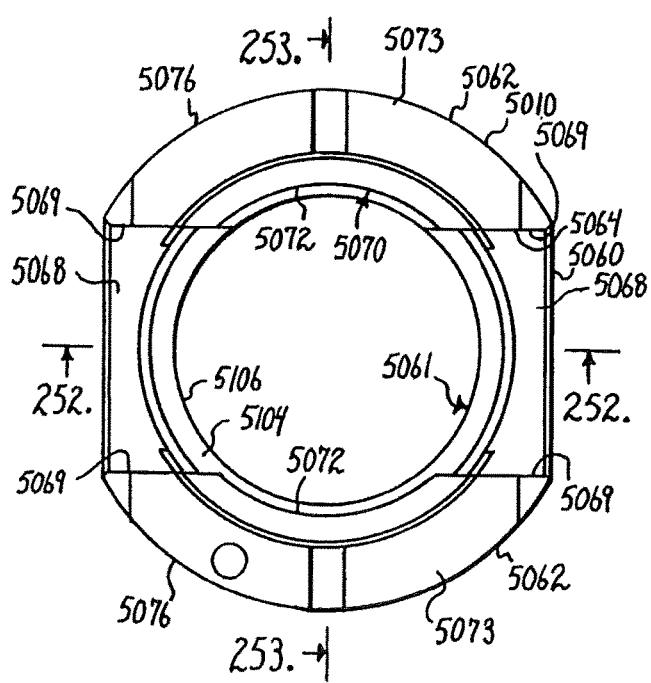

FIG. 250 is a reduced top plan view of the receiver of FIG. 248.

Figure 251:
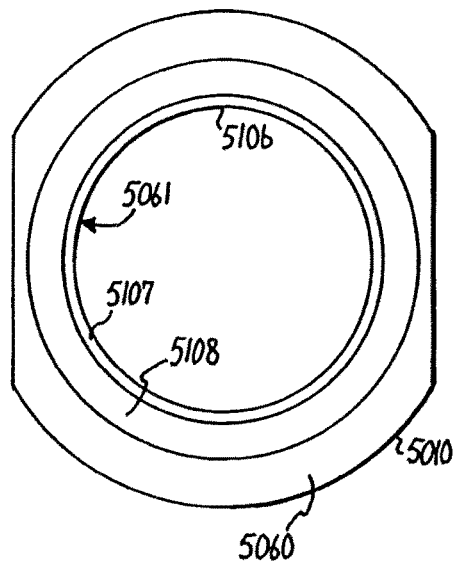

FIG. 251 is a reduced bottom plan view of the receiver of FIG. 248.

Figure 252:
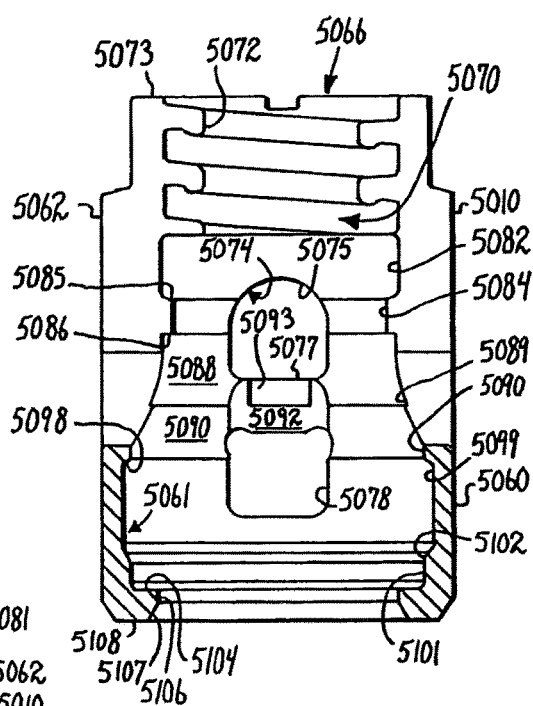

FIG. 252 is a reduced cross-sectional view taken along the line 252-252 of FIG. 250.

Figure 253:
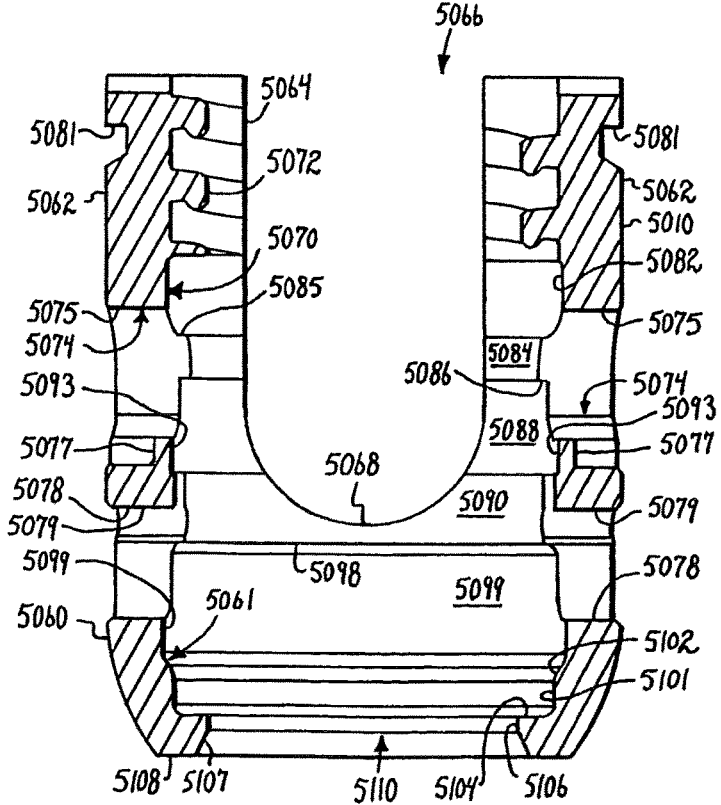

FIG. 253 is an enlarged cross-sectional view taken along the line 253-253 of FIG. 250.

Figure 254:
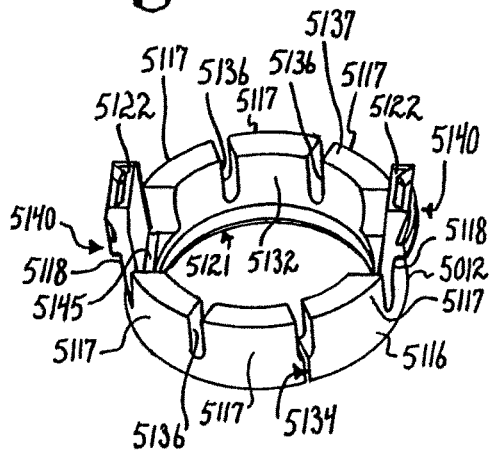

FIG. 254 is an enlarged perspective view of the retainer of FIG. 245.

Figure 255:
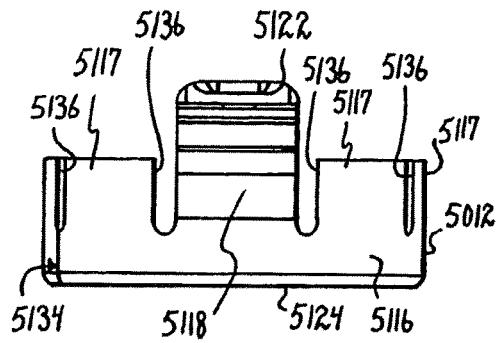

FIG. 255 is an enlarged side elevational view of the retainer of FIG. 254.

Figure 256:
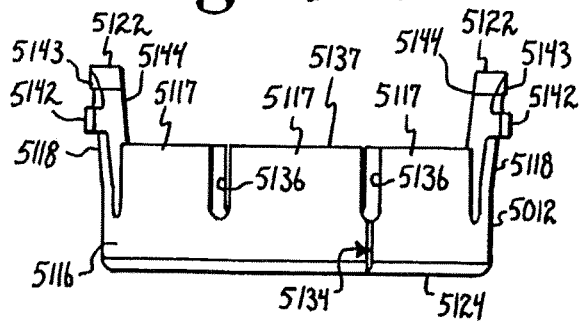

FIG. 256 is an enlarged front elevational view of the retainer of FIG. 254.

Figure 257:
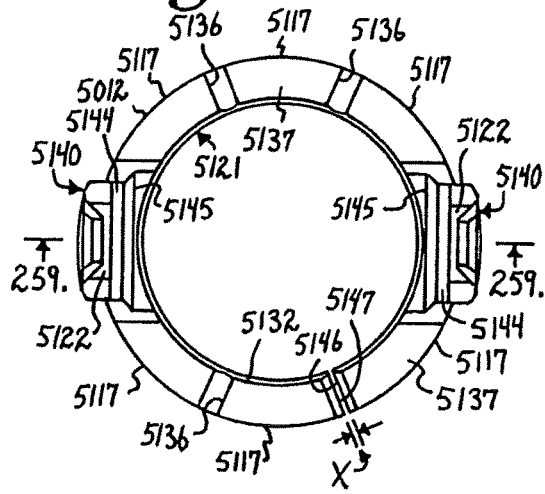

FIG. 257 is an enlarged top plan view of the retainer of FIG. 254.

Figure 258:
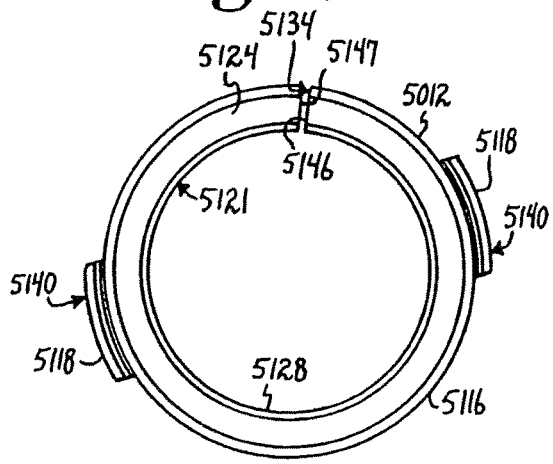

FIG. 258 is an enlarged bottom plan view of the retainer of FIG. 254.

Figure 259:
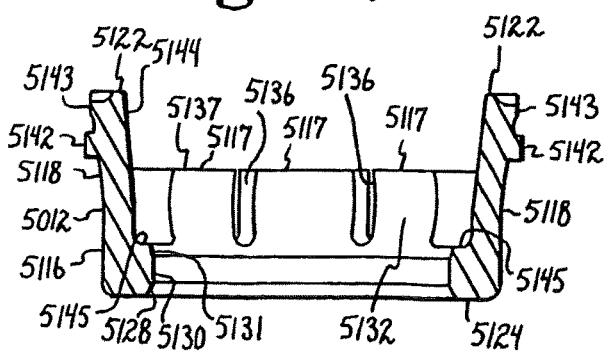

FIG. 259 is a cross-sectional view taken along the line 259-259 of FIG. 257.

Figure 260:
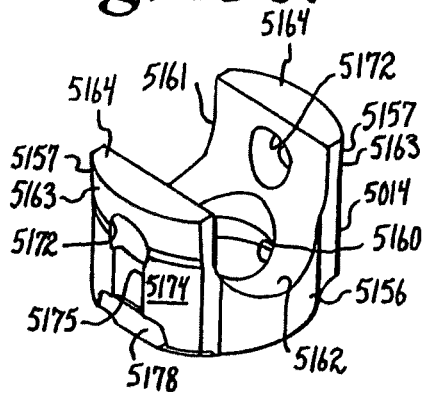

FIG. 260 is an enlarged perspective view of the insert of FIG. 245.

Figure 261:
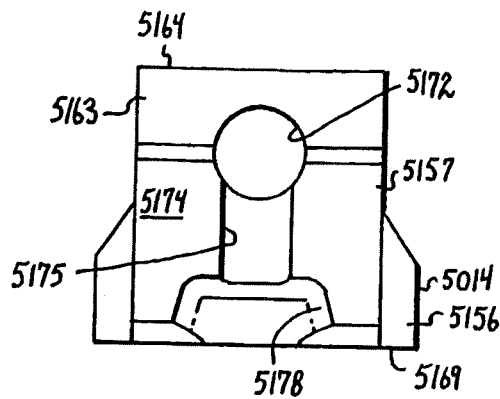

FIG. 261 is an enlarged side elevational view of the insert of FIG. 260.

Figure 262:
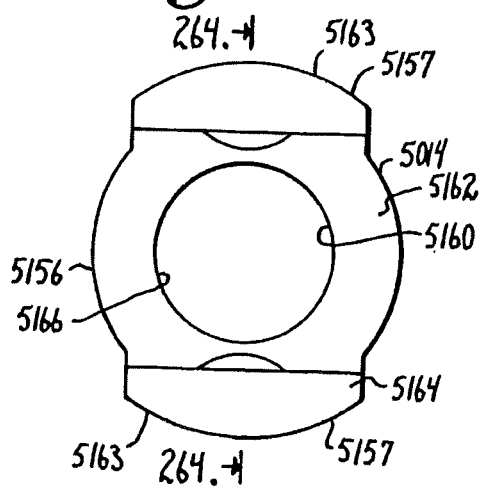

FIG. 262 is an insert of FIG. 260.

Figure 263:
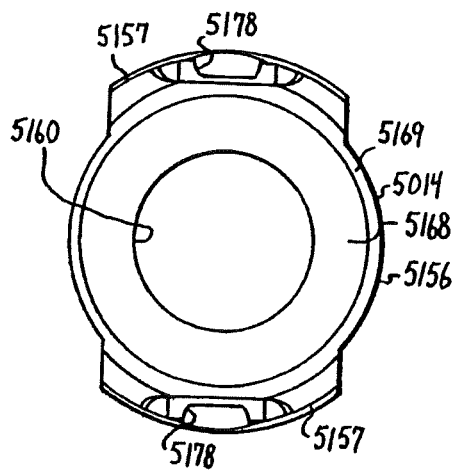

FIG. 263 is an insert of FIG. 260.

Figure 264:
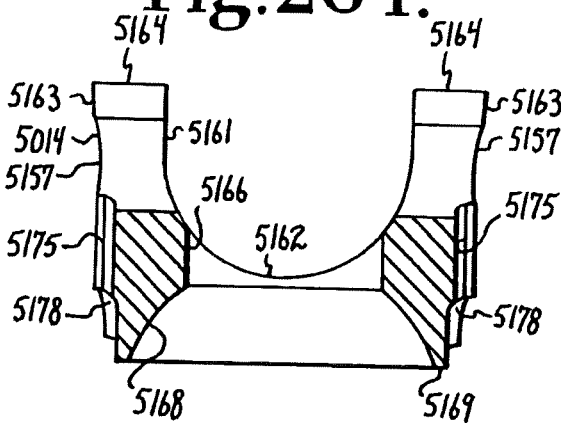

FIG. 264 is an enlarged top plan view of the enlarged bottom plan view of the cross-sectional view taken along the line 264-264 of FIG. 262.

Figure 265:
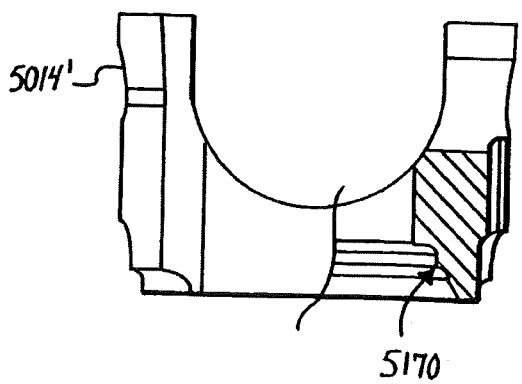

FIG. 265 is an enlarged front elevational view of an alternative insert according to the invention for use in lieu of the insert shown in FIG. 245, with portions broken away to show the detail thereof.

Figure 271:
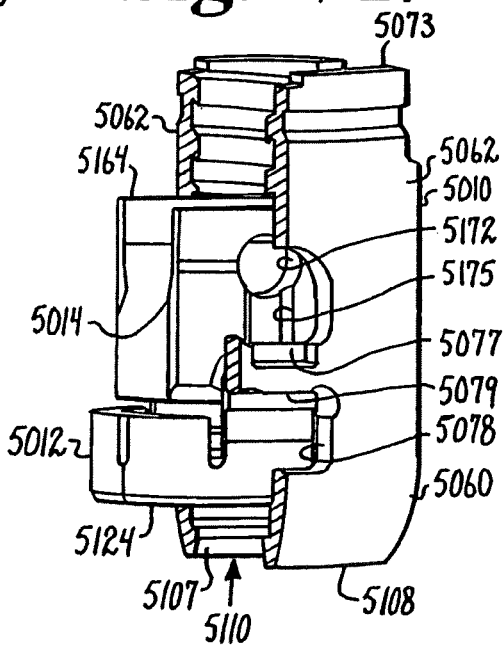

FIG. 266 is an enlarged front elevational view of the retainer and receiver of FIG. 245 with portions of the receiver broken away (as illustrated in FIG. 271) to show the detail thereof, the retainer being shown downloaded into the receiver (in phantom) to a partially inserted stage of assembly.

FIG. 267 is a front elevational view of the retainer and receiver with portions broken away, similar to that shown in FIG. 266, further showing the retainer seated within the receiver and also showing the insert of FIG. 245 in side elevation (in phantom) above the receiver and then being downloaded into the receiver to a partially inserted stage of assembly.

FIG. 268 is a front elevational view with portions broken away, similar to FIG. 267, showing the insert rotated into a position in alignment with the receiver.

FIG. 269 is a front elevational view with portions broken away, similar to FIG. 268 showing arms of the retainer being pinched (with a tool not shown) towards one another and the retainer partially moved upwardly within the receiver.

Figure 270:
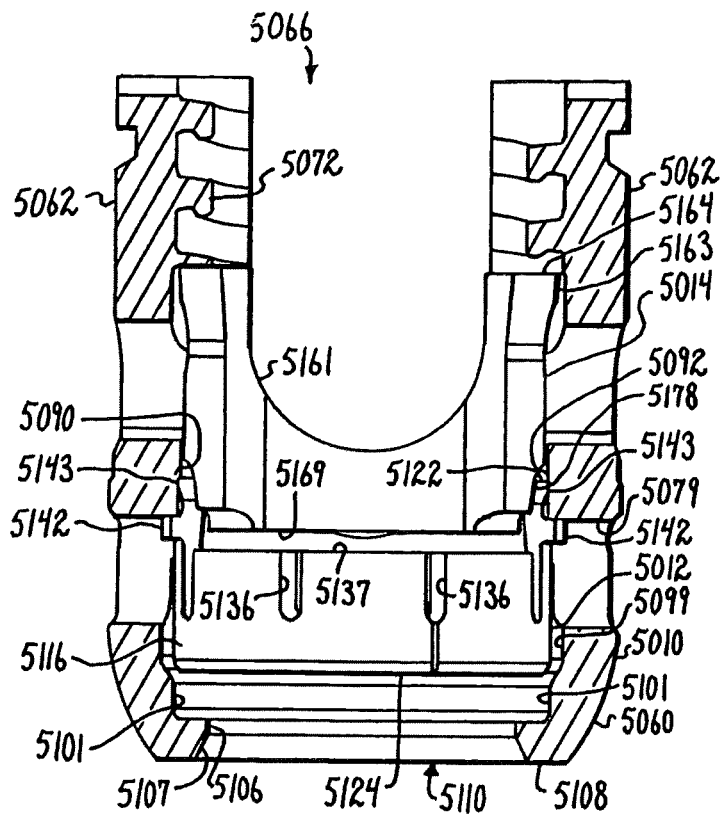

FIG. 270 is a front elevational view similar to FIG. 269 showing the retainer arms placed in a desired upward position within the receiver and the pinching tool removed so that the retainer pushes outwardly against the receiver and is held against the receiver during shipping.

FIG. 271 is a reduced perspective view with portions broken away of the assembly as shown in FIG. 270.

Figure 272:
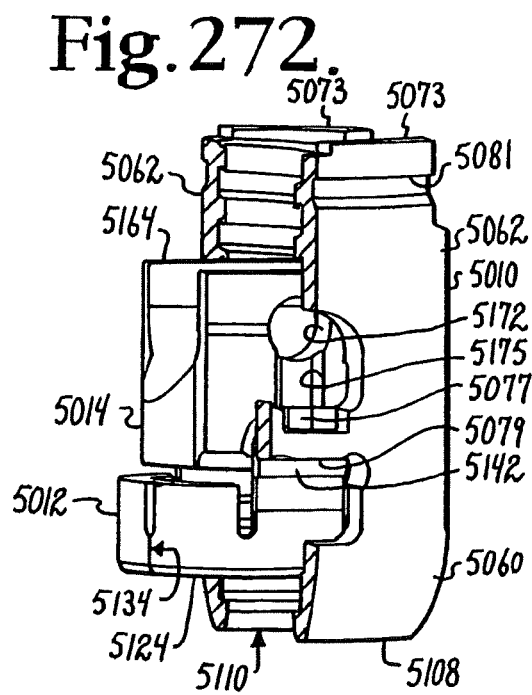

FIG. 272 is a perspective view with portions broken away, similar to FIG. 271, showing a portion of the receiver crimped against the insert.

FIG. 273 is an enlarged front elevational view with portions broken away, similar to FIG. 270, also including the crimping of FIG. 272 and further showing an enlarged and partial shank of FIG. 245 in a first stage of assembly with the retainer, a hemisphere of the shank head and a vertebra portion are both shown in phantom.

FIG. 274 is a partial front elevational view with portions broken away, similar to FIG. 273, showing the retainer lower portion in an expanded state about a mid-portion of the shank head, the head hemisphere shown in phantom.

Figure 275:
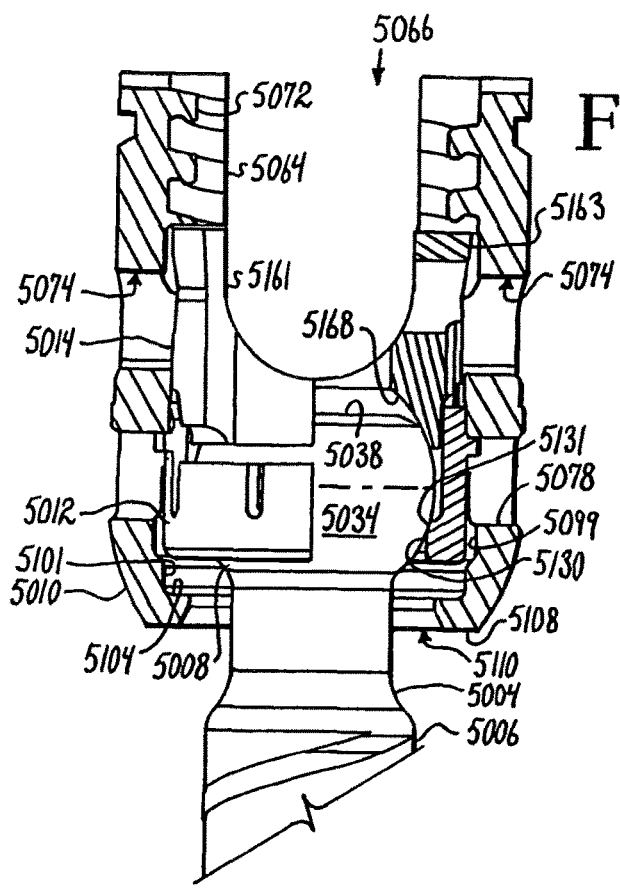

FIG. 275 is a reduced partial front elevational view with portions broken away, similar to FIG. 274, the shank upper portion or head in frictional engagement with an upper portion of the retainer.

Figure 276:
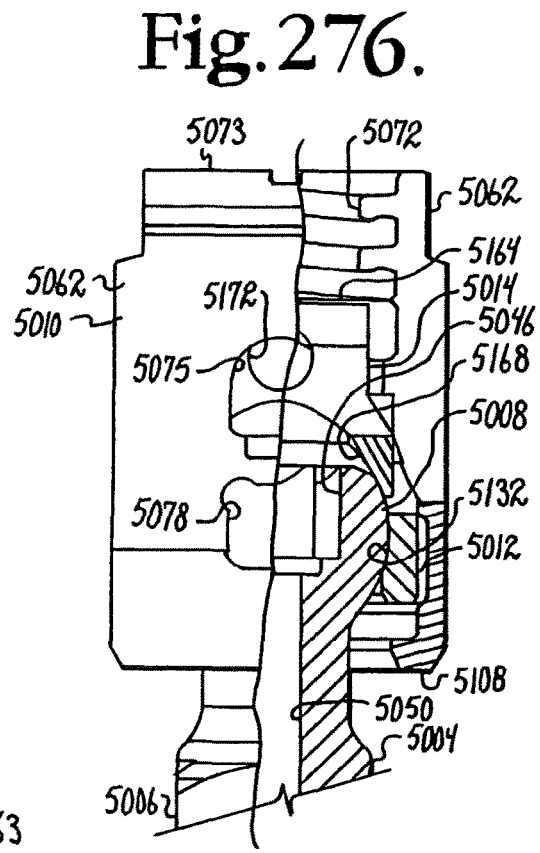

FIG. 276 is a partial side elevational view with portions broken away of the assembly in a stage as shown in FIG. 275.

Figure 277:
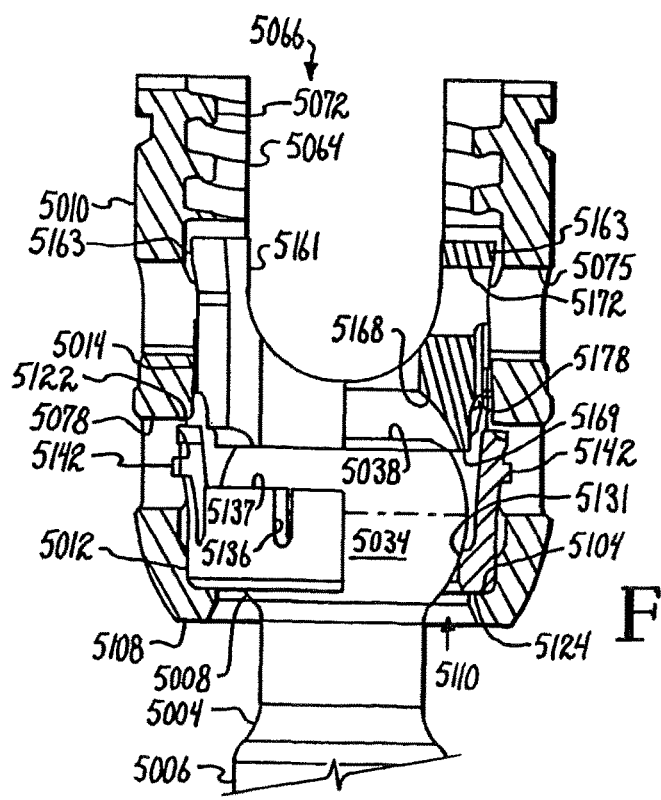

FIG. 277 is a partial front elevational view with portions broken away, similar to FIG. 275, the shank upper portion with attached retainer being shown pulled down into a seated position within the lower receiver cavity.

Figure 278:
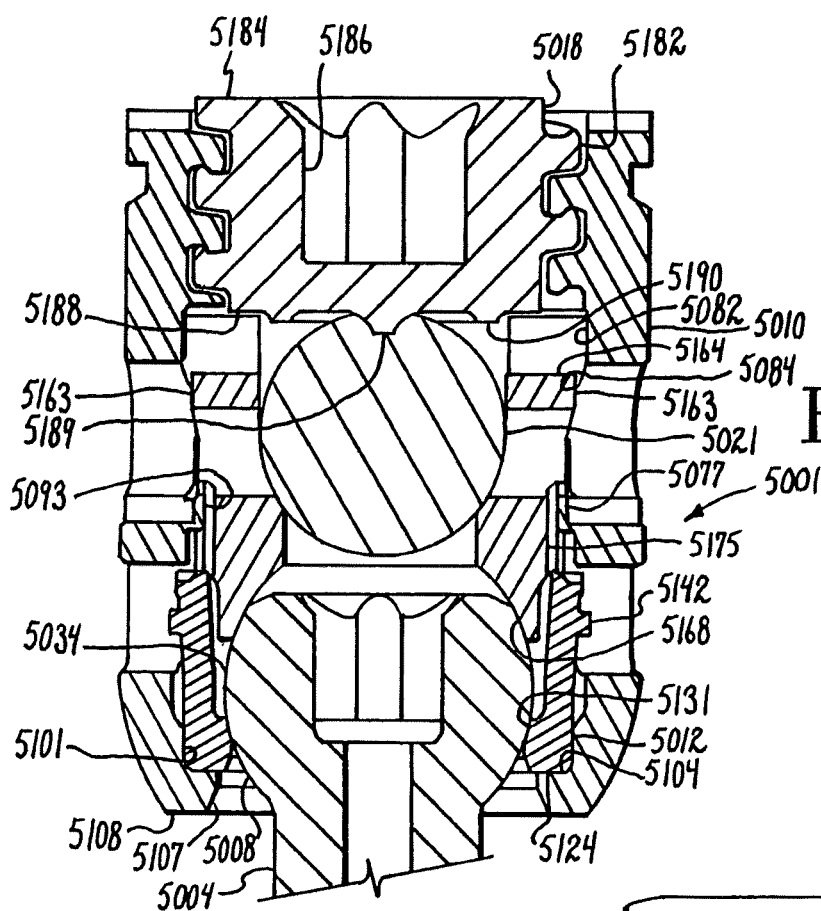

FIG. 278 is an enlarged and partial front elevational view with portions broken away of the entire assembly of FIG. 245, the assembly shown in a locked position with the insert wedged against surfaces of the receiver.

Figure 279:
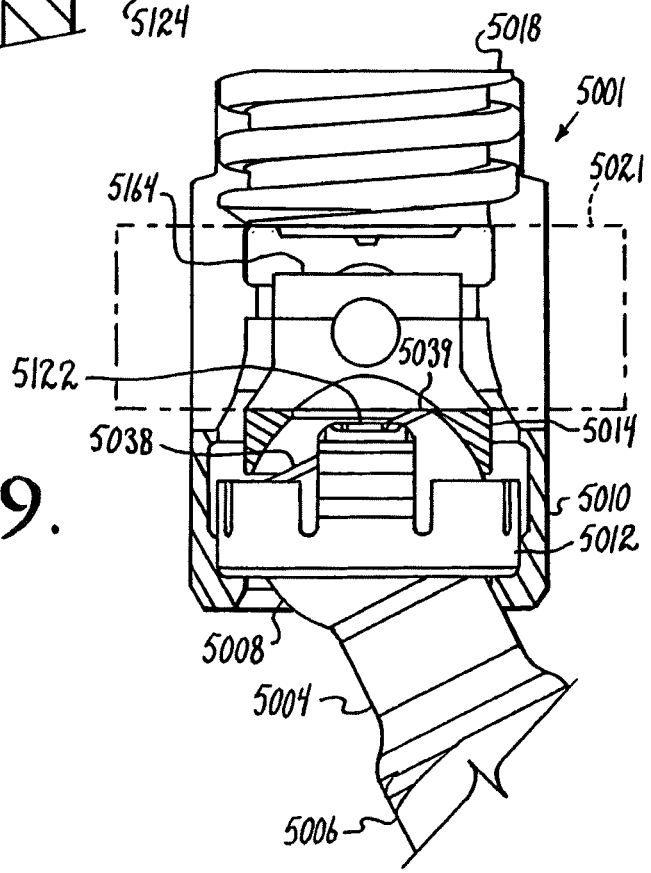

FIG. 279 is an enlarged and partial side elevational view with portions broken away of the entire assembly of FIG. 245, shown locked into position with the shank disposed at an angle with respect to the receiver, the rod being shown in phantom.

Figures 280, 281:
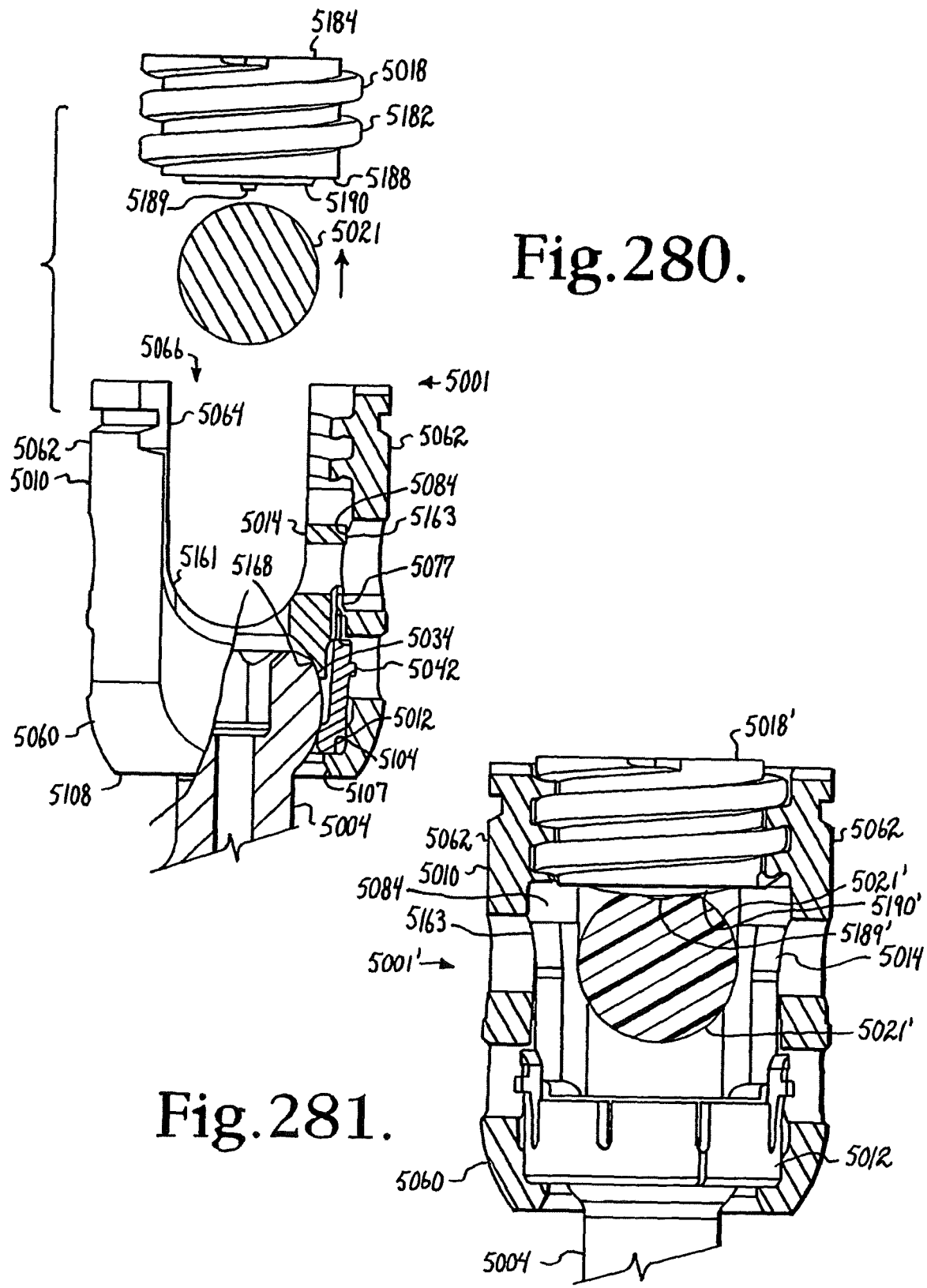

FIG. 280 is a reduced and partial front elevational view with portions broken away, similar to FIG. 278, showing the insert retaining the assembly in a locked position when the closure top and the rod are removed.

FIG. 281 is an enlarged and partial front elevational view with portion broken away, similar to FIG. 280, further showing the assembly with a replacement deformable rod and alternative closure top.

Figure 282:
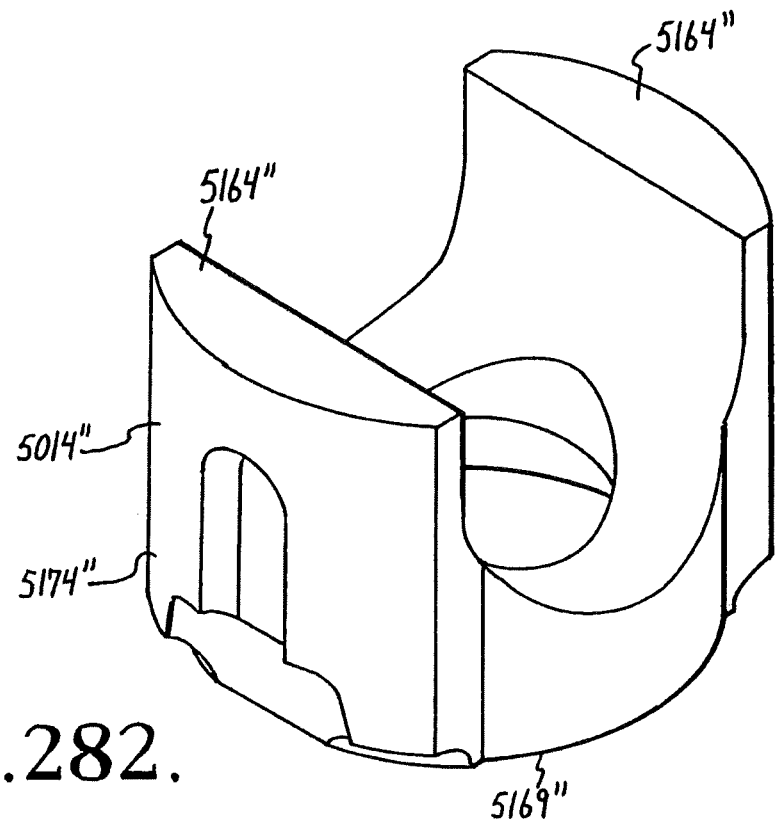

FIG. 282 is an enlarged perspective view of an alternative non-locking insert according to the invention for use with the assembly of FIG. 245.

Figure 283:
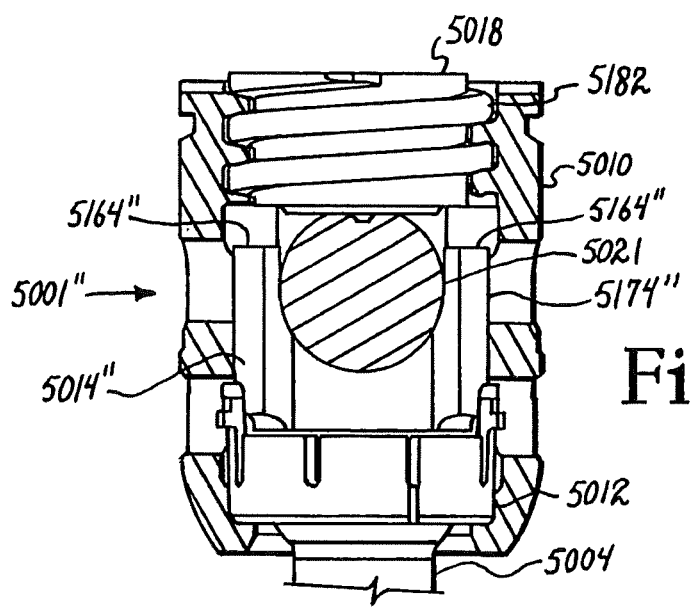

FIG. 283 is an enlarged and partial front elevational view of the assembly of FIG. 245 shown in a fully assembled locked position with the non-locking insert of FIG. 282 in lieu of the locking insert shown in FIG. 245, with portions broken away to show the detail thereof.

Figure 284:
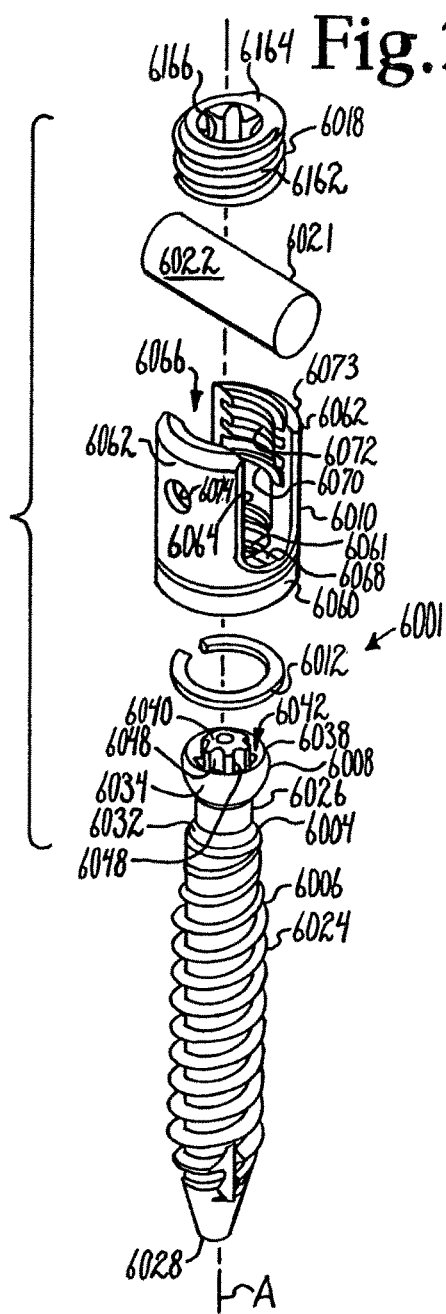

FIG. 284 is an exploded perspective view of another embodiment of a polyaxial bone screw assembly according to the present invention including a shank, a receiver and a retainer ring, further shown with a portion of a longitudinal connecting member in the form of a rod and a closure top.

Figure 285:
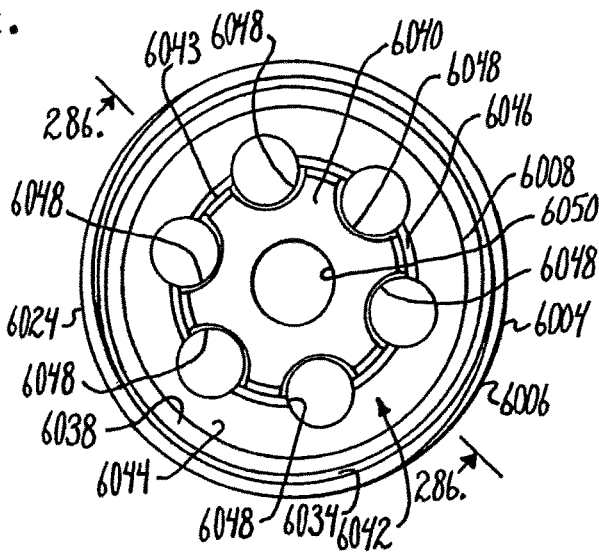

FIG. 285 is an enlarged top plan view of the shank of FIG. 284.

Figure 286:
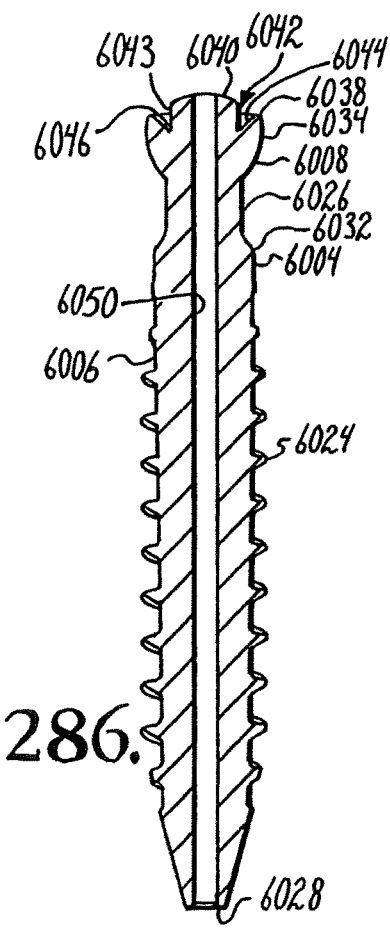

FIG. 286 is reduced cross-sectional view taken along the line 286-286 of FIG. 285.

Figure 287:
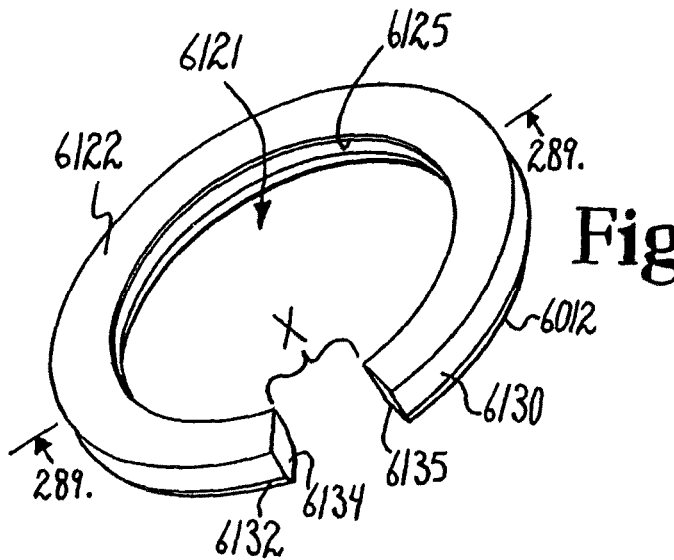

FIG. 287 is an enlarged perspective view of the lower retainer of FIG. 284.

Figure 288:
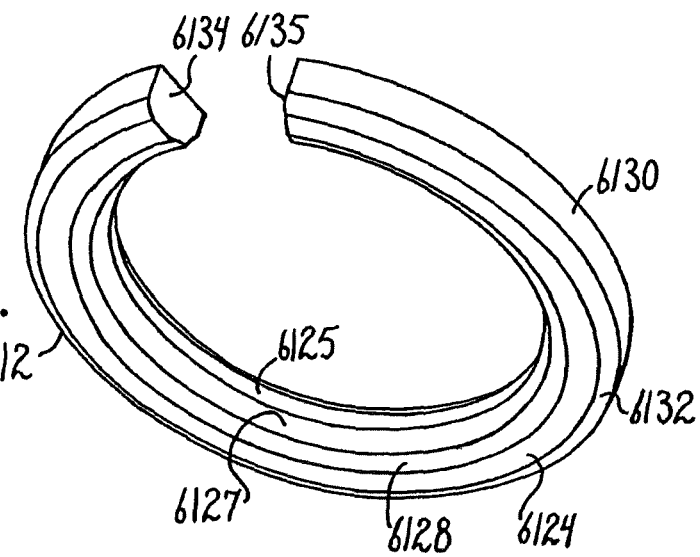

FIG. 288 is another perspective view of the retainer of FIG. 287.

Figure 289:
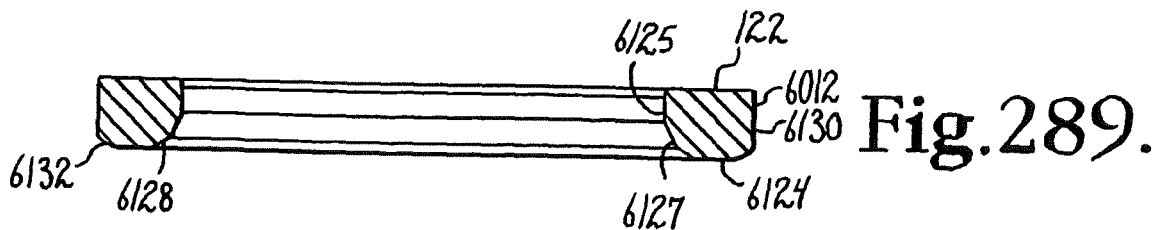

FIG. 289 is a cross-sectional view taken along the line 289-289 of FIG. 287.

Figure 290:
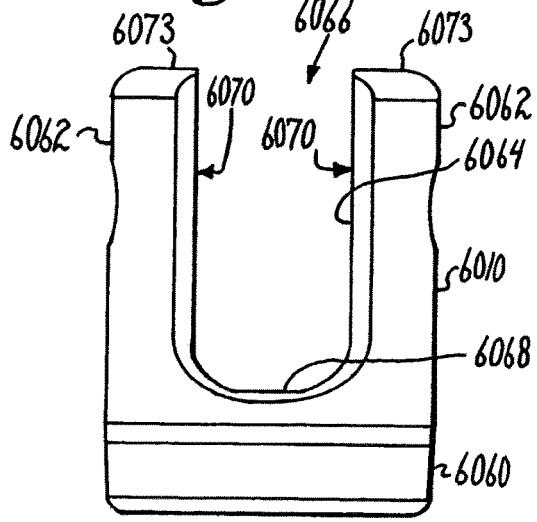

FIG. 290 is an enlarged front elevational view of the receiver of FIG. 284.

Figure 291:
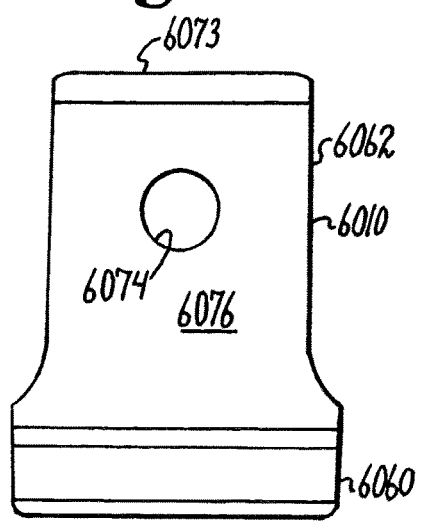

FIG. 291 is a side elevational view of the receiver of FIG. 290.

Figure 292:
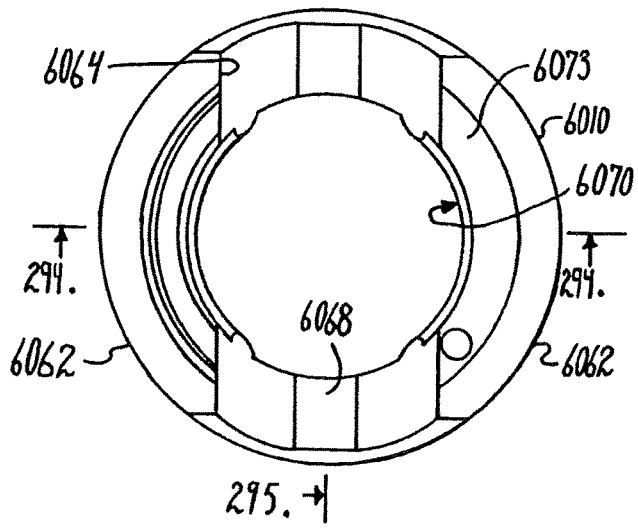

FIG. 292 is a top plan view of the receiver of FIG. 290.

Figure 293:
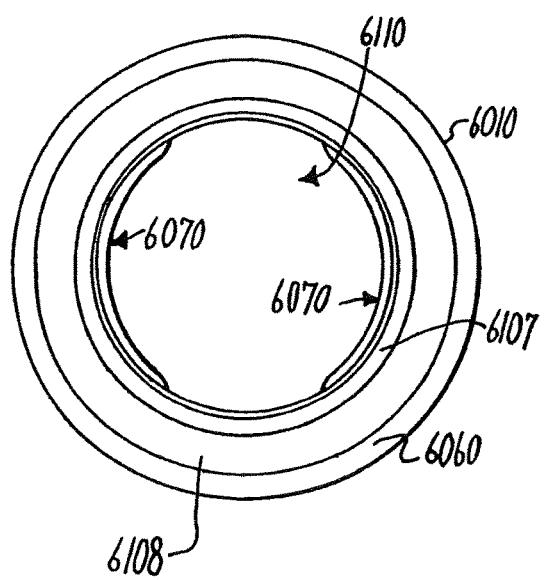

FIG. 293 is a bottom plan view of the receiver of FIG. 290.

Figure 294:
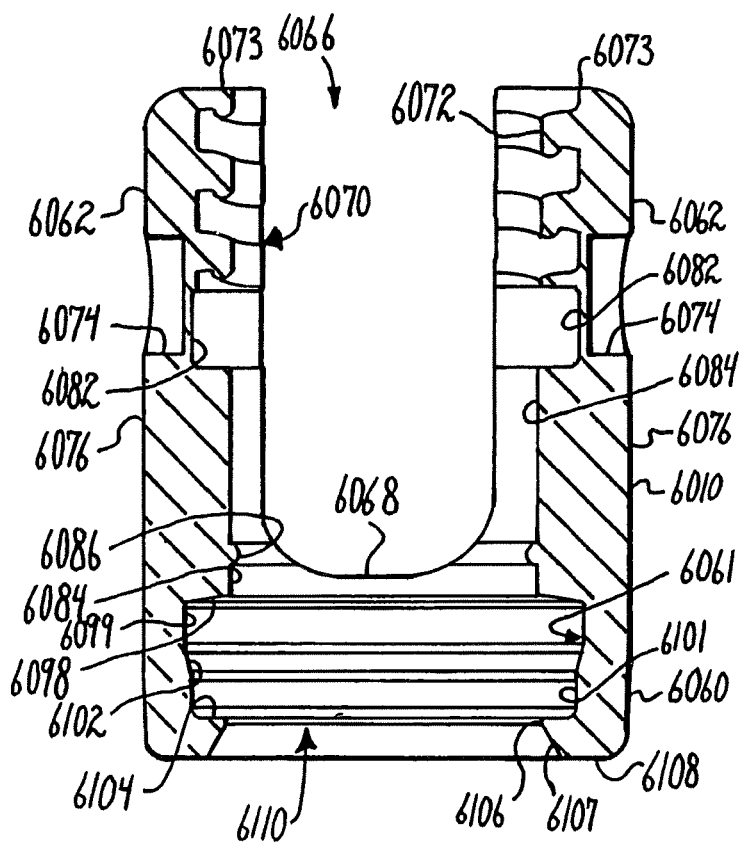

FIG. 294 is a cross-sectional view taken along the line 294-294 of FIG. 292.

Figure 295:
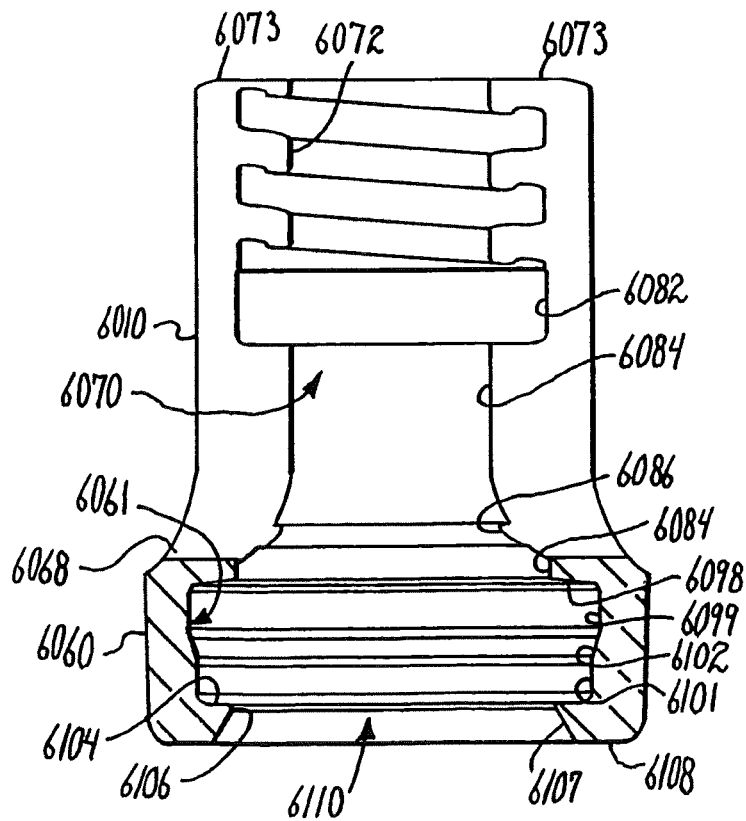

FIG. 295 is a cross-sectional view taken along the line 295-295 of FIG. 292.

Figure 296:
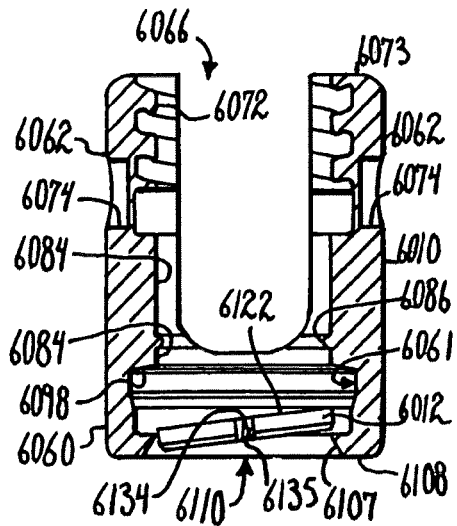

FIG. 296 is an enlarged front elevational view of the receiver and retainer of FIG. 284 with portions of the receiver broken away to show the detail thereof, the retainer being shown in a compressed insertion stage of assembly.

Figure 297:
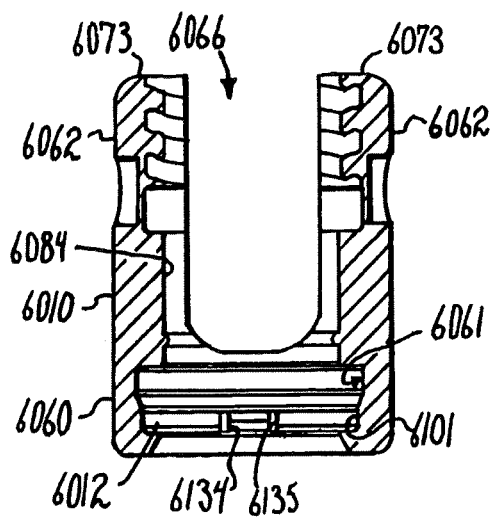

FIG. 297 is a front elevational view with portions broken away, similar to FIG. 296, showing the retainer in a neutral position, assembled with the receiver.

Figure 298:
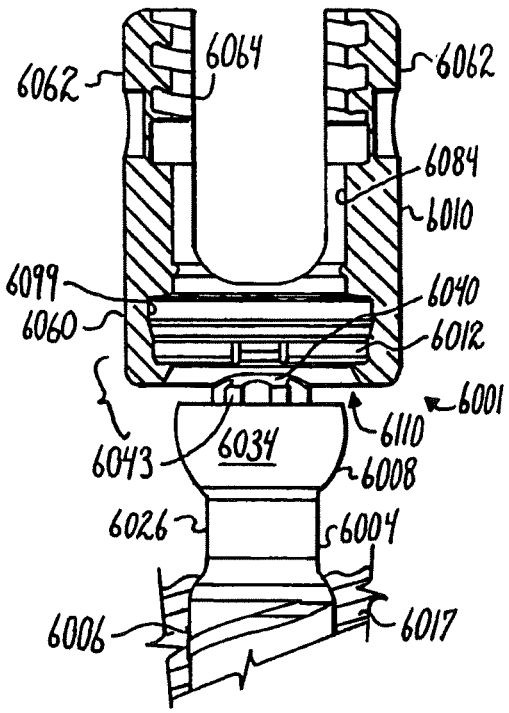

FIG. 298 is a front elevational view with portions broken away, similar to FIG. 297 and further showing the shank of FIG. 284 in partial front elevation and implanted in a vertebra.

Figure 299:
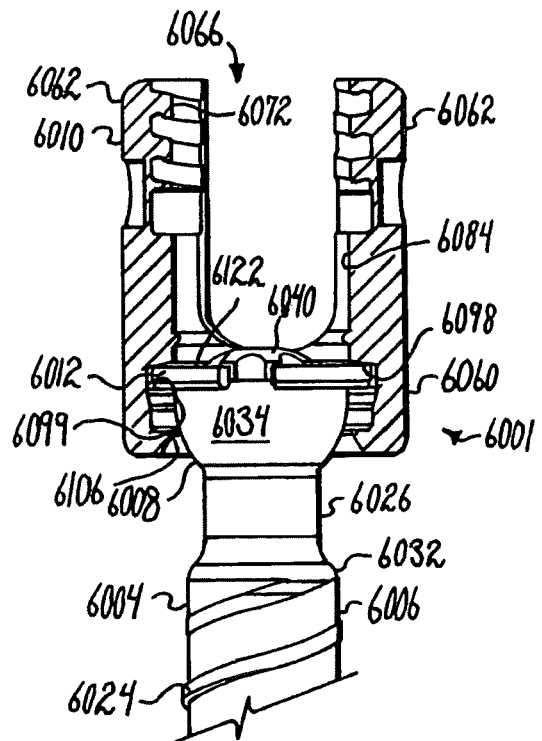

FIG. 299 is a partial front elevational view with portions broken away, similar to FIG. 298 showing the shank in a stage of assembly with the lower retainer ring, the lower retainer ring being pushed up into engagement with the receiver.

Figure 300:
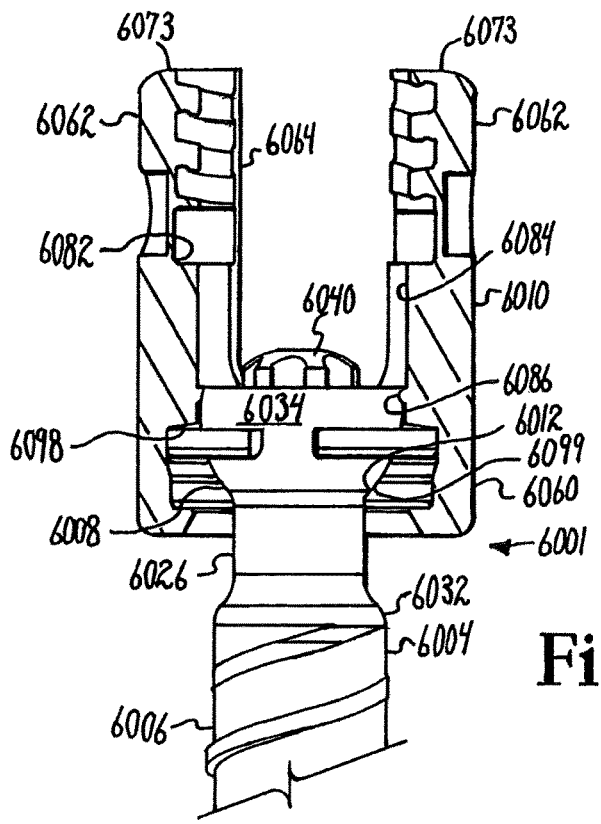

FIG. 300 is a partial front elevational view with portions broken away, similar to FIG. 299, showing the lower retainer in an expanded state about an upper portion of the shank.

Figure 301:
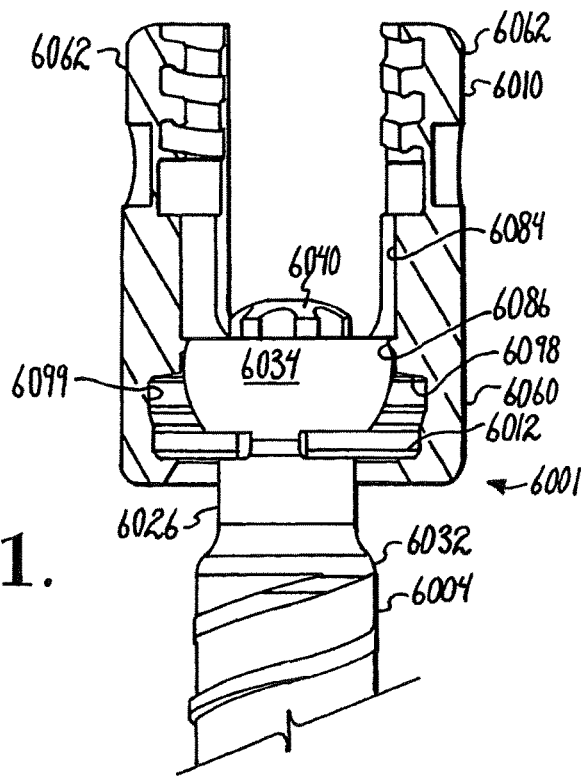

FIG. 301 is a partial front elevational view with portions broken away, similar to FIG. 300, the shank upper portion in engagement with a portion of the receiver and the retainer in a substantially neutral state.

Figure 302:
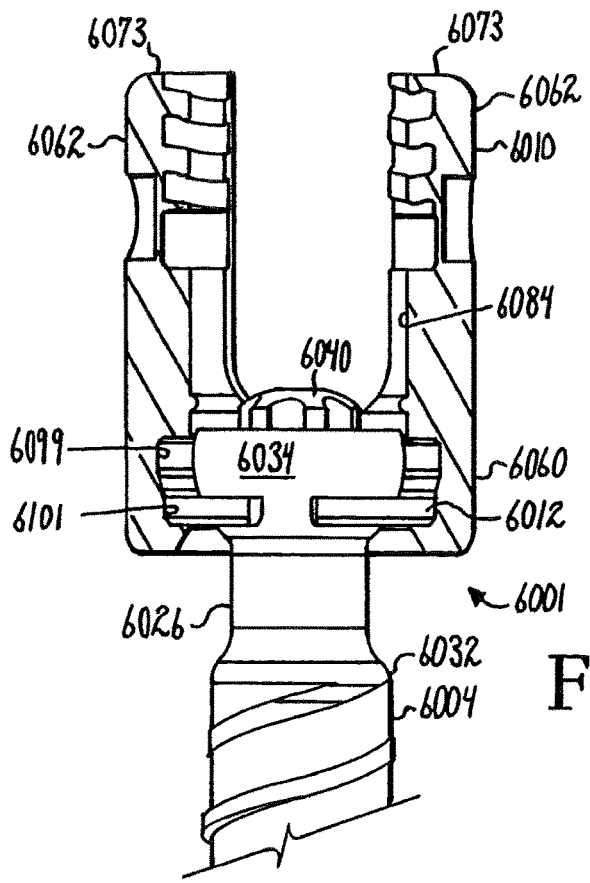

FIG. 302 is a partial front elevational view with portions broken away, similar to FIG. 301, the shank upper portion being in a downward, fully assembled position, the retainer being in a substantially neutral or slightly contracted state.

Figure 303:
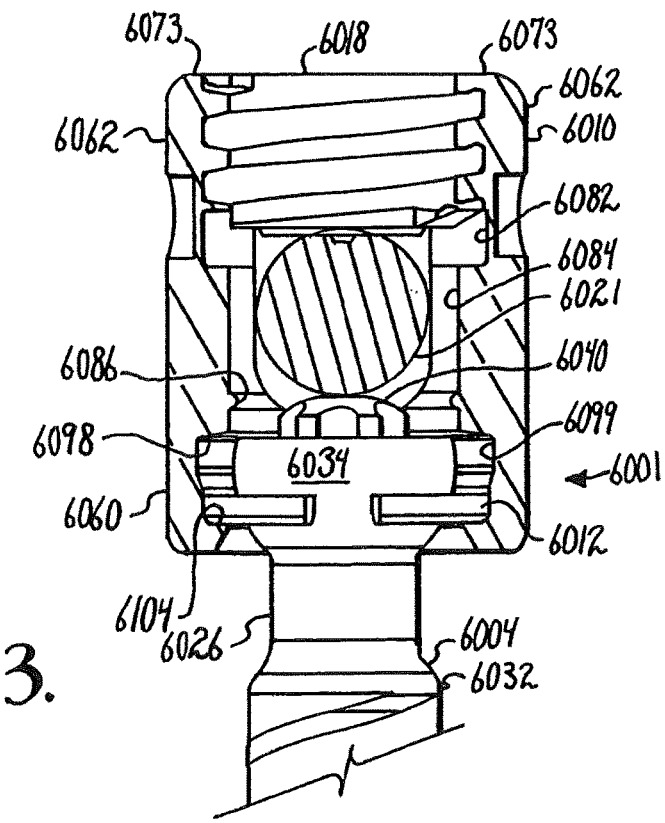

FIG. 303 is a partial front elevational view of the assembly of FIG. 302, with portions broken away and shown in a locked position with the rod portion and closure top of FIG. 284.

Figure 304:
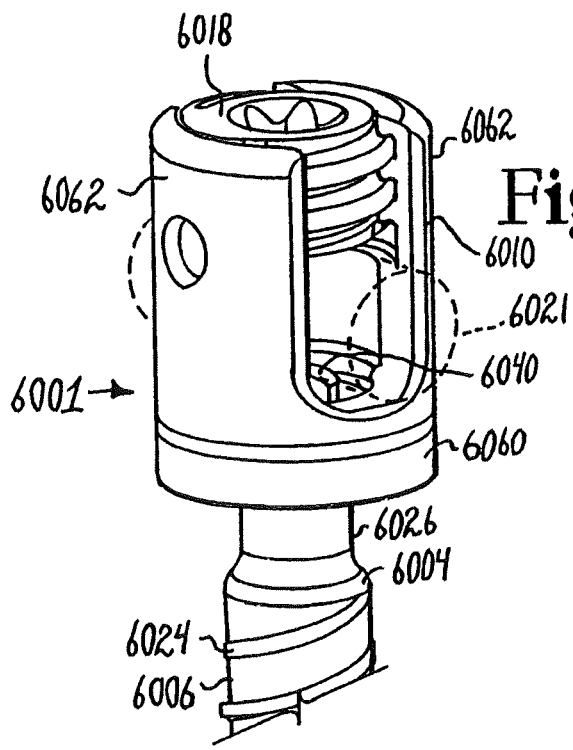

FIG. 304 is a partial perspective view of the assembly of FIG. 303 with the rod shown in phantom.

Figure 305:
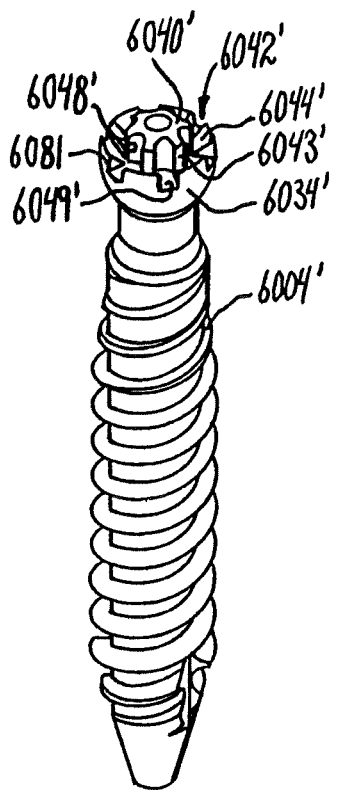

FIG. 305 is a perspective view of an alternative shank according to the invention that may be used with the assembly of FIG. 284 in lieu of the shank shown in FIG. 284.

Figure 306:
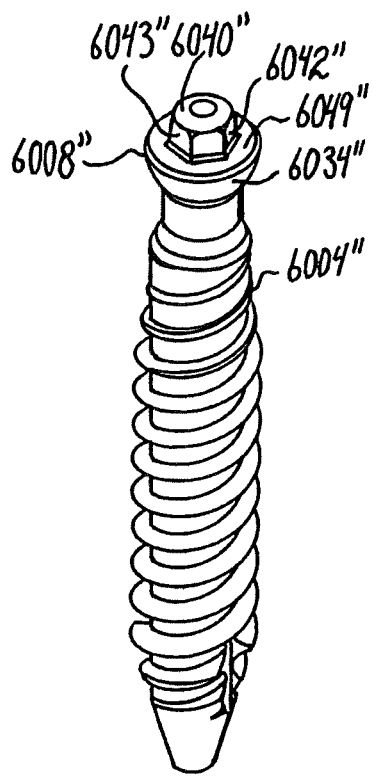

FIG. 306 is a perspective view of another alternative shank according to the invention that may be used with the assembly of FIG. 284 in lieu of the shank shown in FIG. 284.

FIG. 307 is an exploded front elevational view of another polyaxial bone screw assembly according to the present invention including a shank, a receiver and a friction fit retainer, further shown with a portion of a longitudinal connecting member in the form of a rod and a closure top.

FIG. 308 is an enlarged top plan view of the shank of FIG. 307.

FIG. 309 is reduced cross-sectional view taken along the line 309-309 of FIG. 308.

Figure 310:
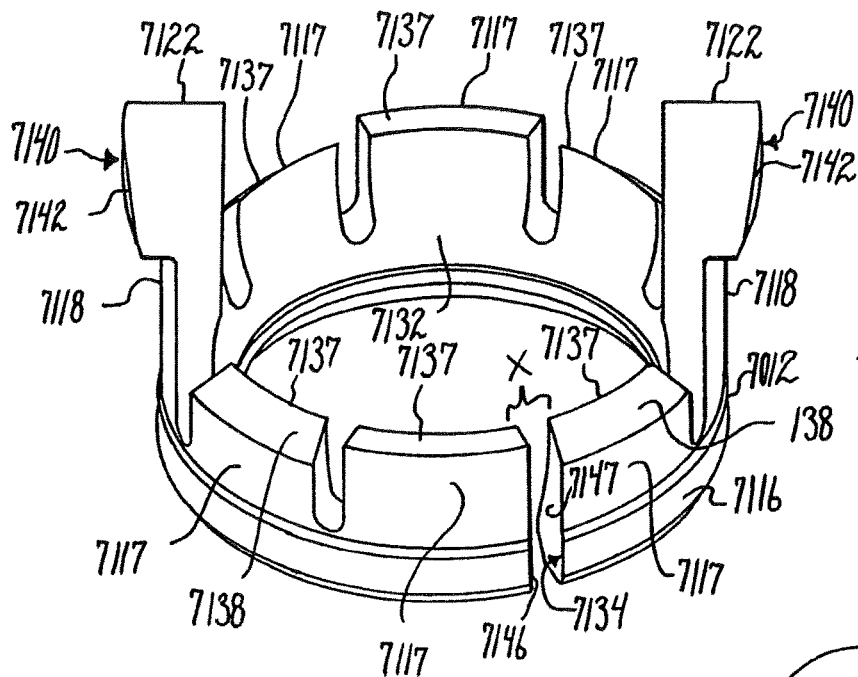

FIG. 310 is an enlarged perspective view of the retainer of FIG. 307.

Figure 311:
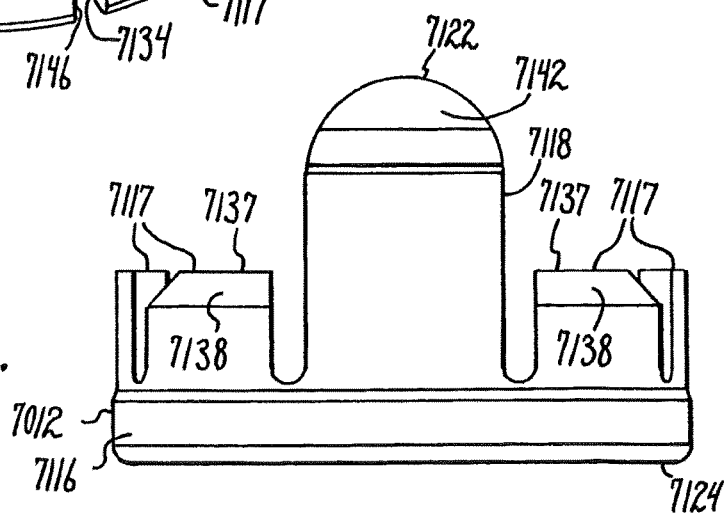

FIG. 311 is side elevational view of the retainer of FIG. 310.

Figure 312:
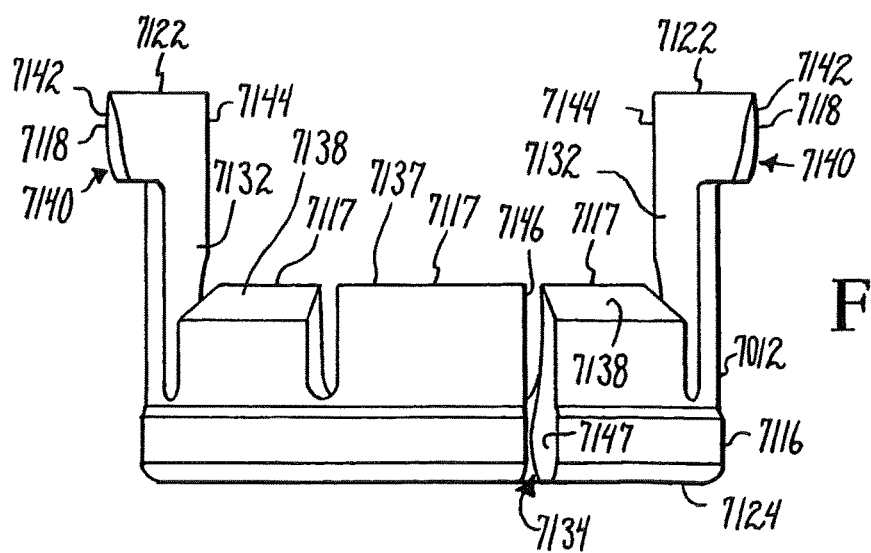

FIG. 312 is a front elevational view of the retainer of FIG. 310.

FIG. 313 is a top plan view of the retainer of FIG. 310.

FIG. 314 is a bottom plan view of the retainer of a cross-sectional view taken along the line 315-315 of FIG. 310.

FIG. 315 is a bottom plan view of the retainer of a cross-sectional view taken along the line 315-315 of FIG. 313.

Figure 316:
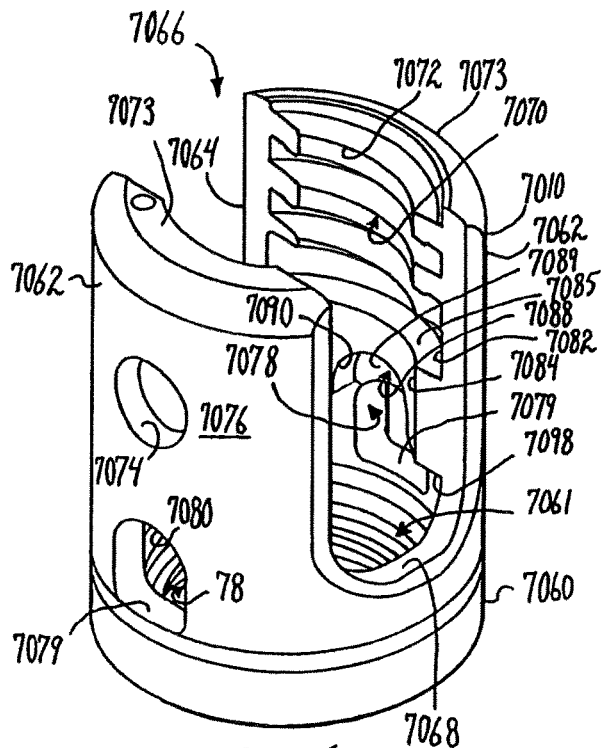

FIG. 316 is an enlarged perspective view of the receiver of FIG. 307.

Figure 317:
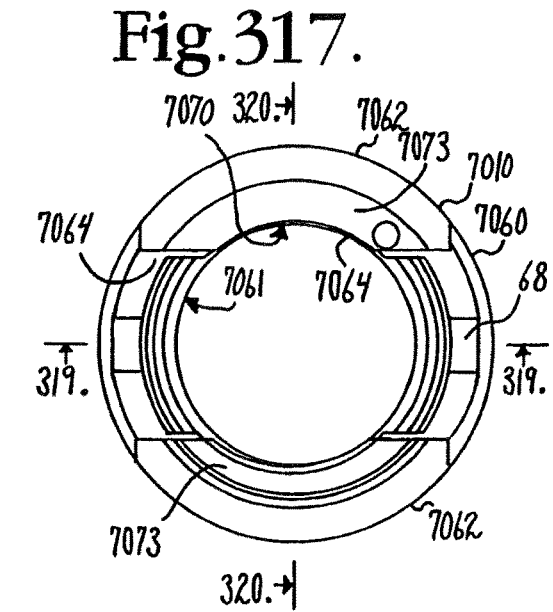

FIG. 317 is a top plan view of the receiver of a bottom plan view of the receiver of FIG. 316.

Figure 318:
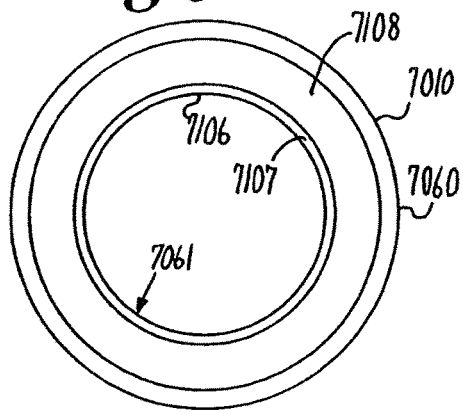

FIG. 318 is a bottom plan view of the receiver of FIG. 316.

Figure 319:
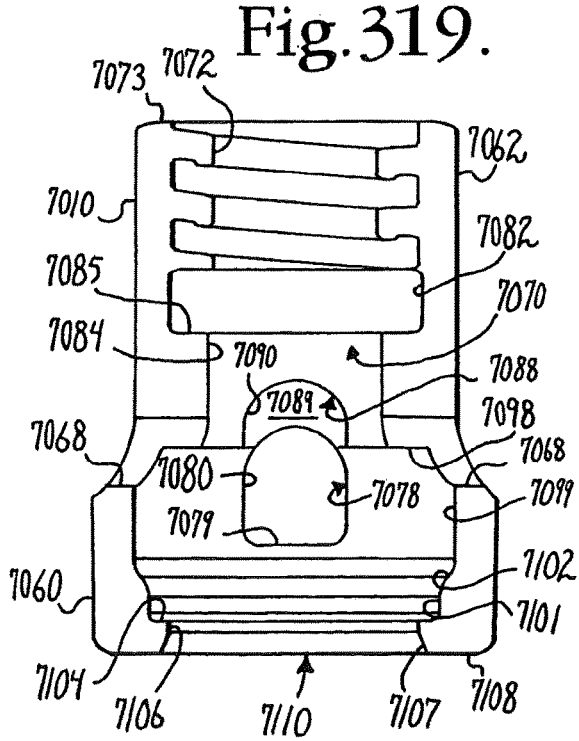

FIG. 319 is a cross-sectional view taken along the line 319-319 if FIG. 317.

FIG. 320 is a cross-sectional view taken along the line 320-320 of FIG. 317.

FIG. 321 is a reduced cross-sectional view of the receiver of FIG. 320 and a reduced front elevational view of the retainer of FIG. 312 shown in a stage of assembly with the receiver.

FIG. 322 is a reduced cross-sectional view of the receiver of FIG. 320 and a reduced front elevational view of the retainer of FIG. 312 shown in a stage of assembly with the receiver subsequent to what is shown in FIG. 321.

FIG. 323 is a reduced cross-sectional view of the receiver of FIG. 320 and a reduced front elevational view of the retainer of FIG. 312 shown in a stage of assembly with the receiver subsequent to what is shown in FIG. 322.

Figure 324:
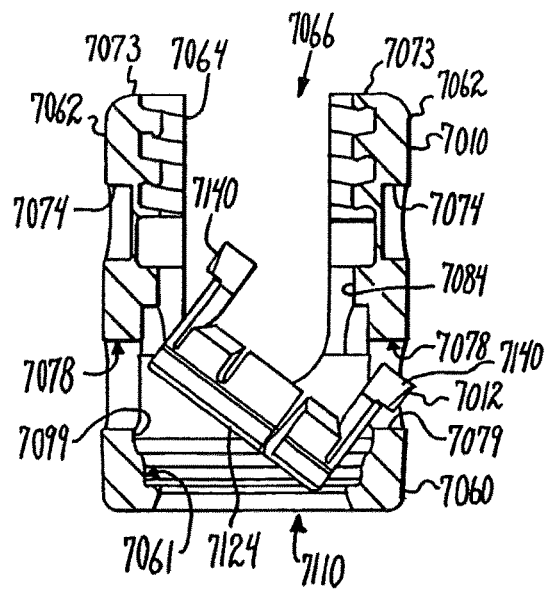

FIG. 324 is a reduced cross-sectional view of the receiver of FIG. 320 and a reduced front elevational view of the retainer of FIG. 312 shown in a stage of assembly with the receiver subsequent to what is shown in FIG. 323.

Figure 325:
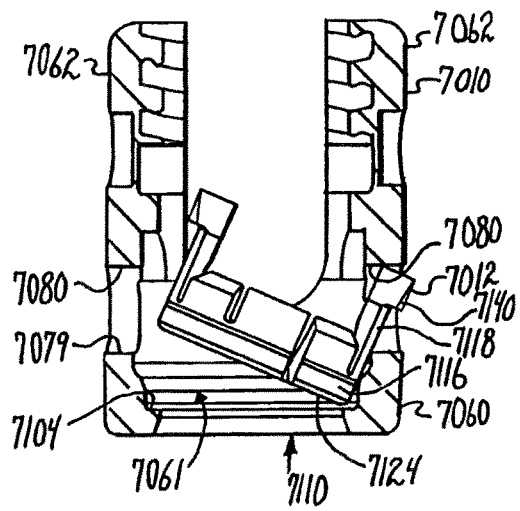

FIG. 325 is a reduced cross-sectional view of the receiver of FIG. 320 and a reduced front elevational view of the retainer of FIG. 312 shown in a stage of assembly with the receiver subsequent to what is shown in FIG. 324.

Figure 326:
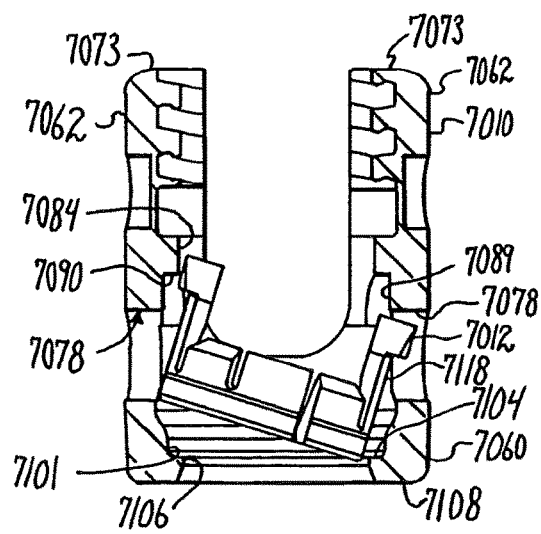

FIG. 326 is a reduced cross-sectional view of the receiver of FIG. 320 and a reduced front elevational view of the retainer of FIG. 312 shown in a stage of assembly with the receiver subsequent to what is shown in FIG. 325.

Figure 327:
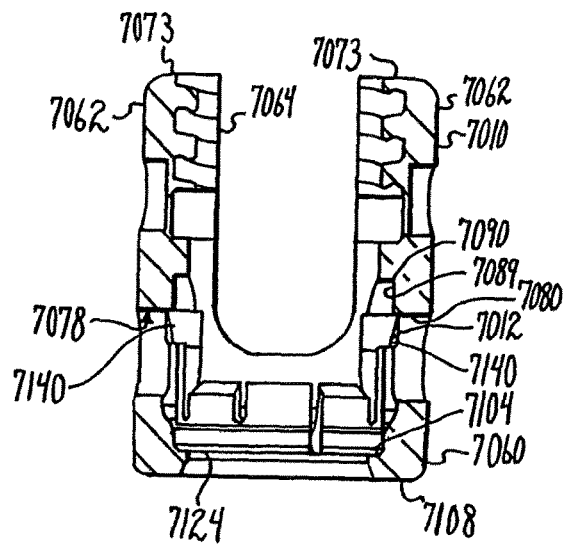

FIG. 327 is a reduced cross-sectional view of the receiver of FIG. 320 and a reduced front elevational view of the retainer of FIG. 312 shown in a stage of assembly with the receiver subsequent to what is shown in FIG. 326.

Figure 328:
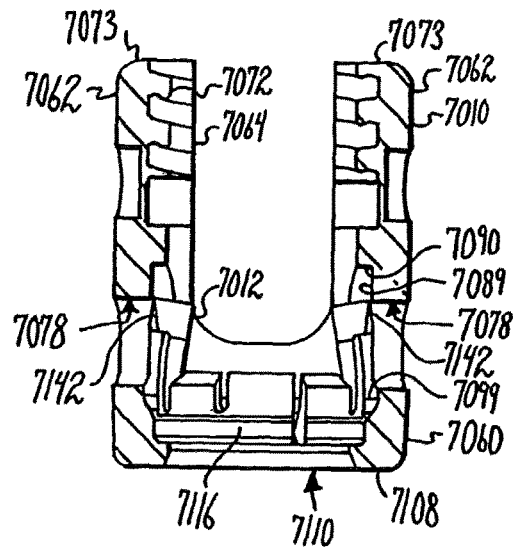

FIG. 328 is a reduced cross-sectional view of the receiver of FIG. 320 and a reduced front elevational view of the retainer of FIG. 312 shown in a stage of assembly with the receiver subsequent to what is shown in FIG. 327.

Figure 329:
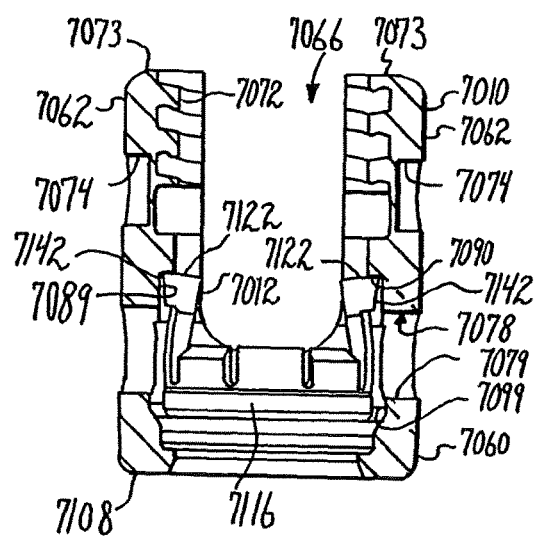

FIG. 329 is a reduced cross-sectional view of the receiver of FIG. 320 and a reduced front elevational view of the retainer of FIG. 312 shown in a stage of assembly with the receiver subsequent to what is shown in FIG. 328.

Figure 330:
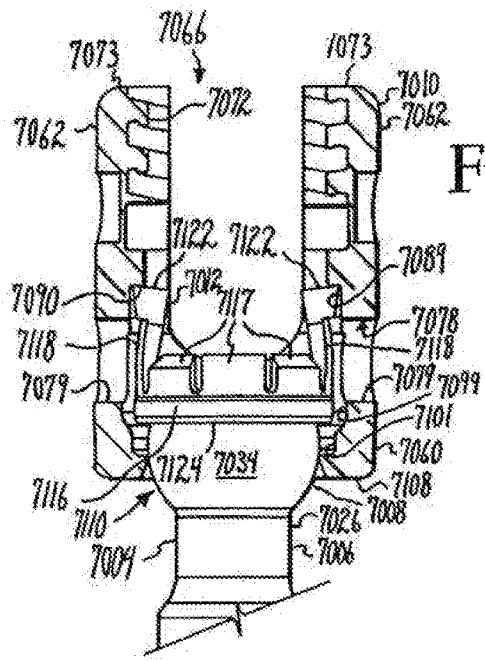

FIG. 330 is an enlarged cross-sectional view of the receiver and front elevational view of the retainer, similar to FIG. 329 and further showing a partial front elevational view of the shank of FIG. 307 shown in a stage of assembly with the receiver and retainer.

Figure 331:
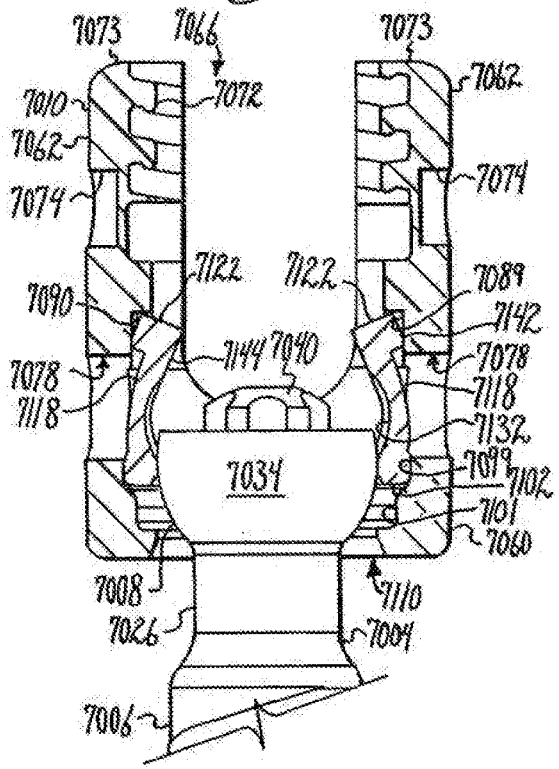

FIG. 331 is an enlarged and partial front elevational view, similar to FIG. 330, with portions broken away to show the detail thereof and showing the shank in a stage of assembly with the receiver and retainer subsequent to what is shown in FIG. 330.

Figure 332:
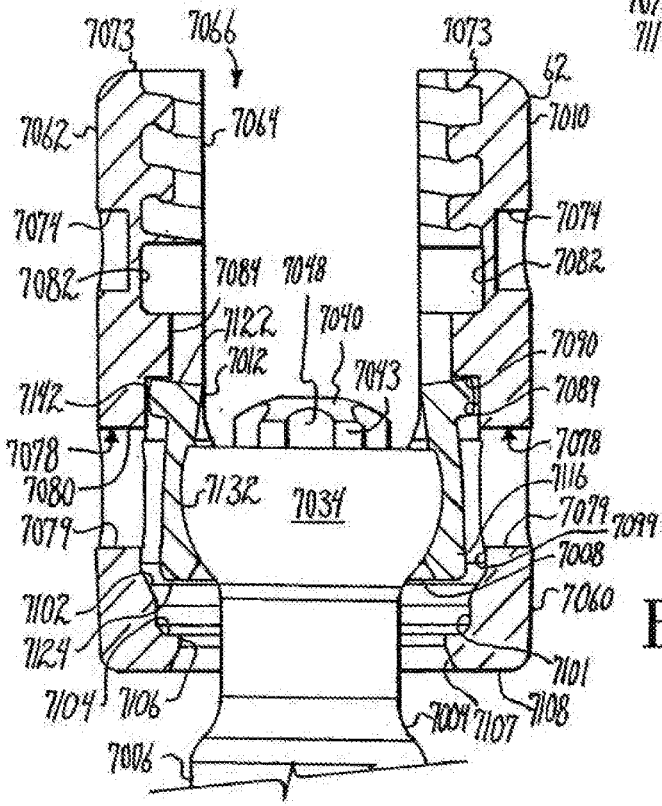

FIG. 332 is an enlarged and partial front elevational view with portions broken away, similar to FIG. 331, showing the shank in a stage of assembly with the receiver and retainer subsequent to what is shown in FIG. 331.

Figure 333:
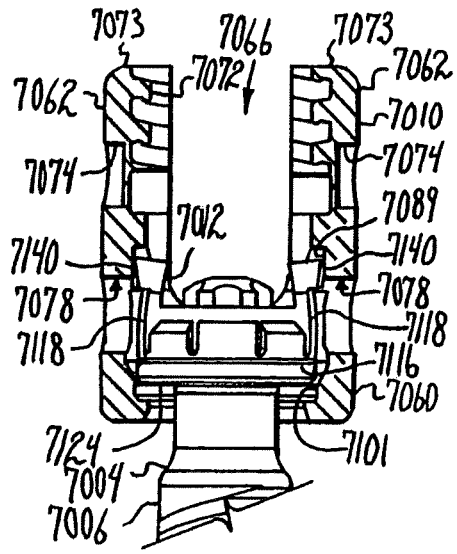

FIG. 333 is a reduced and partial front elevational view with portions broken away, similar to FIG. 332, showing the retainer in a stage of assembly with the receiver subsequent to what is shown in FIG. 332.

Figure 334:
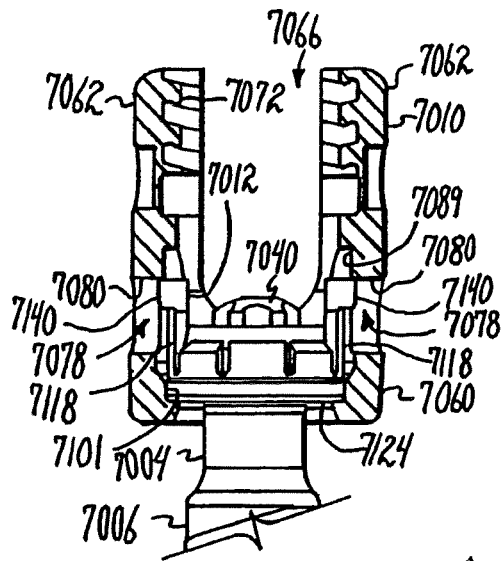

FIG. 334 is a partial front elevational view with portions broken away, similar to FIG. 333, showing the retainer in a stage of assembly with the receiver subsequent to what is shown in FIG. 333.

Figure 335:
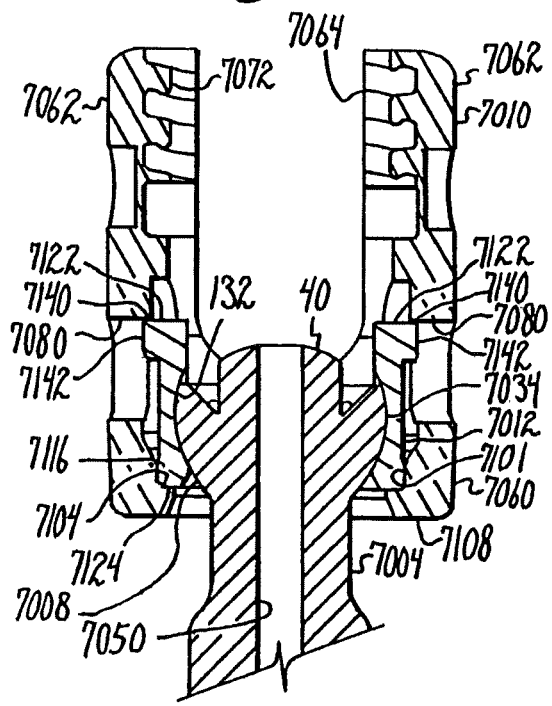

FIG. 335 is an enlarged and partial front elevational view, similar to FIG. 334, with further portions broken away to shown the detail thereof.

Figure 336:
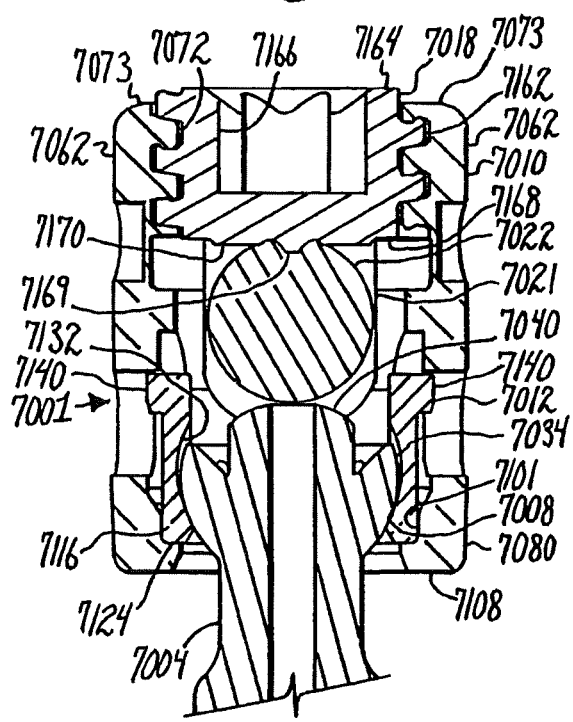

FIG. 336 is an enlarged and partial front elevational view of a fully assembled shank, retainer, receiver, rod and closure top of FIG. 307 with portions broken away to show the detail thereof.

Figure 337:
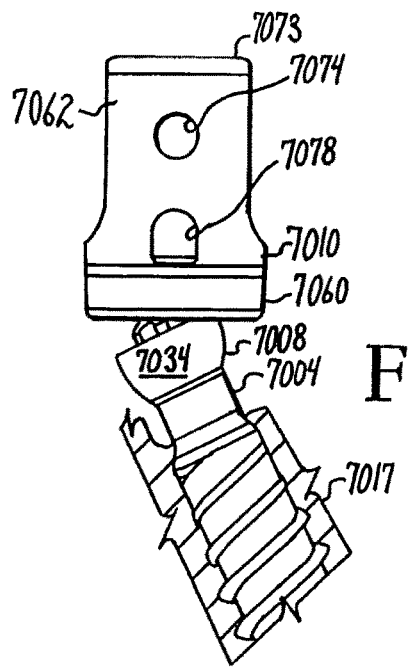

FIG. 337 is a partial side elevational view of the shank of FIG. 307 shown implanted in a vertebra and in an early stage of assembly with a retainer and receiver of FIG. 307, also shown in side elevation.

Figure 338:
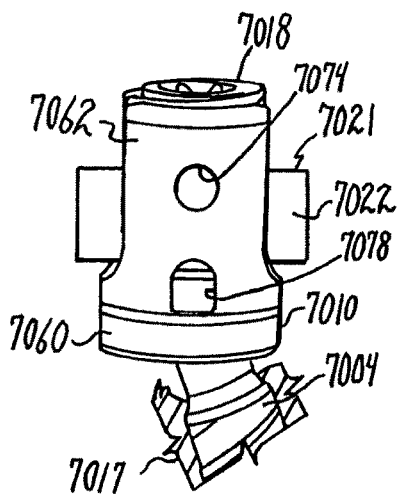

FIG. 338 is a partial side elevational view of the shank, retainer and receiver of FIG. 337, shown fully assembled and further shown assembled with the rod and closure top of FIG. 307, also in side elevation.

Figure 339:
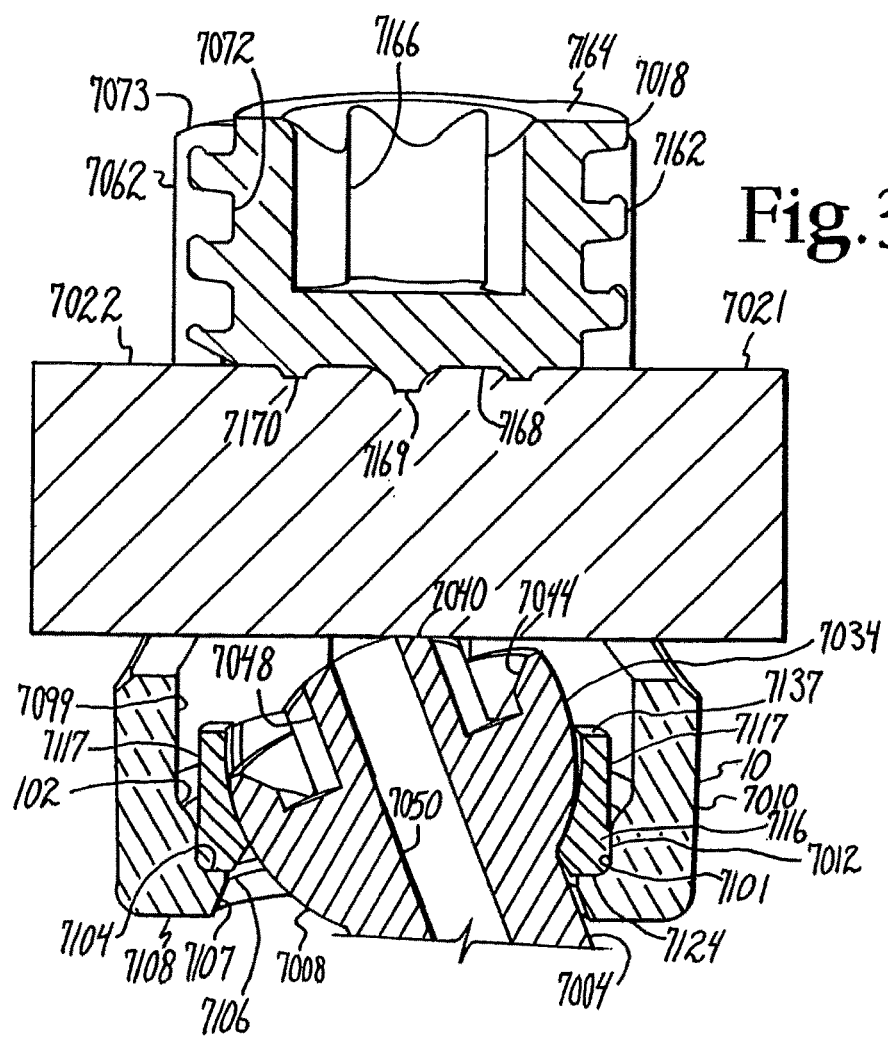

FIG. 339 is an enlarged and partial side elevational view of the shank, retainer, receiver, rod and closure top of FIG. 338 with portions broken away to show the detail thereof.

FIG. 340 is an exploded front elevational view of another embodiment of a polyaxial bone screw assembly according to the present invention including a shank, a receiver, a friction fit retainer and a lock and release insert, further shown with a portion of a longitudinal connecting member in the form of a rod and a closure top.

FIG. 341 is an enlarged top plan view of the shank of FIG. 340.

FIG. 342 is reduced cross-sectional view taken along the line 342-342 of FIG. 341.

Figure 343:
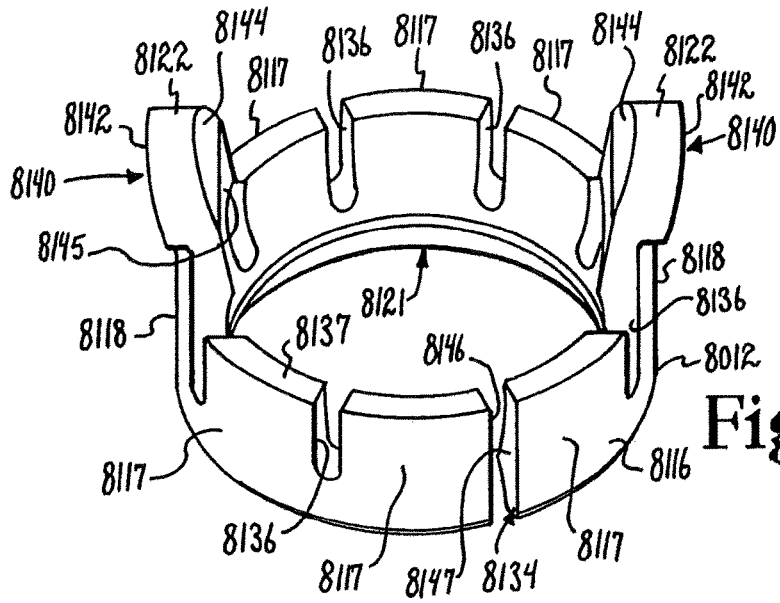

FIG. 343 is an enlarged perspective view of the retainer of FIG. 340.

Figure 344:
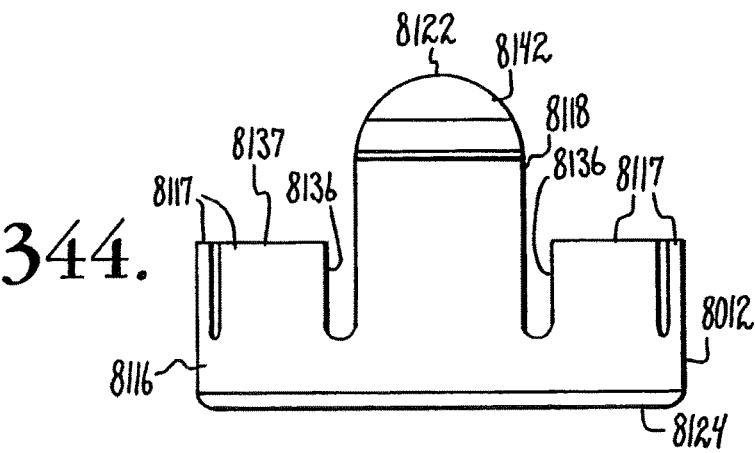

FIG. 344 is side elevational view of the retainer of FIG. 343.

Figure 345:
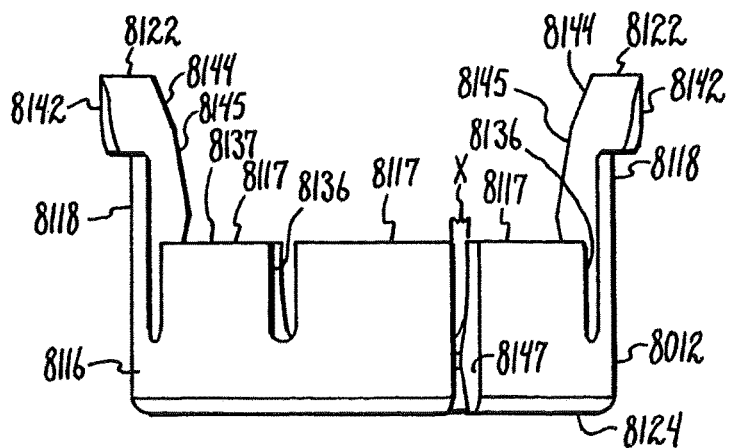

FIG. 345 is a front elevational view of the retainer of FIG. 343.

Figure 346:
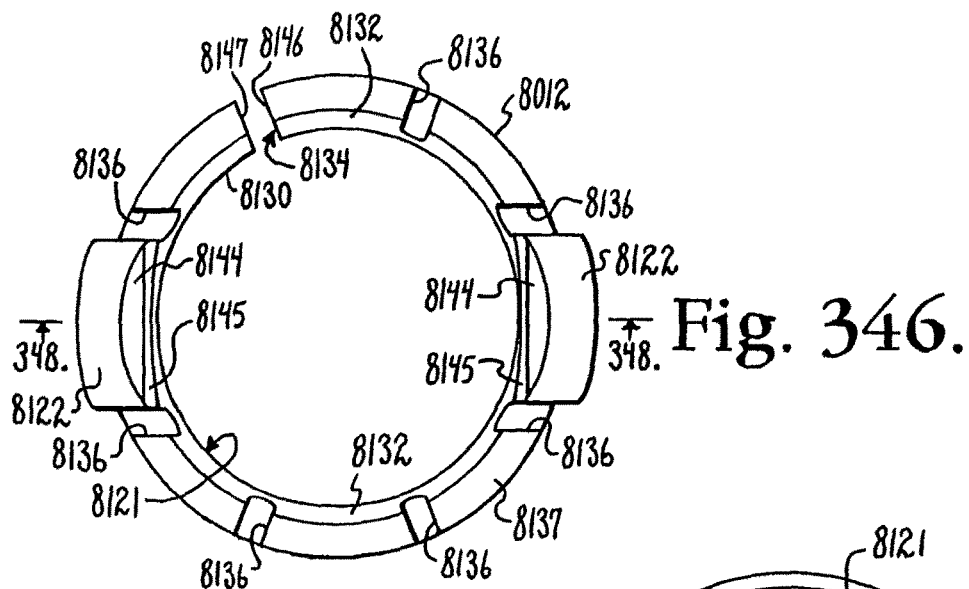

FIG. 346 is a top plan view of the retainer of FIG. 343.

Figure 347:
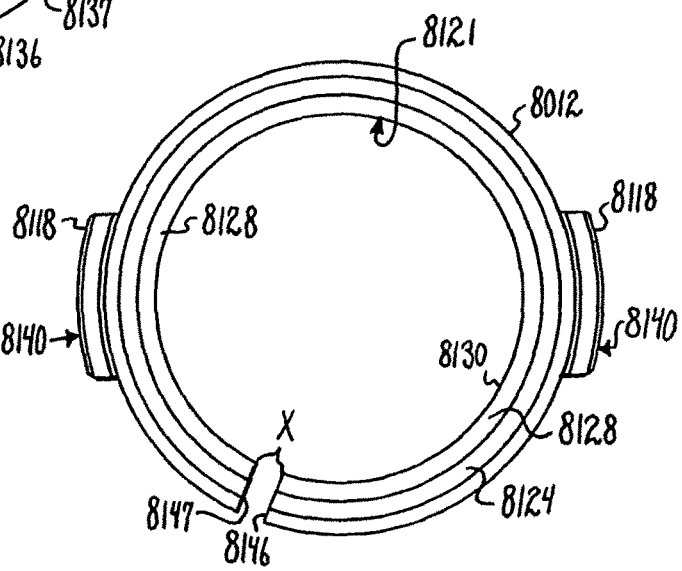

FIG. 347 is a bottom plan view of the retainer of FIG. 343.

Figure 348:
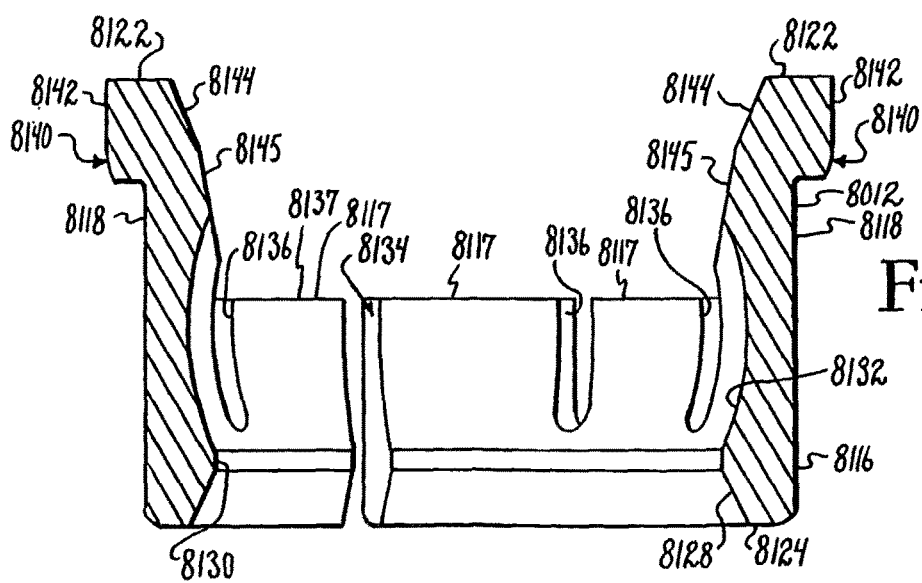

FIG. 348 is a cross-sectional view taken along the line 348-348 of FIG. 346.

Figure 349:
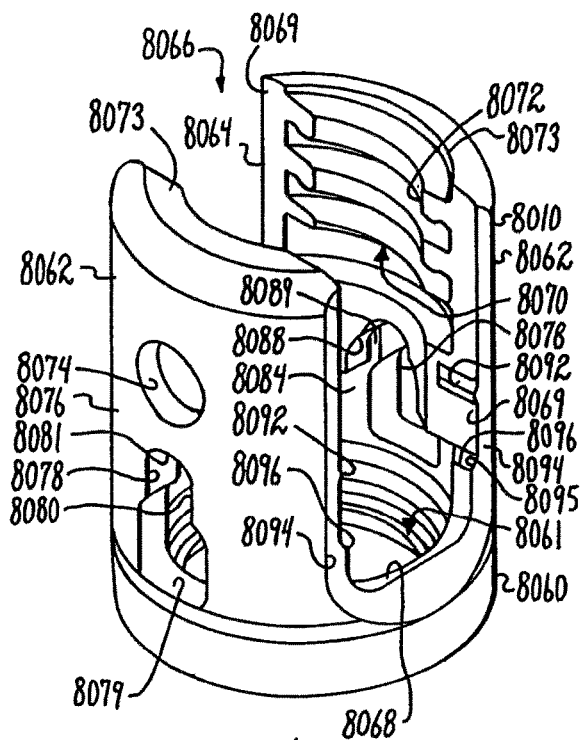

FIG. 349 is an enlarged perspective view of the receiver of FIG. 340.

Figure 350:
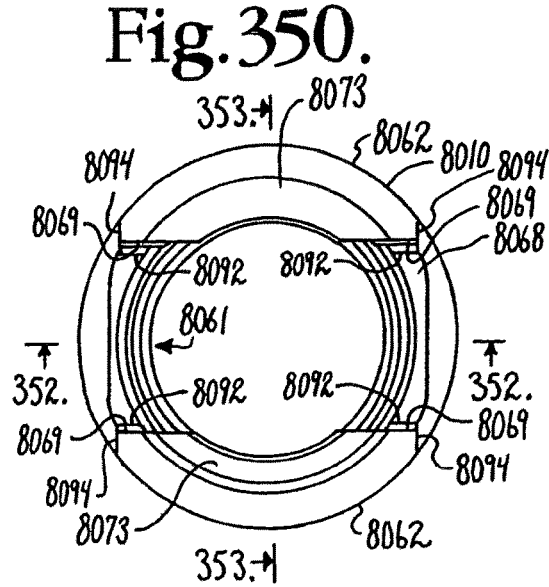

FIG. 350 is a top plan view of the receiver of FIG. 349.

Figure 351:
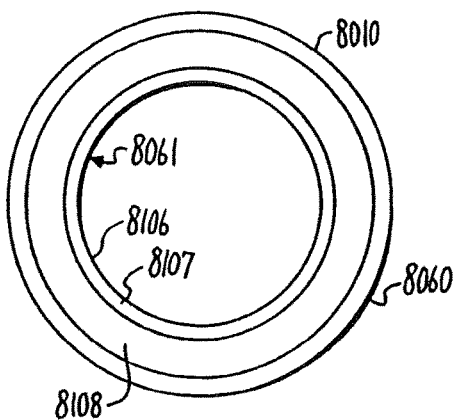

FIG. 351 is a bottom plan view of the receiver of FIG. 349.

Figure 352:
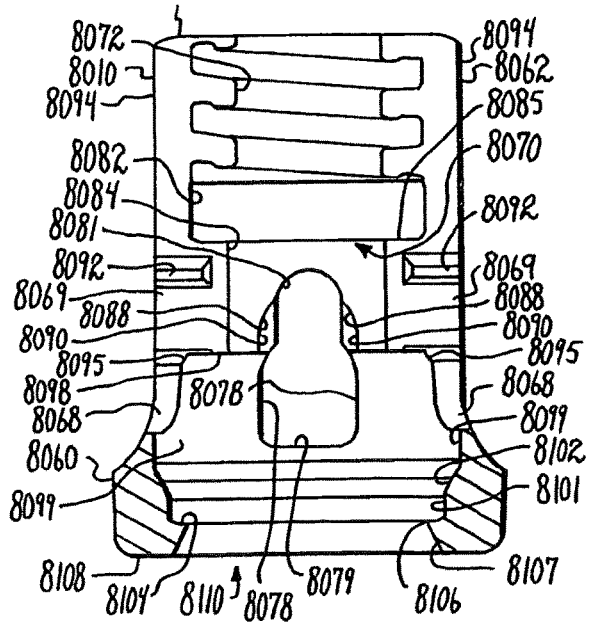

FIG. 352 is a cross-sectional view taken along the line 352-352 of FIG. 350.

Figure 353:
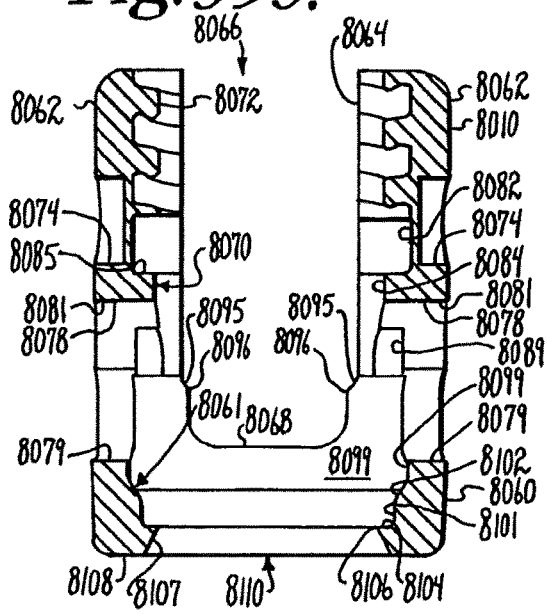

FIG. 353 is a cross-sectional view taken along the line 353-353 of FIG. 350.

Figure 354:
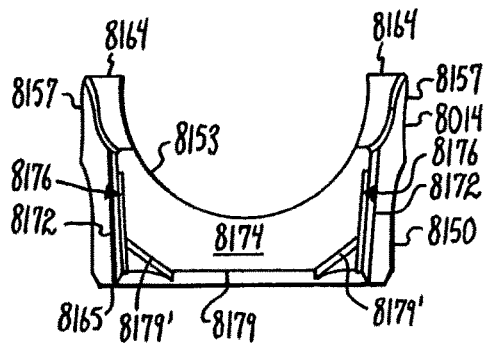

FIG. 354 is an enlarged side elevational view of the insert of FIG. 340.

Figure 355:
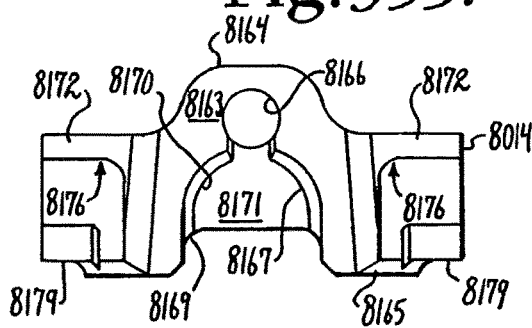

FIG. 355 is a front elevational view of the insert of FIG. 354.

Figure 356:
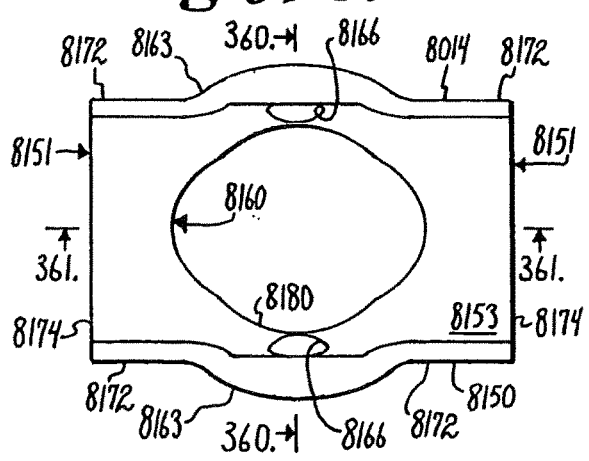

FIG. 356 is a top plan view of the insert of FIG. 354.

Figure 357:
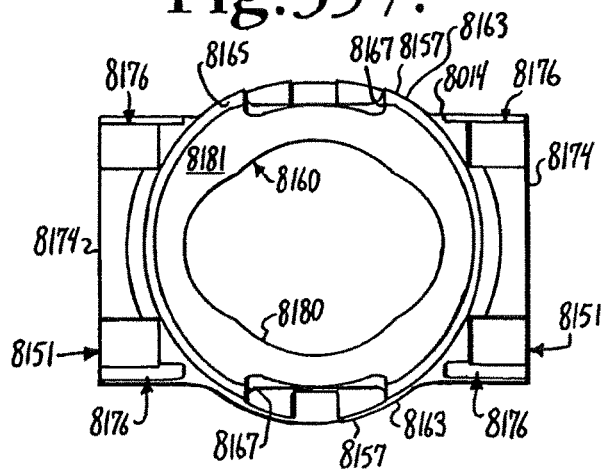

FIG. 357 is a bottom plan view of the insert of FIG. 354.

Figure 358:
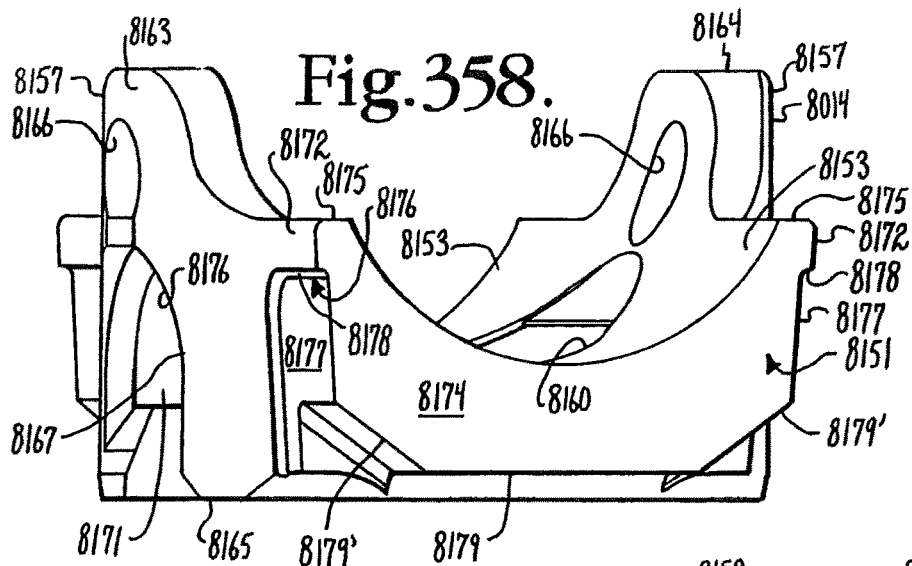

FIG. 358 is an enlarged perspective view of the insert of FIG. 354.

Figure 359:
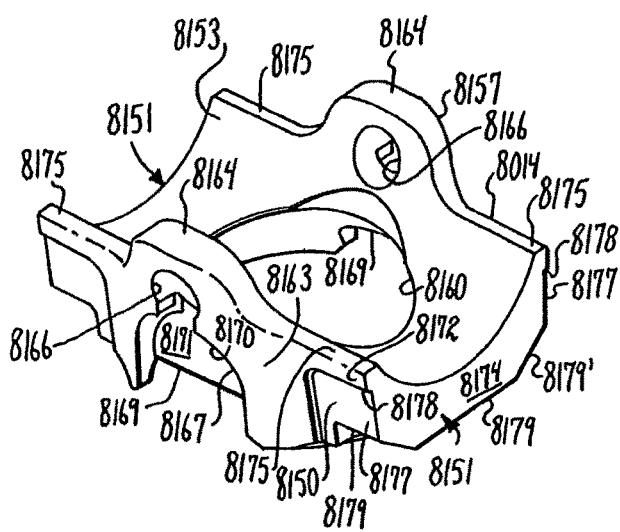

FIG. 359 is another perspective view of the insert of FIG. 354.

Figure 360:
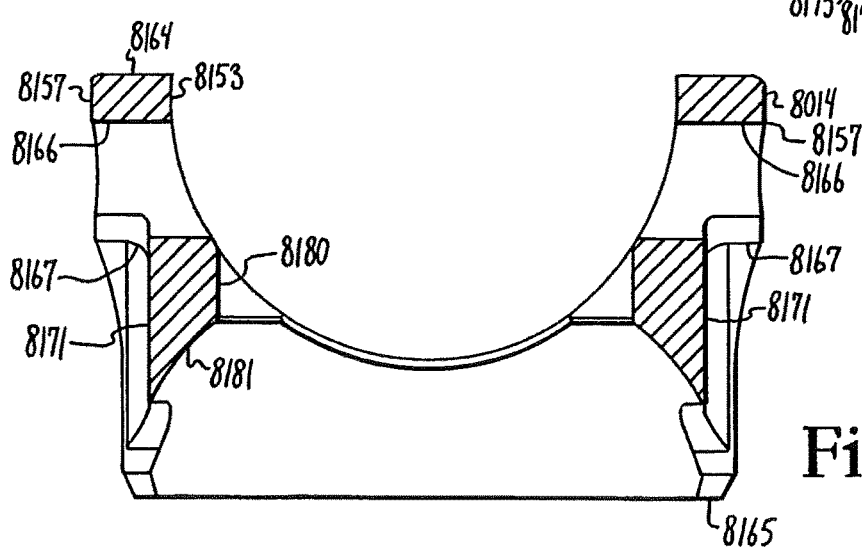

FIG. 360 is a cross-sectional view taken along the line 360-360 of FIG. 356.

Figure 361:
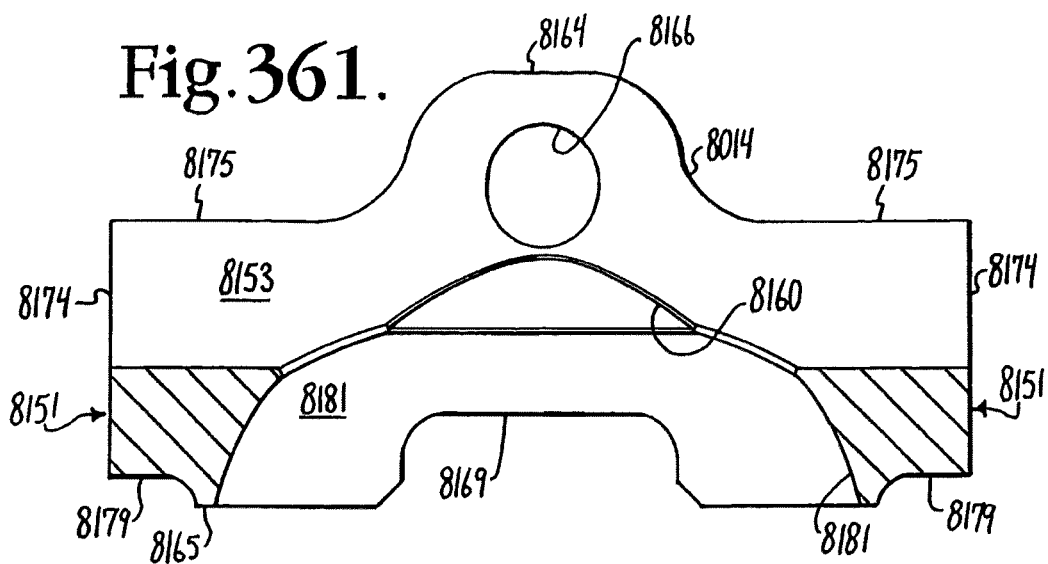

FIG. 361 is a cross-sectional view taken along the line 361-361 of FIG. 356.

Figure 362:
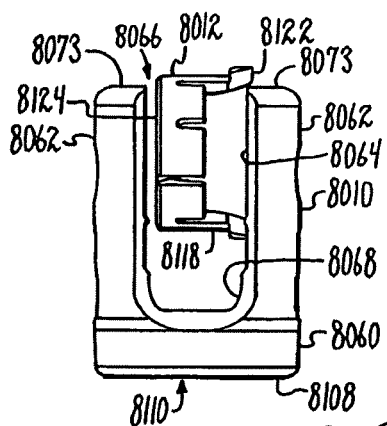

FIG. 362 is a reduced front-elevational view of the receiver of FIG. 349 and a reduced front elevational view of the retainer of FIG. 345 shown in a stage of assembly with the receiver.

Figure 363:
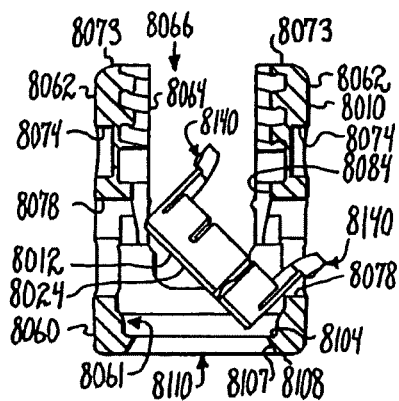

FIG. 363 is a reduced cross-sectional view of the receiver as in FIG. 353 and a reduced front elevational view of the retainer of FIG. 345 shown in a stage of assembly with the receiver subsequent to what is shown in FIG. 362.

Figure 364:
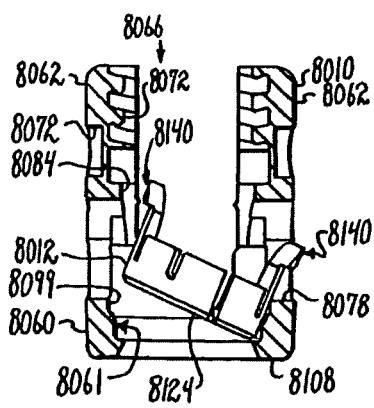

FIG. 364 is a reduced cross-sectional view of the receiver of FIG. 353 and a reduced front elevational view of the retainer of FIG. 345 shown in a stage of assembly with the receiver subsequent to what is shown in FIG. 363.

Figure 365:
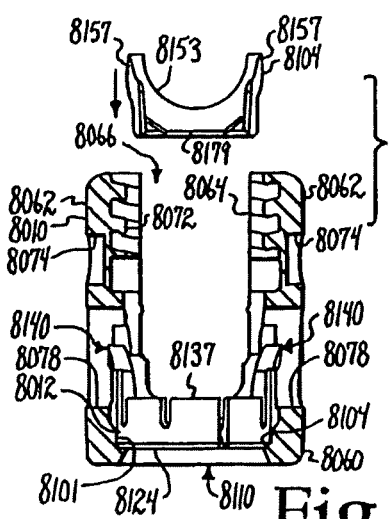

FIG. 365 is a reduced cross-sectional view of the receiver of FIG. 353 and a reduced front elevational view of the retainer of FIG. 345 shown in a stage of assembly with the receiver subsequent to what is shown in FIG. 364 and further shown in a first stage of loading with the insert of FIG. 354, also in reduced front elevational view.

Figure 366:
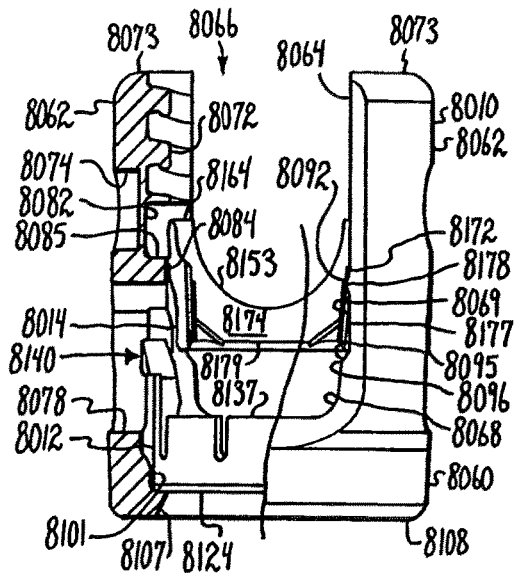

FIG. 366 is an enlarged front elevational view of the receiver, retainer and insert of FIG. 365 with portions broken away to show the detail thereof and shown in an initial stage of assembly of the insert into the receiver.

Figure 367:
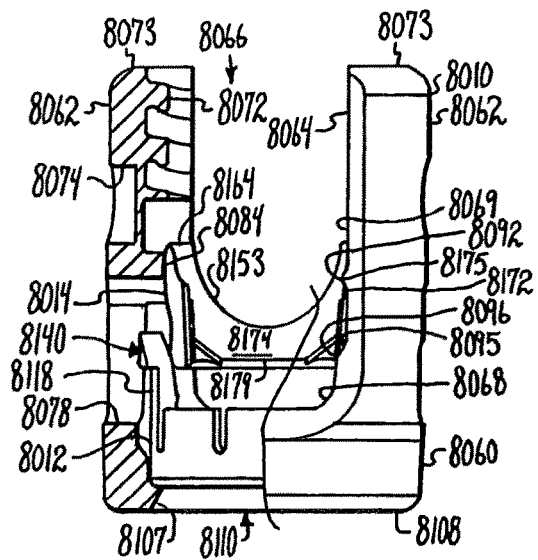

FIG. 367 is a front elevational view of the receiver, retainer and insert of FIG. 366 with portions broken away to show the detail thereof and shown in a stage of assembly subsequent to what is shown in FIG. 366.

Figure 368:
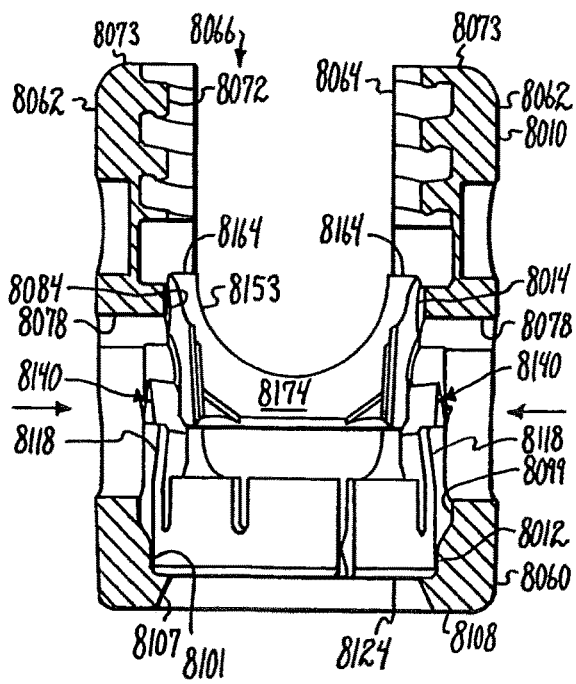

FIG. 368 is an enlarged front elevational view of the receiver, retainer and insert of FIG. 367 with portions broken away to show the detail thereof and shown in a stage of assembly subsequent to what is shown in FIG. 367.

Figure 369:
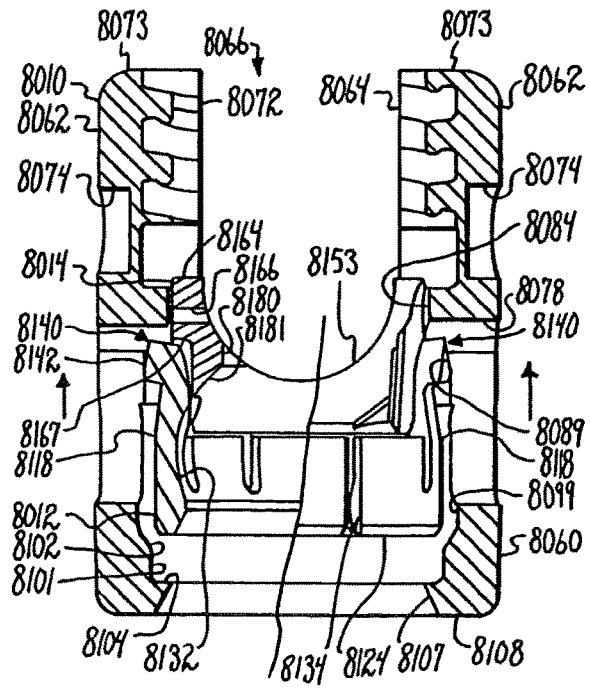

FIG. 369 is a front elevational view of the receiver, retainer and insert of FIG. 368 with portions broken away to show the detail thereof and shown in a stage of assembly subsequent to what is shown in FIG. 368.

Figure 370:
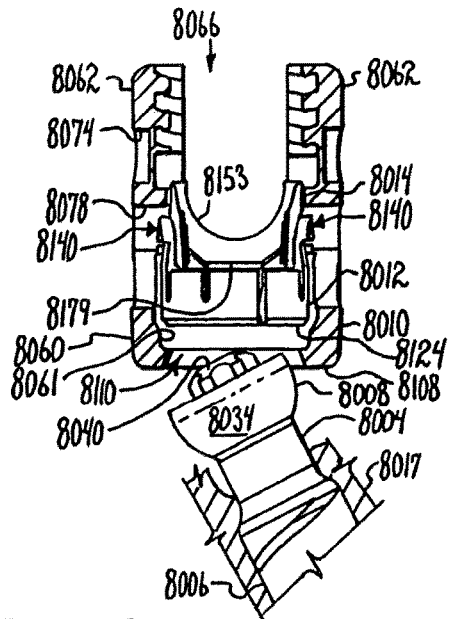

FIG. 370 is a reduced front elevational view of the receiver, retainer and insert of FIG. 369 with portions broken away to show the detail thereof and shown in a first stage of assembly with a shank of FIG. 340, in reduced and partial front elevational view and shown implanted in a vertebra.

Figure 371:
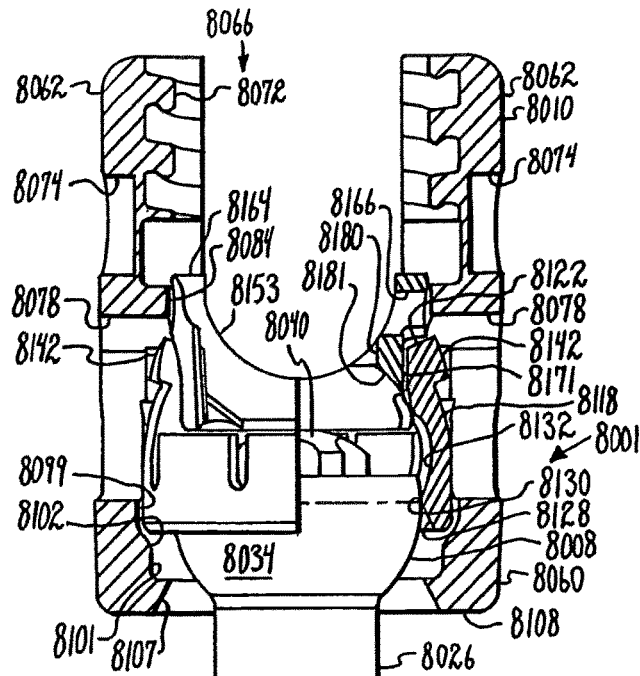

FIG. 371 is an enlarged and partial front elevational view of the receiver, retainer, insert and shank of FIG. 370 with portions broken away to show the detail thereof and shown in a stage of assembly subsequent to what is shown in FIG. 370.

Figure 372:
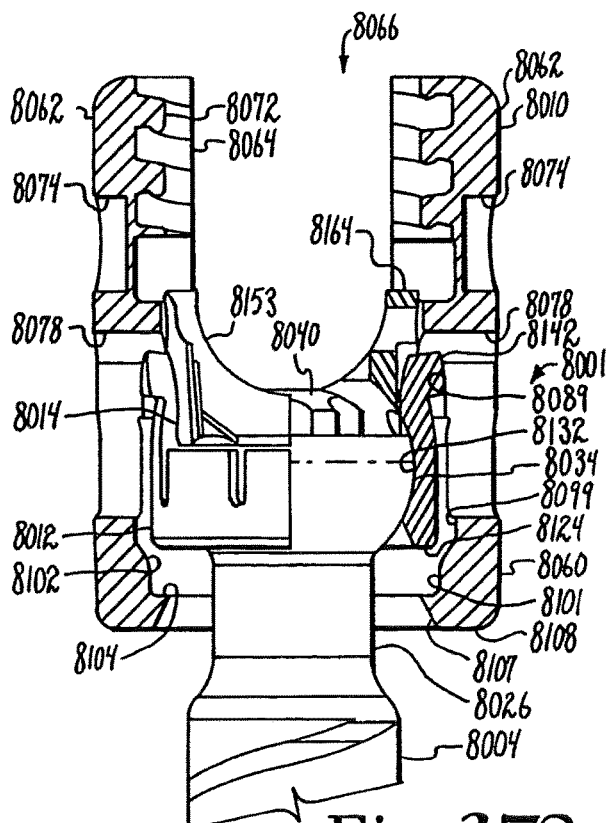

FIG. 372 is a partial front elevational view of the receiver, retainer, insert and shank of FIG. 371 with portions broken away to show the detail thereof and shown in a stage of assembly subsequent to what is shown in FIG. 371.

Figure 373:
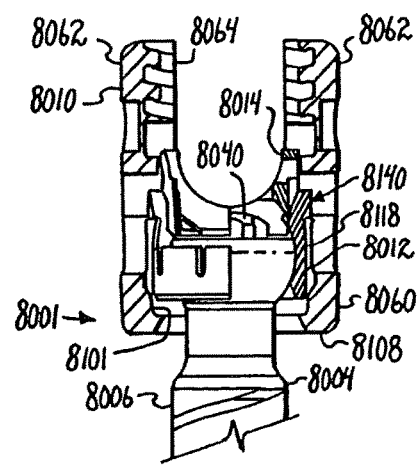

FIG. 373 is a reduced and partial front elevational view of the receiver, retainer, insert and shank of FIG. 372 with portions broken away to show the detail thereof and shown in a stage of assembly subsequent to what is shown in FIG. 372.

Figure 374:
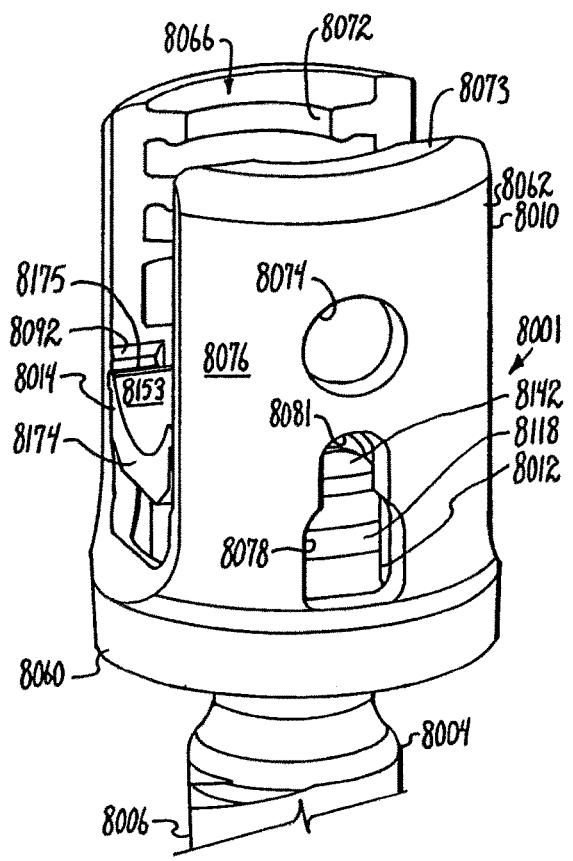

FIG. 374 is an enlarged and partial perspective view of the assembly of FIG. 373.

Figure 375:
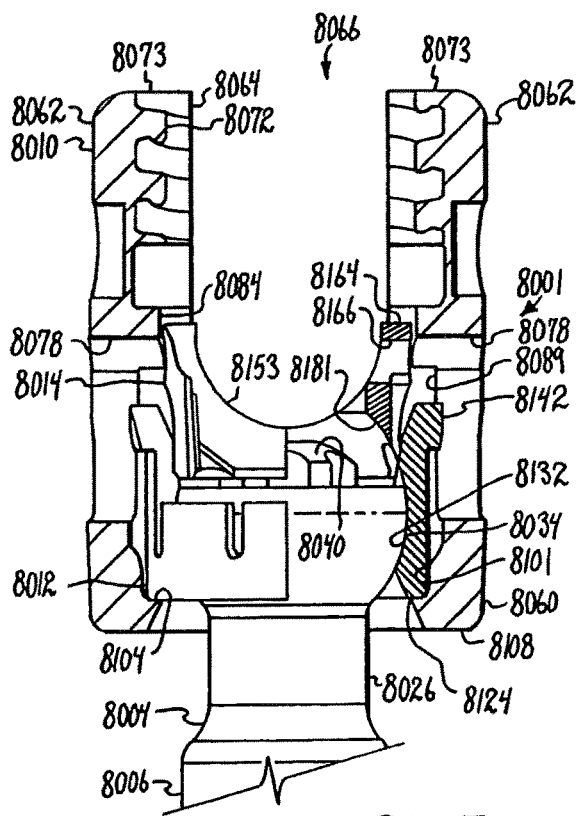

FIG. 375 is an enlarged and partial front elevational view of the receiver, retainer, insert and shank of FIG. 373 with portions broken away to show the detail thereof and shown in a stage of assembly subsequent to what is shown in FIGS. 373 and 374.

Figure 376:
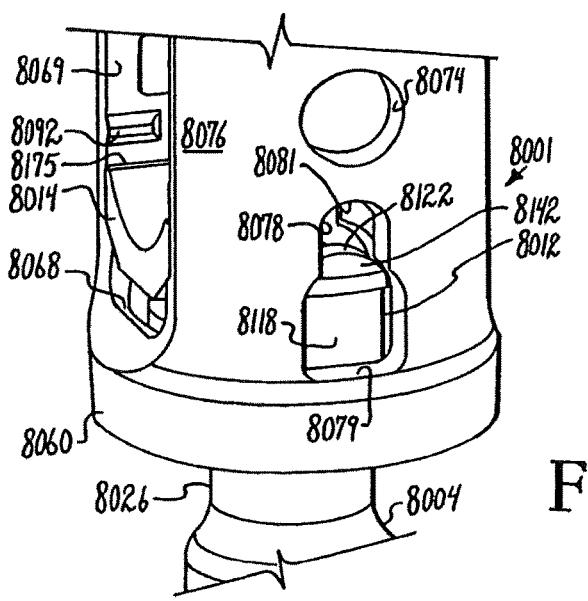

FIG. 376 is an enlarged and partial perspective view of the assembly of FIG. 375.

Figure 377:
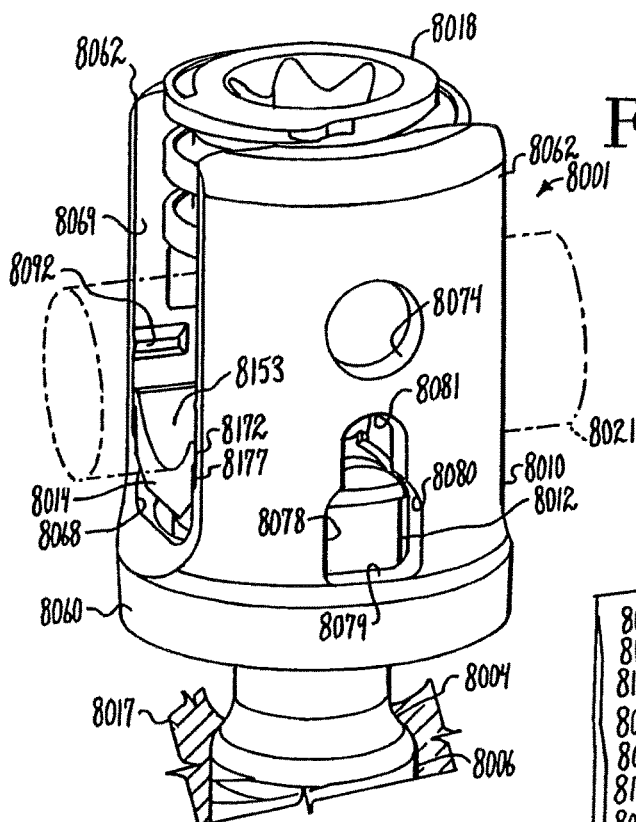

FIG. 377 is an enlarged and partial perspective view, similar to FIG. 376 and further showing the rod (in phantom) and closure of FIG. 340 in a stage of assembly and also in enlarged perspective view.

Figure 378:
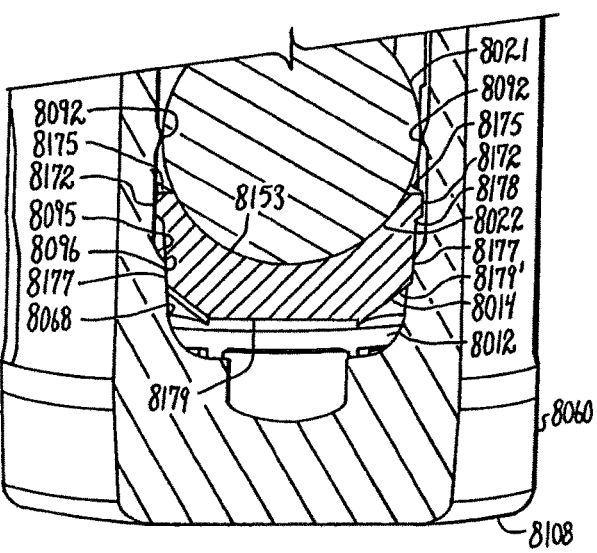

FIG. 378 is an enlarged and partial front elevational view of the assembly of FIG. 377, with a portion of the receiver broken away to show the detail thereof.

Figure 379:
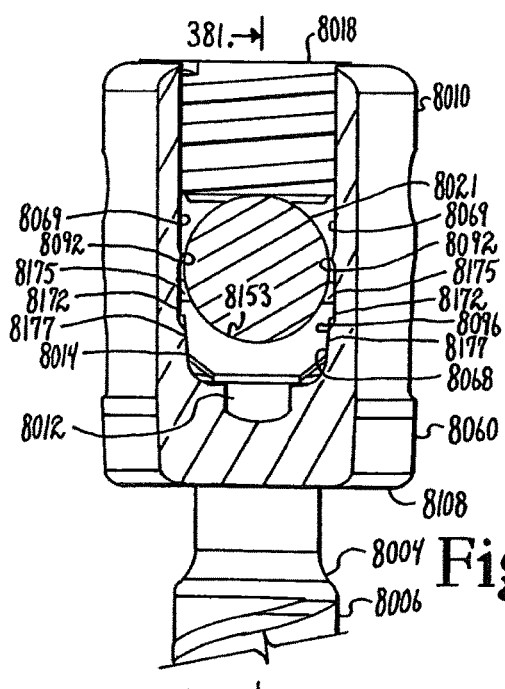

FIG. 379 is a reduced and partial front elevational view, similar to FIG. 378, with a portion of the receiver broken away to show the detail thereof, and shown in a final stage of assembly subsequent to that shown in FIGS. 377 and 378.

Figure 380:
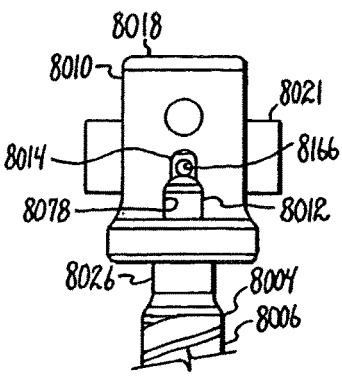

FIG. 380 is a reduced and partial side elevational view of the final assembly of FIG. 379.

Figure 381:
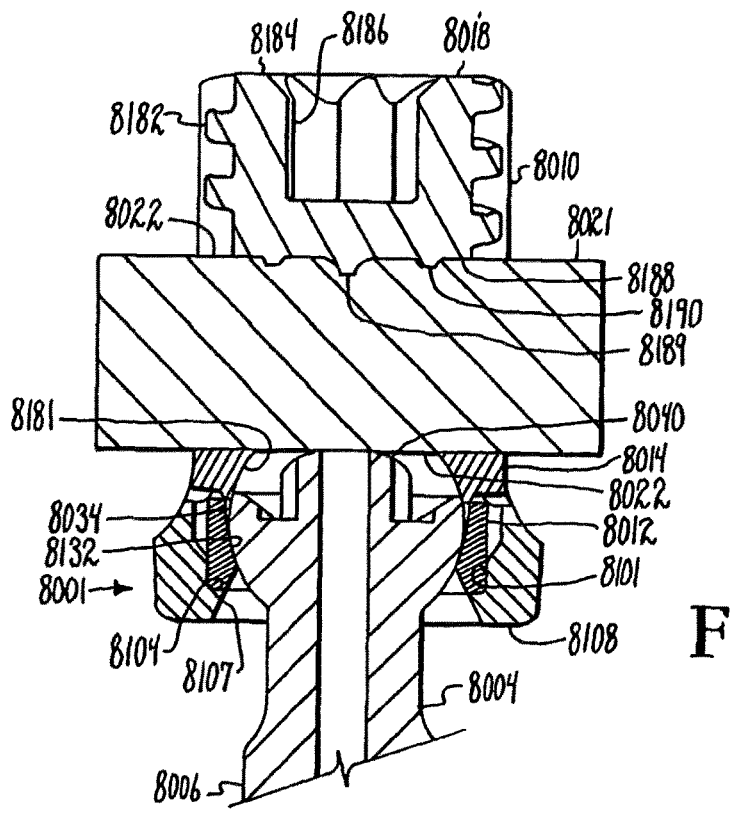

FIG. 381 is an enlarged and partial cross-sectional view taken along the line 381-381 of FIG. 379.

Figure 382:
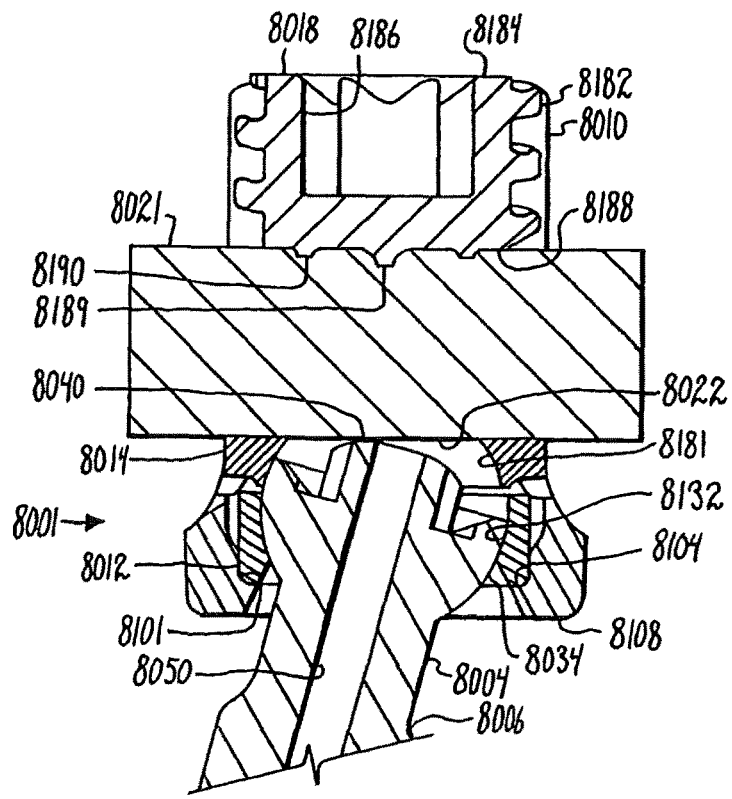

FIG. 382 is a partial cross-sectional view, similar to FIG. 381, showing an alternative position of the shank with respect to the receiver.

FIG. 383 is a reduced and partial perspective and partially exploded view of the assembly of FIG. 382, showing the closure and rod being removed from the receiver and the insert retaining the shank in a locked position.

FIG. 384 is a partial perspective and partially exploded view similar to FIG. 383, showing the closure and hard rod of FIG. 383 being replaced by an alternative closure and a deformable rod.

FIG. 385 is an enlarged and partial side elevational view of the assembly of FIG. 384 with portions broken away to show the detail thereof.

Figure 386:
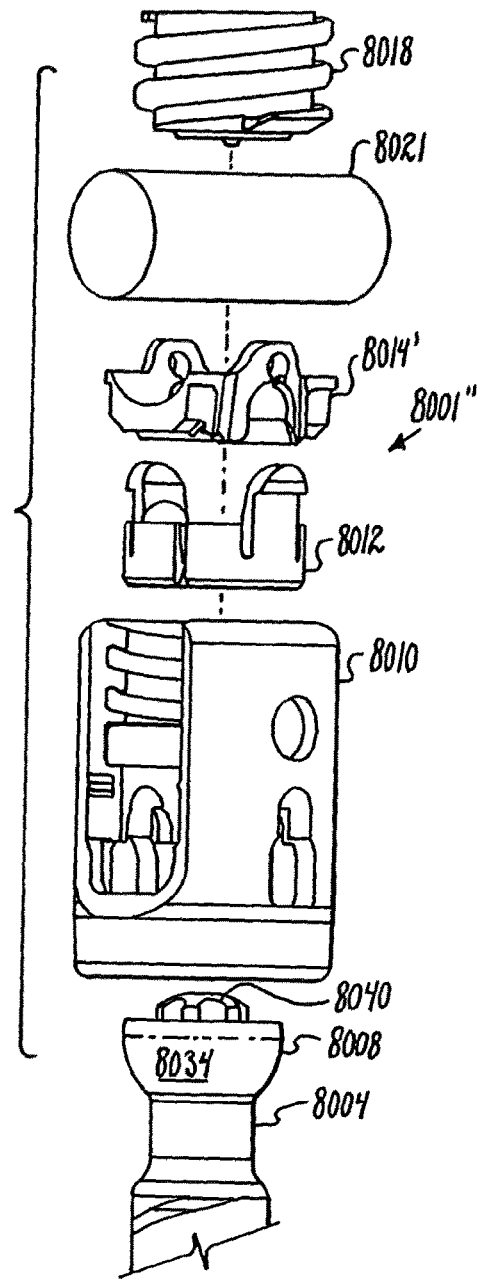

FIG. 386 is an exploded and partial perspective view of an alternative bone screw assembly according to the invention including a shank, a receiver, a retainer and a non-locking insert, and further shown with a rod and a closure top.

Figure 387:
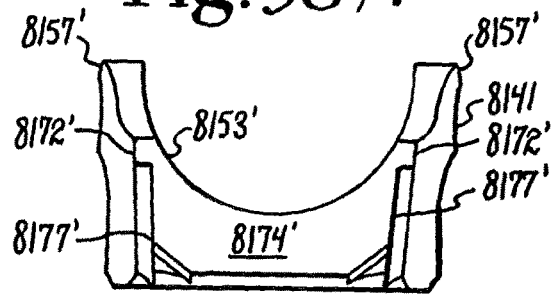

FIG. 387 is an enlarged front elevational view of the insert of FIG. 386.

Figure 388:
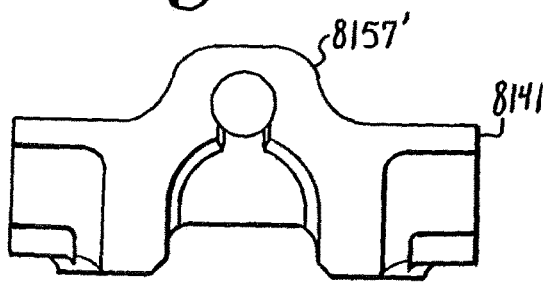

FIG. 388 is a side elevational view of the insert of FIG. 387.

Figure 389:
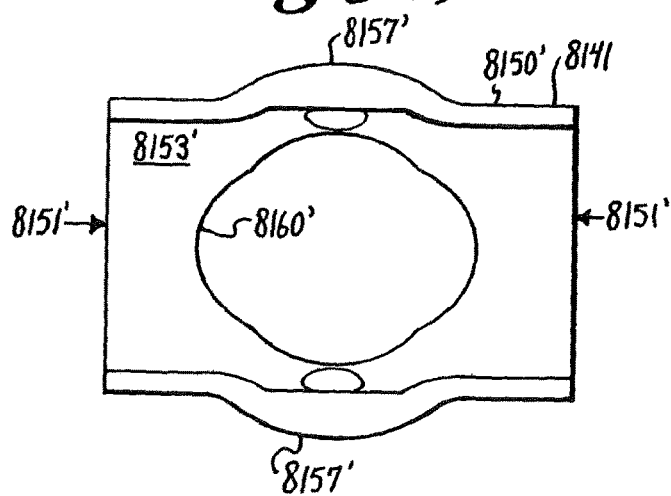

FIG. 389 is a top plan view of the insert of FIG. 387.

Figure 390:
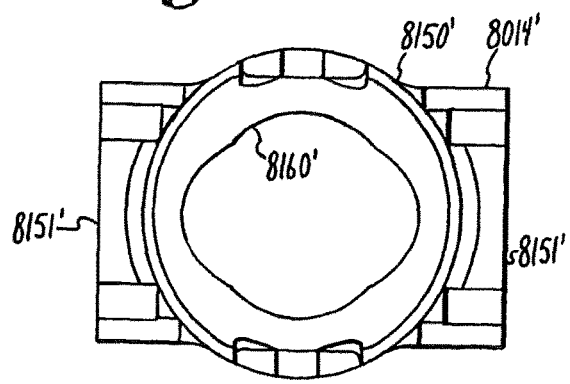

FIG. 390 is a bottom plan view of the insert of FIG. 387.

Figure 391:
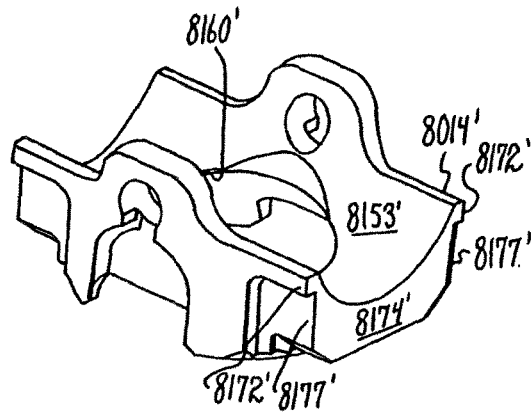

FIG. 391 is a perspective view of the insert of FIG. 387.

Figure 392:
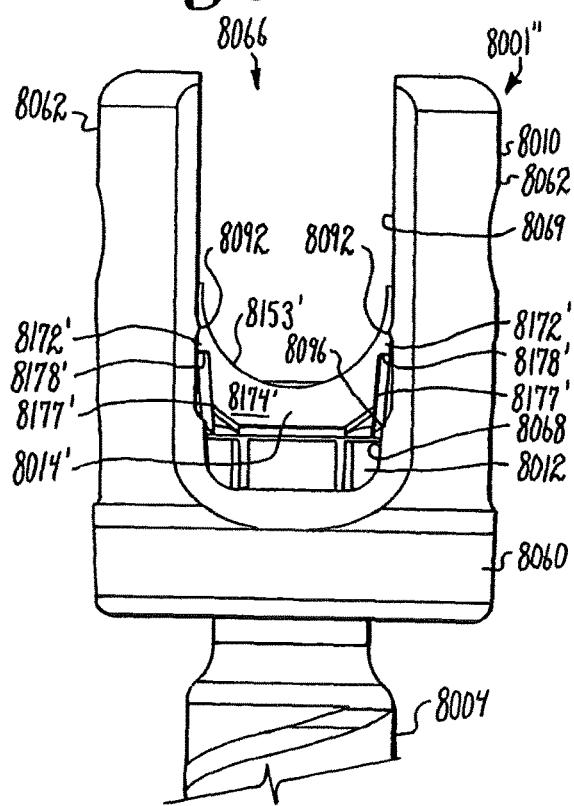

FIG. 392 is an enlarged and partial front elevational view of the receiver, the shank, the retainer and the insert of FIG. 386 shown in a stage of assembly.

Figure 393:
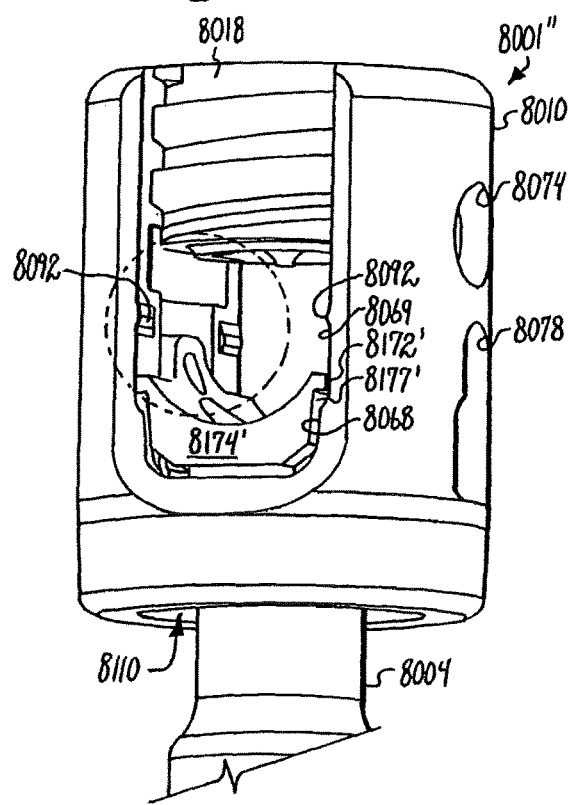

FIG. 393 is an enlarged and partial perspective view of the assembly of FIG. 386 shown fully assembled and with the rod in phantom.

Figure 394:
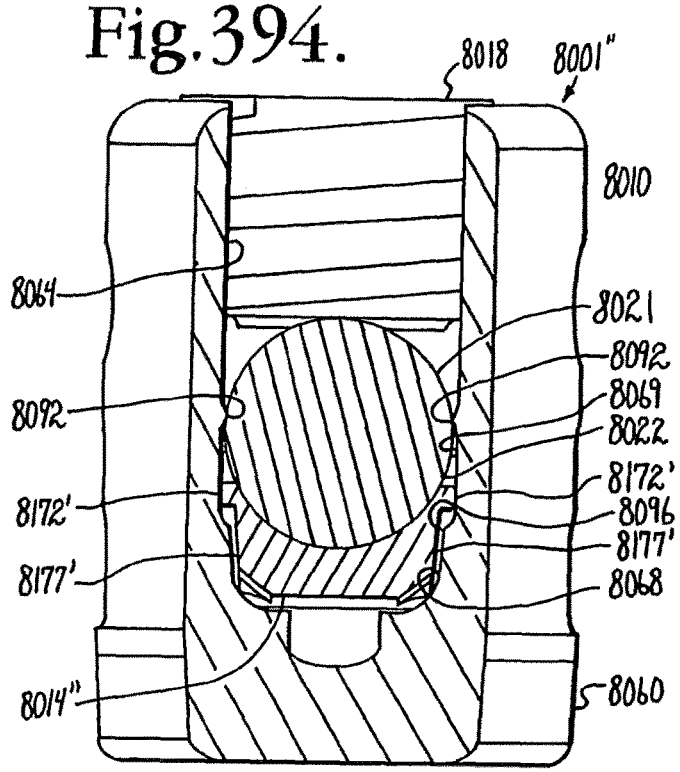

FIG. 394 is an enlarged and partial front elevational view if the assembly of FIG. 393 with portions broken away to show the detail thereof.

Figure 395:
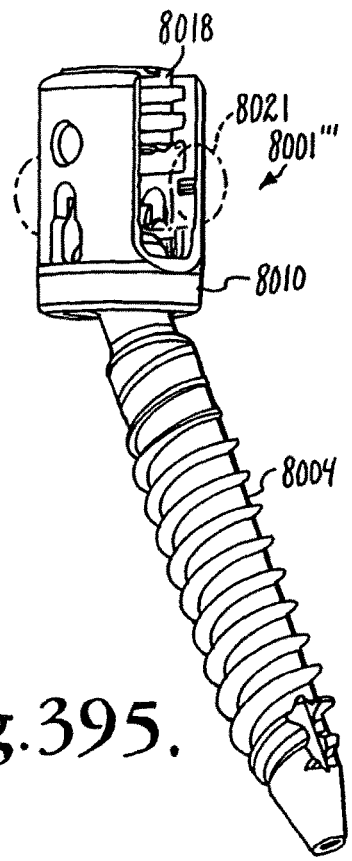

FIG. 395 is a reduced perspective view, similar to FIG. 393, showing an alternative angular position of the shank with respect to the receiver.

Figure 396:
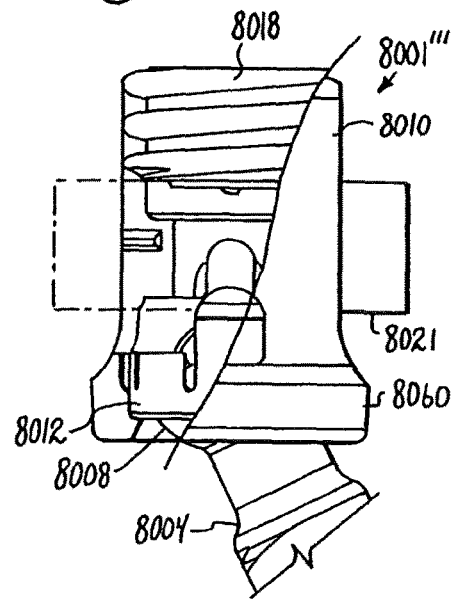

FIG. 396 is an enlarged and partial side elevational view of the assembly as shown in FIG. 395 with portions broken away to show the detail thereof.

Figure 397:
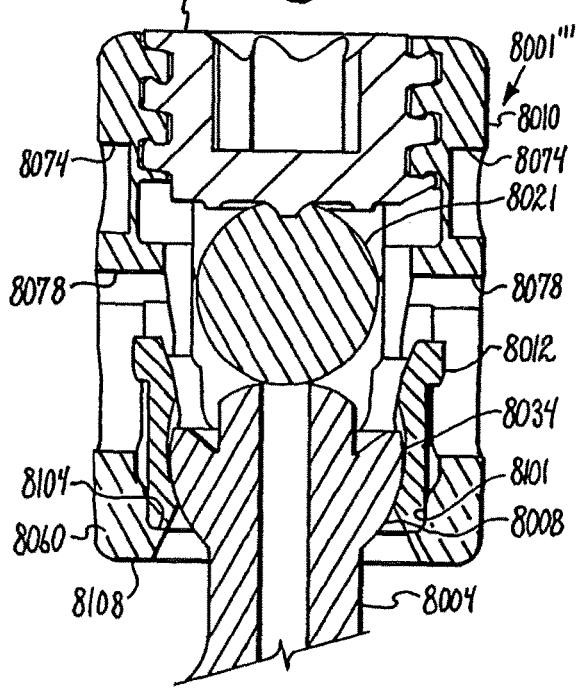

FIG. 397 is a reduced and partial front elevational view of the assembly of FIG. 394 with further portions broken away to show the detail thereof.

Figure 398:
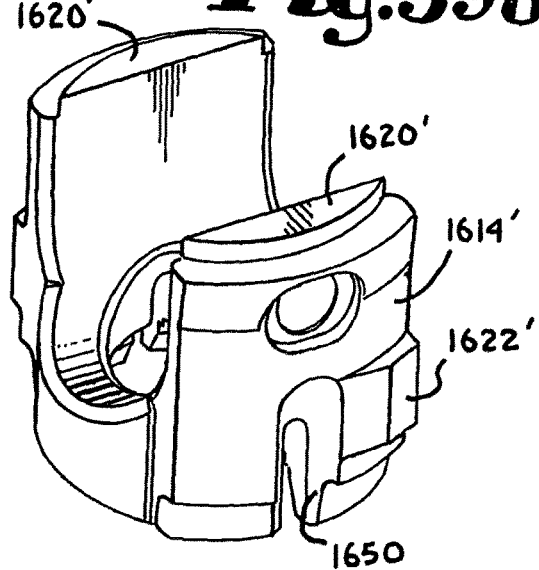

FIG. 398 is a perspective view of an alternative insert for use with the assembly of FIG. 91.

Figure 399:
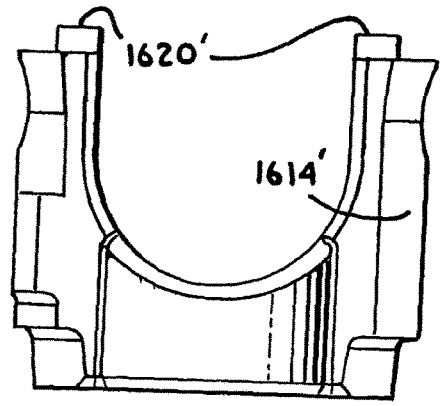

FIG. 399 is a front elevational view of the insert of FIG. 398.

Figure 400:
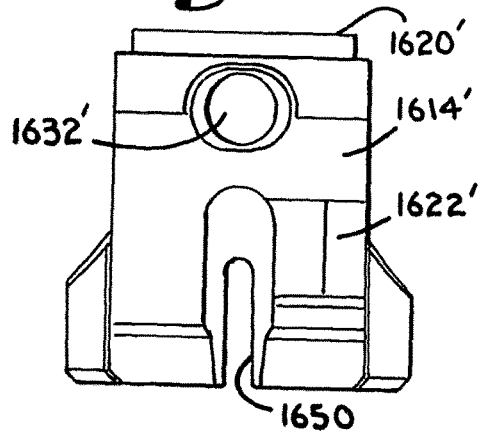

FIG. 400 is a side elevational view of the insert of FIG. 398.

Figure 401:
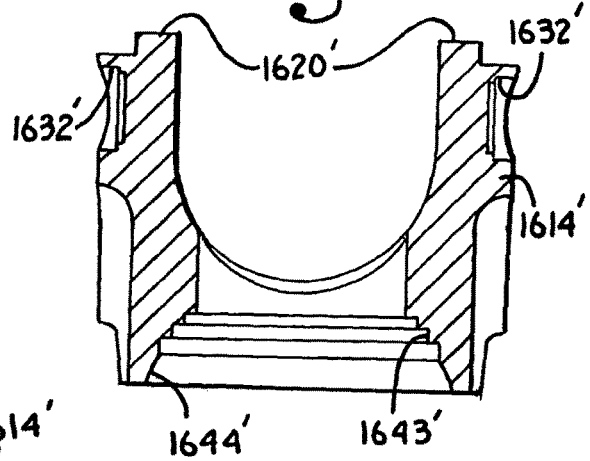

FIG. 401 is a front elevational view, similar to FIG. 399 with portions broken away to show the detail thereof.

Figure 402:
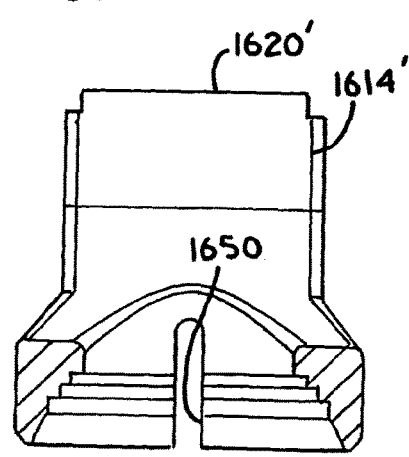

FIG. 402 is a side elevational view, similar to FIG. 400 with portions broken away to show the detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-31 the reference number 1 generally represents a polyaxial bone screw apparatus or assembly according to the present invention. The assembly 1 includes a shank 4, that further includes a body 6 integral with an upwardly extending upper portion or capture structure 8; a receiver 10; a retainer structure 12 and a compression or pressure insert 14. The receiver 10, retainer 12 and compression insert 14 are initially assembled and may be further assembled with the shank 4 either prior or subsequent to implantation of the shank body 6 into a vertebra 13, as will be described in greater detail below. FIG. 1 further shows a closure structure 18 of the invention for capturing a longitudinal member, for example, a rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 13. The illustrated rod 21 is hard, stiff, nonelastic and cylindrical, having an outer cylindrical surface 22. It is foreseen that in other embodiments, the rod 21 may be elastic, deformable and/or of a different cross-sectional geometry. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

The shank 4, best illustrated in FIGS. 1-3 and 22, is elongate, with the shank body 6 having a helically wound bone implantable thread 24 (single or dual lead thread form) extending from near a neck 26 located adjacent to the upper portion or capture structure 8, to a tip 28 of the body 6 and extending radially outwardly therefrom. During use, the body 6 utilizing the thread 24 for gripping and advancement is implanted into the vertebra 13 leading with the tip 28 and driven down into the vertebra with an installation or driving tool 29, so as to be implanted in the vertebra to near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion 8 that provides a connective or capture apparatus disposed at a distance from the upper end 32 and thus at a distance from the vertebra 13 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 and terminates at a substantially planar top surface 38. The spherical surface 34 has an outer radius configured for sliding cooperation and ultimate frictional mating with a concave surface of the compression insert 14 having a substantially similar radius, and also a flat or, in some embodiments, curved surface of the retainer 12, discussed more fully in the paragraphs below. The top surface 38 is substantially perpendicular to the axis A. The spherical surface 34 shown in the present embodiment is substantially smooth with the exception of a stepped or graduated upper surface portion 40 located adjacent to the top surface 38 and sized and shaped for cooperation and ultimate frictional engagement with the compression insert 14. In the illustrated embodiment the surface portion 40 includes at least three graduated cylindrical surfaces disposed substantially parallel to the axis A and adjacent perpendicular step surfaces that are disposed generally perpendicular to the axis A. It is foreseen that the surface portion 40 may include greater or fewer number of stepped surfaces. It is foreseen that the surface portion 40 and also the rest of the surface 34 may additionally or alternatively include a roughened or textured surface or surface finish, or may be scored, knurled, or the like, for enhancing frictional engagement with the retainer 12 and/or the compression insert 14.

Figure 22:
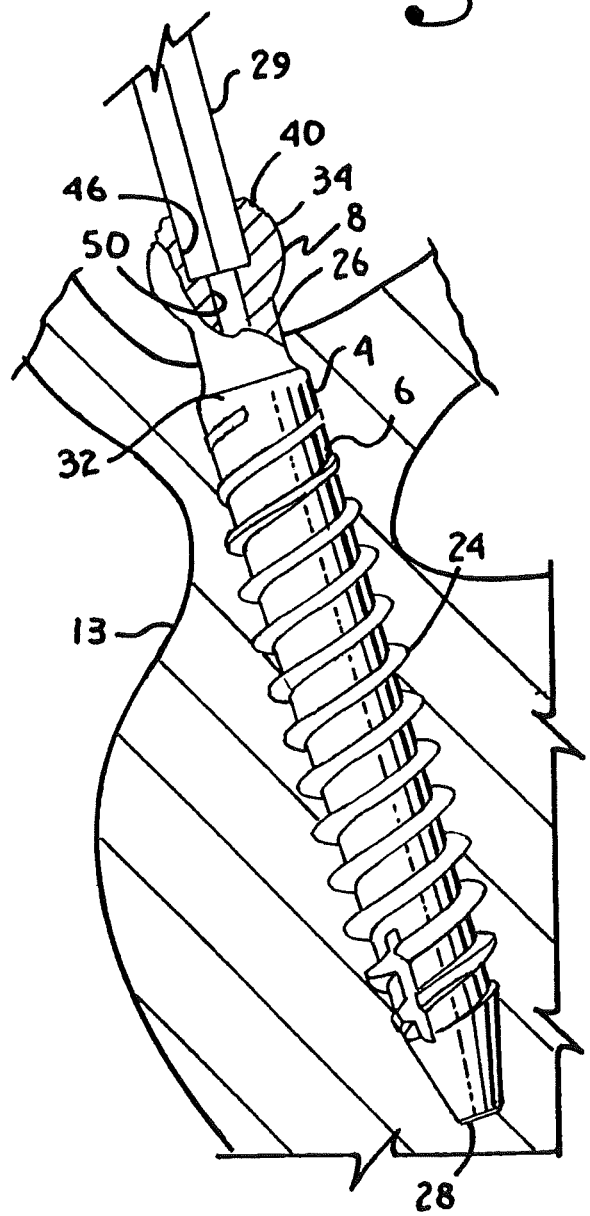
FIG. 22 is an enlarged and partial front elevational view of the shank of FIG. 1 with portions broken away to show the detail thereof, shown with a driving tool in a stage of implantation in a vertebra.
Figure 23:
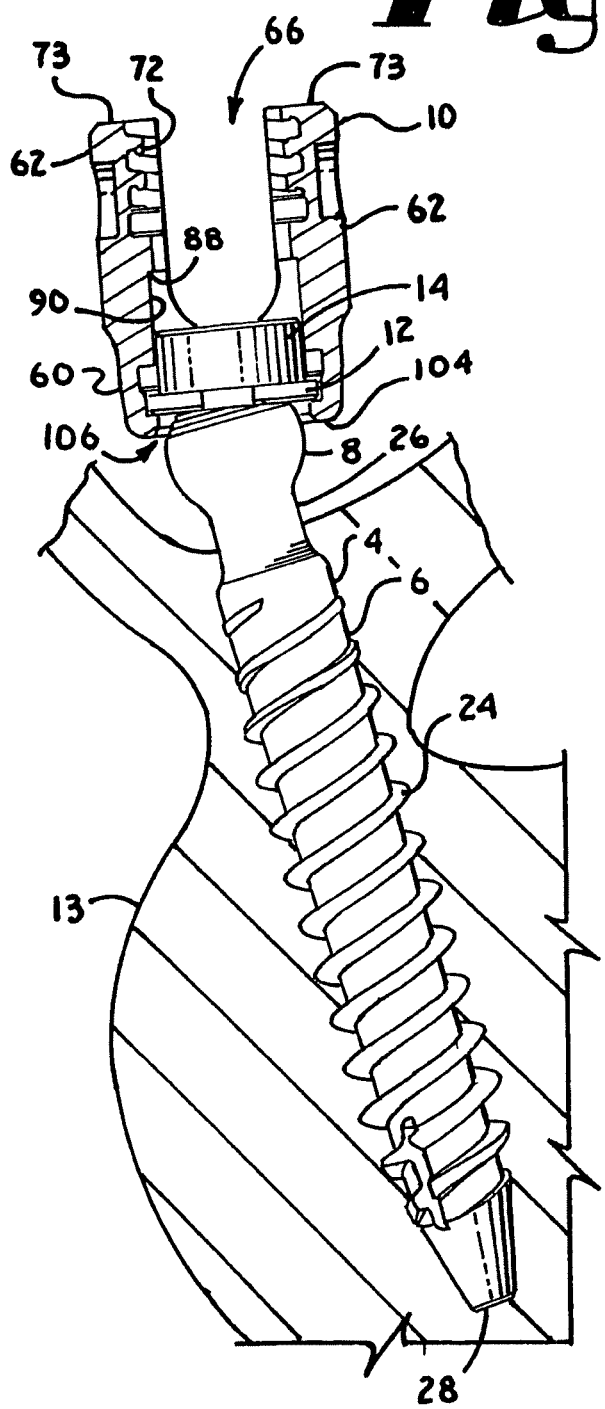
FIG. 23 is a partial front elevational view, similar to FIG. 22 and further showing an early stage of assembly of the shank with the pre-assembled receiver, compression insert and retainer of FIGS. 20 and 21.
Figure 26:
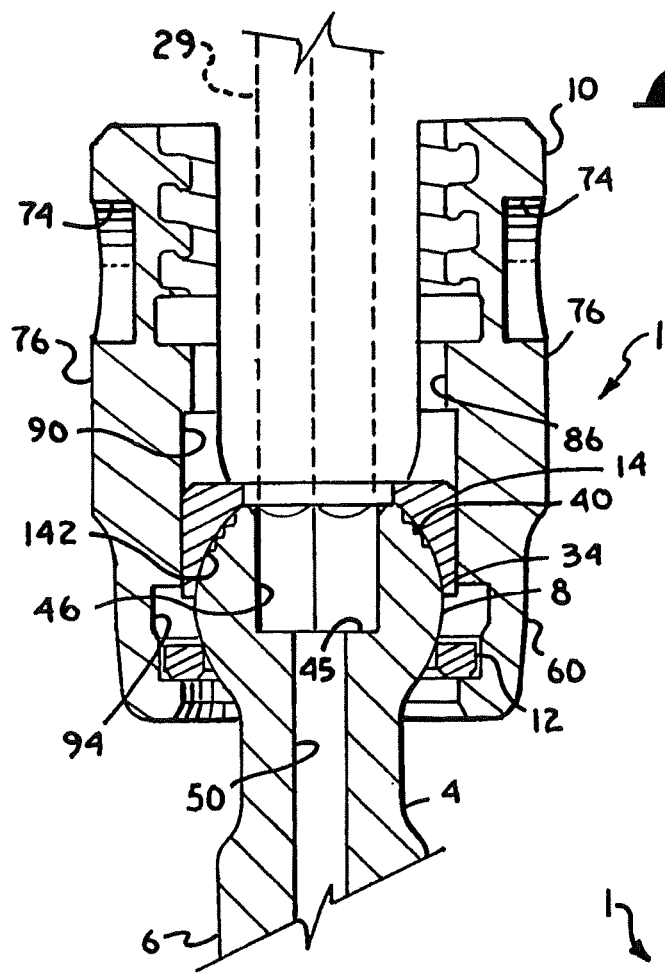
FIG. 26 is a partial front elevational view with portions broken away, similar to FIG. 25, showing the shank fully assembled with the receiver, compression insert and retainer and in a position ready to receive the longitudinal connecting member shown in FIG. 1 and further shown with a driving tool in phantom.
Figure 27:
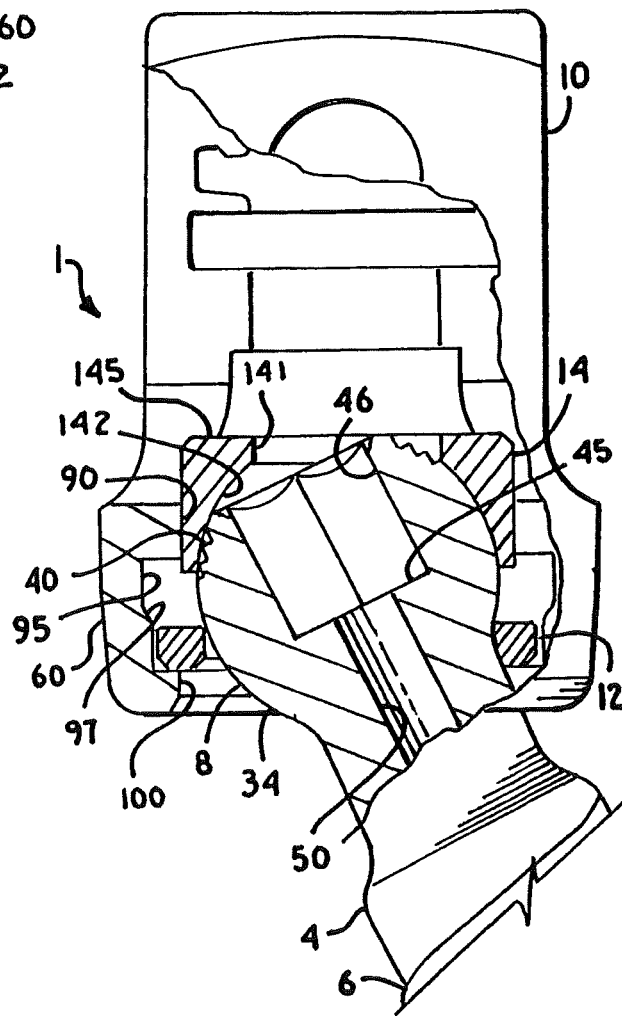
FIG. 27 is a partial side elevational view of the shank, receiver, compression insert and retainer of FIG. 26, with portions broken away to show the detail thereof and further shown with the shank disposed at an angle with respect to the receiver.

A counter sunk substantially planar base or seating surface 45 partially defines an internal drive feature or imprint 46. The illustrated internal drive feature 46 is an aperture formed in the top surface 38 and has a hex shape designed to receive the hex tool 29 of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like. The seat or base 45 of the drive feature 46 is disposed perpendicular to the axis A with the drive feature 46 otherwise being coaxial with the axis A. In operation, the driving tool 29 is received in the internal drive feature 46, being seated at the base 45 and engaging the six faces of the drive feature 46 for both driving and rotating the shank body 6 into the vertebra 13, either before the shank 4 is attached to the receiver 10 as shown in FIG. 22 or after the shank 4 is attached to the receiver 10 as shown in FIG. 26, with the shank body 6 being driven into the vertebra 13 with the driving tool extending into the receiver 10 as shown in phantom.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper opening communicating with the external drive 46 at the surface 45. The bore 50 is coaxial with the threaded body 6 and the upper portion 8. The bore 50 provides a passage through the shank 4 interior for a length of wire (not shown) inserted into the vertebra 13 prior to the insertion of the shank body 6, the wire providing a guide for insertion of the shank body 6 into the vertebra 13.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Cal^o$ ($^PO4$) 6 (OH)$_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-7, the receiver 10 has a generally U-shaped appearance with a partially discontinuous substantially cylindrical inner and outer profile. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 13, the axis B is typically disposed at an angle with respect to the axis A, as shown, for example, in FIGS. 27-29.

The receiver 10 includes a substantially cylindrical base 60 integral with a pair of opposed upstanding arms 62 forming a cradle and defining a channel 64 between the arms 62 with an upper opening, generally 66, and a U-shaped lower seat 68, the channel 64 having a width for operably snugly receiving the rod 21 between the arms 62. Each of the arms 62 has an interior surface, generally 70, that includes various inner cylindrical profiles, an upper of which is a partial helically wound guide and advancement structure 72 located adjacent top surfaces 73 of each of the arms 62. In the illustrated embodiment, the guide and advancement structure 72 is a partial helically wound interlocking flange-form configured to mate under rotation with a similar structure on the closure structure 18, as described more fully below. However, it is foreseen that the guide and advancement structure 72 could alternatively be a square-shaped thread, a buttress thread, a reverse angle thread or other thread-like or non-threadlike helically wound discontinuous advancement structure for operably guiding under rotation and advancing the closure structure 18 downward between the arms 62, as well as eventual torquing when the closure structure 18 abuts against the rod 21.

An opposed pair of tool receiving and engaging apertures 74 are formed on outer surfaces 76 of the arms 62. Furthermore, two pair of tool receiving and engaging apertures 77 are formed in front and rear surfaces 78 of the arms 62. Some or all of the apertures 74 and 77 may be used for holding the receiver 10 during assembly with the shank 4 and the retainer 12, during the implantation of the shank body 6 into a vertebra when the shank is pre-assembled with the receiver 10, and during assembly of the bone anchor assembly 1 with the rod 21 and the closure structure 18. It is foreseen that tool receiving grooves or apertures may be configured in a variety of shapes and sizes and be disposed at other locations on the receiver arms 62.

Returning to the interior surface 70 of the receiver arms 62, located below the guide and advancement structure 72 is a cylindrical surface 82 partially defining a run-out feature for the guide and advancement structure 72. The cylindrical surface 82 has a diameter equal to or slightly greater than a greater diameter of the guide and advancement structure 72. Moving downwardly, in a direction toward the base 60, adjacent the cylindrical surface 82 is a run-out seat or surface 84 that extends inwardly toward the axis B and runs perpendicular to the axis B. Adjacent to and located below the surface 84 is another cylindrical surface 86 having a diameter smaller than the diameter of the surface 82. A discontinuous annular surface 88 that provides an abutment surface or stop for capturing the compression insert 14 in the receiver 10 is located below and adjacent to the cylindrical surface 86. The abutment surface 88 is disposed substantially perpendicular to the axis B. Another cylindrical surface 90 is located below and adjacent to the surface 88. The cylindrical surface 90 is oriented substantially parallel to the axis B and is sized and shaped to slidingly receive the compression insert 14 as will be described in greater detail below. The surface 90 surrounds the U-shaped channel seat 68 and extends downwardly into the base 60. Thus, a portion of the surface 90 extends upwardly into the arms 62. The cylindrical surface 90 has a diameter greater than the diameter of the cylindrical surface 86. A continuous annular surface 92 is located below and adjacent to the cylindrical surface 90. The surface 92 is disposed in the base 60 and forms a stop for the resilient retainer 12, prohibiting the retainer 12 (when in an uncompressed configuration) from moving upwardly into a space or cavity 91 defined by the cylindrical surface 90 that holds the compression insert 14.

Another cylindrical surface 94 is located below and adjacent to the surface 92. The cylindrical surface 94 is oriented substantially parallel to the axis B and is sized and shaped to receive an expanded retainer 12 as will be described in greater detail below. The surfaces 92 and 94 partially define a circumferential recess or expansion chamber 95 that is sized and shaped to receive the retainer 12 as it expands around the shank upper portion 8 as the shank 8 moves upwardly toward the channel 64 during assembly, as well as form a restriction to prevent the expanded retainer 12 from moving upwardly with the shank portion 8, the surface 92 preventing the retainer 12 from passing from the chamber 95 into the cavity 91 whether the retainer 12 is in an expanded position as shown in FIG. 24, or in a neutral or original operative position as shown in FIG. 25. A cylindrical surface 96 located below the cylindrical surface 94 of the expansion chamber is sized and shaped to closely receive the retainer 12 when the retainer is in a neutral interim position as shown in FIG. 26, for example, or expanded operative position as shown in FIG. 29, for example. Thus, the cylindrical surface 96 has a diameter smaller than the diameter of the cylindrical surface 94 that defines the expansion chamber 95. The surface 96 also has a diameter larger than an outside diameter of the retainer 12 so that the retainer may expand outwardly into contact with the surface 96 when the bone screw shank upper portion 8 presses downwardly during locking of the shank 4 against the retainer 12. The surface 96 is joined or connected to the surface 94 by one or more beveled, curved or conical surfaces 97. The surfaces 97 allow for sliding gradual movement and/or contraction of the retainer 12 into the space defined by the surface 96 and ultimate seating of the retainer 12 on a lower annular seating surface 99 located below and adjacent to the cylindrical surface 96. The surfaces 96 and 99 provide a seating chamber for the retainer 12 wherein the retainer expands out to the surface 96 when in a locked position as shown, for example, in FIG. 29. Located below and adjacent to the annular seating surface 99 is another cylindrical surface 100 that communicates with a beveled or flared bottom opening surface 102, the surface 102 communicating with an exterior base surface 104 of the base 60, defining a lower opening, generally 106, of the receiver 10. The illustrated surface 100 has a diameter that is substantially the same as the diameter of the surface 90, allowing for slidable uploading of the compression insert 14 while requiring compression or squeezing of the retainer 12 during uploading of the retainer 12 through the lower opening 106 (see FIGS. 18 and 19).

Figure 19:
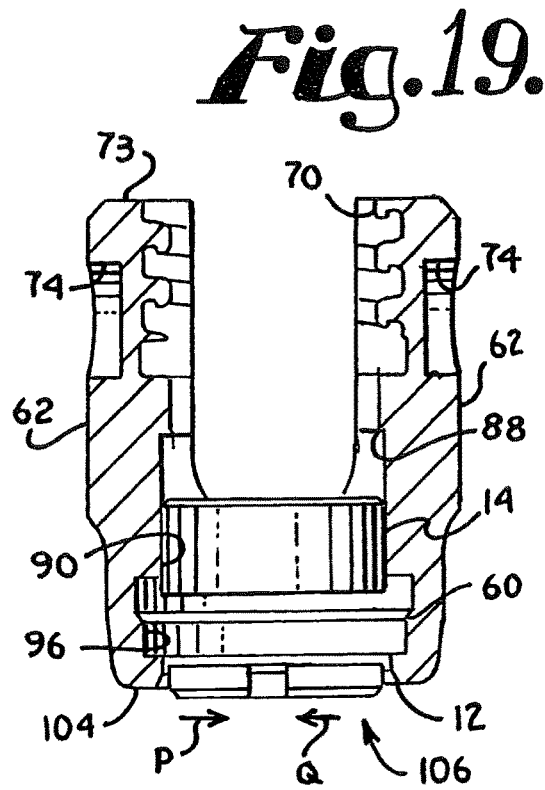
FIG. 19 is an enlarged an partial front elevational view of the receiver, compression insert and retainer of FIG. 1 with portions broken away to show the detail thereof and shown in a stage of assembly subsequent to that shown in FIG. 18.

With particular reference to FIGS. 1 and 8-12, the retainer 12 that operates to capture the shank upper portion 8 and the compression insert 14 within the receiver 10 has a central axis C that is operationally the same as the axis B associated with the receiver 10 when the shank upper portion 8 and the retainer 12 are installed within the receiver 10. The retainer 12 is made from a resilient material, such as a stainless steel or titanium alloy, so that the retainer 12 may be both compressed and expanded during various steps of assembly as will be described in greater detail below. The retainer 12 has a central channel or hollow through bore, generally 121, that passes entirely through the structure 12 from a top surface 122 to a bottom surface 124 thereof. Surfaces that define the channel or bore 121 include a discontinuous inner cylindrical surface 125 adjacent the top surface 122 and a discontinuous frusto-conical or beveled surface 127 adjacent the surface 125, both surfaces coaxial with the axis C when the retainer 12 is in a neutral non-compressed, non-expanded orientation. The retainer 12 further includes an outer cylindrical surface 130 located adjacent the top surface 122 and an outer beveled or frusto-conical surface 132 adjacent the bottom surface 124. The surface 130 is oriented parallel to the axis C. Two or more evenly spaced notches 133 are formed in the cylindrical surface 130 to more evenly distribute stress across the entire retainer during contraction and expansion thereof. In other embodiments of the invention, the notches 133 may be on the inside of the ring or they may be omitted. The resilient retainer 12 further includes first and second end surfaces, 134 and 135 disposed in spaced relation to one another when the retainer is in a neutral non-compressed state. Both end surfaces 134 and 135 are disposed substantially perpendicular to the top surface 122 and the bottom surface 124. A width X between the surfaces 134 and 135 is determined by a desired amount of compressibility of the open retainer 12 when loaded into the receiver 10. The space X shown in FIG. 8 provides adequate space between the surfaces 134 and 135 for the retainer 12 to be pinched, with the surfaces 134 and 135 compressed toward one another (as shown by arrows P and Q in FIG. 19) to a closely spaced or even touching configuration, if necessary, to an extent that the compressed retainer 12 is up or bottom loadable through the receiver opening 106 as shown in FIG. 19. After passing through the opening 106 and along a portion of the lower inner surface, the retainer 12 expands or springs back to an original uncompressed, rounded or collar-like configuration of FIGS. 8-12, see, e.g., FIG. 21. The embodiment shown in FIGS. 8-12 illustrates the surfaces 134 and 135 as substantially parallel, however, it is foreseen that it may be desirable to orient the surfaces obliquely or at a slight angle depending upon the amount of compression desired during loading of the retainer 12 into the receiver 10.

With reference to FIGS. 1 and 13-17, the compression insert 14 is illustrated that is sized and shaped to be received by and up-loaded into the receiver 10 at the lower opening 106. The compression insert 14 has an operational central axis that is the same as the central axis B of the receiver 10. The compression insert 14 has a central channel or through bore substantially defined by an inner cylindrical surface 141 coaxial with an inner partially spherical surface 142. The compression insert 14 through bore is sized and shaped to receive the driving tool 29 therethrough that engages the shank drive feature 46 when the shank body 6 is driven into bone with the receiver 10 attached. The surface 142 is sized and shaped to slidingly receive and ultimately frictionally engage the substantially spherical or domed surface 34 of the shank upper portion 8, in particular the stepped or ridged surface 40 such that the surface 142 initially slidingly and pivotally mates with the spherical surface 34 to create a ball-and-socket type joint. The surface 142 may include a roughening or surface finish to aid in frictional contact between the surface 142 and the surfaces 34 and/or 40, once a desired angle of articulation of the shank 4 with respect to the receiver 10 is reached.

The compression insert 14 also includes an outer cylindrical surface 144 terminating at a top surface 145. The top surface 145 engages the rod 21 or other longitudinal connecting member during operation of the assembly 1 and locates the rod above the lower seat 68 of the receiver. The top surface 145 may further include an outer bevel 147 that is located adjacent the outer cylindrical surface 144. A bottom surface 149 extends between the spherical surface 142 and the outer cylindrical surface 144.

It is foreseen that in some embodiments of the invention the compression insert 14 may further include upstanding arms that cradle the rod 21 or other connecting member. Such arms may be located spaced from the closure top 18 in some embodiments and may be sized and shaped to contact the closure top 18 in other embodiments in order to provide locking of the polyaxial mechanism of the assembly with capture but without fixing of the rod 21 or other longitudinal connecting member with respect to the closure top 18.

The compression or pressure insert 14 ultimately seats on the shank upper portion 8 and is disposed substantially within the upper cylindrical wall 90. In operation, the insert 14 extends at least partially in the channel 64 of the receiver 10 such that the top surface 145 substantially contacts and engages the outer surface 22 of the rod 21 when such rod is placed in the receiver 10 and the closure structure or top 18 is tightened thereon.

With reference to FIGS. 1 and 28-31, the illustrated elongate rod or longitudinal connecting member 21 can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys and deformable and less compressible plastics, including, but not limited to rods made of elastomeric, polyetheretherketone (PEEK) and other types of materials.

Longitudinal connecting members for use with the assembly 1 may take a variety of shapes, including but not limited to rods or bars of oval, rectangular or other curved or polygonal cross-section. The shape of the insert 14 may be modified so as to closely hold, and if desired, fix or slidingly capture the longitudinal connecting member to the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped channel (or rectangular- or other-shaped channel) for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 28-31, the closure structure or closure top 18 shown with the assembly 1 is rotatably received between the spaced arms 62. It is noted that the closure 18 can be any of a variety of different types of closure structures for use in conjunction with the present invention with suitable mating structure on the upstanding arms 62. It is also foreseen that the closure top could be a twist-in or slide-in closure structure. The illustrated closure structure 18 is substantially cylindrical and includes an outer helically wound guide and advancement structure 162 in the form of a flange form that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 18 downward between the arms 62 and having such a nature as to resist splaying of the arms 62 when the closure structure 18 is advanced into the U-shaped channel 64. The illustrated closure structure 18 also includes a top surface 164 with an internal drive 166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 166 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 168 of the closure is planar and further includes a point 169 and a rim 170 for engagement and penetration into the surface 22 of the rod 21 in certain embodiments of the invention. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

Preferably, the receiver 10, the retainer 12 and the compression insert 14 are assembled at a factory setting that includes tooling for holding and alignment of the component pieces and pinching or compressing of the retainer 12. In some circumstances, the shank 4 is also assembled with the receiver 10, retainer 12 and compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way.

Figure 13:
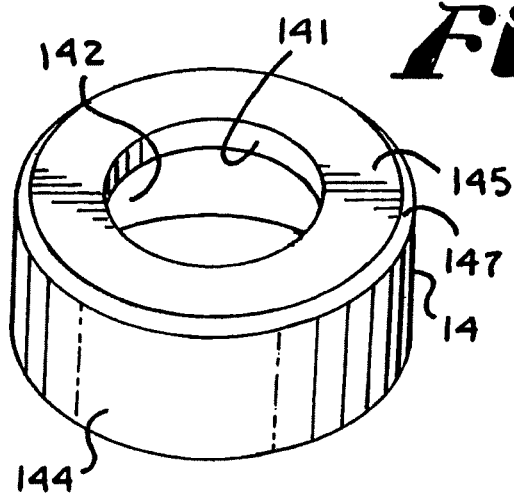
FIG. 13 is an enlarged perspective view of the compression insert of FIG. 1.
Figure 15:
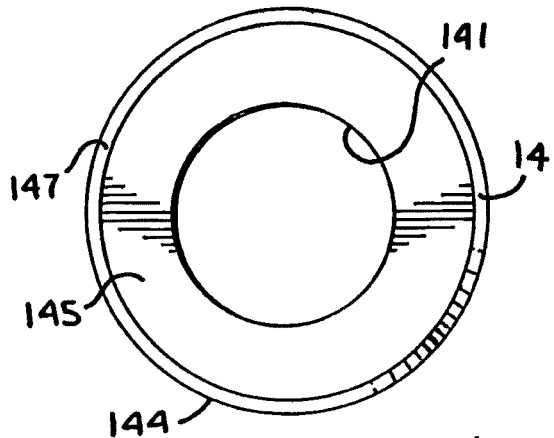
FIG. 15 is a top plan view of the compression insert of FIG. 13.
Figure 14:
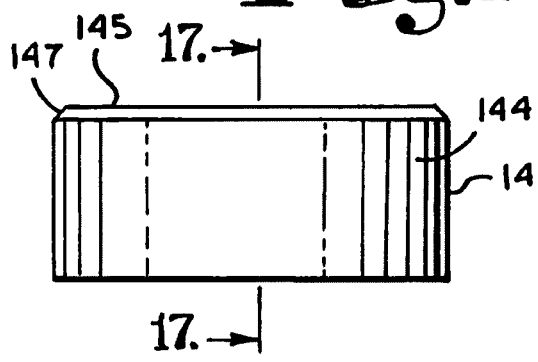
FIG. 14 is a front elevational view of the compression insert of FIG. 13.
Figure 16:
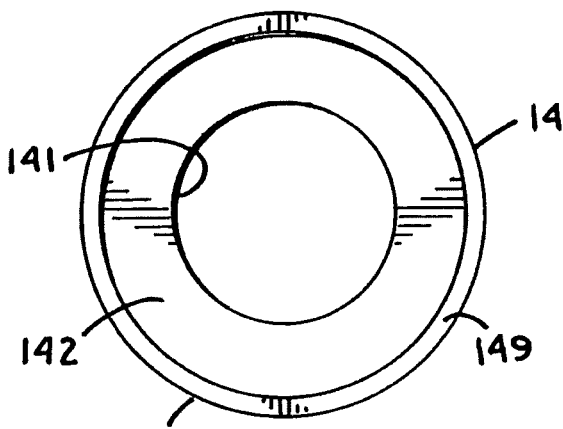
FIG. 16 is a bottom plan view of the compression insert of FIG. 13.
Figure 17:
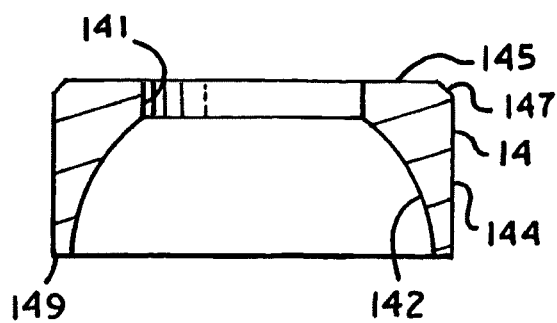
FIG. 17 is a cross-sectional view taken along the line 17-17 of FIG. 14.
Figure 18:
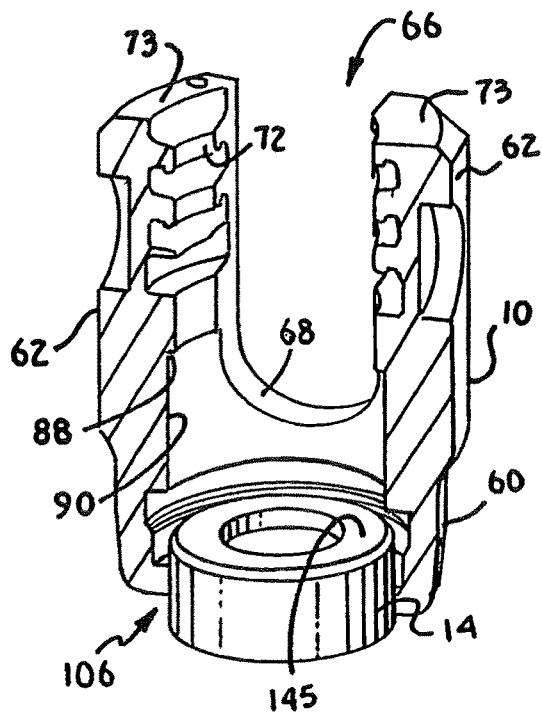
FIG. 18 is an enlarged and partial perspective view of the receiver and compression insert of FIG. 1 with portions broken away to show the detail thereof and shown in an early stage of assembly.
Figure 20:
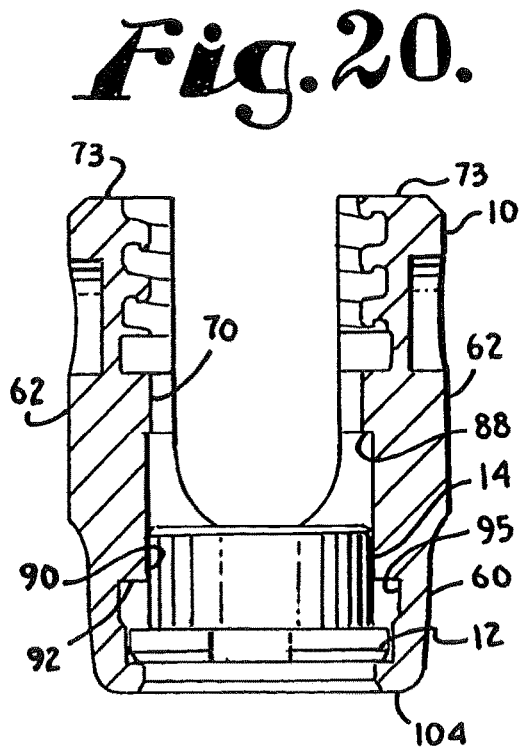
FIG. 20 is a partial front elevational view, similar to FIG. 19, with portions broken away to show the detail thereof and showing the receiver, compression insert and retainer in a pre-assembled orientation with the compression insert and retainer captured within the receiver.
Figure 21:
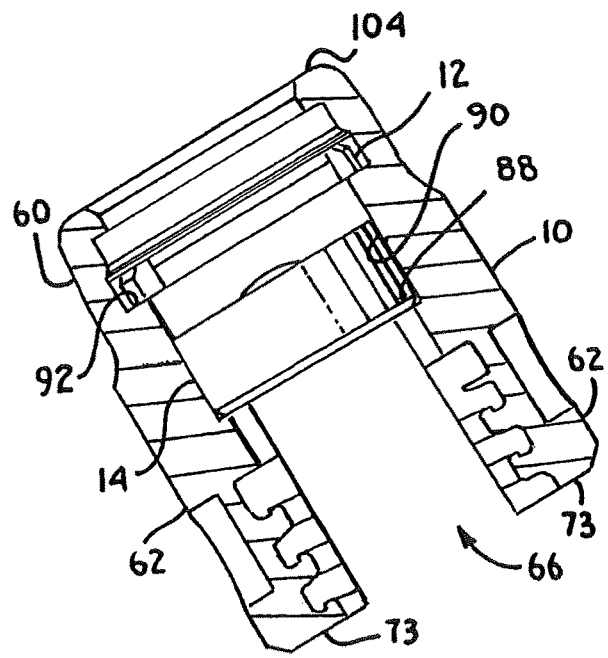
FIG. 21 is a partial front elevational view with portions broken away, similar to FIG. 20, illustrating capture of the compression insert within the receiver when the receiver is rotated or otherwise moved.

Pre-assembly of the receiver 10, retainer 12 and compression insert 14 is shown in FIGS. 18-20. First, the compression insert 14 is uploaded into the receiver 10 through the lower opening 106 with the insert top surface 145 facing the receiver bottom surface 104. The insert 14 is slid upwardly toward the channel seat 68 until the insert is within the cylindrical wall 90. If pressed further upwardly, the insert top surface 145 abuts against the receiver surface 88. Then, the resilient open retainer 12 is prepared for insertion into the receiver 10 by squeezing or pressing the retainer end surfaces 134 and 135 toward one another as shown by the arrows P and Q in FIG. 19. The compressed retainer 12 is inserted into the lower opening 106 with the top surface 122 facing the receiver bottom surface 104. The retainer 12 is typically moved upwardly into the receiver 10 and past the cylindrical surface 96 and allowed to expand to a neutral uncompressed state within the cylindrical surface 94 as shown in FIG. 21. Also as shown in FIG. 21, at this time, both the compression insert 14 and the retainer 12 are captured within the receiver 10. The insert 14 is captured by the retainer 12 at the bottom surface 149 thereof and the top surface 145 abuts against the receiver 88 if the receiver 10 is tipped upside down as shown in FIG. 21. The retainer 12 cannot move beyond the receiver surface 92 at the top 122 thereof and cannot move beyond the receiver surface 99 at the bottom 124 thereof when in a neutral, non-compressed state. At this time the receiver 10, compression insert 14 and retainer 12 combination is pre-assembled and ready for assembly with the shank 4 either at the factory, by surgery staff prior to implantation, or directly upon an implanted shank 4 as will be described herein.

As illustrated in FIG. 22, the bone screw shank 4 (or as shown in FIG. 26, an entire assembly 1 made up of the assembled shank 4, receiver 10, retainer 12 and compression insert 14) is screwed into a bone, such as the vertebra 13, by rotation of the shank 4 using a suitable driving tool 29 that operably drives and rotates the shank body 6 by engagement thereof at the internal drive 46. Specifically, the vertebra 13 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank or assembly is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires.

Again with respect to FIGS. 22 and 23, when the shank 4 is driven into the vertebra 13 without the remainder of the assembly 1, the shank 4 may either be driven to a desired final location or may be driven to a location slightly above or proud to provide for ease in assembly with the pre-assembled receiver, compression insert and retainer. With reference to FIGS. 23-26, the pre-assembled receiver, insert and retainer are placed above the shank upper portion 8 until the shank upper portion is received within the opening 106. As the shank is moved into the interior of the receiver base, the shank upper portion 8 presses the retainer 12 upwardly into the groove 95 (if the retainer is not already located within such groove). As the portion 8 continues to move upwardly toward the channel 64, the retainer top surface 122 abuts against the annular surface 92 stopping upward movement of the retainer 12 and forcing outward movement of the retainer 12 towards the cylindrical surface 94 defining the expansion groove 95 as the spherical surface 34 continues in an upward direction. The retainer 12 begins to contract about the spherical surface 34 as the center of the sphere passes beyond the center of the retainer expansion groove 95 (see FIG. 25). The retainer 12 is then moved down into a final operative position shown in FIG. 26 by either an upward pull on the receiver 10 or, in some cases, by driving the shank 4 further into the vertebra 13 as shown in phantom in FIG. 26. Also, in some embodiments, when the receiver 10 is pre-assembled with the shank 4, the entire assembly 1 may be implanted at this time by inserting the driving tool 20 into the receiver and the shank drive 46 as shown in FIG. 26 and rotating and driving the shank 4 into a desired location of the vertebra 13. At this time, the receiver 10 may be articulated to a desired position with respect to the shank 4 as shown, for example, in FIG. 27.

Figure 30:
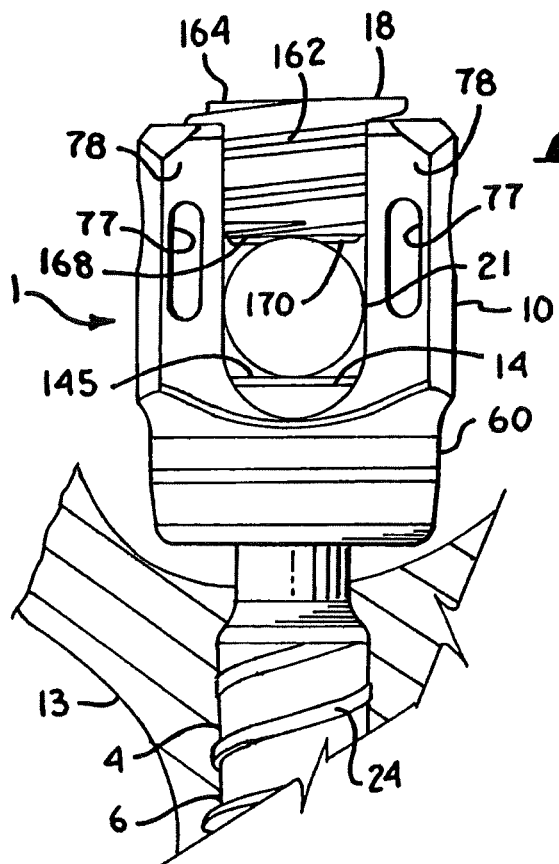
FIG. 30 is an enlarged and partial front elevational view of the entire assembly of FIG. 1 shown with the shank disposed axially aligned with the receiver as shown in FIG. 26 and further shown with a vertebra with portions broken away.
Figure 31:
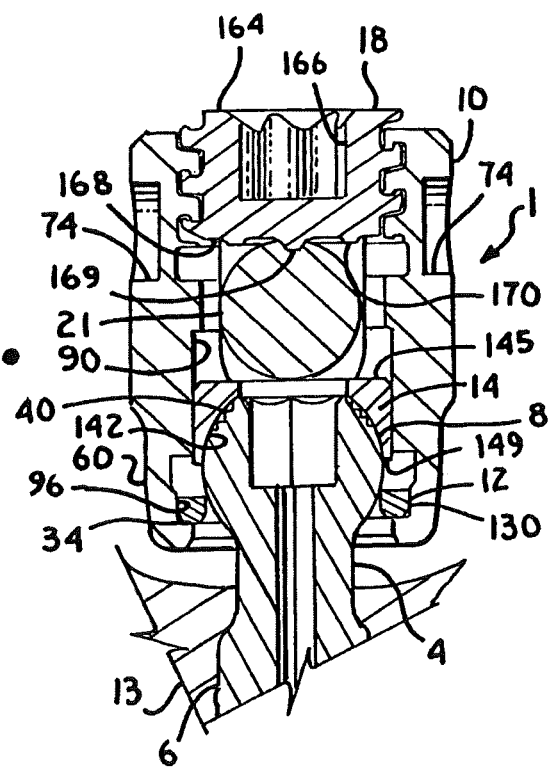
FIG. 31 is a partial front elevational view, similar to FIG. 30, with portions broken away to show the detail thereof.
Figure 44:
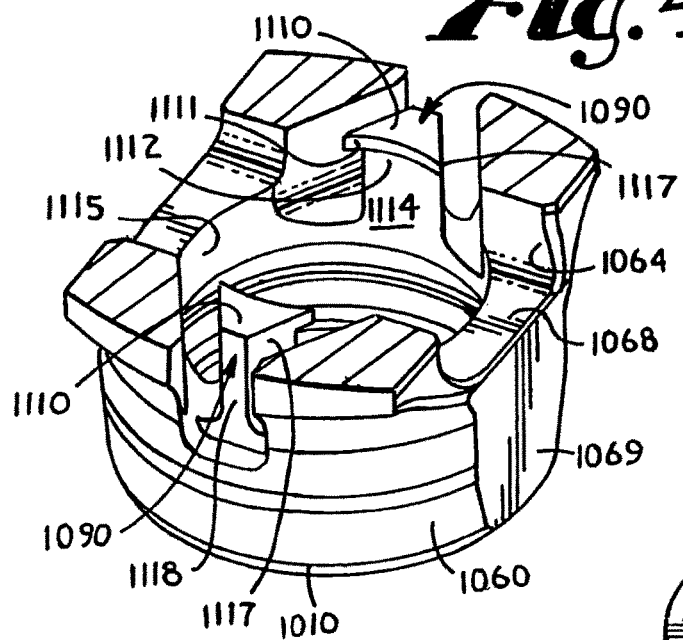
FIG. 44 is a reduced perspective view of the receiver of FIG. 40 with portions broken away to show the detail thereof.
Figure 45:
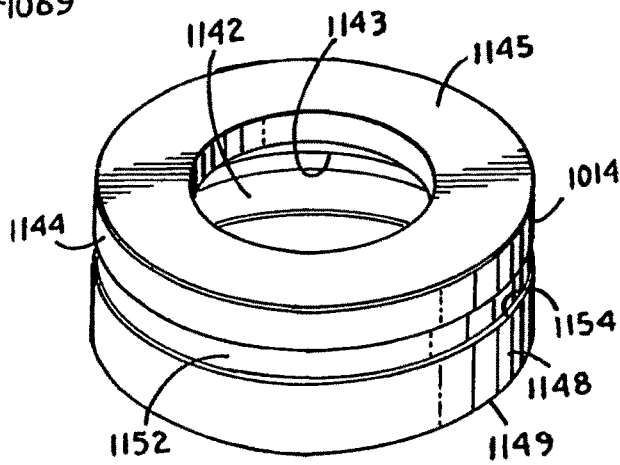
FIG. 45 is an enlarged perspective view of the compression insert of FIG. 32.
Figure 46:
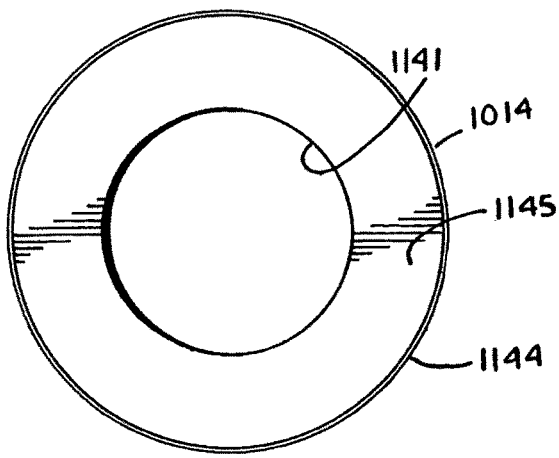
FIG. 46 is a top plan view of the compression insert of FIG. 45.
Figure 47:
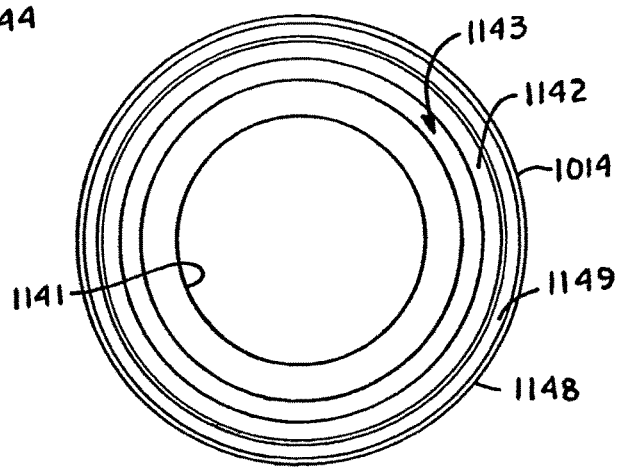
FIG. 47 is a bottom plan view of the compression insert of FIG. 45.

With reference to FIGS. 28-31, the rod 21 is eventually positioned in an open or percutaneous manner in cooperation with the at least two bone screw assemblies 1. The closure structure 18 is then inserted into and advanced between the arms 62 of each of the receivers 10. The closure structure 18 is rotated, using a tool engaged with the inner drive 166 until a selected pressure is reached at which point the rod 21 engages the flat top surface 145 of the compression insert 14, biasing the insert spherical surface 142 against the shank spherical surface 34. As shown in FIG. 29, when the shank 4 is articulated at an angle with respect to the receiver 10 both smooth and stepped 40 surface portions of the spherical surface 34 are in frictional engagement with the spherical surface 142 of the compression insert. When the shank 4 is axially aligned with the receiver 10 as shown in FIGS. 30 and 31, the surface 142 primarily engages the stepped surface portion 40 of the shank upper portion 8.

As the closure structure 18 rotates and moves downwardly into the respective receiver 10, the point 169 and rim 170 engage and penetrate the rod surface 22, the closure structure 18 pressing downwardly against and biasing the rod 21 (in a direction illustrated by the arrow M in FIG. 29) into engagement with the insert 14 that urges the shank upper portion 8 toward the retainer 12 and into locking engagement therewith, the retainer 12 frictionally abutting the surface 99 and expanding outwardly against the cylindrical surface 96. For example, about 80 to about 120 inch pounds of torque on the closure top may be applied for fixing the bone screw shank 6 with respect to the receiver 10.

If removal of the rod 21 from any of the bone screw assemblies 1 is necessary, or if it is desired to release the rod 21 at a particular location, disassembly is accomplished by using the driving tool (not shown) that mates with the internal drive 166 on the closure structure 18 to rotate and remove such closure structure from the cooperating receiver 10. Disassembly is then accomplished in reverse order to the procedure described previously herein for assembly.

Figure 57:
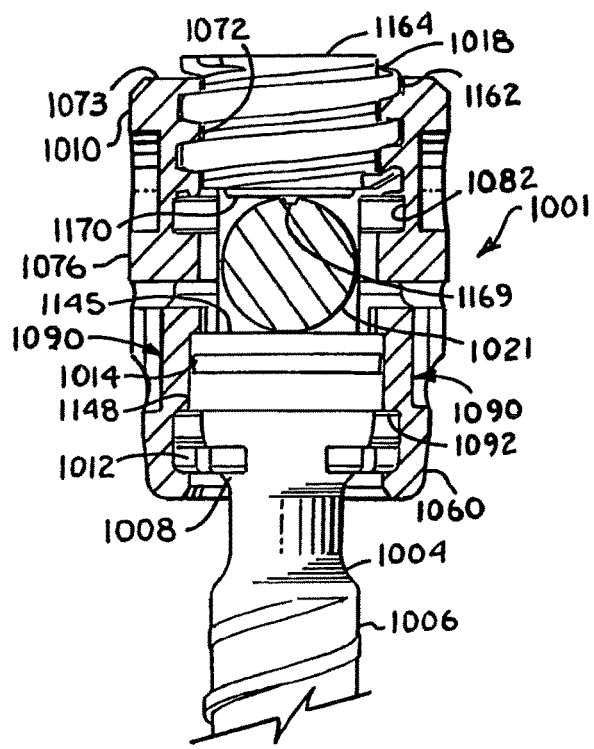
FIG. 57 is a reduced and partial front elevational view with portions broken away, similar to FIG. 56, showing the shank fully assembled with the receiver, compression insert and retainer and further including a longitudinal connecting member and a closure top.
Figure 59:
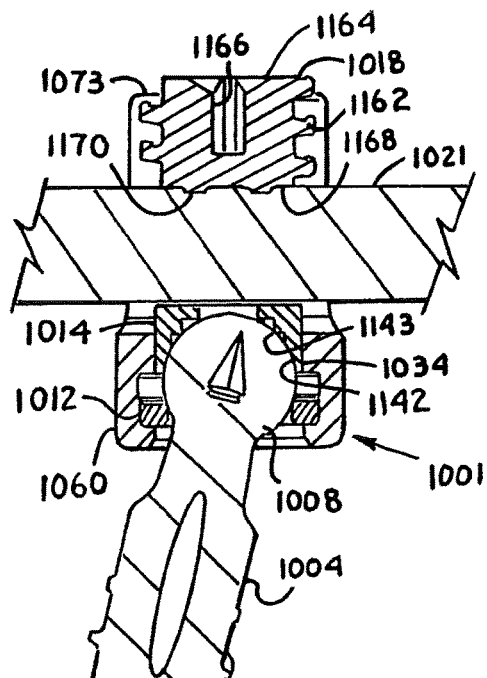
FIG. 59 is a partial side elevational view with portions broken away, similar to FIG. 58 showing the shank disposed at an alternative angle with respect to the receiver.
Figure 58:
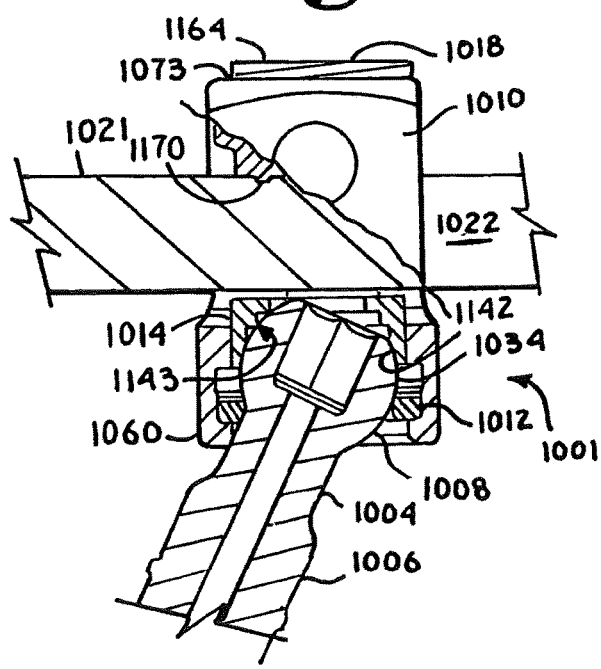
FIG. 58 is a partial side elevational view of the shank, receiver, compression insert and retainer of FIG. 57, with portions broken away to show the detail thereof and further shown with the shank disposed at an angle with respect to the receiver.
Figure 63:
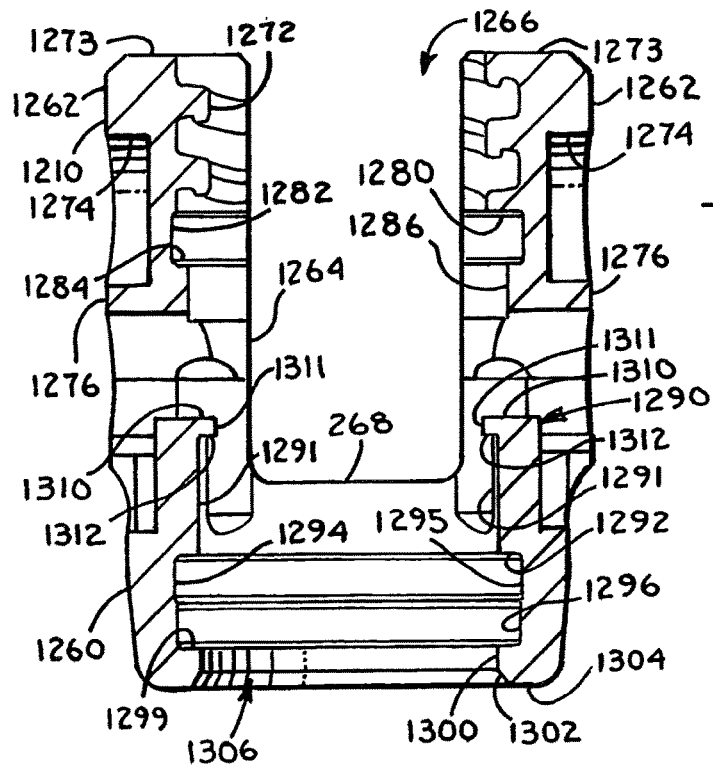
FIG. 63 is a cross-sectional view taken along the line 63-63 of FIG. 62.
Figure 64:
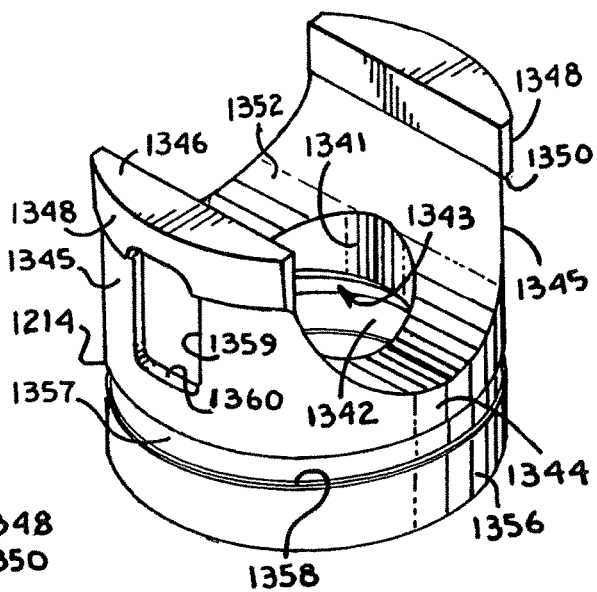
FIG. 64 is an enlarged perspective view of the insert of FIG. 60.
Figure 65:
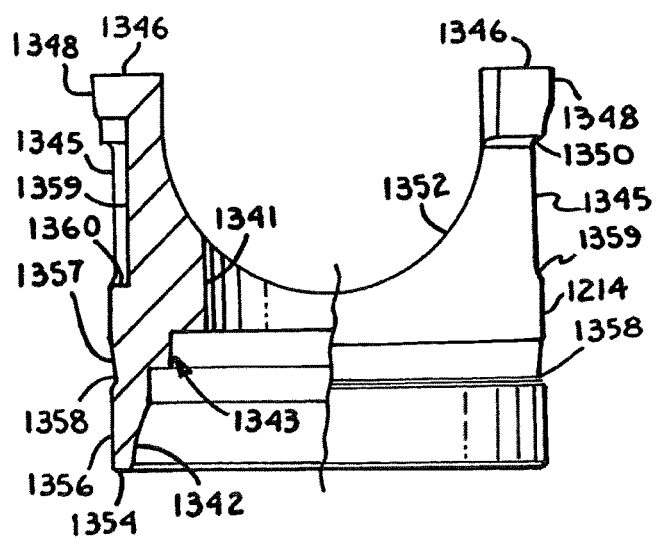
FIG. 65 is a front elevational view of the insert of FIG. 64 with portions broken away to show the detail thereof.
Figure 66:
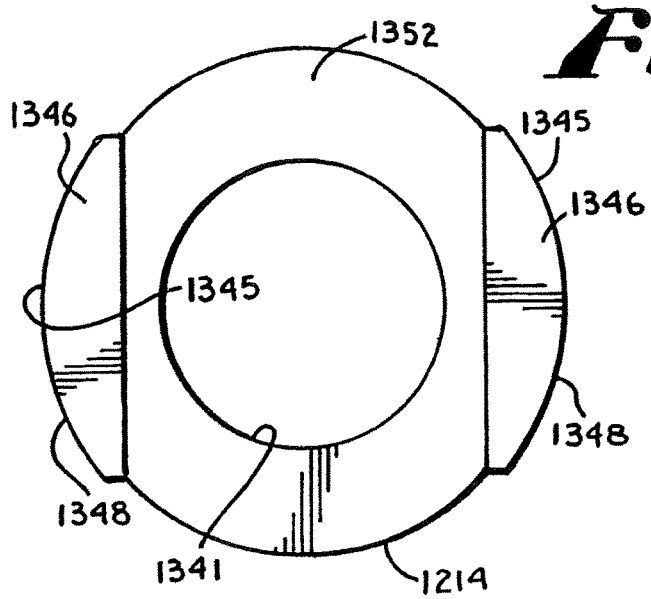
FIG. 66 is a top plan view of the insert of FIG. 64.
Figure 67:
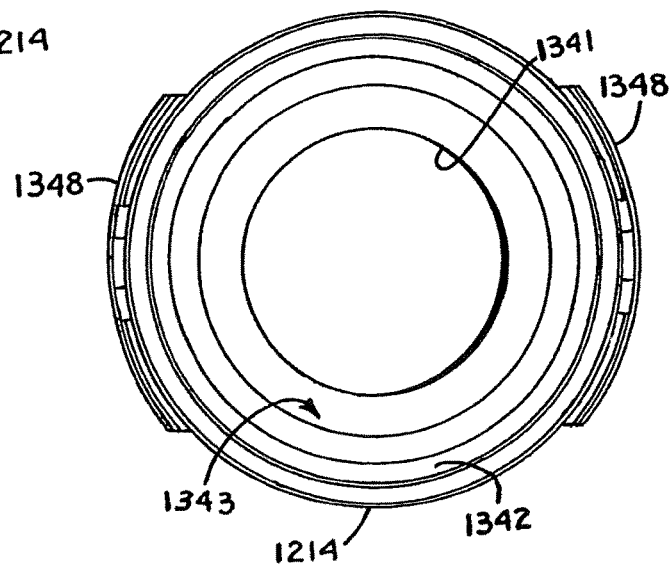
FIG. 67 is a bottom plan view of the insert of FIG. 64.

With reference to FIGS. 32-59 the reference number 1001 generally represents a polyaxial bone screw apparatus or assembly according to the present invention. The assembly 1001 includes a shank 1004, that further includes a body 1006 integral with an upwardly extending upper portion or capture structure 1008; a receiver 1010; a retainer structure 1012 and a compression or pressure insert 1014. The receiver 1010, retainer 1012 and compression insert 1014 are initially assembled and may be further assembled with the shank 1004 either prior or subsequent to implantation of the shank body 1006 into a vertebra 1013. FIGS. 57-59 further show a closure structure 1018 of the invention for capturing a longitudinal connecting member, for example, a rod 1021 which in turn engages the compression insert 1014 that presses against the shank upper portion 1008 into fixed frictional contact with the retainer 1012, so as to capture, and fix the longitudinal connecting member 1021 within the receiver 1010 and thus fix the member 1021 relative to the vertebra 1013. The illustrated rod 1021 is hard, stiff, non-elastic and cylindrical, having an outer cylindrical surface 1022. It is foreseen that in other embodiments, the rod 1021 may be elastic, deformable and/or of a different cross-sectional geometry as previously described herein with respect to the rod 21 of the assembly 1. The receiver 1010 and the shank 1004 cooperate in such a manner that the receiver 1010 and the shank 1004 can be secured at any of a plurality of angles, articulations or rotational alignments relative to one another and within a selected range of angles both from side to side and from front to rear, to enable flexible or articulated engagement of the receiver 1010 with the shank 1004 until both are locked or fixed relative to each other near the end of an implantation procedure.

The shank 1004, best illustrated in FIGS. 32-34 is substantially similar to the shank 4 previously described herein with respect to the assembly 1. Thus, the shank 1004 includes the shank body 1006, upper portion or head 1008, a shank thread 1024, a neck 1026, a tip 1028, a top of thread 1032, an upper portion spherical surface 1034 a top surface 1038, an internal drive 1046 with a base surface 1045 and an cannulation bore 1050 the same or substantially similar to the respective body 6, upper portion or head 8, shank thread 24, neck 26, tip 28, top of thread 32, spherical surface 34, top surface 38, internal drive 46 with base surface 45 and cannulation bore 50 previously described herein with respect to the shank 4 of the assembly 1. Unlike the shank 4, the shank 1004 does not include ridges 40 on the spherical surface 1034. Rather ridges or gripping surfaces are located on the insert 1014 as will be described in greater detail below. To provide a biologically active interface with the bone, the threaded shank body 1006 may be coated, perforated, made porous or otherwise treated as previously discussed herein with respect to the shank body 6 of the assembly 1.

With particular reference to FIGS. 32 and 40-44, the receiver 1010 has a generally squared-off U-shaped appearance with partially discontinuous and partially cylindrical inner and outer profiles. The receiver 1010 has an axis of rotation B that is shown in FIG. 32 as being aligned with and the same as an axis of rotation A of the shank 1004, such orientation being desirable, but not required during assembly of the receiver 1010 with the shank 1004. After the receiver 1010 is pivotally attached to the shank 1004, either before or after the shank 1004 is implanted in a vertebra 1013, the axis B is typically disposed at an angle with respect to the axis A, as shown, for example, in FIGS. 58 and 59.

The receiver 1010 includes a substantially cylindrical base 1060 defining an inner cavity 1061, the base 1060 being integral with a pair of opposed upstanding arms 1062 forming a cradle and defining a channel 1064 between the arms 1062 with an upper opening, generally 1066, and a squared-off U-shaped lower seat 1068, the channel 1064 having a width for operably snugly receiving the rod 1021 between the arms 1062, the channel 1064 communicating with the base cavity 1061. The squared-off geometry of the channel 1064 and lower seat 1068 allow for use with a variety of longitudinal connecting members, including, but not limited to those with circular, oblong, oval, square and rectangular cross-sections. As compared to a U-shaped channel that includes a lower seat having a surface with a radius the same or slightly larger than a cooperating cylindrical rod or other connecting member, the squared-off seat 1068 of the present invention provides improved stress management, moving stress risers outwardly toward the two arms 1062 rather than being focused primarily at a center base line of the radiused lower seat. Furthermore, outer front and rear opposed substantially planar base surfaces 1069 that partially define the squared-off lower seat 1068 advantageously reduce the run on the rod (i.e., provide a more narrow receiver that in turn provides more space and thus more access between bone anchors along the rod or other connecting member) and provide a planar surface for flush or close contact with other connecting member components in certain embodiments, such as for bumpers or spacers that surround a hard or deformable rod or provide support for cord-type connecting members.

Each of the arms 1062 has an interior surface, generally 1070, that includes various inner cylindrical profiles, an upper one of which is a partial helically wound guide and advancement structure 1072 located adjacent top surfaces 1073 of each of the arms 1062. In the illustrated embodiment, the guide and advancement structure 1072 is a partial helically wound interlocking flangeform configured to mate under rotation with a similar structure on the closure structure 1018. However, it is foreseen that the guide and advancement structure 1072 could alternatively be a square-shaped thread, a buttress thread, a reverse angle thread or other thread-like or non-thread-like helically wound discontinuous advancement structure for operably guiding under rotation and advancing the closure structure 1018 downward between the arms 1062, as well as eventual torquing when the closure structure 1018 abuts against the rod 1021 or other longitudinal connecting member.

An opposed pair of tool receiving and engaging apertures 1074 are formed on outer surfaces 1076 of the arms 1062. Furthermore, two pair of tool receiving and engaging apertures 1077 are formed in front and rear surfaces 1078 of the arms 1062. Some or all of the apertures 1074 and 1077 may be used for holding the receiver 1010 during assembly with the insert 1014, the retainer 1012 and the shank 1004, during the implantation of the shank body 1006 into a vertebra when the shank is pre-assembled with the receiver 1010, and during assembly of the bone anchor assembly 1001 with the rod 1021 and the closure structure 1018. It is foreseen that tool receiving grooves or apertures may be configured in a variety of shapes and sizes and be disposed at other locations on the receiver arms 1062.

Returning to the interior surface 1070 of the receiver arms 1062, located below the guide and advancement structure 1072 is a discontinuous cylindrical surface 1082 partially defining a run-out feature for the guide and advancement structure 1072. The cylindrical surface 1082 has a diameter equal to or slightly greater than a greater diameter of the guide and advancement structure 1072. Moving downwardly, in a direction toward the base 1060, adjacent the cylindrical surface 1082 is a run-out seat or surface 1084 that extends inwardly toward the axis B and runs perpendicular to the axis B. Adjacent to and located below the surface 1084 is another cylindrical surface 1086 having a diameter smaller than the diameter of the surface 1082. A discontinuous annular surface 1088 that provides an upper abutment surface or stop for capturing the compression insert 1014 in the receiver 1010 is located below and adjacent to the cylindrical surface 1086. The abutment surface 1088 is disposed substantially perpendicular to the axis B. As shown in FIG. 51 and discussed in greater detail below, the assembly 1001 is typically provided to a user with the insert 1014 being held within the receiver by a pair of spring tabs, generally 1090, that resiliently hold the insert 1014 and keep the insert stationary with respect to the receiver 1010 and slightly spaced from the upper stop 1088 until the insert 1014 is pressed down by the user into a friction fit working position wherein the insert 1014 is in frictional contact with the shank upper portion 1008, the shank still movable with respect to the insert 1014, but not in a loose or floppy manner. Each spring tab 1090 generally extends from a location spaced from the surface 1088 and along one of the arms 1062 downwardly to the base 1060; each spring tab 1090 being integral with the base 1060. The opposed spring tabs 1090 include various surfaces for contacting the insert 1014 at different stages of assembly and will be discussed in greater detail in the paragraphs below. A continuous annular surface 1092 is located below and adjacent to the spring tabs 1090. The surface 1092 is disposed in the base 1060, partially forming the base cavity 1061 and forms a stop for the resilient retainer 1012, prohibiting the retainer 1012 (when in an uncompressed configuration) from moving upwardly into a space or cavity 1091 defined by the spring tab 1090 inner surfaces that hold the compression insert 1014. Another cylindrical surface is located below and adjacent to the surface 1092. The cylindrical surface 1094 is oriented substantially parallel to the axis B and is sized and shaped to receive an expanded retainer 1012. The surfaces 1092 and 1094 define a circumferential recess, groove or chamber 1095 that is sized and shaped to receive the retainer 1012 as it expands around the shank upper portion 1008 as the shank 1008 moves upwardly toward the channel 1064 during assembly, as well as form a restriction to prevent the expanded retainer 1012 from moving upwardly with the shank portion 1008, the surface 1092 preventing the retainer 1012 from passing from the groove 1095 into the cavity 1091 whether the retainer 1012 is in a partially or fully expanded position, or in a neutral or original or operative position (see, e.g., FIG. 54). A cylindrical surface 1096 located below the cylindrical surface 1094 is sized and shaped to closely receive the retainer 1012 when the retainer is in a neutral or slightly expanded position as shown in FIG. 57, for example. Thus, the cylindrical surface 1096 has a diameter smaller than the diameter of the cylindrical surface 1094 that defines the expansion chamber 1095. The surface 1096 is joined or connected to the surface 1094 by one or more beveled, curved or conical surfaces 1097. The surfaces 1097 allow for sliding gradual movement and/or contraction of the retainer 1012 into the space defined by the surface 1096 and ultimate seating and slight expansion of the retainer 1012 on a lower annular surface 1099 located below and adjacent to the cylindrical surface 1096. Located below and adjacent to the annular seating surface 1099 is another cylindrical surface 1100 that communicates with a beveled or flared bottom opening surface 1102, the surface 1102 communicating with an exterior base surface 1104 of the base 1060, defining a lower opening, generally 1106, into the base cavity 1061 of the receiver 1010. The illustrated surface 1100 has a diameter that is substantially the same as an inner diameter of the spring tabs 1090, when in a neutral, unsprung position as will be described in greater detail below, allowing for slidable uploading of the compression insert 1014 while requiring compression or squeezing of the retainer 1012 during uploading of the retainer 1012 through the lower opening 1106 (see FIGS. 50 and 51, for example).

Returning to the spring tabs 1090, each spring tab includes a top surface 1110 and a first radiused inner surface 1111 perpendicular to a lower lip or abutment surface 1112. The abutment surface 1112 extends from the surface 1111 to another radiused surface 1114 having a radius larger than a radius of the surface 1111. The surface 1114 is integral with a cylindrical surface 1115 that extends into the base 1060 defining an upper portion of the base cavity 1061, the surface 1115 terminating at the annular abutment surface 1092. Each spring tab 1090 is further defined by diverging side surfaces 1117 and an outer surface 1118. The surfaces 1117 diverge at the inner surfaces 1111 and 1114 and converge toward the outer surface 1118, the illustrated pairs of surfaces 1117 being at an acute angle with respect to one another. The top surface 1110 is spaced from the annular abutment surface 1088 and is substantially parallel thereto when the spring tabs 1090 are in a neutral, non-sprung state. Also, as will be described in greater detail below, when the tabs 1090 are in a neutral, non-spring state, the surfaces 1111 form a discontinuous cylindrical surface having a diameter smaller than an outer diameter of the insert 1014, while the inner surfaces 1114 form a discontinuous cylindrical surface having a diameter slightly larger than a largest outer diameter of the insert 1014, the insert 1014 being snugly held thereby under the lip surface 1112 when in a fully assembled, friction fit position within the receiver 1010. When the tabs 1090 are in an outwardly directed sprung state as shown on FIGS. 51 and 52, for example, the surfaces 1111 frictionally engage the insert 1014, prohibiting both upward and downward movement of the insert 1014 within the receiver 1010, advantageously keeping the insert 1014 clear of other tools and components prior to assembly with other components and during the insertion of the retainer 1012 into the receiver 1010 and the bone screw shank upper portion 1008 into the retainer 1012 within the receiver 1010. As best shown in FIG. 54, the somewhat trapezoidal spring tabs 1090 are created by a machining process in which at least two cuts, at an acute angle to one another, are made in each receiver arm 1062. The angular cuts advantageously create spring tabs 1090 having greater surface contact area with the insert 1014 than would occur with spring tabs having parallel side surfaces formed by parallel cuts. A further advantage of angular cuts over parallel cuts is that angular cuts advantageously provide access to and removal of material from the inner receiver arms 1062 that then allow for the arms to receive the insert 1014 during the assembly step of springing the tabs 1090 outwardly and pushing the insert 1014 upwardly into frictional engagement with the surfaces 1111 that was mentioned above and will be described in greater detail below.

Figure 52:
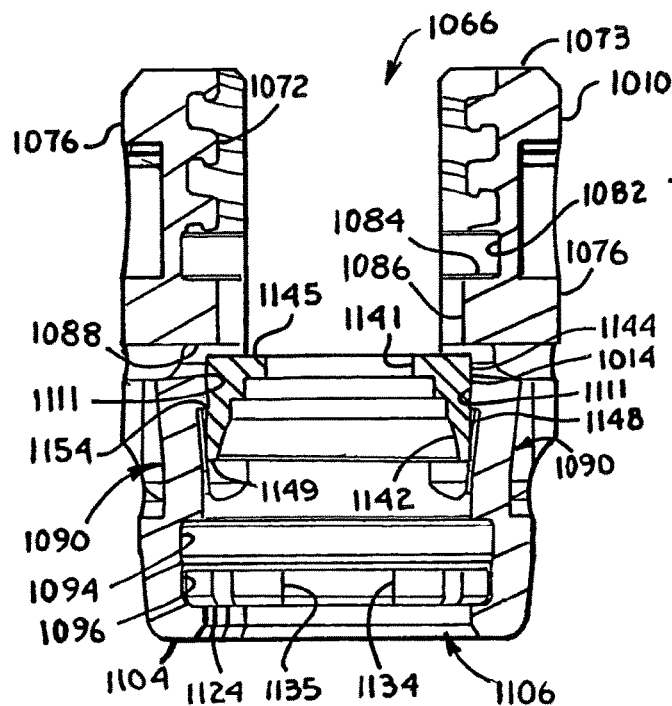
FIG. 52 is a partial front elevational view, similar to FIG. 50, with portions broken away to show the detail thereof and showing the receiver, compression insert and retainer in a pre-assembled orientation with the compression insert and retainer captured within the receiver.

With particular reference to FIGS. 32, 35-39 and 51-52, the retainer 1012 that operates to capture the shank upper portion 1008 and the compression insert 1014 within the receiver 1010 has a central axis C that is operationally the same as the axis B associated with the receiver 1010 when the shank upper portion 1008 and the retainer 1012 are installed within the receiver 1010. The retainer 1012 is made from a resilient material, such as a stainless steel or titanium alloy, so that the retainer 1012 may be both compressed and expanded during various steps of assembly as will be described in greater detail below. The retainer 1012 has a central channel or hollow through bore, generally 1121, that passes entirely through the structure 1012 from a top surface 1122 to a bottom surface 1124 thereof. Surfaces that define the channel or bore 1121 include a discontinuous inner cylindrical surface 1125 adjacent the top surface 1122 and a discontinuous frusto-conical or beveled surface 1127 adjacent the surface 1125, both surfaces coaxial with the axis C when the retainer 1012 is in a neutral non-compressed, non-expanded orientation. The retainer 1012 further includes an outer cylindrical surface 1130 located adjacent the top surface 1122 and an outer beveled or frusto-conical surface 1132 adjacent the bottom surface 1124. The surface 130 is oriented parallel to the axis C. A pair of spaced notches 1133 are formed in the cylindrical surface 1130. The notches 1130 receive a holding and manipulation tool (not shown) used for contraction and insertion of the retainer 1012 into the receiver. In some embodiments further notches may be made to evenly distribute stress across the entire retainer during contraction and expansion thereof. In other embodiments of the invention, such notches may be on the inside of the ring. In some embodiments, the ring can have no notches. The resilient retainer 1012 further includes first and second end surfaces, 1134 and 1135 disposed in spaced relation to one another when the retainer is in a neutral non-compressed state. Both end surfaces 1134 and 1135 are disposed substantially perpendicular to the top surface 1122 and the bottom surface 1124. A width X between the surfaces 1134 and 1135 is determined by a desired amount of compressibility of the open retainer 1012 when loaded into the receiver 1010. The space X shown in FIG. 35 provides adequate space between the surfaces 1134 and 1135 for the retainer 1012 to be pinched, with the surfaces 1134 and 1135 compressed toward one another (as shown in FIG. 51) to a closely spaced or even touching configuration, if necessary, to an extent that the compressed retainer 1012 is up or bottom loadable through the receiver opening 1106 as shown in FIGS. 51 and 52. After passing through the opening 1106 and along a portion of the lower inner surface, the retainer 1012 expands or springs back to an original uncompressed, rounded or collar-like configuration of FIGS. 35-39, see, e.g., FIG. 52. The embodiment shown in FIGS. 35-39 illustrates the surfaces 1134 and 1135 as substantially parallel, however, it is foreseen that it may be desirable to orient the surfaces obliquely or at a slight angle depending upon the amount of compression desired during loading of the retainer 1012 into the receiver 1010.

With reference to FIGS. 32 and 45-51, the compression insert 1014 is illustrated that is sized and shaped to be received by and up-loaded into the receiver 1010 at the lower opening 1106. The compression insert 1014 has an operational central axis that is the same as the central axis B of the receiver 1010. The compression insert 1014 has a central channel or through bore defined by an inner cylindrical surface 1141, an inner partially spherical surface 1142 and a shank gripping surface portion, generally 1143, extending between the surface 1141 and the surface 1142. The gripping surface portion 1143 preferably includes two or more graduated cylindrical surfaces disposed substantially parallel to the axis B and adjacent perpendicular step surfaces that are disposed generally perpendicular to the axis B. It is foreseen that the stepped surface portion 1143 may include greater or fewer number of stepped surfaces. It is foreseen that the shank gripping surface portion 1143 and also the surface 1142 may additionally or alternatively include a roughened or textured surface or surface finish, or may be scored, knurled, or the like, for enhancing frictional engagement with the shank upper portion 1008.

The compression insert 1014 through bore is sized and shaped to receive the driving tool 1029 therethrough that engages the shank drive feature 1046 when the shank body 1006 is driven into bone with the receiver 1010 attached. The surfaces 1142 and 1143 are sized and shaped to initially slidingly receive and ultimately frictionally engage the substantially spherical or domed surface 1034 of the shank upper portion 1008, in particular the stepped or ridged surface 1143 that will initially frictionally but slidingly and pivotally mate with the spherical surface 1034 to create a ball-and-socket type joint, but ultimately dig into and thus be securely fixed with the domed surface 1034.

The compression insert 1014 also includes a first outer and upper cylindrical surface 1144 adjacent to a top surface 1145. The top surface 1145 engages the rod 1021 or other longitudinal connecting member during operation of the assembly 1001 and locates the rod above the lower seat 1068 of the receiver. The insert 1014 also includes an outer lower cylindrical surface 1148 adjacent to a bottom surface 1149. The cylindrical surfaces 1144 and 1148 have the same or substantially the same outer diameter, sized to be received by the receiver surface 1100 when loaded into the receiver 1010 and also be snugly received by spring tab 1090 surfaces 1114 when the spring tabs are in a neutral or relaxed state. Located between the surfaces 1144 and 1148 is a frusto-conical surface 1152 that extends from the surface 1144 inwardly toward the axis B and terminates at an annular ledge 1154. The ledge 1154 extends from the frusto-conical surface 1152 to the surface 1148 and is substantially perpendicular to the surface 1148. As will be described in greater detail below, during early stages of assembly, the insert 1014 outer surfaces 1144 and 1152 are resiliently gripped by the spring tab surfaces 1111 with the spring tab lower lip 1112 engaging the ledge 1154 to hold the insert 1014 in a desired stationary position with respect to the receiver 1010. When the insert 1014 is lowered into a second or friction fit position in frictional engagement with the bone screw shank, the lower lip 1112 extends over the insert top surface 1145.

It is foreseen that in some embodiments of the invention the compression insert 1014 may further include upstanding arms that cradle the rod 1021 or other connecting member. Such arms may be located spaced from the closure top 1018 in some embodiments and may be sized and shaped to contact the closure top 1018 in other embodiments in order to provide locking of the polyaxial mechanism of the assembly with capture but without fixing of the rod 1021 or other longitudinal connecting member with respect to the closure top 1018.

The compression or pressure insert 1014 ultimately seats on the shank upper portion 1008 and is disposed substantially within the spring tab cylindrical wall 1114. In operation, the insert 1014 extends at least partially in the channel 1064 of the receiver 1010 such that the top surface 1145 substantially contacts and engages the outer surface 1022 of the rod 1021 when such rod is placed in the receiver 1010 and the closure structure or top 1018 is tightened thereon.

With reference to FIGS. 57-59, the illustrated elongate rod or longitudinal connecting member 1021 is the same or substantially similar to the rod 21 previously described herein and thus can be any of a variety of implants utilized in reconstructive spinal surgery, but is typically a cylindrical, elongate structure having the outer substantially smooth, cylindrical surface 1022 of uniform diameter. The rod 1021 may be made from a variety of metals, metal alloys and deformable and less compressible plastics, including, but not limited to rods made of elastomeric, polyetheretherketone (PEEK) and other types of materials. Longitudinal connecting members for use with the assembly 1001 may take a variety of shapes as previously described with respect to the assembly 1, including outer sleeve and inner cord connecting member assemblies as shown and described, for example, in U.S. patent application Ser. No. 12/802,849 filed Jun. 15, 2010 that is incorporated by reference herein.

With reference to FIGS. 57-59, the closure structure or closure top 1018 shown with the assembly 1001 is the same or substantially similar in form and function to the closure top 18 previously described herein with respect to the assembly 1 and can be any of a variety of different types of closure structures for use in conjunction with the present invention with suitable mating structure on the upstanding arms 1062. The illustrated closure structure 1018 is substantially cylindrical and includes a an outer helically wound guide and advancement structure 1162 in the form of a flange form that operably joins with the guide and advancement structure 1072 disposed on the arms 1062 of the receiver 1010. The illustrated closure structure 1018 also includes a top surface 1164 with an internal drive 1166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 1166 is used for both rotatable engagement and, if needed, disengagement of the closure 1018 from the receiver arms 1062. It is also foreseen that the closure structure 1018 may alternatively include a break-off head designed to allow such a head to break from a base of the closure at a preselected torque, for example, 70 to 140 inch pounds. Such a closure structure would also include a base having an internal drive to be used for closure removal. A base or bottom surface 1168 of the closure is planar and further includes a point 1169 and a rim 1170 for engagement and penetration into the surface 1022 of the rod 1021 in certain embodiments of the invention. The closure top 1018 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 1062.

Preferably, the receiver 1010, the retainer 1012 and the compression insert 1014 are assembled at a factory setting that includes tooling for holding and alignment of the component pieces and pinching or compressing of the retainer 1012 as well as spreading of the spring tabs 1090. As described herein with respect to the assembly 1, similarly, the shank 1004 may be assembled with the receiver 1010, retainer 1012 and compression insert 1014 at the factory or it may be desirable to "pop" the shank 1004 into the receiver assembly at a later time, either before or after implantation of the shank 1004 in the vertebra 1013.

Pre-assembly of the receiver 1010, retainer 1012 and compression insert 1014 is shown in FIGS. 50-52. First, the compression insert 1014 is uploaded into the receiver 1010 through the lower opening 1106 with the insert top surface 1145 facing the receiver bottom surface 1104. The insert 1014 is slid upwardly toward the channel seat 1068 until the insert is within the cylindrical walls 1114 of the spring tabs 1090. If pressed further upwardly without expanding the spring tabs 1090, the insert top surface 1145 would simply abut against the surface 1112. A tool or tools (not shown) are used to pull or otherwise spread the spring tabs 1090 away from one another and allow the insert 1014 to be placed therebetween at the outer surfaces 1144 and/or 1152. Then the resilient tabs 1090 are released and the surfaces 1111 of the tabs 1090 engage the surface 1144 or 1152, preferably engaging the surface 1152 adjacent to the ledge 1154. The surface 1112 advantageously abuts against the ledge 1154, stopping the insert 1014 from any further upward movement towards the surface 1088 and providing adequate clearance for the later step of pushing the bone screw shank upper portion 1008 through the spring ring retainer 1112. Although the surface 1088 would prohibit the insert 1014 from moving out the upper opening 1066, engagement with the resilient spring tabs 1090 also prohibits downward movement of the insert 1014 and keeps the insert 1014 away from the lower opening 1106 during assembly with the retainer 1012 and subsequent assembly with the shank 1004. Then, the resilient open retainer 1012 is prepared for insertion into the receiver 1010 by squeezing or pressing the retainer end surfaces 1134 and 1135 toward one another as shown in FIG. 51. The compressed retainer 1012 is inserted into the lower opening 1106 with the top surface 1122 facing the receiver bottom surface 1104. The retainer 1012 is typically moved upwardly into the receiver 1010 and past the cylindrical surface 1096 and allowed to expand to a neutral uncompressed state within the cylindrical surface 1096 as shown in FIG. 52. Also as shown in FIG. 52, at this time, both the compression insert 1014 and the retainer 1012 are captured within the receiver 1010. The receiver 1010, compression insert 1014 and the retainer 1012 combination is now pre-assembled and ready for assembly with the shank 1004 either at the factory, by surgery staff prior to implantation, or directly upon an implanted shank 1004.

Figure 53:
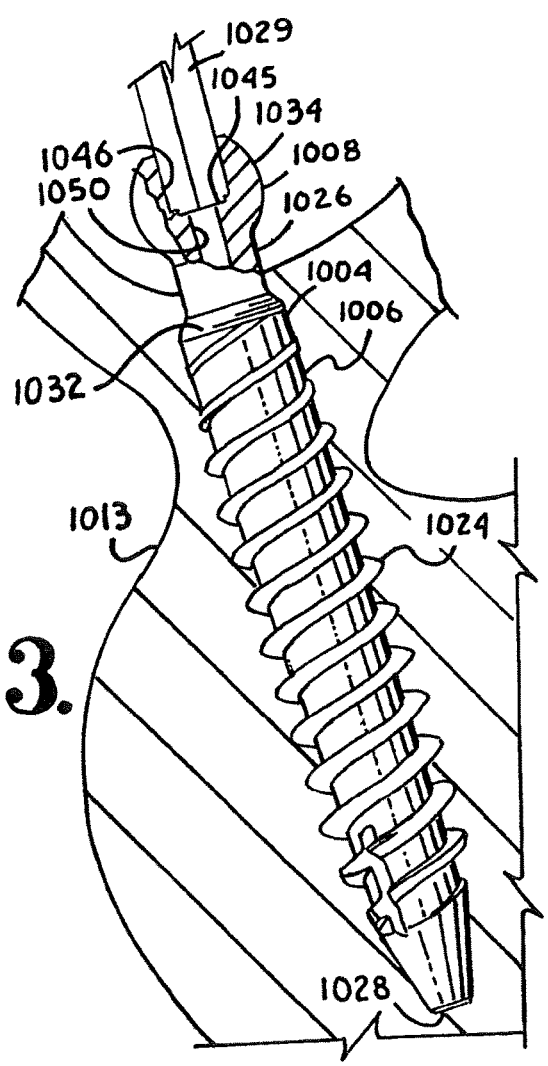
FIG. 53 is an enlarged and partial front elevational view of the shank of FIG. 32 with portions broken away to show the detail thereof, shown with a driving tool in a stage of implantation in a vertebra.

As illustrated in FIG. 53, the bone screw shank 1004 (or an entire assembly 1001 made up of the assembled shank 1004, receiver 1010, retainer 1012 and compression insert 1014) is screwed into a bone, such as the vertebra 1013, by rotation of the shank 1004 using a suitable driving tool 1029 that operably drives and rotates the shank body 1006 by engagement thereof at the internal drive 1046. It is foreseen that the shank and other bone screw assembly parts, the rod 2021 (also having a central lumen in some embodiments) and the closure top 2018 (also with a central bore) can be inserted in a percutaneous or minimally invasive surgical manner, utilizing guide wires.

Again with respect to FIGS. 53 and 54, when the shank 1004 is driven into the vertebra 1013 without the remainder of the assembly 1001, the shank 1004 may either be driven to a desired final location or may be driven to a location slightly above or proud to provide for ease in assembly with the pre-assembled receiver, compression insert and retainer. With reference to FIGS. 54-57, the pre-assembled receiver, insert and retainer are placed above the shank upper portion 1008 until the shank upper portion is received within the opening 1106. As the shank is moved into the interior of the receiver base, the shank upper portion 1008 presses the retainer 1012 upwardly into the chamber 1095 (if the retainer is not already located within such chamber). As the portion 1008 continues to move upwardly toward the channel 1064, the retainer top surface 1122 abuts against the annular surface 1092 stopping upward movement of the retainer 1012 and forcing outward movement of the retainer 1012 towards the cylindrical surface 1094 defining the expansion chamber or groove 1095 as the spherical surface 1034 continues in an upward direction. The retainer 1012 begins to contract about the spherical surface 1034 as the center of the sphere passes beyond the center of the retainer expansion chamber 1095 (see FIG. 55). The retainer 1012 can then move down into a final operative location within the seating chamber or groove, shown in FIGS. 56 and 57 by either gravity and/or an upward pull on the receiver 1010 or, in some cases, by driving the shank 1004 further into the vertebra 1013. Also, in some embodiments, when the receiver 1010 is pre-assembled with the shank 1004, the entire assembly 1001 may be implanted at this time by inserting the driving tool 1020 into the receiver and the shank drive 1046 and rotating and driving the shank 1004 into a desired location of the vertebra 1013.

With reference to FIG. 56, at this time, the compression insert 1014 is pressed downwardly with a tool (not shown), or with the rod, toward the shank upper portion 1008 and out of engagement with the spring tab surfaces 1111. Once the insert surface 1144 clears the tab surfaces 1111, the insert snaps into place and the spring tabs 1090 return to an original, relaxed orientation with the surfaces 1112 located over the insert top surface 1145 and frictionally engaging such surface. The spring tabs 1090 are sized such that when the surfaces 1112 frictionally engage the top surface 1145 of the insert, the insert 1014 surfaces 1142 and 1143 in turn press against the shank upper portion 1008 at the spherical surface 1034. The friction fit between the compression insert 1014 and the shank upper portion 1008 is not totally locked or fixed, but at the same time not loose or floppy either, advantageously allowing the user to articulate the shank 1004 with respect to the receiver 1010, but with some resistance, so that when the shank 1004 is placed in a desired orientation with respect to the receiver 1010, the assembly 1001 remains substantially frictionally set in such desired orientation unless purposefully manipulated into another position. For example, at this time, the receiver 1010 may be articulated to a desired position with respect to the shank 1004, for example, as shown in FIG. 58 or FIG. 59, but prior to locking of such position that is shown in those drawings.

With reference to FIGS. 57-59, the rod 1021 is eventually positioned in an open or percutaneous manner in cooperation with the at least two bone screw assemblies 1001. The closure structure 1018 is then inserted into and advanced between the arms 1062 of each of the receivers 1010. The closure structure 1018 is rotated, using a tool engaged with the inner drive 1166 until a selected pressure is reached at which point the rod 1021 engages the flat top surface 1145 of the compression insert 1014, further pressing the insert spherical surface 1142 and stepped surfaces 1143 against the shank spherical surface 1034, the edges of the stepped surfaces penetrating into the spherical surface 1034.

As the closure structure 1018 rotates and moves downwardly into the respective receiver 1010, the point 1169 and rim 1170 engage and penetrate the rod surface 1022, the closure structure 1018 pressing downwardly against and biasing the rod 1021 into engagement with the insert 1014 that urges the shank upper portion 1008 toward the retainer 1012 and into locking engagement therewith, the retainer 1012 frictionally abutting the surface 1099 and expanding outwardly against the cylindrical surface 1096. For example, about 80 to about 120 inch pounds of torque on the closure top may be applied for fixing the bone screw shank 1006 with respect to the receiver 1010.

If removal of the rod 1021 from any of the bone screw assemblies 1001 is necessary, or if it is desired to release the rod 1021 at a particular location, disassembly is accomplished by using the driving tool (not shown) that mates with the internal drive 1166 on the closure structure 1018 to rotate and remove such closure structure from the cooperating receiver 1010. Disassembly is then accomplished in reverse order to the procedure described previously herein for assembly.

With reference to FIGS. 60-83, the reference numeral 1201 generally represents another embodiment of a polyaxial bone screw according to the invention. The assembly 1201 includes a shank 1204, that further includes a body 1206 integral with an upwardly extending upper portion or capture structure 1208; a receiver 1210; a retainer structure 1212 and a compression or pressure insert 1214. The receiver 1210, retainer 1212 and compression insert 1214 are initially assembled and may be further assembled with the shank 1204 either prior or subsequent to implantation of the shank body 1206 into a vertebra, as will be described in greater detail below. FIG. 60 further shows a closure structure 1218 of the invention for capturing a longitudinal connecting member, for example, a rod 1221 which in turn engages the compression insert 1214 that presses against the shank upper portion 1208 into fixed frictional contact with the retainer 1212, so as to capture, and fix the longitudinal connecting member 1221 within the receiver 1210 and thus fix the member 1221 relative to the vertebra. The illustrated rod 1221 is hard, stiff, non-elastic and cylindrical, having an outer cylindrical surface 1222. It is foreseen that in other embodiments, the rod 1221 may be elastic, deformable and/or of a different cross-sectional geometry. The receiver 1210 and the shank 1204 cooperate in such a manner that the receiver 1210 and the shank 1204 can be secured at any of a plurality of angles, articulations or rotational alignments relative to one another and within a selected range of angles both from side to side and from front to rear, to enable flexible or articulated engagement of the receiver 1210 with the shank 1204 until both are locked or fixed relative to each other near the end of an implantation procedure.

The shank 1204 is the same or substantially similar in form and function to the shank 1004 previously described herein and includes the body 1206, upper portion or head 1208 having a spherical surface 1234 and an internal drive feature 1246 the same or similar to the respective body 1006, upper portion 1008, spherical surface 1034 and drive feature 1046 previously described herein with respect to the shank 1004 of the assembly 1001.

The receiver 1210 is also substantially similar in form and function to the receiver 1010 previously described herein. However, there are differences between the two receivers as the receiver 1210 cooperates with the insert 1214 that varies in many respects from the insert 1014 previously described herein. Therefore, the receiver 1210 and the insert 1214 will be described in greater detail below.

With particular reference to FIGS. 60-63 and 72, the receiver 1210 has a generally squared-off U-shaped appearance with partially discontinuous and partially cylindrical inner and outer profiles. The receiver 1210 has an axis of rotation that is shown in FIG. 60 as being aligned with and the same as an axis of rotation of the shank 1204, such orientation being desirable, but not required during assembly of the receiver 1210 with the shank 1204. The receiver 1210 includes a substantially cylindrical base 1260 defining an inner cavity 1261, the base 1260 being integral with a pair of opposed upstanding arms 1262 forming a cradle and defining a channel 1264 between the arms 1262 with an upper opening, generally 1266, and a squared-off U-shaped lower seat 1268, the channel 1264 having a width for operably snugly receiving the rod 1221 between the arms 1262, the channel 1264 communicating with the base inner cavity 1261. The squared-off geometry of the channel 1264 and lower seat 1268 allow for use with a variety of longitudinal connecting members, including, but not limited to those with circular, square and rectangular cross-sections. As compared to a U-shaped channel that includes a lower seat having a surface with a radius the same or slightly larger than a cooperating cylindrical rod or other connecting member, the squared-off seat 1268 of the present invention provides improved stress management, moving stress risers outwardly toward the two arms 1262 rather than being focused primarily at a center base line of the radiused lower seat. Furthermore, outer front and rear opposed substantially planar base surfaces 1269 that partially define the squared-off lower seat 1268 advantageously reduce the run on the rod (i.e., provide a more narrow receiver that in turn provides more space and thus more access between bone anchors along the rod or other connecting member) and provide a planar surface for flush or close contact with other connecting member components in certain embodiments, such as for bumpers or spacers that surround a hard or deformable rod or provide support for cord-type connecting members. The planar surfaces can also better cooperate with compression and distraction tools.

Each of the arms 1262 has an interior surface, generally 1270, that includes various inner cylindrical profiles, an upper one of which is a partial helically wound guide and advancement structure 1272 located adjacent top surfaces 1273 of each of the arms 1262. In the illustrated embodiment, the guide and advancement structure 1272 is a partial helically wound interlocking flangeform configured to mate under rotation with a similar structure on the closure structure 1218. However, it is foreseen that the guide and advancement structure 1272 could alternatively be a square-shaped thread, a buttress thread, a reverse angle thread or other thread-like or non-thread-like helically wound discontinuous advancement structure for operably guiding under rotation and advancing the closure structure 1018 downward between the arms 1262, as well as eventual torquing when the closure structure 1218 abuts against the rod 1221 or other longitudinal connecting member.

An opposed pair of tool receiving and engaging apertures 1274 are formed on outer surfaces 1276 of the arms 1262. Furthermore, two pair of tool receiving and engaging apertures 1277 are formed in front and rear surfaces 1278 of the arms 1262. Some or all of the apertures 1274 and 1277 may be used for holding the receiver 1210 during assembly with the insert 1214, the retainer 1212 and the shank 1204, during the implantation of the shank body 1206 into a vertebra when the shank is pre-assembled with the receiver 1210, and during assembly of the bone anchor assembly 1201 with the rod 1221 and the closure structure 1218. It is foreseen that tool receiving grooves or apertures may be configured in a variety of shapes and sizes and be disposed at other locations on the receiver arms 1262.

Returning to the interior surface 1270 of the receiver arms 1262, located below the guide and advancement structure 1272, adjacent a bottom surface 1280 thereof, is a discontinuous cylindrical surface 1282 partially defining a run-out feature for the guide and advancement structure 1272. The cylindrical surface 1282 has a diameter equal to or slightly greater than a greater diameter of the guide and advancement structure 1272. Moving downwardly, in a direction toward the base 1260, adjacent the cylindrical surface 1282 is a run-out seat or surface 1284 that extends inwardly toward the central axis of the receiver and is perpendicular thereto. Adjacent to and located below the surface 1284 is another discontinuous cylindrical surface 1285 having a diameter smaller than the diameter of the surface 1282. The surface 1285 terminates at a narrow ledge 1286 that in turn partially defines another discontinuous cylindrical surface 1287 having a diameter slightly smaller than the diameter of the surface 1285. With particular reference to FIGS. 76 and 77 an edge or rim 1288 that defines the junction of the ledge 286 and the cylindrical surface 287 is shown cooperating with the insert 214 as will be described in greater detail below, providing an advantageous shank lock and release feature of the assembly 201.

As discussed in greater detail below, the assembly 1201 is typically provided to a user with the insert 1214 being held within the receiver by a pair of spring tabs, generally 1290, that resiliently hold the insert 1214 and keep the insert stationary with respect to the receiver 1210 in an upward position between the arms 1262 until the insert 1214 is pressed by the user into a friction fit working position wherein the insert 1214 is in frictional contact with the shank upper portion 1208, the shank still movable with respect to the insert 1214, but not in a loose or floppy manner. In a later stage of assembly, the spring tabs 1290 advantageously hold the insert 1214 in a centered position (the insert arms being held in alignment with the receiver arms) during rotation and torquing of the closure top 1218 onto the rod 1221 or other connecting member. Each spring tab 1290 generally extends from a location spaced from the surface 1287 and along one of the arms 1262 downwardly to the base 1260; each spring tab 1290 being integral with the base 1260. The opposed spring tabs 1290 include various surfaces for contacting the insert 1214 at different stages of assembly and will be discussed in greater detail in the paragraphs below.

Returning to FIGS. 62 and 63, the lower cavity 1261 within the base 1260 includes an inner cylindrical surface 1291, portions of which extend up into and partially form the spring tabs 1290. A continuous annular surface 1292 is located below and adjacent to the cylindrical surface 1291. The surface 1292 is disposed in the base 1260, partially defining the base cavity 1261 and providing a stop for the resilient retainer 1212, prohibiting the retainer 1212 (when in an uncompressed configuration) from moving upwardly into a space or cavity defined by the cylindrical surface 1291 and the spring tab 1290 inner surfaces that hold the compression insert 1214. Another cylindrical surface 1294 is located below and adjacent to the surface 1292. The cylindrical surface 1294 is oriented substantially parallel to the receiver central axis and is sized and shaped to receive an expanded retainer 1212. The surfaces 1292 and 1294 define a circumferential recess, groove or chamber 1295 that is sized and shaped to receive the retainer 1212 as it expands around the shank upper portion 1208 as the shank 1208 moves upwardly toward the channel 1264 during assembly, as well as form a restriction to prevent the expanded retainer 1212 from moving upwardly with the shank portion 1208, the surface 1292 preventing the retainer 1212 from passing from the groove 1295 into the cavity defined by the surface 1291 whether the retainer 1212 is in a partially or fully expanded position, or in a neutral or original operative position. A cylindrical surface 1296 located below the cylindrical surface 1294 is sized and shaped to closely receive the retainer 1212 when the retainer is in a neutral or operative position, for example. Thus, the cylindrical surface 1296 has a diameter smaller than the diameter of the cylindrical surface 1294 that defines the expansion groove 1295. The surface 1296 is joined or connected to the surface 1294 by one or more beveled, curved or conical surfaces 1297. The surfaces 1297 allow for sliding gradual movement and/or contraction of the retainer 1212 into the space defined by the surface 1296 and ultimate seating of the retainer 1212 on a lower annular surface 1299 located below and adjacent to the cylindrical surface 1296. Located below and adjacent to the annular seating surface 1299 is another cylindrical surface 1300 that communicates with a beveled or flared bottom opening surface 1302, the surface 1302 communicating with an exterior base surface 1304 of the base 1260, defining a lower opening, generally 1306, of the receiver 1210. The illustrated surface 1300 has a diameter that is substantially the same as an inner diameter of the surface 1291 that extends up into the spring tabs 1290, when in a neutral, un-sprung position as will be described in greater detail below, allowing for slidable uploading of the compression insert 1214 (with minor squeezing of the insert arms toward one another) while requiring substantial compression or squeezing of the retainer 1212 during uploading of the retainer 1212 through the lower opening 1306.

Returning to the spring tabs 1290, each spring tab includes a top surface 1310 and a first radiused inner surface 1311 perpendicular to a lower lip or abutment surface 1312.

The abutment surface 1312 extends from the surface 1311 to the inner cylindrical surface 1291 that has a radius larger than a radius of the surface 1311. Each spring tab 1290 is further defined by a pair of opposed parallel side surfaces 1314, a pair of angled or diverging side surfaces 1315 and an outer surface 1317. The parallel surfaces 1314 are located on either side of the inner surface 1311 and the top surface 1310. The diverging side surfaces 1315 each run from the outer surface 1317 outwardly toward an adjacent surface 1314, the illustrated pairs of surfaces 1317 being at an acute angle with respect to one another. The top surface 1310 is spaced from the cylindrical surface 1287. When the tabs 1290 are in a neutral, non-sprung state, the surfaces 1311 define a diameter smaller than an outer diameter of the insert 1214, while the inner surface 1291 forms a discontinuous cylindrical surface having a diameter slightly larger than a lower outer diameter of the insert 1214, the insert 1214 being snugly held thereby and centered by the spring tabs 1290 that are positioned within a groove of the insert 1214 as will be discussed in greater detail below. When the tabs 1290 are in an outwardly sprung state as shown on FIG. 72, for example, the surfaces 1311 frictionally engage the insert 1214, prohibiting both upward and downward movement of the insert 1214 within the receiver 1210, advantageously keeping the insert 1214 clear of other tools and components prior to assembly with other components and during the insertion of the retainer 1212 into the receiver 1210 and the bone screw shank upper portion 1208 into the retainer 1212 within the receiver 1210. When the spring tabs 1290 are later placed back into a neutral un-spring state, the lip surface 1312 of the tabs 1290 press downwardly on the insert 1214, holding the insert 1214 in a friction fit orientation with respect to the shank upper portion 1208.

As best shown in FIG. 78, the somewhat trapezoidal spring tabs 1290 are created by a machining process in which at least two cuts, at an acute angle to one another, are made into each receiver arm 1262. In order for the spring tabs 1290 to fit within grooves of the compression insert 1214, two parallel cuts are also made to form the opposed side surfaces 1314 of the spring tab 1290. Similar to that described with respect to the receiver 1010, an advantage of making angular cuts into the receiver 1210 to create the spring tabs 1290 is that angular cuts advantageously provide access to and removal of material from the inner receiver arms 1262 that then allow for the arms 1262 to receive the insert 1214 during the assembly step of springing the tabs 1290 outwardly and pushing the insert 1214 upwardly into frictional engagement with the surfaces 1311. This material clearing step is of special interest when the insert 1214 rather than the insert 1014 is being used according to the invention as the insert 1214 includes a pair of opposed arms that are taller than, and thus take up greater space within the receiver than the substantially cylindrical insert 1014.

With reference to FIGS. 60, 72-75 and 79, the retainer 1212 is substantially similar in form and function to the retainer 1012 previously described herein. Therefore, the retainer 1212 includes a top surface 1322, a bottom surface 1324, an inner cylindrical surface 1325, an inner frusto-conical surface 1327, an outer cylindrical surface 1330 and opposed ends 1334 and 1335 that are the same or substantially similar to the respective top surface 1122, bottom surface 1124, inner cylindrical surface 1125, inner frusto-conical surface 1127, outer cylindrical surface 1130 and opposed ends 1134 and 1135 of the retainer 1012 previously described herein with respect to the assembly 1001.

With reference to FIGS. 60 and 64-72, the compression insert 1214 is illustrated that is sized and shaped to be received by and up-loaded into the receiver at the lower opening 1306. The compression insert 1214 has an operational central axis that is the same as the central axis of the receiver 1210. The compression insert 1214 has a central channel or through bore defined by an inner cylindrical surface 1341, an inner partially spherical surface 1342 and a shank gripping surface portion, generally 1343, extending between the surface 1341 and the surface 1342. The gripping surface portion 1343 preferably includes two or more graduated cylindrical surfaces disposed substantially parallel to the insert central axis and adjacent perpendicular step surfaces that are disposed generally perpendicular to the insert central axis. It is foreseen that the stepped surface portion 1343 may include greater or fewer number of stepped surfaces. It is foreseen that the shank gripping surface portion 1343 and also the surface 1342 may additionally or alternatively include a roughened or textured surface or surface finish, or may be scored, knurled, or the like, for enhancing frictional engagement with the shank upper portion 1208.

The compression insert 1214 through bore is sized and shaped to receive a driving tool (such as the driving tool 1029 shown with the assembly 1001) therethrough that engages the shank drive feature 1246 when the shank body 1206 is driven into bone with the receiver 1210 attached. The surfaces 1342 and 1343 are sized and shaped to initially frictionally but slidingly receive and ultimately frictionally engage and fix onto the substantially spherical or domed surface 1234 of the shank upper portion 1208, in particular the stepped or ridged surface 1343 that will initially frictionally but slidingly and pivotally mate with the spherical surface 1234 to create a ball-and-socket type joint, but ultimately dig or penetrate into and thus be securely fixed with the domed surface 1234.

The compression insert 1214 also includes an outer and upper cylindrical surface 1344 that further extends upwardly on either side of the insert to form a pair of opposed arms 1345. Each arm 1345 further includes a top surface 1346 and an outer frusto-conical surface portion 1348 terminating at a lower surface or lip 1350. The frusto-conical surface portion 1348 flares outwardly and upwardly, having a largest radius thereof at the juncture of the surface 1348 with the top surface 1346. As will be described in greater detail below, frictional engagement between the surface portion 1348 and the cylindrical surface 1287 associated with the driving and downward movement of the closure top 1218 on the rod 1221 results in a locking of the polyaxial screw mechanism of the assembly 1201 that remains locked even if the closure top 1218 and the rod 1221 are subsequently loosened, allowing for all type and manner of manipulation of the bone screw and/or the rod 1221 by the surgeon while the polyaxial mechanism of the assembly 1201 remains rigidly fixed in the desired orientation previously chosen and locked down by the surgeon. However, if it is desired to loosen the polyaxial mechanism, the surgeon may do so by squeezing the arms 1345 toward one another with a tool (not shown) and moving the insert 1214 away from the shank 1204, thereby releasing the frusto-conical surface 1348 from the receiver cylindrical surface 1287 and thus loosening the polyaxial mechanism.

Extending between the insert arms 1345 is a U-shaped, saddle like surface 1352 that forms a seat for the rod 1221 or other longitudinal connecting member. Portions of the saddle surface 1352 communicate with the bore defined by the cylindrical surface 1341. The surface 1352 is sized and shaped to closely receive the cylindrical rod 1221 at a location spaced from the lower seat 1268 of the receiver 1210. A bottom surface 1354 communicates with the inner spherical surface 1342, the insert 1214 being sized and shaped such that the surface 1354 is always spaced from the retainer 1212 as shown, for example, in FIGS. 75 and 80. The insert 1214 also includes an outer lower cylindrical surface 1356 adjacent to the bottom surface 1354. The cylindrical surfaces 1344 and 1356 have the same or substantially the same outer diameter, sized to be received by the receiver surface 1300 when loaded into the receiver 1210 and also be snugly received by spring tab 1290 and receiver base inner surfaces 1291 when the spring tabs 1290 are in a neutral or relaxed state. Located between the surfaces 1344 and 1356 is a frusto-conical surface 1357 that extends from the surface 1344 inwardly toward the insert central axis and terminates at an annular ledge 1358. The ledge 1358 extends from the frusto-conical surface 1357 to the surface 1356 and is substantially perpendicular to the surface 1356. As will be described in greater detail below, during early stages of assembly, the insert 1214 outer surface 1357 is resiliently gripped by the spring tab surfaces 1311 with the spring tab lower lip 1312 engaging the ledge 1358 to hold the insert 1214 in a desired stationary position with respect to the receiver 1210. When the insert 1214 is lowered into a second or friction fit position in frictional engagement with the bone screw shank, the lower lip 1312 extends into one of a pair of opposed grooves 1359 as described below. The grooves 1359 are formed in the arm surfaces 1344 and extend upwardly into the upper frusto-conical surface 1348 and are located centrally with respect to each arm 1345. Each illustrated groove 1359 is sized and shaped to cooperate with the spring tabs 1290 at the surfaces 1311. The grooves 1359 are elongate, running parallel to a central axis of the insert 1214. Each groove 1359 has a lower seat or shelf 1360 positioned to engage the spring tab surface 1312 when the insert 1214 is in friction fit working engagement with the shank upper portion 1208 as will be described in greater detail below.

In operation, the insert 1214 extends at least partially in the channel 1264 of the receiver 1210 such that the saddle 1352 surface substantially contacts and engages the outer surface 1222 of the rod 1221 when such rod is placed in the receiver 1210 and the closure structure or top 1218 is tightened thereon. As will also be described below, the cooperation between the insert grooves 1359 and the spring tabs 1290 prohibits additional rotation of the insert 1214 with respect to the receiver 1210 during rotation and torquing of the closure top 1218 against the rod 1221 within the receiver arms 1262. The compression or pressure insert 1214 ultimately seats on the shank upper portion 1208 and is disposed partially within the spring tab cylindrical wall 1291 and partially between the receiver arms 1262.

With reference to FIGS. 60 and 75-80, the illustrated closure top 1218 and illustrated elongate rod or longitudinal connecting member 1221 are the same or substantially similar to the closure top 1018 and the rod 1021 previously described herein, and or alternatives also previously described herein. Thus, with respect to the closure top 218, components of such closure top 1218 include a guide and advancement structure 1362, a top surface 1364, an internal drive 1366, a bottom surface 1368, a point 1369 and a rim 1370 that are the same or substantially similar to the respective guide and advancement structure 1162, top surface 1164, internal drive 1166, bottom surface 1168, point 1169 and rim 1170 of the closure top 1018 previously described herein with respect to the assembly 1001.

Preferably, the receiver 1210, the retainer 1212 and compression insert 1214 are assembled at a factory setting that includes tooling for holding and alignment of the component pieces and pinching or compressing of the retainer 1212 and pinching the insert 1214 as well as spreading of the spring tabs 1290. In some circumstances, the shank 1204 is also assembled with the receiver 1210, retainer 1212 and compression insert 1214 at the factory. In other instances, it is desirable to first implant the shank 1204, followed by addition of the pre-assembled receiver 1210, retainer 1212 and compression insert 1214 at the insertion point. In this way, the surgeon may advantageously and more easily implant and manipulate the shanks 1204, distract or compress the vertebrae with the shanks and work around the shank upper portions or heads without the cooperating receivers being in the way. Furthermore, the assembly 1201 allows for manipulation of the rod 1221 subsequent to a complete lock down of the insert 1214 on the bone screw shank upper portion 1208 that completely locks the polyaxial mechanism of the assembly 1201, as will be described in greater detail below. In other instances, it is desirable for the surgical staff to pre-assemble a shank of a desired size with the receiver 1210, retainer 1212 and compression insert 1214. Allowing the surgeon to choose the appropriately sized shank 1204 advantageously reduces inventory requirements, thus reducing overall cost.

Figure 68:
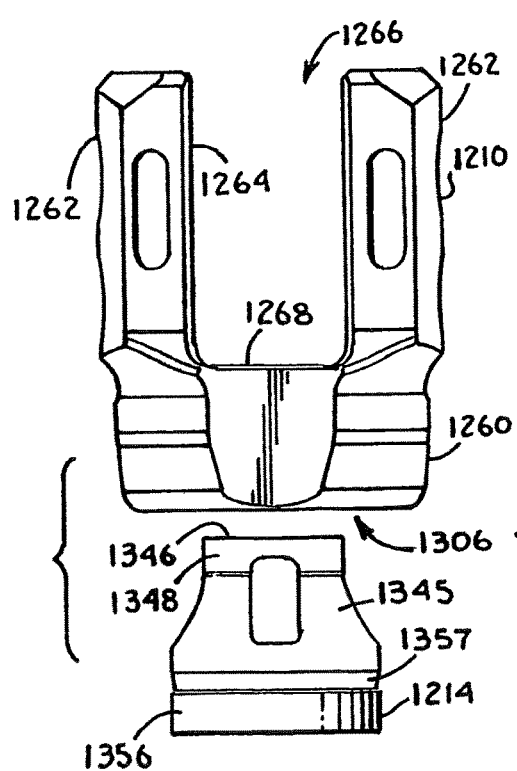
FIG. 68 is an enlarged front elevational view of the receiver of FIG. 60 shown in a stage of assembly with the insert of FIG. 60, shown in enlarged side elevational view.

Pre-assembly of the receiver 1210, retainer 1212 and compression insert 1214 is shown in FIGS. 68-72. First, the compression insert 1214 is prepared for uploading into the receiver 1210 through the lower opening 3106 using a holding tool (not shown) that squeezes or presses the insert arms 1345 toward one another at the upper frusto-conical surfaces 3148 so that the surfaces 1348 are received within the cylindrical surface 1300 during insertion of the insert 1214 into the receiver opening 1306. As illustrated in FIG. 68, the insert 1214 (in squeezed orientation) is inserted into the opening 1306 with the arms 1345 being aligned with the receiver channel 1264. During insertion, the spring tabs 2190 are also pulled apart as shown, for example in FIG. 70 until the spring tab surfaces 1311 are located adjacent the frusto-conical surface 1357. At this time, the insert 1214, no longer in a squeezed state, is rotated as illustrated by an arrow K in FIG. 70 about the central axis thereof until the insert arms 1345 are located within the receiver run-out defined by the cylindrical surface 1282 located directly below the guide and advancement structure 1272 as shown in FIG. 71. As shown in FIG. 71, the guide and advancement structure 1272 prohibits further upward movement of the insert 1214. The spring tabs 1290 are allowed to resiliently move into contact with the insert surface 1357, preferably engaging such surface 1357 adjacent to the ledge 1358. The surface 1312 advantageously abuts against the ledge 1358, stopping the insert 1214 from any further upward movement towards the guide and advancement structure 1272 and providing adequate clearance for the later step of pushing the bone screw shank upper portion 1208 through the spring ring retainer 1212. Although the guide and advancement structure 1272 would prohibit the insert 1214 from moving out the upper opening 1266, engagement with the resilient spring tabs 1290 also prohibits rotational and downward movement of the insert 1214 and keeps the insert 1214 away from the lower opening 1306 during assembly of the retainer 1212.

Figure 72:
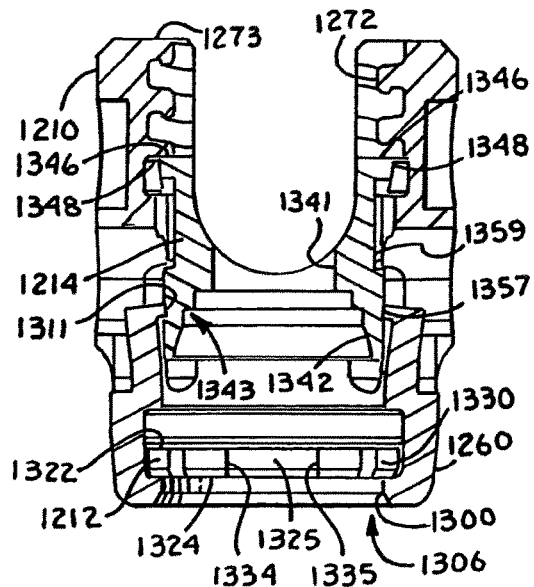
FIG. 72 is an enlarged front elevational view of the receiver, insert and retainer of FIG. 60 with portions broken away to show the detail thereof shown in a pre-assembled orientation with the insert and retainer captured within the receiver.
Figure 73:
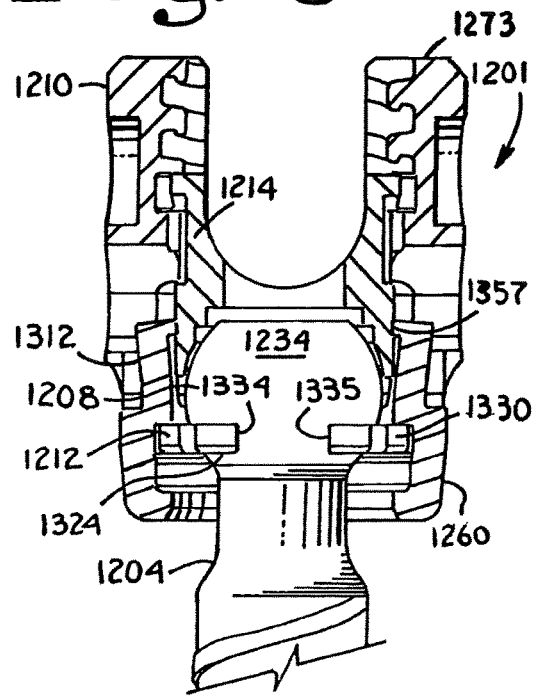
FIG. 73 is a partial front elevational view of the receiver, insert and retainer with portions broken away to show the detail thereof, similar to FIG. 72, and further showing a stage of assembly with the shank of FIG. 60, shown in partial enlarged front elevational view.

With reference to FIGS. 72-75, the resilient open retainer 1212 is prepared for insertion into the receiver 1210 by squeezing or pressing the retainer end surfaces 1334 and 1335 toward one another. The compressed retainer 1212 is inserted into the lower opening 1306 with the top surface 1322 facing the receiver bottom surface 1304. The retainer 1212 is typically moved upwardly into the receiver 1210 and past the cylindrical surface 1296 and allowed to expand to a neutral uncompressed state within the cylindrical surface 1296 as shown in FIG. 72. Also as shown in FIG. 72, at this time, both the compression insert 1214 and the retainer 1212 are captured within the receiver 1210. The receiver 1210, compression insert 1214 and the retainer 1212 combination is now pre-assembled and ready for assembly with the shank 1204 either at the factory, by surgery staff prior to implantation, or directly upon an implanted shank 1204.

The bone screw shank 1204 (or an entire assembly 1201 made up of the assembled shank 1204, receiver 1210, retainer 1212 and compression insert 1214) is screwed into a bone, such as the vertebra 1013 as previously described herein with respect to the shank 1004 and cooperating assembly 1001 and the shank 4 and assembly 1. The pre-assembled receiver, insert and retainer are placed above the shank upper portion 1208 until the shank upper portion is received within the opening 1306. As the shank is moved into the interior of the receiver base, the shank upper portion 1208 presses the retainer 1212 upwardly into the chamber 1295 (if the retainer is not already located within such chamber). As the portion 1208 continues to move upwardly toward the channel 1264, the retainer top surface 1322 abuts against the annular surface 1292 stopping upward movement of the retainer 1212 and forcing outward movement of the retainer 1212 towards the cylindrical surface 1294 defining the expansion chamber 1295 as the spherical surface 1234 continues in an upward direction. The retainer 1212 begins to contract about the spherical surface 1234 as the center of the sphere passes beyond the center of the retainer expansion groove 1295 (see FIG. 73). The retainer is then free to be moved down into an operative position by either gravity and/or an upward pull on the receiver 1210 or, in some cases, by driving the shank 1204 further into the vertebra 1013. Also, in some embodiments, when the receiver 1210 is pre-assembled with the shank 1204, the entire assembly 1201 may be implanted at this time by inserting the driving tool into the receiver and the shank drive 1246 and rotating and driving the shank 1204 into a desired location of the vertebra.

Figure 74:
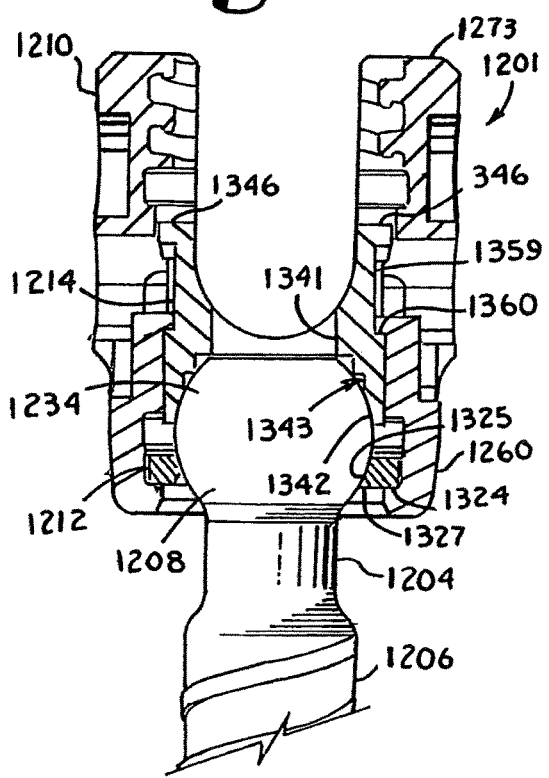
FIG. 74 is a partial front elevational view with portions broken away, similar to FIG. 73 and showing a friction fit stage of assembly subsequent to that shown in FIG. 73.
Figure 75:
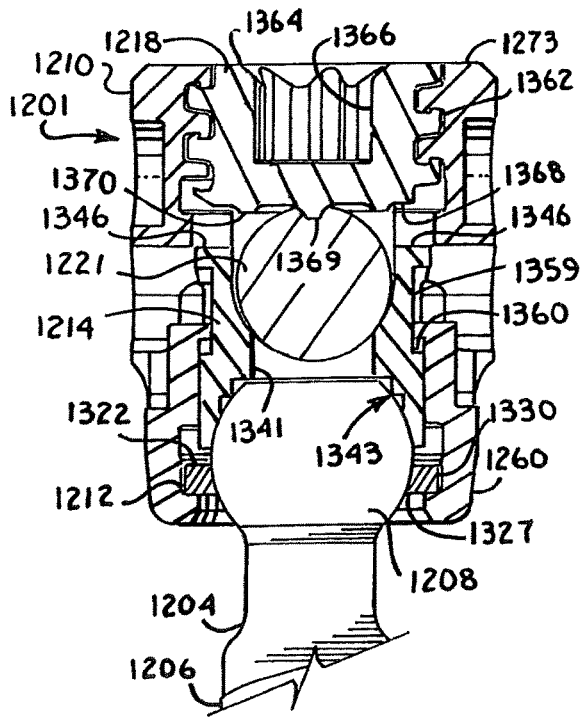
FIG. 75 is a partial front elevational view of the receiver, shank, retainer and insert with portions broken away, similar to FIG. 74, further showing the rod and closure top of FIG. 60, also in front elevational view with portions broken away, the assembly being in a locking stage of assembly subsequent to that shown in FIG. 74.

With reference to FIG. 74, at this time, the compression insert 1214 is pressed downwardly manually, with a rod or with a tool (not shown) toward the shank upper portion 1208, the insert surfaces 1357 and 1344 being moved out of engagement with the spring tab surfaces 1311 when the surfaces 1311 enter into the insert grooves 1359. Once the spring tabs 1290 move into the grooves 1359, the insert 1214 snaps into place and the spring tabs 1290 return to an original, relaxed or only slightly expanded orientation with the surfaces 1312 located over the groove seat 1360 and frictionally engaging such surface. The spring tabs 1290 are sized such that when the surfaces 1312 frictionally engage the surfaces 1360 of the insert, the insert 1214 surfaces 1342 and 1343 in turn press against the shank upper portion 1208 at the spherical surface 1234. The friction fit between the compression insert 1214 and the shank upper portion 1208 is not fixed but at the same time not loose or floppy either, advantageously allowing the user to articulate the shank 1204 with respect to the receiver 1210, but with some resistance, so that when the shank is placed in a desired orientation with respect to the receiver, the assembly 1201 remains substantially frictionally set in such desired orientation unless purposefully manipulated into another position. For example, at this time, the receiver 1210 may be articulated to a desired position with respect to the shank 1204 as shown, for example, as shown in FIG. 80, but prior to locking of such position that is shown in those drawings.

With reference to FIGS. 75-78, the rod 1221 is eventually positioned in an open or percutaneous manner in cooperation with the at least two bone screw assemblies 1201. The closure structure 1218 is then inserted into and advanced between the arms 1262 of the receiver 1210. The closure structure 1218 is rotated, using a tool engaged with the inner drive 1366 until a selected pressure is reached at which point the rod 1221 engages the insert saddle 1352, further pressing the insert spherical surface 1342 and stepped surfaces 1343 against the shank spherical surface 1234, the edges of the stepped surfaces penetrating into the spherical surface 1234. As the closure structure 1218 rotates and moves downwardly into the respective receiver 1210, the point 1369 and rim 1370 engage and penetrate the rod surface 1222, the closure structure 1218 pressing downwardly against and biasing the rod 1221 into full engagement with the insert 1214 that urges the shank upper portion 1208 toward the retainer 1212 and into locking engagement therewith, the retainer 1212 frictionally abutting the surface 1299 and expanding outwardly against the cylindrical surface 1296. For example, about 80 to about 120 inch pounds of torque on the closure top may be applied for fixing the bone screw shank 1206 with respect to the receiver 1210. As shown in FIG. 78, during rotation and downward movement of the closure top 1218, the insert 1214 arms 1345 are retained in alignment with the receiver arms 1262 and thus the saddle surface 1352 is retained in alignment within the receiver channel 1264 by the spring tabs 1290 located within the insert grooves 1359. Also, as shown in FIGS. 76 and 77, during rotation and downward movement of the closure top 1218, the rod 1221 presses the insert 1214 in a direction towards the receiver base 1260, pressing the frusto-conical insert surfaces 1348 into engagement with the cylindrical receiver surfaces 1287, thereby wedging and compression locking the insert 1214 into and against the receiver 1210. If the closure top 1218 is then loosened and rotated to an upward unlocked position, for example as shown in FIG. 79, the rod 1221 is also loosened, but the insert 1214 remains in a downward position, wedged against the receiver walls 1287. This advantageously allows the surgeon to slide or otherwise manipulate the bone anchor and/or the rod 1221 with respect to the assembly 1201 while the assembly 1201 is otherwise in a totally locked position with the shank 1204 in a desired fixed, unmovable angular orientation with respect to the receiver 1210. Once any desirable movement or manipulation of the rod 1221 is completed, the closure top 1218 is simply rotated back into the position shown in FIG. 75, locking the rod 1221 back into place. Furthermore, if the polyaxial mechanism needs to be unlocked, the insert surfaces 1348 are squeezed toward one another using a tool (not shown) that is inserted into the insert grooves 1359 at a location above the spring tabs 1290. The squeezed insert 1214 is then pulled or moved slightly upwardly toward the opening 1266 disengaging the surfaces 1348 from the receiver walls 1287 and unlocking the polyaxial mechanism of the assembly 1201.

Figure 81:
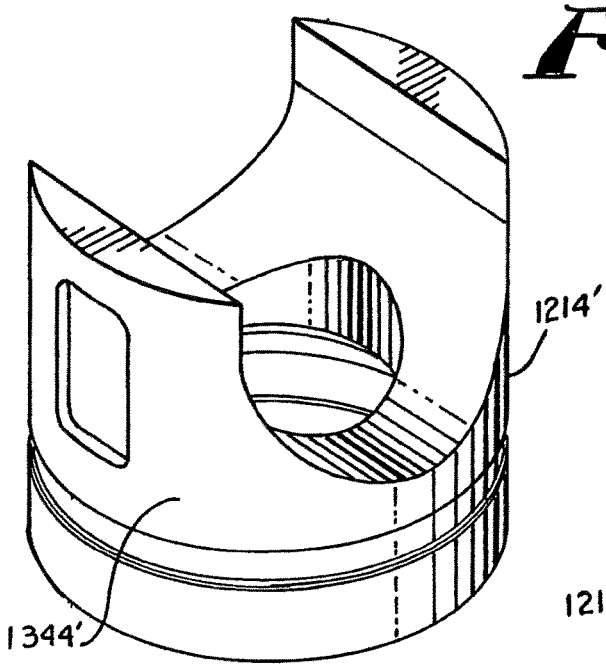
FIG. 81 is an enlarged perspective view of an alternative compression insert for use with the assembly of FIG. 60.
Figure 82:
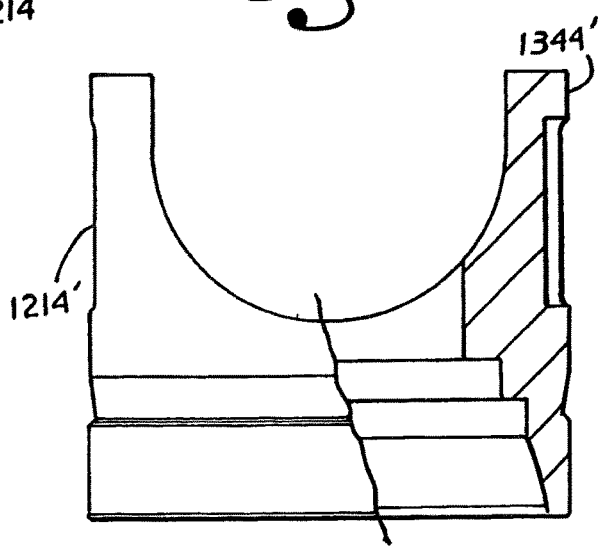
FIG. 82 is a front elevational view of the insert of FIG. 81 with portions broken away to show the detail thereof.
Figure 83:
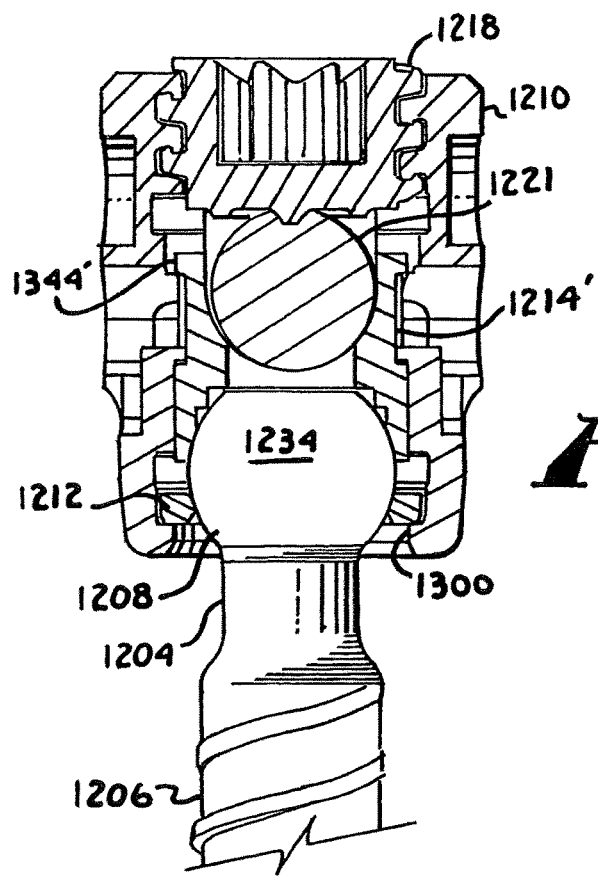
FIG. 83 is an enlarged and partial front elevational view of the assembly of FIG. 60 shown with the alternative insert of FIG. 81 and with portions broken away to show the detail thereof.

With reference to FIGS. 81-83, an alternative compression insert 1214' is shown that is substantially similar to the insert 1214 with the exception that the insert 1214' does not include the compression lock and squeeze release feature of the frusto-conical upper surfaces 1348. Thus, the insert 1214' may be utilized in embodiments wherein the lock and release feature is not desired. The insert 1214' advantageously does not require any squeezing or other manipulation when uploaded into the receiver 1210 as it includes a cylindrical outer surface 1344' that is receivable within the receiver lower opening cylindrical surface 1300.

With reference to FIG. 84 and to U.S. patent application Ser. No. 12/802,849 filed Jun. 15, 2010 (hereafter the '849 application) that is incorporated by reference herein, polyaxial bone screws 1, 1001 and 1010 according to the invention (as well as the other polyaxial screws described later in this application) may be attached to a dynamic stabilization longitudinal connecting member assembly according to the present invention, generally 1401. The connecting member assembly 1401 is elongate, having a substantially central axis. With particular reference to FIG. 84, the connecting member assembly 1401 more fully described in the '849 application is illustrated that generally includes at least one inelastic sleeve, that may be flanged or not, such as, for example, the sleeves 1406 and 1406' with spacers 1415 or spacer/liner 1416 combinations located between the bone screws and attached sleeves. The illustrated connector 1401 is further shown with a hard rod 1121' and a rod cord connector 1424 as well as a cord 1422. Two bone screws 1001 are shown, one of which is attached to the sleeve 1406' and the other to the hard rod 1121'. As more fully discussed in the '849 application, either a slide or slip closure top, such as the tops 18 and 1018 previously described herein or the break-off head closure tops 1430 and 1432 shown in FIGS. 87-90 (and shown in phantom in FIG. 84) engage a respective sleeve (or a hard rod) but not the cord 1422, allowing the cord to slip or slide within the polyaxial screw; or a grip closure top 1431 is used that extends through the sleeve and grips and fixes the cord 1422 against a surface of the sleeve and thus fixes the cord in relation to the polyaxial screw 1001. The closure tops 1430, 1431 and 1432 are shown in greater detail in FIGS. 85-90.

Figure 89:
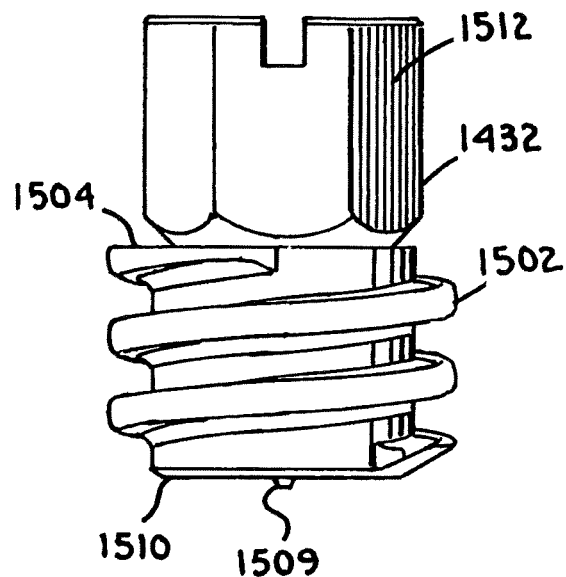
FIG. 89 is an enlarged front elevational view of another closure top also shown in FIG. 84.
Figure 90:
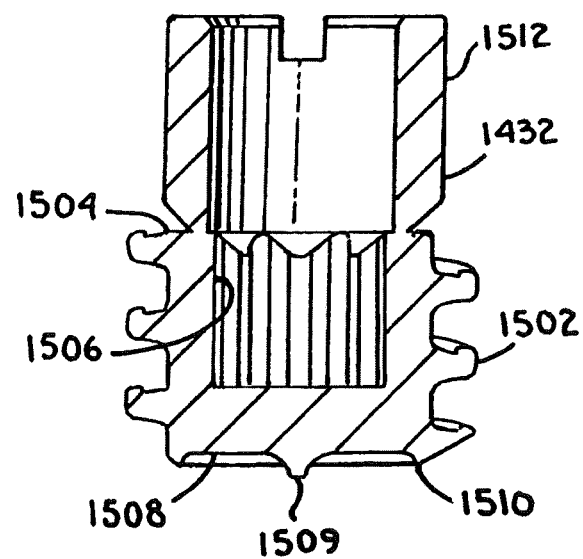
FIG. 90 is a front elevational view of the closure top of FIG. 89 with portions broken away to show the detail thereof.
Figure 98:
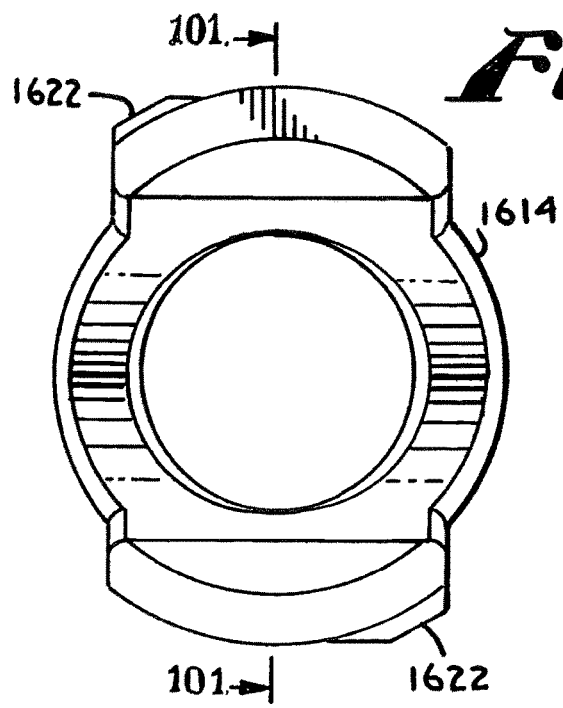
FIG. 98 is a top plan view of the insert of FIG. 96.
Figure 99:
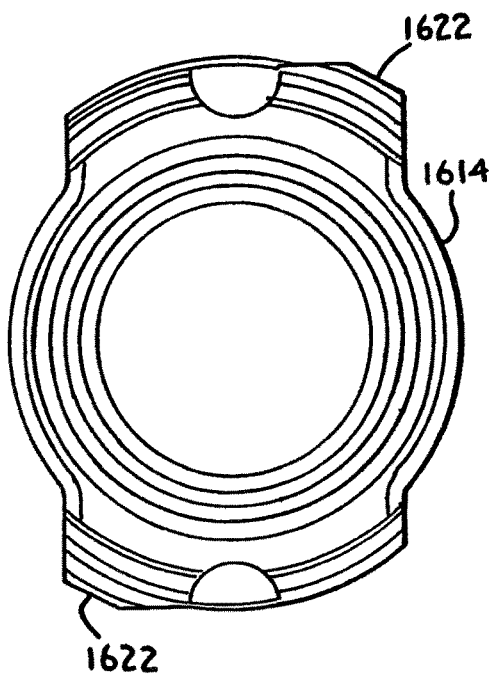
FIG. 99 is a bottom plan view of the insert of FIG. 96.
Figure 100:
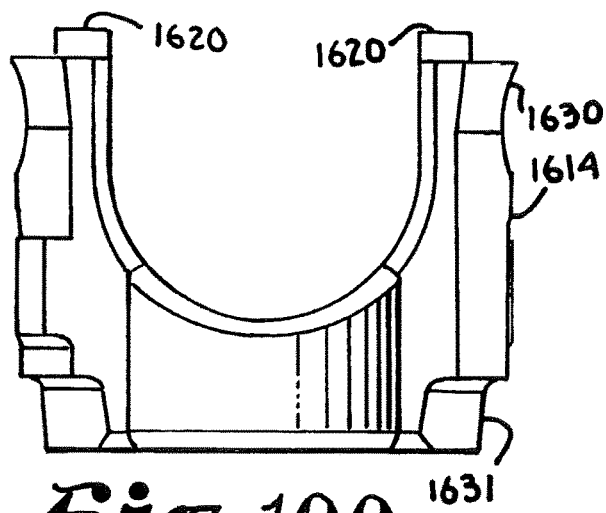
FIG. 100 is a front elevational view of the insert of FIG. 96.
Figure 101:
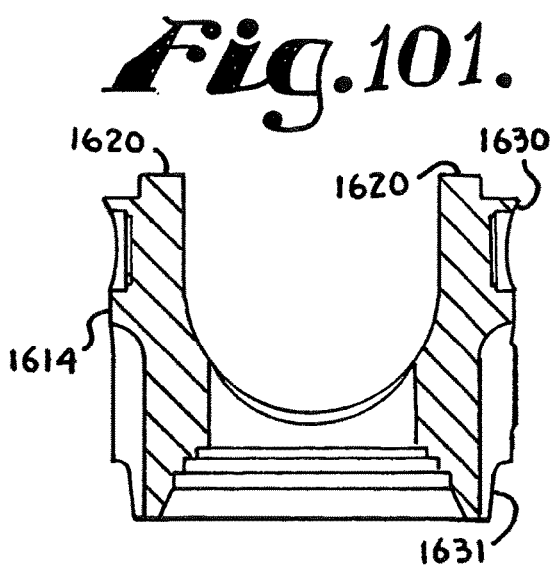
FIG. 101 is a cross-sectional view taken along the line 101-101 of FIG. 98.
Figure 102:
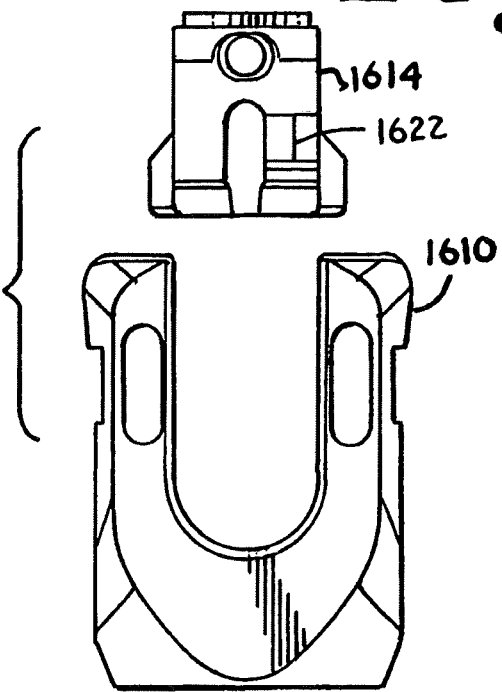
FIG. 102 is an enlarged front elevational view of the receiver and an enlarged side elevational view of the insert of FIG. 91 shown in a stage of assembly.
Figure 103:
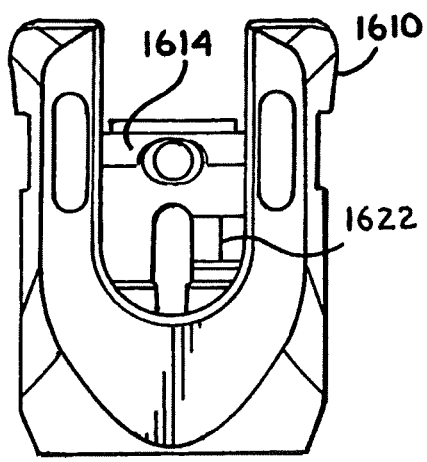
FIG. 103 is a front elevational view, similar to FIG. 102 showing a later stage of assembly.
Figure 104:
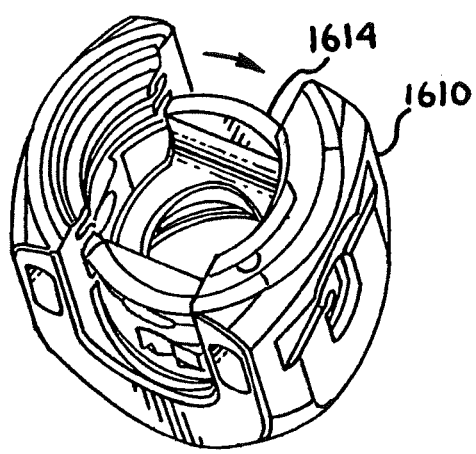
FIG. 104 is a perspective view showing the assembly step of FIG. 103.
Figure 105:
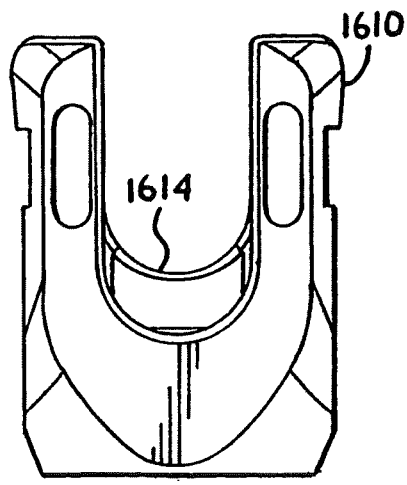
FIG. 105 is a front elevational view, similar to FIG. 103 showing a later stage of assembly.
Figure 108:
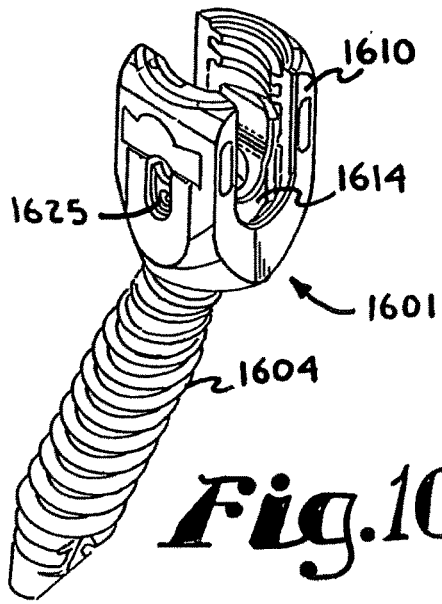
FIG. 108 is a reduced perspective view similar to FIG. 107 showing the shank at an angle with respect to the receiver.
Figure 109:
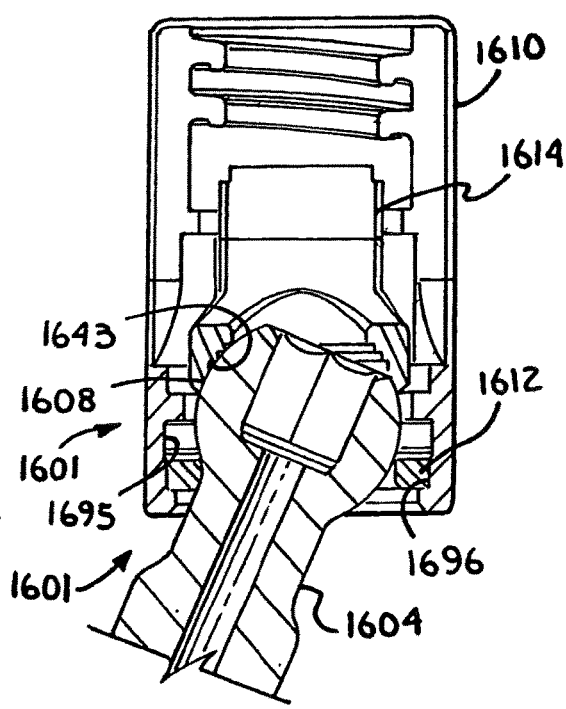
FIG. 109 is an enlarged side elevational view similar to FIG. 108 with portions broken away to show the detail thereof.
Figure 110:
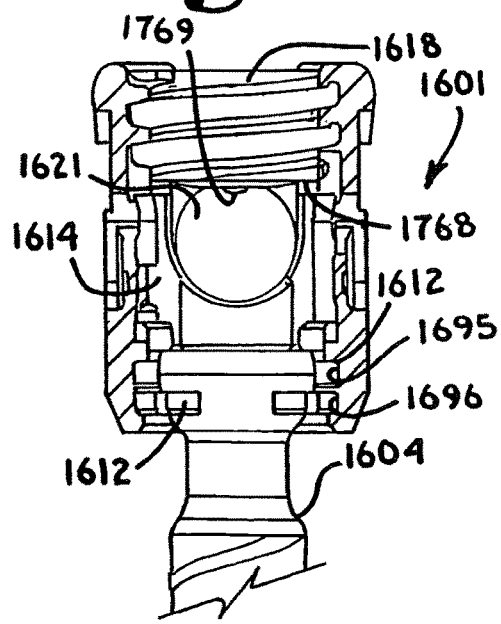
FIG. 110 is an enlarged front elevational view of the assembly of FIG. 91 with portions broken away showing a penultimate stage of assembly.
Figure 111:
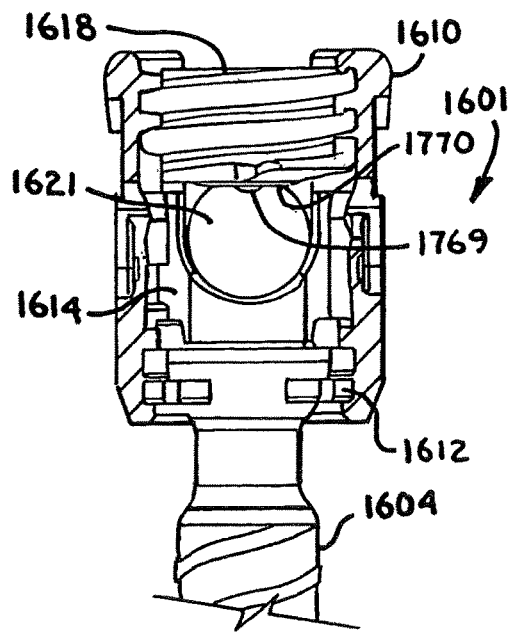
FIG. 111 is a front elevational view with portions broken away, similar to FIG. 110, showing a final locked down stage of assembly.
Figure 112:
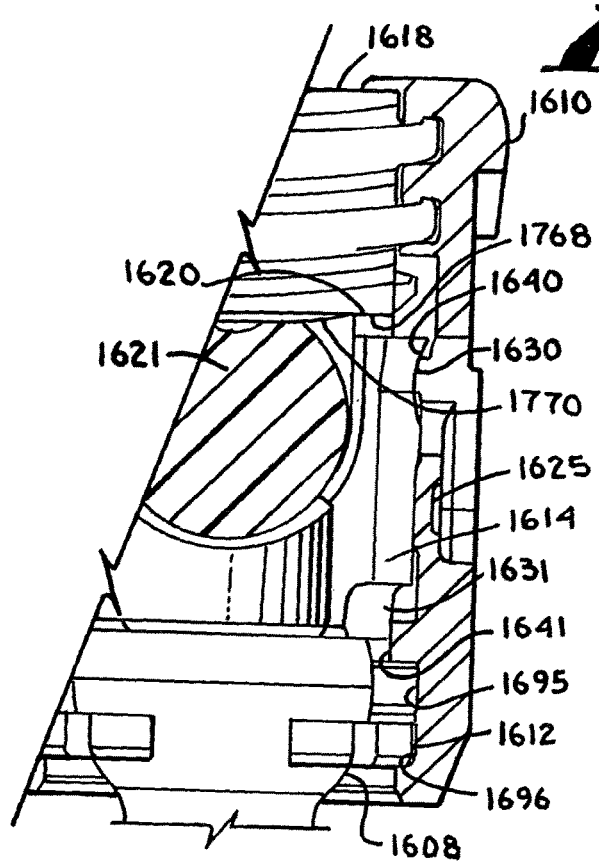
FIG. 112 is an enlarged and partial view of the assembly as in FIG. 110 with portions broken away to show the detail thereof.
Figure 113:
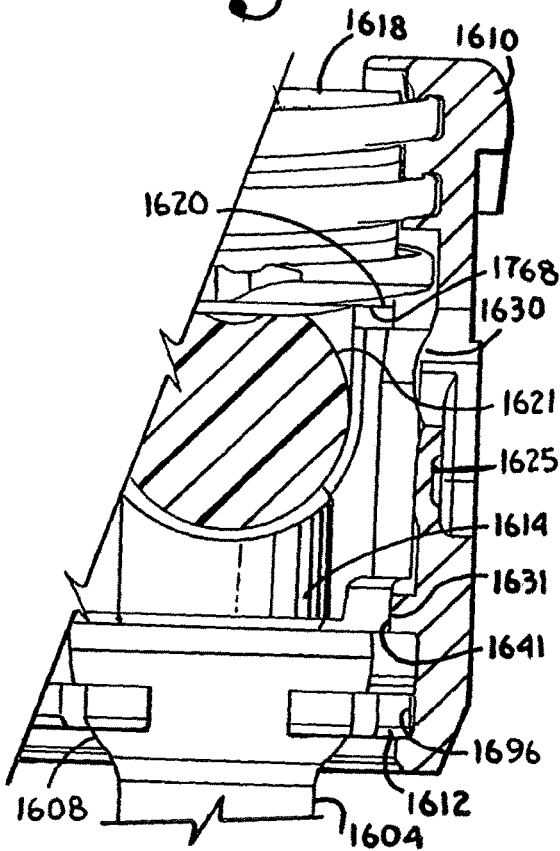
FIG. 113 is an enlarged and partial view of the assembly fully locked down as in FIG. 111 with portions broken away to show the detail thereof.

With further reference to FIGS. 85-90, various closure tops for use with the bone screw assemblies according to the invention and the connecting assembly 1401 are shown. The bone screw 1432 shown in FIGS. 89 and 90 is identical to the closure tops 18 and 1018 previously described herein with the exception that it includes a break-off head designed to allow such a head to break from a base of the closure at a preselected torque, for example, 70 to 140 inch pounds. Thus, the closure structure 1432 includes an outer helically wound guide and advancement structure 1502, a top surface 1504 of the guide and advancement structure, an internal drive 1506, a bottom surface 1508, a point 1509 and a rim 1510, the same or similar to the respective guide and advancement structure 1162, top surface 1164, internal drive 1166, bottom surface 1168, point 1169 and rim 1170 previously discussed herein with respect to the closure structure 1018. Located above the guide and advancement structure top surface is a break-off head 1512.

With reference to FIGS. 85 and 86, also cooperating with the bone anchors 1 and 1001 is the closure top 1431 having an outer helically wound guide and advancement structure 1522, a top surface 1524 of the guide and advancement structure, an internal drive 1526 and a break-off head 1532, the same or similar to the respective guide and advancement structure 1502, top surface 1504, internal drive 1506 and break-off head 1512 previously discussed herein with respect to the closure top 1432. In lieu of the point and rim of the closure top 1432, the closure top 1431 has a lower cylindrical portion 1527 having a substantially planar bottom surface 1528. The portion 1527 is sized and shaped to be received by a bore of the cooperating sleeve, for example, the sleeve 1406', the bottom surface 1528 pressing the cord 1422 into fixed engagement with the sleeve.

With reference to FIGS. 87 and 88, also cooperating with the bone anchors 1 and 1001 is the closure top 1430 having a an outer helically wound guide and advancement structure 1542, a top surface 1544 of the guide and advancement structure, an internal drive 1546 and a break-off head 1552, the same or similar to the respective guide and advancement structure 1522, top surface 1524, internal drive 1526 and break-off head 1532 previously discussed herein with respect to the closure top 1431. The closure top 1430 includes a planar bottom surface 1548 adjacent the guide and advancement structure 1542. The planar bottom surface 1548 remains flush with a corresponding sleeve surface and does not enter into the bore of the sleeve, allowing sliding movement of the cord 1422 with respect to the bone screw receivers 1010 cooperating with the closure tops 1430.

With reference to FIGS. 91-114, the reference numeral 1601 generally represents another embodiment of a polyaxial bone screw according to the invention. The assembly 1601 includes a shank 1604, that further includes a body 1606 integral with an upwardly extending upper portion or capture structure 1608; a receiver 1610; a retainer structure 1612 and a compression or pressure insert 1614. The receiver 1610, retainer 1612 and compression insert 1614 are initially assembled and may be further assembled with the shank 1604 either prior or subsequent to implantation of the shank body 1606 into a vertebra. The shank 1604 and the retainer 1612 are substantially the same in form and function as the respective shank 1204 and retainer 1212 previously discussed herein. With particular reference to FIGS. 106-109, the receiver 1610 is also similar in form and function to the receiver 1210 and other receivers previously discussed herein in that the receiver 1610 provides an expansion chamber 1695 for the retainer to expand about the shank upper portion 1608 allowing the shank to "pop" or "snap" on to the assembly, and a receiver lower seat 1696 for the retainer 1612 to slightly expand into when the shank upper portion 1608 is locked against the retainer 1612. The receiver 1610 differs from the receiver 1210 in that the receiver 1610 does not include spring tabs, but rather has a blocking feature 1623 as will be described below and crimping walls 1625. Furthermore, the receiver 1610 includes surfaces 1640 and 1641 for engagement with the insert 1614, first to hold the insert 1614 in an upper portion of the receiver during shipping and assembly with the shank 1604, the surfaces facilitating a friction fit between the insert 1614 and the shank head 1608 during manipulation of the bone screw 1601 and then locking of the shank 1604 with respect to the receiver by the insert 1614 even if a rod and closure top is loosened or removed from the assembly 1601.

FIGS. 91 and 110-114 further show a closure structure 1618 that is the same as the closure 1018 previously described herein with the exception that the point and rim have been replaced by a bottom outer planar annular rim 1768, a central point or knob 1769 and a domed surface 1770 running from the point 1769 to the rim 1768, the closure 1618 for capturing a longitudinal connecting member, for example, a deformable rod 1621 in the form of a PEEK rod which in turn engages the compression insert 1614 that presses against the shank upper portion 1608 into fixed frictional contact with the retainer 1612, so as to capture, and fix the longitudinal connecting member 1621 within the receiver 1610 and thus fix the member 1621 relative to the vertebra. Furthermore, the insert 1614 includes top surfaces 1620 of arms thereof that engage the closure top 1618 at an annular bottom rim 1768, providing for a locked polyaxial mechanism in the event that the deformable rod 1621 loosens within the receiver 1610. The receiver 1610 and the shank 1604 cooperate in such a manner that the receiver 1610 and the shank 1604 can be secured at any of a plurality of angles, articulations or rotational alignments relative to one another and within a selected range of angles both from side to side and from front to rear, to enable flexible or articulated engagement of the receiver 1610 with the shank 1604 until both are locked or fixed relative to each other near the end of an implantation procedure.

Features of the assembly 1601 include, but are not limited to the downloaded lock and release insert 1614 that includes a rotation block feature 1622 that abuts against the stop or wall 1623 of the receiver 1610 upon insertion, placing the insert 1614 into alignment with the receiver 1610. With reference to FIGS. 102-105, the block feature 1622 and the drop-down insertion of the insert into the receiver followed by rotation thereof until the insert feature abuts the wall 1623 of the receiver is described in greater detail in the '849 patent application that is fully incorporated by reference herein. With reference to FIG. 106, thereafter, thin crimp walls 1625 of the receiver 1610 are pressed inwardly into grooves 1626 of the insert 1614 to block reverse rotation of the insert 1614 out of the receiver and to also frictionally hold the receiver in a desired location, including an upward location shown in FIG. 106 during shipping and early assembly and a down, shank engaging location shown in FIG. 109, for example. Furthermore, in some embodiments of the invention, the insert arms have some flexibility and the arm surfaces 1630 abutting against surfaces 1640 of the receiver may also aid in keeping the insert in the upward location shown in FIG. 106 until the insert is pushed downwardly toward the receiver base in a later stage of assembly.

Figure 114:
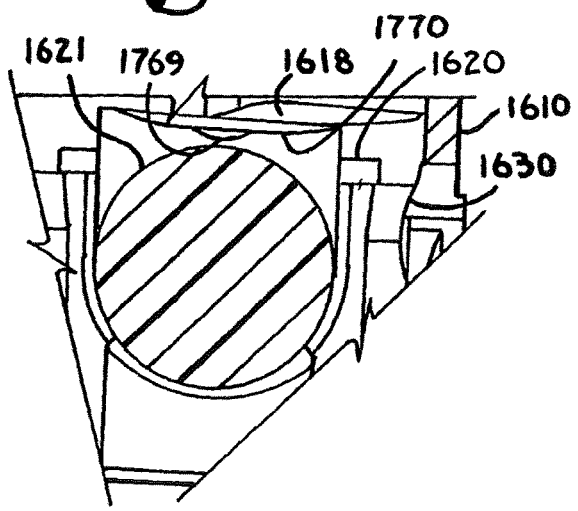
FIG. 114 is an enlarged and partial view, similar to FIG. 113 showing a loosened closure top with a fully locked down assembly.

With further particular reference to FIGS. 110-114, the insert 1614 upper surface 1630 is frusto-conical or otherwise tapered, sized and shaped for wedging against the receiver cylindrical surface 1640 and the insert further includes a lower frusto-conical surface 1631 sized and shaped for wedging into the lower cylindrical surface 1641 of the receiver 1610. Similar to the assembly 1200, as the closure top is advanced downwardly, the frusto-conical surfaces of the insert 1614 wedge into the cylindrical surfaces of the receiver 1610, locking the insert against the shank 1604 and thus locking the polyaxial mechanism, even if the closure top 1618 is later backed out as shown in FIG. 114, allowing for manipulation of the rod 1621 with an advantageously fully locked polyaxial mechanism. If it is desired to loosen the polyaxial mechanism, a tool, not shown may be inserted into the receiver 1610 to push arms of the insert 1614 toward one another and upwardly, loosening the surfaces 1630 and 1631 from the respective receiver surfaces 1640 and 1641.

Furthermore, prior to locking of the insert 1614 against the receiver 1610, the insert may be pressed downwardly into engagement with the shank upper portion 1608 to provide a friction fit between the insert 1615 and the upper portion 1608, either one or both of the upper and lower receiver engagement surfaces 1640 and 1641 engaging with the respective insert surfaces 1630 and 1631 to provide enough downward force or frictional fit between the insert inner stepped surfaces 1643 and/or spherical surface 1644 to provide a non-floppy friction fit with the shank spherical upper portion or head 1608 when the surgeon is manipulating the unlocked assembly 1601 during surgery. Upon locking of the shank in place the stepped surfaces 1643 engage and penetrate the shank spherical head 1608. A squeeze release feature or aperture 1632 located on each insert arm may be accessed through the receiver 1610 apertures to press the insert arms toward one another to lift the insert away from the shank upper portion 1608 and thus unlock the polyaxial mechanism if desired.

With reference to FIGS. 398-402, an alternative insert 1614' for use with the assembly 1601 is substantially identical to the insert 1614 (having the same reference numerals marked with a "'" to indicate features the same or similar to the features identified on the insert 1614). The insert 1614' further includes optional lower slots or slits 1650 for enhancing friction fit with the shank upper portion 1608 and for ease of removal from a locking fit with the receiver 1610, if required.

With reference to FIGS. 115-152 the reference number 2001 generally represents a polyaxial bone screw apparatus or assembly according to the present invention. The assembly 2001 includes a shank 2004, that further includes a body 2006 integral with an upwardly extending upper portion or head-like capture structure 2008; a receiver 2010; a lower retainer structure illustrated as a resilient open ring 2012, a friction fit crown collet compression or pressure insert 2014, and an upper retainer structure illustrated as an open resilient snap ring 2016. The receiver 2010, retainer structures 2012 and 2016 and compression insert 2014 are initially assembled and may be further assembled with the shank 2004 either prior or subsequent to implantation of the shank body 2006 into a vertebra 2017, as will be described in greater detail below. FIGS. 115 and 151-152 further show a closure structure 2018 for capturing a longitudinal connecting member, for example, a rod 2021 which in turn engages the compression insert 2014 that presses against the shank upper portion 2008 into fixed frictional contact with the lower retainer 2012, so as to capture, and fix the longitudinal connecting member 2021 within the receiver 2010 and thus fix the member 2021 relative to the vertebra 2017. The illustrated rod 2021 is hard, stiff, non-elastic and cylindrical, having an outer cylindrical surface 2022. It is foreseen that in other embodiments, the rod 2021 may be elastic, deformable and/or of a different cross-sectional geometry. The receiver 2010 and the shank 2004 cooperate in such a manner that the receiver 2010 and the shank 2004 can be secured at any of a plurality of angles, articulations or rotational alignments relative to one another and within a selected range of angles both from side to side and from front to rear, to enable flexible or articulated engagement of the receiver 2010 with the shank 2004 until both are locked or fixed relative to each other near the end of an implantation procedure.

Figure 116:
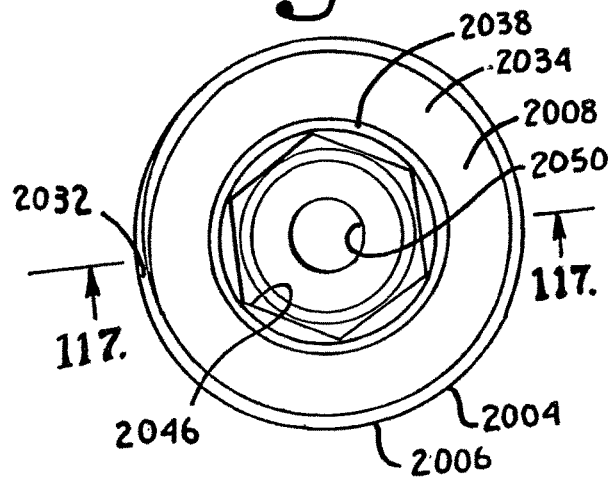
FIG. 116 is an enlarged top plan view of the shank of FIG. 115.
Figure 117:
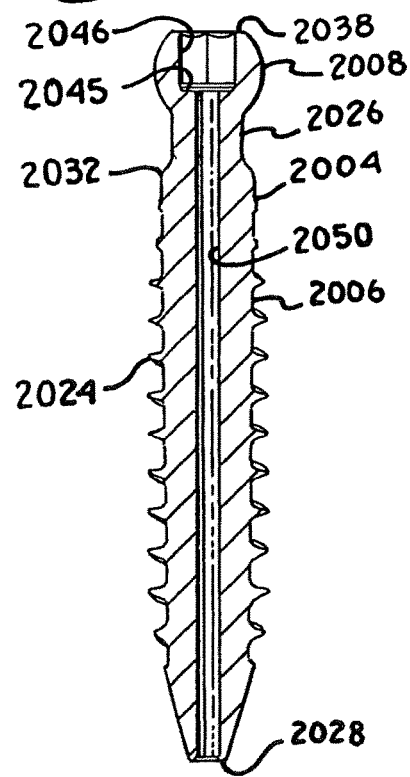
FIG. 117 is reduced cross-sectional view taken along the line 117-117 of FIG. 116.
Figure 128:
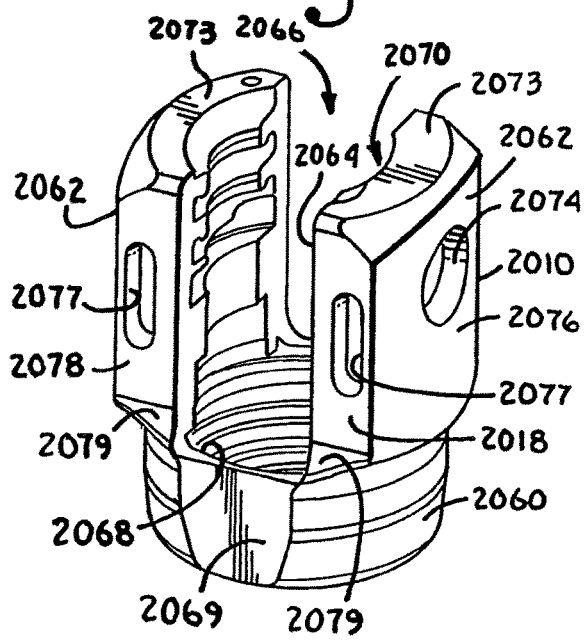
Figure 129:
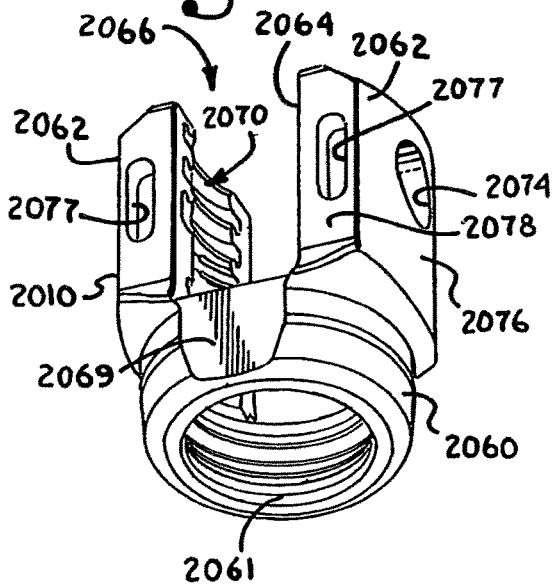

The shank 2004, best illustrated in FIGS. 115-117 is substantially similar to the shank 1004 previously described herein with respect to the assembly 1000. Thus, the shank 2004 includes the shank body 2006, upper portion or head 2008, a shank thread 2024, a neck 2026, a tip 2028, a top of thread 2032, an upper portion spherical surface 2034 a top surface 2038, an internal drive 2046 with a base surface 2045 and an cannulation bore 2050 the same or substantially similar to the respective body 1006, upper portion or head 1008, shank thread 1024, neck 1026, tip 1028, top of thread 1032, spherical surface 1034, top surface 1038, internal drive 1046 with base surface 1045 and cannulation bore 1050 previously described herein with respect to the shank 1004 of the assembly 1001. To provide a biologically active interface with the bone, the threaded shank body 2006 may be coated, perforated, made porous or otherwise treated as previously discussed herein with respect to the shank body 6 of the assembly 1. The shank spherical surface 2034 has an outer radius configured for frictional, non-floppy, sliding cooperation with a discontinuous concave surface 2142 of the compression insert 2014 having a substantially similar or slightly smaller radius, as well as ultimate frictional engagement and penetration by a stepped, gripping portion 2143 of the insert 2014, as will be discussed more fully in the paragraphs below. The spherical surface 2034 shown in the present embodiment is substantially smooth, but in some embodiments may include a roughening or other surface treatment and is sized and shaped for cooperation and ultimate frictional engagement with the compression insert 2014 as well as ultimate frictional engagement with the lower retainer 2012. The shank spherical surface is locked into place exclusively by the insert 2014 and the retainer 2012 and not by inner surfaces defining the receiver cavity.

With particular reference to FIGS. 115 and 128-133, the receiver 2010 has a generally squared-off U-shaped appearance with partially discontinuous and partially cylindrical inner and outer profiles. The receiver 2010 has an axis of rotation B that is shown in FIG. 115 as being aligned with and the same as an axis of rotation A of the shank 2004, such orientation being desirable, but not required during assembly of the receiver 2010 with the shank 2004.

The receiver 2010 includes a substantially cylindrical base 2060 defining a bore or inner cavity 2061, the base 2060 being integral with a pair of opposed upstanding arms 2062 forming a cradle and defining a channel 2064 between the arms 2062 with an upper opening, generally 2066, and a squared off lower channel portion including a substantially planar lower seat 2068, the channel 2064 having a width for operably snugly receiving the rod 2021 or portion of another longitudinal connector between the arms 2062, the channel 2064 communicating with the base cavity 2061. The squared-off geometry of the channel 2064 and lower seat 2068 allow for use with a variety of longitudinal connecting members, including, but not limited to those with circular, square and rectangular cross-sections. As compared to a U-shaped channel that includes a lower seat having a surface with a radius the same or slightly larger than a cooperating cylindrical rod or other connecting member, the squared-off seat 2068 of the present invention provides improved stress management, moving stress risers outwardly toward the two arms 2062 rather than being focused primarily at a center base line of the radiused lower seat. Furthermore, outer front and rear opposed substantially planar base surfaces 2069 that partially define the squared-off lower seat 2068 advantageously reduce the run on the rod (i.e., provide a more narrow receiver that in turn provides more space and thus more access between bone anchors along the rod or other connecting member) and provide the planar surface 2069 for flush or close contact with other connecting member components in certain embodiments, such as for bumpers or spacers that surround a hard or deformable rod or provide support for cord-type connecting members.

Each of the arms 2062 has an interior surface, generally 2070, that includes various inner cylindrical profiles, an upper one of which is a partial helically wound guide and advancement structure 2072 located adjacent top surfaces 2073 of each of the arms 2062. In the illustrated embodiment, the guide and advancement structure 2072 is a partial helically wound interlocking flangeform configured to mate under rotation with a similar structure on the closure structure 2018, as described more fully below. However, it is foreseen that for certain embodiments of the invention, for example, when the receiver 2010 includes a thicker body having a U-shaped channel (as compared to the squared-off channel of the illustrated receiver), the guide and advancement structure 2072 could alternatively be a square-shaped thread, a buttress thread, a reverse angle thread or other thread-like or non-thread-like helically wound discontinuous advancement structures, for operably guiding under rotation and advancing the closure structure 2018 downward between the arms 2062, as well as eventual torquing when the closure structure 2018 abuts against the rod 2021 or other longitudinal connecting member. It is foreseen that the arms could have break-off extensions.

As an example of an alternative closure mechanism, with reference to FIGS. 153-156, an alternative embodiment or assembly 2001' cooperating with a reverse-angle thread form closure top 2018' is shown that is substantially similar to the assembly 2001 with the exception that reverse angle threads 2072' are used in lieu of the flange form 2072 with a receiver 2010' that is substantially similar to the receiver 2010 with the exception of having a U-shaped channel 2064'. The assembly 2001' otherwise includes a shank 2004', a receiver 2010', a lower retainer structure illustrated as a resilient open ring 2012', a friction fit crown collet compression or pressure insert 2014', and an upper retainer structure illustrated as an open resilient snap ring 2016' that are the same or substantially similar in form and function to the respective shank 2004, receiver 2010, lower retainer 2012', friction fit insert 2014 and upper retainer 2016 of the assembly 2001. The assembly 2001' is shown with a rod 2021' that is the same or substantially similar to the rod 2021 shown with the assembly 2001. A more detailed description of the assembly 2001' utilizing the reverse angle thread closure top 2018' is provided in Applicants' Provisional Application Ser. No. 61/343,737 filed May 3, 2010 that is incorporated herein by reference.

Returning to the assembly 2001 shown in FIGS. 115-152, and in particular to FIGS. 128-133, an opposed pair of tool receiving and engaging apertures 2074 are formed on outer surfaces 2076 of the arms 2062. Furthermore, two pair of tool receiving and engaging apertures 2077 are formed in front and rear surfaces 2078 of the arms 2062. Transition base surfaces 2079 span between the surfaces 2078 and the planar base surfaces 2069, the surfaces 2069 and 2078 both running substantially parallel to the receiver axis B, the surfaces 2079 sloping downwardly toward the base 2060 at an angle with respect to the axis B. Some or all of the apertures 2074 and 2077 may be used for holding the receiver 2010 during assembly with the insert 2014, the retainers 2012 and 2016 and the shank 2004, during the implantation of the shank body 2006 into a vertebra when the shank is pre-assembled with the receiver 2010, and during assembly of the bone anchor assembly 2001 with the rod 2021 and the closure structure 2018. It is foreseen that tool receiving grooves or apertures may be configured in a variety of shapes and sizes and be disposed at other locations on the receiver arms 2062.

Returning to the interior surface 2070 of the receiver arms 2062, located below the guide and advancement structure 2072 is a discontinuous cylindrical surface 2082 partially defining a run-out feature for the guide and advancement structure 2072. The cylindrical surface 2082 has a diameter equal to or slightly greater than a greater diameter of the guide and advancement structure 2072. Moving downwardly, in a direction toward the base 2060, adjacent the cylindrical surface 2082 of each arm is a run-out seat or surface 2084 that extends inwardly toward the axis B and runs perpendicular to the axis B. Adjacent to and located below the surface 2084 is another cylindrical surface 2086 having a diameter smaller than the diameter of the surface 2082. A discontinuous annular surface 2088 that provides an upper abutment surface or stop for capturing the compression insert 2014 in the receiver 2010 is located below and adjacent to the cylindrical surface 2086. The abutment surface 2088 is disposed substantially perpendicular to the axis B. As shown in FIG. 144 and discussed in greater detail below, the assembly 2001 is typically provided to a user with the insert 2014 being held within the receiver by the upper snap-ring retainer 2016 that resiliently holds the insert 2014 and keeps the insert stationary with respect to the receiver 2010 and abutting against or slightly spaced from the upper stop 2088 until the insert 2014 is friction fitted about the shank upper portion 2008, also described in greater detail below. The insert 2014 and the shank 2004 are then moved downwardly toward the base 2060 into a working position shown in FIGS. 149 and 150 wherein the insert 2014 is in frictional contact with the shank upper portion 2008, the shank still being movable, with some force, with respect to the insert 2014, and thus advantageously placeable and then held in a selected angular position with respect to the insert 2014 and the receiver 2010, due to the friction fit between the insert 2014 and the shank upper portion 2008.

The inner surfaces 2070 of the arms 2062 include an additional discontinuous cylindrical surface 2090 adjacent the annular surface 2088 and extending downwardly toward the receiver base 2060. The surface 2090 is disposed parallel to the receiver axis B. The surface 2090 has a diameter greater than the diameter of the surface 2086 but less than the diameter of the surface 2082. In some embodiments of the invention, the surface 2090 terminates near a discontinuous annular surface 2092. In the present invention, another cylindrical surface 2093 spans between the surface 2090 and the annular surface 2092, the surface 2093 having a diameter slightly larger than the diameter of the surface 2090. The surfaces 2090 and 2093 are sized and shaped to receive the compression insert 2014 as shown, for example, in FIGS. 144 and 145 when in a pre-assembled configuration, and also during assembly with the shank 2004 as shown in FIGS. 146-148. The surface 2092 is perpendicular to the receiver axis B. A cylindrical surface 2094 adjacent and perpendicular to the surface 2092 is formed in the arm surfaces 2070 and also partially extends into the base 2060. The surface 2094 has a diameter greater than the diameters of the surfaces 2090 and 2093 and also greater than the diameter of the surface 2082. The surface 2094 terminates at a continuous annular seating surface 2095 formed in the receiver base 2060. The surface 2095 is substantially parallel to the surface 2092. The surfaces 2092, 2094 and 2095 form a recess in each arm 2062 for holding the open retainer 2016. As shown in FIGS. 139-149 and discussed in greater detail below, the open snap ring 2016 of the assembly 2001 is compressed and inserted into the channel 2064 from the top opening 2066 and then allowed to expand to a neutral state at a location beneath the surface 2092 and above the surface 2095, the retainer having room to expand outwardly to or near the cylindrical surface 2094 when required. As the compression insert 2014 is placed in different stages of assembly with the shank 2004 (see, e.g., FIGS. 148 and 149), the retainer 2016 expands into the discontinuous recess formed by the surfaces 2092, 2094 and 2095 in the arm surfaces 2070 and then returns to a neutral state during operation of the assembly 2001, the surface 2092 serving as an upper stop, capturing the retainer 2016 in the lower portion of the arms 2062 near the channel seat 2068 and the continuous surface 2095 serving as a stable lower seat for the open retainer 2016.

A cylindrical surface 2096 formed in the base 2060 and partially defining the base cavity 2061 is adjacent to the annular surface 2095 and perpendicular thereto. A diameter of the surface 2096 is smaller than the diameter of the surface 2094. A continuous annular upper rim or stop 2098 is located below and adjacent to the cylindrical surface 2096. The surface 2098 is disposed in the base 2060, partially forming the base cavity 2061 and forms an abutment stop for the resilient retainer 2012, prohibiting the retainer 2012 (when in an uncompressed configuration) from moving upwardly into the space defined by the cylindrical surface 2096 and the channel 2064. Another cylindrical surface 2099 is located below and adjacent to the surface 2098. The cylindrical surface 2099 is oriented substantially parallel to the axis B and is sized and shaped to provide an expansion chamber for receiving an expanded retainer 2012. The surfaces 2098 and 2099 define a circumferential recess that is sized and shaped to receive the retainer 2012 as it expands around the shank upper portion 2008 as the shank 2008 moves upwardly toward the channel 2064 during assembly, as well as form a restriction to prevent the expanded retainer 2012 from moving upwardly with the shank portion 2008, the surface 2098 preventing the retainer 2012 from passing upwardly out of the cavity 2061 whether the retainer 2012 is in a partially or fully expanded position or state, or in a neutral or original or operative position or state (see, e.g., FIGS. 146 and 147). A cylindrical surface 2101 located below the cylindrical surface 2099 is sized and shaped to closely receive the retainer 2012 when the retainer is in a neutral or slightly expanded operative position as shown in FIG. 152, for example. Thus, the cylindrical surface 2101 has a diameter smaller than the diameter of the cylindrical surface 2099 that defines the expansion area for the retainer 2012. The surface 2101 is joined or connected to the surface 2099 by one or more beveled, curved or conical surfaces 2102. The surfaces 2102 allow for sliding gradual movement and/or contraction of the retainer 2012 into the space defined by the surface 2101 and ultimate seating of the retainer 2012 on a lower annular surface 2104 located below and adjacent to the cylindrical surface 2101.

Located below and adjacent to the annular seating surface 2104 is another substantially cylindrical surface 2106 that communicates with a beveled or flared bottom opening surface 2107, the surface 2107 communicating with an exterior base surface 2108 of the base 2060, defining a lower opening, generally 2110, into the base cavity 2061 of the receiver 2010. The illustrated surface 2100 has a diameter allowing for slidable uploading of the compression insert 2014 (with some compression of a portion of the insert 2014 as will be described below) while requiring compression or squeezing of the retainer 2012 during uploading of the retainer 2012 through the lower opening 2110 (see FIGS. 141 and 143, for example).

With particular reference to FIGS. 115 and 118-122, the lower open retainer ring 2012 that operates to capture the shank upper portion 2008 and attached compression insert 2014 within the receiver 2010 has a central axis that is operationally the same as the axis B associated with the receiver 2010 when the shank upper portion 2008 and the retainer 2012 are installed within the receiver 2010. The retainer ring 2012 is made from a resilient material, such as a stainless steel or titanium alloy, so that the retainer 2012 may be both compressed and expanded during various steps of assembly as will be described in greater detail below. The lower retainer 2012 has a central channel or hollow through bore, generally 2121, that passes entirely through the ring 2012 from a top surface 2122 to a bottom surface 2124 thereof. Surfaces that define the channel or bore 2121 include a discontinuous inner cylindrical surface adjacent the top surface 2122 and a discontinuous frusto-conical or beveled surface 2127 adjacent the surface 2125, both surfaces coaxial when the retainer 2012 is in a neutral non-compressed, non-expanded orientation. The retainer 2012 further includes an outer cylindrical surface 2130 located adjacent the top surface 2122 and an outer beveled or frusto-conical surface 2132 adjacent the bottom surface 2124. The surface 2130 is oriented parallel to the central axis of the retainer 2012. In some embodiments of the invention spaced notches (not shown) may be formed in the cylindrical surface 2130 to receive a holding and manipulation tool (not shown) used for contraction and insertion of the retainer 2012 into the receiver 2010. In some embodiments further notches may be made to evenly distribute stress across the entire retainer 2012 during contraction and expansion thereof. In other embodiments of the invention, such notches may be on the inside of the retainer 2012 ring. The resilient retainer 2012 further includes first and second end surfaces, 2134 and 2135 disposed in spaced relation to one another when the retainer is in a neutral non-compressed state. Both end surfaces 2134 and 2135 are disposed substantially perpendicular to the top surface 2122 and the bottom surface 2124. A width X between the surfaces 2134 and 2135 is determined by a desired amount of compressibility of the open retainer 2012 when loaded into the receiver 2010. The space X shown in FIG. 118 provides adequate space between the surfaces 2134 and 2135 for the retainer 2012 to be pinched, with the surfaces 2134 and 2135 compressed toward one another (as shown in FIG. 143) to a closely spaced or even touching configuration, if necessary, to an extent that the compressed retainer 2012 is up or bottom loadable through the receiver opening 2110. After passing through the opening 2110 and along a portion of the lower inner surface 2106, the retainer 2012 expands or springs back to an original uncompressed, rounded or collar-like configuration of FIGS. 118-122, see, e.g., FIG. 144. The embodiment shown in FIGS. 118-122 illustrates the surfaces 2134 and 2135 as substantially parallel, however, it is foreseen that it may be desirable to orient the surfaces obliquely or at a slight angle depending upon the amount of compression desired during loading of the retainer 2012 into the receiver 2010. With particular reference to FIGS. 115 and 123-127, the friction fit crown compression insert 2014 is illustrated that is sized and shaped to be received by and up-loaded into the receiver 2010 at the lower opening 2110. The compression insert 2014 has an operational central axis that is the same as the central axis B of the receiver 2010. In operation, the insert advantageously frictionally engages the bone screw shank upper portion 2008, allowing for unlocked but non-floppy placement of the angle of the shank 2004 with respect to the receiver 2010 during surgery prior to locking of the shank with respect to the receiver near the end of the procedure. The insert 2014 is thus preferably made from a resilient material, such as a stainless steel or titanium alloy, so that portions of the insert may be expanded about and then contracted, snapped or popped onto the shank upper portion 2008. Furthermore, in operation, the insert 2014 is suspended within the receiver 2010, being frictionally held in place by the shank upper portion at a lower end thereof and prohibited from moving upward by the upper resilient retainer 2016. As will be explained in greater detail below, after initial assembly and during operation of the assembly 2001, neither the retainer 2016 nor the inner surfaces of the receiver 2010 that define the cavity 2061 place any compressive force on the insert 2014 to hold the shank portion 2008 therein.

The crown collet compression insert 2014 has a central channel or through bore, generally 2138 running from an annular planar top surface 2139 to an annular planar and discontinuous bottom surface 2140 thereof, the bore 2138 defined by an inner cylindrical surface 2141, an inner partially spherical surface 2142 and a shank gripping surface portion, generally 2143, extending between the surface 2141 and the surface 2142. The gripping surface portion 2143 preferably includes two or more graduated cylindrical surfaces disposed substantially parallel to the axis B and adjacent perpendicular step surfaces that are disposed generally perpendicular to the axis B when the insert 2014 is mounted within the receiver 2010. It is foreseen that the stepped surface portion 2143 may include greater or fewer number of stepped surfaces. It is foreseen that the shank gripping surface portion 2143 and also the surface 2142 may additionally or alternatively include a roughened or textured surface or surface finish, or may be scored, knurled, or the like, for enhancing frictional engagement with the shank upper portion 2008. A plurality of slits or slots 2145 are formed in the spherical surface 2142, running through the bottom surface 2140 and terminating near or slightly extending into the graduated surface portion 2143. The illustrated embodiment includes six slots 2145. It is foreseen that other embodiments of the invention may include more or fewer slots 2145. Each pair of slots 2145 forms a distinct resilient, partially spherical finger, tab or panel 2146 that extends from the shank gripping portion 2143 to the bottom surface 2140. In other words, the inner spherical surface 2142 is separated into six surface portions 2146, each being partially spherical and sized and shaped to resiliently expand about the spherical surface 2034 of the shank upper portion 2008 and then snap on and frictionally grip the surface 2034. Preferably, the spherical surface 2142 is designed such that the gripping tabs or panels 2146 have a neutral or non-expanded radius that is slightly smaller than a radius of the shank surface 2034 so that when the tabs or panels 2146 are gripping the surface 2034, the insert is in a slightly expanded state. When the shank 2004 is locked into position by a rod 2021 or other connecting member being pressed downwardly on the insert top surface 2139 by the closure top 2018, the insert 2014 shank gripping portion 2143 that is initially slidable along the shank surface 2034 then digs or penetrates into the surface 2034 and thus securely fixes the shank upper portion 2008 to the insert at the portion 2143.

The compression insert 2014 through bore 2138 is sized and shaped to receive the driving tool (not shown) therethrough that engages the shank drive feature 2046 when the shank body 2006 is driven into bone with the receiver 2010 attached. The compression insert 2014 also includes a first outer and upper cylindrical surface 2148 adjacent to the top surface 2139. The top surface 2139 engages the rod 2021 or other longitudinal connecting member during operation of the assembly 2001 and locates the rod above the lower seat 2068 of the receiver. The insert 2014 also includes an outer lower and discontinuous cylindrical surface 2150 adjacent to the bottom surface 2140. A discontinuous annular ledge 2151 extends between and connects the upper and lower cylindrical surfaces 2148 and 2150. The cylindrical surface 2148 is sized and shaped to be received within the receiver surface 2106 when loaded through the receiver bottom opening 2110 as shown, for example, in FIG. 141. The surface 2150, on the other hand, has a neutral diameter that is larger than the diameter of the receiver surface 2106. Therefore, during assembly, the resilient insert fingers or panels 2146 are pressed inwardly toward the receiver axis B to allow for insertion of the entire insert 2014 into the receiver opening 2110. As best shown in FIG. 152, the outer cylindrical surface 2150 is sized and shaped so that once the insert 2014 is in an operational position, and the panels 2146 are frictionally mated about the shank upper portion 2008, the outer cylindrical surface 2150 is in slidable engagement or slightly spaced from the receiver inner cylindrical wall 2096. The location of the ledge or lip 2151 is designed such that the upper open retainer 2016 seats on the ledge 2151 when in an operational position as also shown in FIG. 152, for example. As will be described in greater detail below, during early stages of assembly, the insert 2014 outer surface 2150 is gripped by the resilient retainer 2016 pre-assembled within the receiver 2010, the retainer 2016 holding the insert 2014 in a desired stationary position in the receiver for ultimate assembly with the shank upper portion 2008.

It is foreseen that in some embodiments of the invention the compression insert 2014 may further include upstanding arms that cradle the rod 2021 or other connecting member. Such arms may be located spaced from the closure top 2018 in some embodiments and may be sized and shaped to contact the closure top 2018 in other embodiments in order to provide locking of the polyaxial mechanism of the assembly with capture but without fixing of the rod 2021 or other longitudinal connecting member with respect to the closure top 2018.

With particular reference to FIGS. 125 and 134-136, the open upper resilient, ring-like retainer 2016 that operates to capture the compression inert 2014 within the receiver 2010 has a central axis that is operationally the same as the axis B associated with the receiver 2010 when the retainer 2016, the insert 2014, the shank upper portion 2008 and the retainer 2012 are installed within the receiver 2010. The retainer 2016 is made from a resilient material, such as a stainless steel or titanium alloy, so that the retainer 2016 may be both compressed and expanded during various steps of assembly as will be described in greater detail below. The upper retainer 2016 has a central channel or hollow through bore, generally 2153, that passes entirely through the structure 2016 from a top surface 2154 to a bottom surface 2156 thereof. The channel or bore 2153 is defined by a discontinuous inner cylindrical surface 2157 adjacent to both the top surface 2154 and the bottom surface 2156. A discontinuous outer cylindrical surface 2158 is also adjacent to both the top surface 2154 and the bottom surface 2156. In some embodiments of the invention spaced notches (not shown) may be formed in the cylindrical surfaces to receive a holding and manipulation tool (not shown) used for contraction and insertion of the retainer 2016 into the receiver 2010. In some embodiments further notches may be made to evenly distribute stress across the entire retainer 2016 during contraction and expansion thereof. In other embodiments of the invention, such notches may be on the inside of the retainer 2016 ring. It is further noted that the geometry of the retainer 2016 (as well as that of the retainer 2012) is not limited to the particular cylindrical or planar surface shapes shown in the drawings figures. The retainers 2016 and 2012 may be of a rounded ring-shape, for example, or include more or fewer planar surfaces. The resilient retainer 2016 further includes first and second end surfaces, 2159 and 2160 disposed in spaced relation to one another when the retainer is in a neutral non-compressed state. Both end surfaces 2159 and 2160 are disposed substantially perpendicular to the top surface 2154 and the bottom surface 2156. A width X' between the surfaces 2159 and 2160 is determined by a desired amount of compressibility of the open retainer 2016 when loaded into the receiver 2010. The space X' shown in FIG. 134 provides adequate space between the surfaces 2159 and 2160 for the retainer 2016 to be pinched, with the surfaces 2159 and 2160 compressed toward one another (as shown in FIG. 139) to a closely spaced or even touching configuration, if necessary, to an extent that the compressed retainer 2016 is top loadable through the receiver channel opening 2066. After passing through the opening 2066 and along the channel 2064, the retainer 2016 is allowed to expand or spring back to an original uncompressed, rounded or collar-like configuration in the receiver arm recess formed in part by the cylindrical surface 2094, see, e.g., FIG. 140. The embodiment of the retainer 2016 shown in FIGS. 134-136 illustrates the surfaces 2159 and 2160 as substantially parallel, however, it is foreseen that it may be desirable to orient the surfaces obliquely or at a slight angle depending upon the amount of compression desired during loading of the retainer 2016 into the receiver 2010.

With reference to FIGS. 115, 151 and 152, the illustrated elongate rod or longitudinal connecting member 2021 (of which only a portion has been shown) can be any of a variety of implants utilized in reconstructive spinal surgery, but is typically a cylindrical, elongate structure having the outer substantially smooth, cylindrical surface 2022 of uniform diameter. The rod 2021 is the same or substantially similar to the rods previously described herein, such as the rods 21 and 1021. With reference to the '849 patent application, polyaxial bone screw assemblies 2001 according to the invention may be used with soft or dynamic stabilization longitudinal connecting member assemblies that may include, but are not limited to one or more sleeves with cooperating, spacers, bumpers and an inner tensioned cord.

With reference to FIGS. 115, 137 and 138, the closure structure or closure top 2018 shown with the assembly 2001 is rotatably received between the spaced arms 2062 of the receiver 2010. It is noted that the closure 2018 top could be a twist-in or slide-in closure structure. The illustrated closure structure 2018 is substantially cylindrical and includes a an outer helically wound guide and advancement structure 2162 in the form of a flange that operably joins with the guide and advancement structure 2072 disposed on the arms 2062 of the receiver 2010. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 2018 downward between the arms 2062 and having such a nature as to resist splaying of the arms 2062 when the closure structure 2018 is advanced into the channel 2064, the flange form illustrated herein as described more fully in Applicant's U.S. Pat. No. 6,726,689 is preferred as the added strength provided by such flange form beneficially cooperates with and counters any reduction in strength caused by the squared off U-shape channel of the illustrated receiver 2010 and reduced profile of the receiver 2010 that advantageously engages longitudinal connecting member components as will be further described below. The illustrated closure structure 2018 also includes a top surface 2164 with an internal drive 2166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 2166 is used for both rotatable engagement and, if needed, disengagement of the closure 2018 from the receiver arms 2062. It is also foreseen that the closure structure 2018 may alternatively include a break-off head designed to allow such a head to break from a base of the closure at a preselected torque, for example, 70 to 140 inch pounds. Such a closure structure would also include a base having an internal drive to be used for closure removal. A base or bottom surface 2168 of the closure is planar and further includes a point 2169 and a rim 2170 for engagement and penetration into the surface 2022 of the rod 2021 in certain embodiments of the invention. The closure top 2018 may further include a cannulation through bore (not shown) extending along a central axis thereof and through the top and bottom surfaces thereof. Such a through bore provides a passage through the closure 2018 interior for a length of wire (not shown) inserted therein to provide a guide for insertion of the closure top into the receiver arms 2062.

Preferably, the receiver 2010, the retainers 2012 and 2016 and the compression insert 2014 are assembled at a factory setting that includes tooling for holding and alignment of the component pieces and pinching or compressing of the retainers 2012 and 2016 as well as compressing or expanding the insert 2014 panels 2146. In some circumstances, the shank 2004 is also assembled with the receiver 2010, the retainers 2012 and 2016 and the compression insert 2014 at the factory. In other instances, it is desirable to first implant the shank 2004, followed by addition of the pre-assembled receiver, retainers and compression insert at the insertion point. In this way, the surgeon may advantageously and more easily implant and manipulate the shanks 2004, distract or compress the vertebrae with the shanks and work around the shank upper portions or heads without the cooperating receivers being in the way. In other instances, it is desirable for the surgical staff to pre-assemble a shank of a desired size with the receiver, retainer and compression insert. Allowing the surgeon to choose the appropriately sized shank advantageously reduces inventory requirements, thus reducing overall cost.

Pre-assembly of the receiver 2010, retainers 2012 and 2016 and compression insert 2014 is shown in FIGS. 139-144. First, the retainer 2016 is top loaded into the receiver 2010 through the opening 2066 of the channel 2064. The resilient open retainer 2016 is prepared for insertion into the receiver 2010 by squeezing or pressing the retainer end surfaces 2159 and 2160 toward one another as shown in FIG. 139. The compressed retainer 2016 is inserted into the upper opening 2066 with the bottom surface 2156 facing the receiver cavity 2061. However, in the present embodiment, as the top and bottom surfaces are identical, either surface 2154 or 2156 may serve as a bottom or top surface. The retainer 2016 is typically moved downwardly into the channel 2064 and past the cylindrical surface 2090 and allowed to expand to a neutral uncompressed state within the cylindrical surface 2094 of each of the arms 2062 as shown in FIG. 140.

Then, the compression insert 2014 is uploaded into the receiver 2010 through the lower opening 2110 with the insert top surface 2139 facing the receiver bottom surface 2108. The insert 2014 is slid upwardly toward the channel seat 2068 until the ledge 2151 nears the receiver bottom 2108. Then, the insert panels 2146 are pressed radially inwardly toward the axis B to compress the insert slightly so that the outer lower cylindrical surface 2150 clears the receiver surface 2106 at the opening 2110. With reference to FIG. 142, the insert 2014 is pressed upwardly within the inner surface 2157 of the open retainer 2016, expanding the retainer into the arm recesses formed by the cylindrical surfaces 2094. The surface 2092 prohibits upward movement of the retainer 2016 as the insert 2014 is moved upwardly to a desired pre-assembly position with the insert bottom surface 2140 being substantially aligned with the annular receiver surface 2098, the insert 2014 being located above the receiver cylindrical surface 2099 that functions as an expansion recess or chamber for the lower retainer 2012. As the insert lower cylindrical surface 2150 has a diameter in a neutral state that is greater than an inner diameter of the retainer 2016, also in a neutral state, the resilient retainer 2016 expands about and grips the insert 2014 within the receiver 2010. The cylindrical surface 2096 of the receiver, now located about the insert 2014 is sized slightly larger than the outer diameter of the insert cylindrical surface 2150, in a neutral state, so the surface 2096 does not function to compress or otherwise engage the insert panels 2146, but the surface 2096 does block the retainer 2016 from moving in a downward direction. Also, the receiver upper stop 2088 abuts the insert top surface 2139, prohibiting the pre-assembled insert from traveling any further up the receiver channel 2064.

With reference to FIGS. 143 and 144, the retainer 2012 is then prepared for insertion into the receiver 2010 by squeezing or pressing the retainer end surfaces 2134 and 2135 toward one another as shown in FIG. 143. The compressed retainer 2012 is inserted into the lower opening 2110 with the planar top surface 2122 facing the receiver bottom surface 2108. The retainer 2012 is typically moved upwardly into the receiver 2010 and past the cylindrical surface 2106 and allowed to expand to an almost neutral or slightly compressed state within the cylindrical surface 2101 as shown in FIG. 144. Also as shown in FIG. 144, at this time, both the compression insert 2014 and the retainer 2012 are captured within the receiver 2010 in a manner that substantially prevents movement or loss of such parts out of the receiver 2010. The receiver 2010, compression insert 2014 (held by the retainer 2012) and the retainer 2012 (held by the cylindrical surface 2101) combination is now pre-assembled and ready for assembly with the shank 2004 either at the factory, by surgery staff prior to implantation, or directly upon an implanted shank 2004 as will be described herein.

As illustrated in FIG. 151, the bone screw shank 2004 or an entire assembly 2001 made up of the assembled shank 2004, receiver 2010, retainers 2012 and 2016 and compression insert 2014, is screwed into a bone, such as the vertebra 2017, by rotation of the shank 2004 using a suitable driving tool (not shown) that operably drives and rotates the shank body 2006 by engagement thereof at the internal drive 2046.

When the shank 2004 is driven into the vertebra 2017 without the remainder of the assembly 2001, the shank 2004 may either be driven to a desired final location or may be driven to a location slightly above or proud to provide for ease in assembly with the pre-assembled receiver, compression insert and retainer. With reference to FIGS. 145-150 the pre-assembled receiver, insert and retainers are placed above the shank upper portion 2008 until the shank upper portion is received within the opening 2110. With particular reference to FIGS. 146 and 147, as the shank is moved into the interior of the receiver base, the shank upper portion 2008 presses the retainer 2012 upwardly into the recess or expansion chamber partially defined by the cylindrical surface 2099 (if the retainer is not already located within such recess). As the portion 2008 continues to move upwardly toward the channel 2064, the top surface 2122 of the retainer 2012 abuts against the insert bottom surface 2140 as well as the annular rim stop 2098 of the receiver 2010, stopping upward movement of the retainer 2012 and forcing outward movement of the retainer 2012 towards the cylindrical surface 2099 defining the receiver expansion recess as the spherical surface 2034 continues in an upward direction. The retainer 2012 begins to contract about the spherical surface 2034 as the center of the sphere passes beyond the center of the retainer expansion recess defined by the surface 2099

(see FIG. 148). At this time also (back to FIG. 147), the spherical surface 2034 moves into engagement with the insert 2014 spherical surface 2142 with the panels 2146 expanding slightly outwardly to receive the surface 2034 and pushing outwardly against the resilient upper retainer 2016. The panels 2146 press outwardly against the surface 2096 that provides enough clearance for the spherical surface 2034 to enter into full frictional engagement with the panels 2146 as shown in FIG. 148. At this time, the insert 2014 and the surface 2034 are in a fairly tight friction fit, the surface 2034 being pivotable with respect to the insert 2014 with some force. Thus, a tight, non-floppy ball and socket joint is now created between the insert 2014 and the shank upper portion 2008.

With reference to FIG. 149, the retainer 2012 and attached insert 2014 are then moved down into a final operative position shown in FIGS. 149-152 by either an upward pull on the receiver 2010 or, in some cases, by driving the shank 2004 further into the vertebra 2017. Also, in some embodiments, when the receiver 2010 is pre-assembled with the shank 2004, the entire assembly 2001 may be implanted at this time by inserting the driving tool into the receiver and the shank drive 2046 and rotating and driving the shank 2004 into a desired location of the vertebra 2017.

Also with reference to FIG. 149, at this time, the compression insert 2014 lower cylindrical surface 2150 is located below the open retainer 2016 and the retainer 2016 is disposed at or near the insert ledge 2151 and about the substantially non-compressible cylindrical surface 2148. The insert 2014 is thus prohibited from moving upwardly at the ledge 2151 by the retainer 2016, but the retainer 2016 is otherwise in a neutral state and does not place a compressive force on the insert 2014. With reference to FIG. 150, at this time, the receiver 2010 may be articulated to a desired angular position with respect to the shank 2004, that will be held, but not locked, by the frictional engagement between the insert 2014 and the shank upper portion 2008.

With reference to FIGS. 151-152, the rod 2021 is eventually positioned in an open or percutaneous manner in cooperation with the at least two bone screw assemblies 2001. The closure structure 2018 is then inserted into and advanced between the arms 2062 of each of the receivers 2010. The closure structure 2018 is rotated, using a tool engaged with the inner drive 2166 until a selected pressure is reached at which point the rod 2021 engages the flat top surface 2139 of the compression insert 2014, further pressing the insert stepped surfaces 2143 against the shank spherical surface 2034, the edges of the stepped surfaces penetrating into the spherical surface 2034 and also pressing the shank upper portion 2008 into locked frictional engagement with the retainer 2012. Specifically, as the closure structure 2018 rotates and moves downwardly into the respective receiver 2010, the point 2169 and rim 2170 engage and penetrate the rod surface 2022, the closure structure 2018 pressing downwardly against and biasing the rod 2021 into compressive engagement with the insert 2014 that urges the shank upper portion 2008 toward the retainer 2012 and into locking engagement therewith, the retainer 2012 frictionally abutting the surface 2104 and expanding outwardly against the cylindrical seating surface 2101. For example, about 80 to about 120 inch pounds of torque on the closure top may be applied for fixing the bone screw shank 2006 with respect to the receiver 2010.

If removal of the rod 2021 from any of the bone screw assemblies 2001 is necessary, or if it is desired to release the rod 2021 at a particular location, disassembly is accomplished by using the driving tool (not shown) that mates with the internal drive 2166 on the closure structure 2018 to rotate and remove such closure structure from the cooperating receiver 2010. Disassembly is then accomplished in reverse order to the procedure described previously herein for assembly.

With reference to FIGS. 157-187 the reference number 3001 generally represents a polyaxial bone screw apparatus or assembly according to the present invention. The assembly 3001 includes a shank 3004, that further includes a body 3006 integral with an upwardly extending upper portion or head-like capture structure 3008; a receiver 3010; a retainer structure illustrated as a resilient open ring 3012, and a friction fit crown collet compression or pressure insert 3014. The receiver 3010, retainer 3012 and compression insert 3014 are initially assembled and may be further assembled with the shank 3004 either prior or subsequent to implantation of the shank body 3006 into a vertebra 3017, as will be described in greater detail below. FIGS. 157 and 185-187 further show a rod 3021 and closure structure 3018 the same or similar to rods and closures previously described herein, for example, the rod 2021 and the closure 2018 described with reference to the assembly 2001. As with other assemblies of the invention, the receiver 3010 and the shank 3004 cooperate in such a manner that the receiver 3010 and the shank 3004 can be secured at any of a plurality of angles, articulations or rotational alignments relative to one another and within a selected range of angles both from side to side and from front to rear, to enable flexible or articulated engagement of the receiver 3010 with the shank 3004 until both are locked or fixed relative to each other near the end of an implantation procedure.

The shank 3004, best illustrated in FIGS. 157-159 is substantially similar to the shank 1004 previously described herein with respect to the assembly 1000. Thus, the shank 3004 includes the shank body 3006, upper portion or head 3008, a shank thread 3024, a neck 3026, a tip 3028, a top of thread 3032, an upper portion spherical surface 3034 a top surface 3038, an internal drive 3046 with a base surface 3045 and an cannulation bore 3050 the same or substantially similar to the respective body 1006, upper portion or head 1008, shank thread 1024, neck 1026, tip 1028, top of thread 1032, spherical surface 1034, top surface 1038, internal drive 1046 with base surface 1045 and cannulation bore 1050 previously described herein with respect to the shank 1004 of the assembly 1001. To provide a biologically active interface with the bone, the threaded shank body 3006 may be coated, perforated, made porous or otherwise treated as previously discussed herein with respect to the shank body 6 of the assembly 1. The shank spherical surface 3034 has an outer radius configured for frictional, non-floppy, sliding cooperation with a discontinuous concave surface 3152 of the compression insert 3014 having a substantially similar or slightly smaller or slightly larger radius, as well as ultimate frictional engagement and penetration by a stepped, gripping portion 3150 of the insert 3014, as will be discussed more fully in the paragraphs below. The top surface 3038 is substantially perpendicular to a central axis A. The spherical surface 3034 shown in the present embodiment is substantially smooth, but in some embodiments may include a roughening or other surface treatment and is sized and shaped for cooperation and ultimate frictional engagement with the compression insert 3014 as well as ultimate frictional engagement with the retainer 3012. The shank spherical surface 3034 is locked into place exclusively by the insert 3014 and the retainer 3012 and not by inner surfaces defining the receiver cavity.

With particular reference to FIGS. 157 and 171-175, the receiver 3010 has a generally U-shaped appearance with partially discontinuous and partially cylindrical inner and outer profiles. The receiver 3010 has an axis of rotation B that is shown in FIG. 157 as being aligned with and the same as the axis of rotation A of the shank 3004, such orientation being desirable, but not required during assembly of the receiver 3010 with the shank 3004 (see, e.g., FIG. 179 showing a receiver 3010 being "popped on" to a shank 3006 that is implanted in a vertebra 3017 and disposed at an angle with respect to the receiver). After the receiver 3010 is pivotally attached to the shank 3004, either before or after the shank 3004 is implanted in a vertebra 3017, the axis B is typically disposed at an angle with respect to the axis A, as shown, for example, in FIG. 187.

The receiver 10 includes a substantially cylindrical base 3060 defining a bore or inner cavity, generally 3061, the base 3060 being integral with a pair of opposed upstanding arms 3062 forming a cradle and defining a channel 3064 between the arms 3062 with an upper opening, generally 3066, and a U-shaped lower channel portion or seat 3068, the channel 3064 having a width for operably snugly receiving the rod 3021 or portion of another longitudinal connector between the arms 3062, the channel 3064 communicating with the base cavity 3061. Outer front and rear opposed substantially planar arm surfaces 3069 partially define the channel 3064 directly above the seat 3068, the surfaces 3069 advantageously reduce the run on the rod (i.e., provide a more narrow receiver portion that in turn provides more space and thus more access between bone anchors along the rod or other connecting member) and provide the planar surface 3069 for flush or close contact with other connecting member components in certain embodiments, such as for bumpers or spacers that surround a hard or deformable rod or provide support for cord-type connecting members, such as those shown in the '849 application, incorporated by reference herein.

Each of the arms 3062 has an interior surface, generally 3070, that includes various inner cylindrical profiles, an upper one of which is a partial helically wound guide and advancement structure 3072 located adjacent top surfaces 3073 of each of the arms 3062. In the illustrated embodiment, the guide and advancement structure 3072 is a partial helically wound interlocking flangeform configured to mate under rotation with a similar structure on the closure structure 3018, as described more fully below. However, it is foreseen that for certain embodiments of the invention, the guide and advancement structure 3072 could alternatively be a square-shaped thread, a buttress thread, a reverse angle thread or other thread-like or non-threadlike helically wound discontinuous advancement structures, for operably guiding under rotation and advancing the closure structure 18 downward between the arms 3062, as well as eventual torquing when the closure structure 3018 abuts against the rod 3021 or other longitudinal connecting member. It is foreseen that the arms could have break-off extensions.

An opposed pair of key-hole like shallow tool receiving and engaging grooves or apertures 3074, each having a through bore 3075, are formed on outer surfaces 3076 of the arms 3062. Each through bore 3075 extends between the outer surface 3076 and the inner surface 3070 and is located between upper and lower shallow grooved or recessed portions that do not extend completely through the respective arm 3062. In the present embodiment, part of the grooved portion directly below the through bore 3075 is defined by a thin wall 3077 that is crimped into the insert 3014 during assembly thereof with the receiver 3010 as will be described in greater detail below. In other embodiments of the invention, other surfaces forming the groove or aperture 3074 may be inwardly crimped. Alternatively, spring tabs or other movable structure may be included on the receiver 3010 or the insert 3014 for retaining the insert 3014 in a desired position, with regard to rotation and axial movement (along the axis A) with respect to the receiver 3010. Preferably the insert and/or receiver are configured with structure for blocking rotation of the insert with respect to the receiver, but allowing some up and down movement of the insert with respect to the receiver during the assembly and implant procedure. Two additional pair of tool receiving and engaging apertures 3078 are also formed in the front and rear surfaces 3069 of the receiver arms 3062. Transition base surfaces 3079 span between the planar surfaces 3069 at the U-shaped seat 3068 and the cylindrical base 3060, the surfaces 3079 sloping downwardly toward the base 3060 at an angle with respect to the axis B. Some or all of the apertures 3074 and 3077 may be used for holding the receiver 3010 during assembly with the insert 3014, the retainer 3012 and the shank 3004; during the implantation of the shank body 3006 into a vertebra when the shank is pre-assembled with the receiver 3010; during assembly of the bone anchor assembly 3001 with the rod 3021 and the closure structure 3018; and during lock and release adjustment of the insert 3014 with respect to the receiver 3010, either into or out of frictional engagement with the inner surfaces of the receiver 3010 as will be described in greater detail below. It is foreseen that tool receiving grooves or apertures may be configured in a variety of shapes and sizes and be disposed at other locations on the receiver arms 3062.

Returning to the interior surface 3070 of the receiver arms 3062, located below the guide and advancement structure 3072 is a discontinuous cylindrical surface 3082 partially defining a run-out feature for the guide and advancement structure 3072. The cylindrical surface 3082 has a diameter equal to or slightly greater than a greater diameter of the guide and advancement structure 3072. Moving downwardly, in a direction toward the base 3060, adjacent the cylindrical surface 3082 of each arm is a run-out seat or surface 3084 that extends inwardly toward the axis B and runs perpendicular to the axis B. Adjacent to and located below the surface 3084 is another cylindrical surface 3086 having a diameter smaller than the diameter of the surface 3082. The through bores 3075 extends through the arms at the surfaces 3086. Located directly below each bore 3075 is a surface portion 3087 that engages the insert 3014 when the thin wall 3077 is crimped toward the insert 3014 during assembly of such insert in the receiver 3010 as will be described in greater detail below. A discontinuous annular surface 3088 is located below and adjacent to the cylindrical surface 3086. The surface 3088 is disposed substantially perpendicular to the axis B. The inner surfaces 3070 of the arms 3062 include an additional partially discontinuous and partially continuous inner cylindrical surface 3090 adjacent the annular surface 3088 and extending downwardly into the receiver base 3060. The surface 3090 is disposed parallel to the receiver axis B. The surface 3090 has a diameter greater than the diameter of the surface 3082. The cylindrical surfaces 3086 and 3090 are sized to receive respective upper- and mid-portions of the insert 3014 as will be described in greater detail below.

Now, with respect to the base 3060 and more specifically, the base cavity 3061, a lower portion of the surface 3090 that extends into the base and partially defines the base cavity 3061 terminates at an annular surface or ledge 3095. The ledge 3095 extends toward the axis B and is substantially perpendicular thereto. Extending downwardly from the ledge 3095 is a cylindrical surface 3096 that partially defines the base cavity 3061, the surface 3096 running parallel to the axis B and having a diameter smaller than the diameter of the surface 3090. The surface 3096 is sized and shaped to initially closely receive a lower portion of the insert 3014 and later frictionally engage a tapered portion of the insert 3014, providing and lock and release function that will be described in greater detail below. The surface 3096 terminates at an annular surface 98 of the base cavity 3061 that functions as an upper stop for the retainer 3012, particularly when in an expanded state as shown in FIG. 181 and as will be described in greater detail below. Another cylindrical surface 3099 is located below and adjacent to the surface 3098. The cylindrical surface 3099 is oriented substantially parallel to the axis B and is sized and shaped to receive an expanded retainer 3012. The surfaces 3098 and 3099 define a circumferential recess or expansion chamber that is sized and shaped give clearance to and to receive the retainer 3012 as it expands around the shank upper portion 3008 as the shank 8 moves upwardly toward the channel 3064 during assembly, as well as form a restriction to prevent the expanded retainer 3012 from moving upwardly with the shank portion 3008, the surface 3098 and the insert 3014 preventing the retainer 3012 from passing upwardly out of the cavity 3061 whether the retainer 3012 is in a partially or fully expanded position or state, or in a neutral or original operative position or state. A cylindrical surface 3101 located below the cylindrical surface 3099 is sized and shaped to closely receive the retainer 3012 when the retainer is in a neutral or slightly compressed operative position as shown in FIGS. 184 and 185, for example. Thus, the cylindrical surface 3101 has a diameter smaller than the diameter of the cylindrical surface 3099 that defines the expansion area for the retainer 3012. The surface 3101 is joined or connected to the surface 3099 by one or more beveled, curved or conical surfaces 3102. The surfaces 3102 allow for sliding gradual movement and/or contraction of the retainer 3012 into the final seating space defined by the surface 3101 and ultimate seating of the retainer 3012 on a lower annular surface 3104 located below and adjacent to the cylindrical surface 3101.

Located below and adjacent to the annular seating surface 3104 is another substantially cylindrical surface 3106 that communicates with a beveled or flared bottom opening surface 3107, the surface 3107 communicating with an exterior base surface 3108 of the base 3060, defining a lower opening, generally 3110, into the base cavity 3061 of the receiver 3010. The illustrated surface 3100 has a diameter requiring compression or squeezing of the retainer 3012 during uploading of the retainer 3012 through the lower opening 3110 (see FIG. 177, for example).

With particular reference to FIGS. 157, 160-164 and 177, the lower open retainer ring 3012 that operates to capture the shank upper portion 3008 and attached compression insert 3014 within the receiver 3010 has a central axis that is operationally the same as the axis B associated with the receiver 3010 when the shank upper portion 3008 and the retainer 3012 are installed within the receiver 3010. The retainer ring 3012 is made from a resilient material, such as a stainless steel or titanium alloy, so that the retainer 3012 may be both compressed and expanded during various steps of assembly as will be described in greater detail below. The retainer 3012 has a central channel or hollow through bore, generally 3121, that passes entirely through the ring 3012 from a top surface 3122 to a bottom surface 3124 thereof. Surfaces that define the channel or bore 3121 include a discontinuous inner cylindrical surface 3125 adjacent the top surface 3122, a discontinuous frusto-conical surface 3127 adjacent the surface 3125 and a beveled surface 3128, all three surfaces coaxial when the retainer 3012 is in a neutral non-compressed, non-expanded orientation. The retainer 3012 further includes an outer cylindrical surface 3130 located adjacent the top surface 3122 and an outer beveled or frusto-conical surface 3132 adjacent the bottom surface 3124. The surface 3130 is oriented parallel to the central axis of the retainer 3012. In some embodiments of the invention, spaced notches (not shown) may be formed in the cylindrical surface 3130 to receive a holding and manipulation tool (not shown) used for contraction and insertion of the retainer 3012 into the receiver 3010. In some embodiments further notches may be made to evenly distribute stress across the entire retainer 3012 during contraction and expansion thereof. In other embodiments of the invention, such notches may be on the inside of the retainer 3012 ring. The resilient retainer 3012 further includes first and second end surfaces, 3134 and 3135 disposed in spaced relation to one another when the retainer is in a neutral non-compressed state. Both end surfaces 3134 and 3135 are disposed substantially perpendicular to the top surface 3122 and the bottom surface 3124. A width X between the surfaces 3134 and 3135 is determined by a desired amount of compressibility of the open retainer 312 when loaded into the receiver 310 as shown in FIG. 177. The space X shown in FIG. 160 provides adequate space between the surfaces 3134 and 3135 for the retainer 3012 to be pinched, with the surfaces 3134 and 3135 compressed toward one another (as shown in FIG. 177) to a closely spaced or even touching configuration, if necessary, to an extent that the compressed retainer 3012 is up or bottom loadable through the receiver opening 3110. After passing through the opening 3110 and along a portion of the lower inner surface 3106, the retainer 3012 expands or springs back to an original uncompressed, rounded or collar-like configuration of FIGS. 160-164, see, e.g., FIG. 178. The embodiment shown in FIGS. 160-164 illustrates the surfaces 3134 and 3135 as substantially parallel, however, it is foreseen that it may be desirable to orient the surfaces obliquely or at a slight angle depending upon the amount of compression desired during loading of the retainer 3012 into the receiver 3010.

With particular reference to FIGS. 157 and 165-170, the friction fit, lock and release crown compression insert 3014 is illustrated that is sized and shaped to be received by and down-loaded into the receiver 3010 at the upper opening 3066. The compression insert 3014 has an operational central axis that is the same as the central axis B of the receiver 3010. In operation, the insert advantageously frictionally engages the bone screw shank upper portion 3008, allowing for un-locked but non-floppy placement of the angle of the shank 3004 with respect to the receiver 3010 during surgery prior to locking of the shank with respect to the receiver near the end of the procedure. Furthermore, as will be described more fully below, an insert 3014 that has locked the shank 3004 in a desired angular position with respect to the receiver 3010, by, for example, compression from the rod 3021 and closure top 3018, is also wedged into engagement with the receiver 3010 at the inner surface 3096 and thus retains the shank 3006 in a locked position even if the rod 3021 and closure top 3018 are removed as shown in FIG. 186. Such locked position may also be released by the surgeon if desired. The insert 3014 is thus preferably made from a resilient material, such as a stainless steel or titanium alloy, so that portions of the insert may be expanded about and then contracted, snapped or popped onto the shank upper portion 3008 as well as pinched and un-wedged from the receiver 3010.

The lock-and-release crown collet compression insert 3014 includes a substantially cylindrical body 3136 integral with a pair of upstanding arms 3137 at an upper end thereof and integral with an opposed pair of crown collet extensions 3138 at a lower end thereof. A bore, generally 3140, is disposed primarily within and through the body 3136 and communicates with a generally U-shaped through channel 3141 that is defined by the upstanding arms 3137. The channel 3141 has a lower seat 3142 sized and shaped to closely, snugly engage the rod 3021. It is foreseen that an alternative embodiment may be configured to include planar holding surfaces that closely hold a square or rectangular bar as well as hold a cylindrical rod-shaped, cord, or sleeved cord longitudinal connecting member. The arms 3137 disposed on either side of the channel 3141 extend upwardly from the body 3136. The arms 3137 are sized and configured for ultimate placement near the cylindrical run-out surface 3082 below the receiver guide and advancement structure 3072. It is foreseen that in some embodiments of the invention, the arms may be extended and the closure top configured such the arms ultimately directly engage the closure top 3018 for locking of the polyaxial mechanism, for example, when the rod 3021 is made from a deformable material. In such embodiments, the insert 3014 would include a rotation blocking structure or feature that abuts against cooperating structure located on an inner wall of the receiver 3010, preventing rotation of the insert with respect to the receiver when the closure top is rotated into engagement with the insert. In the present embodiment, the arms 3137 include outer surfaces 3143 and top surfaces 3144 that are ultimately positioned in spaced relation with the closure top 3018, so that the closure top 3018 frictionally engages the rod 3021 only, pressing the rod 3021 downwardly against the seating surface 3142, the insert 3014 in turn pressing against the shank 3004 upper portion 3008 that presses against the retainer 3012 to lock the polyaxial mechanism of the bone screw assembly 3001 at a desired angle. As will be discussed in greater detail below, frictional engagement between the insert 3014 and the receiver 3010 maintains the upper portion 3008 in locked engagement with the retainer 3012 even if the closure top 3018 and/or rod 3021 are thereafter removed from the receiver 3010.

The bore, generally 3140, is substantially defined at the body 3136 by an inner cylindrical surface 3146 that communicates with a lower collet space that extends to discontinuous bottom surfaces 3148 of the collet extensions 3138. The body 3135 (and bore 3140) is further defined by a shank gripping surface portion, generally 3150, the gripping portion 3150 being adjacent to the cylindrical surface 3146. Located below and adjacent to the gripping portion 3150 is an inner partially spherical surface 3152 that is continuous at the body 3136 and is discontinuous at the extensions 3138 wherein the surface 3152 extends downwardly, defining the inner shank holding portion of each of the collet extensions 3138 and terminating at the extension bottom surfaces 3148. The gripping surface portion 3150 preferably includes two or more graduated cylindrical surfaces disposed substantially parallel to the axis B and adjacent perpendicular step surfaces that are disposed generally perpendicular to the axis B when the insert 3014 is mounted within the receiver 3010. It is foreseen that the stepped surface portion 3150 may include greater or fewer number of stepped surfaces. It is foreseen that the shank gripping surface portion 3150 and also the spherical surface 3152 may additionally or alternatively include a roughened or textured surface or surface finish, or may be scored, knurled, or the like, for enhancing frictional engagement with the shank upper portion 3008. The two collet extensions 3138 that generally extend in a direction opposite to the two arms 3137 and have the discontinuous inner spherical surface 3152, also include through slits or slots 3153 running substantially vertically from adjacent the shank gripping surface portion 3150 through the bottom surfaces 3148. The illustrated embodiment includes one slot 3153 centrally located in each extension 3138. It is foreseen that other embodiments of the invention may include more or fewer slots 3153. The slots 3153 substantially equally partition each of the extensions 3138, forming four distinct resilient, partially spherical fingers, tab or panels 3154 that extend from the shank gripping portion 3150 to the bottom surface 3148. In other words, the discontinuous inner spherical surface 3152 is further separated into four surface portions 3154, each being partially spherical and sized and shaped to resiliently expand about the spherical surface 3034 of the shank upper portion 3008 and then snap on and frictionally grip the surface 3034. The illustrated spherical surface 3152 is designed such that the gripping tabs or panels 3154 have a neutral or non-expanded radius that is the same or in some instances may be slightly smaller than a radius of the shank surface 3034 so that when the tabs or panels 3154 are gripping the surface 3034, the insert 3014 collet extension portion 3138 is in a slightly expanded state. In other embodiments, as illustrated in the embodiment shown in FIG. 222, the non-expanded radius is the same or larger than a radius of the shank surface. The contacting surface area between the shank and the insert is sufficient to provide a non-floppy frictional fit in such instances. Furthermore, the shank surface 3034 and/or the spherical surface 3152 may include a roughened or grooved surface feature to provide for a frictional fit between the shank and the insert. In other embodiments, the resilient panels 3154 having a slightly larger pre-assembly radius than the shank surface 3034 may be bent inwardly to result in a tighter frictional fit with the shank surface. When the shank 3004 is locked into position by a rod 3021 or other connecting member being pressed downwardly on the insert seat 3142 by the closure top 3018, the insert 3014 shank gripping portion 3150 that is initially slidable along the shank surface 3034 then digs or penetrates into the surface 3034 and thus securely fixes the shank upper portion 3008 to the insert at the portion 3150.

The compression insert 3014 through bore 3140 is sized and shaped to receive the driving tool (not shown) therethrough that engages the shank drive feature 3046 when the shank body 3006 is driven into bone with the receiver 3010 attached.

The illustrated insert 3014 further includes features that allow for a lock and release frictional fit between the insert 3014 and the receiver 3010. These features include a shallow, substantially vertical or keyhole like slot 3155 disposed on the outer surface 3143 of each arm 3137, the slot 3155 running substantially vertically from near the top surface 3144 through the body 3136 to near one of the collet extension through slots 3153. In the illustrated embodiment, the slots 3155 and 3153 are substantially aligned and run substantially parallel to the axis B. Each slot 3155 further includes a through bore 3156 at or near a top thereof, the bore 156 running radially through each of the arms 3137 in a direction substantially perpendicular to the axis B. The through bore and slots are directly opposed from one another and are sized and shaped to receive tools for manipulating the insert 3014 with respect to the receiver 3010 as will be described herein as well as for receiving tabs or crimped material from the receiver 3010 for maintaining alignment between the insert 3014 channel 3141 and the receiver 3010 channel 3064. Directly below each arm 3137 and intersecting with a portion of each slot 3155 is a frusto-conical or otherwise outwardly flaring or tapered surface 3158 sized and shaped for engaging with the receiver 3010 at the surface 3096 as will be described more fully below. Each surface 3158 tapers inwardly toward the axis B as the surface runs toward the crown collet extensions 3138. Below and adjacent to each surface 3158 is a cylindrical surface 3159 that partially defines an outer surface of a respective crown collet extension 3138. Another frusto-conical surface 3160 is located below the surface 3159, followed by a substantially cylindrical surface 3161 that defines a lower portion of each extension 3138. The surface 3161 has a diameter smaller than a diameter of the surface 3159. The surface 3161 is sized and shaped for being closely but slidingly received by the receiver cavity 3061 at the cylindrical surface 3096.

The insert body 3136 located between the arms 3137 and the collet extensions 3138 has an outer diameter slightly smaller than a diameter between crests of the guide and advancement structure 3072 of the receiver 3010, allowing for top loading of the compression insert 3014 into the receiver opening 3066, with the arms 3137 of the insert 3014 being located between the receiver arms 3062 during insertion of the insert 3014 into the receiver 3010. Once the arms 3137 of the insert 3014 are generally located beneath the guide and advancement structure 3072, the insert 3014 is rotated into place about the receiver axis B until the top surfaces 3144 are located directly below the guide and advancement structure 3072 as will be described in greater detail below.

With reference to FIGS. 157 and 185-187, the illustrated elongate rod or longitudinal connecting member 3021 (of which only a portion has been shown) can be any of a variety of implants utilized in reconstructive spinal surgery, but is typically a cylindrical, elongate structure having the outer substantially smooth, cylindrical surface 3022 of uniform diameter. The rod 3021 is substantially similar to the rods previously described herein, such as the rods 21, 1021 and 2021 and may be a soft connecting member assembly as described, for example, in the '849 application incorporated by reference herein, and therefore shall not be discussed in any greater detail here.

With reference to FIGS. 157 and 185-187, the closure structure or closure top 3018 shown with the assembly 3001 is rotatably received between the spaced arms of the receiver 3010. It is noted that the closure 3018 top could be a twist-in or slide-in closure structure. The illustrated closure structure 3018 is substantially cylindrical and includes a an outer helically wound guide and advancement structure 3162 in the form of a flange that operably joins with the guide and advancement structure 3072 disposed on the arms 3062 of the receiver 3010. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 3018 downward between the arms 3062 and having such a nature as to resist splaying of the arms 3062 when the closure structure 3018 is advanced into the channel 3064, the flange form illustrated herein as described more fully in Applicant's U.S. Pat. No. 726,689 is preferred as the added strength provided by such flange form beneficially cooperates with and counters any reduction in strength caused by the squared off U-shape channel of the illustrated receiver 3010 and reduced profile of the receiver 3010 that advantageously engages longitudinal connecting member components as will be further described below. The illustrated closure structure 3018 also includes a top surface 3164 with an internal drive 3166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 3166 is used for both rotatable engagement and, if needed, disengagement of the closure 3018 from the receiver arms 3062. It is also foreseen that the closure structure 3018 may alternatively include a break-off head designed to allow such a head to break from a base of the closure at a preselected torque, for example, 70 to 140 inch pounds. Such a closure structure would also include a base having an internal drive to be used for closure removal. A base or bottom surface 3168 of the closure is planar and further includes a point 3169 and a rim 3170 for engagement and penetration into the surface 3022 of the rod 3021 in certain embodiments of the invention. The closure top 3018 may further include a cannulation through bore (not shown) extending along a central axis thereof and through the top and bottom surfaces thereof. Such a through bore provides a passage through the closure 3018 interior for a length of wire (not shown) inserted therein to provide a guide for insertion of the closure top into the receiver arms 3062.

Preferably, the receiver 3010, the retainer 3012 and the compression insert 3014 are assembled at a factory setting that includes tooling for holding and alignment of the component pieces and pinching or compressing of the retainer 3012 as well as compressing or expanding the insert 3014 arms and collet extensions, if needed, as well as crimping a portion of the receiver 3010 toward the insert 3014. In some circumstances, the shank 3004 is also assembled with the receiver 3010, the retainer 3012 and the compression insert 3014 at the factory. In other instances, it is desirable to first implant the shank 3004, followed by addition of the pre-assembled receiver, retainer and compression insert at the insertion point. In this way, the surgeon may advantageously and more easily implant and manipulate the shanks 3004, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 3008 and/or hydroxyapatite on the shank 3006), with the receiver, retainer and compression insert. Allowing the surgeon to choose the appropriately sized or treated shank 3004 advantageously reduces inventory requirements, thus reducing overall cost.

Pre-assembly of the receiver 3010, retainer 3012 and compression insert 3014 is shown in FIGS. 175-177. First, the compression insert 3014 is downloaded into the receiver 3010 through the upper opening 3066 with the crown collet extension bottom surfaces 3148 facing the receiver arm top surfaces 3073 and the insert arms 3137 as well as the insert collet extensions 3138 located between the opposed receiver arms 3062. The insert 3014 is then lowered toward the channel seat 3068 until the insert 3014 arm upper surfaces 3144 are adjacent the run-out area below the guide and advancement structure 3072 defined in part by the cylindrical surface 3082. Thereafter, the insert 3014 is rotated in a clockwise or counter-clockwise manner about the receiver axis B until the upper arm surfaces 3144 are directly below the guide and advancement structure 3072 as illustrated in FIG. 176 with the U-shaped channel 3141 of the insert 3014 aligned with the U-shaped channel 3064 of the receiver 3010. In some embodiments, the insert arms 3137 and collet extensions 3138 may need to be compressed slightly during rotation to clear inner surfaces of the receiver arms 3062. As shown in FIGS. 176 and 177, the outer lower cylindrical surface 3161 of the insert 3014 is received with the cylindrical surface 3096 of the receiver. With reference to FIG. 177, the receiver thin walls 3077 are then crimped inwardly toward the axis B by inserting a tool (not shown) through the receiver apertures 3074, the tool pressing the walls 3077 until the wall surface 3087 engages the insert 3014 at the shallow central slot 3155 formed on the outer surface 3143 of each of the insert arms 3137. The crimping of the wall surface 3087 into the slot 3155 keeps the insert 3014 U-shaped channel 3141 aligned with the receiver U-shaped channel 3064 and also retains the insert 3014 at the upward location shown in FIG. 177 with the insert arm top surfaces 3144 adjacent the guide and advancement structure 3072 until the insert 3014 is pushed downwardly toward the receiver base 3060 after assembly with the shank 3004. Thus, the crimping of the receiver walls 3077 prohibits rotation of the insert 3014 about the receiver axis B but allows for limited axial movement of the insert 3014 with respect to the receiver 3010 along the axis B when some force is exerted to slide the crimped surface 3087 up or down along the groove 3155. The insert 3014 is fully captured within the receiver 3010 by the guide and advancement structure 3072 prohibiting movement of the insert 3014 up and out through the receiver opening 3066 as well as by the frusto-conical surface 3158 of the insert 3014 that is sized to engage and wedge against the cylindrical surface 3096 of the receiver, preventing movement of the insert 3014 out of the lower receiver opening 3110. In some embodiments of the invention, top or side surfaces of the insert 3014 may include a resilient projection or projections for temporarily frictionally engaging with an inner surface of the receiver 3010 to hold the insert 3014 in an upper portion of the receiver 3010 during some of the assembly steps, also providing a frictional but slidable fit between the insert 3014 and the receiver 3010. In some embodiments, the insert 3014 may also be freely slidable in the upper portion of the receiver 3010 in an axial direction, but preferably kept above the receiver cylindrical surface 3099 that functions as an expansion recess or chamber for the retainer 3012.

Also with reference to FIG. 177, the retainer 3012 is then prepared for insertion into the receiver 3010 by squeezing or pressing the retainer end surfaces 3134 and 3135 toward one another. The compressed retainer 3012 is inserted into the lower opening 3110 with the planar top surface 3122 facing the receiver bottom surface 3108. The retainer 3012 is typically moved upwardly into the receiver 3010 and past the cylindrical surface 3106 and allowed to expand to a substantially neutral state within the cylindrical surface 3101 as shown in FIG. 178. Also as shown in FIG. 178, at this time, both the compression insert 3014 and the retainer 3012 are captured within the receiver 3010 in a manner that substantially prevents movement or loss of such parts out of the receiver 3010. The receiver 3010, compression insert 3014 and the retainer 3012 combination is now pre-assembled and ready for assembly with the shank 3004 either at the factory, by surgery staff prior to implantation, or directly upon an implanted shank 3004 as shown, for example, in FIG. 179, with the shank axis A and the receiver axis B either being aligned during assembly as shown in FIG. 178 and most of the drawings figures illustrating the assembly process, or the axes being at an angle with respect to one another as shown in FIG. 179.

As illustrated in FIG. 179, the bone screw shank 3004 or an entire assembly 3001 made up of the assembled shank 3004, receiver 3010, retainer 3012 and compression insert 3014, is screwed into a bone, such as the vertebra 3017, by rotation of the shank 3004 using a suitable driving tool (not shown) that operably drives and rotates the shank body 3006 by engagement thereof at the internal drive 3046.

With reference to FIGS. 178 and 179, the pre-assembled receiver, insert and retainers are placed above the shank upper portion 3008 until the shank upper portion is received within the opening 3110. With particular reference to FIGS. 180 and 181, as the shank upper portion 3008 is moved into the interior 3061 of the receiver base, the shank upper portion 3008 presses the retainer 3012 upwardly into the recess partially defined by the cylindrical surface 3099 (if the retainer is not already located within such recess). As the portion 3008 continues to move upwardly toward the channel 3064, the top surface 3122 of the retainer 3012 abuts against the insert bottom surfaces 3148 as well as the annular rim stop 3098 of the receiver 3010, stopping upward movement of the retainer 3012 and forcing outward movement of the retainer 3012 towards the cylindrical surface 3099 defining the receiver expansion recess as the spherical surface 3034 continues in an upward direction. The retainer 3012 begins to contract about the spherical surface 3034 as the center of the sphere passes beyond the center of the retainer expansion recess defined by the surface 3099. At this time also, the spherical surface 3034 moves into engagement with the insert 3014 spherical surface 3152 with the collet panels 3154 expanding slightly outwardly to receive the surface 3034. The panels 3154 press outwardly against the surface 3096 that provides enough clearance for the spherical surface 3034 to enter into full frictional engagement with the panel inner surfaces 3152 as shown in FIG. 182. At this time, the insert 3014 and the surface 3034 are in a fairly tight friction fit, the surface 3034 being pivotable with respect to the insert 3014 with some force. Thus, a tight, non-floppy ball and socket joint is now created between the insert 3014 and the shank upper portion 3008.

With reference to FIGS. 183 and 184, the shank 3004 and attached insert 3014 are then moved downwardly into a desired position for receiving the rod 3021 or other longitudinal connecting member by either an upward pull on the receiver 3010 or, in some cases, by driving the shank 3004 further into the vertebra 3017. Also, in some embodiments, when the receiver 3010 is pre-assembled with the shank 3004, the entire assembly 3001 may be implanted at this time by inserting the driving tool (not shown) into the receiver and the shank drive 3046 and rotating and driving the shank 3004 into a desired location of the vertebra 3017.

Also with reference to FIG. 184, at this time, the compression insert 3014 cylindrical surface 3159 is located within the receiver cylindrical surface 3096 with the insert frusto-conical surface 3158 at or near the surface 3096 at an edge thereof defining a juncture of the surface 3096 and the annular seat 3095. The insert 3014 is thus prohibited from moving any further downwardly at the ledge or seat 3095 unless forced downwardly by a tool or by the closure top pressing downwardly on the rod that in turn presses downwardly on the insert 3014 in a later stage of assembly as shown in FIG. 185. With further reference to FIG. 184, at this time, the receiver 310 may be articulated to a desired angular position with respect to the shank 3004, that will be held, but not locked, by the frictional engagement between the insert 3014 and the shank upper portion 3008.

With reference to FIGS. 185-187, the rod 21 is eventually positioned in an open or percutaneous manner in cooperation with the at least two bone screw assemblies 3001 (or combination of 1, 1001, 2001 and 3001, for example). The closure structure 3018 is then inserted into and advanced between the arms 3062 of each of the receivers 3010. The closure structure 3018 is rotated, using a tool engaged with the inner drive 3166 until a selected pressure is reached at which point the rod 3021 engages the U-shaped seating surface 3142 of the compression insert 3014, further pressing the insert stepped shank gripping surfaces 3150 against the shank spherical surface 3034, the edges of the stepped surfaces penetrating into the spherical surface 3034 and also pressing the shank upper portion 3008 into locked frictional engagement with the retainer 3012. Specifically, as the closure structure 3018 rotates and moves downwardly into the respective receiver 3010, the point 3169 and rim 3170 engage and penetrate the rod surface 3022, the closure structure 3018 pressing downwardly against and biasing the rod 3021 into compressive engagement with the insert 3014 that urges the shank upper portion 3008 toward the retainer 3012 and into locking engagement therewith, the retainer 3012 frictionally abutting the surface 3104 and expanding outwardly against the cylindrical surface 3101. For example, about 80 to about 120 inch pounds of torque on the closure top may be applied for fixing the bone screw shank 3006 with respect to the receiver 3010.

Also, as the closure structure 3018 and the rod 3021 press the insert 3014 downwardly toward the base of the receiver 3010, the insert frusto-conical surface 3158 is forced into the receiver cylindrical surface 3096, wedging the insert 3014 into fixed frictional engagement with the receiver surface 3096. With reference to FIG. 186, at this time, the closure top 3018 may be loosened or removed and/or the rod 3021 may be adjusted and/or removed and the frictional engagement between the insert 3014 and the receiver 3010 at the receiver surface 3096 will remain locked in place, advantageously maintaining a locked angular position of the shank 3004 with respect to the receiver 3010. If the user wishes to release the insert 3014 from the receiver 3010 and unlock the polyaxial mechanism, a tool (not shown) may be used that includes extensions or prongs that are received by and through the opposed through bores 3075 of the receiver 3010 and received into the through bores 3156 of the insert 3014. Such tool is then pulled upwardly in a direction along the axis B away from the receiver base 3060, thereby pulling the insert slightly upwardly and away from the receiver base 3060 and releasing the frusto-conical surface 3158 from the cylindrical surface 3096. Alternatively, if both the closure top 3018 and the rod 3021 are already removed from the receiver 3010, another manipulation tool (not shown) may be used that is inserted into the receiver at the opening 3066 and into the insert channel 3141, with prongs or extensions thereof extending outwardly into the insert through bores 3156; a piston-like portion of the tool thereafter pushing directly on the shank upper portion 3008, thereby pulling the insert 3014 surface 3158 away from the receiver surface 3096 and thus releasing the polyaxial mechanism. At such time, the shank 3004 may be articulated with respect to the receiver 3010, but the desired friction fit remains or returns between the insert 3014 and the shank surface 3034, so that an adjustable, but non-floppy relationship exists between the shank 3004 and the receiver 3010. If further disassembly if the assembly 3001 is desired, such is accomplished in reverse order to the procedure described previously herein for assembly.

With reference to FIGS. 188-221 the reference number 3201 generally represents another embodiment of a polyaxial bone screw apparatus or assembly according to the present invention. The assembly 3201 includes a shank 3204, that further includes a body 3206 integral with an upwardly extending upper portion or head-like capture structure 3208; a receiver 3210; a retainer structure illustrated as a resilient open ring 3212, and a friction fit crown collet compression or pressure insert 3214. The receiver 3210, retainer 3212 and compression insert 3214 are initially assembled and may be further assembled with the shank 3204 either prior or subsequent to implantation of the shank body 3206 into a vertebra 3217, as will be described in greater detail below. FIGS. 188, 220 and 221 further show a closure structure 3218 for capturing a longitudinal connecting member, for example, a rod 3221 which in turn engages the compression insert 3214 that presses against the shank upper portion 3208 into fixed frictional contact with the retainer 3212, so as to capture, and fix the longitudinal connecting member 3221 within the receiver 3210 and thus fix the member relative to the vertebra 3217. The illustrated rod 3221 is substantially similar to the hard, stiff rod 3021 previously described herein, having an outer cylindrical surface 3222. In other embodiments, the stiff rod 3221 may take other shapes and/or be made from other materials or be part of a longitudinal connecting member assembly that may include sleeves that are fixable to a core member or slidable with respect thereto, spacers (compressible or not) and cords, for example, all as previously described herein with respect to the rods 21, 1021, 2021 and 3021, for example, and fully incorporated by reference herein with respect to the rod 3221.

The receiver 3210 and the shank 3204 cooperate in such a manner that the receiver 3210 and the shank 3204 can be secured at any of a plurality of angles, articulations or rotational alignments relative to one another and within a selected range of angles both from side to side and from front to rear, to enable flexible or articulated engagement of the receiver 3210 with the shank 3204 until both are locked or fixed relative to each other near the end of an implantation procedure.

The shank 3204, best illustrated in FIGS. 188-190, is the same or substantially similar to the shank 3004 previously described herein. Therefore, the shank 3204 includes the body 3206, the upper portion or head 3208, a thread 3224, a neck 3226, a shank body top 3232, an upper portion spherical surface 3234, an upper portion planar top surface 3238, an aperture with a stepped base 3245 partially defining an internal drive feature 3246 and a cannulation bore 3250, all the same or substantially similar to the respective body 3006, upper portion or head 3008, thread 3024, neck 3026, shank body top 3032, upper portion spherical surface 3034, upper portion planar top surface 3038, aperture with stepped base 3045, internal drive feature 3046 and cannulation bore 3050 of the shank 3004 previously described herein with respect to the assembly 3001.

With particular reference to FIGS. 188 and 202-208, the receiver 3210 has a generally squared-off, U-shaped appearance with partially discontinuous and partially cylindrical inner and outer profiles. The receiver 3210 has an axis of rotation BB that is shown in FIG. 188 as being aligned with and the same as the axis of rotation AA of the shank 3204, such orientation being desirable, but not required during assembly of the receiver 3210 with the shank 3204. After the receiver 3210 is pivotally attached to the shank 3204, either before or after the shank 3204 is implanted in a vertebra 3217, the axis BB is typically disposed at an angle with respect to the axis AA, as shown, for example, in FIG. 221.

The receiver 3210 includes a substantially cylindrical base 3260 defining a bore or inner cavity, generally 3261, the base 3260 being integral with a pair of opposed upstanding arms 3262 forming a cradle and defining a channel 3264 between the arms 3262 with an upper opening, generally 3266, and a substantially planar lower channel portion or seat 3268, the channel 3264 having a width for operably snugly receiving the rod 3221 or portion of another longitudinal connector between the arms 3262, the channel 3264 communicating with the base cavity 3261. Directly below each channel seat 3268, the cylindrical base 3260 is cut or truncated, forming opposed planar surfaces 3267. Outer front and rear opposed substantially planar arm surfaces 3269 partially define the channel 3264 substantially directly above the seat 3268, the arm surfaces 3269 as well as the base surfaces 3267 advantageously reducing the run on the rod (i.e., providing a more narrow receiver portion that in turn provides more space and thus more access between bone anchors along the rod or other connecting member) and providing planar contact surfaces for flush or close cooperation with other connecting member components in certain embodiments, such as for bumpers or spacers that surround a hard or deformable rod or provide support for elastic or cord-type connecting members. The squared-off geometry of the channel 3264 and lower seat 3268 allow for use with a variety of longitudinal connecting members, including, but not limited to those with circular, square and rectangular cross-sections. As compared to a U-shaped channel that includes a lower seat having a surface with a radius the same or slightly larger than a cooperating cylindrical rod or other connecting member, the squared-off seat 3268 provides improved stress management, moving stress risers outwardly toward the two arms 3262 rather than being focused primarily at a center base line of the radiused lower seat.

Each of the arms 3262 has an interior surface, generally 3270, that includes various inner cylindrical profiles, an upper one of which is a partial helically wound guide and advancement structure 3272 located adjacent top surfaces 3273 of each of the arms 3262. In the illustrated embodiment, the guide and advancement structure 3272 is a partial helically wound interlocking flangeform configured to mate under rotation with a similar structure on the closure structure 3218, the same or similar to the guide and advancement structure 3072 previously described herein with respect to the receiver 3010 of the assembly 3001. However, it is foreseen that for certain embodiments of the invention, the guide and advancement structure 3272 could alternatively be a square-shaped thread, a buttress thread, a reverse angle thread or other thread-like or non-threadlike helically wound discontinuous advancement structures, for operably guiding under rotation and advancing the closure structure 3218 downward between the arms 3262, as well as eventual torquing when the closure structure 3218 abuts against the rod 3221 or other longitudinal connecting member. It is foreseen that the arms could have break-off extensions.

An opposed pair of substantially circular shallow tool receiving and engaging apertures 3274 are formed on outer surfaces 3276 of the arms 3262. Two additional pair of tool receiving and engaging apertures 3278 are also formed in the front and rear surfaces 3269 of the receiver arms 3262. Transition base surfaces 3279 span between the planar surfaces 3269 and the planar seating surface 3268 at either side of the planar base surfaces 3267. Some or all of the apertures 3274 and 3278 may be used for holding the receiver 3210 during assembly with the insert 3214, the retainer 3212 and the shank 3204; during the implantation of the shank body 3206 into a vertebra when the shank is pre-assembled with the receiver 3210; during assembly of the bone anchor assembly 3201 with the rod 3221 and the closure structure 3218; and during disassembly of the component parts, when needed. It is foreseen that tool receiving grooves or apertures may be configured in a variety of shapes and sizes and be disposed at other locations on the receiver arms 3262.

Returning to the interior surface 3270 of the receiver arms 3262, located below the guide and advancement structure 3272 is a discontinuous cylindrical surface 3282 partially defining a run-out feature for the guide and advancement structure 3272. The cylindrical surface 3282 has a diameter equal to or slightly greater than a greater diameter of the guide and advancement structure 3272. Moving downwardly, in a direction toward the base 3260, adjacent the cylindrical surface 3282 of each arm is a run-out seat or surface 3284 that extends inwardly toward the axis BB and runs perpendicular to the axis BB. Adjacent to and located below the surface 3284 is another cylindrical surface 3286 having a diameter smaller than the diameter of the surface 3282. Four inner crimping structures, generally 3288, for keeping the insert 3214 in a desired alignment within the receiver 3210 are each cut or otherwise formed in the receiver 3210 below the surface 3286 and extend downwardly into the base cavity 3261. The crimping structures 3288 may be made, for example, by making electrical discharge machining (EDMO) cuts below the surface 3286, creating a pair of opposed discontinuous annular surfaces 3289 and 3290, the surfaces 3290 defining upper surfaces of the structures 3288. Substantially parallel vertical EDM cuts (parallel to the axis BB) located near each channel seat 3268 create outer surfaces 3292 of each of the structures 3288. A discontinuous cylindrical surface 3293 defines a contact surface of each of the crimping structures 3288. The surfaces 3293 have a diameter smaller than the diameter of the run-out surface 3282 but larger than the diameter of the discontinuous cylindrical surface 3286. Each structure 3288 terminates in the base cavity 3261 at a partially annular surface or lower rim 3294 disposed perpendicular to the axis BB. As best shown in FIGS. 206 and 213, the crimping structures 3288 are deployed by bending each structure toward the insert 3214 at the surface 3293 as will be described in greater detail below. It is foreseen that the structures 3288 may have other geometries for cooperating with the insert 3214 and/or other structure, such as spring tabs or thin crimped walls may alternatively be utilized to retain the insert 3214 in a desired position within the receiver 3210.

Each inner arm surface 3270 further includes a substantially centrally located recess or partial curvate groove, generally 3295, for receiving portions of the insert 3214 in a neutral state thereof as will be described in greater detail below. The recess 3295 is defined by an upper partially annular surface or stop 3296 disposed perpendicular to the axis BB and a curvate or partially cylindrical surface 3297 that cuts into the cylindrical surface 3293. Each recess 3295 generally terminates at or aligned with the discontinuous lower rim 3294.

The EDM cuts that form the outer surfaces 3292 of the crimping structures 3288 also form planar surfaces 3298 partially defining an upper portion of the cavity 3261 located below and at either side of each channel seat 3268. A pair of opposed centrally located curved or partially cylindrical surfaces 3299 also partially define an upper portion of the cavity 3261, each surface 3299 spanning between planar surfaces 3298. A diameter of each surface 3299 is the same as the un-crimped diameter of the crimping structure 3288 inner cylindrical surfaces 3293 as best illustrated in FIG. 206.

Further with respect to the base 3260 and more specifically, the base cavity 3261, located below and adjacent to the discontinuous lower rim 3294 is a cylindrical surface 3300 oriented substantially parallel to the axis BB and sized and shaped to receive an expanded retainer 3212. The surfaces 3294 and 3300 define a circumferential recess or chamber that is sized and shaped to receive the retainer 3212 as it expands around the shank upper portion 3208 as the shank 3204 moves upwardly toward the channel 3264 during assembly, the insert 3214 forming a restriction to prevent the neutral or expanding retainer 3212 from moving upwardly with the shank portion 3208. Prior to assembly of the insert 3214 with the receiver 3210, the discontinuous rim 3294 aids in keeping the retainer 3212 within the receiver cavity 3261. A cylindrical surface 3301 located below the cylindrical surface 3300 is sized and shaped to closely receive the retainer 3212 when the retainer is in a neutral or operative position as shown in FIGS. 219 and 220, for example. Thus, the cylindrical surface 3301 has a diameter smaller than the diameter of the cylindrical surface 3300 that defines the expansion area for the retainer 3212. The surface 3301 is joined or connected to the surface 3300 by one or more beveled, curved or conical surfaces 3302. The surfaces 3302 allow for sliding gradual movement and/or contraction of the retainer 3212 into the space defined by the surface 3301 and ultimate seating of the retainer 3212 on a lower annular surface 3304 located below and adjacent to the cylindrical surface 3301. Located below and adjacent to the annular seating surface 3304 is another substantially cylindrical surface 3306 that communicates with a beveled or flared bottom opening surface 3307, the surface 3307 communicating with an exterior base surface 3308 of the base 3260, defining a lower opening, generally 3310, into the base cavity 3261 of the receiver 3210.

With particular reference to FIGS. 188, 191-195 and 207, the open retainer ring 3212 that operates to capture the shank upper portion 3208 and attached compression insert 3214 within the receiver 3210 has a central axis that is operationally the same as the axis BB associated with the receiver 3210 when the shank upper portion 3208 and the retainer 3212 are installed within the receiver 3210. The retainer ring 3212 is made from a resilient material, such as a stainless steel or titanium alloy, so that the retainer 3212 may be expanded during assembly as will be described in greater detail below. The retainer 3212 has a central channel or hollow through bore, generally 3321, that passes entirely through the ring 3212 from a top surface 3322 to a bottom surface 3324 thereof. Surfaces that define the channel or bore 3321 include a discontinuous inner cylindrical surface 3325 adjacent the top surface 3322, a discontinuous frusto-conical surface 3327 adjacent the surface 3325 and a beveled surface 3328, all three surfaces coaxial when the retainer 3212 is in a neutral, non-expanded orientation. The retainer 3212 further includes an outer cylindrical surface 3330 located adjacent the top surface 3322 and an outer beveled or frusto-conical surface 3332 adjacent the bottom surface 3324. The surface 3330 is oriented parallel to the central axis of the retainer 3212. The resilient retainer 3212 further includes first and second end surfaces, 3334 and 3335 disposed in spaced relation to one another (they may also be touching) when the retainer is in a neutral state. Both end surfaces 3334 and 3335 are disposed substantially perpendicular to the top surface 3322 and the bottom surface 3324. A width XX between the surfaces 3334 and 3335 is very narrow as compared to the width X between the surfaces 3034 and 3035 of the retainer 3012 of the assembly 3001. Unlike the retainer 3012 and receiver 3010 of the assembly 3001, the retainer 3212 and the receiver 3210 are sized and shaped for top loading of the insert 3212 into the receiver 3210 which does not require compressing or pinching of the surfaces and 3335 toward one another during the loading step. Therefore, the gap between the surfaces 3334 and 3335 functions only in expansion to allow the retainer 3212 to expand about the shank upper portion 3208 and ultimately against the receiver when finally locked in place. This results in a stronger retainer that provides more surface contact with the shank upper portion 3208, resulting in a sturdier connection with less likelihood of failure than a retainer ring having a greater gap. Furthermore, because the retainer 3212 is only expanded and not compressed and expanded like the retainer 3012, the retainer 3212 does not undergo the mechanical stress that typically is placed on the retainer 3012.

With particular reference to FIGS. 188 and 196-201, the friction fit crown compression insert 3214 is illustrated that is sized and shaped to be received by and down-loaded into the receiver 3210 at the upper opening 3266. The compression insert 3214 has an operational central axis that is the same as the central axis BB of the receiver 3210. In operation, the insert 3214 advantageously frictionally engages the bone screw shank upper portion 3208, allowing for un-locked but non-floppy placement of the angle of the shank 3204 with respect to the receiver 3210 during surgery prior to locking of the shank 3204 with respect to the receiver 3210 near the end of the procedure. The insert 3214 is thus preferably made from a resilient material, such as a stainless steel or titanium alloy, so that portions of the insert may be expanded about and then contracted, snapped or popped onto the shank upper portion 3208 as well as pinched and un-wedged from the receiver 3210.

The crown collet compression insert 3214 includes a partially cylindrical body 3336 having a planar top surface 3337 and being integral with an opposed pair of crown collet extensions, generally 3338 at a lower end thereof opposite the planar top surface 3337. Furthermore, extending opposite the extensions 3338 are two upwardly and outwardly extending resilient structures or prongs 3339 that engage the receiver 3210 during certain steps of the assembly process as will be described in greater detail below. A bore 3340 extends through the body 3336 with the collet extensions 3338 and the prongs 3339 being located generally on opposed sides of the bore 3340. The prongs 3339 may be formed in a variety of ways. In the illustrated embodiment, the top surface 3337 is initially substantially rectangular and opposed side surfaces taper outwardly (e.g. frusto-conical). EDM cut-outs are made near each of the tapered side surfaces, forming the prong inner curved surfaces 3342 and facing substantially planar body surfaces 3343 as well as a groove or base surface 3344 that spans between each surface 3342 and 3343. Each prong 3339 further includes an outer tapered or frusto-conical (or otherwise curved) surface 3345 and a top surface 3346. In a neutral state, the top surface 3346 is level or flush with the top surface 3337 of the body 3336. It is noted that in other embodiments of the invention, the prongs 3339 may be made into an insert having outer cylindrical surfaces, for example, by making a straight cut into the surface 3337 and then bending each prong 3339 outwardly from the body 3336 into a position wherein the prong top surfaces 3346 are spaced from the body top surface 3337 similar to what is shown in the drawings. However formed, the prongs 3339 are sized, shaped and positioned to extend outwardly from the body 3336 when in a neutral state and to fit within the central recesses 3295 of the receiver 3210 when in a deployed or operating position as shown, for example in FIGS. 219 and 220, with each prong top surface 3346 located directly beneath a respective receiver surface 3296 and each prong outer surface 3345 engaging or extending outwardly near the receiver surface 3297. The prongs 3339 have adequate resilience to be pinched or squeezed toward the insert body 3336 at the receiver arm surfaces 3293 when being rotated into an initial position in the receiver 3210 as shown, for example, in FIG. 210 in preparation for assembly with the shank upper portion 3208 as described in greater detail below.

The bore 3340 is disposed generally centrally through the body 3336 and is further defined by an inner cylindrical surface 3347 that communicates with a lower collet space that extends to discontinuous bottom surfaces 3348 of the collet extensions 3338. The body 3335 (and bore 3340) is further defined by a shank gripping surface portion, generally 3350, the gripping portion 3350 being adjacent to the cylindrical surface 3347. Located below and adjacent to the gripping portion 3350 is an inner partially spherical surface 3352 that is continuous at the body 3336 and is discontinuous at the extensions 3338 wherein the surface 3352 extends downwardly, defining the inner shank holding portion of each of the collet extensions 3338 and terminating at the extension bottom surfaces 3348. The gripping surface portion 3350 preferably includes two or more graduated cylindrical surfaces disposed substantially parallel to the axis BB and adjacent perpendicular step surfaces that are disposed generally perpendicular to the axis BB when the insert 3214 is mounted within the receiver 3210. It is foreseen that the stepped surface portion 3350 may include greater or fewer number of stepped surfaces. It is foreseen that the shank gripping surface portion 3350 and also the spherical surface 3352 may additionally or alternatively include a roughened or textured surface or surface finish, or may be scored, knurled, or the like, for enhancing frictional engagement with the shank upper portion 3208. The two collet extensions 3338 that generally extend in a direction opposite to the prongs 3339 and have the discontinuous inner spherical surface 3352, also include through slits or slots 3353 running substantially vertically from adjacent the shank gripping surface portion 3350 through the bottom surfaces 3348. The illustrated embodiment includes two substantially equally spaced slots 3353 located in each extension 3338. It is foreseen that other embodiments of the invention may include more or fewer slots 3353. The slots 3353 substantially equally partition each of the extensions 3338, forming a total of six distinct resilient, partially spherical fingers, tab or panels 3354 that extend from the shank gripping portion 3350 to the bottom surface 3348. In other words, the discontinuous inner spherical surface 3352 is further separated into two opposed pairs of three surface portions 3354 each, with each portion 3354 being partially spherical and sized and shaped to resiliently expand about the spherical surface 3234 of the shank upper portion 3208 and then snap on and frictionally grip the surface 3234. Preferably, the spherical surface 3352 is designed such that the gripping tabs or panels 3354 have a neutral or non-expanded radius that is slightly smaller than a radius of the shank surface 3234 so that when the tabs or panels 3354 are gripping the surface 3234, the insert 3214 collet extension portion 3338 is in a slightly expanded state. When the shank 3204 is locked into position by a rod 3221 or other connecting member being pressed downwardly on the insert seat 3342 by the closure top 3218, the insert 3214 shank gripping portion 3350 that is initially slidable along the shank surface 3234 then digs or penetrates into the surface 3234 and thus securely fixes the shank upper portion 3208 to the insert at the portion 3350.

The compression insert 3214 through bore 3340 is sized and shaped to receive the driving tool (not shown) therethrough that engages the shank drive feature 3246 when the shank body 3206 is driven into bone with the receiver 3210 attached. The illustrated insert 3214 further includes surface features located primarily on the insert body 3336 that cooperate with the receiver crimping structures 3288. Specifically, the insert body 3336 includes a centrally located substantially cylindrical portion 3356 located about and co-axial with the bore 3340. The portion 3356 includes opposed cylindrical surfaces 3357 that run from the top surface 3337 to a lower or bottom surface 3358 located substantially centrally between the collet extensions 3338. Located on either side of each surface 3357 is a curvate transition surface 3359 followed by a substantially planar surface 3360 that extends substantially to the body surface 3343 and is substantially perpendicular thereto. Each surface 3359 runs from the planar top surface 3337 to the respective bottom surface 3358. The portion of the bottom surface 3358 that is adjacent to the surface 3359 curves downwardly in a direction toward the respective collet extension bottom surface 3348. Each surface 3360 runs from the planar top surface 3337 and along each crown collet extension 3338 to bottom surfaces 3348 thereof. With particular reference to FIGS. 211-213 and as will be described in greater detail below, the four inner crimping structures 3288 of the receive 3210 are crimped or bent to a location at or near the four surfaces 3360 of the insert 3214, the structures 3288 being crimped or bent toward the insert 3214 spanning from a location near the insert top surface 3337 to a location near the collet bottom surfaces 3348, substantially limiting or prohibiting rotation of the insert 3214 with respect to the receiver 3210 about the axis BB (only a 2.5 degree collet rotation possible in the illustrated embodiment). However, the crimping structures 3288 advantageously allow for up and down movement of the insert 3214 with respect to the receiver 3210 along the axis BB.

The opposed cylindrical insert body surfaces 3357 have an outer diameter slightly smaller than a diameter between crests of the guide and advancement structure 3272 of the receiver 3210, allowing for top loading of the compression insert 3214 into the receiver opening 3266, with the collet extensions 3338 and the prongs 3339 of the insert 3214 being located between the receiver arms 3262 during insertion of the insert 3214 into the receiver 3210. Once the upper prongs 3339 the insert 3214 are generally located below the discontinuous annular surface 3289, the insert 3214 is rotated into place about the receiver axis BB until the prong top surfaces 3346 are located directly beneath the surfaces 3289, the prong outer surfaces 3345 engaging the receiver discontinuous cylindrical surface 3293 during rotation of the insert 3214, the prongs 3339 being pressed inwardly toward the axis BB as will be described in greater detail below. The frictional engagement between the prong surfaces 3345 and the receiver arm surfaces 3293 advantageously maintains the insert 3214 in an upper portion of the receiver cavity 3261 prior to and during assembly with the shank 3204.

The closure top 3218 illustrated in FIGS. 188, 220 and 221 is the same or substantially similar to the closure top 3018 previously described herein. Therefore, the closure top 3218 includes a guide and advancement structure 3362, a top surface 3364, an internal drive feature 3366, and a bottom surface 3368 further having a point 3369 and a rim 3370 the same or similar to the respective guide and advancement structure 3162, top surface 3164, internal drive feature 3166, and bottom surface 3168 with point 3169 and rim 3170 of the closure top 3018 of the assembly 3001 previously described herein.

Preferably, the receiver 3210, the retainer 3212 and the compression insert 3214 are assembled at a factory setting that includes tooling for holding, alignment, compression and expansion of the component pieces, if needed, as well as crimping the structures 3288 of the receiver 3210 toward the insert 3214. In some circumstances, the shank 3204 is also assembled with the receiver 3210, the retainer 3212 and the compression insert 3214 at the factory. In other instances, it is desirable to first implant the shank 3204, followed by addition of the pre-assembled receiver, retainer and compression insert at the insertion point. In this way, the surgeon may advantageously and more easily implant and manipulate the shanks 3204, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 3208 and/or hydroxyapatite on the shank 3206), with the receiver, retainer and compression insert. Allowing the surgeon to choose the appropriately sized or treated shank 3204 advantageously reduces inventory requirements, thus reducing overall cost.

Pre-assembly of the receiver 3210, retainer 3212 and compression insert 3214 is shown in FIGS. 207-214. With particular reference to FIGS. 207 and 208, first the retainer 3212 is inserted into the upper receiver opening 3266 with the planar top surface 3322 facing one of the receiver guide and advancement structures 3272 (not shown), the retainer 3212 lowered into the channel 3264 and partially into the receiver cavity 3261, followed by turning the retainer 3212 such that the top surface 3322 is moved into a position within the cavity facing upwardly toward the receiver channel opening 3266. The retainer 3212 may then be pressed downwardly into a lower portion of the receiver cavity 3261, preferably to a position wherein the retainer 3212 bottom surface 3324 engages the receiver annular surface 3304, the retainer 3212 being slightly compressed with the outer cylindrical surface 3330 frictionally engaging the receiver cylindrical surface 3301.

With particular reference to FIGS. 208-210, the compression insert 3214 is downloaded into the receiver 3210 through the upper opening 3266 with the crown collet extension bottom surfaces 3348 facing the receiver arm top surfaces 3273 and the insert upper prongs 3339 as well as the insert collet extensions 3338 being located between the opposed receiver arms 3262. The insert 3214 is then lowered toward the receiver base 3260 until the insert 3214 body top surface 3337 is substantially adjacent to and located slightly below the receiver arm surfaces 3289 that are located directly below the arm cylindrical surfaces 3286. Thereafter, the insert 3214 is rotated in a clockwise or counter-clockwise manner about the receiver axis BB until the prong upper surfaces 3346 are each directly below the surfaces 3289. As the insert 3214 is rotated, the prongs 3339 are squeezed toward one another so that each prong outer surface 3345 slidingly frictionally engages the receiver surfaces 3293. With reference to FIG. 210, the insert 3213 is rotated until the prongs 3339 and the collet extensions 3338 are centrally located beneath the surfaces 3289 and centrally aligned with each of the receiver arms 3262. With particular reference to FIGS. 211-213, each of the four receiver crimping structures 3288 are then crimped or bent towards the insert surfaces 3360, limiting any further rotation of the insert 3214 with respect to the receiver 3210 about the axis BB to no more than a few degrees. At this time, the surfaces 3289 prevent upward movement of the insert 3214, but with some force, the insert 3214 may be moved downwardly toward the receiver base 3260. However, it is desirable at this time to keep the insert 3214 wedged at the arm surfaces 3293 and the retainer 3212 engaged with the cavity surface 3301.

The receiver 3210, compression insert 3214 and the retainer 3212 combination is now pre-assembled and ready for assembly with the shank 3204 either at the factory, by surgery staff prior to implantation, or directly upon an implanted shank 3204, with the shank axis AA and the receiver axis BB either being aligned during assembly as shown in FIG. 214 and most of the drawings figures illustrating the assembly process, or the axes being at an angle with respect to one another as shown, for example, in FIG. 221.

The bone screw shank 3204 or an entire assembly 3201 made up of the assembled shank 3204, receiver 3210, retainer 3212 and compression insert 3214, is screwed into a bone, such as the vertebra 3217, by rotation of the shank 3204 using a suitable driving tool (not shown) that operably drives and rotates the shank body 3206 by engagement thereof at the internal drive 3246. Specifically, the vertebra 3217 may be pre-drilled to minimize stressing the bone and have a guide wire (not shown) inserted therein to provide a guide for the placement and angle of the shank 3204 with respect to the vertebra. A further tap hole may be made using a tap with the guide wire as a guide. Then, the bone screw shank 3204 or the entire assembly 3201 is threaded onto the guide wire utilizing the cannulation bore 3250 by first threading the wire into the opening at the bottom 3228 and then out of the top opening at the drive feature 3246. The shank 3204 is then driven into the vertebra using the wire as a placement guide. It is foreseen that the shank and other bone screw assembly parts, the rod 3221 (also having a central lumen in some embodiments) and the closure top 3218 (also with a central bore) can be inserted in a percutaneous or minimally invasive surgical manner, utilizing guide wires. When the shank 3204 is driven into the vertebra 3217 without the remainder of the assembly 3201, the shank 3204 may either be driven to a desired final location or may be driven to a location slightly above or proud to provide for ease in assembly with the pre-assembled receiver, compression insert and retainer.

With reference to FIGS. 214-219, the pre-assembled receiver, insert and retainer are placed above the shank upper portion 3208 until the shank upper portion is received within the opening 3310. With particular reference to FIG. 215, as the shank upper portion 3208 is moved into the interior 3261 of the receiver base, the shank upper portion 3208 presses the retainer 3212 upwardly into the recess partially defined by the cylindrical surface 3300 (if the retainer is not already located within such recess). With particular reference to FIG. 216, as the portion 3208 continues to move upwardly toward the channel 3264, the top surface 3322 of the retainer 3212 abuts against the insert bottom surfaces 3348, stopping upward movement of the retainer 3212 and forcing outward movement of the retainer 3212 towards the cylindrical surface 3300 as the shank spherical surface 3234 continues in an upward direction. With further reference to FIG. 216, the retainer 3212 contracts about the spherical surface 3234 as the center of the sphere passes beyond the center of the retainer expansion recess. At this time also, the spherical surface 3234 moves into engagement with the insert 3214 spherical surface 3352 with the collet panels 3354 expanding slightly outwardly to receive the surface 3234. The spherical surface 3352 then enters frictional engagement with the panel inner surfaces 3352 as shown in FIG. 217. At this time, the insert 3214 and the surface 3234 are in a fairly tight friction fit, the surface 3234 being pivotable with respect to the insert 3214 with some force. Thus, a tight, non-floppy ball and socket joint is now created between the insert 3214 and the shank upper portion 3208. At this time the retainer 3212 has returned to a neutral position and is typically located within the receiver transition surface or surfaces 3302.

With reference to FIGS. 218 and 219, the shank upper portion 3208 and attached insert 3214 are then moved downwardly into a desired position for receiving the rod 3221 or other longitudinal connecting member by either an upward pull on the receiver 3210 or, in some cases, by driving the shank 3204 further into the vertebra 3217. Also with reference to FIGS. 217-219, as the shank 3204 is moved downwardly toward the receiver base 3260, the insert prongs 3339 slide along the surfaces 3293 until top surfaces 3346 thereof clear the surfaces 3293, allowing the prongs 3330 to snap outwardly to a neutral position located below the surfaces 3293 and within the central recesses 3295 of each of the receiver arms 3262. The prong top surfaces 3346 now being located beneath surfaces 3296 of the central recesses 3295, thus retaining the insert 3214 in a desired location within the receiver cavity 3261, the shank upper portion 3208 pressing downwardly on the retainer 3212 and the retainer seated on the receiver surface 3304. In some embodiments, when the receiver 3210 is pre-assembled with the shank 3204, the entire assembly 3201 may be implanted at this time by inserting the driving tool (not shown) into the receiver and the shank drive 3246 and rotating and driving the shank 3204 into a desired location of the vertebra 3217.

With reference to FIG. 220, the rod 3221 is eventually positioned in an open or percutaneous manner in cooperation with the at least two bone screw assemblies 3201 (or with other bone screws of the invention). The closure structure 3218 is then inserted into and advanced between the arms 3262 of each of the receivers 3210. The closure structure 3218 is rotated, using a tool engaged with the inner drive 3366 until a selected pressure is reached at which point the rod 3221 engages the planar surface 3337 of the compression insert 3214, further pressing the insert stepped shank gripping surfaces 3350 against the shank top 3238 and/or spherical surface 3234, the edges of the stepped surfaces penetrating into the spherical surface 3234 and also pressing the shank upper portion 3208 into locked frictional engagement with the retainer 3212. Specifically, as the closure structure 3218 rotates and moves downwardly into the respective receiver 3210, the point 3369 and rim 3370 engage and penetrate the rod surface 3222, the closure structure 3218 pressing downwardly against and biasing the rod 3221 into compressive engagement with the insert 3214 that urges the shank upper portion 3208 toward the retainer 3212 and into locking engagement therewith, the retainer 3212 frictionally abutting the surface 3304 and expanding outwardly against the cylindrical surface 3301. For example, about 80 to about 120 inch pounds of torque on the closure top may be applied for fixing the bone screw shank 3206 with respect to the receiver 3210.

With reference to FIGS. 222-234 the reference number 3401 generally represents another embodiment of a polyaxial bone screw apparatus or assembly according to the present invention. The assembly 3401 includes a shank 3404, that further includes a body 3406 integral with an upwardly extending upper portion or head-like capture structure 3408; a receiver 3410; a retainer structure illustrated as a resilient open ring 3412, and a lock and release friction fit compression or pressure insert 3414. The receiver 3410, retainer 3412 and compression insert 3414 are initially assembled and may be further assembled with the shank 3404 either prior or subsequent to implantation of the shank body 3406 into a vertebra, such as the vertebra 3017 or 3217 previously shown herein. FIG. 222 also shows a closure structure 3418 for capturing a longitudinal connecting member, for example, a rod 3421 which in turn engages the compression insert 3414 that presses against the shank upper portion 3408 into fixed frictional contact with the retainer 3412, so as to capture, and fix the longitudinal connecting member 3421 within the receiver 3410 and thus fix the member 3421 relative to the vertebra. The illustrated rod 3421 is substantially similar to the hard, stiff rod 3021 previously described herein, having an outer cylindrical surface. In other embodiments, the stiff rod 3421 may take other shapes and/or be made from other materials or be part of a longitudinal connecting member assembly that may include rigid sleeves that are fixable to a core member or slidable with respect thereto, spacers (compressible or not) and cords, for example, all as previously described herein with respect to the rods 21, 1021, 2021 and 3021, for example, and fully incorporated by reference herein with respect to the rod 3421.

The receiver 3410 and the shank 3404 cooperate in such a manner that the receiver 3410 and the shank 3404 can be secured at any of a plurality of angles, articulations or rotational alignments relative to one another and within a selected range of angles both from side to side and from front to rear, to enable flexible or articulated engagement of the receiver 3410 with the shank 3404 until both are locked or fixed relative to each other near the end of an implantation procedure.

The shank 3404 is identical or substantially similar to the shank 3004 previously described herein. The receiver 3410 is identical or substantially similar to the receiver 3010 previously described herein, thus having an inner bore or cavity 3461 with an insert locking inner cylindrical surface 3496 and inner arm surfaces 3470, as well as other features that are the same or similar to the cavity 3061, cylindrical surface 3096 and inner arm surfaces 3070 previously described herein with respect to the receiver 3010.

The retainer 3412 is the same or substantially the same as the top loading retainer 3212 previously described herein. Thus, with reference to FIG. 223, the retainer 3412 is open, but includes a very narrow slit, providing a strong retainer that is not compressed during assembly with the receiver because it is top loaded and is only expanded about the shank head 3408 during assembly as shown in FIGS. 226 and 227 and also expands slightly within the receiver upon final locking with the shank 3404 as shown, for example in FIG. 228.

The insert 3414 is substantially similar or identical to the insert 3014 previously described herein with respect to the assembly 3001. Thus, the insert 3414 includes a pair of upstanding arms 3537 and a pair of crown collet extensions 3538 the same or similar to the respective arms 3137 and extensions 3138 of the insert 3014 previously described herein. The insert 3414 extension 3538 further include panels 3554 having inner spherical gripping surfaces as well as an outer frusto-conical surface 3558 for frictional locking with the inner cylindrical surface 3496 of the receiver 3410, such features being the same or similar to the respective panels 3154, with spherical surfaces 3152 and the outer frusto-conical surface 3158 of the insert 3014. The inner spherical surfaces 3552 preferably have a pre-assembly radius that is the same or slightly larger than a radius of the shank upper portion or head 3408. As discussed above with respect to the insert 3014, the insert 3414 and/or the shank head 3408 may include surface treatments or the panels may be crimped or bent to result in a desired frictional fit between the insert 3414 and the shank head 3408 during the temporary steps of manipulating the bone screws 3401 during assembly with the rod. As with the assembly 3001, the final locking of the assembly 3401 is accomplished by frictional contact between the bone screw shank upper portion 3408 and the retainer ring 3412 when the insert 3414 presses down upon the shank upper portion 3408.

Thus, the assembly 3401 includes features of both the assembly 3001 and the assembly 3201 to result in a polyaxial assembly wherein the shank 3404 may be snapped or popped onto the receiver 3410 either before or after implantation of the shank 3404 into a vertebra. As shown in FIG. 223, the retainer 3412 is initially top loaded into the receiver 3410 followed by top loading of the insert 3414 with the insert arms 3437 located between arms of the receiver 3410. With reference to FIGS. 224 and 225, the insert 3414 is rotated into place. With reference to FIGS. 226 and 227, the shank 3404 is bottom loaded by pressing the shank head or upper portion 3408 through the open retainer 3412 within an expansion area of the receiver 3410 followed by non-floppy frictional engagement between the shank upper portion 3408 and the flexible tabs or panels 3554. FIGS. 228-230 illustrate the locking of the insert 3414 frusto-conical surface 3558 against the receiver surface 3496, the same or similar to what was described above with respect to the assembly 3001. Thus, as shown in FIG. 229, the closure top 3418 and/or the hard rod 3421 may be removed without unlocking the polyaxial mechanism of the screw 3401. With reference to FIG. 230, a deformable rod 3421', such as a PEEK rod with a cooperating alternative closure top 3418' may be placed in the receiver 3410 and secured therein. The deformable rod 3421' does not compromise the secure lock of a desired angle between the shank 3404 and the receiver 3410 provided by the wedging of the insert 3414 into the receiver 3410 at the respective surfaces 3496 and 3558.

With reference to FIGS. 231-233, an alternative insert 3414' for use in the assembly 3001 or the assembly 3401 in lieu of the insert 3014 or the insert 3414 is shown. The insert 3414' is substantially similar or identical to the inserts 3014 and 3414 previously described above with the exception that the substantially curved or spherical surfaces 3152 or 3552 and been replaced by planar surfaces 3552'. Thus, the insert 3414' includes four planar surfaces 3552' that frictionally grip the shank upper portion 3008 or the shank upper portion 3408 to provide a friction fit between the respective shank and the insert 3414'. It is foreseen that more or fewer planar surfaces may be included to grip the shank upper portion 3008 or the shank upper portion 3408.

With reference to FIG. 234, another alternative non-locking insert 3414" is shown that is identical to the insert 3414' with the exception that a frusto-conical outer surface 3558' of the insert 3414' has been replaced by a cylindrical surface 3558". Thus, when used with the receiver 3410, for example, the cylindrical surface 3558' is slidingly received by the inner cylindrical surface 3496 and does not wedge or lock into the receiver 3410.

With reference to FIGS. 235-244 an alternative receiver 4010, open retainer 4012 and compression insert 4014 are shown that may be used with the shank 3404, rod 3421 and closure top 3418 previously described herein with respect to the assembly 3401. Furthermore, the open, top loadable retainer 4012 is identical to the retainer 3412 of the assembly 3401. The alternative receiver 4010 and cooperating insert 4014 differ only slightly from the receiver 3410 and cooperating insert 3414 of the assembly 3401. The receiver 4010 includes features of both the receiver 3410 and the receiver 1210 of the assembly 1201 previously described herein. In particular, the receiver 4010 has spring tabs 4290 with insert engaging surfaces 4311 substantially similar to the respective spring tabs 1290 with inner engaging surfaces 1311 of the receiver 1210. However, the receiver 4010 also includes an inner cylindrical surface 4096 located at a base of the spring tabs 1290, the surface 4096 sized and shaped to frictionally engage and lock a tapered or frusto-conical surface 4158 of the insert 4014 so that the insert 4014 locks against the receiver, substantially similar to the cooperation between the insert 3414 and the receiver 3410 previously described herein. The insert further includes grooves 4159 in the arms thereof for receiving the receiver spring tabs 4290 at the surfaces 4311. As shown in FIGS. 238 and 239, when the insert 4014 is dropped down into the receiver 4010 and rotated into position, the spring tabs 4290 are pushed outward and away from the insert 4014. However, once the insert 4014 completes its rotation when the insert U-shaped channel is aligned with the receiver U-shaped channel, the spring tabs 4290 snap into grooves 4159 of the insert 4014, capturing the insert 4014 in the receiver 4010, keeping the insert in alignment with the receiver and allowing only some upward and downward movement of the insert with respect to the receiver 4010. The tabs 4290 frictionally retain the insert in an upper portion of the receiver during the "pop-on" attachment to the bone screw shank 3404. As shown in FIG. 241, a downward force upon the insert 4014, such as by the rod 3421 and closure top 3418 causes the insert tapered surface 4158 to wedge up against the cylindrical surface 4096 of the receiver 4010, locking the polyaxial mechanism.

With reference to FIGS. 242-244 a two-piece tool 4600 is illustrated for releasing the insert 4014 from the receiver 4010. The tool 4600 includes an inner flexible tube-like structure with opposed inwardly facing prongs 4312 located on either side of a through-channel 4616. The channel 4616 may terminate at a location spaced from the prongs 4312 or may extend further upwardly through the tool, resulting in a two-piece tool 4610. The tool 4600 includes an outer, more rigid tubular member 4620 having a smaller through channel 4622. The member 4620 slidingly fits over the tube 4610 after the flexible member 4610 prongs 4612 are fitted within opposed apertures 4074 of the receiver 4010 and aligned opposed apertures 4156 located on arms of the insert 4014. In FIG. 242, the tool 4600 is shown having unlocked the insert 4014 from the receiver 4010 with the outer member 4620 surrounding the inner member 4610 and holding the prongs 4612 within the receiver and insert apertures while the tool 4600 is pulled upwardly away from the shank 3404. It is foreseen that another tube within a tube type tool may be used for locking the lower pressure insert downward into the receiver 4010 wherein prongs of an inner flexible tubular member that are larger than the prongs 4612 drive the insert 4014 downwardly into locking engagement with the receiver 4010 as the prongs enter the larger receiver apertures 4074 and then the insert apertures 4156.

With reference to FIGS. 245-283 the reference number 5001 generally represents a polyaxial bone screw apparatus or assembly according to the present invention. The assembly 5001 includes a shank 5004, that further includes a body 5006 integral with an upwardly extending upper portion or head structure 5008; a receiver 5010; a friction fit retainer 5012, and a crown-like compression or pressure insert 5014. The receiver 5010, retainer 5012 and compression insert 5014 are initially assembled and may be further assembled with the shank 5004 either prior or subsequent to implantation of the shank body 5006 into a vertebra 5017, as will be described in greater detail below. FIGS. 1 and 278-280 further show a closure structure 5018 for capturing a longitudinal connecting member, for example, a rod 5021 which in turn engages the compression insert 5014 that presses against the shank upper portion 5008 into fixed frictional contact with the retainer 5012, so as to capture, and fix the longitudinal connecting member 5021 within the receiver 5010 and thus fix the member 5021 relative to the vertebra 5017. The closure top 5018 and the rod 2010 are identical or substantially similar to many of the closure tops and rods previously described herein, for example, the closure top 4018 and the rod 4021 of the assembly 4001 having the same form and function and therefore shall not be discussed any further here.

The shank 5004, best illustrated in FIGS. 245-247, is substantially similar to the shank 3004 previously described herein with respect to the assembly 3001. Thus, the shank 5004 includes the shank body 5006, upper portion or head 5008, a shank thread 5024, a neck 5026, a tip 5028, a top of thread 5032, an upper portion spherical surface 5034 a top surface 5038, an internal drive 5046 with a base surface 5045 and an cannulation bore 5050 the same or substantially similar to the respective body 3006, upper portion or head 3008, shank thread 3024, neck 3026, tip 3028, top of thread 3032, spherical surface 3034, top surface 3038, internal drive 3046 with base surface 3045 and cannulation bore 3050 previously described herein with respect to the shank 3004 of the assembly 3001.

To provide a biologically active interface with the bone, the threaded shank body 5006 may be coated, perforated, made porous or otherwise treated as previously discussed herein with respect to the shank body 6 of the assembly 1. In the illustrated embodiment, a frusto-conical surface 5039 extends from the spherical surface 5034 to the top surface 5038, providing additional clearance during shank angulation as best shown in FIG. 279. The spherical surface 5034 has an outer radius configured for temporary frictional, non-floppy, sliding cooperation with panels of the retainer 5012 having concave or flat surfaces, as well as ultimate frictional engagement with the insert 5014 at an inner partially spherical surface thereof, as will be discussed more fully in the paragraphs below. The top surface 5038 is substantially perpendicular to the axis A. The spherical surface 5034 shown in the present embodiment is substantially smooth, but in some embodiments may include a roughening or other surface treatment and is sized and shaped for cooperation and ultimate frictional engagement with the compression insert 5014 as well as ultimate frictional engagement with a lower ring-like portion of the retainer 5012. The shank spherical surface 5034 is locked into place exclusively by the insert 5014 and the retainer 5012 lower portion and not by inner surfaces defining the receiver cavity. The illustrated internal drive feature 5046 differs from the feature 3046 of the shank 3004 in that the feature 5046 is an aperture formed in the top surface 5038 that has a star shape designed to receive a tool (not shown) of an Allen wrench type, into the aperture for rotating and driving the bone screw shank 5004. As illustrated in FIGS. 246 and 247, the drive seat 5045 may include beveled or stepped surfaces that may further enhance gripping with the driving tool. In operation, a driving tool (not shown) is received in the internal drive feature 5046, being seated at the base 5045 and engaging the faces of the drive feature 5046 for both driving and rotating the shank body 5006 into the vertebra 5017, either before the shank 5004 is attached to the receiver 5010 or after the shank 5004 is attached to the receiver 5010, with the shank body 5006 being driven into the vertebra 5017 with the driving tool extending into the receiver 5010.

With particular reference to FIGS. 245 and 248-253, the receiver 5010 has a generally U-shaped appearance with partially discontinuous and partially cylindrical inner and outer profiles. The receiver 5010 has an axis of rotation B that is shown in FIG. 245 as being aligned with and the same as an axis of rotation A of the shank 5004, such orientation being desirable, but not required during assembly of the receiver 5010 with the shank 5004. After the receiver 5010 is pivotally attached to the shank 5004, either before or after the shank 5004 is implanted in a vertebra 5017, the axis B is typically disposed at an angle with respect to the axis A, as shown, for example, in FIG. 279.

The receiver 5010 includes a substantially cylindrical base 5060 defining a bore or inner cavity, generally 5061, the base 5060 being integral with a pair of opposed upstanding arms 5062 forming a cradle and defining a channel 5064 between the arms 5062 with an upper opening, generally 5066, and a U-shaped lower channel portion or seat 5068, the channel 5064 having a width for operably snugly receiving the rod 5021 or portion of another longitudinal connector between the arms 5062, the channel 5064 communicating with the base cavity 5061. Inner opposed substantially planar arm surfaces 5069 partially define the channel 5064 directly above the seat 5068 and are located on either side of each arm interior surface generally 5070, that includes various inner cylindrical profiles, an upper one of which is a partial helically wound guide and advancement structure 5072 located adjacent top surfaces 5073 of each of the arms 62. In the illustrated embodiment, the guide and advancement structure 5072 is a partial helically wound interlocking flangeform configured to mate under rotation with a similar structure on the closure structure 5018, as described more fully below. However, it is foreseen that for certain embodiments of the invention, the guide and advancement structure 5072 could alternatively be a square-shaped thread, a buttress thread, a reverse angle thread or other thread-like or non-thread-like helically wound discontinuous advancement structures, for operably guiding under rotation and advancing the closure structure 5018 downward between the arms 5062, as well as eventual torquing when the closure structure 5018 abuts against the rod 5021 or other longitudinal connecting member. It is foreseen that the arms 5062 could have break-off extensions.

An opposed pair of key-hole like tool receiving and engaging grooves or apertures, generally 5074, each having an upper arched through bore 5075, are formed on outer surfaces 5076 of the arms 5062. Each through bore 5075 extends between the outer surface 5076 and the inner surface 5070 and is located above a rectangular shaped shallow recessed arm portion or crimp wall 5077 that defines the portion of the aperture 5074 that does not extend completely through the respective arm 5062. The thin walled portion 5077 is pressed or crimped into the insert 5014 to prohibit rotation and misalignment of the insert 5014 with respect to the receiver 5010 as will be described in greater detail below. In other embodiments of the invention, other surfaces forming the groove or aperture 5074 may be inwardly crimped. Alternatively, spring tabs or other movable structure may be included on the receiver 5010 or the insert 5014 for retaining the insert 5014 in a desired position, with regard to rotation and axial movement (along the axis A) with respect to the receiver 5010. Preferably the insert and/or receiver are configured with structure for blocking rotation of the insert with respect to the receiver, but allowing some up and down movement of the insert with respect to the receiver during the assembly and implant procedure. Two additional rectangular shaped through bores 5078 are also formed in the arms 5062 and located directly below the apertures 5074. The through bores 5078 are sized and shaped for receiving portions of the retainer 5012 during top loading of the retainer 5012 into the receiver 5010 as will be described more fully below and as shown, for example, in FIG. 266. An upper surface 5079 defining each bore 5078 functions as an upper stop for a portion of the retainer 5012, during shipping and during assembly, as shown, for example, in FIG. 272, and as will be described in greater detail below. Also formed in each outer arm surface 5076 near the top surface 5073 is an undercut tool receiving and engaging groove 5081. Some or all of the apertures 5074 and 5078 and the groove 5081 may be used for holding the receiver 5010 during assembly with the insert 5014, the retainer 5012 and the shank 5004; during the implantation of the shank body 5006 into a vertebra when the shank is pre-assembled with the receiver 5010; during assembly of the bone anchor assembly 5001 with the rod 5021 and the closure structure 5018; and during lock and release adjustment of the insert 5014 with respect to the receiver 5010, either into or out of frictional engagement with the inner surfaces of the receiver 5010 as will be described in greater detail below. It is foreseen that tool receiving grooves or apertures may be configured in a variety of shapes and sizes and be disposed at other locations on the receiver arms 5062.

Returning to the interior surface 5070 of the receiver arms 5062, located below the guide and advancement structure 5072 is a discontinuous cylindrical surface 5082 partially defining a run-out feature for the guide and advancement structure 5072. The cylindrical surface 5082 has a diameter equal to or slightly greater than a greater diameter of the guide and advancement structure 5072. Moving downwardly, in a direction toward the base 5060, following the cylindrical surface 5082 of each arm is a cylindrical surface 5084 partially defined by a run-out seat or surface 5085 that extends inwardly toward the axis B and runs perpendicular to the axis B. The surface 5084 has a diameter smaller than the diameter of the surface 5082. The surface 5084 is sized and shaped to initially closely receive a lower portion of the insert 5014 and later frictionally engage a tapered or frusto-conical upper portion of the insert 5014, providing a lock and release function that will be described in greater detail below. A discontinuous annular surface 5086 is located below and adjacent to the surface 5084. The surface 5086 is substantially perpendicular to the axis B. Another discontinuous cylindrical surface 5088 is located below and adjacent to the surface 5086. The surface 5088 has a diameter slightly larger than the diameter of the surface 5084. A discontinuous annular surface or narrow ledge 5089 is located below the surface 5088 and is substantially perpendicular to the axis B. A partially discontinuous cylindrical surface 5090 is located one each arm below and adjacent to the surface 5089. The surface 5090 also defines an upper cylindrical surface of the base cavity 5061. The surface 5090 has a diameter slightly smaller than the diameter of the surface 5088 but larger than the diameter of the surface 5084. It is noted that in some embodiments of the invention, the surfaces 5088 and 5090 are combined and form a single smooth cylindrical surface.

The through bores 5075 each extend through the arms at the surfaces 5082, 5084 and 5088. The crimping wall 5077 is located in an inner recessed surface area 5092 that is formed in both the surfaces 5088 and 5090. In the illustrated embodiment, the crimping wall 5077 has an inner surface 5093 that is primarily located at the portion of the area 5092 that is formed in the cylindrical surface 5088. Each through bore 5078 is located directly below the area 5092.

An annular surface 5098 partially defining the base cavity 5061 is located below and adjacent to the cylindrical surface 5090. The surface 5098 is disposed substantially perpendicular to the axis B. Another cylindrical surface 5099 is located below and adjacent to the surface 5098. The cylindrical surface 5099 is oriented substantially parallel to the axis B and is sized and shaped to receive an expanded portion of retainer 5012. The surfaces 5098 and 5099 define a circumferential recess or expansion chamber that is sized and shaped to receive the retainer 5012 as it expands around the shank upper portion 5008 as the shank 5008 moves upwardly toward the channel 5064 during assembly. A cylindrical surface 5101 located below the cylindrical surface 5099 is sized and shaped to closely receive a lower portion of the retainer 5012 when the retainer is in a substantially neutral position as shown in FIG. 267, for example. Thus, the cylindrical surface 5101 has a diameter smaller than the diameter of the cylindrical surface 5099 that defines the expansion area for the retainer 5012. The surface 5101 is joined or connected to the surface 5099 by one or more beveled, curved or conical surfaces 5102. The surfaces 5102 allow for sliding gradual movement and/or contraction of the retainer 5012 into the space defined by the surface 5101 and ultimate seating of the retainer 5012 on a lower annular surface 5104 located below and adjacent to the cylindrical surface 5101.

Located below and adjacent to the annular seating surface 5104 is another substantially cylindrical surface 5106 that communicates with a beveled or flared bottom opening surface 5107, the surface 5107 communicating with an exterior base surface 5108 of the base 5060, defining a lower opening, generally 5110, into the base cavity 5061 of the receiver 5010.

With particular reference to FIGS. 245 and 254-259, the lower open friction fit retainer 5012 that operates to capture the shank upper portion 5008 and attached compression insert 5014 within the receiver 5010 has a central axis that is operationally the same as the axis B associated with the receiver 5010 when the shank upper portion 5008 and the retainer 5012 are installed within the receiver 5010. The retainer 5012 includes a substantially cylindrical discontinuous lower body 5116, a plurality of flex fingers or panels, 5117 extending upwardly from the body 5116 and a pair of opposed spring arms or tabs 5118, also extending upwardly from the body 5116. The retainer ring 5012 is made from a resilient material, such as a stainless steel or titanium alloy, so that the retainer 5012 body 5116 may be expanded and the fingers and tabs (5117 and 5118) of the retainer may be manipulated during various steps of assembly as will be described in greater detail below. The retainer 5012 has a central channel or hollow through bore, generally 5121, that passes entirely through the retainer 5012 from tab 5118 top surfaces 5122 to a bottom surface 5124 of the retainer body 5116. Surfaces that define the channel or bore 5121 include an inner lower frusto-conical surface 5128 adjacent to the retainer body bottom surface 5124, a substantially cylindrical surface 5130 adjacent the frusto-conical surface 5128, a narrow frusto-conical or beveled surface 5131 adjacent the cylindrical surface 5130 and a partially continuous partially discontinuous substantially spherical surface 5132 adjacent the surface 5131, the surface 5132 being substantially continuous near the cylindrical surface 5130 with the exception of the opposed spring tabs 5118 and a through slot or slit, generally 5134. The surface 5132 is in a plurality of segments or pieces at the flex fingers 5117 wherein a plurality of substantially evenly spaced slots 5136 running outwardly and upwardly through an upper surface 5137 separate the surface 5132 into the individual flex fingers 5117. In the illustrated embodiment, the slots 5136 and the through slit 5134 form the six substantially uniform flex fingers or tabs 5117 as well as partially define the two spring tabs 5118, each finger having the inner spherical surface 5132. It is foreseen that more or fewer flex fingers may be made by the forming of more or fewer slots 5136. The discontinuous spherical surface 5132 is sized and shaped to closely fit about and snap onto the shank surface 5034 during assembly as will be described in greater detail below. Preferably the surface 5132 has a radius the same, slightly smaller or slightly larger than the radius of the spherical shank surface 5034. In operation, the discontinuous surface 5132 advantageously frictionally engages the bone screw shank upper portion 5008, allowing for un-locked but non-floppy placement of the angle of the shank 5004 with respect to the receiver 5010 during surgery prior to locking of the shank 5004 with respect to the receiver 5010 near the end of the procedure. At the time of locking engagement, as shown in FIG. 278, for example, downward and outward force placed on the retainer 5012 by the shank upper portion 5008 expands the retainer body 5116 at the slit 5134 and the individual flex fingers 5117 no longer frictionally grip the spherical surface 5034 of the upper portion 5008. To aid in bending flexibility and resiliency, certain flex fingers 5117 may have sloping outer surfaces or other geometry to gain the level of resiliency desired for expansion and gripping of the fingers 5117 about the shank upper portion 5008. The spherical surfaces 5132 may include a surface treatment or roughening to provide a desired friction fit. It is noted that the surfaces 5132 need not be spherical and may be planar or faceted or include other surface geometries that resiliently grip the shank upper portion or head 5008. In some embodiments, the flexible tabs 5117 may be bent to further enhance frictional engagement. It is noted that the fingers 5117 that are directed generally upwardly toward the receiver channel 5064 advantageously sufficiently snap about and then grip the shank surface 5034 to an extent to provide the friction fit desired for non-floppy placement of the shank body 5006 at a desired angle with respect to the receiver 5010 during manipulation of the bone screws 5001 and the rod 5021 or other longitudinal connecting member during surgery. However, as compared to bone screw inserts such as collets known in the art that include downwardly directed portions or panels that are ultimately wedged between a receiver surface and a shank surface upon final locking of the shank to the receiver, the thin upwardly directed fingers 5117 that extend away from the shank locking surface that are not as strong as the retainer body 5116 or the insert 5014, do not participate or cooperate with the final locking of the insert 5014 to the shank upper portion 5008, the shank upper portion 5008 to the retainer 5012, and the retainer 5012 to the receiver inner surfaces 5101 and 5104. For such purpose, the more substantial retainer body 5116 having only the very narrow slit 5134, used for expansion purposes only, is the component that locks the shank upper portion 5008 between the receiver 5010, the insert 5014 and the rod 5021 or other longitudinal connecting member.

The retainer body 5116, the flex fingers 5117 and a portion of each of the spring tabs 5118 have an outer substantially cylindrical profile, sized and shaped to closely and slidingly fit within the receiver cavity 5061 with the exception of outward extensions or wings, generally 5140, of the spring tabs 5118 that are located adjacent to the upper surfaces 5122, each wing extending outwardly away from the respective tab body 5118 and having a projected outward surface 5142 spaced from each top surface 5122 that is sized and shaped to closely cooperate and frictionally engage upper surfaces 5079 defining the through bores 5078. Outer surfaces 5143 located directly beneath each upper surface 5122 and above the surfaces 5142 are sized and shaped to cooperate with and frictionally engage the cylindrical surface 5090 during assembly and shipping as shown, for example, in FIG. 270. The tab wings 5140 may include more or fewer projections or notches as needed for tooling to resiliently hold the retainer in an upper portion of the cavity 5061 when desired, but readily release the retainer 5012 into a lower portion of the receiver cavity 5061 once the retainer flex tabs 5117 engage the shank head 5008. The illustrated spring tabs 5118 each includes one or more planar or curved inner surfaces 5144 running from the top surface 5122 to a tab base surface or seat 5145 located adjacent to the surface 5131. The surfaces 5144 extend both outwardly and upward from the base surface 5145. It is foreseen that in other embodiments of the invention, fewer or greater number of planar or other surfaces with other geometries may extend between the top surface 5122 and the inner surfaces defining the body 5116 of the retainer 5012.

The through slit 5134 of the resilient retainer 5012 is defined by first and second end surfaces, 5146 and 5147 disposed in spaced relation to one another (they may also be touching) when the retainer is in a neutral state. Both end surfaces 5146 and 5147 are disposed substantially perpendicular to the bottom surface 5124. A width X between the surfaces 5146 and 5147 is very narrow (slit may be made by EDM process) to provide stability to the retainer 5012 during operation. Because the retainer 5012 is top loadable in a neutral state and the retainer 5012 does not need to be compressed to fit within the receiver cavity 5061, the width X may be much smaller than might be required for a bottom loaded compressible retainer ring. The gap X functions only in expansion to allow the retainer 5012 to expand about the shank upper portion 5008. This results in a stronger retainer that provides more surface contact with the shank upper portion 5008 upon locking, resulting in a sturdier connection with less likelihood of failure than a retainer ring having a greater gap. Furthermore, because the retainer 5012 body 5116 is only expanded and not compressed, the retainer 5012 does not undergo the mechanical stress that typically is placed on spring ring type retainers that are both compressed and expanded during assembly.

It is foreseen that in some embodiments of the invention, the retainer 5012 inner surfaces may include a roughening or additional material to increase the friction fit against the shank upper portion 5008 prior to lock down by the rod 5021 or other longitudinal connecting member. Also, the embodiment shown in FIGS. 254-259 illustrates the surfaces 5146 and 5147 as substantially parallel, however, it is foreseen that it may be desirable to orient the surfaces obliquely or at a slight angle.

With particular reference to FIGS. 245 and 260-265, the lock and release crown compression insert 5014 is illustrated that is sized and shaped to be received by and down-loaded into the receiver 5010 at the upper opening 5066. The compression insert 5014 has an operational central axis that is the same as the central axis B of the receiver 5010. In operation, the insert advantageously frictionally engages the bone screw shank upper portion 5008. Furthermore, as will be described more fully below, an insert 5014 that has locked the shank 5004 in a desired angular position with respect to the receiver 5010, by, for example, compression from the rod 5021 and closure top 5018, is also wedged into engagement with the receiver 5010 at the inner surface 5084 and thus retains the shank 5006 in a locked position even if the rod 5021 and closure top 5018 are removed as shown in FIG. 280. Such locked position may also be released by the surgeon if desired. The insert 5014 is thus preferably made from a resilient material, such as a stainless steel or titanium alloy, so that portions of the insert may be expanded about and then contracted, snapped or popped onto the shank upper portion 5008 as well as pinched and un-wedged from the receiver 5010.

The lock-and-release compression insert 5014 includes a substantially cylindrical body 5156 integral with a pair of upstanding arms 5157. A bore, generally 5160, is disposed primarily within and through the body 5156 and communicates with a generally U-shaped through channel 5161 that is defined by the upstanding arms 5157. The channel 5161 has a lower seat 5162 sized and shaped to closely, snugly engage the rod 5021. It is foreseen that an alternative embodiment may be configured to include planar holding surfaces that closely hold a square or rectangular bar as well as hold a cylindrical rod-shaped, cord, or sleeved cord longitudinal connecting member. The arms 5157 disposed on either side of the channel 5141 extend upwardly from the body 5156. The arms 5157 are sized and configured for ultimate placement beneath the cylindrical run-out surface 5082 located below the receiver guide and advancement structure 5072. It is foreseen that in some embodiments of the invention, for example, when the insert is non-locking as the insert 5014" shown in FIGS. 282 and 283, the arms may be extended and the closure top configured such the arms ultimately directly engage the closure top 5018 for locking of the polyaxial mechanism, for example, when the rod 5021 is made from a deformable material. In such embodiments, the insert 5014 would include a rotation blocking structure or feature that abuts against cooperating structure located on an inner wall of the receiver 5010, preventing rotation of the insert with respect to the receiver when the closure top is rotated into engagement with the insert. In the present embodiment, the arms 5157 include outer upper flared or frusto-conical surfaces 5163 and top surfaces 5164 that are ultimately positioned in spaced relation with the closure top 5018, so that the closure top 5018 frictionally engages the rod 5021 only, pressing the rod 5021 downwardly against the seating surface 5162, the insert 5014 in turn pressing against the shank 5004 upper portion 5008 that presses against the retainer 5012 to lock the polyaxial mechanism of the bone screw assembly 5001 at a desired angle. As will be discussed in greater detail below, frictional engagement between the insert 5014 and the receiver 5010, more particularly, the wedging of the tapered surfaces 5163 into the cylindrical surfaces 5084, provides independent locking of the polyaxial mechanism of the assembly 5001, maintaining the upper shank portion 5008 in locked engagement by and between the retainer 5012 and the insert 5014 even if the closure top 5018 and/or rod 5021 are thereafter removed from the receiver 5010.

The bore, generally 5160, is substantially defined at the body 5156 by an inner cylindrical surface 5166 that communicates with the seat 5162 and a lower concave substantially spherical surface 5168 having a radius the same or substantially similar to a radius of the surface 5034 of the shank upper portion 5008. The surface 5168 terminates at an annular and substantially planar base surface 5169 of the body 5156. In some embodiments of the invention, located between the cylindrical surface 5166 and the spherical surface 5168 or located along the spherical surface 5168 is a shank gripping surface portion, generally 5170, illustrated in FIG. 265 on an alternative insert 5014' that is otherwise identical to the insert 5014. The gripping surface portion 5170 includes one or more stepped surfaces or ridges sized and shaped to grip and penetrate into the shank head 5008 when the insert 5014' is locked against the head surface 5034. It is foreseen that the stepped surface portion 5170 may include greater or fewer number of stepped surfaces. It is foreseen that the shank gripping surface portion 5170 and also the spherical surface 5168 may additionally or alternatively include a roughened or textured surface or surface finish, or may be scored, knurled, or the like, for enhancing frictional engagement with the shank upper portion 5008.

The compression insert 5014 through bore 5160 is sized and shaped to receive the driving tool (not shown) therethrough that engages the shank drive feature 5046 when the shank body 5006 is driven into bone with the receiver 5010 attached. Also, the bore 5160 receives a manipulation tool (not shown) used for releasing the insert 5014 from a locked position with the receiver, the tool pressing down on the shank and also gripping the insert 5014 at through bores 5172 located in the arms 5157 or with other tool engaging features. A manipulation tool for un-wedging the insert 5014 from the receiver 5010 may also access the bores 5172 from the receiver through bores 5075 (see, e.g., FIG. 242244)

The illustrated insert 5014 further includes other features for manipulating and holding the insert 5014 within the receiver 5010. Each insert arm 5157 includes an outer surface 5174 having a substantially vertical groove 5175 formed thereon, the groove 5175 located below the through bore 5172. The grooves 5175 cooperate with the receiver crimp wall 5077 to aid in alignment of the insert channel 5161 with the receiver channel 5064. Located beneath each groove 5175 is a recessed area or portion 5178 sized and shaped to receive the upper surface 5122 of the retainer wings 5140, as shown, for example, in FIG. 270, during assembly and shipping of the pre-assembled receiver 5010, retainer 5012 and insert 5014.

The insert body 5156 has an outer diameter slightly smaller than a diameter between crests of the guide and advancement structure 5072 of the receiver 5010, allowing for top loading of the compression insert 5014 into the receiver opening 5066, with the arms 5157 of the insert 5014 being located between the receiver arms 5062 during insertion of the insert 5014 into the receiver 5010. Once the arms 5157 of the insert 5014 are generally located beneath the guide and advancement structure 5072, the insert is rotated into place about the receiver axis B until the top surfaces 5164 are located directly below the guide and advancement structure 5072 as will be described in greater detail below.

With reference to FIGS. 282 and 283, an alternative non-locking insert 5014" is identical or substantially similar to the insert 5014 with the exception of outer arm surfaces 5174" that are substantially cylindrical and extend from a top surface 5164" to near a bottom surface 5169" of the insert 5014". In other words, the insert 5014" does not include the tapered surfaces 5163 of the insert 5014. The arm surfaces 5174" are fully and slidingly received by the receiver surfaces 5084 as well as the other receiver 5010 inner arm surfaces and thus the insert 5014" cannot be wedged into the receiver 5010 to independently lock the polyaxial mechanism of the assembly 5001. In all other respects, the insert 5014" functions the same as the insert 5014.

With reference to FIGS. 245 and 278-280, the closure structure or closure top 5018 shown with the assembly 5001 includes a guide and advancement structure 5182 that is a flange form as described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 5018 downward between the arms 5062 and having such a nature as to resist splaying of the arms 5062 when the closure structure 5018 is advanced into the channel 5064, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 5010 that may more advantageously engage longitudinal connecting member components. The illustrated closure structure 5018 also includes a top surface 5184 with an internal drive 5186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 5186 is used for both rotatable engagement and, if needed, disengagement of the closure 5018 from the receiver arms 5062. It is also foreseen that the closure structure 5018 may alternatively include a break-off head designed to allow such a head to break from a base of the closure at a preselected torque, for example, 70 to 140 inch pounds. Such a closure structure would also include a base having an internal drive to be used for closure removal. A base or bottom surface 5188 of the closure is planar and further includes a point 5189 and a rim 5190 for engagement and penetration into the surface 5022 of the rod 5021 in certain embodiments of the invention.

An alternative closure top 5018' for use with a deformable rod 5021', such as a PEEK rod, is shown in FIG. 281. The top 5018' is identical to the top 5018 with the exception that a point 5189' is located on a domed surface 5190' in lieu of the planar bottom with point and rim of the closure top 5018.

Preferably, the receiver 5010, the retainer 5012 and the compression insert 5014 are assembled at a factory setting that includes tooling for holding and alignment of the component pieces and pinching or compressing of the retainer 5012 spring tabs 5118 and rotating and otherwise manipulating the insert 5014 arms, as well as crimping a portion of the receiver 5010 toward the insert 5014. In some circumstances, the shank 5004 is also assembled with the receiver 5010, the retainer 5012 and the compression insert 5014 at the factory. In other instances, it is desirable to first implant the shank 5004, followed by addition of the pre-assembled receiver, retainer and compression insert at the insertion point. In this way, the surgeon may advantageously and more easily implant and manipulate the shanks 5004, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 5008 and/or hydroxyapatite on the shank 5006), with the receiver, retainer and compression insert. Allowing the surgeon to choose the appropriately sized or treated shank 5004 advantageously reduces inventory requirements, thus reducing overall cost.

Pre-assembly of the receiver 5010, retainer 5012 and compression insert 5014 is shown in FIGS. 266-272. With particular reference to FIG. 266, first the retainer 5012 is inserted into the upper receiver opening 5066, leading with one of the spring tabs 5118 with both of the spring tab top surfaces 5122 facing one arm 5062 and the retainer bottom surface 5124 facing the opposing arm 5062 (shown in phantom). The retainer 5012 is then lowered in such sideways manner into the channel 5064 and partially into the receiver cavity 5061, followed by tilting the retainer 5012 such that the top surface 5122 and thereafter the outer tab or wing 5140 of the leading spring tab 5118 is moved into a nearby receiver arm through bore 5078. With reference to FIG. 267, the retainer 5012 is then further tilted or turned and manipulated within the receiver to a position within the cavity until the retainer 5012 bottom surface 5124 is directed toward the receiver cavity 5061 and the spring tab upper surfaces 5122 are facing upwardly toward the receiver channel opening 5066. To accomplish such tilting and turning of the retainer 5012, the spring tab arm 5118 located within the receiver bore 5078 is manipulated downwardly and then upwardly within the bore 5078 and finally shifted out of the bore 5078 when the opposed spring tab arm 5118 outer tab or wing 5140 moves past and clears the cylindrical surface 5084 of the receiver 5010. Once the retainer bottom surface 5124 seats on the receiver surface 5104, both of the spring tab wings 5140 are partially located in opposed receiver bores 5078.

With reference to FIGS. 267 and 268, the compression insert 5014 is then downloaded into the receiver 5010 through the upper opening 5066 with the bottom surface 5169 facing the receiver arm top surfaces 5073 and the insert arms 5157 located between the opposed receiver arms 5062. The insert 5014 is then lowered toward the channel seat 5068 until the insert 5014 arm upper surfaces 5164 are adjacent the run-out area below the guide and advancement structure 5072 defined in part by the cylindrical surface 5082. Thereafter, the insert 5014 is rotated in a clockwise or counter-clockwise manner about the receiver axis B until the upper arm surfaces 5164 are directly below the guide and advancement structure 5072 as illustrated in FIG. 268 with the U-shaped channel 5161 of the insert 5014 aligned with the U-shaped channel 5064 of the receiver 5010. In some embodiments, the insert arms 5157 may need to be compressed slightly during rotation to clear inner surfaces of the receiver arms 5062. As shown in FIGS. 269 and 270, the outer lower cylindrical surface 5174 of the insert 5014 is received within the cylindrical surface 5090 of the receiver.

With further reference to FIGS. 268 and 269, a tool (not shown) is then used to grip the retainer spring tab arms 5118 at outer surfaces thereof and squeeze or press the tabs 5118 toward one another while moving the retainer 5012 in an upward direction away from the surface 5104. With reference to FIG. 270, when the spring tab wing surface projections 5142 abut against the surface 5079, the tool (not shown) is released and a portion or portions 5143 of each spring tab 5118 spring out to engage the surface portion 5092 formed in the receiver cylindrical surface 5090. With reference to FIGS. 270-272, the retainer 5012 is now in a desired position for shipping and with assembly with the shank 5004. The insert 5014 recessed areas 5178 are located adjacent to the retainer spring tab top surfaces 5122.

With reference to FIGS. 271 and 272, the receiver thin walls 5077 are then crimped inwardly toward the axis B by inserting a tool (not shown) through the receiver apertures 5074, the tool pressing the walls 5077 until the wall surface 5087 engages the insert 5014 at the shallow central grooves 5175 formed on the outer surface 5174 of each of the insert arms 5157. The crimping of the wall surface 5093 into the groove 5175 keeps the insert 5014 U-shaped channel 5161 aligned with the receiver U-shaped channel 5064 and also helps retain the insert 5014 at the upward location shown in FIG. 270 with the insert arm top surfaces 5164 adjacent the guide and advancement structure 5072 until the insert 5014 is pushed downwardly toward the receiver base 5060 after assembly with the shank 5004. Thus, the crimping of the receiver walls 5077 prohibits rotation of the insert 5014 about the receiver axis B but allows for limited axial movement of the insert 5014 with respect to the receiver 5010 along the axis B when some force is exerted to slide the crimped surface 5093 up or down along the groove 5175. The insert 5014 is fully captured within the receiver 5010 by the guide and advancement structure 5072 prohibiting movement of the insert 5014 up and out through the receiver opening 5066 as well as by retainer 5012 located below the insert.

Typically, the receiver and retainer combination are shipped or otherwise provided to the end user with the spring tab outer wings 5140 wedged against the receiver as shown in FIG. 270. The receiver 5010, retainer 5012 and insert 5014 combination is now pre-assembled and ready for assembly with the shank 5004 either at the factory, by surgery staff prior to implantation, or directly upon an implanted shank 5004 as will be described herein.

As illustrated in FIG. 273, the bone screw shank 5004 or an entire assembly 5001 made up of the assembled shank 5004, receiver 5010, retainer 5012 and compression insert 5014, is screwed into a bone, such as the vertebra 5017 (shown in phantom), by rotation of the shank 5004 using a suitable driving tool (not shown) that operably drives and rotates the shank body 5006 by engagement thereof at the internal drive 5046.

With further reference to FIG. 273, the pre-assembled receiver, insert and retainer are placed above the shank upper portion 5008 until the shank upper portion is received within the opening 5110. With particular reference to FIGS. 274 and 275, as the shank upper portion 5008 is moved into the interior 5061 of the receiver base, the shank upper portion 5008 presses upwardly against the retainer 5012 in the recess partially defined by the cylindrical surface 5099. As the portion 5008 continues to move upwardly toward the channel 5064, the surface 5034 forces outward movement of the retainer 5012 towards the cylindrical surface 5099 defining the receiver expansion recess or chamber. The retainer 5012 begins to contract about the spherical surface 5034 as the center of the sphere (shown in dotted lines) passes beyond the center of the retainer expansion recess. At this time also, the spherical surface 5034 moves into engagement with the surfaces 5132 of the retainer flex tabs 5117, the tabs 5117 expanding slightly outwardly to receive the surface 5034. With reference to FIG. 276, the spherical surface 5034 then enters into full frictional engagement with the panel inner surfaces 5132. At this time, the retainer 5012 panels and the surface 5034 are in a fairly tight friction fit, the surface 5034 being pivotable with respect to the retainer 5012 with some force. Thus, a tight, non-floppy ball and socket joint is now created between the retainer 5012 and the shank upper portion 5008.

With reference to FIG. 277, the shank 5004 and attached retainer 5012 are then moved downwardly into a desired position with the retainer seated on the surface 5104. This may be accomplished by either an upward pull on the receiver 5010 or, in some cases, by driving the shank 5004 further into the vertebra 5017. The insert 5014 may be pressed downwardly by a tool or by a rod and closure top as shown in FIG. 278. Also, in some embodiments, when the receiver 5010 is pre-assembled with the shank 5004, the entire assembly 5001 may be implanted at this time by inserting the driving tool (not shown) into the receiver and the shank drive 5046 and rotating and driving the shank 5004 into a desired location of the vertebra 5017.

Also with reference to FIGS. 277 and 278, prior to assembly with the rod 5021 and the closure top 5018, the compression insert 5014 frusto-conical surface 5163 is near the surface 5084. The insert 5014 is prohibited from moving any further downwardly at the beginning of the surface 5084 unless forced downwardly by a tool or by the closure top pressing downwardly on the rod that in turn presses downwardly on the insert 5014 as shown in FIG. 278. With further reference to FIG. 277 and also to FIG. 279, at this time, the receiver 5010 may be articulated to a desired angular position with respect to the shank 5004, such as that shown in FIG. 279, that will be held, but not locked, by the frictional engagement between the retainer 5012 and the shank upper portion 5008.

The rod 5021 is eventually positioned in an open or percutaneous manner in cooperation with the at least two bone screw assemblies 5001. The closure structure 5018 is then inserted into and advanced between the arms 5062 of each of the receivers 5010. The closure structure 5018 is rotated, using a tool engaged with the inner drive 5186 until a selected pressure is reached at which point the rod 5021 engages the U-shaped seating surface 5162 of the compression insert 5014, further pressing the insert spherical surface 5168 (or stepped shank gripping surfaces 5170 of the insert 5014') against the shank spherical surface 5034, (the edges of the stepped surfaces 5170 penetrating into the spherical surface 5034), pressing the shank upper portion 5008 into locked frictional engagement with the retainer 5012. Specifically, as the closure structure 5018 rotates and moves downwardly into the respective receiver 5010, the point 5189 and rim 5190 engage and penetrate the rod surface 5022, the closure structure 5018 pressing downwardly against and biasing the rod 5021 into compressive engagement with the insert 5014 that urges the shank upper portion 5008 toward the retainer 5012 and into locking engagement therewith, the retainer 5012 frictionally abutting the surface 5104 and expanding outwardly against the cylindrical surface 5101. For example, about 80 to about 120 inch pounds of torque on the closure top may be applied for fixing the bone screw shank 5006 with respect to the receiver 5010.

Also, as the closure structure 5018 and the rod 5021 press the insert 5014 downwardly toward the base of the receiver 5010, the insert frusto-conical surface 5163 is forced into the receiver cylindrical surface 5084, wedging the insert 5014 into fixed frictional engagement with the receiver surface 5084. With reference to FIG. 280, at this time, the closure top 5018 may be loosened or removed and/or the rod 5021 may be adjusted and/or removed and the frictional engagement between the insert 5014 and the receiver 5010 at the receiver surface 5084 will remain locked in place, advantageously maintaining a locked angular position of the shank 5004 with respect to the receiver 5010. If the user wishes to release the insert 5014 from the receiver 5010 and unlock the polyaxial mechanism, a tool (not shown) may be used that includes extensions or prongs that are received by and through the opposed through bores 5075 of the receiver 5010 and received into the through bores 5172 of the insert 5014. Such tool is then pulled upwardly in a direction along the axis B away from the receiver base 5060, thereby pulling the insert slightly upwardly and away from the receiver base 5060 and releasing the frusto-conical surface 5163 from the cylindrical surface 5084. Alternatively, if both the closure top 5018 and the rod 5021 are already removed from the receiver 5010, another manipulation tool (not shown) may be used that is inserted into the receiver at the opening 5066 and into the insert channel 5161, with prongs or extensions thereof extending outwardly into the insert through bores 5172; a piston-like portion of the tool thereafter pushing directly on the shank upper portion 5008, thereby pulling the insert 5014 surface 5163 away from the receiver surface 5084 and thus releasing the polyaxial mechanism. At such time, the shank 5004 may be articulated with respect to the receiver 5010, and the desired friction fit returns between the retainer 5012 and the shank surface 5034, so that an adjustable, but non-floppy relationship still exists between the shank 5004 and the receiver 5010. If further disassembly if the assembly is desired, such is accomplished in reverse order to the procedure described previously herein for assembly.

With reference to FIG. 281, an alternative assembly 5001' is shown in which the rod 5021 and closure top 5018 of the assembly 5001 of FIG. 280 are replaced with a deformable rod 5018' and alternative closure top 5018'. Because of the lock between the insert 5014 and the receiver 5010, any loosening of the rod 5021' from the receiver 5010 that may occur due to rod deformation does not compromise the locked polyaxial mechanism formed by the wedged in insert 5014, the shank upper portion 5008, the retainer 5012 and the receiver 5010.

With reference to FIGS. 284-306 the reference number 6001 generally represents a polyaxial bone screw apparatus or assembly according to the present invention. The assembly 6001 includes a shank 6004, that further includes a body 6006 integral with an upwardly extending upper portion or head-like capture structure 6008; a receiver 6010; and a lower retainer structure illustrated as a resilient open ring 6012. The receiver 6010 and retainer structure 6012 are initially assembled and may be further assembled with the shank 6004 either prior or subsequent to implantation of the shank body 6006 into a vertebra 6017, as will be described in greater detail below. FIG. 284 further shows a closure structure 6018 for capturing a longitudinal connecting member, for example, a rod 6021 which in turn presses against the shank upper portion 6008 into fixed frictional contact with the lower retainer 6012, so as to capture, and fix the longitudinal connecting member 6021 within the receiver 6010 and thus fix the member 6021 relative to the vertebra 6017. The illustrated rod 6021 is hard, stiff, non-elastic and cylindrical, having an outer cylindrical surface 6022. The rod 6021 is the same or substantially similar to the rods previously discussed herein, such as the rods 21, 1021, 2021, 3021, 4021, 5021 and 6021. It is foreseen that in other embodiments, the rod 6021 may be elastic, deformable and/or of a different cross-sectional geometry. The receiver 6010 and the shank 6004 cooperate in such a manner that the receiver 6010 and the shank 6004 can be secured at any of a plurality of angles, articulations or rotational alignments relative to one another and within a selected range of angles both from side to side and from front to rear, to enable flexible or articulated engagement of the receiver 6010 with the shank 6004 until both are locked or fixed relative to each other near the end of an implantation procedure.

The shank 6004, best illustrated in FIGS. 284-286, is elongate, with the shank body 6006 having a helically wound bone implantable thread 6024 (single or dual lead thread form) extending from near a neck 6026 located adjacent to the upper portion or head 6008, to a tip 6028 of the body 6006 and extending radially outwardly therefrom. During use, the body 6006 utilizing the thread 6024 for gripping and advancement is implanted into the vertebra 6017 leading with the tip 6028 and driven down into the vertebra with an installation or driving tool (not shown), so as to be implanted in the vertebra to a location at or near the neck 6026, as more fully described in the paragraphs below. The shank 6004 has an elongate axis of rotation generally identified by the reference letter A.

The neck 6026 extends axially upward from the shank body 6006. The neck 6026 may be of the same or is typically of a slightly reduced radius as compared to an adjacent upper end or top 6032 of the body 6006 where the thread 6024 terminates. Further extending axially and outwardly from the neck 6026 is the shank upper portion or head 6008 that provides a connective or capture apparatus disposed at a distance from the upper end 6032 and thus at a distance from the vertebra 6017 when the body 6006 is implanted in such vertebra.

The shank upper portion 6008 is configured for a pivotable connection between the shank 6004 and the retainer 6012 and receiver 6010 prior to fixing of the shank 6004 in a desired position with respect to the receiver 6010. The shank upper portion 6008 has an outer, convex and substantially spherical surface 6034 that extends outwardly and upwardly from the neck 6026 and terminates at an outer annular rim surface 6038. The spherical surface 6034 has an outer radius configured for frictional, sliding cooperation with the retainer 6012 as will be described in greater detail below. The top surface 6038 is substantially perpendicular to the axis A. The spherical surface 6034 shown in the present embodiment is substantially smooth, but in some embodiments may include a roughening or other surface treatment and is sized and shaped for cooperation and ultimate frictional engagement with the lower retainer 12. The shank spherical surface 6034 is locked into place exclusively by the rod 6021 and the retainer 6012 and not by inner surfaces defining the receiver cavity.

The shank upper portion 6008 further includes a substantially spherical, curved or domed top surface 6040. In operation, the surface 6040 directly engages the rod 6021 within the channel of the receiver 6010. The domed surface 6040 is located above and is spaced from the annular rim 6038 where the surface 6034 terminates. A counter sunk feature, generally 6042 separates the domed surface 6040 from the annular rim 6038. The feature 6042 is further defined by a discontinuous cylindrical surface 6043 located about the domed surface 6040 and a frusto-conical surface 6044 extending from the rim 6038 downwardly and inwardly toward the surface 6043. The surface 6043 runs parallel to the axis A. The surface 6044 terminates at a narrow annular track 6046 that encircles the cylindrical surface 6043. Six evenly spaced cylindrical cut-outs, 6048 are formed primarily into the cylindrical surface 6043 and also partially into the frusto-conical surface 6044, each of the cutouts 6048 running parallel to the shank axis A. Cylindrical surfaces created by the cutouts 6048 and the surfaces 6043 and 6044 provide a partially external and partially internal drive feature for receiving a driving tool (not shown) for rotating and driving the bone screw shank body 6006 into the vertebra 6017. It is foreseen that the shank driving feature may take on other various shapes and forms, as for example, will be described herein with respect to the alternative bone screw shanks 6004' and 6004" shown in FIGS. 305 and 306, respectively. Other forms may include more or fewer apertures of various shapes. As illustrated in FIGS. 285 and 386, the external and internal portions of the drive may also include beveled or stepped surfaces that may further enhance gripping with the driving tool. In operation, a driving tool (not shown) is received in the drive feature 6042, being seated at the frusto-conical surface 6044 and engaging the various curved faces at and about the cylindrical surface 6043 for both driving and rotating the shank body 6006 into the vertebra 6017, either before the shank 6004 is attached to the receiver 6010 or after the shank 6004 is attached to the receiver 6010, with the shank body 6006 being driven into the vertebra 6017 with the driving tool extending into the receiver 6010.

The shank 6004 shown in the drawings is cannulated, having a small central bore 6050 extending an entire length of the shank 6004 along the axis A. The bore 6050 is defined by an inner cylindrical wall of the shank 6004 and has a circular opening at the shank tip 6028 and an upper opening communicating with the top surface 6040. The bore 6050 is coaxial with the threaded body 6006 and the upper portion 6008. The bore 6050 provides a passage through the shank 6004 interior for a length of wire (not shown) inserted into the vertebra 6013 prior to the insertion of the shank body 6006, the wire providing a guide for insertion of the shank body 6006 into the vertebra 6017.

To provide a biologically active interface with the bone, the threaded shank body 606 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bioceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 284 and 290-295, the receiver 6010 has a generally cylindrical and U-shaped appearance. The receiver 6010 has an axis of rotation B that is shown in FIG. 284 as being aligned with and the same as the axis of rotation A of the shank 6004, such orientation being desirable, but not required during assembly of the receiver 6010 with the shank 6004. After the receiver 6010 is pivotally attached to the shank 6004, either before or after the shank 6004 is implanted in a vertebra 6017, the axis B is typically disposed at an angle with respect to the axis A.

The receiver 6010 includes a substantially cylindrical base 6060 defining a bore or inner cavity, generally 6061, the base 6060 being integral with a pair of opposed upstanding arms 6062 forming a cradle and defining a channel 6064 between the arms 6062 with an upper opening, generally 6066, and a lower channel portion including a partially planar and partially U-shaped lower seat 6068, the channel 6064 having a width for operably snugly receiving the rod 6021 or portion of another longitudinal connector between the arms 6062, the channel 6064 communicating with the base cavity 6061.

Each of the arms 6062 has an interior surface, generally 6070, that includes various inner cylindrical profiles, an upper one of which is a partial helically wound guide and advancement structure 6072 located adjacent top surfaces 6073 of each of the arms 6062. In the illustrated embodiment, the guide and advancement structure 6072 is a partial helically wound interlocking flangeform configured to mate under rotation with a similar structure on the closure structure 18, as described more fully below. However, it is foreseen that for certain embodiments of the invention, the guide and advancement structure 6072 could alternatively be a square-shaped thread, a buttress thread, a reverse angle thread or other thread-like or non-threadlike helically wound discontinuous advancement structures, such as a flange form, for operably guiding under rotation and advancing the closure structure 6018 downward between the arms 6062, as well as eventual torquing when the closure structure 6018 abuts against the rod 6021 or other longitudinal connecting member. It is foreseen that the arms could have break-off extensions.

An opposed pair of tool receiving and engaging apertures 6074 are formed on outer surfaces 6076 of the arms 62. It is foreseen that tool receiving grooves or apertures may be configured in a variety of shapes and sizes and be disposed at other locations on the receiver arms 6062.

Returning to the interior surface 6070 of the receiver arms 6062, located below the guide and advancement structure 6072 is a run-out feature for the guide and advancement structure 6072 partially defined by a discontinuous cylindrical surface 6082 having a diameter approximately the same or slightly greater than a greater diameter of the guide and advancement structure 6072. Below the surface 6082, moving in a direction toward the base 6060, is another cylindrical surface 6084 having a diameter smaller than the diameter of the surface 6082 and illustrated as substantially the same as an inner or lesser diameter of the guide and advancement structure 6072. The surface 6084 is initially discontinuous (at the arms 6062) and transitions into a continuous surface at the channel seat 6068. Directly above the seat 6068, located in each of the arms 6062 is a discontinuous, radially extending, rounded lip 6086 extending inwardly toward the axis B from each of the surfaces 6084. As will be described in greater detail below, the lip 6086 provides a frictional stop for the shank upper portion 6008 during pop-on assembly with the retainer 6012 within the receiver 6010. A continuous, beveled annular upper rim or stop surface 6098 is located below and adjacent to the cylindrical surface 6084. The surface 6098 is disposed in the base 6060, partially forming the base cavity 6061 and forms an abutment stop for the resilient retainer 6012, prohibiting the retainer 6012 (when in an uncompressed configuration) from moving upwardly into the space defined by the cylindrical surface 6084 and the channel 6064. Another cylindrical surface 6099 is located below and adjacent to the surface 6098. The cylindrical surface 6099 is oriented substantially parallel to the axis B and is sized and shaped to receive an expanded retainer 6012. The surfaces 6098 and 6099 define a circumferential recess that is sized and shaped to receive the retainer 6012 as it expands around the shank upper portion 6008 as the shank 6008 moves upwardly toward the channel 6064 during assembly, as well as form a restriction to prevent the expanded retainer 6012 from moving upwardly with the shank portion 6008, the surface 6098 preventing the retainer 6012 from passing upwardly out of the cavity 6061 whether the retainer 6012 is in a partially or fully expanded position or state, or in a neutral or original operative position or state (see, e.g., FIGS. 299 and 300). A cylindrical surface 6101 located below the cylindrical surface 6099 is sized and shaped to closely receive the retainer 6012 when the retainer is in a neutral or slightly compressed operative position as shown in FIGS. 297 and 301, for example. Thus, the cylindrical surface 6101 has a diameter smaller than the diameter of the cylindrical surface 6099 that defines the expansion area for the retainer 6012. The surface 6101 is joined or connected to the surface 6099 by one or more beveled, curved or conical surfaces 6102. The surfaces 6102 allow for sliding gradual movement and/or contraction of the retainer 6012 into the space defined by the surface 6101 and ultimate seating of the retainer 6012 on a lower annular surface 6104 located below and adjacent to the cylindrical surface 6101.

Located below and adjacent to the annular seating surface 6104 is another substantially cylindrical surface 6106 that communicates with a beveled or flared bottom opening surface 6107, the surface 6107 communicating with an exterior base surface 6108 of the base 6060, defining a lower opening, generally 6110, into the base cavity 6061 of the receiver 6010. The illustrated surface 6106 has a diameter requiring compression or squeezing of the retainer 6012 during uploading of the retainer 6012 through the lower opening 6110 (see FIG. 296, for example).

With particular reference to FIGS. 284 and 287-289, the lower open retainer ring 6012 that operates to capture the shank upper portion 6008 within the receiver 6010 has a central axis that is operationally the same as the axis B associated with the receiver 6010 when the shank upper portion 6008 and the retainer 6012 are installed within the receiver 6010. The retainer ring 6012 is made from a resilient material, such as a stainless steel or titanium alloy, so that the retainer 6012 may be both compressed and expanded during various steps of assembly as will be described in greater detail below. The lower retainer 6012 has a central channel or hollow through bore, generally 6121, that passes entirely through the ring 6012 from a top surface 6122 to a bottom surface 6124 thereof. Surfaces that define the channel or bore 6121 include a discontinuous inner cylindrical surface 6125 near or adjacent the top surface 6122, a first discontinuous frusto-conical or curved surface 6127 adjacent the surface 6125 and a second frusto-conical or beveled surface 6128 adjacent the surface 6127 and also adjacent to the bottom 6124, all three surfaces 6125, 6127 and 6128 being coaxial when the retainer 6012 is in a neutral non-compressed, non-expanded orientation. The retainer 6012 further includes an outer cylindrical surface 6130 located adjacent the top surface 6122 and an outer beveled or frusto-conical surface 6132 adjacent the bottom surface 6124. The surface 6130 is oriented parallel to the central axis of the retainer 6012. In some embodiments of the invention spaced notches (not shown) may be formed in the cylindrical surface 6130 to receive a holding and manipulation tool (not shown) used for contraction and insertion of the retainer 6012 into the receiver 6010. In some embodiments further notches may be made to evenly distribute stress across the entire retainer 6012 during contraction and expansion thereof. In other embodiments of the invention, such notches may be on the inside of the retainer 6012 ring. It is also foreseen that in some embodiments of the invention, the retainer 6012 inner surfaces may include a roughening or additional material to provide a friction fit against the shank upper portion 6008 prior to lock down by the rod 6021 or other longitudinal connecting member. The resilient retainer 6012 further includes first and second end surfaces, 6134 and 6135 disposed in spaced relation to one another when the retainer is in a neutral non-compressed state. Both end surfaces 6134 and 6135 are disposed substantially perpendicular to the top surface 6122 and the bottom surface 6124. A width X between the surfaces 6134 and 6135 is determined by a desired amount of compressibility of the open retainer 6012 when loaded into the receiver 6010. The space X shown in FIG. 287 provides adequate space between the surfaces 6134 and 6135 for the retainer 6012 to be pinched, with the surfaces 6134 and 6135 compressed toward one another (as shown in FIG. 296) to a closely spaced or even touching configuration, if necessary, to an extent that the compressed retainer 6012 is up or bottom loadable (as illustrated) through the receiver opening 6110 or alternatively top loaded through the channel opening 6066 (not shown). After passing through the opening 6110 and along a portion of the lower inner surface 6106, the retainer 6012 expands or springs back to an original uncompressed, rounded or collar-like configuration of FIGS. 287-289, see, e.g., FIG. 297. The embodiment shown in FIGS. 287-289 illustrates the surfaces 6134 and 6135 as substantially parallel, however, it is foreseen that it may be desirable to orient the surfaces obliquely or at a slight angle depending upon the amount of compression desired during loading of the retainer 6012 into the receiver 6010. It is further noted that the geometry of the retainer 6012 is not limited to the particular cylindrical or planar surface shapes shown in the drawings figures. The retainer 6012 may be of a rounded ring-shape, for example, or include more or fewer planar, conical or curved surfaces.

With reference to FIGS. 284, 303 and 304, the illustrated elongate rod or longitudinal connecting member 6021 (of which only a portion has been shown) can be any of a variety of implants utilized in reconstructive spinal surgery, but is typically a cylindrical, elongate structure having the outer substantially smooth, cylindrical surface 6022 of uniform diameter. The rod 6021 may be made from a variety of metals, metal alloys and deformable and less compressible plastics, including, but not limited to rods made of elastomeric, polyetheretherketone (PEEK) and other types of materials.

Longitudinal connecting members for use with the assembly 6001 may take a variety of shapes, including but not limited to rods or bars of oval, rectangular or other curved or polygonal cross-section. The shape of the receiver 6010 may be modified so as to closely hold, and if desired, fix or slidingly capture the longitudinal connecting member to the assembly 6001. Some embodiments of the assembly 6001 may also be used with a tensioned cord. Such a cord may be made from a variety of materials, including polyester or other plastic fibers, strands or threads, such as polyethyleneterephthalate. Furthermore, the longitudinal connector may be a component of a longer overall dynamic stabilization connecting member, with cylindrical or bar-shaped portions sized and shaped for being received by the receiver 6010 or alternative receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 6001, for example. A damping component or bumper may be attached to the longitudinal connecting member at one or both sides of the bone screw assembly 6001. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIG. 284, the closure structure or closure top 6018 shown with the assembly 6001 is rotatably received between the spaced arms 6062 of the receiver 6010. It is noted that the closure 6018 top could be a twist-in or slide-in closure structure. The illustrated closure structure 6018 is substantially cylindrical and includes a an outer helically wound guide and advancement structure 6162 in the form of a flange that operably joins with the guide and advancement structure 6072 disposed on the arms 6062 of the receiver 6010. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 6018 downward between the arms 6062 and having such a nature as to resist splaying of the arms 6062 when the closure structure 6018 is advanced into the channel 6064, the flange form illustrated herein as described more fully in Applicant's U.S. Pat. No. 6,726,689 is preferred as the added strength provided by such flange form beneficially cooperates with and counters any reduction in strength caused by the reduced profile of the receiver 6010 that advantageously engages longitudinal connecting member components as will be further described below. The illustrated closure structure 6018 also includes a top surface 6164 with an internal drive 6166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 6166 is used for both rotatable engagement and, if needed, disengagement of the closure 6018 from the receiver arms 6062. It is also foreseen that the closure structure 6018 may alternatively include a break-off head designed to allow such a head to break from a base of the closure at a preselected torque, for example, 6070 to 6140 inch pounds. Such a closure structure would also include a base having an internal drive to be used for closure removal. A base or bottom surface 6168 of the closure is planar and further includes a point 6169 and a rim 6170 for engagement and penetration into the surface 6022 of the rod 6021 in certain embodiments of the invention. The closure top 6018 may further include a cannulation through bore (not shown) extending along a central axis thereof and through the top and bottom surfaces thereof. Such a through bore provides a passage through the closure 6018 interior for a length of wire (not shown) inserted therein to provide a guide for insertion of the closure top into the receiver arms 6062.

Preferably, the receiver 6010 and the retainers 6012 are assembled at a factory setting that includes tooling for holding and alignment of the component pieces and pinching or compressing of the retainer 6012. In some circumstances, the shank 6004 is also assembled with the receiver 6010 and the retainer 6012 at the factory. In other instances, it is desirable to first implant the shank 6004, followed by addition of the pre-assembled receiver and retainer at the insertion point. In this way, the surgeon may advantageously and more easily implant and manipulate the shanks 6004, distract or compress the vertebrae with the shanks and work around the shank upper portions or heads without the cooperating receivers being in the way. In other instances, it is desirable for the surgical staff to pre-assemble a shank of a desired size with the already assembled receiver and retainer. Allowing the surgeon to choose the appropriately sized shank advantageously reduces inventory requirements, thus reducing overall cost.

Pre-assembly of the receiver 6010 and the retainer 6012 is shown in FIGS. 296-297. The retainer 6012 is prepared for insertion into the receiver 6010 by squeezing or pressing the retainer end surfaces 6134 and 6135 toward one another as shown in FIG. 296. The compressed retainer 6012 is inserted into the lower opening 6110 with the planar top surface 6122 facing the receiver bottom surface 6108. The retainer 6012 is typically moved upwardly into the receiver 6010 and past the cylindrical surface 106 and allowed to expand to an almost neutral or slightly compressed state within the cylindrical surface 101 as shown in FIG. 297. The receiver 6010 and the retainer 6012 (held by the cylindrical surface 6101) combination is now pre-assembled and ready for assembly with the shank 6004 either at the factory, by surgery staff prior to implantation, or directly upon an implanted shank 6004 as will be described herein.

As illustrated in FIG. 298, the bone screw shank 6004 alone (or an entire assembly 6001 made up of the assembled shank 6004, receiver 6010 and retainer 6012) is screwed into a bone, such as the vertebra 6017, by rotation of the shank 6004 using a suitable driving tool (not shown) that operably drives and rotates the shank body 6006 by engagement thereof at the drive feature 6042. Specifically, the vertebra 6017 may be pre-drilled to minimize stressing the bone and have a guide wire (not shown) inserted therein to provide a guide for the placement and angle of the shank 6004 with respect to the vertebra. A further tap hole may be made using a tap with the guide wire as a guide. Then, the bone screw shank 6004 or the assembly 6001 is threaded onto the guide wire utilizing the cannulation bore 6050 by first threading the wire into the opening at the bottom 6028 and then out of the top opening at the top surface 6040. The shank 6004 is then driven into the vertebra using the wire as a placement guide. It is foreseen that the shank and other bone screw assembly parts, the rod 6021 (also having a central lumen in some embodiments) and the closure top 18 (also with a central bore) can be inserted in a percutaneous or minimally invasive surgical manner, utilizing guide wires.

When the shank 6004 is driven into the vertebra 6017 without the remainder of the assembly 6001, the shank 6004 may either be driven to a desired final location or may be driven to a location slightly above or proud to provide for ease in assembly with the pre-assembled receiver, compression insert and retainer. With reference to FIG. 298, the pre-assembled receiver and retainer is placed above the shank upper portion 6008 until the shank upper portion is received within the opening 6110. With particular reference to FIGS. 299-300, as the shank is moved into the interior of the receiver base, the shank upper portion 6008 presses the retainer 6012 upwardly into the recess partially defined by the cylindrical surface 6099 (if the retainer is not already located within such recess). As the portion continues to move upwardly toward the channel 6064, the top surface 6122 of the retainer 6012 abuts against the receiver surface 6098. At this time, the shank upper portion moves upwardly into the channel 6064 until the outer surface 6034 frictionally engages the lip 6086 on the receiver cylindrical surface 6084, stopping upward movement of the shank upper portion 6008. As the retainer 6012 presses up against the surface 6098, the shank upper portion 6008 forces outward movement of the retainer 6012 towards the cylindrical surface 6099 defining the receiver expansion recess as the spherical surface 6034 continues in an upward direction. The retainer 6012 begins to contract about the spherical surface 6034 as the center of the sphere passes beyond the center of the retainer expansion recess defined by the surface 6099. At this time also, the spherical surface 6034 is in engagement with the receiver lip 6086, prohibiting further upward movement of the shank 6004 into the channel 6064.

With reference to FIG. 302, the retainer 6012 and attached insert 6014 are ultimately moved down into a final operative position by either an upward pull on the receiver 6010 or, in some cases, by driving the shank 6004 further into the vertebra 6017. Also, in some embodiments, when the receiver 6010 is pre-assembled with the shank 6004, the entire assembly 6001 may be implanted at this time by inserting the driving tool (not shown) into the receiver and the shank drive 6042 and rotating and driving the shank 4 into a desired location of the vertebra 6017.

With reference to FIG. 303-304, the rod 6021 is eventually positioned in an open or percutaneous manner in cooperation with the at least two bone screw assemblies 6001. The closure structure 6018 is then inserted into and advanced between the arms 6062 of each of the receivers 6010. The closure structure 6018 is rotated, using a tool engaged with the inner drive 6166 until a selected pressure is reached at which point the rod 6021 engages the curved top surface 6040 of the shank 6004, pressing the shank upper portion 6008 into locked frictional engagement with the retainer 6012. Specifically, as the closure structure 6018 rotates and moves downwardly into the respective receiver 6010, the point 6169 and rim 6170 engage and penetrate the rod surface 6022, the closure structure 6018 pressing downwardly against and biasing the rod 6021 into compressive engagement with the shank upper surface 6040 that urges the shank upper portion 6008 toward the retainer 6012 and into locking engagement therewith, the retainer 6012 frictionally abutting the surface 6104 and expanding outwardly against the cylindrical surface 6101. For example, about 6080 to about 6120 inch pounds of torque on the closure top may be applied for fixing the bone screw shank 6006 with respect to the receiver 6010.

If removal of the rod 6021 from any of the bone screw assemblies 6001 is necessary, or if it is desired to release the rod 6021 at a particular location, disassembly is accomplished by using the driving tool (not shown) that mates with the internal drive 6166 on the closure structure 6018 to rotate and remove such closure structure from the cooperating receiver 6010. Disassembly is then accomplished in reverse order to the procedure described previously herein for assembly.

With reference to FIGS. 305 and 306, alternative bone screw shanks 6004' and 6004" according to the invention may include alternative drive features 6042' and 6042", respectively. The bone screws 6004' and 6004" may be used in lieu of a screw 6004 in the assembly 1 described above.

The bone screw 6004' and 6004" include respective outer lower spherical surface 6034' and 6034" and respective upper or top domed shaped surfaces 6040' and 6040", that are the same or substantially similar to the respective spherical surface 6034 and top domed surface 6040 previously described herein with respect to the shank 6004 of the assembly 6001. The bone screw 6004' is identical to the screw 6004 with the exception that the six cylindrical cutouts 6048 are replaced by six partially cylindrical grooves 6048' that in addition to forming cylindrical surfaces in an upstanding surface 6043' (that is otherwise identical to the surface 6043 of the shank 6004), also carve a groove into the frusto-conical surface 6044' (that is otherwise identical to the surface 6044) and through the outer spherical surface 6034', the grooves 6048' each having a substantially planar bottom surface 6049' that extends from the surface 6043' radially outwardly and through the spherical surface 6034'. With respect to the bone screw 6004", the cylindrical surface 6043 of the bone screw 6004 is replaced by a faceted surface 6043" and a portion of the spherical surface 6034 is completely removed to result in an annular planar tool seating surface 6049". In the illustrated embodiment, the faceted surface 6043" includes six surfaces sized and shaped to be received in a hex shaped socket type driving tool (not shown), the tool seatable on the planar surface 6049".

With reference to the '849 patent application incorporated by reference herein, polyaxial bone screws 6001 according to the invention may be used with dynamic stabilization longitudinal connecting member assemblies that include one or more sleeves with cooperating, spacers, bumpers and an inner tensioned cord.

With reference to FIGS. 307-339 the reference number 7001 generally represents a polyaxial bone screw apparatus or assembly according to the present invention. The assembly 7001 includes a shank 7004, that further includes a body 7006 integral with an upwardly extending upper portion or head-like capture structure 7008; a receiver 7010; and a lower retainer structure illustrated as a resilient open ring-like structure 7012. The receiver 7010 and retainer structure 7012 are initially assembled and may be further assembled with the shank 7004 either prior or subsequent to implantation of the shank body 7006 into a vertebra 7017, as will be described in greater detail below. FIG. 307 further shows a closure structure 7018 for capturing a longitudinal connecting member, for example, a rod 7021 which in turn presses against the shank upper portion 7008 into fixed frictional contact with the lower retainer 7012, so as to capture, and fix the longitudinal connecting member 7021 within the receiver 7010 and thus fix the member 7021 relative to the vertebra 7017. The illustrated rod 7021 is hard, stiff, non-elastic and cylindrical, having an outer cylindrical surface 7022. It is foreseen that in other embodiments, the rod 7021 may be elastic, deformable and/or of a different cross-sectional geometry. The receiver 7010 and the shank 7004 cooperate in such a manner that the receiver 7010 and the shank 7004 can be secured at any of a plurality of angles, articulations or rotational alignments relative to one another and within a selected range of angles both from side to side and from front to rear, to enable flexible or articulated engagement of the receiver 7010 with the shank 7004 until both are locked or fixed relative to each other near the end of an implantation procedure.

The shank 7004, best illustrated in FIGS. 307-309, is substantially similar to the shank 6004 previously described herein with respect to the assembly 6001. Thus, the shank 7004 includes the shank body 7006, upper portion or head 7008, a shank thread 7024, a neck 7026, a tip 7028, a top of thread 7032, an upper portion spherical surface 7034 a top surface 7040, a drive feature 7042 and a cannulation bore 7050 the same or substantially similar to the respective body 6006, upper portion or head 6008, shank thread 6024, neck 6026, tip 6028, top of thread 6032, spherical surface 6034, domed top surface 6040, drive feature 6042 and cannulation bore 6050 previously described herein with respect to the shank 6004 of the assembly 6001. To provide a biologically active interface with the bone, the threaded shank body 7006 may be coated, perforated, made porous or otherwise treated as previously discussed herein with respect to the shank body 6 of the assembly 1.

With particular reference to FIGS. 307 and 316-320, the receiver 7010 has a generally cylindrical and U-shaped appearance. The receiver 7010 has an axis of rotation B that is shown in FIG. 307 as being aligned with and the same as the axis of rotation A of the shank 7004, such orientation being desirable, but not required during assembly of the receiver 7010 with the shank 7004, as shown, for example, in FIG. 337. After the receiver 7010 is pivotally attached to the shank 7004, either before or after the shank 7004 is implanted in a vertebra 7017, the axis B is typically disposed at an angle with respect to the axis A, as shown, for example, in FIG. 338.

The receiver 7010 includes a substantially cylindrical base 7060 defining a bore or inner cavity, generally 7061, the base 7060 being integral with a pair of opposed upstanding arms 7062 forming a cradle and defining a channel 7064 between the arms 7062 with an upper opening, generally 7066, and a lower channel portion including a partially planar and partially U-shaped lower seat 7068, the channel 7064 having a width for operably snugly receiving the rod 7021 or portion of another longitudinal connector between the arms 7062, the channel 7064 communicating with the base cavity 7061.

Each of the arms 7062 has an interior surface, generally 7070, that includes various inner cylindrical profiles, an upper one of which is a partial helically wound guide and advancement structure 7072 located adjacent top surfaces 7073 of each of the arms 7062. In the illustrated embodiment, the guide and advancement structure 7072 is a partial helically wound interlocking flangeform configured to mate under rotation with a similar structure on the closure structure 7018, as described more fully below. However, it is foreseen that for certain embodiments of the invention, the guide and advancement structure 7072 could alternatively be a square-shaped thread, a buttress thread, a reverse angle thread or other thread-like or non-threadlike helically wound discontinuous advancement structures, such as a flange form, for operably guiding under rotation and advancing the closure structure 7018 downward between the arms 7062, as well as eventual torquing when the closure structure 7018 abuts against the rod 7021 or other longitudinal connecting member. It is foreseen that the arms could have break-off extensions.

An opposed pair of upper tool receiving and engaging apertures or grooves 7074 are formed on outer surfaces 7076 of the arms 7062. It is foreseen that tool receiving grooves or apertures may be configured in a variety of shapes and sizes and be disposed at other locations on the receiver arms 7062. Located directly below the apertures are another pair of tool receiving and engaging apertures or through bores, generally 7078, that extend from the surfaces 7076 to the inner surfaces 7070. The through bores 7078 each have a substantially planar bottom surface 7079 and arched or U-shaped upper and side surfaces 7080. It is foreseen that other geometries are possible. As will be described in greater detail below, the through bores 7078 are sized and shaped to provide clearance within the receiver 7010 for down-loading the retainer 7012 from the receiver upper opening 7066 and between the interior surfaces 7070 of the arms 7062 and into the receiver cavity 7061. The bores 7078 also provide access into the receiver 7010 for manipulating the retainer 7012 after loading and during assembly with the shank 7004.

Returning to the interior surface 7070 of the receiver arms 7062, located below each guide and advancement structure 7072 is a run-out feature for the guide and advancement structure 7072 partially defined by a discontinuous cylindrical surface 7082 having a diameter approximately the same or slightly greater than a greater diameter of the guide and advancement structure 7072. Below the surface 7082, moving in a direction toward the base 7060, is another cylindrical surface 7084 having a diameter smaller than the diameter of the surface 7082 and illustrated as slightly greater than an inner or lesser diameter of the guide and advancement structure 7072. The surface 7084 is also discontinuous, being formed only at the arms 7062. Located between each of the surfaces 7082 and 7084 is a discontinuous annular surface 7085 running substantially perpendicular to the axis B. Formed in each of the surfaces 7084 is a curved recess or aperture, generally 7088, that is located adjacent to and directly above the respective through bore 7078, an upper portion of the bore 7078 also formed in and through the surface 7084. Each recess 7088 is partially defined by a substantially cylindrical surface 7089 and also by an arched or upside-down U-shaped surface 7090 that runs from the surface 7084 to the surface 7089. The recesses 7088 cooperate with the retainer 7012 during assembly with the receiver 7010 and the shank 7004 as will be described in greater detail below.

The surface 7084 terminates at a lower ledge 7098 that runs radially outwardly from the surface 7084 to another cylindrical surface 7099. The ledge 7098 is substantially perpendicular to the axis B. The cylindrical surface 7099 is partially discontinuous at the arms 7062 and also extends downwardly into the base 7060, defining a continuous upper cylindrical portion of the base cavity 7061. Each bore 7078 is substantially formed in the surface 7099 and extends outwardly to the arm surface 7076. The cylindrical surface 7099 is oriented substantially parallel to the axis B and is sized and shaped to receive an expanded retainer 7012. The surfaces 7098 and 7099 define a circumferential recess that is sized and shaped to receive a portion of the retainer 7012 as it expands around the shank upper portion 7008 at the surface 7034 as the shank 8 moves upwardly toward the channel 7064 during assembly. A cylindrical surface 7101 located below the cylindrical surface 7099 is sized and shaped to closely receive the retainer 7012 when the retainer is in a neutral or slightly expanded position as will be described in greater detail below. Thus, the cylindrical surface 7101 has a diameter smaller than the diameter of the cylindrical surface 7099 that defines the expansion area for the retainer 7012. The surface 7101 is joined or connected to the surface 7099 by one or more beveled, curved or conical surfaces 7102. The surfaces 7102 allow for sliding gradual movement of the retainer 7012 into the space defined by the surface 6101 and ultimate seating of the retainer 7012 on a lower annular surface 7104 located below and adjacent to the cylindrical surface 7101. Located below and adjacent to the annular seating surface 7104 is another substantially cylindrical surface 7106 that communicates with a beveled or flared bottom opening surface 7107, the surface 7107 communicating with an exterior base surface 7108 of the base 7060, defining a lower opening, generally 7110, into the base cavity 7061 of the receiver 7010.

With particular reference to FIGS. 307 and 310-315, the open, friction fit retainer 7012 that operates to capture and frictionally engage the shank upper portion 7008 within the receiver 7010 has a central axis that is operationally the same as the axis B associated with the receiver 7010 when the shank upper portion 7008 and the retainer 7012 are installed within the receiver 7010. The retainer 7012 includes a substantially cylindrical discontinuous lower body 7116, a plurality of flex fingers or panels, 7117 extending upwardly from the body 7116 and a pair of opposed spring arms or tabs 7118, also extending upwardly from the body 7116. The retainer ring 7012 is made from a resilient material, such as a stainless steel or titanium alloy, so that the retainer 7012 body 7116 may be expanded and the fingers and tabs (7117 and 7118) of the retainer may be manipulated during various steps of assembly as will be described in greater detail below. The retainer 7012 has a central channel or hollow through bore, generally 7121, that passes entirely through the retainer 7012 from curved retainer arm or tab 7118 top surfaces 7122 to a bottom surface 7124 of the retainer body 7116. Surfaces that define the channel or bore 7121 include an inner lower frusto-conical surface 7128 adjacent to the retainer body bottom surface 7124, a substantially cylindrical surface 7130 adjacent the frusto-conical surface 7128, a narrow frusto-conical or beveled surface 7131 adjacent the cylindrical surface 7130 and a partially discontinuous substantially spherical surface 7132 adjacent the surface 7131, the surface 7132 being continuous near the cylindrical surface 7130 with the exception of a through slot or slit, generally 7134. The surface 7132 is in a plurality of segments or pieces at the flex fingers 7117 wherein a plurality of substantially evenly spaced slots 7136 running outwardly and upwardly through an upper surface 7137 separate the surface 7132 into the individual flex fingers 7117. In the illustrated embodiment, the slots 7136 and the through slit 7134 form six substantially uniform flex fingers or tabs 7117 as well as partially define the two spring tabs 7118, each finger and tab having the inner spherical surface 7132. It is foreseen that more or fewer flex fingers may be made by the forming of more or fewer slots 7136. The discontinuous spherical surface 7132 is sized and shaped to closely fit about and snap onto the shank surface 7034 during assembly as will be described in greater detail below. Preferably the surface 7132 has a radius the same or slightly smaller than the radius of the spherical shank surface 7034. In operation, the discontinuous surface 7132 advantageously frictionally engages the bone screw shank upper portion 7008, allowing for un-locked but non-floppy placement of the angle of the shank 7004 with respect to the receiver 7010 during surgery prior to locking of the shank 7004 with respect to the receiver 7010 near the end of the procedure. At the time of locking engagement, as shown in FIG. 336, for example, downward and outward force placed on the retainer 7012 by the shank upper portion 7008 expands the retainer body 7116 at the slit 7134 and the individual flex fingers 7117 no longer frictionally grip the spherical surface 7034 of the upper portion 7008. To aid in bending flexibility and resiliency, certain flex fingers 7117 have sloping outer surfaces 7138, reducing a width of, or, as illustrated, substantially eliminating, the top planar surface 7137, resulting in four of the fingers 7117 having a combination of a narrow top edge surface 7137 with an outwardly and downwardly sloping frusto-conical surface 7138. It is foreseen that in other embodiments of the invention other surface geometries may be used to gain the level of resiliency desired for expansion and gripping of the fingers 7117 about the shank upper portion 7008. It is noted that the fingers 7117 that are directed generally upwardly toward the receiver channel 7064, some of which that include narrow top edges, advantageously sufficiently snap about and then grip the shank surface 7034 to an extent to provide the friction fit desired for non-floppy placement of the shank body 7006 at a desired angle with respect to the receiver 7010 during manipulation of the bone screws 7001 and the rod 7021 or other longitudinal connecting member during surgery. However, as compared to bone screw inserts such as collets known in the art that include downwardly directed portions or panels that are ultimately wedged between a receiver surface and a shank surface upon final locking of the shank to the receiver, the thin upwardly directed fingers 7117 that extend away from the shank locking surface that are not as strong as the retainer body 7116 do not participate or cooperate with the final locking of the shank upper portion 7008 to the retainer 7012 and the retainer 7012 to the receiver inner surfaces 7101 and 7104. For such purpose, the more substantial retainer body 7116 having only the very narrow slit 7134 used for expansion purposes only is the component that locks the shank upper portion 7008 between the receiver 7010 and the rod 7021 or other longitudinal connecting member.

The retainer body 7116, the flex fingers 7117 and a substantial part of each of the spring tabs 7118 have an outer substantially cylindrical profile, sized and shaped to closely and slidingly fit within the receiver cavity 7061 with the exception of outward extensions or wings, generally 7140, of the spring tabs 7118 that are located adjacent to the upper surfaces 7122, each extending outwardly away from the respective tab and having a curved outward surface 7142 that is substantially cylindrical, being sized and shaped to closely cooperate and frictionally engage the cylindrical surface 7089 of the receiver recess 7088. Each spring tab 7118 further includes an inner planar surface 7144 that runs from the curved top surface 7122 to the inner cylindrical surface 7132.

The through slit 7134 of the resilient retainer 7012 is defined by first and second end surfaces, 7146 and 7147 disposed in spaced relation to one another (they may also be touching) when the retainer is in a neutral state. Both end surfaces 7146 and 7147 are disposed substantially perpendicular to the bottom surface 7124. A width X between the surfaces 7146 and 7147 is very narrow, in some embodiments of about or less than 0.004 inches, the narrow slit functioning to provide stability to the retainer 7012 during operation, specifically retention of the shank upper portion 7008 within the receiver 7010 that must withstand extreme pressure both during assembly and subsequent patient movement. The slit 7134 may be made, for example, by an electrical discharge machining (EDM) process with the resulting surfaces 7146 and 7147 almost touching. Because the retainer 7012 is top loadable in a neutral state and the retainer 7012 does not need to be compressed to fit within the receiver cavity 7061, the width X may be much smaller than what is often required for a bottom loaded compressible retainer ring. The gap X functions only in expansion to allow the retainer 7012 to expand about the shank upper portion 8 both during assembly and during locking of the polyaxial mechanism. The narrow gap X provides for a stronger retainer that has more surface contact with the shank upper portion 7008 upon locking, resulting in a sturdier connection with less likelihood of failure than a retainer ring having a greater gap. Furthermore, because the retainer 7012 body 7116 is only expanded and not compressed, the retainer 7012 does not undergo the mechanical stress that typically is placed on spring ring type retainers that may be both compressed and expanded more than once during assembly and locking.

It is foreseen that in some embodiments of the invention, the retainer 7012 inner surfaces may include a roughening or additional material to increase the friction fit against the shank upper portion 7008 prior to lock down by the rod 7021 or other longitudinal connecting member. Also, the embodiment shown in FIGS. 310-315 illustrates the surfaces 7146 and 7147 as substantially parallel, however, it is foreseen that it may be desirable to orient the surfaces obliquely or at a slight angle.

With reference to FIGS. 307, 336 and 339, the illustrated elongate rod or longitudinal connecting member 7021 (of which only a portion has been shown) can be any of a variety of implants utilized in reconstructive spinal surgery, but is typically a cylindrical, elongate structure having the outer substantially smooth, cylindrical surface 7022 of uniform diameter. The rod 7021 may be made from a variety of metals, metal alloys and deformable and less compressible plastics, including, but not limited to rods made of elastomeric, polyetheretherketone (PEEK) and other types of materials.

Longitudinal connecting members for use with the assembly 7001 may take a variety of shapes, including but not limited to rods or bars of oval, rectangular or other curved or polygonal cross-section. The shape of the receiver 7010 may be modified so as to closely hold, and if desired, fix or slidingly capture the longitudinal connecting member to the assembly 7001. Some embodiments of the assembly 7001 may also be used with a tensioned cord. Such a cord may be made from a variety of materials, including polyester or other plastic fibers, strands or threads, such as polyethyleneterephthalate. Furthermore, the longitudinal connector may be a component of a longer overall dynamic stabilization connecting member, with cylindrical or bar-shaped portions sized and shaped for being received by the receiver 7010 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 7001, for example. A damping component or bumper may be attached to the longitudinal connecting member at one or both sides of the bone screw assembly 7001. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 307 and 336, the closure structure or closure top 7018 shown with the assembly 7001 is rotatably received between the spaced arms 7062 of the receiver 7010. It is noted that the closure 7018 top could be a twist-in or slide-in closure structure. The illustrated closure structure 7018 is substantially cylindrical and includes a an outer helically wound guide and advancement structure 7162 in the form of a flange that operably joins with the guide and advancement structure 7072 disposed on the arms 7062 of the receiver 7010. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 7018 downward between the arms 7062 and having such a nature as to resist splaying of the arms 7062 when the closure structure 7018 is advanced into the channel 7064, the flange form illustrated herein as described more fully in Applicant's U.S. Pat. No. 6,726,689 is preferred in some embodiments due to the added strength provided by such flange form that beneficially cooperates with and counters any reduction in receiver strength that may occur in some embodiments that have a receiver of reduced profile designed for closely fitting with sleeves or other longitudinal connecting member components. The illustrated closure structure 7018 also includes a top surface 7164 with an internal drive 7166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 7166 is used for both rotatable engagement and, if needed, disengagement of the closure 7018 from the receiver arms 7062. It is also foreseen that the closure structure 7018 may alternatively include a break-off head designed to allow such a head to break from a base of the closure at a preselected torque, for example, 70 to 140 inch pounds. Such a closure structure would also include a base having an internal drive to be used for closure removal. A base or bottom surface 7168 of the closure is planar and further includes a point 7169 and a rim 7170 for engagement and penetration into the surface 7022 of the rod 7021 in certain embodiments of the invention. The closure top 7018 may further include a cannulation through bore (not shown) extending along a central axis thereof and through the top and bottom surfaces thereof. Such a through bore provides a passage through the closure 7018 interior for a length of wire (not shown) inserted therein to provide a guide for insertion of the closure top into the receiver arms 7062.

Preferably, the receiver 7010 and the retainer 7012 are assembled at a factory setting that includes tooling for holding and alignment of the component pieces and pinching or compressing of the retainer spring tabs 7118 toward one another. In some circumstances, the shank 7004 is also assembled with the receiver 7010 and the retainer 7012 at the factory. In other instances, it is desirable to first implant the shank 7004, followed by addition of the pre-assembled receiver and retainer at the insertion point. In this way, the surgeon may advantageously and more easily implant and manipulate the shanks 7004, distract or compress the vertebrae with the shanks and work around the shank upper portions or heads without the cooperating receivers being in the way. In other instances, it is desirable for the surgical staff to pre-assemble a shank of a desired size with the receiver, retainer and compression insert. Allowing the surgeon to choose the appropriately sized shank advantageously reduces inventory requirements, thus reducing overall cost.

Pre-assembly of the receiver 10 and the retainer 7012 is shown in FIGS. 321-329. With particular reference to FIG. 321, first the retainer 7012 is inserted into the upper receiver opening 7066, leading with one of the spring tabs 7118 with both of the spring tab top surfaces 7122 facing one arm 7062 and the retainer bottom surface 7124 facing the opposing arm 7062. The retainer 7012 is then lowered in such sideways manner into the channel 7064 and partially into the receiver cavity 7061, followed by tilting the retainer 7212 such that the top surface 7122 and thereafter the outer tab or wing 7140 of the leading spring tab 7118 is moved into a nearby receiver arm through bore 7078 as shown in FIGS. 322 and 323. With reference to FIGS. 323-326, the retainer 7012 is then further tilted or turned and manipulated within the receiver to a position within the cavity until the retainer 7012 bottom surface 7124 is directed toward the receiver cavity 7061 and the spring tab upper surfaces 7122 are facing upwardly toward the receiver channel opening 7066. To accomplish such tilting and turning of the retainer 7012, the spring tab arm 7118 located within the receiver bore 7078 is manipulated downwardly and then upwardly within the bore 7078 and finally shifted out of the bore 7078 when the opposed spring tab arm 7118 outer tab or wing 7140 moves past and clears the cylindrical surface 7084 of the receiver 7010 as shown in FIG. 326. Once the retainer bottom surface 7124 seats on the receiver surface 7104, both of the spring tab wings 7140 are partially located in opposed receiver bores 7078. With reference to FIGS. 328 and 329, a tool (not shown) is then used to grip the spring tab arms 7118 at outer surfaces thereof and squeeze or press the tabs 7118 toward one another while moving the retainer 7012 in an upward direction away from the surface 7104. When the spring tab wing surfaces 7122 abut against the surface 7090, the tool (not shown) is released and a portion or portions of each spring tab 7118 curved outer surface 7142 spring out to engage the cylindrical surface 7089 that defines a portion of the receiver recess or aperture 7088. With reference to FIG. 329, the retainer 7012 is now in a desired position for assembly with the shank 7004 with the retainer body 7116 located near and centrally within the cylindrical surface 7099. Typically, the receiver and retainer combination are shipped or otherwise provided to the end user with the spring tab outer wings 7140 wedged against the receiver as shown in FIG. 329. The receiver 7010 and the retainer 7012 combination is now pre-assembled and ready for assembly with the shank 7004 either at the factory, by surgery staff prior to implantation, or directly upon an implanted shank 7004 as will be described herein.

As illustrated in FIG. 337, the bone screw shank 7004 or an entire assembly 7001 made up of the assembled shank 7004, receiver 7010 and retainer 7012 is screwed into a bone, such as the vertebra 7017, by rotation of the shank 7004 using a suitable driving tool (not shown) that operably drives and rotates the shank body 7006 by engagement thereof at the drive feature 7042. Specifically, the vertebra 7017 may be pre-drilled to minimize stressing the bone and have a guide wire (not shown) inserted therein to provide a guide for the placement and angle of the shank 7004 with respect to the vertebra. A further tap hole may be made using a tap with the guide wire as a guide. Then, the bone screw shank 7004 or the assembly 7001 is threaded onto the guide wire utilizing the cannulation bore 7050 by first threading the wire into the opening at the bottom 7028 and then out of the top opening at the drive feature 7042. The shank 7004 is then driven into the vertebra using the wire as a placement guide. It is foreseen that the shank and other bone screw assembly parts, the rod 7021 (also having a central lumen in some embodiments) and the closure top 7018 (also with a central bore) can be inserted in a percutaneous or minimally invasive surgical manner, utilizing guide wires.

When the shank 7004 is driven into the vertebra 7017 without the remainder of the assembly 7001, the shank 7004 may either be driven to a desired final location or may be driven to a location slightly above or proud to provide for ease in assembly with the pre-assembled receiver, compression insert and retainer. With reference to FIGS. 330 and 337, the pre-assembled receiver and retainer is placed above the shank upper portion 708 until the shank upper portion is received within the opening 7110. As shown in these two figures, the receiver may be snapped or popped on to the shank with the shank and receiver axes aligned or at an angle with respect to one another. With particular reference to FIGS. 331-332, as the shank is moved into the interior of the receiver base, the shank upper portion 7008 presses upwardly against the retainer 7012, the engagement of the retainer spring tabs with the receiver surfaces 7090 keeping the retainer body 7116 in the space defined by the cylindrical surface 7099. As the retainer 7012 presses up against the surface 7090, the shank upper portion 7008 forces outward movement of the retainer body 7116 towards the cylindrical surface 7099 defining the receiver expansion recess as the spherical surface 7034 continues in an upward direction. With reference to FIG. 331, the spring tabs 7118 may bow outwardly as the retainer body 7116 expands. The retainer 7012 body 7116 then begins to contract about the spherical surface 7034 as the center of the sphere passes beyond the center of the retainer expansion recess defined by the surface 7099. At this time also, the spherical surface 7034 engages the spherical surfaces 7132 of the retainer flex fingers 7117, the fingers 7117 also prohibiting further upward movement of the shank 7004 into the channel 7064. The frictional engagement between the surface 7034 and the surfaces 7132 provide for a desired friction fit between such components that is snug or close, but not locked. Furthermore, the position of the spring tab outer wings 7140 within the receiver recesses 7088 prohibits rotation of the now coupled retainer 7012 and shank 7004 about the receiver axis B which might otherwise occur if the retainer 7012 was equipped with flex fingers 7117 but not the upwardly and outwardly extending spring tabs 7118.

With reference to FIGS. 333-335, the shank 7004 and attached retainer 7012 are then moved down into a final operative position by either an upward pull on the receiver 7010 or a downward pull on the shank, and/or, in some cases, by driving the shank 7004 further into the vertebra 7017. As best shown in FIG. 335, such movements snaps the retainer 7012 into place with the wings 7140 moving outwardly and being ultimately located in opposed bores 7078 of the receiver 7010 directly beneath the arched surfaces 7080, the spring tabs 7118 now in a neutral position with the receiver surface 7080 prohibiting upward movement of the retainer 7012 and attached shank 7004 within the receiver 7010. Furthermore, capture of the spring tab portions 7140 within the opposed receiver bores 7078 prevent rotation (about the axis B) of the retainer 7012 and shank 7004 combination with respect to the receiver 7010. The shank body 7006 may now only be manipulated (pivoted and rotated) in a non-floppy manner with respect to the receiver 7010. As also illustrated in FIG. 335, the retainer body 7116 is now seated on the receiver surface 7104. However, there is still space between the outer surface of the retainer body and the cylindrical surface 7101 of the receiver to allow for expansion locking of the retainer 7012 with respect to the receiver 7010 surface 7101 when a downward force is placed upon a rod or other captured connecting member as shown, for example, in FIG. 336. In some embodiments, when the receiver 7010 is pre-assembled with the shank 7004, the entire assembly 7001 may be implanted at this time by inserting the driving tool (not shown) into the receiver and the shank drive 7042 and rotating and driving the shank 7004 into a desired location of the vertebra 7017.

With reference to FIGS. 336, 338 and 339, the rod 7021 is eventually positioned in an open or percutaneous manner in cooperation with the at least two bone screw assemblies 7001. The closure structure 7018 is then inserted into and advanced between the arms 7062 of each of the receivers 7010. The closure structure 7018 is rotated, using a tool engaged with the inner drive 7166 until a selected pressure is reached at which point the rod 7021 engages the curved top surface 7040 of the shank 7004, pressing the shank upper portion 7008 into locked frictional engagement with the retainer 7012. Specifically, as the closure structure 7018 rotates and moves downwardly into the respective receiver 7010, the point 7169 and rim 7170 engage and penetrate the rod surface 7022, the closure structure 7018 pressing downwardly against and biasing the rod 7021 into compressive engagement with the shank upper surface that urges the shank upper portion 7008 toward the retainer 7012 and into locking engagement therewith, the retainer 7012 frictionally abutting the surface 7104 and expanding outwardly against the cylindrical surface 7101. For example, about 7080 to about 7120 inch pounds of torque on the closure top may be applied for fixing the bone screw shank 7006 with respect to the receiver 7010. It is noted that at this time, the retainer flex finger 7117 inner spherical surfaces 7132 may pull away from the shank spherical surface 7034 as shown in FIG. 336. As the final locking of the shank 7004 with respect to the receiver 7010 has now been accomplished, such a pulling away of the retainer fingers from the shank upper portion 7008 is of no consequence. The non-floppy, friction fit relationship between the retainer flex fingers 7117 and the shank surface 7034 is a temporary, advantageous engagement providing bone anchor stability and maneuverability during the bone anchor implantation and rod placement process.

If removal of the rod 7021 from any of the bone screw assemblies 7001 is necessary, or if it is desired to release the rod 7021 at a particular location, disassembly is accomplished by using the driving tool (not shown) that mates with the internal drive 7166 on the closure structure 7018 to rotate and remove such closure structure from the cooperating receiver 7010. Disassembly is then accomplished in reverse order to the procedure described previously herein for assembly.

With particular reference to FIGS. 340-385 the reference number 8001 generally represents a polyaxial bone screw apparatus or assembly according to the present invention. The assembly 8001 includes a shank 8004, that further includes a body 8006 integral with an upwardly extending upper portion or head-like capture structure 8008; a receiver 8010; and a lower retainer structure illustrated as a resilient open ring-like structure 8012. The receiver 8010 and retainer structure 8012 are initially assembled and may be further assembled with the shank 8004 either prior or subsequent to implantation of the shank body 8006 into a vertebra 8017, as will be described in greater detail below. FIG. 340 further shows a closure structure 8018 for capturing a longitudinal connecting member, for example, a rod 8021 which in turn presses against the shank upper portion 8008 into fixed frictional contact with the lower retainer 8012, so as to capture, and fix the longitudinal connecting member 8021 within the receiver 8010 and thus fix the member 8021 relative to the vertebra 8017. The illustrated rod 8021 is hard, stiff, non-elastic and cylindrical, having an outer cylindrical surface 8022. It is foreseen that in other embodiments, the rod 8021 may be elastic, deformable and/or of a different cross-sectional geometry. Furthermore, the assembly 8001 may cooperate with longitudinal connecting members that include sleeves. The receiver 8010 and the shank 8004 cooperate in such a manner that the receiver 8010 and the shank 8004 can be secured at any of a plurality of angles, articulations or rotational alignments relative to one another and within a selected range of angles both from side to side and from front to rear, to enable flexible or articulated engagement of the receiver 8010 with the shank 8004 until both are locked or fixed relative to each other near the end of an implantation procedure.

The shank 8004 is substantially similar to the shank 6004 previously described herein with respect to the assembly 6001. Thus, the shank 8004 includes the shank body 8006, upper portion or head 8008, a shank thread 8024, a neck 8026, a tip 8028, a top of thread 8032, an upper portion spherical surface 8034 a top surface 8040, a drive feature 8042 and a cannulation bore 8050 the same or substantially similar to the respective body 6006, upper portion or head 6008, shank thread 6024, neck 6026, tip 6028, top of thread 6032, spherical surface 6034, domed top surface 6040, drive feature 6042 and cannulation bore 6050 previously described herein with respect to the shank 6004 of the assembly 6001. To provide a biologically active interface with the bone, the threaded shank body 8006 may be coated, perforated, made porous or otherwise treated as previously discussed herein with respect to the shank body 6 of the assembly 1.

With particular reference to FIGS. 340 and 349-353, the receiver 8010 has a generally cylindrical and U-shaped appearance. The receiver 8010 has an axis of rotation B that is shown in FIG. 340 as being aligned with and the same as the axis of rotation A of the shank 8004, such orientation being desirable, but not required during assembly of the receiver 8010 with the shank 8004, as shown, for example, in FIG. 370. After the receiver 8010 is pivotally attached to the shank 8004, either before or after the shank 8004 is implanted in a vertebra 8017, the axis B is typically disposed at an angle with respect to the axis A, as shown, for example, in FIG. 382.

The receiver 8010 includes a substantially cylindrical base 8060 defining a bore or inner cavity, generally 8061, the base 8060 being integral with a pair of opposed upstanding arms 8062 forming a cradle and defining a channel 8064 between the arms 8062 with an upper opening, generally 8066, and a lower channel portion including a partially planar and partially U-shaped lower seat 8068, as well as pairs of opposed, facing substantially planar perimeter surfaces extending upwardly from either side of the u-shaped seat 8068, the channel 8064 having a width between the opposed surfaces 8069 for operably snugly receiving the insert 8014 and the rod 8021 or portion of another longitudinal connector between the arms 8062, the channel 8064 communicating with the base cavity 8061.

Each of the arms 8062 has a pair of perimeter surfaces 8069 and an interior surface, generally 8070 located therebetween, the surface 8070 including various inner concave and substantially cylindrical profiles, an upper one of which is a partial helically wound guide and advancement structure 8072 located adjacent top surfaces 8073 of each of the arms 8062. In the illustrated embodiment, the guide and advancement structure 8072 is a partial helically wound interlocking flangeform configured to mate under rotation with a similar structure on the closure structure 8018, as described more fully below. However, it is foreseen that for certain embodiments of the invention, the guide and advancement structure 8072 could alternatively be a square-shaped thread, a buttress thread, a reverse angle thread or other thread-like or non-threadlike helically wound discontinuous advancement structures, such as a flange form, for operably guiding under rotation and advancing the closure structure 8018 downward between the arms 8062, as well as eventual torquing when the closure structure 8018 abuts against the rod 8021 or other longitudinal connecting member. It is foreseen that the arms could have break-off extensions.

An opposed pair of upper tool receiving and engaging apertures or grooves 8074 are formed on outer surfaces 8076 of the arms 8062. It is foreseen that tool receiving grooves or apertures may be configured in a variety of shapes and sizes and be disposed at other locations on the receiver arms 8062. Located directly below the apertures are another pair of tool receiving and engaging apertures or through bores, generally 8078, that are illustrated as having a keyhole shape, and extend from the surfaces 8076 to the inner surfaces 8070. The through bores 8078 each have a substantially planar bottom surface 8079 and keyhole-like curved side surfaces 8080 and an upper arched surface 8081. It is foreseen that other geometries are possible. As will be described in greater detail below, the through bores 8078 are sized and shaped to provide clearance within the receiver 8010 for down-loading the retainer 8012 from the receiver upper opening 8066 and between the interior surfaces 8070 of the arms 8062 and into the receiver cavity 8061. The bores 8078 also provide access into the receiver 8010 for manipulating the retainer 8012 and/or the insert 8014 during and after assembly.

Returning to the interior surface 8070 of the receiver arms 8062, located below each guide and advancement structure 8072 is a run-out feature for the guide and advancement structure 8072 partially defined by a discontinuous cylindrical surface 8082 having a diameter approximately the same or slightly greater than a greater diameter of the guide and advancement structure 8072. Below the surface 8082, moving in a direction toward the base 8060, is another cylindrical surface 8084 having a diameter smaller than the diameter of the surface 8082 and illustrated as slightly greater than an inner or lesser diameter of the guide and advancement structure 8072. The surface 8084 is also discontinuous, being formed only at the arms 8062. Located between each of the surfaces 8082 and 8084 is a discontinuous annular surface 8085 running substantially perpendicular to the axis B. Formed in each of the surfaces 8084 are curved recesses or apertures, generally 8088, each partially formed by a cylindrical surface 8089 and arched surfaces 8090 extending from the surface 8089 to the surface 8084. The recesses 8088 are located adjacent to and at either side of the respective through bore 8078, the upper arched portion 8081 of the bore 8078 also being formed in and through the surface 8084. The surfaces forming the recesses 8088 cooperate with the retainer 8012 during assembly with the receiver 8010 and the shank 8004, allowing the resilient retainer 8012 to be temporarily retained in an upper portion of the receiver as will be described in greater detail below.

Returning to the substantially planar peripheral surfaces 8069, each arm 8062 includes a pair of projecting ridges or stops 8092, located on each surface 8069, for a total of four stops 8092 that are located near the annular surface 8085 and are spaced from the cylindrical surface 8084. The stops 8092 of one arm 8062 face the opposing pair of stops 8092 on the other arm 8062, each stop 8092 projecting outwardly from the respective planar surface 8069. The illustrated stops 8092 are elongate, running from arm outside or edge surfaces 8094 toward the respective cylindrical surface 8084 in a direction perpendicular to the axis B. As will be described in greater detail below, the stops 8092 cooperate with surfaces of the insert 8014 to retain the insert 8014 within the channel 8064 of the receiver 8010. In the illustrated embodiment, at a location below the stops 8092, each arm includes a curved surface 8095 connecting each substantially planar surface 8069 with the U-shaped seat 8068, an edge 8096 forming a juncture of the curved surface 8095 and the U-shaped seat 8068. As will be described in greater detail below and is shown in FIGS. 374-379, for example, when the insert 8014 is positioned in the receiver channel 8064 between the surfaces 8069 and below the stops 8092, the insert 8014 initially typically rests or seats at or near the surface 8095 and the edge 8096 and is later pressed along and below the edge 8096 and into the seat 8068 into frictional, locking engagement with the receiver 8010.

Returning to FIGS. 349-353, the surface 8084 terminates at a lower ledge 8098 that runs radially outwardly from the surface 8084 to another cylindrical surface 8099. The ledge 8098 is substantially perpendicular to the axis B and located adjacent the curved surfaces 8095 that partially form the edges 8096. The cylindrical surface 8099 is partially discontinuous at the arms 8062 and also extends downwardly into the base 8060, defining a continuous upper cylindrical portion of the base cavity 8061. Each bore 8078 is substantially formed in the surface 8099 (with the exception of the upper arched portion 8081 that is formed in the surface 8084), the bore 8078 extending outwardly to the arm surface 8076. The cylindrical surface 8099 is oriented substantially parallel to the axis B and is sized and shaped to receive an expanded retainer 8012. The surfaces 8098 and 8099 define a circumferential recess that is sized and shaped to receive a portion of the retainer 8012 as it expands around the shank upper portion 8008 at the surface 8034 as the shank 8008 moves upwardly toward the channel 8064 during assembly. A cylindrical surface 8101 located below the cylindrical surface 8099 is sized and shaped to closely receive the retainer 8012 when the retainer is in a neutral or slightly expanded position as will be described in greater detail below. Thus, the cylindrical surface 80101 has a diameter smaller than the diameter of the cylindrical surface 8099 that defines the expansion area for receiving the retainer 8012. The surface 8101 is joined or connected to the surface 8099 by one or more beveled, curved or frusto-conical surfaces 8102. The surfaces 8102 allow for sliding gradual movement of the retainer 8012 into the space defined by the surface 8101 and ultimate seating of the retainer 8012 on a lower annular surface 8104 located below and adjacent to the cylindrical surface 8101. Located below and adjacent to the annular seating surface 8104 is a circular edge or narrow substantially cylindrical surface 8106 that communicates with a beveled or flared bottom opening surface 8107, the surface 8107 communicating with an exterior base surface 8108 of the base 8060, defining a lower opening, generally 8110, into the base cavity 8061 of the receiver 8010.

With particular reference to FIGS. 340 and 343-348, the open, friction fit retainer 8012 that operates to capture and frictionally engage the shank upper portion 8008 within the receiver 8010 has a central axis that is operationally the same as the axis B associated with the receiver 8010 when the shank upper portion 8008 and the retainer 8012 are installed within the receiver 8010. The retainer 8012 includes a substantially cylindrical discontinuous lower body 8116, a plurality of flex fingers or panels, 8117 extending upwardly from the body 116 and a pair of opposed spring arms or tabs 8118, also extending upwardly from the body 8116. The retainer ring 8012 is made from a resilient material, such as a stainless steel or titanium alloy, so that the retainer 8012 body 8116 may be expanded and the fingers and tabs (8117 and 8118) of the retainer may be manipulated during various steps of assembly as will be described in greater detail below. The retainer 8012 has a central channel or hollow through bore, generally 8121, that passes entirely through the retainer 8012 from curved retainer arm or tab 8118 top surfaces 8122 to a bottom surface 8124 of the retainer body 8116. Surfaces that define the channel or bore 8121 include an inner lower frusto-conical surface 8128 adjacent to the retainer body bottom surface 8124, a substantially cylindrical surface 8130 adjacent the frusto-conical surface 8128 and a partially discontinuous substantially spherical surface 8132 adjacent the surface 8130, the surface 8132 being continuous near the cylindrical surface 8130 with the exception of a through slot or slit, generally 8134. The surface 8132 is in a plurality of segments or pieces at the flex fingers 8117 wherein a plurality of substantially evenly spaced slots 8136 running outwardly and upwardly through an upper surface 8137 separate the surface 8132 into the individual flex fingers 8117. In the illustrated embodiment, the slots 8136 and the through slit 8134 form six substantially uniform flex fingers or tabs 8117 as well as partially define the two spring tabs 8118, each finger and tab having the inner spherical surface 8132. It is foreseen that more or fewer flex fingers may be made by the forming of more or fewer slots 8136. The discontinuous spherical surface 8132 is sized and shaped to closely fit about and snap onto the shank surface 8034 during assembly as will be described in greater detail below. The surface 8132 may have a radius the same, slightly larger or slightly smaller than the radius of the spherical shank surface 8034. The surface 8132 and/or the shank surface 8034 may include a surface treatment for enhancing friction between such surfaces. In some embodiments, the flexible tabs 8117 may be bent to further enhance frictional engagement. In other embodiments, some or all of the spherical surface 8132 may be replaced by planar or faceted surfaces. In operation, the discontinuous surface 8132 advantageously frictionally engages the bone screw shank upper portion 8008, allowing for un-locked but non-floppy placement of the angle of the shank 8004 with respect to the receiver 8010 during surgery prior to locking of the shank 8004 with respect to the receiver 8010 near the end of the procedure. At the time of locking engagement, downward and outward force placed on the retainer 8012 by the shank upper portion 8008 expands the retainer body 8116 at the slit 8134 and the individual flex fingers 8117 no longer frictionally grip the spherical surface 8034 of the upper portion 8008. In some embodiments, to aid in bending flexibility and resiliency, certain flex fingers 8117 may have sloping outer surfaces (not shown) that reduce a width of, or substantially eliminate the top planar surface 8137. It is foreseen that in other embodiments of the invention other surface geometries may be used to gain a level of resiliency desired for expansion and gripping of the fingers 8117 about the shank upper portion 8008. It is noted that the fingers 8117 that are directed generally upwardly toward the receiver channel 8064 advantageously sufficiently snap about and then grip the shank surface 8034 to an extent to provide the friction fit desired for non-floppy placement of the shank body 8006 at a desired angle with respect to the receiver 8010 during manipulation of the bone screws 8001 and the rod 8021 or other longitudinal connecting member during surgery. However, as compared to bone screw inserts such as collets known in the art that include downwardly directed portions or panels that are ultimately wedged between a receiver surface and a shank surface upon final locking of the shank to the receiver, the thin upwardly directed fingers 8117 that extend away from the shank locking surface that are not as strong as the retainer body 8116, do not participate or cooperate with the final locking of the shank upper portion 8008 to the retainer 8012 and the retainer 8012 to the receiver inner surfaces 8101 and 8104. For such purpose, the more substantial retainer body 8116 having only the very narrow slit 8134, used for expansion purposes only, is the component that locks the shank upper portion 8008 between the receiver 8010 and the rod 8021 or other longitudinal connecting member.

The retainer body 8116, the flex fingers 8117 and a substantial part of each of the spring tabs 8118 have an outer substantially cylindrical profile, sized and shaped to closely and slidingly fit within the receiver cavity 8061 with the exception of outward extensions or wings, generally 8140, of the spring tabs 8118 that are located adjacent to the upper surfaces 8122, each wing extending outwardly away from the respective tab body 8118 and having a curved outward surface 8142 that is substantially cylindrical with a curved or frusto-conical lower portion, the surfaces 8142 being sized and shaped to closely cooperate and frictionally engage the cylindrical surface 8089 of the receiver recess 8088. Each spring tab 8118 further includes first and second inner planar surfaces 8144 and 8145, the surface 8144 running from the curved top surface 8122 to the surface 8145 and the surface 8145 running from the surface 8144 to the inner spherical surface 8132. It is foreseen that in other embodiments of the invention, fewer or greater number of planar or other surfaces with other geometries may extend between the top surface 8122 and the spherical surface 8132.

The through slit 8134 of the resilient retainer 8012 is defined by first and second end surfaces, 8146 and 8147 disposed in spaced relation to one another (they may also be touching) when the retainer is in a neutral state. Both end surfaces 8146 and 8147 are disposed substantially perpendicular to the bottom surface 8124. A width X between the surfaces 8146 and 8147 is very narrow, in some embodiments of about or less than 0.004 inches, the narrow slit functioning to provide stability to the retainer 8012 during operation, specifically retention of the shank upper portion 8008 within the receiver 8010 that must withstand extreme pressure both during assembly and subsequent patient movement. The slit 8134 may be made, for example, by an electrical discharge machining (EDM) process with the resulting surfaces 8146 and 8147 almost touching. Because the retainer 8012 is top loadable in a neutral state and the retainer 8012 does not need to be compressed to fit within the receiver cavity 8061, the width X may be much smaller than what is often required for a bottom loaded compressible retainer ring. The gap X functions only in expansion to allow the retainer 8012 to expand about the shank upper portion 8 both during assembly and during locking of the polyaxial mechanism. The narrow gap X provides for a stronger retainer that has more surface contact with the shank upper portion 8008 upon locking, resulting in a sturdier connection with less likelihood of failure than a retainer ring having a greater gap. Furthermore, because the retainer 8012 body 8116 is only expanded and not compressed, the retainer 8012 does not undergo the mechanical stress that typically is placed on spring ring type retainers that may be both compressed and expanded more than once during assembly and locking.

It is foreseen that in some embodiments of the invention, the retainer 8012 inner surfaces may include a roughening or additional material to increase the friction fit against the shank upper portion 8008 prior to lock down by the rod 8021 or other longitudinal connecting member. Also, the embodiment shown in FIGS. 343-348 illustrates the surfaces 8146 and 8147 as substantially parallel, however, it is foreseen that it may be desirable to orient the surfaces obliquely or at a slight angle.

With particular reference to FIGS. 340 and 354-361, the lock and release insert 8014 is illustrated that is sized and shaped to be received by and down-loaded into the receiver 8010 at the upper opening 8066. The insert 8014 has an operational central axis that is the same as the central axis B of the receiver 8010. In operation, an insert 8014 that has been pressed downwardly during the locking of the shank 8004 in a desired angular position with respect to the receiver 8010, by, for example, compression from the rod 8021 and closure top 8018, is wedged into engagement with the receiver 8010 at outer edge surfaces of the receiver arms, the insert retaining the shank 8006 in a locked position even if the rod 8021 and closure top 8018 are removed as shown in FIG. 383. Such locked position may also be released by the surgeon if desired. The insert 8014 is thus preferably made from a resilient material, such as a stainless steel or titanium alloy, so that portions of the insert may be pinched and un-wedged from the receiver 8010.

The insert 8014 includes a substantially U-shaped body 8150 having opposed ends, generally 8151, the body 8150 being sized and shaped to extend completely through the U-shaped channel 8064 between the opposed outer surfaces 8094 of the arms 8062 so as to cooperate with the receiver arm outer side surfaces 8069, the stops 8092, and the insert wedging edge surfaces 8096 formed by each curved surface 8095 and the channel seat 8068. A U-shaped channel surface or saddle 8153 formed in the body 8150 also extends between the insert ends 8151 and when the insert 8014 is assembled with the receiver 8010, the saddle 8153 substantially aligns with the receiver channel 8064. The saddle 8153 is formed by the insert body 8150 and by two upstanding arms 8157 and is sized and shaped to closely receive the rod 8021 or other longitudinal connecting member. A bore, generally 8160, is disposed primarily within and through the insert body 8156 that runs along the axis B and communicates with the U-shaped channel formed by the saddle 8153 and upstanding arms 8157. The bore 8160 is sized and shaped to provide space and clearance for the shank head portion 8040 to extend therethrough so that a rod 8021 or other connecting member seated on the saddle 8153 also directly frictionally engages the spherical surface 8040. The bore 8160 is also sized such that in any angular position of the shank 8004 with respect to the receiver 8010, the spherical surface 8040 does not directly engage the insert 8014, but rather is in contact with the rod 8021 or other longitudinal connecting member. As best shown in FIGS. 381 and 382, when the shank 8004 is locked in any angular position by the rod 8021, the insert 8014 contacts the shank 8004 at the spherical surface 8034 and not the spherical surface 8040. It is foreseen that an alternative insert embodiment may be configured to include planar holding surfaces that closely hold a square or rectangular bar as well as hold a cylindrical rod-shaped, cord, or sleeved cord longitudinal connecting member.

The arms 8157 disposed on either side of the saddle 8153 and extend upwardly therefrom are sized and configured for ultimate placement above the retainer spring tabs 8118 and beneath the cylindrical run-out surface 8082 located below the receiver guide and advancement structure 8072. The arms 8157 include outer curved, convex surfaces 8163 that is illustrated as partially cylindrical and curved top surfaces 8164 that are ultimately positioned in spaced relation with the closure top 8018, so that the closure top 8018 frictionally engages the rod 8021 only, pressing the rod 8021 downwardly against both the shank top surface 8040 and the insert saddle 8153, the shank 8004 upper portion 8008 then pressing against the retainer 8012 to lock the polyaxial mechanism of the bone screw assembly 8001 at a desired angle. The partially cylindrical surface 8163 extends from the top surface 8164 to a bottom surface 8165 of the insert 8014. The surface 8163 is sized and shaped to generally fit within the receiver surface 8084. Formed in each surface 8163 and extending through the saddle 8153 surface is a through bore 8166, the bore 8166 used for manipulation and removal of the insert 8014 from the receiver through the receiver bore 8074. A recessed surface portion 8167 located beneath each bore 8166 is sized and shaped to receive the curved upper surface 8122 of a wing 8140 of a retainer 8012 spring tab 8118. A portion of the recessed portion 8167 extends completely through the insert 8014 and is defined by a lower notched surface 8169. The recessed portion 8167 is further defined by an upper arched surface 8170 that communicates with the bore 8166 and a flat or slightly convex surface 8171 that extends from the arched surface 8170 to the lower notched surface 8169.

The insert 8014 extends from the substantially cylindrical outer arms surfaces 8163 equally outwardly to each end 8151. Substantially planar outer side surfaces 8172 extend from each arm surface 8163 to a substantially planar surface 8174 disposed perpendicular thereto, the surfaces 8174 substantially defining each of the ends 8151. Also, adjacent to the side surfaces 8172, substantially planar upper surfaces 8175 run from the arms 8157 to the end surface 8174. A recess, generally 8176, is located directly beneath the side surfaces 8172 and is also formed in each end surface 8174. Each recess 8176 extends all the way from the end surface 8174 to the arm surface 8163 and is substantially defined by a substantially planar tapering surface 8177 and an upper lip 8178. Pairs of opposed surfaces 8177 are sized and shaped to wedge against and between opposed surfaces 8068 forming the seat of the receiver channel 8064 to lock the insert 8014 against the receiver 8012 and thus lock the polyaxial mechanism of the assembly 8001 as best shown in FIGS. 378 and 379, for example. Portions of the surfaces 8177 and respective adjacent end surfaces 8174 terminate at a lower surface 8179 that curves or tapers downwardly to the base rim 8165. Further cut-outs, tapers or bevels may be made to the surfaces to provide adequate clearance and ease of manipulation of the insert 8014 within the receiver 8010, such as the angular surfaces 8179' running from the surface 179 to each of the surfaces 8177.

The insert bore, generally 8160, is substantially defined at the body 8150 by an inner cylindrical surface 8180 that communicates with the saddle 8153 and a lower concave substantially spherical surface 8181 having a radius the same or substantially similar to a radius of the surface 8034 of the shank upper portion 8008. The surface 8181 terminates at the base 8165 and the lower notched surface 8169. The through bore 8160 is not completely cylindrical at the saddle surface 8153, with portions of the bore extending outwardly towards each end 8151 to provide more than adequate clearance for the shank upper portion surface to fully and directly engage the rod 8021 or other longitudinal connecting member at any and all angular positions of the shank 8004 with respect to the receiver 8010. The bore 8160 is also sized and shaped to receive the driving tool (not shown) therethrough that engages the shank drive feature when the shank body 8006 is driven into bone with the receiver 8010 attached. Also, the bore 8160 receives a manipulation tool (not shown) used for releasing the insert 8014 from a locked position with the receiver, the tool pressing down on the shank and also gripping the insert 8014 at the opposed through bores 8166 or with other tool engaging features. A manipulation tool for un-wedging the insert 8014 from the receiver 8010 may also access the bores 8166 from the receiver through bores 8074. The illustrated insert 8014 may further include other features, including grooves and recesses for manipulating and holding the insert 8014 within the receiver 8010 and providing adequate clearance between the retainer 8012 and the insert 8014.

As will be discussed in greater detail below, frictional engagement between the insert 8014 and the receiver 8010, more particularly, the wedging of the tapered surfaces 8177 into the edge 8096 defined by the seat surfaces 8068, provides independent locking of the polyaxial mechanism of the assembly 8001, maintaining the upper shank portion 8008 in locked engagement by and between the retainer 8012 and the insert 8014 even if the closure top 8018 and/or rod 8021 are thereafter removed from the receiver 8010.

With reference to FIGS. 340 and 377-382, the illustrated elongate rod or longitudinal connecting member 8021 (of which only a portion has been shown) can be any of a variety of implants utilized in reconstructive spinal surgery, but is typically a cylindrical, elongate structure having the outer substantially smooth, cylindrical surface 8022 of uniform diameter. The rod 8021 may be made from a variety of metals, metal alloys and deformable and less compressible plastics, including, but not limited to rods made of elastomeric, polyetheretherketone (PEEK) and other types of materials, such as polycarbonate urethanes (PCU).

Longitudinal connecting members for use with the assembly 1 may take a variety of shapes, including but not limited to rods or bars of oval, rectangular or other curved or polygonal cross-section. The shape of the insert 8014 may be modified so as to closely hold the particular longitudinal connecting member used in the assembly 8001. Some embodiments of the assembly 8001 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 8014 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 8001, for example. A damping component or bumper may be attached to the longitudinal connecting member at one or both sides of the bone screw assembly 8001. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 340 and 377-382, the closure structure or closure top 18 shown with the assembly 8001 is rotatably received between the spaced arms 8062 of the receiver 8010. It is noted that the closure 8018 top could be a twist-in or slide-in closure structure. The illustrated closure structure 8018 is substantially cylindrical and includes a an outer helically wound guide and advancement structure 8182 in the form of a flange that operably joins with the guide and advancement structure 8072 disposed on the arms 8062 of the receiver 8010. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 8018 downward between the arms 8062 and having such a nature as to resist splaying of the arms 8062 when the closure structure 8018 is advanced into the channel 8064, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 8010 that may more advantageously engage longitudinal connecting member components. The illustrated closure structure 8018 also includes a top surface 184 with an internal drive 8186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 8186 is used for both rotatable engagement and, if needed, disengagement of the closure 8018 from the receiver arms 8062. It is also foreseen that the closure structure 80 18 may alternatively include a break-off head designed to allow such a head to break from a base of the closure at a preselected torque, for example, 8070 to 8140 inch pounds. Such a closure structure would also include a base having an internal drive to be used for closure removal. A base or bottom surface 8188 of the closure is planar and further includes a point 8189 and a rim 8190 for engagement and penetration into the surface 8022 of the rod 8021 in certain embodiments of the invention. The closure top 8018 may further include a cannulation through bore (not shown) extending along a central axis thereof and through the top and bottom surfaces thereof. Such a through bore provides a passage through the closure 8018 interior for a length of wire (not shown) inserted therein to provide a guide for insertion of the closure top into the receiver arms 8062.

An alternative closure top 8018' for use with a deformable rod 8021', such as a PEEK rod, is shown in FIGS. 384 and 385. The top 8018' is identical to the top 8018 with the exception that a point 8189' is located on a domed surface 8190' in lieu of the planar bottom with point and rim of the closure top 8018.

Preferably, the receiver 8010, the retainer 8012 and the insert 8014 are assembled at a factory setting that includes tooling for holding and alignment of the component pieces and pinching or compressing of the retainer 8012 spring tabs 8118 and manipulating the insert 8014. In some circumstances, the shank 8004 is also assembled with the receiver 8010, the retainer 8012 and the insert 8014 at the factory. In other instances, it is desirable to first implant the shank 8004, followed by addition of the pre-assembled receiver, retainer and insert at the patient's insertion point. In this way, the surgeon may advantageously and more easily implant and manipulate the shanks 8004, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8008 and/or hydroxyapatite on the shank 8006), with the receiver, retainer and compression insert. Allowing the surgeon to choose the appropriately sized or treated shank 8004 advantageously reduces inventory requirements, thus reducing overall cost.

Pre-assembly of the receiver 8010, the retainer 8012 and the insert 8014 is shown in FIGS. 362-369. With particular reference to FIG. 362, first the retainer 8012 is inserted into the upper receiver opening 8066, leading with one of the spring tabs 8118 with both of the spring tab top surfaces 8122 facing one arm 8062 and the retainer bottom surface 8124 facing the opposing arm 8062. With reference to FIG. 362 and also FIGS. 363 and 364, the retainer 8012 is then lowered in such sideways manner into the channel 8064 and partially into the receiver cavity 8061, followed by tilting the retainer 8212 such that the top surface 8122 and thereafter the outer tab or wing 8140 of the leading spring tab 8118 is moved into a nearby receiver arm through bore 8078. With reference to FIG. 365, the retainer 8012 is then further tilted or turned and manipulated within the receiver to a position within the cavity until the retainer 8012 bottom surface 8124 is directed toward the receiver cavity 8061 and the spring tab upper surfaces 8122 are facing upwardly toward the receiver channel opening 8066. To accomplish such tilting and turning of the retainer 8012, the spring tab arm 8118 located within the receiver bore 8078 is manipulated downwardly and then upwardly within the bore 8078 and finally shifted out of the bore 8078 when the opposed spring tab arm 8118 outer tab or wing 8140 moves past and clears the cylindrical surface 8084 of the receiver 8010. Once the retainer bottom surface 8124 seats on the receiver surface 8104, both of the spring tab wings 8140 are partially located in opposed receiver bores 8078.

With reference to FIGS. 365 and 366, the compression insert 8014 is then downloaded into the receiver 8010 through the upper opening 8066 with the bottom surface 8179 facing the receiver arm top surfaces 8073 and the insert arms 8157 aligned with the receiver arms 8062. The insert 8014 is then lowered toward the channel seat 8068 until the insert 8014 arm upper surfaces 8164 are adjacent the run-out area below the guide and advancement structure 8072 defined in part by the cylindrical surface 8082, with the U-shaped channel or saddle surface 8153 of the insert 8014 aligned with the channel 8064 of the receiver 8010. With reference to FIG. 366, at this time, the side surfaces 8172 at the insert ends 8151 are located above the four stops 8092 located on the receiver inner side surfaces 8069 with the lips 8178 resting on each of the stops 8092. With reference to FIG. 367, the insert 8014 is then pushed downwardly toward the receiver base 8060, the resilient u-shaped saddle 8153 being slightly compressed inwardly until the surfaces 8172 pass over the stops 8092. At this time, the insert 8014 is captured within the receiver 8010 between the stops 8092 and the retainer 8012.

With reference to FIGS. 368 and 369, a tool (not shown) is then used to grip the retainer spring tab arms 8118 at outer surfaces thereof and squeeze or press the tabs 8118 toward one another while moving the retainer 8012 in an upward direction away from the receiver surface 8104. With reference to FIG. 369, when the spring tab wing surface projections 8142 face the receiver surface 8089, the tool (not shown) is released and a portion or portions of each spring tab 8118 spring out to engage the surface 8089. The retainer 8012 and the insert 8014 are now in a desired position for shipping and also for assembly with the shank 8004. The insert 8014 recessed areas 8167 are located adjacent to the retainer spring tab top surfaces 8122. The insert 8014 is fully captured within the receiver 8010 by the stops 8092 and the geometry of the insert 8014 that extends fully within the channel 8064 of the receiver 8010 advantageously provides an insert 8014 with a saddle 8153 fully aligned with the receiver channel 8064 that cannot be rotated out of alignment as may occur with known inserts that are substantially cylindrical in form.

Typically, the receiver, insert and retainer combination are shipped or otherwise provided to the end user with the spring tab outer wings 8140 wedged against the receiver as shown in FIG. 369. The receiver 8010, retainer 8012 and insert 8014 combination is now pre-assembled and ready for assembly with the shank 8004 either at the factory, by surgery staff prior to implantation, or directly upon an implanted shank 8004 as will be described herein.

As illustrated in FIG. 370, the bone screw shank 8004 or an entire assembly 8001 made up of the assembled shank 8004, receiver 8010, retainer 8012 and compression insert 8014, is screwed into a bone, such as the vertebra 8017, by rotation of the shank 8004 using a suitable driving tool (not shown) that operably drives and rotates the shank body 8006 by engagement thereof at the drive 8042. Specifically, the vertebra 8017 may be pre-drilled to minimize stressing the bone and have a guide wire (not shown) inserted therein to provide a guide for the placement and angle of the shank 8004 with respect to the vertebra. A further tap hole may be made using a tap with the guide wire as a guide. Then, the bone screw shank 8004 or the entire assembly 8001 is threaded onto the guide wire utilizing the cannulation bore 8050 by first threading the wire into the opening at the bottom 8028 and then out of the top opening at the drive feature 8042. The shank 8004 is then driven into the vertebra using the wire as a placement guide. It is foreseen that the shank and other bone screw assembly parts, the rod 8021 (also having a central lumen in some embodiments) and the closure top 8018 (also with a central bore) can be inserted in a percutaneous or minimally invasive surgical manner, utilizing guide wires. When the shank 8004 is driven into the vertebra 8017 without the remainder of the assembly 8001, the shank 8004 may either be driven to a desired final location or may be driven to a location slightly above or proud to provide for ease in assembly with the pre-assembled receiver, compression insert and retainer.

With further reference to FIG. 370, the pre-assembled receiver, insert and retainer are placed above the shank upper portion 8008 until the shank upper portion is received within the opening 8110. With particular reference to FIGS. 371 and 372, as the shank upper portion 8008 is moved into the interior 8061 of the receiver base, the shank upper portion 8008 presses upwardly against the retainer 8012 in the recess partially defined by the cylindrical surface 8099. As the portion 8008 continues to move upwardly toward the channel 8064, the surface 8034 forces outward movement of the retainer 8012 towards the cylindrical surface 8099 defining the receiver expansion recess. The retainer 8012 begins to contract about the spherical surface 8034 as the center of the sphere (shown in dotted lines) passes beyond the center of the retainer expansion recess. At this time also, the spherical surface 8034 moves into engagement with the surfaces 8132 of the retainer flex tabs 8117, the tabs 8117 expanding slightly outwardly to receive the surface 8034. With reference to FIG. 372, the spherical surface 8034 then enters into full frictional engagement with the panel inner surfaces 8132. At this time, the retainer 8012 panels and the surface 8034 are in a fairly tight friction fit, the surface 8034 being pivotable with respect to the retainer 8012 with some force. Thus, a tight, non-floppy ball and socket joint is now created between the retainer 8012 and the shank upper portion 8.

With reference to FIGS. 373 and 374, the shank 8004 and attached retainer 8012 are then moved partially downwardly and then into a fully locked desired position (FIG. 375) with the retainer 8012 bottom surface 8124 seated on the receiver surface 8104. This may be accomplished by either an upward pull on the receiver 8010 or, in some cases, by driving the shank 8004 further into the vertebra 8017. Also with reference to FIGS. 375 and 376, the insert 8014 may be pressed downwardly by a tool (not shown) and/or ultimately by a rod and closure top as shown in FIGS. 377-380. Also, in some embodiments, when the receiver 8010 is pre-assembled with the shank 8004, the entire assembly 8001 may be implanted at this time by inserting the driving tool (not shown) into the receiver and the shank drive 8042 and rotating and driving the shank 8004 into a desired location of the vertebra 8017. With further reference to FIGS. 375 and 376, at this time, the receiver 8010 may be articulated to a desired angular position with respect to the shank 8004, such as that shown in FIG. 382, that will be held, but not locked, by the frictional engagement between the retainer 8012 panels 8117 and the shank upper portion 8008.

With particular reference to FIGS. 374-376, prior to assembly with the rod 8021 and the closure top 8018, the compression insert 8014 upper end surfaces 8175 are located directly below the receiver stops 8092 (see FIG. 374) and the sloping or tapering surfaces 8177 are resting on or near the edge 8096 that defines the beginning of the receiver channel seat 8068 that is either substantially vertical or may also have an inward slope. With particular reference to FIGS. 378 and 379, as the closure top and rod press down upon both the shank upper portion 8008 and the insert saddle 8153, the surfaces 8177 of the insert are wedged against the receiver edges 8096, pressing the insert into a full frictional engagement with the receiver 8010. With reference to FIG. 380, at this time, the insert through bores 8166 are aligned with the upper arched portion 81 of the receiver keyhole like through bores 8078. Thus, a tool (not shown) may be used to press inwardly on the insert 8014 at either side thereof at the bores 8166 and pull the insert 8014 upwardly away from the receiver seat 8068 and edge surface 8096.

The rod 8021 is eventually positioned in an open or percutaneous manner in cooperation with the at least two bone screw assemblies 8001. The closure structure 8018 is then inserted into and advanced between the arms 8062 of each of the receivers 8010. The closure structure 8018 is rotated, using a tool engaged with the inner drive 8186 until a selected pressure is reached at which point the rod 8021 engages the bone screw shank 8004 at the upper surface 8004 as well as the saddle 8153 of the compression insert 8014, pressing the insert spherical surface 8181 against the shank spherical surface 8034, the rod 8021 pressing the shank upper portion 8008 into locked frictional engagement with the retainer 8012. Specifically, as the closure structure 8018 rotates and moves downwardly into the respective receiver 8010, the point 8189 and rim 8190 engage and penetrate the rod surface 8022, the closure structure 8018 pressing downwardly against and biasing the rod 8021 into direct compressive engagement with the shank upper portion 8008 toward the retainer 8012 and into locking engagement therewith, the retainer 8012 frictionally abutting the surface 8104 and expanding outwardly against the cylindrical surface 8101. For example, about 8080 to about 8120 inch pounds of torque on the closure top may be applied for fixing the bone screw shank 8006 with respect to the receiver 8010. As best shown in FIGS. 381 and 382, as the retainer 8012 expands outwardly against the receiver cylindrical surface 8101, the panels 8117 are pulled away from the shank upper portion 8008, pulling the friction fit surface 8132 away from the spherical surface 8034. This is not of concern at this time as the friction fit feature, temporarily advantageous for articulation and placement of the shanks 8004 with respect to the receivers 8010 during the surgical process, is no longer required.

With reference to FIGS. 381 and 382, two different angular configurations of the shank 8004 and receiver 8010 are shown. With respect to both of the drawing figures, the rod 8021 bears down directly on the shank upper surface 8040 when the assembly 8001 is in a locked position. Also, when in a locked position, the insert surface 8181 directly engages a portion of the shank spherical surface 8034. Thus, the closure top 8018 can then be loosened without loosening the lock on the polyaxial mechanism provided by the insert 8014 pressing on the shank surface 8034. With reference to FIGS. 383-385, the rod 8021 and closure 8018 are shown removed at FIG. 383 and replaced by a deformable rod 8021' and cooperating closure top 8018' to result in an alternative assembly 8001'.

If a user wishes to unlock the insert 8014 from the receiver 8010, a tool (not shown) may be used that includes extensions or prongs that are received by and through the opposed through bores 8078 of the receiver 8010 and received into the through bores 8166 of the insert 8014. Such tool is then pulled upwardly in a direction along the axis B away from the receiver base 8060, thereby pulling the insert slightly upwardly and away from the receiver base 8060 and releasing the surface 8177 from the receiver surface 8096. Alternatively, if both the closure top 8018 or 8018' and the rod 8021 or 8021' are already removed from the receiver 8010, another manipulation tool (not shown) may be used that is inserted into the receiver at the opening 8066 and between the insert arms 8157, with prongs or extensions thereof extending outwardly into the insert through bores 8166; a piston-like portion of the tool thereafter pushing directly on the shank upper portion 8008, thereby pulling the insert 8014 surface 8177 away from the receiver surface 8096 and thus releasing the polyaxial mechanism. At such time, the shank 8004 may be articulated with respect to the receiver 8010, and the desired friction fit returns between the retainer 8012 and the shank surface 8034, so that an adjustable, but non-floppy relationship still exists between the shank 8004 and the receiver 8010. If further disassembly if the assembly 8001 is desired, such is accomplished in reverse order to the procedure described previously herein for assembly.

With reference to FIGS. 386-394, an alternative polyaxial bone screw 8011" according to the invention is shown that includes the shank 8004, receiver 8010 retainer 8012, rod 8021 and closure top 8018 of the assembly 8001 previously described herein. An insert 8014' is included in the assembly 8001" that is substantially similar to the insert 8014 previously described herein. Thus, the insert 8014' includes a body 8150', opposed ends 8151', a saddle 8153', upstanding arms 8157', a through bore 8160' the same or similar to the respective body 8150, opposed ends 8151, saddle 8153, upstanding arms 8157 and through bore 8160 previously described herein with respect to the insert 8014. The insert 8014' also includes pairs of side surfaces 8172', a pair of outer end surfaces 8174', a recess with tapered surfaces 8177' and a lip 8178' located between the surfaces 8177' and the side surfaces 8172' that are substantially similar to the respective side surfaces 8172, end surfaces 8174, tapered surfaces 8177 and lip 8178 previously described herein with respect to the insert 8014 with the exception that the surfaces 8177' are located further inwardly than the similar surfaces 8177 such that the insert 8014' does not lock up against the receiver edge 8096 when the insert 8014' is pressed downwardly toward the receiver base 8060. Thus, with particular reference to FIGS. 392-394, when the closure top 18 presses the rod 8021 into direct locking engagement with the shank top surface 8040, the insert surfaces 8177' move downwardly in spaced relation with the receiver channel seat surfaces 8068 and do not wedge against or otherwise engage the edge surface 8096. When the closure top 8018 is removed from the assembly 8001", the insert 8014' loosens also and the polyaxial mechanism is unlocked. As with the assembly 8001, once the shank upper portion 8008 is unlocked from the retainer 8012, the retainer flex panels 8117 resiliently move back into engagement with the shank surface 8034, once again providing a friction fit relationship between the shank upper portion 8008 and the retainer 8012.

With reference to FIGS. 395-397, a polyaxial bone screw assembly 8001' is shown having the bone screw shank 8004, retainer 8012, rod 8021 and closure top 8018 identical or substantially similar to the assembly 8001 and 8001" previously described herein. The assembly 8001' however, does not include an insert 8014 or 8014'.

It is to be understood that while certain forms of the present invention have been illustrated and described herein, it is not to be limited to the specific forms or arrangement of parts described and shown.

What is claimed is:

1. A receiver assembly for securing a rod to a capture head of a bone anchor that is implantable into a bone of a patient, the receiver assembly comprising:
   a receiver including an upper opening, a bottom opening opposite the upper opening, a base cavity extending upward from the bottom opening, a first channel configured to receive the rod and extending downward from the upper opening into communication with the base cavity to form a through-space extending between the upper opening and the bottom opening, the through-space including a helically wound guide and advancement structure extending along an upper portion of the first channel, at least one internal recess beneath the helically wound guide and advancement structure, and at least one internal ridge projecting inwardly below the at least one internal recess; and
   an insert having a second channel configured to receive the rod, top surfaces adjacent the second channel, side structures protruding laterally outward and spaced below the top surfaces, and opposed lower extensions extending downwardly below the second channel, the insert configured for loading into a non-aligned position within the through-space of the receiver with the second channel being in non-alignment with the first channel,
   wherein the insert is non-threadably rotatable in the through-space of the receiver from the non-aligned position to an aligned position, so as to align the second channel with the first channel and to rotate the side structures into the at least one internal recess with the side structures being adjacent to and above the at least one internal ridge, and
   wherein upon a forced downward displacement of the insert within the through-space of the receiver, the the side structures are configured to engage the at least one internal ridge so as to inhibit the insert from moving upward within the through-space of receiver.

2. The receiver assembly of claim 1, further comprising at least one gap between the opposed lower extensions of the insert.

3. The receiver assembly of claim 1, further comprising side recesses or notches formed into outer surfaces of the insert and configured to engage with internal surfaces of the through-space of the receiver to inhibit further rotation of the insert within the receiver.

4. The receiver assembly of claim 1,
   wherein the receiver further comprises a base and a pair of upright arms extending upward from a base to define the first channel, and
   wherein the helically wound guide and advancement structure is a discontinuous helically wound guide and advancement structure.

5. The receiver assembly of claim 4, wherein the upright arms include upwardly-extending break-off extensions.

6. The receiver assembly of claim 1, wherein the the engagement between the side structures of the insert and the at least one internal ridge of the through space of the receiver is an increasingly frictional interference engagement.

7. The receiver assembly of claim 6, wherein the forced downward displacement towards the bottom opening within the through-space is brought about by a closure being rotated downwardly along the helically wound guide and advancement structure so as to drive the rod against the insert and move the insert downwardly within the through-space of the receiver.

8. A bone anchor assembly comprising the receiver assembly of claim 1 and the bone anchor, the bone anchor comprising the capture head having an at least partially spherical outer surface and an anchor portion opposite the capture head implantable into the bone of the patient.

9. The bone anchor assembly of claim 8, wherein the opposed lower extensions of the insert are configured to frictionally engage the at least partially spherical outer surface of the capture head of the bone anchor.

10. The bone anchor assembly of claim 8 and further comprising a retainer positionable within the base cavity of the receiver and configured to capture and pivotably secure the capture head of the bone anchor in the base cavity of the receiver.

11. The bone anchor assembly of claim 10, wherein the retainer is uploadable into base cavity through the bottom opening of the receiver.

12. The bone anchor assembly of claim 10, wherein the retainer is configured for positioning in the base cavity of the receiver prior to the capture head of the bone anchor being uploaded into the receiver via the bottom opening.

13. The bone anchor assembly of claim 10, wherein the retainer further comprises a ring-shaped body having at least one slit or slot extending at least partially through the body of the retainer.

14. The bone anchor assembly of claim 13, wherein the base cavity is sized and shaped to allow for expansion of the retainer when the capture head of the bone anchor is uploaded via the bottom opening, so as to capture the capture head in the base cavity.

15. The bone anchor assembly of claim 8 and further comprising the rod and a closure,
wherein the closure is configured to be rotated downwardly along the helically wound guide and advancement structure so as to drive the rod against the insert and move the insert downwardly within the through-space of the receiver, and
wherein the insert is configured to exert force against the capture head of the bone anchor sufficient to lock an orientation of the bone anchor relative to the receiver.

16. The bone anchor assembly of claim 15, wherein the closure is configured as a two-piece threaded closure with an outer threaded ring and an inner threaded set screw.

17. The bone anchor assembly of claim 16, wherein the outer threaded ring is configured to engage an upper end of the insert.

18. The bone anchor assembly of claim 8, wherein upon the forced downward displacement of the insert within the through-space of the receiver, the opposed lower extensions of the insert are configured to engage the capture head of the bone anchor with a frictional engagement so as to inhibit the bone anchor from moving upward within the through-space of receiver.

* * * * *